(12) United States Patent
Luo et al.

(10) Patent No.: US 10,981,910 B2
(45) Date of Patent: *Apr. 20, 2021

(54) BIARYL KINASE INHIBITORS

(71) Applicant: BRISTOL-MYERS SQUIBB COMPANY, Princeton, NJ (US)

(72) Inventors: Guanglin Luo, Newtown, PA (US); Carolyn Diane Dzierba, Middletown, CT (US); John E. Macor, Washington Crossing, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/913,064

(22) Filed: Jun. 26, 2020

(65) Prior Publication Data

US 2020/0317671 A1 Oct. 8, 2020

Related U.S. Application Data

(63) Continuation of application No. 16/443,929, filed on Jun. 18, 2019, which is a continuation of application No. 16/168,533, filed on Oct. 23, 2018, now Pat. No. 10,351,563, which is a continuation of application No. 15/865,848, filed on Jan. 9, 2018, now Pat. No. 10,155,760, which is a continuation of application No. 15/300,618, filed as application No. PCT/US2015/023805 on Apr. 1, 2015, now Pat. No. 9,902,722.

(60) Provisional application No. 62/061,591, filed on Oct. 8, 2014, provisional application No. 61/973,942, filed on Apr. 2, 2014.

(51) Int. Cl.
| | |
|---|---|
| C07D 401/04 | (2006.01) |
| A61K 31/4427 | (2006.01) |
| A61P 25/28 | (2006.01) |
| A61P 29/00 | (2006.01) |
| C07D 471/04 | (2006.01) |
| C07D 401/14 | (2006.01) |
| C07D 213/74 | (2006.01) |
| C07D 309/18 | (2006.01) |
| C07D 237/08 | (2006.01) |
| A61K 31/50 | (2006.01) |
| C07C 233/25 | (2006.01) |
| C07D 213/30 | (2006.01) |
| C07D 213/34 | (2006.01) |
| C07D 213/57 | (2006.01) |
| C07D 213/61 | (2006.01) |
| C07D 213/64 | (2006.01) |
| C07D 213/73 | (2006.01) |
| C07D 213/75 | (2006.01) |
| C07D 213/80 | (2006.01) |
| C07D 215/14 | (2006.01) |
| C07D 239/26 | (2006.01) |
| C07D 309/22 | (2006.01) |
| C07D 413/10 | (2006.01) |

(52) U.S. Cl.
CPC ........ *C07D 471/04* (2013.01); *A61K 31/4427* (2013.01); *A61K 31/50* (2013.01); *A61P 25/28* (2018.01); *C07C 233/25* (2013.01); *C07D 213/30* (2013.01); *C07D 213/34* (2013.01); *C07D 213/57* (2013.01); *C07D 213/61* (2013.01); *C07D 213/64* (2013.01); *C07D 213/73* (2013.01); *C07D 213/74* (2013.01); *C07D 213/75* (2013.01); *C07D 213/80* (2013.01); *C07D 215/14* (2013.01); *C07D 237/08* (2013.01); *C07D 239/26* (2013.01); *C07D 309/18* (2013.01); *C07D 309/22* (2013.01); *C07D 401/04* (2013.01); *C07D 401/14* (2013.01); *C07D 413/10* (2013.01)

(58) Field of Classification Search
CPC ... C07D 401/04; A61K 31/4427; A61P 25/28; A61P 29/00
USPC .......................................... 546/261; 514/335
See application file for complete search history.

(56) References Cited

U.S. PATENT DOCUMENTS

| | | | |
|---|---|---|---|
| 9,708,337 B2 | 7/2017 | Vrudhula et al. | |
| 9,902,722 B2 * | 2/2018 | Luo .................. | C07D 401/14 |
| 10,155,760 B2 * | 12/2018 | Luo .................. | C07D 213/30 |
| 10,253,027 B2 | 4/2019 | Hartz et al. | |
| 10,351,563 B2 | 7/2019 | Luo et al. | |
| 10,723,734 B2 | 7/2020 | Luo et al. | |
| 2013/0237555 A1 * | 9/2013 | Vrudhula .............. | A61P 25/00 |
| | | | 514/278 |

FOREIGN PATENT DOCUMENTS

| | | |
|---|---|---|
| WO | WO 2004/041810 A1 | 5/2004 |
| WO | WO 2013/134036 A1 | 9/2013 |
| WO | WO 2013/134336 A2 | 9/2013 |
| WO | WO 2014/022167 A1 | 2/2014 |
| WO | WO 2014/130258 A1 | 8/2014 |
| WO | WO 2015/006100 A1 | 1/2015 |
| WO | WO 2015/038112 A1 | 3/2015 |
| WO | WO 2015/116060 A1 | 8/2015 |

(Continued)

OTHER PUBLICATIONS

Kostich et al. J Pharmacol Exp Ther 358:371-386, Sep. 2016.*

(Continued)

*Primary Examiner* — Venkataraman Balasubramanian
(74) *Attorney, Agent, or Firm* — Mary K. VanAtten

(57) ABSTRACT

The present disclosure is generally directed to compounds which can inhibit AAK1 (adaptor associated kinase 1), compositions comprising such compounds, and methods for inhibiting AAK1.

2 Claims, 1 Drawing Sheet
Specification includes a Sequence Listing.

(56) References Cited

FOREIGN PATENT DOCUMENTS

| WO | WO 2015/116492 A1 | 8/2015 |
|----|-------------------|--------|
| WO | WO 2016/053794 A1 | 4/2016 |
| WO | WO 2016/164295 A2 | 10/2016 |
| WO | WO 2017/059080 A1 | 4/2017 |
| WO | WO 2017/059085 A1 | 4/2017 |

OTHER PUBLICATIONS

Cecil Textbook of Medicine, edited by Bennet, J.C., and Plum F., 20th edition, vol. 1, 1004-1010, 1996.*
Cohen et al., Current Opinion in Chemical Biology, 3,459-465, 1999.*
Freshney et al., Culture of Animal Cells, A Manual of Basic Technique, Alan R. Liss, Inc., 1983, New York, p. 4.*
Dermer et al., Bio/Technology, 1994, 12:320.*
Buonanno, A., "The neuregulin signaling pathway and schizophrenia: From genes to synapses and neural circuits", Brain Research Bulletin, vol. 83, pp. 122-131 (2010).
Conner, S.D. et al., "AAK-1 Mediated µ2 Phosphorylation is Stimulated by Assembled Clathrin", Traffic, vol. 4, pp. 885-890 (2003).
Conner, S.D. et al., "Identification of an adaptor-associated kinase, AAK1, as a regulator of clathrin-mediated endocytosis", The Journal of Cell Biology, vol. 156, No. 5, pp. 921-929 (2002).
Greenwood, T.A. et al., "Analysis of 94 Candidate Genes and 12 Endophenotypes for Schizophrenia", Am. J. Psychiatry, vol. 168, No. 9, pp. 930-946 (2011).
Henderson, D.M. et al., "A Novel AAK1 Splice Variant Functions at Multiple Steps of the Endocytic Pathway", Molecular Biology of the Cell, vol. 18, pp. 2698-2706 (2007).
Jaaro-Peled, H. et al., "Review of Pathological Hallmarks of Schizophrenia: Comparison of Genetic Models with Patients and Nongenetic Models", Schizophrenia Bulletin, vol. 36, No. 2, pp. 301-313 (2010).
Jackson, A.P. et al., "Clathrin promotes incorporation of cargo into coated pits by activation of the AP2 adaptor µ2 kinase", The Journal of Cell Biology, vol. 163, No. 2, pp. 231-236 (2003).
Kuai, L. et al., "AAK1 Identified as an Inhibitor of Neuregulin-1/ErbB4-Dependent Neurotrophic Factor Signaling Using Integrative Chemical Genomics and Proteomics", Chemistry & Biology, vol. 18, pp. 891-906 (2011).
Latourelle, J.C. et al., "Genomewide association study for onset age in Parkinson disease", BMC Medical Genetics, 10:98 (2009).
Motley, A.M. et al., Functional Analysis of AP-2 α and µ2 Subunits, Molecular Biology of the Cell, vol. 17, pp. 5298-5308 (2006).
Ricotta, D. et al., "Phosphorylation of the AP2 µ subunit by AAK1 mediates high affinity binding to membrane protein sorting signals", The Journal of Cell Biology, vol. 156, No. 5, pp. 791-795 (2002).
Wen, L. et al., "Neuregulin 1 regulates pyramidal neuron activity via ErbB4 in parvalbumin-positive interneurons", Proc. Natl. Acad. Sci. USA, vol. 107, No. 3, pp. 1211-1216 (2010).
Kostich, W. et al., "Inhibition of AAK1 Kinase as a Novel Therapeutic Approach to Treat Neuropathic Pain," The Journal of Pharmacology and Experimental Therapeutics, 358, pp. 371-386, (Sep. 2016).

\* cited by examiner

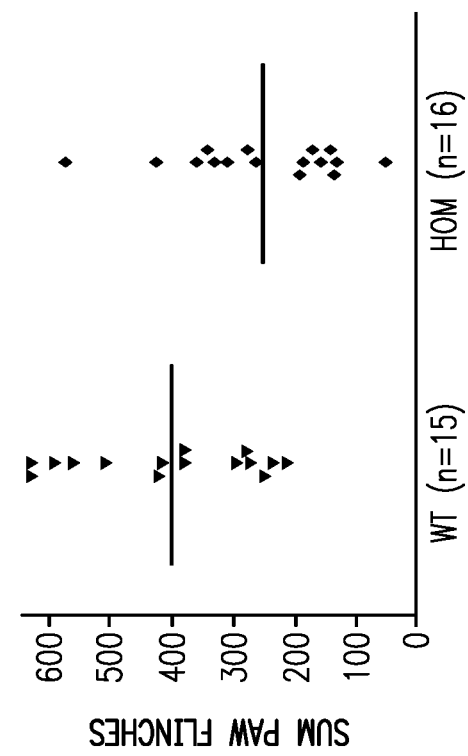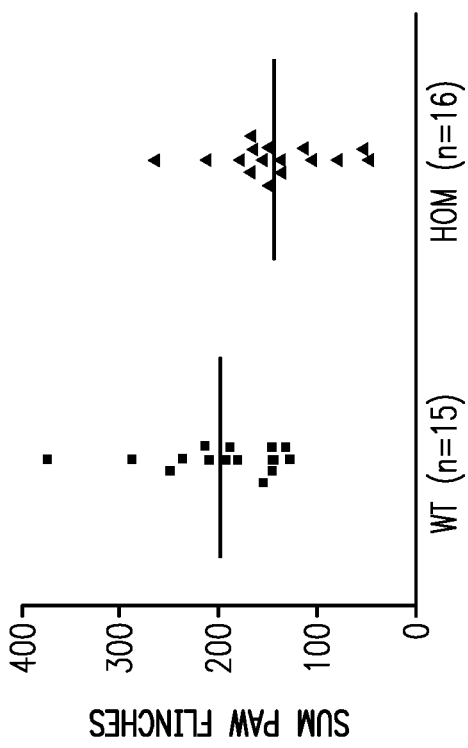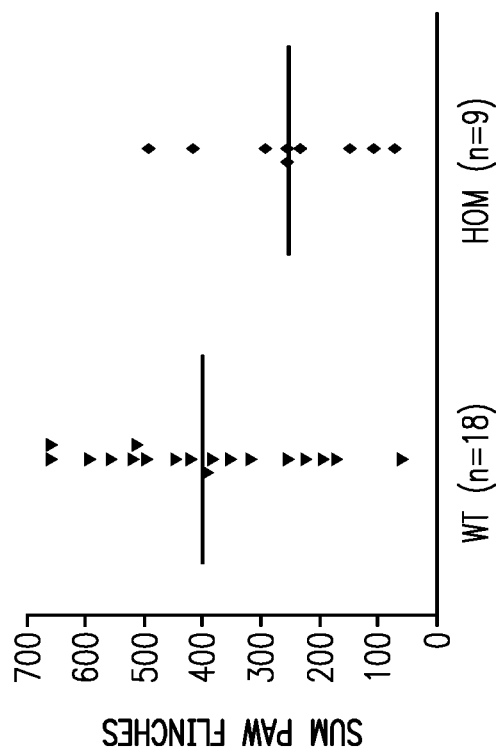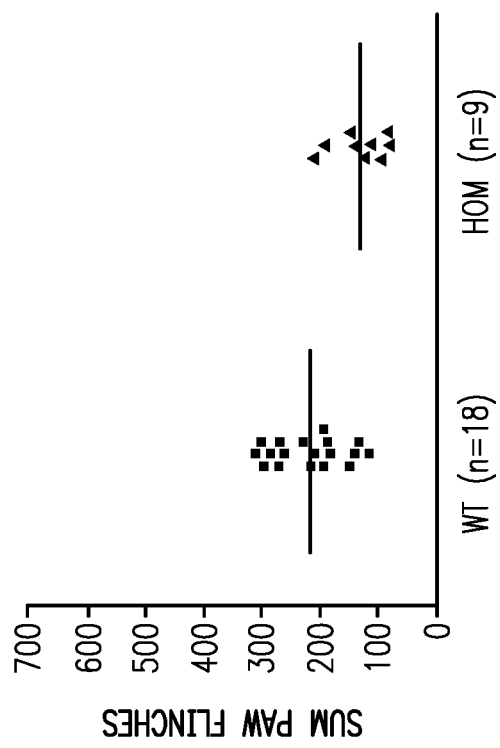

SEQUENCE LISTING

```
<160> NUMBER OF SEQ ID NOS: 1

<210> SEQ ID NO 1
<211> LENGTH: 18
<212> TYPE: PRT
<213> ORGANISM: Artificial Sequence
<220> FEATURE:
<223> OTHER INFORMATION: fluoresceinated peptide
```

```
<400> SEQUENCE: 1

Lys Glu Glu Gln Ser Gln Ile Thr Ser Gln Val Thr Gly Gln Ile Gly
1               5                   10                  15

Trp Arg
```

BIARYL KINASE INHIBITORS

CROSS-REFERENCE TO RELATED APPLICATIONS

This Continuation application claims the benefit of U.S. Ser. No. 16/443,929, filed Jun. 18, 2019, now allowed, which claims the benefit of U.S. Ser. No. 16/168,533, filed Oct. 23, 2018, now U.S. Pat. No. 10,351,563, which claims the benefit of U.S. Ser. No. 15/865,848 filed Jan. 9, 2018, now U.S. Pat. No. 10,155,760, which claims the benefit of U.S. Ser. No. 15/300,618 filed Sep. 29, 2016, now U.S. Pat. No. 9,902,722, which is a 371 of PCT/US2015/023805 filed Apr. 1, 2015, which claims the benefit of Provisional application U.S. Ser. No. 61/973,942 filed Apr. 2, 2014, and Provisional application U.S. Ser. No. 62/061,591 filed Oct. 8, 2014, hereby incorporated by reference in their entireties.

The present disclosure is generally directed to compounds which can inhibit adaptor associated kinase 1 (AAK1), compositions comprising such compounds, and methods for inhibiting AAK1.

Adaptor associated kinase 1 (AAK1) is a member of the Ark1/Prk1 family of serine/threonine kinases. AAK1 mRNA exists in two splice forms termed short and long. The long form predominates and is highly expressed in brain and heart (Henderson and Conner, *Mol. Biol. Cell.* 2007, 18, 2698-2706). AAK1 is enriched in synaptosomal preparations and is co-localized with endocytic structures in cultured cells. AAK1 modulates clatherin coated endocytosis, a process that is important in synaptic vesicle recycling and receptor-mediated endocytosis. AAK1 associates with the AP2 complex, a hetero-tetramer which links receptor cargo to the clatherin coat. The binding of clatherin to AAK1 stimulates AAK1 kinase activity (Conner et. al., *Traffic* 2003, 4, 885-890; Jackson et. al., *J. Cell. Biol.* 2003, 163, 231-236). AAK1 phosphorylates the mu-2 subunit of AP-2, which promotes the binding of mu-2 to tyrosine containing sorting motifs on cargo receptors (Ricotta et. al., *J. Cell Bio.* 2002, 156, 791-795; Conner and Schmid, *J. Cell Bio.* 2002, 156, 921-929). Mu2 phosphorylation is not required for receptor uptake, but phosphorylation enhances the efficiency of internalization (Motely et. al., *Mol. Biol. Cell.* 2006, 17, 5298-5308).

AAK1 has been identified as an inhibitor of Neuregulin-1/ErbB4 signaling in PC12 cells. Loss of AAK1 expression through RNA interference mediated gene silencing or treatment with the kinase inhibitor K252a (which inhibits AAK1 kinase activity) results in the potentiation of Neuregulin-1 induced neurite outgrowth. These treatments result in increased expression of ErbB4 and accumulation of ErbB4 in or near the plasma membrane (Kuai et. al., *Chemistry and Biology* 2011, 18, 891-906). NRG1 and ErbB4 are putative schizophrenia susceptibility genes (Buonanno, *Brain Res. Bull.* 2010, 83, 122-131). SNPs in both genes have been associated with multiple schizophrenia endophenotypes (Greenwood et. al., *Am. J. Psychiatry* 2011, 168, 930-946). Neuregulin 1 and ErbB4 KO mouse models have shown schizophrenia relevant morphological changes and behavioral phenotypes (Jaaro-Peled et. al., *Schizophrenia Bulletin* 2010, 36, 301-313; Wen et. al., Proc. Natl. Acad. Sci. USA. 2010, 107, 1211-1216). In addition, a single nucleotide polymorphism in an intron of the AAK1 gene has been associated with the age of onset of Parkinson's disease (Latourelle et. al., *BMC Med. Genet.* 2009, 10, 98). These results suggest that inhibition of AAK1 activity may have utility in the treatment of schizophrenia, cognitive deficits in schizophrenia, Parkinson's disease, neuropathic pain, bipolar disorder, and Alzheimer's disease.

In addition, studies using Huh-7.5 cells indicate a potential utility for AAK1 kinase inhibitors in the treatment of hepatitis C (HCV) infection. Reduction of AAK1 protein using RNA interference mediated gene silencing, treatment with the kinase inhibitor sunitinib (a potent AAK1 inhibitor), and overexpression of Mu2 (AAK1 substrate) phosphorylation site mutant all result in reduced HCV virion assembly. Furthermore the same treatments were shown to inhibit HCV entry, suggesting AAK1 inhibitors can disrupt two host dependent stages of the virus life cycle (Neveu et. al., *PLoS Pathog.* 2012, 8, 1-16; Neveu et. al., *J. Virol.* 2015, posted online 4 February). AAK1 inhibitors may also be useful against HIV and HBV (see, for example, Boge et al., *J. Biol. Chem.* 1998, 273, 15773-15778).

In its first aspect the present disclosure provides a compound of formula (I) A compound of formula (I)

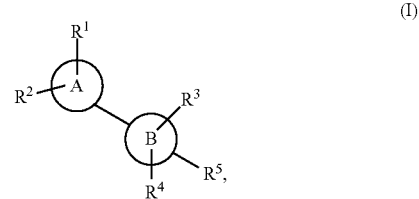

or a pharmaceutically acceptable salt thereof, wherein:

A is selected from

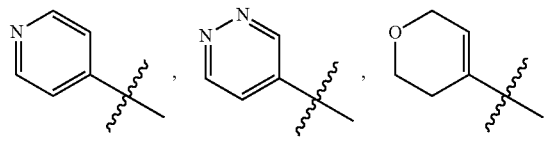

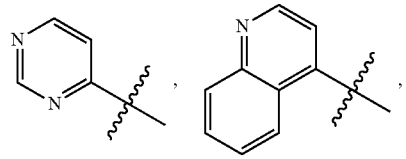

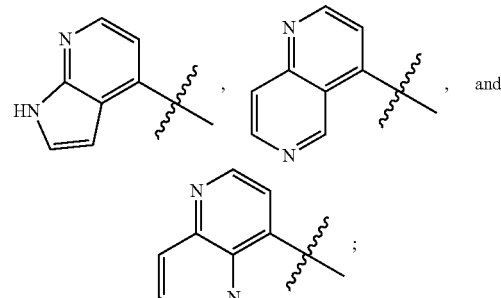

wherein "⸸" denotes the point of attachment to B;

B is selected from

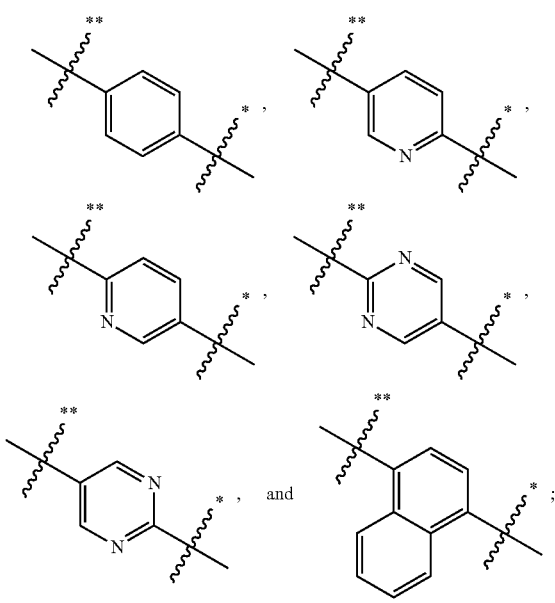

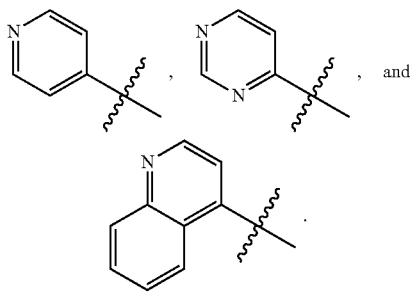

wherein "*" indicates the point of attachment to R5 and "**" indicates the point of attachment to ring A;

R$^1$ is selected from hydrogen, amino, —CO$_2$H, difluoromethyl, ethyl, halo, hydroxymethyl, methoxy, methyl, —NHC(O)CH$_3$, —NHCO$_2$CH$_3$, trifluoromethoxy, and trifluoromethyl;

R$^2$ is selected from hydrogen, cyano, —CH$_2$OH, halo, and methyl;

R$^3$ is selected from hydrogen, cyano, cyclopropyl, difluoromethyl, halo, hydroxymethyl, methoxy, methyl, methylsulfonyl, trifluoromethoxy, trifluoromethyl, —CH$_2$N(CH$_3$)$_2$, and a five-membered aromatic ring containing one, two, or three heteroatoms selected from nitrogen, oxygen, and sulfur;

R$^4$ is selected from hydrogen, halo, and methyl;

R$^5$ is selected from

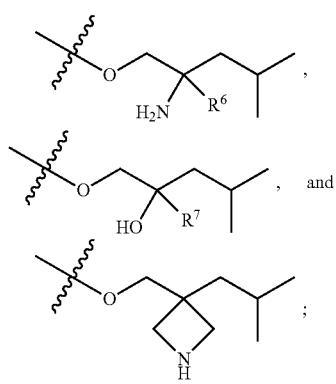

R$^6$ is selected from hydrogen, ethyl, fluoromethyl, difluoromethyl, methyl, and trifluoromethyl; and R$^7$ is methyl.

In a first embodiment of the first aspect the present disclosure provides a compound of formula (I), or a pharmaceutically acceptable salt thereof, wherein A is selected from In a second embodiment of the first aspect the present disclosure provides a compound of formula (I), or a pharmaceutically acceptable salt thereof, wherein B is selected from

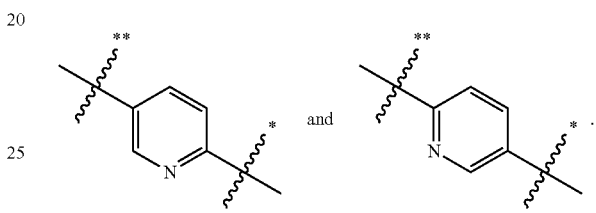

In a third embodiment, B is.

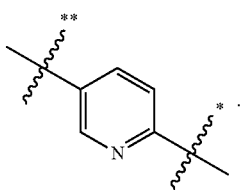 [SMILES: *c1ccc(*)nc1]

In a fourth embodiment of the first aspect the present disclosure provides a compound of formula (I), or a pharmaceutically acceptable salt thereof, wherein R$^5$ is

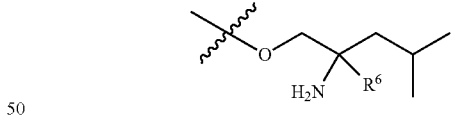

In a second aspect the present disclosure provides a compound of formula (II)

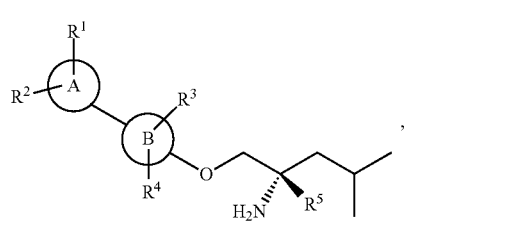

(II)

or a pharmaceutically acceptable salt thereof, wherein:

A is selected from

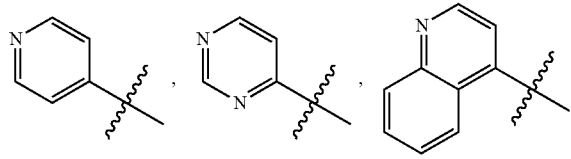,

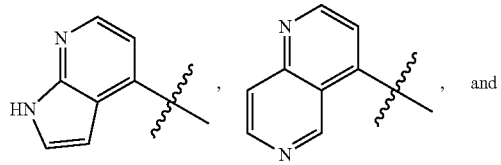, and

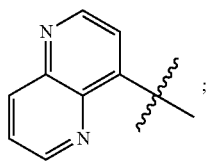;

wherein " ⌇ " denotes the point of attachment to B;

B is selected from phenyl and pyridinyl;

R¹ is selected from hydrogen, difluoromethyl, halo, methoxy, methyl, —NHC(O)CH₃, —NHCO₂CH₃, and trifluoromethyl;

R² is selected from hydrogen, —CH₂OH, and halo;

R³ is selected from hydrogen, cyano, cyclopropyl, difluoromethyl, halo, hydroxymethyl, methoxy, methyl, trifluoromethoxy, trifluoromethyl, and a five-membered aromatic ring containing one, two, or three heteroatoms selected from nitrogen, oxygen, and sulfur;

R⁴ is selected from hydrogen, halo, and methyl; and

R⁵ is selected from hydrogen, ethyl, fluoromethyl, difluoromethyl, methyl, and trifluoromethyl.

In a first embodiment of the second aspect the present disclosure provides a compound of formula (II), or a pharmaceutically acceptable salt thereof, wherein A is selected from

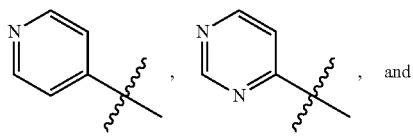

In a second embodiment of the second aspect the present disclosure provides a compound of formula (II), or a pharmaceutically acceptable salt thereof, wherein B is pyridinyl. In a third embodiment B is.

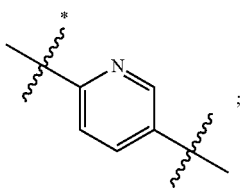 [SMILES: *c1ccc(*)nc1];

wherein " ⌇* " denotes the point of attachment to A and " ⌇ " denotes the point of attachment to the oxygen atom.

In a fourth embodiment of the second aspect the present disclosure provides a compound of formula (II), or a pharmaceutically acceptable salt thereof, wherein wherein A is selected from

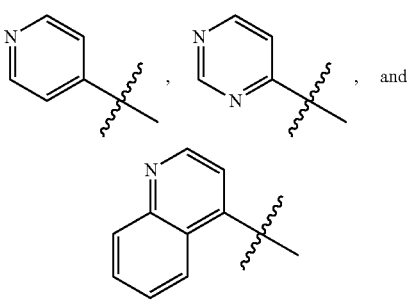

and

B is

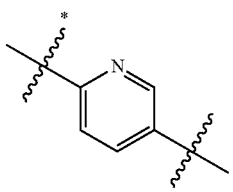.

In a third aspect the present disclosure provides a composition comprising a pharmaceutically acceptable amount of a compound of formula (I), or a pharmaceutically acceptable salt thereof, and a pharmaceutically acceptable carrier.

In a fourth aspect the present disclosure provides a method of inhibiting adaptor associated kinase 1 (AAK1) activity, comprising contacting AAK1 with a compound of formula (I), or a pharmaceutically acceptable salt thereof.

In a fifth aspect the present disclosure provides a method for treating or managing a disease or a disorder mediated by AAK1 activity, the method comprising administering to a patient in need thereof a therapeutically effective amount of a compound of formula (I), or a pharmaceutically acceptable salt thereof. In a first embodiment of the fifth aspect the disease or disorder is selected from Alzheimer's disease, bipolar disorder, pain, Parkinson's disease, and schizophrenia. In a second embodiment the pain is neuropathic pain. In a third embodiment the neuropathic pain is fibromyalgia or peripheral neuropathy.

Other aspects of the present disclosure may include suitable combinations of embodiments disclosed herein.

Yet other aspects and embodiments may be found in the description provided herein.

BRIEF DESCRIPTION OF THE FIGURES

Aspects of the disclosure are illustrated in FIG. 1, which shows results obtained from a formalin pain model using AAK1 homozygous (−/−) knockout mice and their wild-type (+/+) littermates. The AAK1 homozygous (−/−) knockout mice show a clear reduction in both acute and tonic pain response as compared to their wild-type (+/+) littermates.

This disclosure is based, in part, on the discovery that AAK1 knockout mice exhibit a high resistance to pain. That discovery prompted research that ultimately led to the discovery of AAK1 inhibitors, compositions comprising them, and methods of their use.

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

As used in the present specification, the following terms have the meanings indicated:

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

In some instances, the number of carbon atoms in any particular group is denoted before the recitation of the group. For example, the term "$C_{1-6}$ alkyl" denotes an alkyl group containing one to six carbon atoms. Where these designations exist they supercede all other definitions contained herein.

The term "halo," as used herein, refers to Br, Cl, F, and/or I.

Asymmetric centers may exist in the compounds of the present disclosure. It should be understood that the disclosure encompasses all stereochemical isomeric forms, or mixtures thereof, which possess the ability to inhibit AAK1. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of formula (I), and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, diydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

One embodiment of this disclosure encompasses methods of inhibiting adaptor associated kinase 1 (AAK1), both in vitro and in vivo, which comprise contacting AAK1 with a compound of formula I or a pharmaceutically acceptable salt thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. Unless otherwise indicated, a "therapeutically effective amount" of a compound is an amount sufficient to provide a therapeutic benefit in the treatment or management of a disease or condition, or to delay or minimize one or more symptoms associated with the disease or condition. The term "therapeutically effective amount" can encompass an amount that improves overall therapy, reduces or avoids symptoms or causes of a disease or condition, or enhances the therapeutic efficacy of another therapeutic agent.

The term "therapeutically effective amount," as used herein, refers to an amount of a compound or compounds sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, that provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Compounds of the disclosure may be administered in combination with one or more additional therapeutic or prophylactic agents. For example, when used for the treatment of pain, possible additional agents include immunosuppressive agents, anti-inflammatory agents, and/or other agents used in the treatment of pain.

Immunosuppressants suitable for use in the methods and compositions of this disclosure include those known in the art. Examples include aminopterin, azathioprine, cyclosporin A, D-penicillamine, gold salts, hydroxychloroquine, leflunomide, methotrexate, minocycline, rapamycin, sulfasalazine, tacrolimus (FK506), and pharmaceutically acceptable salts thereof. A particular immunosuppressant is methotrexate.

Additional examples of immunosuppressants include anti-TNF antibodies, such as adalimumab, certolizumab pegol, etanercept, and infliximab. Others include interleukin-1 blockers, such as anakinra. Others include anti-B cell (CD20) antibodies, such as rituximab. Others include T cell activation blockers, such as abatacept.

Other immunosuppressants include inosine monophosphate dehydrogenase inhibitors, such as mycophenolate mofetil (CellCept®) and mycophenolic acid (Myfortic®).

Anti-inflammatory drugs suitable for use in the methods and compositions of this disclosure include those known in the art. Examples include glucocorticoids and NSAIDs. Examples of glucocorticoids include aldosterone, beclometasone, betamethasone, cortisone, deoxycorticosterone, dexamethasone, fludrocortisones, hydrocortisone, methylprednisolone, prednisolone, prednisone, triamcinolone, and pharmaceutically acceptable salts thereof.

Examples of NSAID include salicylates (e.g., aspirin, amoxiprin, benorilate, choline magnesium salicylate, diflunisal, faislamine, methyl salicylate, magnesium salicylate, salicyl salicylate, and pharmaceutically acceptable salts thereof), arylalkanoic acids (e.g., diclofenac, aceclofenac, acemetacin, bromfenac, etodolac, indometacin, nabumetone, sulindac, tolmetin, and pharmaceutically acceptable salts thereof), arylpropionic acids (e.g., ibuprofen, carprofen, fenbufen, fenoprofen, flurbiprofen, ketoprofen, ketorolac, loxoprofen, naproxen, oxaprozin, tiaprofenic acid, suprofen, and pharmaceutically acceptable salts thereof), arylanthranilic acids (e.g., meclofenamic acid, mefenamic acid, and pharmaceutically acceptable salts thereof), pyrazolidine derivatives (e.g., azapropazone, metamizole, oxyphenbutazone, phenylbutazone, sulfinprazone, and pharmaceutically acceptable salts thereof), oxicams (e.g., lornoxicam, meloxicam, piroxicam, tenoxicam, and pharmaceutically acceptable salts thereof), COX-2 inhibitors (e.g., celecoxib, etoricoxib, lumiracoxib, parecoxib, rofecoxib, valdecoxib, and pharmaceutically acceptable salts thereof), and sulphonanilides (e.g., nimesulide and pharmaceutically acceptable salts thereof).

Other agents used in the treatment of pain (including but not limited to neuropathic and inflammatory pain) include, but are not limited to, agents such as pregabalin, lidocaine, duloxetine, gabapentin, carbamazepine, capsaicin, and other serotonin/norepinephrine/dopamine reuptake inhibitors, and opiates (such as oxycontin, morphine, and codeine).

In the treatment of pain caused by a known disease or condition, such as diabetes, infection (e.g., herpes zoster or HIV infection), or cancer, compounds of the disclosure may be administered in combination with one or more additional therapeutic or prophylactic agents directed at the underlying disease or condition. For example, when used to treat diabetic neuropathy, compounds of the disclosure may be administered in combination with one or more anti-diabetic agents, anti-hyperglycemic agents, hypolipidemic/lipid lowering agents, anti-obesity agents, anti-hypertensive agents and appetite suppressants. Examples of anti-diabetic agents include biguanides (e.g., metformin, phenformin), glucosidase inhibitors (e.g., acarbose, miglitol), insulins (including insulin secretagogues and insulin sensitizers), meglitinides (e.g., repaglinide), sulfonylureas (e.g., glimepiride, glyburide, gliclazide, chlorpropamide, and glipizide), biguanide/glyburide combinations (e.g., Glucovance), thiazolidinediones (e.g., troglitazone, rosiglitazone, and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, dipeptidyl peptidase IV (DPP4) inhibitors, and sodium-glucose co-transporter 2 (SGLT2) inhibitors (e.g., dapagliflozin, canagliflozin, and LX-4211).

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals. Unless otherwise indicated, the terms "manage," "managing", and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

This disclosure is intended to encompass compounds having Formula (I) when prepared by synthetic processes or by metabolic processes including those occurring in the human or animal body (in vivo) or processes occurring in vitro.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The abbreviations used in the present application, including particularly in the illustrative schemes and examples which follow, are well-known to those skilled in the art. Some of the abbreviations used are as follows: MeOH for methanol; min for minutes, EtOAc or ETOAC for ethyl acetate; h or hr or hrs for hours; $Ph_3P$ for triphenylphosphine, DIAD for diisopropyl azodicarboxylate; RT or rt or r.t. for room temperature or retention time (context will dictate); $t_R$ for retention time; EtOH for ethanol; DMSO for dimethylsulfoxide; THF for tetrahydrofuran; dppf for diphenylphosphinoferrocene; TFA for trifluoracetic acid; NMP for N-methylpyrrolidine; CBz or Cbz for benzyloxycarbonyl; DCM for dichloromethane; IPA for isopropyl alcohol; DMAP for N,N-dimethylaminopyridine; BOC or Boc for tert-butoxycarbonyl; $(BOC)_2O$ for di-tert-butyl dicarbonate/ DMF for N,N-dimethylformamide; OAc for acetate; Cbz for carbobenzyloxy; TMS for trimethylsilane; LDA for lithium diisopropylamide; MOM-Cl for chloromethyl methyl ether; KHMDS for potassium hexamethyldisilazide; KOtBu for potassium tert-butoxide; DAST for diethylaminosulfur trifloride; BuOH for n-butanol; n-BuLi for n-butyllithium; and NBS for N-bromosuccinimide.

The compounds of the present disclosure may be prepared using the reactions and techniques described in this section as well as other synthetic methods known to those of ordinary skill in the art. The reactions are performed in solvents appropriate to the reagents and materials employed and suitable for the transformation being affected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Compounds of Formula Ia can be synthesized following General Scheme I. The two key reactions, Suzuki coupling and ether formation, could alternate as shown depending on the commercially available starting materials. The Suzuki coupling substrates, boronic acids/boronates, were either commercially available or prepared from corresponding halogen intermediates (Cl/Br/I) with various standard literature conditions. The ether formation can be achieved by $SN_{AR}$ when a fluorine intermediate (Formula IV) is available, by Mitsunobu reaction or alkylation with suitable amino alcohol when an OH is available (Formula III/V), and by Buchwald's Pd-catalyzed ether formation reaction when a Cl intermediate (Formula III/V) is available. In cases where $R^5$ is bigger than H, an activated form of the amino alcohol (Formula VII) was used as the OH-alkylating reagent. Sometimes $NH_2$ and OH were protected and deprotected during the reaction sequence.

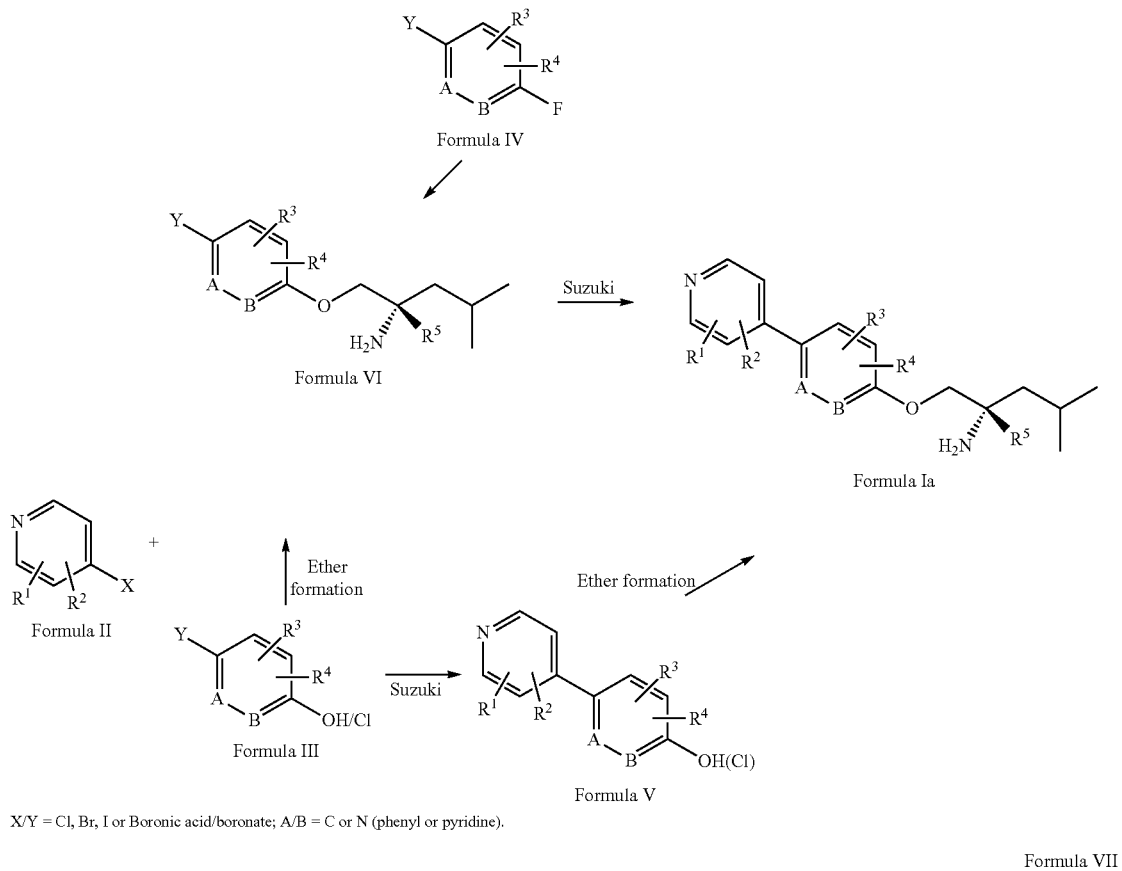

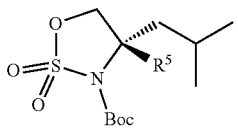

A common activated amino alcohol reagent for ether formation when $R^5$ is not H.

In the following examples, proton NMR spectra were recorded on either a Bruker 400 or 500 MHz NMR spectrometer. Chemical shifts are reported in δ values relative to tetramethylsilane. Liquid chromatography (LC)/mass spectra were run on a Shimadzu LC coupled to a Waters Micromass ZQ using at least one of the following methods.

LC/MS Method A:
Column: Phenomenex LUNA C18, 30×2, 3 µm; Solvent A=5% MeOH: 95%
Water: 10 mM Ammonium Acetate; Solvent B=95% MeOH: 5% Water: 10 mM
Ammonium Acetate; Flow rate: 1 ml/min; Starting B=0%; Final B=100%; Gradient time=2 min; Run time: 3 min.

LC/MS Method B:
Column: Phenomenex LUNA C18, 30×2, 3 µm; Solvent A=10% MeOH: 90%

Water: 0.1% TFA; Solvent B=90% MeOH: 10% Water: 0.1% TFA; Flow rate: 1 ml/min; Starting B=0%; Final B=100%; Gradient time=2 min; Run time: 3 min.
LC/MS Method C:
Column: Phenomenex LUNA C18, 30×2, 3 μm; Solvent A=5% MeOH: 95%
Water: 10 mM Ammonium Acetate; Solvent B=95% MeOH: 5% Water: 10 mM
Ammonium Acetate; Flow rate: 0.8 ml/min; Starting B=0%; Final B=100%; Gradient time=4 min; Run time: 5 min.

Example 1

(S)—N-(4-(4-((2-amino-4-methylpentyl)oxy)-3-fluorophenyl)pyridin-2-yl)acetamide

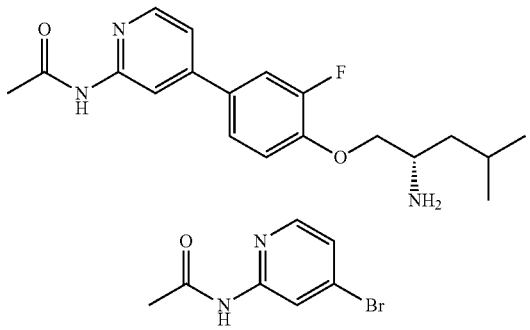

Part A: N-(4-bromopyridin-2-yl)acetamide

To a mixture of 4-bromopyridin-2-amine (3.11 g, 17.98 mmol) in $CH_2Cl_2$ (60 mL) at 0° C. was added acetyl chloride (1.406 mL, 19.77 mmol) and pyridine (1.745 mL, 21.57 mmol). The mixture was warmed to rt and stirred for 2 h. The reaction was quenched with water and diluted with EtOAc. The layers were separated. The organic layer was washed with water, brine, dried ($Na_2SO_4$) and concentrated under reduced pressure to obtain N-(4-bromopyridin-2-yl)acetamide (3.82 g, 17.05 mmol, 95% yield) as a white solid. The material was carried on without further purification. LCMS (ESI) m/e 215.0 [(M+H)$^+$, calcd $C_7H_8Br_1N_2O_1$, 215.0]; LC/MS retention time (method A): $t_R$=2.61 min.

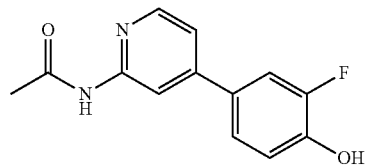 [SMILES: CC(=O)Nc1cc(-c2ccc(O)c(F)c2)ccn1]

Part B: N-(4-(3-fluoro-4-hydroxyphenyl)pyridin-2-yl)acetamide

To a 15 mL vial was added N-(4-bromopyridin-2-yl)acetamide (205.8 mg, 0.957 mmol), (3-fluoro-4-hydroxyphenyl)boronic acid (239 mg, 1.531 mmol), and $Na_2CO_3$ (1.435 mL, 2.87 mmol) in dioxane (3 mL) under nitrogen to give a colorless solution. 1,1'-bis(diphenylphosphino)ferrocenepalladium(II) dichloride, toluene (39.4 mg, 0.048 mmol) was added under nitrogen. The vial was sealed and heated at 130° C. (microwave) for 2 h. The mixture was partitioned between water and EtOAc. The layers were separated. The organic layer was washed with brine, dried ($Na_2SO_4$) and concentrated under reduced pressure to obtain N-(4-(3-fluoro-4-hydroxyphenyl)pyridin-2-yl)acetamide (200 mg, 0.812 mmol, 85% yield) as a tan solid. LCMS (ESI) m/e 247.0 [(M+H)$^+$, calcd $C_{13}H_{12}F_1N_2O_2$, 247.1]; LC/MS retention time (method A): $t_R$=1.51 min.

Part C: (S)-2-(1-hydroxy-4-methylpentan-2-yl)isoindoline-1,3-dione

To a 250 mL round-bottomed flask was added (S)-3-amino-5-methylhexan-1-ol (2.166 g, 16.51 mmol) and isobenzofuran-1,3-dione (2.445 g, 16.51 mmol) in toluene (60 mL) to give a colorless suspension. The mixture was heated at 110° C. for 16 h. The volatiles were removed under high vacuum to afford (S)-2-(1-hydroxy-4-methylpentan-2-yl)isoindoline-1,3-dione (4.08 g, 16.51 mmol, quantitative yield) as a light yellow dense oil. LCMS (ESI) m/e 246.2 [(M−H)$^+$, calcd $C_{14}H_{16}N_1O_3$, 246.1]; LC/MS retention time (method A): $t_R$=1.88 min.

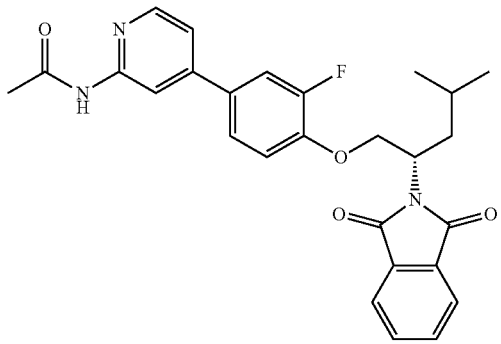 [SMILES: CC(=O)Nc1cc(-c2ccc(OC[C@H](CC(C)C)N3C(=O)c4ccccc4C3=O)c(F)c2)ccn1]

Part D: (S)—N-(4-(4-((2-(1,3-dioxoisoindolin-2-yl)-4-methylpentyl)oxy)-3-fluorophenyl)pyridin-2-yl)acetamide To a 50 mL round-bottomed flask was added (S)-2-(1-hydroxy-4-methylpentan-2-yl)isoindoline-1,3-dione (93 mg, 0.375 mmol), $Ph_3P$ (123 mg, 0.468 mmol), and (S)-2-(1-hydroxy-4-methylpentan-2-yl)isoindoline-1,3-dione (93 mg, 0.375 mmol) in tetrahydrofuran (1 mL) to give a tan suspension. DIAD (0.091 mL, 0.468 mmol) was added dropwise at rt. The resultant clear tan solution was stirred at rt for 19 h. The solution was concentrated under reduced pressure to give a tan oil which was carried directly into the next reaction. LCMS (ESI) m/e 476.3 [(M+H)$^+$, calcd $C_{27}H_{27}F_1N_3O_4$, 476.2]; LC/MS retention time (method A): $t_R$=2.21 min.

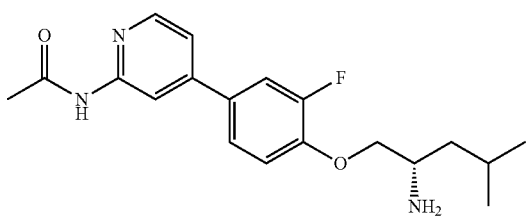

Part E: (S)—N-(4-(4-((2-amino-4-methylpentyl)oxy)-3-fluorophenyl)pyridin-2-yl)acetamide To a 50 mL round-bottomed flask was added (S)—N-(4-(4-((2-(1,3-dioxoisoindolin-2-yl)-4-methylpentyl)oxy)-3-fluorophenyl)pyridin-2-yl)acetamide (148 mg, 0.312 mmol) in EtOH (2 mL) to give a tan solution. Hydrazine (0.049 mL, 1.560 mmol) was added and the mixture was heated at 60° C. for 2 h. The solution was cooled to rt and was concentrated under reduced pressure. The residue was suspended in MeOH, filtered, and purified by prep-HPLC (24 mg, 0.069 mmol, 22% yield for 3 steps): $^1$H NMR (500 MHz, DMSO-d$_6$) δ 10.53 (s, 1H), 8.33 (d, J=4.9 Hz, 2H), 7.61 (dd, J=12.5, 2.2 Hz, 1H), 7.52 (dd, J=8.5, 2.2 Hz, 1H), 7.43-7.37 (m, 1H), 7.32 (t, J=8.7 Hz, 1H), 3.97 (dd, J=9.5, 4.9 Hz, 1H), 3.90 (dd, J=9.5, 6.5 Hz, 1H), 3.12 (dt, J=11.9, 5.4 Hz, 1H), 2.12 (s, 3H), 1.81 (dq, J=13.0, 6.5 Hz, 1H), 1.33 (ddd, J=13.5, 8.5, 5.0 Hz, 1H), 1.26 (ddd, J=13.5, 8.5, 5.5 Hz, 1H), 0.92 (d, J=6.6 Hz, 3H), 0.88 (d, J=6.5 Hz, 3H); LCMS (ESI) m/e 346.2 [(M+H)$^+$, calcd C$_{19}$H$_{25}$F$_1$N$_3$O$_2$, 346.2]; LC/MS retention time (method A): t$_R$=1.89 min.

Alternative Synthesis of Example 1

(S)—N-(4-(4-((2-amino-4-methylpentyl)oxy)-3-fluorophenyl)pyridin-2-yl)acetamide

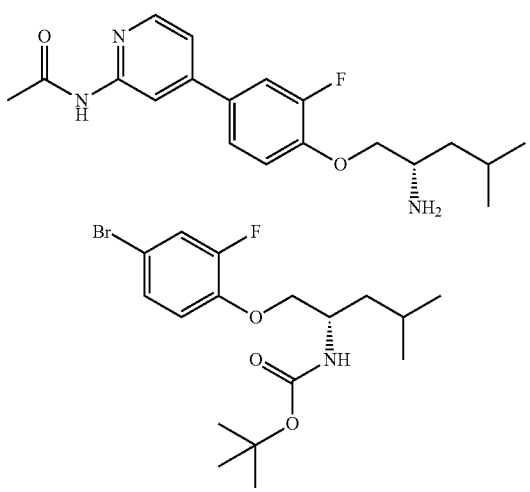

Part 2A: (S)-tert-butyl (1-(4-bromo-2-fluorophenoxy)-4-methylpentan-2-yl)carbamate To a 15 mL vial was added (S)-tert-butyl (1-hydroxy-4-methylpentan-2-yl)carbamate (172 mg, 0.792 mmol), Ph$_3$P (260 mg, 0.990 mmol), and 4-bromo-2-fluorophenol (126 mg, 0.660 mmol) in tetrahydrofuran (2 mL) to give a tan solution. DIAD (0.180 mL, 0.924 mmol) was added at rt. The resulted clear tan solution was stirred at rt for 16 h. The solution was concentrated under reduced pressure to afford a tan oil which was directly purified by silica gel column chromatography (up to 60% EtOAc/hexane to afford (S)-tert-butyl (1-(4-bromo-2-fluorophenoxy)-4-methylpentan-2-yl)carbamate (249 mg, 0.638 mmol, 97% yield) as a colorless oil: $^1$H NMR (400 MHz, Chloroform-d) δ 7.24 (dd, J=10.5, 2.4 Hz, 1H), 7.21-7.16 (m, 1H), 6.90-6.81 (m, 1H), 4.83-4.69 (m, 1H), 4.08-3.92 (m, 3H), 1.71 (dp, J=13.2, 6.6 Hz, 1H), 1.59-1.49 (m, 2H), 1.47 (d, J=3.8 Hz, 9H), 0.96 (dd, J=6.6, 4.4 Hz, 6H); LCMS (ESI) m/e 412.1 [(M+Na)$^+$, calcd C$_{17}$H$_{25}$BrFNNaO$_3$, 412.1]; LC/MS retention time (method B): t$_R$=2.41 min.

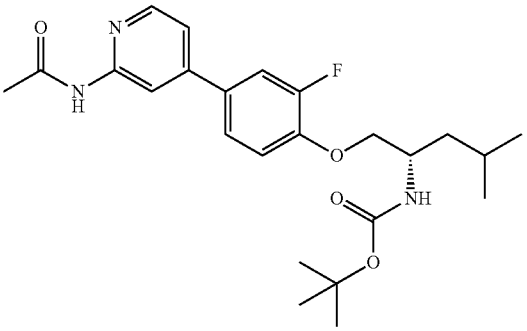 [SMILES: CC(=O)Nc1cc(-c2ccc(OC[C@H](CC(C)C)NC(=O)OC(C)(C)C)c(F)c2)ccn1]

Part 2B: (S)-tert-butyl (1-(4-(2-acetamidopyridin-4-yl)-2-fluorophenoxy)-4-methylpentan-2-yl)carbamate To a 15 mL vial was added N-(4-(4,4,5,5-tetramethyl-1,3,2-dioxaborolan-2-yl)pyridin-2-yl)acetamide (208 mg, 0.792 mmol), (S)-tert-butyl (1-(4-bromo-2-fluorophenoxy)-4-methylpentan-2-yl)carbamate (258 mg, 0.66 mmol), and Na$_2$CO$_3$ (0.990 mL, 1.980 mmol) in dioxane (2 mL) under nitrogen to give a colorless suspension. 1,1'-Bis(diphenylphosphino)ferrocenepalladium(II) dichloride, toluene (27.1 mg, 0.033 mmol) was added under nitrogen. The vial was sealed and heated at 130° C. (microwave) for 2 h. The mixture was diluted with water and EtOAc. The layers were separated. The organic layer was washed with brine, dried (Na$_2$SO$_4$) and concentrated. The residue was purified by silica gel column chromatography (up to 70% EtOAc/hexane) to afford the desired product (200 mg, 0.449 mmol, 68% yield for two steps) as a colorless oil: $^1$H NMR (400 MHz, Chloroform-d) δ 8.79 (s, 1H), 8.46 (s, 1H), 8.29 (d, J=5.4 Hz, 1H), 7.50-7.38 (m, 2H), 7.21 (dd, J=5.2, 1.7 Hz, 1H), 7.06 (t, J=8.7 Hz, 1H), 4.81 (d, J=9.2 Hz, 1H), 4.12-3.96 (m, 3H), 2.25 (s, 3H), 1.74 (dq, J=13.5, 6.5, 6.1 Hz, 1H), 1.63-1.52 (m, 2H), 1.47 (s, 9H), 0.98 (dd, J=6.6, 3.3 Hz, 6H); LCMS (ESI) m/e 446.2 [(M+H)$^-$, calcd C$_{24}$H$_{33}$F$_1$N$_3$O$_4$, 446.2]; LC/MS retention time (method B): t$_R$=2.11 min.

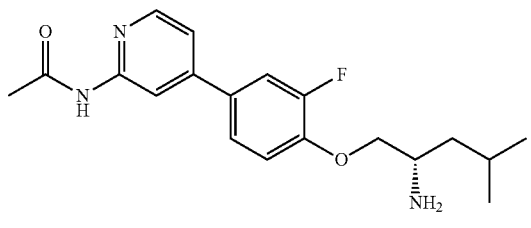

Part 2C: (S)—N-(4-(4-((2-amino-4-methylpentyl)oxy)-3-fluorophenyl)pyridin-2-yl)acetamide To a 50 mL round-bottomed flask was added (S)-tert-butyl (1-(4-(2-acetamidopyridin-4-yl)-2-fluorophenoxy)-4-methylpentan-2-yl)carbamate (202 mg, 0.453 mmol) in dichloromethane (2 mL) to give a colorless solution. TFA (0.5 mL) was added, and the resulted tan solution was stirred at rt for 1 h. The volatiles were removed under reduced pressure. The residue was diluted with EtOAc and basified with 1N NaOH. The layers were separated. The organic layer was washed with brine, dried ($Na_2SO_4$) and concentrated under reduced pressure to afford (S)—N-(4-(4-((2-amino-4-methylpentyl)oxy)-3-fluorophenyl)pyridin-2-yl)acetamide (155 mg, 0.449 mmol, 99% yield) as a slightly tan oil: $^1$H NMR and LCMS matched that of the previously prepared; $^{19}$F NMR (376 MHz, Chloroform-d) δ −133.47.

Example 2

(S)—N-(4-(4-((2-amino-4-methylpentyl)oxy)-3-methoxyphenyl)pyridin-2-yl)acetamide

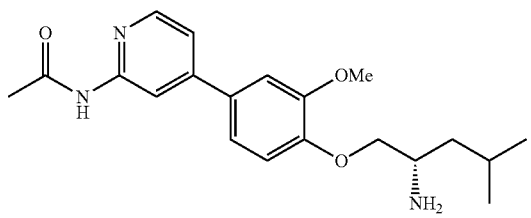

Prepared as described in Example 1.

Part A: N-(4-(3-methoxy-4-hydroxyphenyl)pyridin-2-yl)acetamide

LCMS (ESI) m/e 259.1 [(M+H)$^+$, calcd $C_{14}H_{15}N_2O_3$, 259.3]; LC/MS retention time (method A): $t_R$=1.51 min.

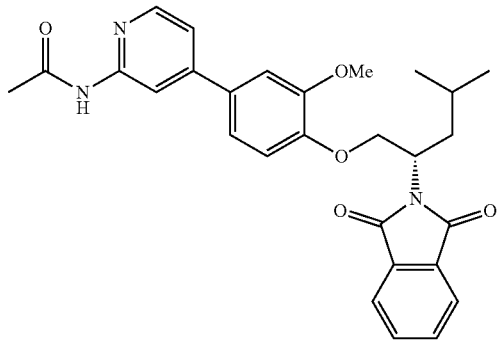 [SMILES: COc1cc(-c2ccnc(NC(C)=O)c2)ccc1OC[C@H](CC(C)C)N1C(=O)c2ccccc2C1=O]

Part B: (S)—N-(4-(4-((2-(1,3-dioxoisoindolin-2-yl)-4-methylpentyl)oxy)-3-methoxyphenyl)pyridin-2-yl)acetamide LCMS (ESI) m/e 488.3 [(M+H)$^+$, calcd $C_2H_{30}N_3O_5$, 488.2]; LC/MS retention time (method A): $t_R$=2.17 min.

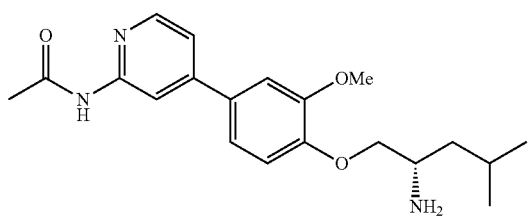 [SMILES: COc1cc(-c2ccnc(NC(C)=O)c2)ccc1OC[C@@H](N)CC(C)C]

Part C: (S)—N-(4-(4-((2-amino-4-methylpentyl)oxy)-3-methoxyphenyl)pyridin-2-yl)acetamide Obtained(S)—N-(4-(4-((2-amino-4-methylpentyl)oxy)-3-methoxyphenyl)pyridin-2-yl)acetamide (14.9 mg, 0.042 mmol, 80% yield for final step) as a slightly tan foam: $^1$H NMR (500 MHz, DMSO-d$_6$) δ 10.50 (s, 1H), 8.35 (s, 1H), 8.32 (d, J=5.2 Hz, 1H), 7.40 (dd, J=5.2, 1.8 Hz, 1H), 7.32-7.22 (m, 2H), 7.12 (d, J=8.2 Hz, 1H), 3.90 (dd, J=9.3, 4.6 Hz, 1H), 3.87 (s, 3H), 3.78 (dd, J=9.4, 6.9 Hz, 1H), 3.09 (p, J=5.5, 5.1 Hz, 1H), 2.12 (s, 3H), 1.82 (dt, J=13.4, 6.7 Hz, 1H), 1.32 (ddd, J=13.5, 8.6, 5.0 Hz, 1H), 1.24 (ddd, J=13.6, 8.7, 5.5 Hz, 1H), 0.92 (d, J=6.6 Hz, 3H), 0.89 (d, J=6.5 Hz, 3H); LCMS (ESI) m/e 358.2 [(M+H)$^+$, calcd $C_{20}H_{28}N_3O_3$, 358.2]; LC/MS retention time (method A): $t_R$=1.70 min.

Example 3

(S)—N-(4-(4-((2-amino-4-methylpentyl)oxy)-3-cyanophenyl)pyridin-2-yl)acetamide

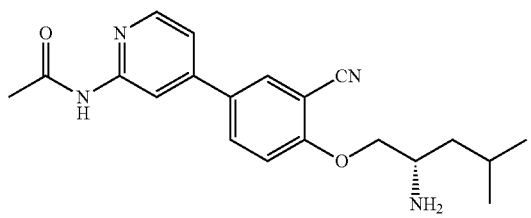

Prepared as described in Example 1.

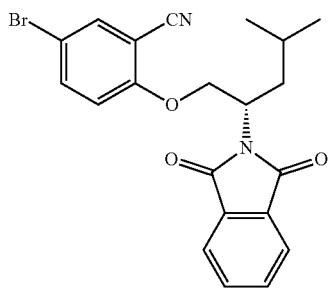 [SMILES: CC(C)C[C@@H](COc1ccc(Br)cc1C#N)N1C(=O)c2ccccc2C1=O]

Part A: (S)-5-bromo-2-((2-(1,3-dioxoisoindolin-2-yl)-4-methylpentyl)oxy)benzonitrile $^1$H NMR (400 MHz, Chloroform-d) δ 7.86 (dd, J=5.4, 3.0 Hz, 2H), 7.74 (dd, J=5.5, 3.1 Hz, 2H), 7.63-7.55 (m, 2H), 6.87 (d, J=8.8 Hz, 1H), 4.85 (tdd, J=9.8, 5.6, 3.9 Hz, 1H), 4.57 (t, J=9.2 Hz, 1H), 4.32 (dd, J=9.3, 5.7 Hz, 1H), 2.28-2.14 (m, 1H), 1.66-1.53 (m, 2H), 1.00 (d, J=5.8 Hz, 3H), 0.96 (d, J=6.0 Hz, 3H); LCMS (ESI) m/e 427.1 [(M+H)$^+$, calcd C$_{21}$H$_2$Br$_1$N$_2$O$_3$, 427.1]; LC/MS retention time (method B): t$_R$=2.29 min.

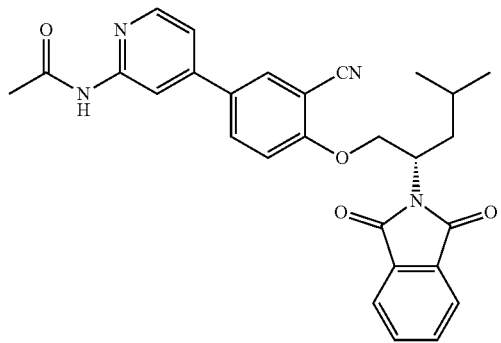 [SMILES: CC(=O)Nc1cc(-c2ccc(OC[C@H](CC(C)C)N3C(=O)c4ccccc4C3=O)c(C#N)c2)ccn1]

Part B: (S)—N-(4-(3-cyano-4-((2-(1,3-dioxoisoindolin-2-yl)-4-methylpentyl)oxy)phenyl)pyridin-2-yl)acetamide LCMS (ESI) m/e 483.3 [(M+H)$^+$, calcd C$_{28}$H$_{27}$N$_4$O$_4$, 483.2]; LC/MS retention time (method B): t$_R$=2.06 min.

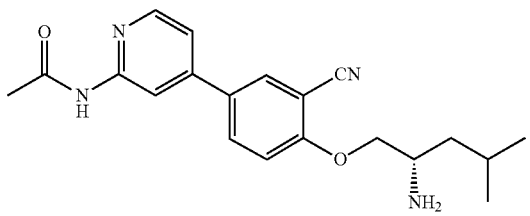

Part C: (S)—N-(4-(4-((2-amino-4-methylpentyl)oxy)-3-cyanophenyl)pyridin-2-yl)acetamide Acetamide was partially hydrolyzed (see Example 4) and the two products were separated and identified. Obtained (S)—N-(4-(4-((2-amino-4-methylpentyl)oxy)-3-cyanophenyl)pyridin-2-yl)acetamide (10.1 mg, 0.028 mmol, 23% yield) as a colorless foam. $^1$H NMR (500 MHz, DMSO-d$_6$) δ 10.58 (s, 1H), 8.39-8.32 (m, 2H), 8.12 (d, J=2.5 Hz, 1H), 8.00 (dd, J=8.8, 2.5 Hz, 1H), 7.44 (d, J=5.4 Hz, 1H), 7.41 (d, J=8.8 Hz, 1H), 4.05 (dd, J=9.3, 5.0 Hz, 1H), 3.99 (t, J=7.9 Hz, 1H), 3.12 (s, 1H), 2.13 (s, 3H), 1.84 (p, J=6.6 Hz, 1H), 1.42-1.31 (m, 1H), 1.27 (dq, J=14.0, 7.0, 6.2 Hz, 1H), 0.93 (d, J=6.6 Hz, 3H), 0.89 (d, J=6.4 Hz, 3H); LCMS (ESI) m/e 353.2 [(M+H)$^+$, calcd C$_2$H$_{25}$N$_4$O$_2$, 353.2]; LC/MS retention time (method B): t$_R$=1.44 min.

Example 4

(S)-2-((2-amino-4-methylpentyl)oxy)-5-(2-amino-pyridin-4-yl)benzonitrile

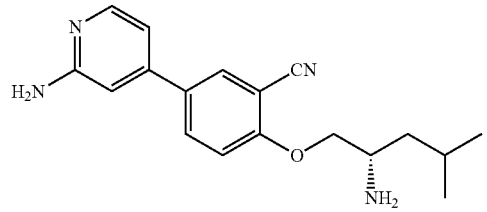 [SMILES: CC(C)C[C@H](N)COc1ccc(-c2ccnc(N)c2)cc1C#N]

The hydrolyzed material from Example 3 was identified as (S)-2-((2-amino-4-methylpentyl)oxy)-5-(2-aminopyridin-4-yl)benzonitrile (10.1 mg, 0.030 mmol, 26% yield) as a colorless foam. $^1$H NMR (500 MHz, DMSO-d$_6$) δ 8.02 (d, J=2.4 Hz, 1H), 7.97 (d, J=5.3 Hz, 1H), 7.93 (dd, J=8.8, 2.4 Hz, 1H), 7.36 (d, J=8.9 Hz, 1H), 6.82 (dd, J=5.3, 1.6 Hz, 1H), 6.70 (s, 1H), 5.97 (s, 2H), 4.03 (dd, J=9.3, 5.1 Hz, 1H), 3.96 (t, J=7.7 Hz, 1H), 3.10 (s, 1H), 1.84 (p, J=6.4 Hz, 1H), 1.35 (q, J=9.3, 6.6 Hz, 1H), 1.26 (dq, J=13.7, 6.8, 6.1 Hz, 1H), 0.92 (d, J=6.6 Hz, 3H), 0.89 (d, J=6.5 Hz, 3H); LCMS (ESI) m/e 311.2 [(M+H)$^+$, calcd C$_{18}$H$_{23}$N$_4$O$_1$, 311.2]; LC/MS retention time (method B): t$_R$=1.35 min.

Example 5

(S)—N-(4-(4-((2-amino-4-methylpentyl)oxy)-3-(trifluoromethyl)phenyl)pyridin-2-yl)acetamide

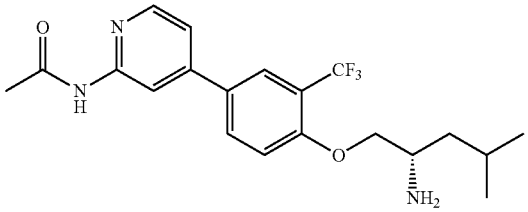

Prepared as described in Example 1.

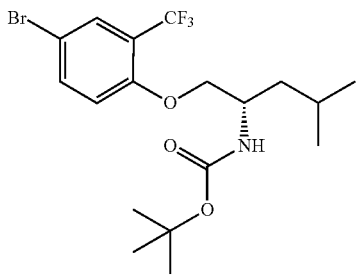 [SMILES: CC(C)C[C@@H](COc1ccc(Br)cc1C(F)(F)F)NC(=O)OC(C)(C)C]

Part A: (S)-tert-butyl (1-(4-bromo-2-(trifluoromethyl)phenoxy)-4-methylpentan-2-yl)carbamate ¹H NMR (400 MHz, Chloroform-d) δ 7.67 (d, J=2.4 Hz, 1H), 7.57 (dd, J=8.8, 2.5 Hz, 1H), 6.88 (d, J=8.8 Hz, 1H), 4.71 (d, J=8.3 Hz, 1H), 4.03 (p, J=7.2 Hz, 3H), 1.68 (hept, J=6.7 Hz, 1H), 1.55-1.48 (m, 2H), 1.44 (s, 9H), 0.95 (dd, J=6.6, 4.2 Hz, 6H); LCMS (ESI) m/e 462.1 [(M+Na)+, calcd $C_{18}H_{25}Br_1F_3N_1Na_1O_3$, 462.1]; LC/MS retention time (method B): $t_R$=2.45 min.

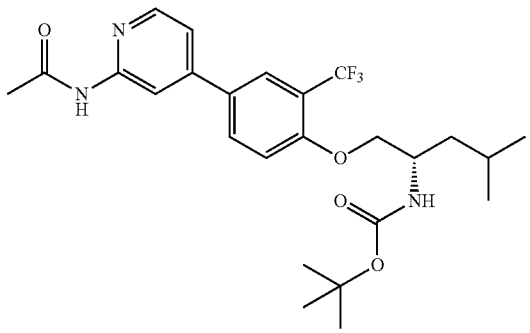 [SMILES: CC(=O)Nc1cc(-c2ccc(OC[C@H](CC(C)C)NC(=O)OC(C)(C)C)c(C(F)(F)F)c2)ccn1]

Part B: (S)-tert-butyl (1-(4-(2-acetamidopyridin-4-yl)-2-(trifluoromethyl)phenoxy)-4-methylpentan-2-yl)carbamate ¹H NMR (400 MHz, Chloroform-d) δ 9.50 (s, 1H), 8.48 (s, 1H), 8.29 (d, J=5.3 Hz, 1H), 7.86 (d, J=2.4 Hz, 1H), 7.81 (dd, J=8.5, 2.4 Hz, 1H), 7.21 (dd, J=5.3, 1.7 Hz, 1H), 7.08 (d, J=8.6 Hz, 1H), 4.79 (d, J=8.7 Hz, 1H), 4.13-4.04 (m, 3H), 2.25 (s, 3H), 1.70 (dt, J=13.6, 6.9 Hz, 1H), 1.54 (t, J=7.2 Hz, 2H), 1.44 (s, 9H), 0.96 (d, J=2.8 Hz, 3H), 0.95 (d, J=2.7 Hz, 3H); LCMS (ESI) m/e 496.2 [(M+H)+, calcd $C_{25}H_{33}F_3N_3O_4$, 446.2]; LC/MS retention time (method A): $t_R$=2.28 min.

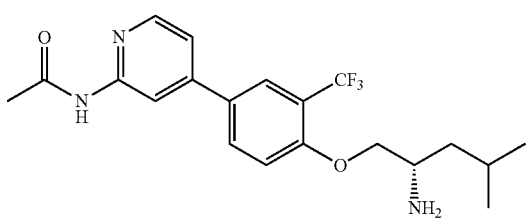 [SMILES: CC(=O)Nc1cc(-c2ccc(OC[C@@H](N)CC(C)C)c(C(F)(F)F)c2)ccn1]

Part C: (S)—N-(4-(4-((2-amino-4-methylpentyl)oxy)-3-(trifluoromethyl)phenyl)pyridin-2-yl)acetamide (221 mg, 0.531 mmol, quantitative yield for final step) as a white foam. ¹H NMR (400 MHz, Chloroform-d) δ 9.15 (s, 1H), 8.48 (s, 1H), 8.30 (d, J=5.3 Hz, 1H), 7.88 (d, J=2.2 Hz, 1H), 7.82 (dd, J=8.7, 2.3 Hz, 1H), 7.23 (dd, J=5.3, 1.7 Hz, 1H), 7.07 (d, J=8.7 Hz, 1H), 4.08 (dd, J=8.7, 3.6 Hz, 1H), 3.85 (dd, J=8.7, 7.1 Hz, 1H), 3.32 (qd, J=7.0, 3.6 Hz, 1H), 2.25 (s, 3H), 1.80 (dp, J=13.5, 6.7 Hz, 1H), 1.57 (s, 2H), 1.38 (t, J=7.0 Hz, 2H), 0.98 (d, J=6.5 Hz, 3H), 0.96 (d, J=6.6 Hz, 3H); ¹⁹F NMR (376 MHz, Chloroform-d) δ −62.40; LCMS (ESI) m/e 394.2 [(M−H), calcd $C_{20}H_{23}F_3N_3O_2$, 394.2]; LC/MS retention time (method A): $t_R$=1.97 min.

Example 6

(S)—N-(4-(4-((2-amino-4-methylpentyl)oxy)-3-(trifluoromethoxy)phenyl)pyridin-2-yl)acetamide

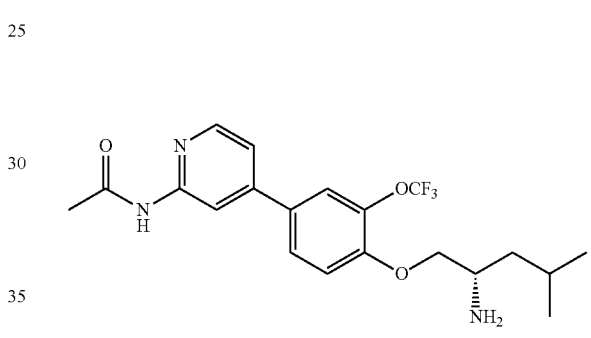

Prepared as described in Example 1.

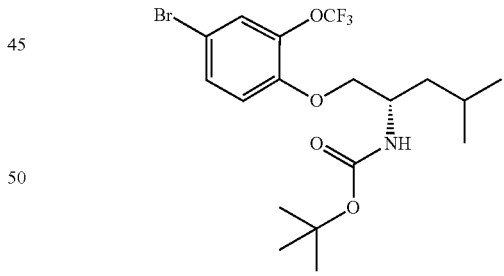

Part A: (S)-tert-butyl (1-(4-bromo-2-(trifluoromethoxy)phenoxy)-4-methylpentan-2-yl)carbamate ¹H NMR (400 MHz, Chloroform-d) δ 7.42-7.33 (m, 2H), 6.89 (d, J=8.8 Hz, 1H), 4.78-4.61 (m, 1H), 4.09-3.90 (m, 3H), 1.68 (dq, J=13.3, 6.7 Hz, 1H), 1.51 (t, J=6.8 Hz, 2H), 1.45 (s, 9H), 0.95 (dd, J=6.6, 5.4 Hz, 6H); LCMS (ESI) m/e 478.1 [(M+Na)+, calcd $C_{18}H_{25}Br_1F_3N_1Na_1O_4$, 478.0]; LC/MS retention time (method B): $t_R$=2.45 min.

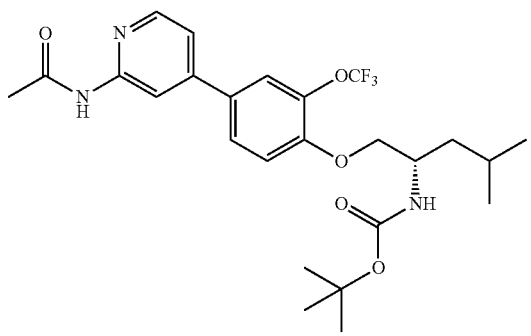 [SMILES: CC(=O)Nc1cc(-c2ccc(OC[C@H](CC(C)C)NC(=O)OC(C)(C)C)c(OC(F)(F)F)c2)ccn1]

Part B: (S)-tert-butyl (1-(4-(2-acetamidopyridin-4-yl)-2-(trifluoromethoxy)phenoxy)-4-methylpentan-2-yl)carbamate $^1$H NMR (400 MHz, Chloroform-d) δ 9.13 (s, 1H), 8.47 (s, 1H), 8.29 (d, J=5.3 Hz, 1H), 7.61 (dd, J=8.5, 2.3 Hz, 1H), 7.56 (q, J=1.3 Hz, 1H), 7.21 (dd, J=5.3, 1.7 Hz, 1H), 7.09 (d, J=8.6 Hz, 1H), 4.77 (d, J=8.3 Hz, 1H), 4.12-3.98 (m, 3H), 2.25 (s, 3H), 1.73 (dq, J=13.7, 7.1, 6.4 Hz, 1H), 1.55 (t, J=7.0 Hz, 2H), 1.46 (s, 9H), 0.97 (dd, J=6.6, 4.1 Hz, 6H); LCMS (ESI) m/e 512.2 [(M+H)$^+$, calcd $C_{25}H_{33}F_3N_3O_5$, 512.2]; LC/MS retention time (method A): $t_R$=2.29 min.

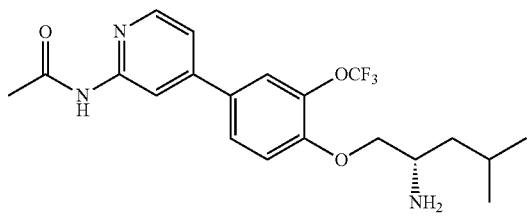

Part C: (S)—N-(4-(4-((2-amino-4-methylpentyl)oxy)-3-(trifluoromethoxy)phenyl)pyridin-2-yl)acetamide (225 mg, 0.520 mmol, 95% yield for final step) as a white foam. $^1$H NMR (400 MHz, Chloroform-d) δ 9.59 (s, 1H), 8.47 (s, 1H), 8.27 (d, J=5.3 Hz, 1H), 7.58 (dd, J=8.5, 2.3 Hz, 1H), 7.55 (d, J=2.0 Hz, 1H), 7.19 (dd, J=5.4, 1.7 Hz, 1H), 7.04 (d, J=8.6 Hz, 1H), 4.00 (dd, J=8.8, 3.7 Hz, 1H), 3.80 (dd, J=8.8, 7.3 Hz, 1H), 3.31 (qd, J=7.1, 3.7 Hz, 1H), 2.23 (s, 3H), 1.86-1.72 (m, J=6.9 Hz, 1H), 1.63 (s, 2H), 1.35 (t, J=7.0 Hz, 2H), 0.95 (dd, J=9.1, 6.6 Hz, 6H); $^{19}$F NMR (376 MHz, Chloroform-d) δ −58.10; LCMS (ESI) m/e 412.1 [(M+H)$^+$, calcd $C_{20}H_{25}F_3N_3O_3$, 412.2]; LC/MS retention time (method A): $t_R$=1.99 min.

Example 7

(S)—N-(4-(4-((2-amino-4-methylpentyl)oxy)-3-methylphenyl)pyridin-2-yl)acetamide

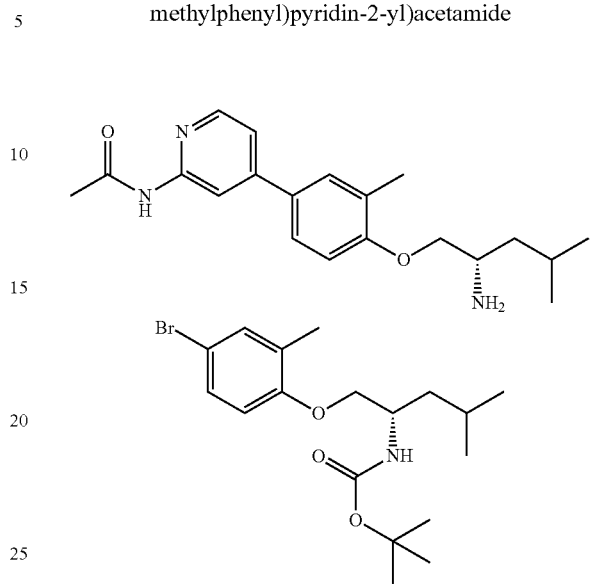

Part A: (S)-tert-butyl(1-(4-bromo-2-methylphenoxy)-4-methylpentan-2-yl)carbamate DIAD (0.090 mL, 0.464 mmol) was added to a solution of triphenylphosphine(0.097 g, 0.371 mmol), 4-bromo-2-methylphenol (0.069 g, 0.371 mmol) and (S)-tert-butyl (1-hydroxy-4-methylpentan-2-yl)carbamate (0.0672 g, 0.309 mmol) in THF (1.5 mL) at rt under $N_2$. The reaction was stirred at room temperature overnight. The solvent was removed under reduced pressure. The residue was purified via silica gel chromatography (0 to 25% ethyl acetate in hexanes). NMR and LCMS showed the product contained the starting material (4-bromo-2-methoxyphenol). This mixture was taken up in ethyl acetate and washed with 1N NaOH (2×) and water (1×). The ethyl acetate layer was separated, dried (Na2SO4), filtered and concentrated under reduced pressure to give (S)-tert-butyl (1-(4-bromo-2-methylphenoxy)-4-methylpentan-2-yl)carbamate (31.2 mg, 0.081 mmol, 26% yield) as a colorless wax. LCMS (ESI) m/e 408.1 [(M+Na)$^+$, calcd $C_{18}H_{28}BrNO_3Na$, 408.1]; LC/MS retention time (method B): $t_R$=2.44 min.

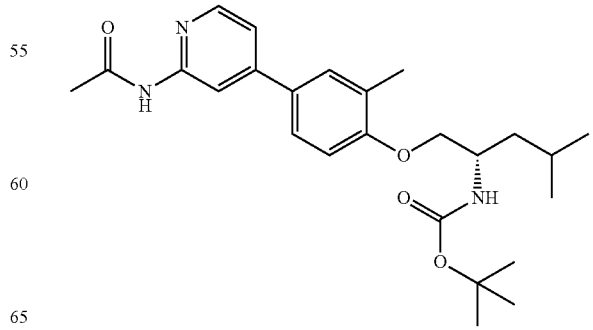

Part B: (S)-tert-butyl (1-(4-(2-acetamidopyridin-4-yl)-2-methylphenoxy)-4-methylpentan-2-yl)carbamate A mixture of sodium carbonate (0.061 mL, 0.121 mmol), N-(4-(4,4,5,5-tetramethyl-1,3,2-dioxaborolan-2-yl)pyridin-2-yl)acetamide (0.028 g, 0.105 mmol), (S)-tert-butyl (1-(4-bromo-2-methylphenoxy)-4-methylpentan-2-yl)carbamate (0.0312 g, 0.081 mmol) in dioxane (1 mL) was purged with nitrogen 5 times. PdCl$_2$(dppf) (5.91 mg, 8.08 μmol) was added to the reaction mixture and the reaction was heated at 80° C. overnight. The reaction was cooled to room temperature and diluted with ethyl acetate. The organic layer was separated and washed with brine (1×). The ethyl acetate layer was separated, dried (Na$_2$SO$_4$), filtered and concentrated under reduced pressure. The crude was used as it is at the next reaction. LCMS (ESI) m/e 442.3 [(M+H)$^+$, calcd C$_{25}$H$_{36}$N$_3$O$_4$, 442.3]; LC/MS retention time (method B): t$_R$=2.13 min.

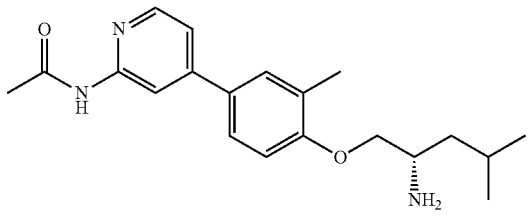 [SMILES: CC(=O)Nc1cc(-c2ccc(OC[C@@H](N)CC(C)C)c(C)c2)ccn1]

Part C: (S)—N-(4-(4-((2-amino-4-methylpentyl)oxy)-3-methylphenyl)pyridin-2-yl)acetamide A mixture of TFA (1 mL, 12.98 mmol) and (S)-tert-butyl (1-(4-(2-acetamidopyridin-4-yl)-2-methylphenoxy)-4-methylpentan-2-yl)carbamate (35.8 mg, 0.081 mmol) in CH$_2$Cl$_2$ (4 mL) was stirred at room temperature for 1 h. The solvent was removed under reduced pressure and the residue was purified via reverse phase HPLC (acetonitrile/water/10 mM ammonium acetate). To afford (S)—N-(4-(4-((2-amino-4-methylpentyl)oxy)-3-methylphenyl)pyridin-2-yl)acetamide (9.7 mg, 0.028 mmol, 35% yield for two steps). $^1$H NMR (500 MHz, DMSO-d$_6$) δ 10.50 (s, 1H), 8.34 (br. s., 1H), 8.30 (d, J=5.2 Hz, 1H), 7.53 (br. s., 2H), 7.35 (d, J=4.6 Hz, 1H), 7.08-7.03 (m, J=9.2 Hz, 1H), 3.92-3.86 (m, 1H), 3.84-3.78 (m, 1H), 3.10 (br. s., 1H), 2.26 (s, 3H), 2.12 (s, 3H), 1.87-1.79 (m, 1H), 1.40-1.31 (m, 1H), 1.27 (d, J=6.4 Hz, 1H), 0.93 (d, J=6.7 Hz, 3H), 0.89 (d, J=6.4 Hz, 3H); LCMS (ESI) m/e 342.2 [(M+H)$^+$, calcd C$_{20}$H$_{28}$N$_3$O$_2$, 342.2]; LC/MS retention time (method B): t$_R$=1.73 min.

Example 8

(S)—N-(4-(4-((2-amino-4-methylpentyl)oxy)-3-chlorophenyl)pyridin-2-yl)acetamide

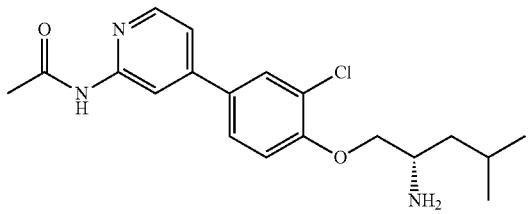

Part A: (S)-tert-butyl (1-(4-bromo-2-chlorophenoxy)-4-methylpentan-2-yl)carbamate Prepared as described in Example 1, Part 2A. $^1$H NMR (400 MHz, CHLOROFORM-d) δ 7.52 (d, J=2.5 Hz, 1H), 7.33 (dd, J=8.8, 2.5 Hz, 1H), 6.82 (d, J=8.8 Hz, 1H), 4.08-3.95 (m, 3H), 1.77-1.66 (m, 1H), 1.57 (br. m, 2H), 1.47 (s, 9H), 0.98 (dd, J=6.5, 3.8 Hz, 6H). LCMS (ESI) m/e 428.0 [(M+Na)$^+$, calcd C$_{17}$H$_{25}$BrClNO$_3$Na, 428.1]; LC/MS retention time (method B): t$_R$=2.47 min.

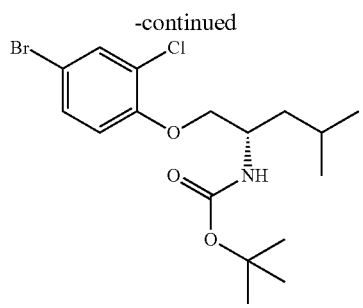

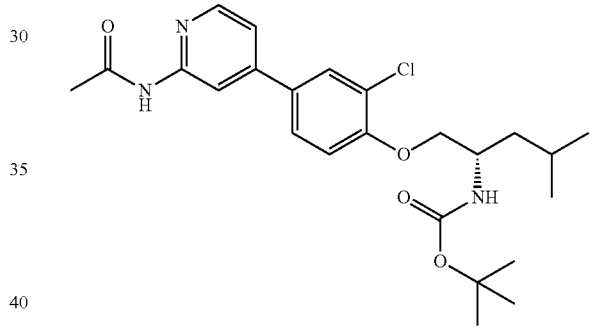

Part B: (S)-tert-butyl (1-(4-(2-acetamidopyridin-4-yl)-2-chlorophenoxy)-4-methylpentan-2-yl)carbamate The mixture of sodium carbonate (0.113 mL, 0.226 mmol), N-(4-(4,4,5,5-tetramethyl-1,3,2-dioxaborolan-2-yl)pyridin-2-yl)acetamide (0.051 g, 0.196 mmol), (S)-tert-butyl (1-(4-bromo-2-chlorophenoxy)-4-methylpentan-2-yl)carbamate (0.0612 g, 0.150 mmol) in dioxane (1 mL) was evacuated and back-filled with N$_2$ (5×). PdCl$_2$(dppf) (0.011 g, 0.015 mmol) was added to the reaction mixture and the reaction was heated at 80° C. overnight. The reaction was diluted with ethyl acetate and washed with brine (1×). The ethyl acetate layer was separated, dried (Na$_2$SO$_4$), filtered and concentrated under reduced pressure. The crude was purified by silica gel chromatography (50% ethyl acetate in hexanes) to afford. (S)-tert-butyl (1-(4-(2-acetamidopyridin-4-yl)-2-chlorophenoxy)-4-methylpentan-2-yl)carbamate (51.7 mg, 0.112 mmol, 74% yield). LCMS (ESI) m/e 462.2 [(M+H)$^+$, calcd C$_{24}$H$_{33}$ClN$_3$O$_4$, 462.2]; LC/MS retention time (method B): t$_R$=2.21 min.

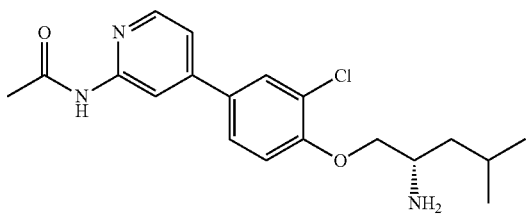 [SMILES: CC(=O)Nc1cc(-c2ccc(OC[C@@H](N)CC(C)C)c(Cl)c2)ccn1]

Part C: (S)—N-(4-(4-((2-amino-4-methylpentyl)oxy)-3-chlorophenyl)pyridin-2-yl)acetamide A mixture of (S)-tert-butyl (1-(4-(2-acetamidopyridin-4-yl)-2-chlorophenoxy)-4-methylpentan-2-yl)carbamate (51.7 mg, 0.112 mmol) and TFA (1 mL, 12.98 mmol) was stirred in CH$_2$Cl$_2$ (3 mL) at room temperature for 2 h. The solvent was removed under reduced pressure and the residue was purified via reverse phase HPLC (acetonitrile/water/10 mM ammonium acetate). (42.7 mg, 0.111 mmol, 99% yield). $^1$H NMR (500 MHz, DMSO-d$_6$) δ 10.58 (br. s., 1H), 8.35 (d, J=4.6 Hz, 2H), 7.81 (s, 1H), 7.70 (d, J=8.9 Hz, 1H), 7.42 (d, J=5.2 Hz, 1H), 7.33 (d, J=8.5 Hz, 1H), 4.18-4.12 (m, 1H), 4.08-4.01 (m, 1H), 3.39-3.35 (m, 1H), 2.13 (s, 3H), 1.86-1.74 (m, 1H), 1.50 (d, J=6.1 Hz, 1H), 1.45-1.36 (m, 1H), 0.92 (dd, J=10.2, 6.6 Hz, 6H); LCMS (ESI) m/e 362.2 [(M+H)$^+$, calcd C$_{19}$H$_{25}$ClN$_3$O$_3$, 362.2]; LC/MS retention time (method B): t$_R$=1.69 min.

Example 9

(S)—N-(4-(4-((2-amino-4-methylpentyl)oxy)-3,5-difluorophenyl)pyridin-2-yl)acetamide

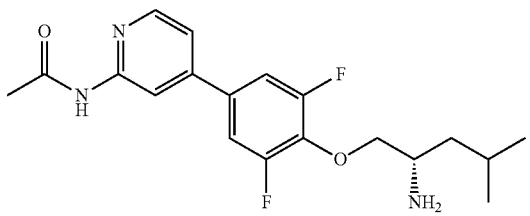

Prepared as described in Example 1.

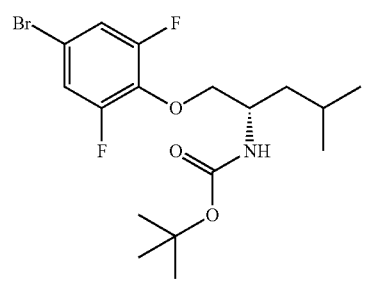 [SMILES: CC(C)C[C@@H](COc1c(F)cc(Br)cc1F)NC(=O)OC(C)(C)C]

Part A: (S)-tert-butyl (1-(4-bromo-2,6-difluorophenoxy)-4-methylpentan-2-yl)carbamate $^1$H NMR (400 MHz, Chloroform-d) δ 7.42-7.33 (m, 2H), 6.89 (d, J=8.8 Hz, 1H), 4.78-4.61 (m, 1H), 4.09-3.90 (m, 3H), 1.68 (dq, J=13.3, 6.7 Hz, 1H), 1.51 (t, J=6.8 Hz, 2H), 1.45 (s, 9H), 0.95 (dd, J=6.6, 5.4 Hz, 6H); LCMS (ESI) m/e 478.1 [(M+Na)$^+$, calcd C$_{18}$H$_{25}$Br$_1$F$_3$N$_1$Na$_1$O$_4$, 478.0]; LC/MS retention time (method B): t$_R$=2.45 min.

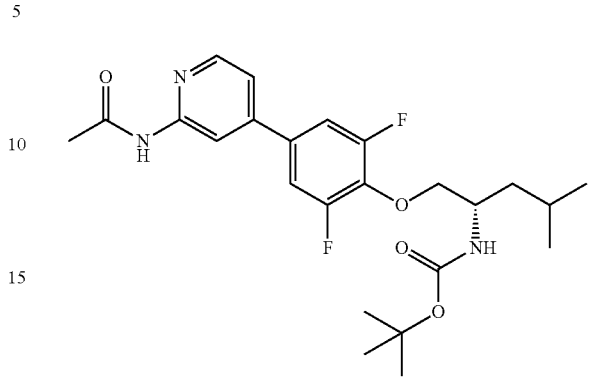

Part B: (S)-tert-butyl (1-(4-(2-acetamidopyridin-4-yl)-2,6-difluorophenoxy)-4-methylpentan-2-yl)carbamate $^1$H NMR (400 MHz, Chloroform-d) δ 9.01 (s, 1H), 8.42 (s, 1H), 8.28 (d, J=5.3 Hz, 1H), 7.22 (d, J=8.7 Hz, 2H), 7.15 (dd, J=5.4, 1.7 Hz, 1H), 4.88 (d, J=9.0 Hz, 1H), 4.24-4.13 (m, 2H), 3.94 (s, 1H), 2.24 (s, 3H), 1.74 (dt, J=13.5, 6.7 Hz, 1H), 1.55 (t, J=7.3 Hz, 2H), 1.24 (s, 9H), 0.97 (d, J=6.5 Hz, 6H); $^{19}$F NMR (376 MHz, Chloroform-d) δ −126.89; LCMS (ESI) m/e 464.2 [(M+H)$^+$, calcd C$_{24}$H$_{32}$F$_2$N$_3$O$_4$, 464.2]; LC/MS retention time (method A): t$_R$=2.24 min.

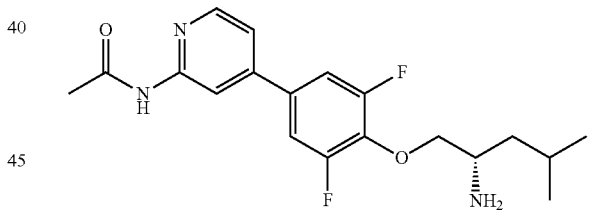

Part C: (S)—N-(4-(4-((2-amino-4-methylpentyl)oxy)-3,5-difluorophenyl)pyridin-2-yl)acetamide Obtained (S)—N-(4-(4-((2-amino-4-methylpentyl)oxy)-3,5-difluorophenyl)pyridin-2-yl)acetamide (48.4 mg, 0.152 mmol, 99% yield for final step) as an off-white foam. $^1$H NMR (500 MHz, DMSO-d$_6$) δ 10.62 (s, 1H), 8.37 (d, J=5.3 Hz, 1H), 8.32 (s, 1H), 7.59-7.48 (m, 2H), 7.42 (dd, J=5.2, 1.8 Hz, 1H), 4.16 (dd, J=10.0, 4.5 Hz, 1H), 4.07 (dd, J=9.9, 5.7 Hz, 1H), 3.24 (dq, J=10.5, 5.8 Hz, 1H), 2.13 (s, 3H), 1.82-1.74 (m, 1H), 1.46 (ddd, J=13.7, 8.1, 5.8 Hz, 1H), 1.35 (ddd, J=13.9, 8.1, 6.3 Hz, 1H), 0.90 (dd, J=9.0, 6.5 Hz, 6H); LCMS (ESI) m/e 364.1 [(M+H)$^+$, calcd C$_{19}$H$_{24}$F$_2$N$_3$O$_2$, 364.2]; LC/MS retention time (method A): t$_R$=1.81 min.

Example 10

(S)—N-(4-(4-((2-amino-4-methylpentyl)oxy)-3-chloro-5-fluorophenyl)pyridin-2-yl)acetamide

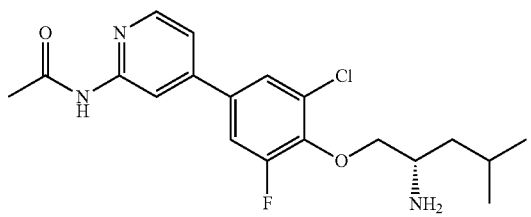 [SMILES: CC(=O)Nc1cc(-c2cc(F)c(OC[C@@H](N)CC(C)C)c(Cl)c2)ccn1]

Prepared as described in Example 1.

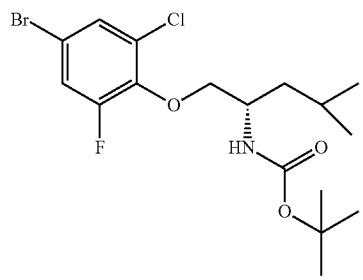 [SMILES: CC(C)C[C@@H](COc1c(F)cc(Br)cc1Cl)NC(=O)OC(C)(C)C]

Part A: (S)-tert-butyl (1-(4-bromo-2,6-difluorophenoxy)-4-methylpentan-2-yl)carbamate LCMS (ESI) m/e 424.2 [(M+H)$^+$, calcd C$_{17}$H$_{25}$Br$_1$Cl$_1$F$_1$N$_1$O$_3$, 424.1]; LC/MS retention time (method A): $t_R$=2.37 min.

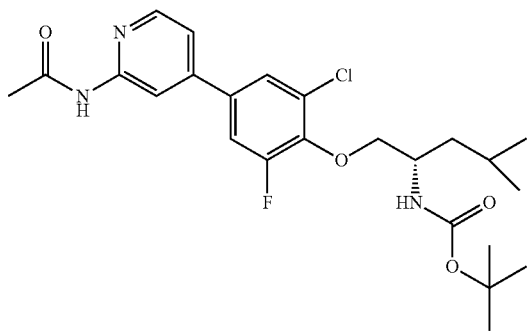 [SMILES: CC(=O)Nc1cc(-c2cc(F)c(OC[C@H](CC(C)C)NC(=O)OC(C)(C)C)c(Cl)c2)ccn1]

Part B (S)-tert-buty (1-(4-(2-acetamdopyridin-4-yl)-2-chloro-6-fluorophenoxy)-4-methylpentan-2-yl)carbamate LCMS (ESI) m/e 480.2 [(M+H)$^+$, calcd C$_{24}$H$_{32}$F$_2$N$_3$O$_4$, 480.2]; LC/MS retention time (method B): $t_R$=2.28 min.

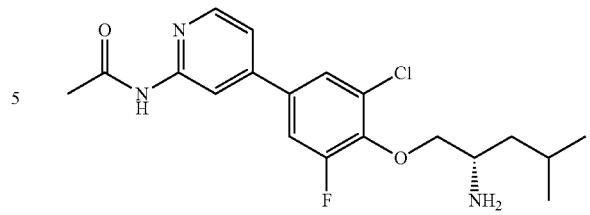

Part C: (S)—N-(4-(4-((2-amino-4-methylpentyl)oxy)-3-chloro-5-fluorophenyl)pyridin-2-yl)acetamide Obtained (S)—N-(4-(4-((2-amino-4-methylpentyl)oxy)-3-chloro-5-fluorophenyl)pyridin-2-yl)acetamide (26.5 mg, 0.066 mmol, 56% yield for final step) as a colorless solid. $^1$H NMR (500 MHz, DMSO-d$_6$) δ 10.60 (s, 1H), 8.37 (d, J=5.2 Hz, 1H), 8.30 (s, 1H), 7.67 (d, J=9.5 Hz, 2H), 7.43 (d, J=5.1 Hz, 1H), 4.04 (dd, J=9.4, 4.7 Hz, 1H), 3.96 (dd, J=9.5, 6.2 Hz, 1H), 3.11 (dq, J=10.7, 5.1 Hz, 1H), 2.12 (s, 3H), 1.79 (dq, J=13.6, 6.4 Hz, 1H), 1.41 (ddd, J=13.6, 8.5, 5.2 Hz, 1H), 1.26 (ddd, J=14.1, 8.6, 5.8 Hz, 1H), 0.91 (d, J=6.5 Hz, 3H), 0.88 (d, J=6.5 Hz, 3H); LCMS (ESI) m/e 380.2 [(M+H)$^+$, calcd C$_{19}$H$_{24}$Cl$_1$F$_1$N$_3$O$_2$, 380.2]; LC/MS retention time (method B): $t_R$=1.82 min.

Example 11

(S)—N-(4-(4-((2-amino-4-methylpentyl)oxy)-3-fluoro-5-(trifluoromethyl)phenyl)pyridin-2-yl)acetamide

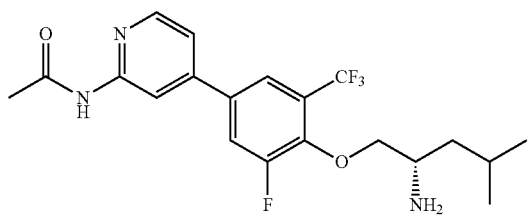

Prepared as described in Example 1.

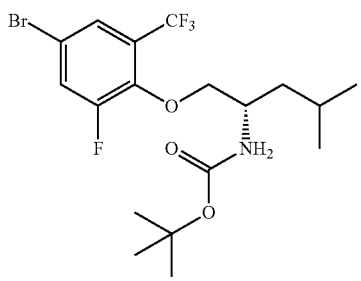 [SMILES: CC(C)C[C@@H](COc1c(F)cc(Br)cc1C(F)(F)F)NC(=O)OC(C)(C)C]

Part A: (S)-tert-butyl (1-(4-bromo-2-fluoro-6-(trifluoromethyl)phenoxy)-4-methylpentan-2-yl)carbamate $^1$H NMR (400 MHz, Chloroform-d) δ 7.52 (t, J=1.9 Hz, 1H), 7.47 (dd, J=10.7, 2.4 Hz, 1H), 4.76 (d, J=9.1 Hz, 1H), 4.19 (s, 2H), 3.96 (d, J=7.7 Hz, 1H), 1.74 (dq, J=13.5, 6.7 Hz, 1H), 1.54 (t, J=7.1 Hz, 2H), 1.47 (s, 9H), 0.98 (d, J=6.6 Hz, 6H); LCMS (ESI) m/e 480.0 [(M+Na)+, calcd C$_{18}$H$_{24}$Br$_1$F$_4$N$_1$Na$_1$O$_3$, 480.1]; LC/MS retention time (method B): t$_R$=2.50 min.

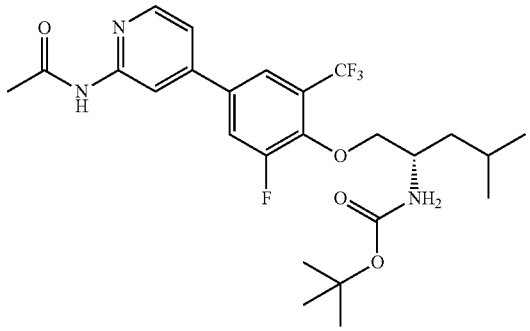 [SMILES: CC(=O)Nc1cc(-c2cc(F)c(OC[C@H](CC(C)C)NC(=O)OC(C)(C)C)c(C(F)(F)F)c2)ccn1]

Part B: (S)-tert-butyl (1-(4-(2-acetamidopyridin-4-yl)-2-fluoro-6-(trifluoromethyl)phenoxy)-4-methylpentan-2-yl)carbamate LCMS (ESI) m/e 536.2 [(M+Na)+, calcd C$_{25}$H$_{31}$F$_4$Na$_1$N$_3$O$_4$, 536.2]; LC/MS retention time (method B): t$_R$=2.34 min.

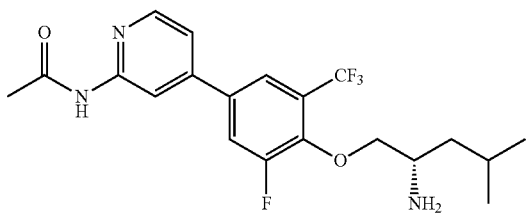

Part C: (S)—N-(4-(4-((2-amino-4-methylpentyl)oxy)-3-fluoro-5-(trifluoromethyl)phenyl)pyridin-2-yl)acetamide Obtained (S)—N-(4-(4-((2-amino-4-methylpentyl)oxy)-3-fluoro-5-(trifluoromethyl)phenyl)pyridin-2-yl)acetamide (49 mg, 0.116 mmol, 75% yield for final step) as a colorless solid. $^1$H NMR (500 MHz, DMSO-d$_6$) δ 10.63 (s, 1H), 8.39 (d, J=5.3 Hz, 1H), 8.35 (s, 1H), 8.01 (dd, J=12.9, 2.2 Hz, 1H), 7.74 (s, 1H), 7.48 (d, J=5.4 Hz, 1H), 4.06 (p, J=8.2 Hz, 2H), 3.12-3.03 (m, 1H), 2.13 (s, 3H), 1.82 (dt, J=13.6, 7.2 Hz, 1H), 1.35 (ddd, J=13.4, 8.9, 4.8 Hz, 1H), 1.22 (ddd, J=13.8, 9.0, 5.5 Hz, 1H), 0.92 (d, J=6.6 Hz, 3H), 0.88 (d, J=6.6 Hz, 3H); LCMS (ESI) m/e 414.2 [(M+H)+, calcd C$_{20}$H$_{24}$F$_4$N$_3$O$_2$, 414.2]; LC/MS retention time (method A): t$_R$=2.01 min.

Example 12

(S)—N-(4-(4-((2-amino-4-methylpentyl)oxy)-2,5-difluorophenyl)pyridin-2-yl)acetamide

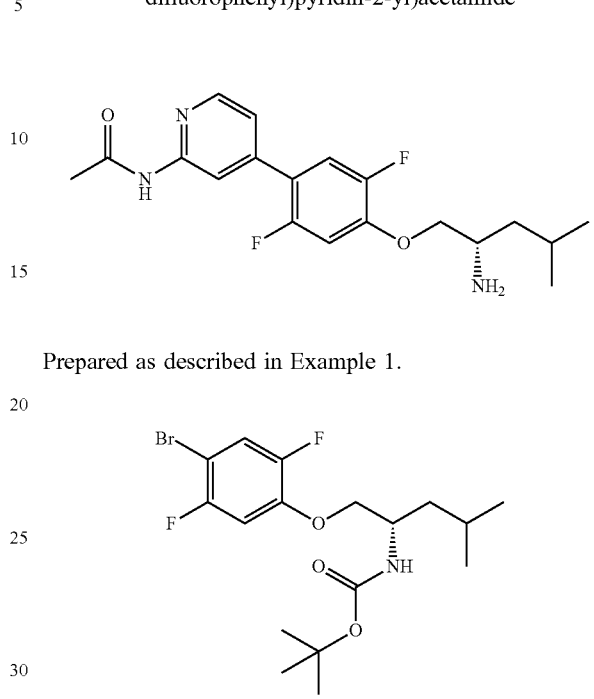

Prepared as described in Example 1.

Part A: (S)-tert-butyl (1-(4-bromo-2,5-difluorophenoxy)-4-methylpentan-2-yl)carbamate $^1$H NMR (400 MHz, Chloroform-d) δ 7.29 (t, J=9.5 Hz, 1H), 6.81 (dd, J=9.5, 7.3 Hz, 1H), 4.68 (s, 1H), 4.09-3.91 (m, 3H), 1.71 (dt, J=13.4, 7.0 Hz, 1H), 1.53 (dd, J=15.3, 7.8 Hz, 2H), 1.47 (s, 9H), 0.97 (dd, J=6.6, 4.5 Hz, 6H); LCMS (ESI) m/e 408.0 [(M+H)+, calcd C$_{17}$H$_{25}$Br$_1$F$_2$N$_1$O$_3$, 408.1]; LC/MS retention time (method A): t$_R$=2.40 min.

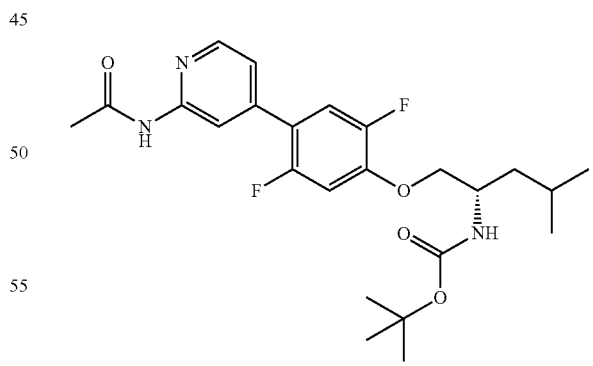

Part B: (S)-tert-butyl (1-(4-(2-acetamidopyridin-4-yl)-2,5-difluorophenoxy)-4-methylpentan-2-yl)carbamate LCMS (ESI) m/e 464.2 [(M+H)+, calcd C$_{24}$H$_{32}$F$_2$N$_3$O$_4$, 464.3]; LC/MS retention time (method A): t$_R$=2.29 min.

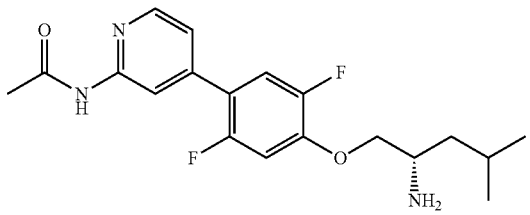

Part C: (S)—N-(4-(4-((2-amino-4-methylpentyl)oxy)-2,5-difluorophenyl)pyridin-2-yl)acetamide Obtained (S)—N-(4-(4-((2-amino-4-methylpentyl)oxy)-2,5-difluorophenyl)pyridin-2-yl)acetamide (46.4 mg, 0.125 mmol, 77% yield for final step) as a colorless solid. $^1$H NMR (500 MHz, DMSO-$d_6$) δ 10.59 (s, 1H), 8.37 (d, J=5.2 Hz, 1H), 8.29 (s, 1H), 7.54 (dd, J=11.8, 7.3 Hz, 1H), 7.34 (dd, J=12.3, 7.2 Hz, 1H), 7.26 (d, J=5.2 Hz, 1H), 4.08 (dd, J=9.8, 4.5 Hz, 1H), 3.98 (dd, J=10.0, 6.4 Hz, 1H), 3.24 (p, J=6.0 Hz, 1H), 2.11 (s, 3H), 1.80 (dq, J=15.3, 8.4, 7.6 Hz, 1H), 1.35 (qt, J=13.7, 6.8 Hz, 2H), 0.91 (dd, J=14.1, 6.6 Hz, 6H); LCMS (ESI) m/e 364.2 [(M+H)$^+$, calcd $C_{19}H_{24}F_2N_3O_2$, 364.2]; LC/MS retention time (method A): $t_R$=1.82 min.

Example 13

(S)-methyl (4-(4-((2-amino-4-methylpentyl)oxy)-3-fluorophenyl)pyridin-2-yl)carbamate

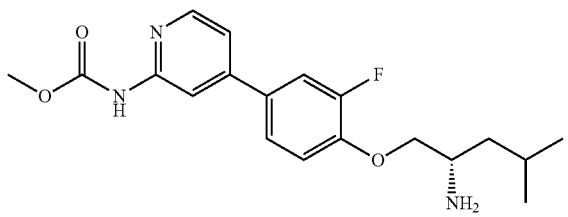 [SMILES: COC(=O)Nc1cc(-c2ccc(OC[C@@H](N)CC(C)C)c(F)c2)ccn1]

Prepared as described in Example 1.

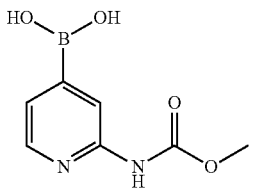

Part A: (2-((methoxycarbonyl)amino)pyridin-4-yl)boronic acid

The mixture of 2-(dicyclohexylphosphino)-2',4',6'-triisopropylbiphenyl(0.079 g, 0.166 mmol), potassium acetate (2.446 g, 24.92 mmol), 2$^{nd}$ generation Xphos precatalyst (0.065 g, 0.083 mmol), methyl (4-chloropyridin-2-yl)carbamate (1.55 g, 8.31 mmol) and hypodiboric acid (1.117 g, 12.46 mmol) in ethanol (80 mL) was degassed three times via vacuum/N$_2$ fill cycle. The reaction mixture was heated at 80° C. for 3 h. The reaction mixture was cooled to rt and the solvent was removed under reduced pressure and the solid was washed with acetone. The remaining solid was suspended with mixture of methanol and CH$_2$Cl$_2$. The suspension was filtered and the filtrate was concentrated under reduced pressure to give the crude product as a solid. The solid was suspended in water and filtered. The solid was washed with acetone to give (2-((methoxycarbonyl)amino)pyridin-4-yl)boronic acid (702 mg, 3.58 mmol, 43% yield) as an off-white solid. LCMS (ESI) m/e 197.2 [(M+H)$^+$, calcd $C_7H_{10}BN_2O_4$, 197.1]; LC/MS retention time (method B): $t_R$=0.46 min.

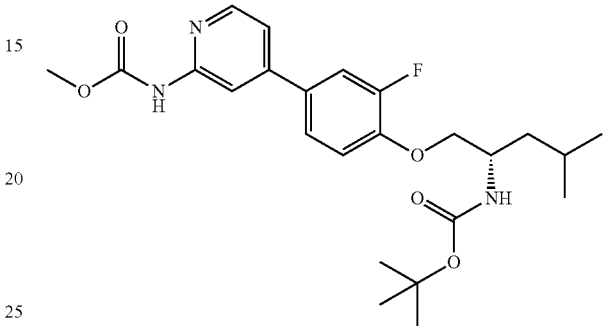

Part B: (S)-tert-butyl (1-(4-(2-aminopyridin-4-yl)-2-fluorophenoxy)-4-methylpentan-2-yl)carbamate $^1$H NMR (400 MHz, Chloroform-d) δ 9.86 (s, 1H), 8.35 (d, J=5.4 Hz, 1H), 8.31-8.24 (m, 1H), 7.52-7.39 (m, 2H), 7.17 (dd, J=5.4, 1.7 Hz, 1H), 7.06 (t, J=8.6 Hz, 1H), 4.84 (d, J=8.5 Hz, 1H), 4.15-3.99 (m, 3H), 3.87 (s, 3H), 1.80-1.67 (m, 1H), 1.56 (dt, J=13.3, 7.8 Hz, 2H), 1.47 (s, 9H), 0.99 (d, J=3.7 Hz, 3H), 0.97 (d, J=3.6 Hz, 3H); $^{19}$F NMR (376 MHz, Chloroform-d) δ −133.39; LCMS (ESI) m/e 462.2 [(M+H)$^+$, calcd $C_{24}H_{33}F_1N_3O_5$, 462.2]; LC/MS retention time (method B): $t_R$=2.20 min.

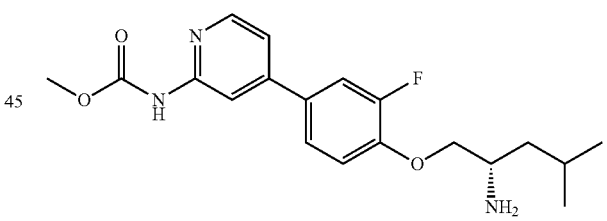

Part C: (S)-methyl (4-(4-((2-amino-4-methylpentyl)oxy)-3-fluorophenyl)pyridin-2-yl)carbamate Obtained (S)-methyl (4-(4-((2-amino-4-methylpentyl)oxy)-3-fluorophenyl)pyridin-2-yl)carbamate (33.2 mg, 0.091 mmol, 93% yield for the final step) as an off-white solid. $^1$H NMR (500 MHz, DMSO-$d_6$) δ 10.26 (s, 1H), 8.30 (d, J=5.3 Hz, 1H), 8.09 (s, 1H), 7.63 (dd, J=12.7, 2.4 Hz, 1H), 7.55-7.49 (m, 1H), 7.37 (dd, J=5.3, 1.9 Hz, 1H), 7.32 (t, J=8.7 Hz, 1H), 3.97 (dd, J=9.4, 5.0 Hz, 1H), 3.90 (dd, J=9.4, 6.5 Hz, 1H), 3.71 (s, 3H), 3.12 (p, J=5.6 Hz, 1H), 1.83 (dt, J=14.1, 6.7 Hz, 1H), 1.33 (ddd, J=13.4, 8.5, 4.9 Hz, 1H), 1.26 (ddd, J=13.9, 8.7, 5.5 Hz, 1H), 0.92 (d, J=6.6 Hz, 3H), 0.89 (d, J=6.5 Hz, 3H); LCMS (ESI) m/e 362.1 [(M+H)$^+$, calcd $C_{19}H_{25}F_1N_3O_3$, 362.2]; LC/MS retention time (method A): $t_R$=1.85 min.

Example 14

(S)-methyl(4-(4-((2-amino-4-methylpentyl)oxy)-3-(isoxazol-5-yl)phenyl)pyridin-2-yl)carbamate

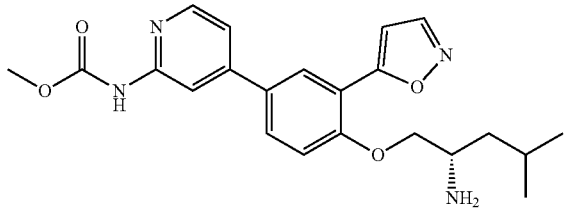 [SMILES: COC(=O)Nc1cc(-c2ccc(OC[C@@H](N)CC(C)C)c(-c3ccno3)c2)ccn1]

Prepared as described in Example 1.

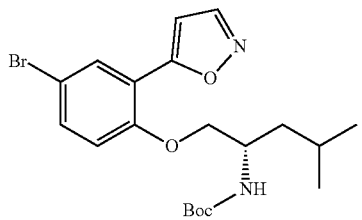 [SMILES: CC(C)C[C@@H](COc1ccc(Br)cc1-c1ccno1)NC(=O)OC(C)(C)C]

Part A: (S)-tert-butyl (1-(4-bromo-2-(isoxazol-5-yl)phenoxy)-4-methylpentan-2-yl)carbamate $^1$H NMR (400 MHz, Chloroform-d) δ 8.31 (s, 1H), 8.09 (d, J=2.4 Hz, 1H), 7.46 (dd, J=9.1, 2.6 Hz, 1H), 6.88 (d, J=9.0 Hz, 2H), 4.60 (d, J=8.9 Hz, 1H), 4.19 (d, J=7.0 Hz, 1H), 4.02 (qd, J=9.2, 5.2 Hz, 2H), 1.75 (dq, J=13.6, 6.7 Hz, 1H), 1.46 (d, J=12.0 Hz, 11H), 0.98 (d, J=6.6 Hz, 6H); LCMS (ESI) m/e 461.0 [(M+Na)$^+$, calcd C$_{20}$H$_{27}$Br$_1$N$_2$Na$_1$O$_4$, 461.1]; LC/MS retention time (method B): t$_R$=2.41 min.

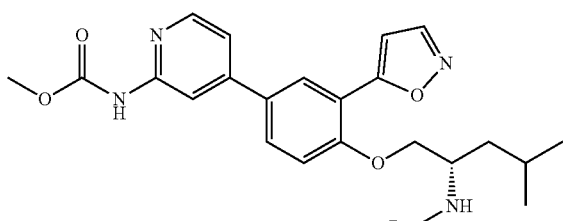

Part B: (S)-methyl (4-(4-((2-Boc-amino-4-methylpentyl)oxy)-3-(isoxazol-5-yl)phenyl)pyridin-2-yl)carbamate LCMS (ESI) m/e 511.4 [(M+H)$^+$, calcd C$_{27}$H$_{35}$N$_4$O$_6$, 511.2]; LC/MS retention time (method A): t$_R$=2.27 min.

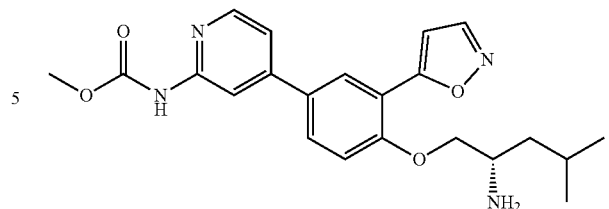

Part C: (S)-methyl (4-(4-((2-amino-4-methylpentyl)oxy)-3-(isoxazol-5-yl)phenyl)pyridin-2-yl)carbamate Obtained (S)-methyl (4-(4-((2-amino-4-methylpentyl)oxy)-3-(isoxazol-5-yl)phenyl)pyridin-2-yl)carbamate (10.9 mg, 0.027 mmol, 34% yield for the final step) as an off-white solid. $^1$H NMR (500 MHz, DMSO-d$_6$) δ 8.74 (d, J=1.7 Hz, 1H), 8.34 (d, J=5.2 Hz, 1H), 8.19 (t, J=2.4 Hz, 2H), 7.89 (dd, J=8.7, 2.4 Hz, 1H), 7.44 (d, J=5.3 Hz, 1H), 7.41 (d, J=8.8 Hz, 1H), 7.05 (d, J=1.9 Hz, 1H), 4.18 (dd, J=9.7, 4.5 Hz, 1H), 4.09 (dd, J=9.6, 6.3 Hz, 1H), 3.72 (s, 3H), 3.36 (d, J=4.3 Hz, 1H), 1.83 (dt, J=13.7, 6.7 Hz, 1H), 1.44 (dt, J=13.6, 7.0 Hz, 1H), 1.41-1.32 (m, 1H), 0.92 (dd, J=9.4, 6.6 Hz, 6H); LCMS (ESI) m/e 411.1 [(M+H)$^+$, calcd C$_{22}$H$_{27}$N$_4$O$_4$, 411.2]; LC/MS retention time (method B): t$_R$=1.63 min.

Example 15

(S)-2-((2-amino-4-methylpentyl)oxy)-5-(2-methylpyridin-4-yl)benzonitrile

Prepared as described in Example 1.

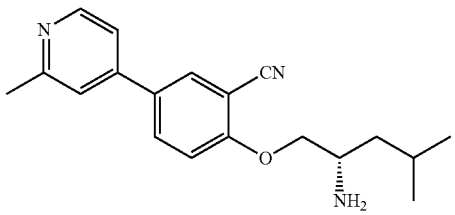

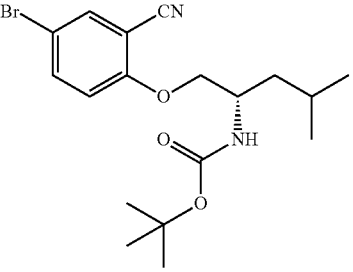

Part A: (S)-tert-butyl (1-(4-bromo-2-cyanophenoxy)-4-methylpentan-2-yl)carbamate $^1$H NMR (400 MHz, Chloroform-d) δ 7.68 (d, J=2.5 Hz, 1H), 7.64 (dd, J=8.9, 2.5 Hz, 1H), 6.91 (d, J=8.9 Hz, 1H), 4.71 (s, 1H), 4.12 (t, J=6.1 Hz, 1H), 4.10-3.98 (m, 2H), 1.79-1.67 (m, 1H), 1.59 (dd, J=13.8, 6.9 Hz, 2H), 1.47 (s, 9H), 0.98 (dd, J=6.5, 5.2 Hz, 6H); LCMS (ESI) m/e 397.1 [(M+H)$^+$, calcd C$_{18}$H$_{26}$Br$_1$N$_2$O$_3$, 397.1]; LC/MS retention time (method A): t$_R$=2.22 min.

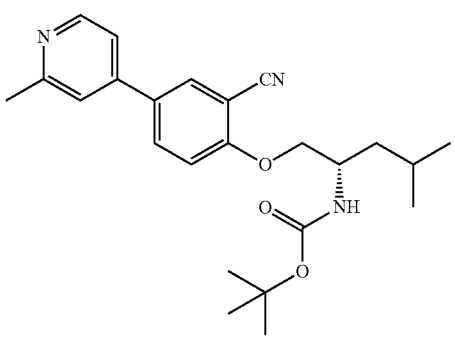 [SMILES: Cc1cc(-c2ccc(OC[C@H](CC(C)C)NC(=O)OC(C)(C)C)c(C#N)c2)ccn1]

Part B: (S)-tert-butyl (1-(2-cyano-4-(2-methylpyridin-4-yl)phenoxy)-4-methylpentan-2-yl)carbamate $^1$H NMR (400 MHz, Chloroform-d) δ 8.56 (d, J=5.3 Hz, 1H), 7.84 (d, J=2.3 Hz, 1H), 7.80 (dd, J=8.8, 2.4 Hz, 1H), 7.31 (d, J=1.7 Hz, 1H), 7.25 (dd, J=5.3, 1.8 Hz, 1H), 7.12 (d, J=8.8 Hz, 1H), 4.81 (d, J=8.6 Hz, 1H), 4.21-4.11 (m, 2H), 4.10-4.03 (m, 1H), 2.64 (s, 3H), 1.76-1.68 (m, 1H), 1.60 (tt, J=15.6, 6.2 Hz, 2H), 1.46 (s, 9H), 0.98 (dd, J=6.5, 5.0 Hz, 6H); LCMS (ESI) m/e 410.2 [(M+H)$^+$, calcd C$_{24}$H$_{32}$N$_3$O$_3$, 410.2]; LC/MS retention time (method A): t$_R$=2.18 min.

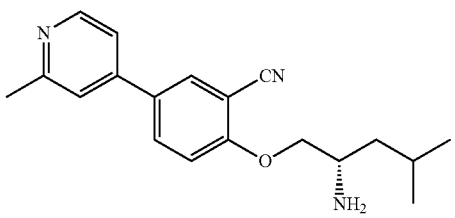

Part C: (S)-2-((2-amino-4-methylpentyl)oxy)-5-(2-methylpyridin-4-yl)benzonitrile Obtained (48.4 mg, 0.152 mmol, 99% yield for the final step) as an off-white solid. $^1$H NMR (500 MHz, DMSO-d$_6$) δ 8.49 (d, J=5.3 Hz, 1H), 8.24 (d, J=2.4 Hz, 1H), 8.11 (dd, J=8.9, 2.4 Hz, 1H), 7.65 (s, 1H), 7.57-7.52 (m, 1H), 7.38 (d, J=8.9 Hz, 1H), 4.09 (dd, J=9.5, 5.1 Hz, 1H), 4.01 (dd, J=9.5, 6.2 Hz, 1H), 3.16 (dq, J=10.8, 5.4 Hz, 1H), 2.53 (s, 3H), 2.51 (s, 2H), 1.83 (dq, J=12.8, 6.5 Hz, 1H), 1.39 (ddd, J=13.5, 8.4, 5.1 Hz, 1H), 1.30 (ddd, J=13.8, 8.6, 5.9 Hz, 1H), 0.93 (d, J=6.6 Hz, 3H), 0.89 (d, J=6.6 Hz, 3H); LCMS (ESI) m/e 310.1 [(M+H)$^+$, calcd C$_{19}$H$_{24}$N$_3$O$_1$, 310.2]; LC/MS retention time (method A): t$_R$=1.82 min.

Example 16

(S)-2-((2-amino-4-methylpentyl)oxy)-5-(2-methoxypyridin-4-yl)benzonitrile

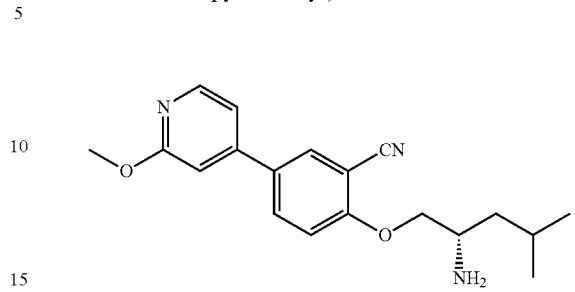

Prepared as described in Example 1.

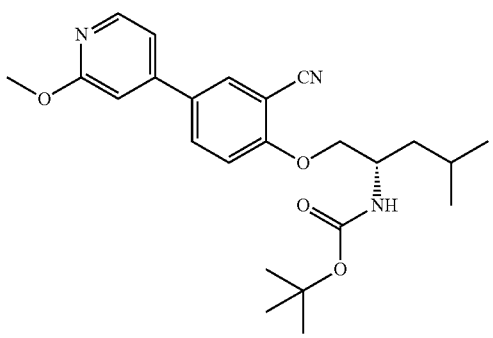 [SMILES: COc1cc(-c2ccc(OC[C@H](CC(C)C)NC(=O)OC(C)(C)C)c(C#N)c2)ccn1]

Part A: (S)-tert-butyl (1-(2-cyano-4-(2-methylpyridin-4-yl)phenoxy)-4-methoxypentan-2-yl)carbamate $^1$H NMR (500 MHz, Chloroform-d) δ 8.20 (dd, J=5.4, 0.7 Hz, 1H), 7.79 (d, J=2.3 Hz, 1H), 7.76 (dd, J=8.7, 2.4 Hz, 1H), 7.11-7.05 (m, 1H), 7.00 (dd, J=5.4, 1.6 Hz, 1H), 6.85 (dd, J=1.6, 0.7 Hz, 1H), 4.84 (d, J=8.7 Hz, 1H), 4.20-4.14 (m, 1H), 4.11 (ddd, J=8.7, 4.6, 2.5 Hz, 1H), 4.07-4.03 (m, 1H), 3.97 (s, 3H), 1.76-1.66 (m, 1H), 1.64-1.52 (m, 2H), 1.44 (s, 9H), 0.96 (dd, J=6.6, 5.7 Hz, 6H); LCMS (ESI) m/e 426.2 [(M+H)$^+$, calcd C$_{24}$H$_{32}$N$_3$O$_4$, 426.2]; LC/MS retention time (method A): t$_R$=2.27 min.

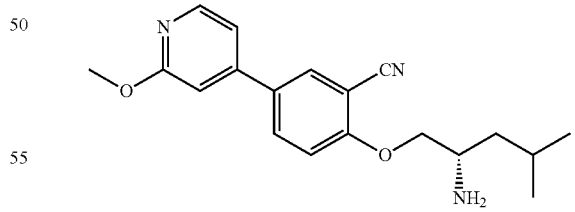

Part B: (S)-2-((2-amino-4-methylpentyl)oxy)-5-(2-methoxypyridin-4-yl)benzonitrile Obtained (S)-2-((2-amino-4-methylpentyl)oxy)-5-(2-methoxypyridin-4-yl)benzonitrile (28.6 mg, 0.088 mmol, 60% yield for the final step) as an off-white solid. $^1$H NMR (500 MHz, DMSO-d$_6$) δ 8.23 (dd, J=6.7, 3.9 Hz, 2H), 8.10 (dd, J=8.9, 2.4 Hz, 1H), 7.41-7.32 (m, 2H), 7.18 (s, 1H), 4.05

(dd, J=9.3, 5.1 Hz, 1H), 3.98 (dd, J=9.4, 6.3 Hz, 1H), 3.90 (s, 3H), 3.12 (dq, J=10.4, 5.4 Hz, 1H), 1.83 (tt, J=13.3, 6.7 Hz, 1H), 1.36 (ddd, J=13.4, 8.5, 4.9 Hz, 1H), 1.26 (ddd, J=13.9, 8.8, 5.7 Hz, 1H), 0.92 (d, J=6.6 Hz, 3H), 0.89 (d, J=6.6 Hz, 3H); LCMS (ESI) m/e 326.1 [(M+H)$^+$, calcd $C_{19}H_{24}N_3O_2$, 326.2]; LC/MS retention time (method A): $t_R$=1.88 min.

Example 17

(S)-2-((2-amino-4-methylpentyl)oxy)-5-(2-(trifluoromethyl)pyridin-4-yl)benzonitrile

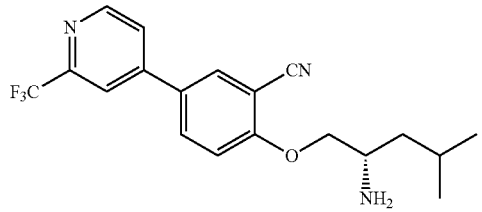 [SMILES: CC(C)C[C@H](N)COc1ccc(-c2ccnc(C(F)(F)F)c2)cc1C#N]

Prepared as described in Example 1.

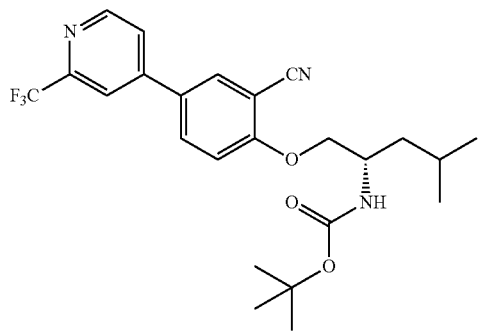 [SMILES: CC(C)C[C@@H](COc1ccc(-c2ccnc(C(F)(F)F)c2)cc1C#N)NC(=O)OC(C)(C)C]

Part A: (S)-tert-butyl (1-(2-cyano-4-(2-(trifluoromethyl)pyridin-4-yl)phenoxy)-4-methylpentan-2-yl)carbamate $^1$H NMR (400 MHz, Chloroform-d) δ 8.80 (d, J=5.1 Hz, 1H), 7.89 (d, J=2.4 Hz, 1H), 7.86 (dd, J=8.8, 2.5 Hz, 1H), 7.84-7.80 (m, 1H), 7.64 (dd, J=5.1, 1.8 Hz, 1H), 7.19 (d, J=8.8 Hz, 1H), 4.79 (d, J=8.5 Hz, 1H), 4.26-4.14 (m, 2H), 4.11-4.04 (m, 1H), 1.73 (p, J=6.5 Hz, 1H), 1.66-1.54 (m, 2H), 1.46 (s, 9H), 0.98 (t, J=6.3 Hz, 6H); $^{19}$F NMR (376 MHz, Chloroform-d) δ −68.06; LCMS (ESI) m/e 486.2 [(M+Na)$^+$, calcd $C_{24}H_{28}F_3NaN_3O_3$, 486.2]; LC/MS retention time (method B): $t_R$=2.35 min.

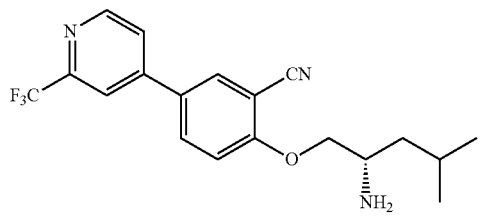 [SMILES: CC(C)C[C@H](N)COc1ccc(-c2ccnc(C(F)(F)F)c2)cc1C#N]

Part B: (S)-2-((2-amino-4-methylpentyl)oxy)-5-(2-(trifluoromethyl)pyridin-4-yl)benzonitrile Obtained (S)-2-((2-amino-4-methylpentyl)oxy)-5-(2-(trifluoromethyl)pyridin-4-yl)benzonitrile (34.3 mg, 0.093 mmol, 93% yield for the final step) as an off-white solid. $^1$H NMR (500 MHz, DMSO-d$_6$) δ 8.81 (d, J=5.2 Hz, 1H), 8.46 (d, J=2.9 Hz, 1H), 8.34-8.21 (m, 2H), 8.11 (d, J=5.1 Hz, 1H), 7.42 (d, J=8.9 Hz, 1H), 4.08 (dd, J=9.9, 5.2 Hz, 1H), 4.05-3.95 (m, 1H), 3.13 (d, J=7.5 Hz, 1H), 1.85 (t, J=7.0 Hz, 1H), 1.43-1.32 (m, 1H), 1.27 (q, J=11.7, 9.8 Hz, 1H), 0.93 (d, J=6.4 Hz, 3H), 0.89 (d, J=6.4 Hz, 3H); LCMS (ESI) m/e 364.1 [(M+H)$^+$, calcd $C_{19}H_2F_3N_3O_1$, 364.2]; LC/MS retention time (method B): $t_R$=1.97 min.

Example 18

(S)-1-(2-(isoxazol-5-yl)-4-(2-methylpyridin-4-yl)phenoxy)-4-methylpentan-2-amine

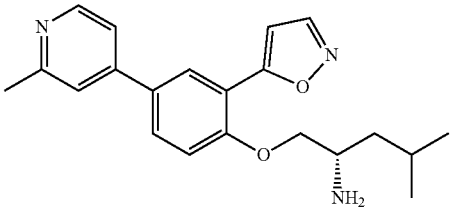

Prepared as described in Example 1.

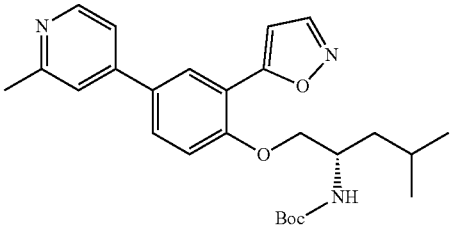 [SMILES: Cc1cc(-c2ccc(OC[C@H](CC(C)C)NC(=O)OC(C)(C)C)c(-c3ccno3)c2)ccn1]

Part A: (S)-tert-butyl (1-(2-(isoxazol-5-yl)-4-(2-methylpyridin-4-yl)phenoxy)-4-methylpentan-2-yl)carbamate LCMS (ESI) m/e 452.1 [(M+H)$^+$, calcd $C_{26}H_{34}N_3O_4$, 452.2]; LC/MS retention time (method B): $t_R$=2.03 min.

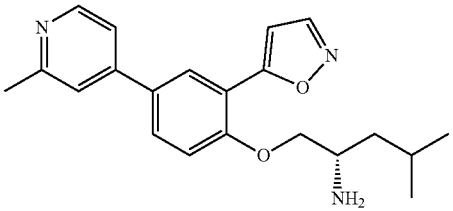 [SMILES: Cc1cc(-c2ccc(OC[C@@H](N)CC(C)C)c(-c3ccno3)c2)ccn1]

Part B: (S)-1-(2-(isoxazol-5-yl)-4-(2-methylpyridin-4-yl)phenoxy)-4-methylpentan-2-amine Obtained(S)-1-(2-(isoxazol-5-yl)-4-(2-methylpyridin-4-yl)phenoxy)-4-methylpentan-2-amine (14.6 mg, 0.041 mmol, 49% yield for the final step) as an off-white solid. ¹H NMR (500 MHz, DMSO-$d_6$) δ 8.72 (d, J=1.9 Hz, 1H), 8.49 (d, J=5.3 Hz, 1H), 8.24 (d, J=2.4 Hz, 1H), 7.93 (dd, J=8.8, 2.4 Hz, 1H), 7.65 (s, 1H), 7.59-7.52 (m, 1H), 7.37 (d, J=8.8 Hz, 1H), 7.03 (d, J=1.9 Hz, 1H), 4.12 (dd, J=9.6, 4.6 Hz, 1H), 4.04 (dd, J=9.5, 6.3 Hz, 1H), 3.27 (dq, J=10.3, 5.3 Hz, 1H), 2.51 (s, 3H), 1.83 (dt, J=14.0, 6.7 Hz, 1H), 1.40 (ddd, J=13.4, 8.4, 5.2 Hz, 1H), 1.32 (ddd, J=13.7, 8.5, 5.7 Hz, 1H), 0.91 (dd, J=10.5, 6.5 Hz, 6H); LCMS (ESI) m/e 352.1 [(M+H)⁺, calcd $C_{21}H_{26}N_3O_2$, 352.2]; LC/MS retention time (method B): $t_R$=1.50 min.

Example 19

(S)—N-(4-(4-((2-amino-2,4-dimethylpentyl)oxy)-3-(trifluoromethyl)phenyl)pyridin-2-yl)acetamide

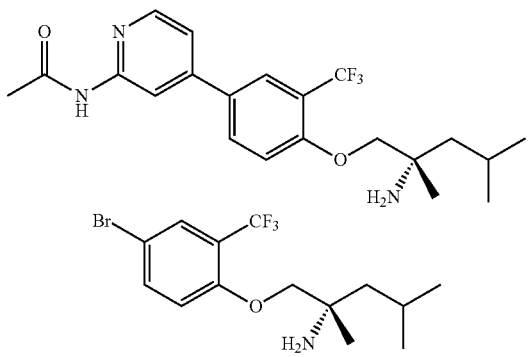

Part A: (S)-1-(4-bromo-2-(trifluoromethyl)phenoxy)-2,4-dimethylpentan-2-amine

To a 50 mL round-bottomed flask was added (S)-2-amino-2,4-dimethylpentan-1-ol (66.1 mg, 0.504 mmol) in tetrahydrofuran (1.5 mL) to give a colorless solution. Potassium tert-butoxide (0.604 mL, 0.604 mmol) (1.0 M in THF) was added dropwise under nitrogen. After 5 min, 4-bromo-1-fluoro-2-(trifluoromethyl)benzene (0.079 mL, 0.604 mmol) was added in one portion. The mixture was stirred at rt for 2 h. The reaction was quenched with water and extracted with EtOAc. The organic layer was washed with brine, dried (Na₂SO₄) and concentrated under reduced pressure to obtain crude (S)-1-(4-bromo-2-(trifluoromethyl)phenoxy)-2,4-dimethylpentan-2-amine (146 mg, 0.412 mmol, 82% yield) as a tan oil which was used as is. ¹H NMR (500 MHz, Chloroform-d) δ 7.70 (d, J=2.5 Hz, 1H), 7.59 (dd, J=8.8, 2.5 Hz, 1H), 6.86 (d, J=8.8 Hz, 1H), 3.80-3.72 (m, 2H), 1.83-1.73 (m, 1H), 1.53-1.44 (m, 2H), 1.23 (s, 3H), 0.98 (dd, J=12.2, 6.7 Hz, 6H); ¹⁹F NMR (470 MHz, Chloroform-d) δ −62.61; LCMS (ESI) m/e 354.0 [(M+H)⁺, calcd $C_{14}H_{20}Br_1F_3N_1O_1$, 354.1]; LC/MS retention time (method B): $t_R$=2.14 min.

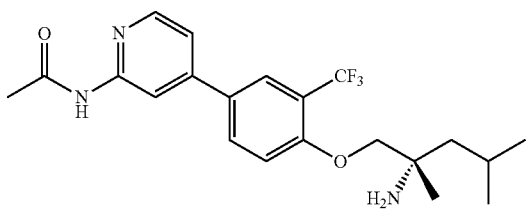 [SMILES: CC(=O)Nc1cc(-c2ccc(OC[C@@](C)(N)CC(C)C)c(C(F)(F)F)c2)ccn1]

Part B: (S)—N-(4-(4-((2-amino-2,4-dimethylpentyl)oxy)-3-(trifluoromethyl)phenyl)pyridin-2-yl)acetamide To a 2 mL vial was added (S)-1-(4-bromo-2-(trifluoromethyl)phenoxy)-2,4-dimethylpentan-2-amine (43.5 mg, 0.123 mmol), N-(4-(4,4,5,5-tetramethyl-1,3,2-dioxaborolan-2-yl)pyridin-2-yl)acetamide (26.5 mg, 0.147 mmol) (prepared as described in Example 1, Part A), and Na₂CO₃ (0.184 mL, 0.368 mmol) in dioxane (0.5 mL) under nitrogen to give a colorless suspension. 1,1'-bis(diphenylphosphino)ferrocene palladium(II) dichloride, toluene (5.05 mg, 6.14 µmol) was added under nitrogen. The vial was sealed and heated at 130° C. (microwave) for 2 h (100° C. oil heating for 2 h was fine and was used for all other examples). The mixture was cooled to rt and diluted with EtOAc then passed through a plug of Na₂SO₄. The organic solution was concentrated under reduced pressure. The residue was purified by reverse phase HPLC (acetonitrile: water with 10 mM ammonium) to give (S)—N-(4-(4-((2-amino-2,4-dimethylpentyl)oxy)-3-(trifluoromethyl)phenyl)pyridin-2-yl)acetamide (24 mg, 0.057 mmol, 47% yield) as an off-white solid. ¹H NMR (500 MHz, DMSO-$d_6$) δ 10.58 (s, 1H), 8.36 (d, J=5.2 Hz, 2H), 7.97 (t, J=8.1 Hz, 1H), 7.89 (s, 1H), 7.44 (d, J=5.4 Hz, 1H), 7.38 (d, J=8.7 Hz, 1H), 3.86 (q, J=8.8 Hz, 2H), 2.13 (s, 3H), 1.79 (dq, J=10.2, 5.2, 4.0 Hz, 1H), 1.39 (d, J=5.5 Hz, 2H), 1.12 (s, 3H), 0.91 (d, J=6.6 Hz, 6H); LCMS (ESI) m/e 410.2 [(M−H), calcd $C_2H_{23}F_3N_3O_2$, 410.2]; LC/MS retention time (method B): $t_R$=1.87 min.

Example 20

(S)-methyl(4-(4-((2-amino-2,4-dimethylpentyl)oxy)-3-(trifluoromethyl)phenyl)pyridin-2-yl)carbamate

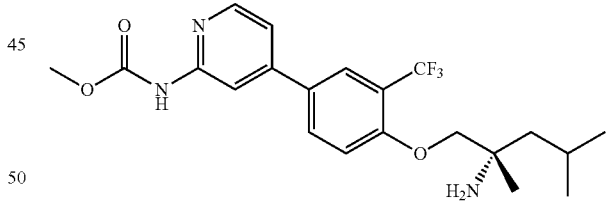

Prepared as described in Example 19 to obtain (S)-methyl (4-(4-((2-amino-2,4-dimethylpentyl)oxy)-3-(trifluoromethyl)phenyl)pyridin-2-yl)carbamate (22.9 mg, 0.051 mmol, 38% yield) as an off-white solid. ¹H NMR (500 MHz, DMSO-$d_6$) δ 10.29 (s, 1H), 8.32 (d, J=5.3 Hz, 1H), 8.11 (s, 1H), 7.99 (d, J=8.7 Hz, 1H), 7.90 (s, 1H), 7.39 (dd, J=12.5, 7.0 Hz, 2H), 3.87 (q, J=8.8 Hz, 2H), 3.71 (s, 3H), 1.79 (dq, J=10.8, 5.6, 4.8 Hz, 1H), 1.40 (d, J=5.6 Hz, 2H), 1.13 (s, 3H), 0.91 (d, J=6.6 Hz, 6H); LCMS (ESI) m/e 426.3 [(M−H)⁺, calcd $C_{21}H_{27}F_3N_3O_3$, 426.2]; LC/MS retention time (method A): $t_R$=2.23 min.

Example 21

(S)—N-(4-(4-((2-amino-2,4-dimethylpentyl)oxy)-3-cyanophenyl)pyridin-2-yl)acetamide

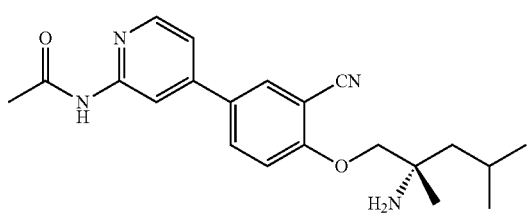 [SMILES: CC(=O)Nc1cc(-c2ccc(OC[C@@](C)(N)CC(C)C)c(C#N)c2)ccn1]

Prepared as described in Example 19

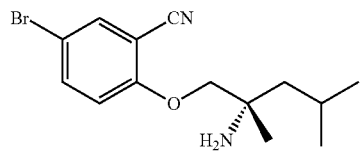 [SMILES: CC(C)C[C@](C)(N)COc1ccc(Br)cc1C#N]

Part A: (S)-2-((2-amino-2,4-dimethylpentyl)oxy)-5-bromobenzonitrile $^1$H NMR (400 MHz, Chloroform-d) δ 7.68 (d, J=2.5 Hz, 1H), 7.63 (dd, J=8.9, 2.4 Hz, 1H), 6.86 (d, J=9.0 Hz, 1H), 3.84-3.77 (m, 2H), 1.87-1.74 (m, 1H), 1.59-1.53 (m, 2H), 1.27 (s, 3H), 1.00 (dd, J=8.3, 6.6 Hz, 6H); LCMS (ESI) m/e 311.1, 313.1 Br pattern [(M+H)$^+$, calcd Cl$_4$H$_{20}$BrN$_2$O, 311.1]; LC/MS retention time (method A): $t_R$=2.01 min.

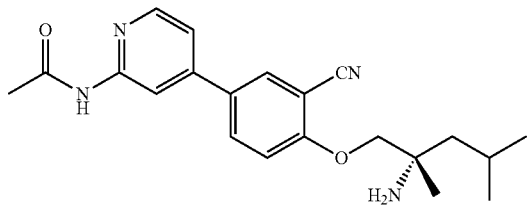 [SMILES: CC(=O)Nc1cc(-c2ccc(OC[C@@](C)(N)CC(C)C)c(C#N)c2)ccn1]

Part B: (S)—N-(4-(4-((2-amino-2,4-dimethylpentyl)oxy)-3-cyanophenyl)pyridin-2-yl)acetamide Obtained (S)—N-(4-(4-((2-amino-2,4-dimethylpentyl)oxy)-3-cyanophenyl)pyridin-2-yl)acetamide (28.9 mg, 0.078 mmol, 70% yield) as an off-white solid. $^1$H NMR (500 MHz, DMSO-d$_6$) δ 10.58 (s, 1H), 8.44-8.29 (m, 2H), 8.12 (s, 1H), 8.00 (d, J=8.9 Hz, 1H), 7.44 (d, J=5.3 Hz, 1H), 7.39 (d, J=8.8 Hz, 1H), 3.91 (t, J=6.7 Hz, 2H), 2.13 (s, 3H), 1.82 (p, J=6.2 Hz, 1H), 1.43 (t, J=5.4 Hz, 2H), 1.15 (s, 3H), 0.93 (dd, J=6.7, 3.7 Hz, 6H); LCMS (ESI) m/e 367.3 [(M+H)$^+$, calcd C$_{21}$H$_{27}$N$_4$O$_2$, 367.2]; LC/MS retention time (method A): $t_R$=1.82 min.

Example 22

(S)-methyl(4-(4-((2-amino-2,4-dimethylpentyl)oxy)-3-cyanophenyl)pyridin-2-yl)carbamate

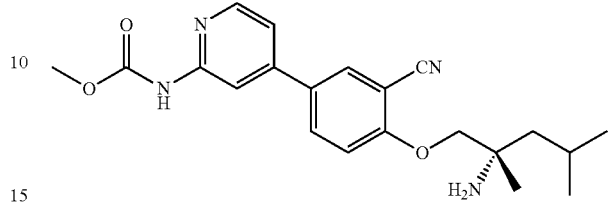

Prepared as described in Example 19 to obtain (S)-methyl (4-(4-((2-amino-2,4-dimethylpentyl)oxy)-3-cyanophenyl) pyridin-2-yl)carbamate (21.1 mg, 0.053 mmol, 47% yield) as an off-white solid. $^1$H NMR (500 MHz, DMSO-d$_6$) δ 10.29 (s, 1H), 8.32 (d, J=5.3 Hz, 1H), 8.13 (s, 1H), 8.10 (s, 1H), 8.01 (d, J=9.1 Hz, 1H), 7.40 (dd, J=11.9, 7.1 Hz, 2H), 3.91 (t, J=6.5 Hz, 2H), 3.71 (s, 3H), 1.81 (dq, J=12.5, 6.2 Hz, 1H), 1.42 (q, J=8.2, 6.6 Hz, 2H), 1.15 (s, 3H), 0.93 (dd, J=6.8, 3.8 Hz, 6H); LCMS (ESI) m/e 405.2 [(M+Na)$^+$, calcd C$_{21}$H$_{26}$N$_4$Na$_1$O$_3$, 405.2]; LC/MS retention time (method B): $t_R$=1.87 min.

Example 23

(S)—N-(4-(4-((2-amino-2,4-dimethylpentyl)oxy)-3-(difluoromethyl)phenyl)pyridin-2-yl)acetamide

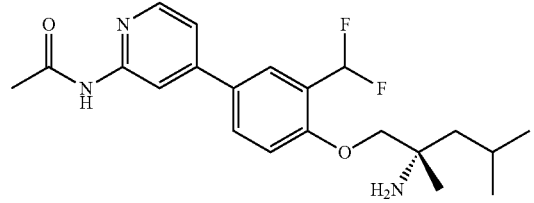 [SMILES: CC(=O)Nc1cc(-c2ccc(OC[C@@](C)(N)CC(C)C)c(C(F)F)c2)ccn1]

Prepared as described in Example 19.

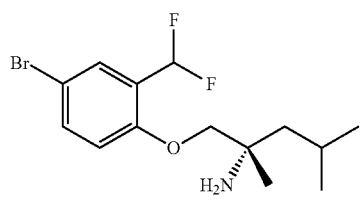 [SMILES: CC(C)C[C@](C)(N)COc1ccc(Br)cc1C(F)F]

Part A: (S)-1-(4-bromo-2-(difluoromethyl)phenoxy)-2,4-dimethylpentan-2-amine $^1$H NMR (400 MHz, Chloroform-d) δ 7.67 (dd, J=2.4, 1.1 Hz, 1H), 7.53 (ddt, J=8.8, 2.3, 1.1 Hz, 1H), 6.93-6.70 (m, 2H), 3.79-3.72 (m, 2H), 1.85-1.73 (m, 1H), 1.52-1.47 (m, 2H), 1.23 (s, 3H), 0.99 (dd, J=7.6, 6.6 Hz, 6H); $^{19}$F NMR (376 MHz, Chloroform-d) δ −116.21; LCMS (ESI) m/e 336.1 [(M+H)$^+$, calcd C$_{14}$H$_{21}$Br$_1$F$_2$N$_1$O$_1$, 336.1]; LC/MS retention time (method A): $t_R$=2.18 min.

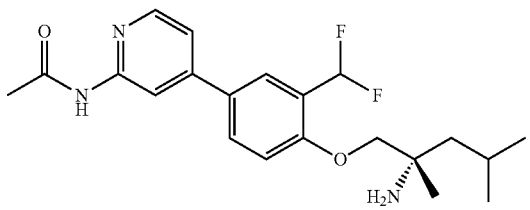 [SMILES: CC(=O)Nc1cc(-c2ccc(OC[C@@](C)(N)CC(C)C)c(C(F)F)c2)ccn1]

Part B: (S)—N-(4-(4-((2-amino-2,4-dimethylpentyl)oxy)-3-(difluoromethyl)phenyl)pyridin-2-yl)acetamide

Obtained (S)—N-(4-(4-((2-amino-2,4-dimethylpentyl)oxy)-3-(difluoromethyl)phenyl)pyridin-2-yl)acetamide (13 mg, 0.033 mmol, 32% yield) as an off-white solid. $^1$H NMR (500 MHz, DMSO-d$_6$) δ 10.56 (s, 1H), 8.45-8.29 (m, 2H), 7.87 (d, J=8.7 Hz, 1H), 7.82 (s, 1H), 7.49-7.12 (m, 3H), 3.84 (s, 2H), 2.13 (s, 3H), 1.79 (dt, J=14.1, 7.3 Hz, 1H), 1.47-1.34 (m, 2H), 1.14 (s, 3H), 0.92 (dd, J=11.3, 6.6 Hz, 6H); LCMS (ESI) m/e 392.3 [(M+H)$^+$, calcd C$_{21}$H$_{2}$F$_2$N$_3$O$_2$, 392.2]; LC/MS retention time (method A): t$_R$=1.90 min.

Example 24

(S)-methyl (4-(4-((2-amino-2,4-dimethylpentyl)oxy)-3-(difluoromethyl)phenyl)pyridin-2-yl)carbamate

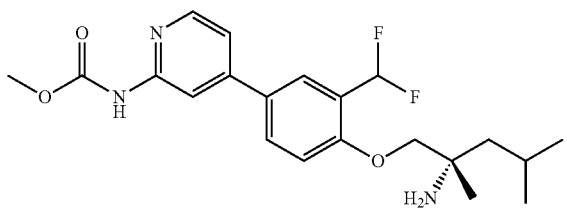 [SMILES: COC(=O)Nc1cc(-c2ccc(OC[C@@](C)(N)CC(C)C)c(C(F)F)c2)ccn1]

Prepared as described in Example 19 to obtain (S)-methyl (4-(4-((2-amino-2,4-dimethylpentyl)oxy)-3-(difluoromethyl)phenyl)pyridin-2-yl)carbamate (15.4 mg, 0.037 mmol, 35% yield) as an off-white solid. $^1$H NMR (500 MHz, DMSO-d$_6$) δ 10.26 (s, 1H), 8.31 (d, J=5.3 Hz, 1H), 8.11 (s, 1H), 7.91-7.85 (m, 1H), 7.83 (s, 1H), 7.42-7.13 (m, 3H), 3.84 (s, 2H), 3.70 (s, 3H), 1.79 (dt, J=12.8, 6.4 Hz, 1H), 1.41 (qd, J=14.0, 5.6 Hz, 2H), 1.14 (s, 3H), 0.92 (dd, J=11.4, 6.6 Hz, 6H); LCMS (ESI) m/e 408.3 [(M+H)$^+$, calcd C$_{21}$H$_{28}$F$_2$N$_3$O$_3$, 408.2]; LC/MS retention time (method A): t$_R$=2.00 min.

Example 25

(S)—N-(4-(4-((2-amino-2,4-dimethylpentyl)oxy)-3-(trifluoromethoxy)phenyl)pyridin-2-yl)acetamide

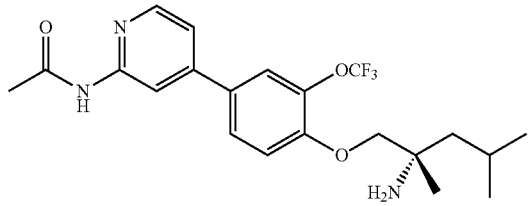 [SMILES: CC(=O)Nc1cc(-c2ccc(OC[C@@](C)(N)CC(C)C)c(OC(F)(F)F)c2)ccn1]

Prepared as described in Example 19.

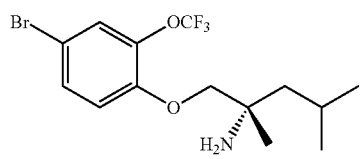 [SMILES: CC(C)C[C@](C)(N)COc1ccc(Br)cc1OC(F)(F)F]

Part A: (S)-1-(4-bromo-2-(trifluoromethoxy)phenoxy)-2,4-dimethylpentan-2-amine

$^1$H NMR (400 MHz, Chloroform-d) δ 7.41-7.34 (m, 2H), 6.87 (d, J=8.6 Hz, 1H), 3.76-3.72 (m, 2H), 1.83-1.76 (m, 1H), 1.49-1.47 (m, 2H), 1.23 (s, 3H), 1.01-0.98 (m, 6H); $^{19}$F NMR (376 MHz, Chloroform-d) δ −58.22; LCMS (ESI) m/e 370.1 [(M+H)$^+$, calcd C$_{14}$H$_{20}$Br$_1$F$_3$N$_1$O$_2$, 370.1]; LC/MS retention time (method A): t$_R$=2.33 min.

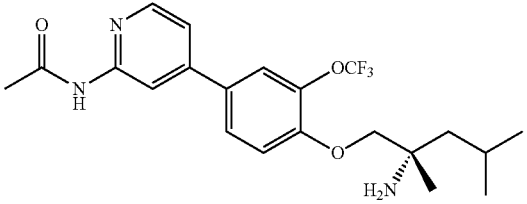 [SMILES: CC(=O)Nc1cc(-c2ccc(OC[C@@](C)(N)CC(C)C)c(OC(F)(F)F)c2)ccn1]

Part B: (S)—N-(4-(4-((2-amino-2,4-dimethylpentyl)oxy)-3-(trifluoromethoxy)phenyl)pyridin-2-yl)acetamide

Obtained (S)—N-(4-(4-((2-amino-2,4-dimethylpentyl)oxy)-3-(trifluoromethoxy)phenyl)pyridin-2-yl)acetamide (14.1 mg, 0.032 mmol, 36% yield) as an off-white as solid. $^1$H NMR (500 MHz, DMSO-d$_6$) δ 10.57 (s, 1H), 8.35 (d, J=4.6 Hz, 2H), 7.74 (d, J=8.8 Hz, 1H), 7.70 (s, 1H), 7.41 (d, J=5.1 Hz, 1H), 7.38 (d, J=8.6 Hz, 1H), 3.83 (t, J=7.3 Hz, 2H), 2.12 (s, 3H), 1.81 (dt, J=13.1, 6.7 Hz, 1H), 1.39 (q, J=7.6, 6.3 Hz, 2H), 1.13 (s, 3H), 0.92 (t, J=5.1 Hz, 6H); LCMS (ESI) m/e 426.2 [(M+H)$^+$, calcd C$_{21}$H$_{27}$F$_3$N$_3$O$_3$, 426.2]; LC/MS retention time (method A): t$_R$=2.08 min.

Example 26

(S)-methyl (4-(4-((2-amino-2,4-dimethylpentyl)oxy)-3-(trifluoromethoxy)phenyl)pyridin-2-yl)carbamate

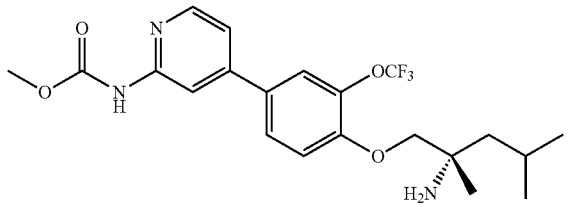 [SMILES: COC(=O)Nc1cc(-c2ccc(OC[C@@](C)(N)CC(C)C)c(OC(F)(F)F)c2)ccn1]

Prepared as described in Example 19 to obtain (S)-methyl (4-(4-((2-amino-2,4-dimethylpentyl)oxy)-3-(trifluoromethoxy)phenyl)pyridin-2-yl)carbamate (11.5 mg, 0.026 mmol, 27% yield) as an off-white solid. $^1$H NMR (500 MHz, DMSO-$d_6$) δ 10.28 (s, 1H), 8.31 (d, J=5.2 Hz, 1H), 8.10 (s, 1H), 7.75 (d, J=8.6 Hz, 1H), 7.71 (s, 1H), 7.43-7.34 (m, 2H), 3.86-3.80 (m, 2H), 3.71 (s, 3H), 1.81 (dt, J=12.7, 6.4 Hz, 1H), 1.39 (q, J=8.2, 6.3 Hz, 2H), 1.13 (s, 3H), 0.92 (dd, J=6.7, 3.8 Hz, 6H); LCMS (ESI) m/e 442.2 [(M+H)$^+$, calcd $C_{21}H_{27}F_3N_3O_4$, 442.2]; LC/MS retention time (method B): $t_R$=2.00 min.

Example 27

(S)—N-(4-(4-((2-amino-2,4-dimethylpentyl)oxy)-3-fluorophenyl)pyridin-2-yl)acetamide

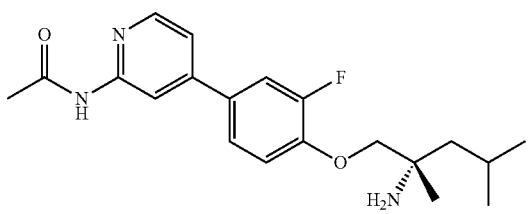 [SMILES: CC(=O)Nc1cc(-c2ccc(OC[C@@](C)(N)CC(C)C)c(F)c2)ccn1]

Prepared as described in Example 19.

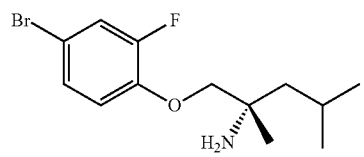

Part A: (S)-1-(2-fluorophenoxy)-2,4-dimethylpentan-2-amine

LCMS (ESI) m/e 226.3 [(M+H)$^+$, calcd $C_{13}H_{21}F_1N_1O_1$, 226.2]; LC/MS retention time (method B): $t_R$=1.93 min.

Part B: (S)-1-(4-bromo-2-(trifluoromethoxy)phenoxy)-2,4-dimethylpentan-2-amine

To a 100 mL round-bottomed flask was added (S)-1-(2-fluorophenoxy)-2,4-dimethylpentan-2-amine (83.4 mg, 0.370 mmol) in CHCl$_3$ (2 mL) to give a colorless solution. Br$_2$ (0.021 mL, 0.407 mmol) was added. The mixture was stirred at 45° C. for 15 h. The reaction mixture cooled to rt and was diluted with EtOAc then treated with aqueous sodium bisulfite solution. The layers were separated. The organic layer was washed with water, brine, dried (Na$_2$SO$_4$) and concentrated under reduced pressure to afford (S)-1-(4-bromo-2-(trifluoromethoxy)phenoxy)-2,4-dimethylpentan-2-amine (84 mg, 0.276 mmol, 75% yield). The crude material was carried on as is. LCMS (ESI) m/e 304.1 [(M+H)$^+$, calcd $C_{13}H_2Br_1F_1N_1O_1$, 304.1]; LC/MS retention time (method A): $t_R$=2.05 min.

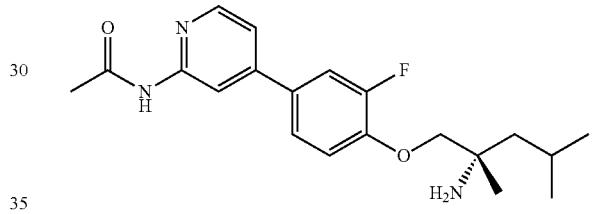

Part C: (S)—N-(4-(4-((2-amino-2,4-dimethylpentyl)oxy)-3-fluorophenyl)pyridin-2-yl)acetamide Obtained (S)—N-(4-(4-((2-amino-2,4-dimethylpentyl)oxy)-3-fluorophenyl)pyridin-2-yl)acetamide (14.5 mg, 0.039 mmol, 31% yield) as an off-white solid. $^1$H NMR (500 MHz, DMSO-$d_6$) δ 10.55 (s, 1H), 8.33 (d, J=6.0 Hz, 2H), 7.61 (d, J=12.3 Hz, 1H), 7.52 (d, J=8.8 Hz, 1H), 7.39 (d, J=5.4 Hz, 1H), 7.30 (t, J=8.8 Hz, 1H), 3.84-3.76 (m, 2H), 2.12 (s, 3H), 1.81 (p, J=6.4 Hz, 1H), 1.38 (q, J=7.9, 6.8 Hz, 2H), 1.12 (s, 3H), 0.93 (t, J=6.6 Hz, 6H); LCMS (ESI) m/e 360.2 [(M+H)$^+$, calcd $C_{20}H_{27}F_1N_3O_2$, 360.2]; LC/MS retention time (method A): $t_R$=1.82 min.

Example 28

(S)-methyl (4-(4-((2-amino-2,4-dimethylpentyl)oxy)-3-fluorophenyl)pyridin-2-yl)carbamate

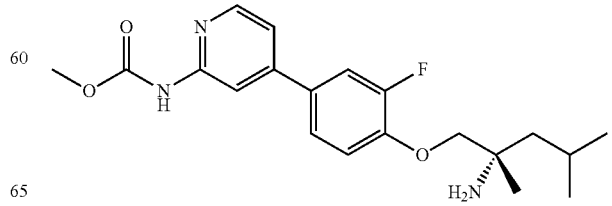

Prepared as described in Example 19 to obtain (S)-methyl (4-(4-((2-amino-2,4-dimethylpentyl)oxy)-3-fluorophenyl)pyridin-2-yl)carbamate (17.1 mg, 0.044 mmol, 30% yield) as an off-white solid. $^1$H NMR (500 MHz, DMSO-d$_6$) δ 10.25 (s, 1H), 8.29 (d, J=5.3 Hz, 1H), 8.09 (s, 1H), 7.62 (d, J=12.4 Hz, 1H), 7.53 (d, J=8.6 Hz, 1H), 7.36 (d, J=5.4 Hz, 1H), 7.30 (t, J=8.7 Hz, 1H), 3.82 (d, J=2.8 Hz, 2H), 3.70 (s, 3H), 1.86-1.74 (m, 1H), 1.46-1.33 (m, 2H), 1.13 (s, 3H), 0.93 (t, J=6.8 Hz, 6H); LCMS (ESI) m/e 376.2 [(M+H)$^+$, calcd C$_{20}$H$_{27}$F$_1$N$_3$O$_3$, 376.2]; LC/MS retention time (method A): t$_R$=1.92 min.

Example 29 methyl (4-(4-((2-amino-2,4-dimethylpentyl)oxy)-3-chlorophenyl)pyridin-2-yl)carbamate

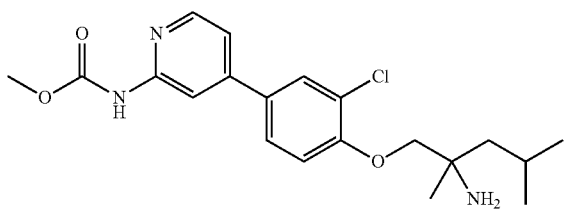

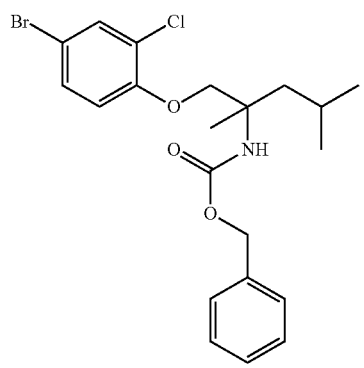

Part A: Benzyl (1-(4-bromo-2-chlorophenoxy)-2,4-dimethylpentan-2-yl)carbamate

An NMP (0.3 mL) suspension of 4-bromo-2-chlorophenol (0.074 g, 0.354 mmol), potassium carbonate (0.037 g, 0.266 mmol) and benzyl 4-isobutyl-4-methyl-1,2,3-oxathiazolidine-3-carboxylate 2,2-dioxide (0.058 g, 0.177 mmol) was heated at 50° C. overnight. The reaction was diluted with ethyl acetate and washed with NaOH (1N) (2×) and water (1×). The ethyl acetate layer was separated, dried (Na$_2$SO$_4$), filtered and concentrated under reduced pressure. The crude material was carried on without further purification. LCMS (ESI) m/e 476.1 [(M+Na)$^+$, calcd C$_{21}$H$_{25}$BrClNaNO$_3$, 476.1]; LC/MS retention time (method B): t$_R$=2.56 min.

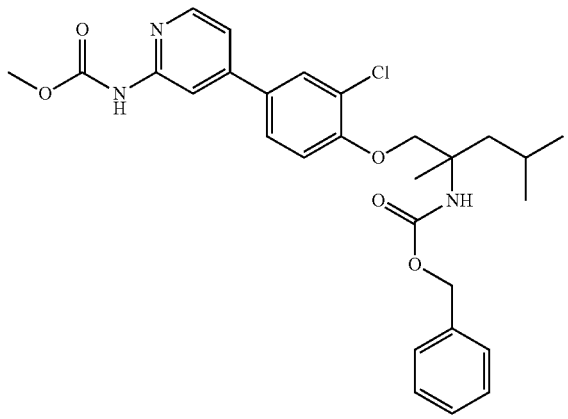 [SMILES: COC(=O)Nc1cc(-c2ccc(OCC(C)(CC(C)C)NC(=O)OCc3ccccc3)c(Cl)c2)ccn1]

Part B: Cbz methyl (4-(4-((2-amino-2,4-dimethylpentyl)oxy)-3-chlorophenyl)pyridin-2-yl)carbamate A mixture of sodium carbonate (0.177 ml, 0.354 mmol), 1,1'-bis(diphenylphosphino)ferrocene-palladium(II)dichloride dichloromethane complex (10.12 mg, 0.012 mmol), (2-((methoxycarbonyl)amino)pyridin-4-yl)boronic acid (0.035 g, 0.177 mmol) and benzyl (1-(4-bromo-2-chlorophenoxy)-2,4-dimethylpentan-2-yl)carbamate (0.080 g, 0.177 mmol) in dioxane (1 mL) (degassed) was heated at 85° C. overnight. The reaction was diluted with ethyl acetate and washed with water (3×). The aqueous layer was extract with ethyl acetate. The ethyl acetate layers were combined, washed with brine, dried (Na$_2$SO$_4$), filtered and concentrated under reduced pressure. The residue was purified via silica gel chromatography (from 0 to 30% ethyl acetate in hexanes) to give Cbz methyl (4-(4-((2-amino-2,4-dimethylpentyl)oxy)-3-chlorophenyl)pyridin-2-yl)carbamate (56.5 mg, 0.107 mmol, 61% yield for two steps) as a tan foam. (0.565 g, 61% yield). LCMS (ESI) m/e 548.2 [(M+Na)$^+$, calcd C$_{28}$H$_{32}$ClN$_3$O$_5$Na, 548.2]; LC/MS retention time (method B): t$_R$=2.25 min.

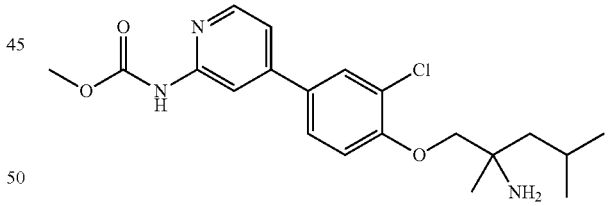

Part C: methyl (4-(4-((2-amino-2,4-dimethylpentyl)oxy)-3-chlorophenyl)pyridin-2-yl)carbamate Triethylsilane(0.026 mL, 0.161 mmol) was added to a CH$_2$Cl$_2$ (0.5 mL) suspension of palladium(II) acetate (2.2 mg, 9.80 μmol) and triethylamine (1 drop) at rt. This solution was stirred at room temperature for 10 min before the addition of a CH$_2$Cl$_2$ (0.5 mL) solution of Cbz protected methyl (4-(4-((2-amino-2,4-dimethylpentyl)oxy)-3-chlorophenyl)pyridin-2-yl)carbamate (0.0565 g, 0.107 mmol) (the flask contain the Cbz protected methyl (4-(4-((2-amino-2,4-dimethylpentyl)oxy)-3-chlorophenyl)pyridin-2-yl)carbamate (0.0565 g, 0.107 mmol) was rinsed with CH$_2$Cl$_2$ (0.5 mL) and added to the reaction mixture). The above reaction was stirred at room temperature overnight. The solvent was removed under reduced pressure and the residue was purified via reverse phase HPLC (acetonitrile/water/10 nM ammonium acetate) to afford methyl (4-(4-((2-amino-2,4-dimethylpentyl)oxy)-3-chlorophenyl)pyridin-2-yl)carbamate (29.6 mg, 0.076 mmol, 70% yield) as an off-white solid. $^1$H NMR (500 MHz, DMSO-$d_6$) δ 10.27 (br. s., 1H), 8.30 (d, J=5.2 Hz, 1H), 8.08 (s, 1H), 7.79 (s, 1H), 7.68 (d, J=8.2 Hz, 1H), 7.37 (d, J=5.2 Hz, 1H), 7.26 (d, J=8.5 Hz, 1H), 3.82 (d, J=2.4 Hz, 2H), 3.70 (s, 3H), 1.85-1.77 (m, 1H), 1.42 (br. s., 2H), 1.14 (s, 3H), 0.92 (m, 6H); LCMS (ESI) m/e 392.2 [(M+H)$^+$, calcd $C_{20}H_{27}ClN_3O_3$, 392.2]; LC/MS retention time (method B): $t_R$=1.75 min.

Example 30 methyl (4-(4-((2-amino-2,4-dimethylpentyl)oxy)-3-methylphenyl)pyridin-2-yl)carbamate Prepared as described in Example 29.

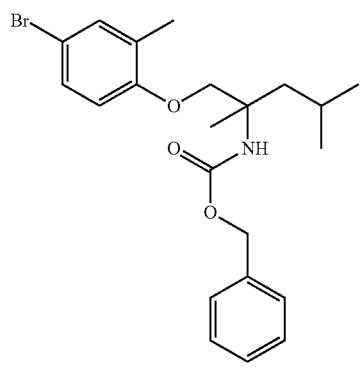 [SMILES: Cc1cc(Br)ccc1OCC(C)(CC(C)C)NC(=O)OCc1ccccc1]

Part A: Benzyl (1-(4-bromo-2-methylphenoxy)-2,4-dimethylpentan-2-yl)carbamate

LCMS (ESI) m/e 456.1 [(M+Na)$^+$, calcd $C_{22}H_{28}BrNO_3Na$, 456.1]; LC/MS retention time (method B): $t_R$=2.56 min.

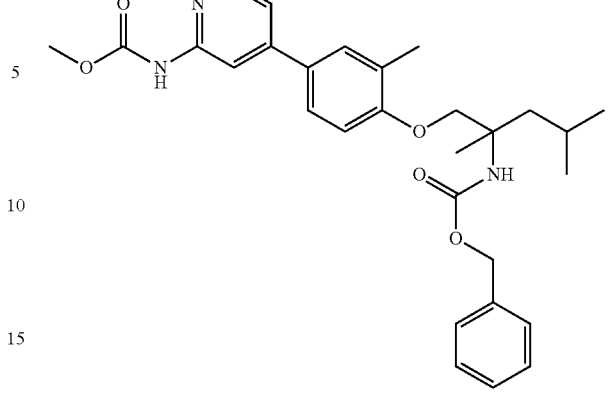

Part B: Cbz methyl (4-(4-((2-amino-2,4-dimethylpentyl)oxy)-3-methylphenyl)pyridin-2-yl)carbamate LCMS (ESI) m/e 506.1 [(M+H)$^+$, calcd $C_{29}H_{36}N_3O_5$, 506.3]; LC/MS retention time (method B): $t_R$=2.21 min.

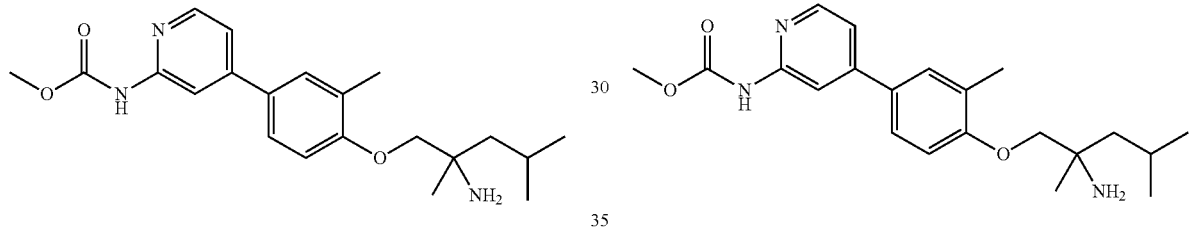

Part C: methyl(4-(4-((2-amino-2,4-dimethylpentyl)oxy)-3-methylphenyl)pyridin-2-yl)carbamate Obtained methyl(4-(4-((2-amino-2,4-dimethylpentyl)oxy)-3-methylphenyl)pyridin-2-yl)carbamate (3.7 mg, 9.96 umol, 35% yield) as an off white solid. $^1$H NMR (600 MHz, DMSO-$d_6$) δ 10.11 (br. s., 1H), 8.26 (d, J=5.1 Hz, 1H), 8.08 (s, 1H), 7.53 (br. s., 2H), 7.34-7.27 (m, 1H), 7.03 (d, J=9.2 Hz, 1H), 3.77-3.68 (m, 5H), 2.28 (s, 3H), 1.86-1.76 (m, 1H), 1.42 (t, J=5.0 Hz, 2H), 1.14 (s, 3H), 0.93 (m, 6H); LCMS (ESI) m/e 372.3 [(M+H)$^+$, calcd $C_{21}H_{30}N_3O_3$, 372.2]; LC/MS retention time (method B): $t_R$=1.71 min.

Example 31 methyl (4-(4-((2-amino-2,4-dimethylpentyl)oxy)-2,3-dimethylphenyl)pyridin-2-yl)carbamate

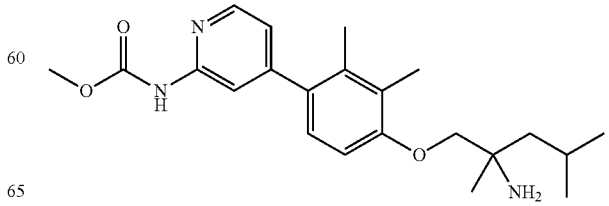

Prepared as described in Example 29.

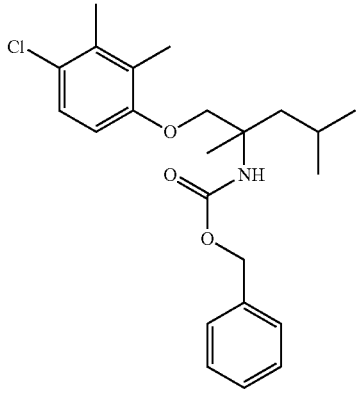 [SMILES: Cc1c(Cl)ccc(OCC(C)(CC(C)C)NC(=O)OCc2ccccc2)c1C]

Part A: Benzyl (1-((5-chloro-3,4-dimethylpyridin-2-yl)oxy)-2,4-dimethylpentan-2-yl)carbamate LCMS (ESI) m/e 426.3 [(M+Na)$^+$, calcd C$_{22}$H$_{29}$ClN$_2$O$_3$Na, 427.2]; LC/MS retention time (method B t$_R$=2.57 min.

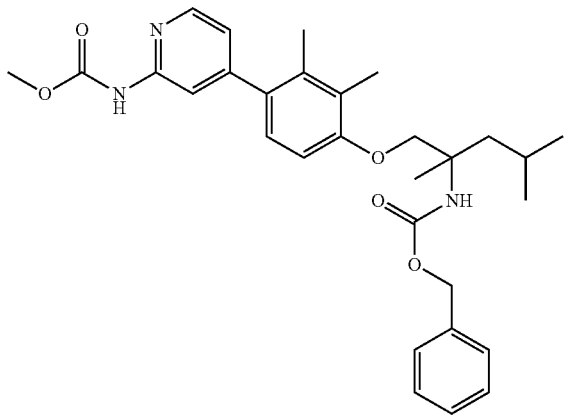 [SMILES: COC(=O)Nc1cc(-c2ccc(OCC(C)(CC(C)C)NC(=O)OCc3ccccc3)c(C)c2C)ccn1]

Part B: Cbz methyl (4-(4-((2-amino-2,4-dimethylpentyl)oxy)-2,3-dimethylphenyl)pyridin-2-yl)carbamate A mixture of 2$^{nd}$ generation Xphos Precatalyst (4 mg, 5.08 μmol), potassium phosphate tribasic (0.5 mL, 0.250 mmol), (2-((methoxycarbonyl)amino)pyridin-4-yl)boronic acid (0.044 g, 0.225 mmol) and benzyl (1-(4-chloro-2,3-dimethylphenoxy)-2,4-dimethylpentan-2-yl)carbamate (0.0385 g, 0.095 mmol) in THF (0.8 mL) was degassed via vacuum/N$_2$ fill cycle three times. The reaction mixture was heated at 80° C. overnight. The reaction was diluted with ethyl acetate and washed with water (2×) followed by brine. The ethyl acetate layer was separated, dried (Na$_2$SO$_4$), filtered and concentrated under reduced pressure. The product was purified via silica gel chromatography (0-30% ethyl acetate in hexanes) to afford Cbz methyl (4-(4-((2-amino-2,4-dimethylpentyl)oxy)-2,3-dimethylphenyl)pyridin-2-yl)carbamate (25 mg, 0.025 mmol, 27% yield) as a white solid. LCMS (ESI) m/e 520.5 [(M+H)$^+$, calcd C$_3$H$_{37}$N$_3$O$_5$, 520.3]; LC/MS retention time (method A): t$_R$=2.38 min.

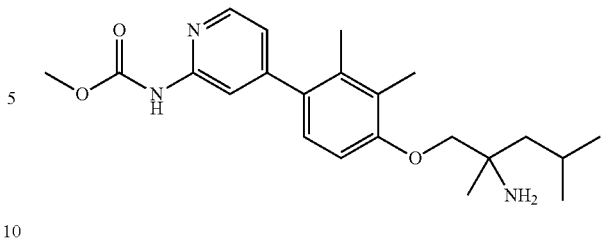

Part C: methyl (4-(4-((2-amino-2,4-dimethylpentyl)oxy)-2,3-dimethylphenyl)pyridin-2-yl)carbamate A mixture of Pd/C (6 mg, 5.64 μmol) and Cbz protected methyl (4-(4-((2-amino-2,4-dimethylpentyl)oxy)-2,3-dimethylphenyl)pyridin-2-yl)carbamate (0.025 g, 0.048 mmol) in ethanol (4 mL) was hydrogenated via a H$_2$ balloon at room temperature overnight. The reaction mixture was filtered through a celite pad and washed with CH$_2$Cl$_2$. The filtrate was concentrated under reduced pressure and the residue was purified by reverse phase HPLC (acetonitrile/water/10 mM ammonium acetate) to afford methyl (4-(4-((2-amino-2,4-dimethylpentyl)oxy)-2,3-dimethylphenyl)pyridin-2-yl)carbamate (2.8 mg, 7.26 umol, 15% yield) as an off-white solid. $^1$H NMR (600 MHz, DMSO-d$_6$) δ 8.26 (d, J=4.8 Hz, 1H), 7.74 (s, 1H), 7.02 (d, J=8.4 Hz, 1H), 6.96 (d, J=5.1 Hz, 1H), 6.86 (d, J=8.8 Hz, 1H), 3.67 (s, 4H), 3.48 (d, J=10.6 Hz, 1H), 2.19 (s, 3H), 1.84 (s, 3H), 1.83-1.74 (m, 1H), 1.42 (t, J=6.1 Hz, 2H), 1.14 (s, 3H), 0.92 (t, J=5.9 Hz, 6H). LCMS (ESI) m/e 369.2 [(M−NH$_2$)$^-$, calcd C$_{22}$H$_{29}$N$_2$O$_3$, 369.2]; LC/MS retention time (method B): t$_R$=1.68 min.

Example 32

(S)-methyl (4-(4-((2-amino-2,4-dimethylpentyl)oxy)-3-(hydroxymethyl)phenyl)pyridin-2-yl)carbamate

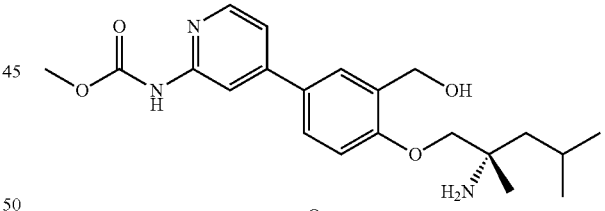

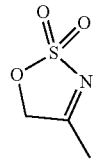

Part A. 4-methyl-5H-1,2,3-oxathiazole 2,2-dioxide

Step 1: Sulfamoyl chloride formation: In a 1000 ml 4 neck round-bottomed flask equipped with a mechanical stirring and an addition funnel, was charged DCM (400 mL) and chlorosulfonyl isocyanate (124 mL, 1430 mmol). Under N$_2$, this solution was cooled to 0° C. Then formic acid (53.9 mL, 1430 mmol) was added to DCM (100 mL) and this solution was transferred to the addition funnel and the solution was added slowly to the vigorously stirring reaction mixture. Gradually a thick slurry formed. A slow exotherm was observed so additional dry ice was added to acetone bath. Once temperature was stabilized, addition of the formic acid was continued. Addition was done in ~25 min. The mixture was allowed to gradually warm to room temperature and was stirred overnight.

Step 2: In a separate 5 L 4 neck reaction flask was charged hydroxyacetone (72.5 mL, 953 mmol), pyridine (116 mL, 1430 mmol), and DCM (2000 mL). This solution was cooled to −5° C. under $N_2$. The sulfamoyl chloride solution was added slowly via Teflon tube over 10 min. After the addition, the reaction was stirred for 15 min then the ice bath was removed and the reaction mixture allowed to warm to room temperature. As the reaction progressed, a gummy material formed. The material was purified via silica gel chromatography (300 g silica gel eluting with DCM). Obtained 4-methyl-5H-1,2,3-oxathiazole 2,2-dioxide (72.4 g, 536 mmol, 56% yield) as a colorless solid. $^1$H NMR (400 MHz, CHLOROFORM-d) δ 5.09 (s, 2H), 2.44 (s, 3H); LCMS (ESI) m/e 136.0 [(M+H)$^+$, calcd for $C_3H_6NO_3S$ 136.0].

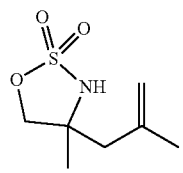

Part B. 2-(tert-butoxycarbonylamino)-2,4-dimethylpentanoic acid 4-methyl-4-(2-methylallyl)-1,2,3-oxathiazolidine 2,2-dioxide A suspension of 4-methyl-5H-1,2,3-oxathiazole 2,2-dioxide (0.541 g, 4 mmol) in methyl tert-butyl ether (30 mL) was cooled below 0° C. with an ice/IPA bath. To the cooled solution was added a solution of (2-methylallyl)magnesium chloride, 0.5 M in THF (9.60 mL, 4.80 mmol). The reaction mixture was allowed to warm to rt overnight. It was then quenched with a saturated solution of $NH_4Cl$ (50 mL) and EtOAc (20 mL) was added. The organic phase was separated, washed with brine (50 mL), dried over $Na_2SO_4$, filtered and concentrated under reduced pressure to give 2-(tert-butoxycarbonylamino)-2,4-dimethylpentanoic acid 4-methyl-4-(2-methylallyl)-1,2,3-oxathiazolidine 2,2-dioxide (0.567 g, 2.96 mmol, 74% yield). $^1$H NMR (400 MHz, CHLOROFORM-d) δ 5.06 (quin, J=1.5 Hz, 1H), 4.87 (dd, J=1.7, 0.8 Hz, 1H), 4.50 (br. s., 1H), 4.40 (d, J=8.6 Hz, 1H), 4.29 (d, J=8.7 Hz, 1H), 2.56 (d, J=13.8 Hz, 1H), 2.40-2.30 (m, 1H), 1.86 (br. s, 3H), 1.49 (s, 3H); LCMS (ESI) m/e 192.1 [(M+H)$^+$, calcd for $C_7H_{14}NO_3S$ 192.1].

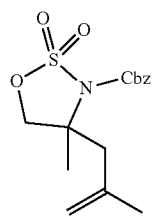 [SMILES: C=C(C)CC1(C)COS(=O)(=O)N1C(=O)OCc1ccccc1]

Part C. benzyl 4-methyl-4-(2-methylallyl)-1,2,3-oxathiazolidine-3-carboxylate 2,2-dioxide To a $N_2$ flushed, 100 mL round-bottomed flask was added a solution of 4-methyl-4-(2-methylallyl)-1,2,3-oxathiazolidine 2,2-dioxide (0.55 g, 2.88 mmol) in THF (10 mL). A solution of potassium tert-butoxide (4.31 mL, 4.31 mmol) in THF was added The temperature rose to 27° C. and the solution became a suspension. The mixture was stirred at room temperature for 1 h. Benzyl carbonochloridate (1.026 mL, 7.19 mmol) was added slowly. The reaction mixture was stirred at room temperature for 2 h. The reaction mixture was then quenched with water (50 mL) and extracted with EtOAc (2×70 mL). The organic extracts were washed with brine (50 mL), dried over $Na_2SO_4$, filtered and concentrated under reduced pressure. The residue was purified by silica gel chromatography (ethyl acetate/hexanes) to give benzyl 4-methyl-4-(2-methylallyl)-1,2,3-oxathiazolidine-3-carboxylate 2,2-dioxide (0.66 g, 2.028 mmol, 71% yield). $^1$H NMR (400 MHz, CHLOROFORM-d) δ 7.58-7.32 (m, 5H), 5.43-5.25 (m, 2H), 5.01 (t, J=1.5 Hz, 1H), 4.81 (d, J=0.9 Hz, 1H), 4.63 (d, J=9.5 Hz, 1H), 4.21 (d, J=9.5 Hz, 1H), 2.87 (d, J=14.1 Hz, 1H), 2.56 (d, J=14.1 Hz, 1H), 1.78 (br. s, 3H), 1.64 (s, 3H); LCMS (ESI) m/e 326.1 [(M+H)$^+$, calcd for $C_{15}H_{20}NO_5S$ 326.1].

The racmeic compounds was separated by chiral super critical fluid chromatography (Column: OJ-H (3×25 cm, 5 µm); Mobile Phase: $CO_2$/MeOH (90/10)) to give the two enantiomers.

Analytical super critical fluid chromatography conditions: Column: OJ-H (0.46×25 cm, 5 µm); BPR pressure: 100 bars; Temperature: 35° C.; Flow rate: 3.0 mL/min; Mobile Phase: $CO_2$/MeOH (90/10); Detector Wavelength: UV 200-400 nm Enantiomer 1: (S)-benzyl 4-methyl-4-(2-methylallyl)-1,2,3-oxathiazolidine-3-carboxylate 2,2-dioxide HPLC retention time=2.53 min.

Enantiomer 2: (R)-benzyl 4-methyl-4-(2-methylallyl)-1,2,3-oxathiazolidine-3-carboxylate 2,2-dioxide HPLC retention time=2.97 min.

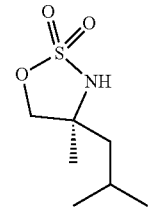

Part D.
(S)-4-isobutyl-4-methyl-1,2,3-oxathiazolidine 2,2-dioxide

To a stirred solution of (S)-benzyl 4-methyl-4-(2-methylallyl)-1,2,3-oxathiazolidine-3-carboxylate 2,2-dioxide (800 mg, 2.459 mmol) in MeOH (20 mL) was added Pd/C (262 mg, 0.246 mmol) under a nitrogen atmosphere and the reaction mixture was stirred under 1 atm hydrogen pressure for 16 h. The reaction mixture was passed through celite pad and the celite pad was washed with EtOAc (15 mL). The organic layer was evaporated under reduced pressure to afford (S)-4-isobutyl-4-methyl-1,2,3-oxathiazolidine 2,2-dioxide (462 mg, 2.39 mmol, 97% yield, 95% purity) as colorless oil. The material was carried forward without further purification. $^1$H NMR (400 MHz, DMSO-$d_6$) δ ppm 7.69 (br, 1H) 4.33 (d, J=8.03 Hz, 1H) 4.17-4.26 (m, 1H) 1.68-1.81 (m, 1H) 1.53-1.63 (m, 1H) 1.43-1.51 (m, 1H) 1.34 (s, 3H) 0.81-1.00 (m, 6H).

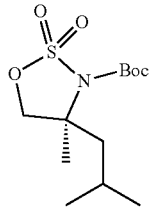

Part E. (S)-tert-butyl 4-isobutyl-4-methyl-1,2,3-oxathiazolidine-3-carboxylate 2,2-dioxide To a stirred solution of (S)-4-isobutyl-4-methyl-1,2,3-oxathiazolidine 2,2-dioxide (7 g, 15.21 mmol) in DCM (70 mL) cooled to 0° C. was added DMAP (1.858 g, 15.21 mmol) and (BOC)$_2$O (5.30 mL, 22.82 mmol) The reaction mixture was stirred at rt for 12 h. The reaction mixture was transfers to a separating funnel containing water (20 ml) and was extracted with DCM (2×60 ml). The combined organic layers were washed with brine (50 mL), dried over (Na$_2$SO$_4$), and concentrated under reduced pressure. The residue was purified via silica gel chromatography (30% ethyl acetate in pet ether) to afford (S)-tert-butyl 4-isobutyl-4-methyl-1,2,3-oxathiazolidine-3-carboxylate 2,2-dioxide (4.4 g, 14.70 mmol, 97% yield) as a colorless oil. $^1$H NMR (400 MHz, CHLOROFORM-d) δ 4.45 (d, J=9.0 Hz, 1H), 4.20 (d, J=9.0 Hz, 1H), 2.07-1.98 (m, J=8.0 Hz, 1H), 1.83-1.69 (m, 2H), 1.59 (s, 3H), 1.56 (s, 9H), 0.99 (dd, J=8.0, 6.5 Hz, 6H).

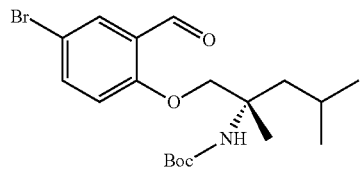 [SMILES: CC(C)C[C@@](C)(COc1ccc(Br)cc1C=O)NC(=O)OC(C)(C)C]

Part F: (S)-tert-butyl (1-(4-bromo-2-formylphenoxy)-2,4-dimethylpentan-2-yl)carbamate To a 20 mL vial was added 5-bromo-2-hydroxybenzaldehyde (81 mg, 0.403 mmol), (S)-tert-butyl 4-isobutyl-4-methyl-1,2,3-oxathiazolidine-3-carboxylate 2,2-dioxide (107.4 mg, 0.366 mmol), and K$_2$CO$_3$ (152 mg, 1.098 mmol) in DMF (1.2 mL) to give a white suspension. The vial was sealed and the mixture was heated at 80° C. for 17 h. The reaction mixture was cooled to rt and partitioned between water and EtOAc. The layers were separated. The organic layer was washed with water, brine, dried (Na$_2$SO$_4$) and concentrated under reduced pressure. The crude residue was purified by silica gel chromatography (up to 40% EtOAc/hexanes) to afford (S)-tert-butyl (1-(4-bromo-2-formylphenoxy)-2,4-dimethylpentan-2-yl)carbamate (115 mg, 0.278 mmol, 76%) as a colorless oil. $^1$H NMR (400 MHz, Chloroform-d) δ 10.43 (s, 1H), 7.89 (d, J=2.6 Hz, 1H), 7.59 (dd, J=8.9, 2.6 Hz, 1H), 6.93 (d, J=8.8 Hz, 1H), 4.58 (s, 1H), 4.29 (d, J=8.8 Hz, 1H), 4.09 (d, J=8.8 Hz, 1H), 1.94-1.74 (m, 2H), 1.48 (dd, J=13.9, 4.8 Hz, 1H), 1.39 (s, 3H), 1.37 (s, 9H), 0.98 (dd, J=6.6, 4.8 Hz, 6H); (ESI) m/e 314.0, 316.0 Br pattern [(M-Boc+H)$^+$, calcd C$_{14}$H$_{21}$BrNO$_2$, 414.1]; LC/MS retention time (method B): $t_R$=2.39 min.

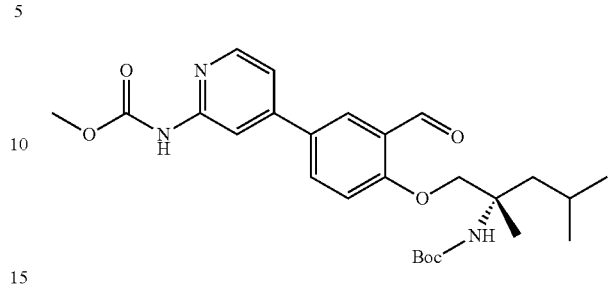

Part G: (S)-methyl (4-(4-((2-Boc-amino-2,4-dimethylpentyl)oxy)-3-carbonylphenyl)pyridin-2-yl)carbamate To a 2 mL vial was added (S)-tert-butyl (1-(4-bromo-2-formylphenoxy)-2,4-dimethylpentan-2-yl)carbamate (27.9 mg, 0.067 mmol), (2-((methoxycarbonyl)amino)pyridin-4-yl)boronic acid (19.79 mg, 0.101 mmol), and Na$_2$CO$_3$ (0.101 mL, 0.202 mmol) in dioxane (0.5 mL) under nitrogen to give a colorless suspension. 1,1'-Bis(diphenylphosphino)ferrocenepalladium(II) dichloride, toluene (2.77 mg, 3.37 µmol) was added under nitrogen. The vial was sealed and heated at 100° C. (bath temp: 105° C.) for 3 h. LCMS showed conversion to the desired product (M+H=486), but with some starting material left. A bit more reagents was added and heating continued for another 3 h. LCMS showed no more starting material. The mixture was diluted with EtOAc and passed through a plug of Na$_2$SO$_4$. The organic solution was concentrated. Obtained (S)-methyl (4-(4-((2-Boc-amino-2,4-dimethylpentyl)oxy)-3-carbonylphenyl)pyridin-2-yl)carbamate as a tan residue which was carried on without further purification. LCMS (ESI) m/e 486.4 [(M+H)$^+$, calcd C$_{26}$H$_{36}$N$_3$O$_6$, 486.3]; LC/MS retention time (method C): $t_R$=4.23 min.

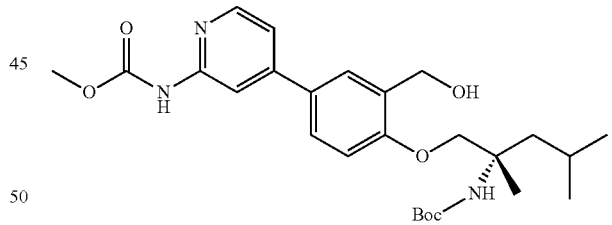

Part H: (S)-methyl (4-(4-((2-Boc-amino-2,4-dimethylpentyl)oxy)-3-(hydroxymethyl)phenyl)pyridin-2-yl)carbamate To a 2 mL vial was added crude aldehyde (10.68 mg, 0.022 mmol) in MeOH (0.5 mL) to give a tan solution. NaBH$_4$ (5 mg, 0.132 mmol) was added. The mixture was stirred at rt for 1 h. The mixture was partitioned between water and EtOAc. The layers were separated. The organic layer was washed with brine, dried (Na$_2$SO$_4$) and concentrated under reduced pressure. The tan residue was directly carried onto next reaction. LCMS (ESI) m/e 488.2 [(M+H)$^+$, calcd C$_{26}$H$_{38}$N$_3$O$_6$, 488.3]; LC/MS retention time (method B): $t_R$=2.00 min.

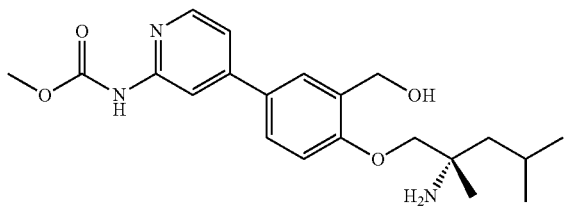 [SMILES: COC(=O)Nc1cc(-c2ccc(OC[C@@](C)(N)CC(C)C)c(CO)c2)ccn1]

Part I: (S)-methyl (4-(4-((2-amino-2,4-dimethylpentyl)oxy)-3-(hydroxymethyl)phenyl)pyridin-2-yl)carbamate To a 25 mL flask was added (S)-methyl (4-(4-((2-Boc-amino-2,4-dimethylpentyl)oxy)-3-(hydroxymethyl)phenyl)pyridin-2-yl)carbamate (10.73 mg, 0.022 mmol) in $CH_2Cl_2$ (1 mL) to give a tan solution. TFA (0.5 ml, 6.49 mmol) was added under nitrogen. The mixture was stirred at rt for 1 h. The mixture was concentrated. The residue was dissolved in MeOH, filtered, and purified by reverse phase HPLC (acetonitrile/water/10 mM ammonium acetate) to afford (S)-methyl (4-(4-((2-amino-2,4-dimethylpentyl)oxy)-3-(hydroxymethyl)phenyl)pyridin-2-yl)carbamate (7.6 mg, 0.019 mmol, 86% yield for three steps) as a colorless solid. $^1$H NMR (500 MHz, DMSO-$d_6$) δ 8.28 (d, J=5.2 Hz, 1H), 8.12 (s, 1H), 7.77 (d, J=2.4 Hz, 1H), 7.61 (dd, J=8.6, 2.4 Hz, 1H), 7.32 (d, J=5.2 Hz, 1H), 7.06 (d, J=8.5 Hz, 1H), 4.63 (s, 2H), 3.77 (s, 2H), 3.70 (s, 3H), 1.79 (td, J=11.7, 10.6, 5.5 Hz, 1H), 1.42 (qd, J=14.0, 5.6 Hz, 2H), 1.14 (s, 3H), 0.93 (t, J=7.2 Hz, 6H); LCMS (ESI) m/e 388.1 [(M+H)$^+$, calcd $C_{21}H_{30}N_3O_4$, 388.2]; LC/MS retention time (method B): $t_R$=1.55 min.

Example 33

(S)-methyl (4-(4-((2-amino-2,4-dimethylpentyl)oxy)-3-cyclopropylphenyl)pyridin-2-yl)carbamate

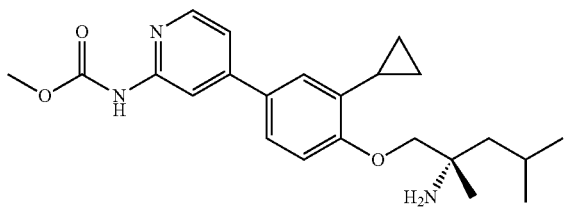 [SMILES: COC(=O)Nc1cc(-c2ccc(OC[C@@](C)(N)CC(C)C)c(C3CC3)c2)ccn1]

Prepared as described in Example 32.

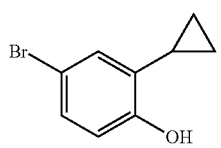 [SMILES: Oc1ccc(Br)cc1C1CC1]

Part A: (S)-tert-butyl (1-(4-bromo-2-cyclopropylphenoxy)-2,4-dimethylpentan-2-yl)carbamate To a 100 mL round-bottomed flask was added 2-cyclopropylphenol (584 mg, 4.35 mmol) in $CH_2Cl_2$ (22 mL) to give a colorless solution. $Br_2$ (0.224 mL, 4.35 mmol) was added dropwise at 0° C. The mixture was stirred at 0° C. for 1 h. The mixture was concentrated under reduced pressure to afford (S)-tert-butyl (1-(4-bromo-2-cyclopropylphenoxy)-2,4-dimethylpentan-2-yl)carbamate (992 mg, 4.35 mmol, 100% yield) as a colorless oil. $^1$H NMR (400 MHz, Chloroform-d) δ 7.24 (dd, J=8.6, 2.5 Hz, 1H), 7.20 (dd, J=2.5, 0.9 Hz, 1H), 6.76 (d, J=8.5 Hz, 1H), 5.43 (s, 1H), 1.82 (tt, J=8.3, 5.3 Hz, 1H), 1.04-0.97 (m, 2H), 0.70-0.64 (m, 2H); LC/MS retention time (method B): $t_R$=2.09 min.

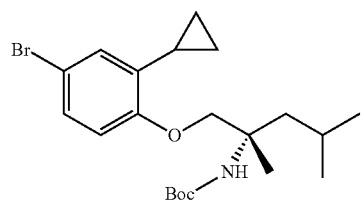 [SMILES: CC(C)C[C@@](C)(COc1ccc(Br)cc1C1CC1)NC(=O)OC(C)(C)C]

Part B: (S)-tert-butyl (1-(4-bromo-2-cyclopropylphenoxy)-2,4-dimethylpentan-2-yl)carbamate $^1$H NMR (400 MHz, Chloroform-d) δ 7.21 (dd, J=8.7, 2.5 Hz, 1H), 6.98 (d, J=2.5 Hz, 1H), 6.71 (d, J=8.7 Hz, 1H), 4.67 (s, 1H), 4.10 (d, J=9.0 Hz, 1H), 3.94 (d, J=8.8 Hz, 1H), 2.16-2.08 (m, 1H), 1.84 (ddt, J=13.0, 10.9, 6.5 Hz, 2H), 1.69-1.59 (m, 1H), 1.43 (s, 3H), 1.42 (s, 9H), 0.99 (dd, J=6.5, 3.1 Hz, 6H), 0.97-0.92 (m, 2H), 0.68-0.61 (m, 2H); LCMS (ESI) m/e 447.9 [(M+Na)$^+$, calcd $C_{21}H_{32}Br_1N_1Na_1O_3$, 448.2]; LC/MS retention time (method B): $t_R$=2.59 min.

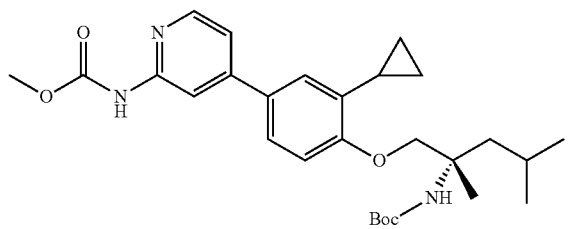 [SMILES: COC(=O)Nc1cc(-c2ccc(OC[C@](C)(CC(C)C)NC(=O)OC(C)(C)C)c(C3CC3)c2)ccn1]

Part C: (S)-methyl (4-(4-((2-Boc-amino-2,4-dimethylpentyl)oxy)-3-cyclopropylphenyl)pyridin-2-yl)carbamate LCMS (ESI) m/e 498.1 [(M+H)$^+$, calcd $C_{28}H_{40}N_3O_5$, 498.3]; LC/MS retention time (method B): $t_R$=2.24 min.

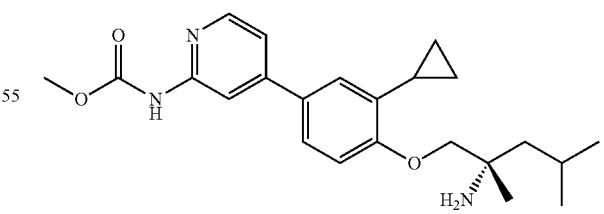

Part D: (S)-methyl (4-(4-((2-amino-2,4-dimethylpentyl)oxy)-3-cyclopropylphenyl)pyridin-2-yl)carbamate $^1$H NMR (500 MHz, DMSO-$d_6$) δ 8.25 (d, J=5.3 Hz, 1H), 8.05 (s, 1H), 7.50 (dd, J=8.5, 2.4 Hz, 1H), 7.32 (d, J=5.4 Hz, 1H), 7.19 (d, J=2.3 Hz, 1H), 7.04 (d, J=8.5 Hz, 1H), 3.81-3.73 (m, 2H), 3.70 (s, 3H), 2.20 (ddd, J=13.9, 8.8, 5.4 Hz, 1H), 1.82 (dt, J=12.8, 6.3 Hz, 1H), 1.49-1.38 (m, 2H), 1.16 (s, 3H), 0.94 (q, J=6.2 Hz, 8H), 0.72 (q, J=5.1 Hz, 2H); LCMS (ESI) m/e 398.1 [(M+H)$^+$, calcd $C_{23}H_{32}N_3O_3$, 398.2]; LC/MS retention time (method B): $t_R$=1.73 min.

Example 34

(S)—N-(4-(4-((2-amino-2,4-dimethylpentyl)oxy)-3-(trifluoromethyl)phenyl)-5-(hydroxymethyl)pyridin-2-yl)acetamide

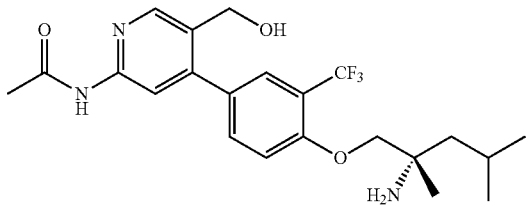 [SMILES: CC(=O)Nc1cc(-c2ccc(OC[C@@](C)(N)CC(C)C)c(C(F)(F)F)c2)c(CO)cn1]

Prepared as described in Example 19.

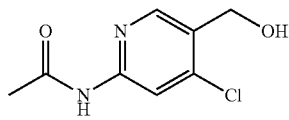

Part A: N-(4-chloro-5-(hydroxymethyl)pyridin-2-yl)acetamide

To a 25 mL vial was added (4,6-dichloropyridin-3-yl)methanol (125.8 mg, 0.707 mmol), and acetamide (62.6 mg, 1.060 mmol) in 1,4-dioxane (4 mL) to give a colorless solution. While degassing with $N_2$, PdOAc$_2$ (7.93 mg, 0.035 mmol), XANTPHOS (30.7 mg, 0.053 mmol), Cs$_2$CO$_3$ (368 mg, 1.131 mmol) were added. The vial was sealed under nitrogen and heated at 110° C. (bath: 112° C.) for 22 h (1:30 pm). The reaction mixture was cooled to rt and partitioned between water and EtOAc. There were some insoluble solids which were removed by filtration. The layers were separated. The aqueous layer was extracted 4 times with EtOAc (there were still product left in aq.). The combined organic layers were washed with brine, dried and concentrated. The residue was purified by silica gel chromatography (up to 10% MeOH/CH$_2$Cl$_2$) to afford N-(4-chloro-5-(hydroxymethyl)pyridin-2-yl)acetamide (90 mg, o.449 mmol, 64% yield) as a white solid: $^1$H NMR (400 MHz, Methanol-d$_4$) δ 8.34 (s, 1H), 8.19 (s, 1H), 4.69 (s, 2H), 2.19 (s, 3H); LCMS (ESI) m/e 201.1 [(M+H)$^+$, calcd $C_8H_{10}ClN_2O_2$, 201.1]; LC/MS retention time (method B): $t_R$=1.73 min.

Part B: (2-acetamido-5-(hydroxymethyl)pyridin-4-yl)boronic acid

To a 20 mL vial was added N-(4-chloro-5-(hydroxymethyl)pyridin-2-yl)acetamide (48 mg, 0.239 mmol), hypodiboric acid (32.2 mg, 0.359 mmol), 2-(dicyclohexylphosphino)-2',4',6'-triisopropylbiphenyl (2.281 mg, 4.79 μmol), Xphos precatalyst (1.882 mg, 2.393 μmol) and potassium acetate (70.4 mg, 0.718 mmol) in ethanol (2.2 mL) to give a tan suspension (degassed with N$_2$ before adding reagents). The bottle was capped and heated at 80° C. for 1.5 h. The mixture was cooled to rt and concentrated under reduced pressure. The crude material was carried on without purification.

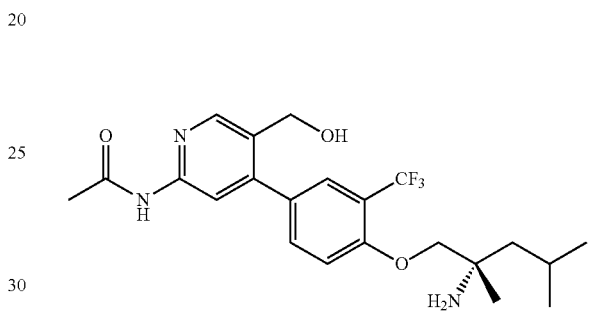

Part C: (S)—N-(4-(4-((2-amino-2,4-dimethylpentyl)oxy)-3-(trifluoromethyl)phenyl)-5-(hydroxymethyl)pyridin-2-yl)acetamide To a 20 mL vial was added (2-acetamido-5-(hydroxymethyl)pyridin-4-yl)boronic acid (50.2 mg, 0.239 mmol) was added potassium phosphate tribasic (2 mL, 1.000 mmol). After degassing with N$_2$ for 5 min, Xphos precatalyst (3.76 mg, 4.78 μmol) and (S)-1-(4-bromo-2-(trifluoromethyl)phenoxy)-2,4-dimethylpentan-2-amine (30 mg, 0.076 mmol) (prepared as described in Example 19. Part A) in tetrahydrofuran (2 mL) were added. The vial was sealed and heated at 80° C. for 18 h. The reaction mixture was cooled to rt and the volatiles were removed under reduced pressure. The residue was partitioned between water and EtOAc. The organic layer was dried, filtered and concentrated. The residue was dissolved in MeOH and purified by reverse phase HPLC (acetonitrile/water/10 mM ammonium acetate) to afford (S)—N-(4-(4-((2-amino-2,4-dimethylpentyl)oxy)-3-(trifluoromethyl)phenyl)-5-(hydroxymethyl)pyridin-2-yl)acetamide (27.7 mg, 0.060 mmol, 79% yield) as an off-white solid. $^1$H NMR (600 MHz, DMSO-d$_6$) δ 10.57 (s, 1H), 8.38 (s, 1H), 8.02 (s, 1H), 7.80 (s, 1H), 7.78-7.71 (m, 1H), 7.35 (d, J=8.6 Hz, 1H), 4.36 (s, 2H), 3.86 (q, J=8.8 Hz, 2H), 2.10 (s, 3H), 1.81 (dt, J=12.6, 6.1 Hz, 1H), 1.45-1.37 (m, 2H), 1.13 (s, 3H), 0.92 (dd, J=6.6, 3.4 Hz, 6H); LCMS (ESI) m/e 440.2 [(M+H)$^+$, calcd $C_{22}H_{29}F_3N_3O_3$, 440.2]; LC/MS retention time (method B): $t_R$=1.67 min.

Example 35

(S)-1-(4-(2-(difluoromethyl)pyridin-4-yl)-2-(trifluoromethyl)phenoxy)-2,4-dimethylpentan-2-amine

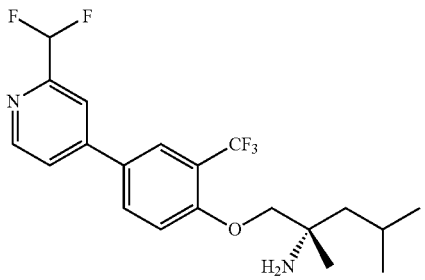 [SMILES: CC(C)C[C@](C)(N)COc1ccc(-c2ccnc(C(F)F)c2)cc1C#N]

Prepared as described in Example 19. Obtained (S)-1-(4-(2-(difluoromethyl)pyridin-4-yl)-2-(trifluoromethyl)phenoxy)-2,4-dimethylpentan-2-amine (25.5 mg, 0.062 mmol, 54% yield) as an off-white solid. $^1$H NMR (600 MHz, DMSO-$d_6$) δ 8.74 (d, J=5.1 Hz, 1H), 8.19 (d, J=8.8 Hz, 1H), 8.11 (s, 1H), 8.06 (s, 1H), 7.96 (d, J=5.1 Hz, 1H), 7.44 (d, J=8.7 Hz, 1H), 7.01 (t, J=54.9 Hz, 1H), 4.05 (q, J=9.6 Hz, 2H), 1.81 (dt, J=12.9, 6.6 Hz, 1H), 1.61-1.47 (m, 2H), 1.25 (s, 3H), 0.92 (t, J=6.9 Hz, 6H); LCMS (ESI) m/e 403.4 [(M+H)$^+$, calcd $C_2H_{24}F_5N_2O_1$, 403.2]; LC/MS retention time (method A): $t_R$=2.13 min.

Example 36

(S)-2-((2-amino-2,4-dimethylpentyl)oxy)-5-(2-(difluoromethyl)pyridin-4-yl)benzonitrile

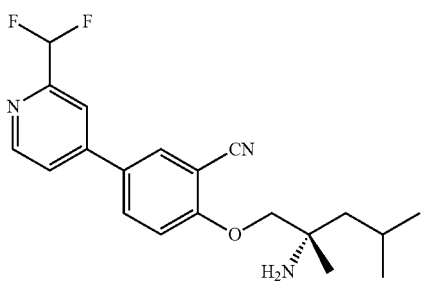

Prepared as described in Example 19. Obtained (S)-2-((2-amino-2,4-dimethylpentyl)oxy)-5-(2-(difluoromethyl)pyridin-4-yl)benzonitrile (32 mg, 0.086 mmol, 60% yield) as an off-white solid. $^1$H NMR (500 MHz, DMSO-$d_6$) δ 8.48 (d, J=5.2 Hz, 1H), 8.11 (d, J=2.5 Hz, 1H), 7.95 (dd, J=9.0, 2.4 Hz, 1H), 7.80 (s, 1H), 7.69 (d, J=5.2 Hz, 1H), 7.14 (d, J=8.9 Hz, 1H), 6.73 (t, J=54.8 Hz, 1H), 3.80-3.68 (m, 2H), 1.56 (dp, J=12.5, 6.4 Hz, 1H), 1.23 (qd, J=14.0, 5.5 Hz, 2H), 0.95 (s, 3H), 0.68 (dd, J=6.7, 4.7 Hz, 6H); $^{19}$F NMR (376 MHz, DMSO-d6) δ -115.30 (d, J=54.0 Hz); LCMS (ESI) m/e 360.2 [(M+H)$^+$, calcd $C_{20}H_{24}F_2N_3O_1$, 360.2]; LC/MS retention time (method B): $t_R$=1.69 min.

Example 37

(S)-1-(2-(difluoromethyl)-4-(2-(difluoromethyl)pyridin-4-yl)phenoxy)-2,4-dimethylpentan-2-amine

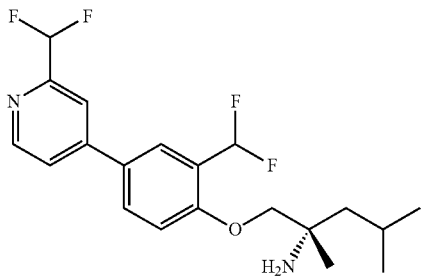 [SMILES: CC(C)C[C@](C)(N)COc1ccc(-c2ccnc(C(F)F)c2)cc1C(F)F]

Prepared as described in Example 19. Obtained (S)-1-(2-(difluoromethyl)-4-(2-(difluoromethyl)pyridin-4-yl)phenoxy)-2,4-dimethylpentan-2-amine (31.9 mg, 0.080 mmol, 61% yield) as an off-white solid. $^1$H NMR (500 MHz, DMSO-$d_6$) δ 8.48 (d, J=5.1 Hz, 1H), 7.81 (dd, J=8.9, 2.4 Hz, 1H), 7.76 (d, J=3.6 Hz, 2H), 7.67 (d, J=5.1 Hz, 1H), 7.22-6.94 (m, 2H), 6.76 (t, J=54.9 Hz, 1H), 3.68 (d, J=2.2 Hz, 2H), 1.54 (dp, J=12.7, 6.3 Hz, 1H), 1.30-1.13 (m, 2H), 0.95 (s, 3H), 0.67 (dd, J=15.9, 6.6 Hz, 6H); $^{19}$F NMR (376 MHz, DMSO-d6) δ -73.65, -115.33; LCMS (ESI) m/e 407.2 [(M+Na)$^+$, calcd $C_{20}H_{24}F_4N_2Na_1O_1$, 407.2]; LC/MS retention time (method B): $t_R$=1.89 min.

Example 38

(S)-1-(4-(2-(difluoromethyl)pyridin-4-yl)-2-(trifluoromethoxy)phenoxy)-2,4-dimethylpentan-2-amine

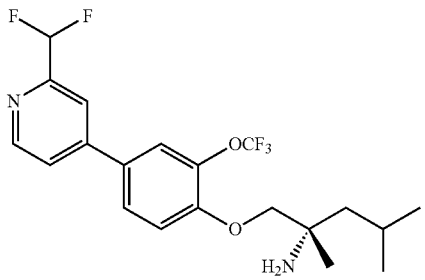 [SMILES: CC(C)C[C@](C)(N)COc1ccc(-c2ccnc(C(F)F)c2)cc1OC(F)(F)F]

Prepared as described in Example 19. Obtained (S)-1-(4-(2-(difluoromethyl)pyridin-4-yl)-2-(trifluoromethoxy)phenoxy)-2,4-dimethylpentan-2-amine (21.1 mg, 0.050 mmol, 39% yield) as an off-white solid. $^1$H NMR (500 MHz, DMSO-$d_6$) δ 8.55 (d, J=5.2 Hz, 1H), 7.85 (s, 1H), 7.78 (dd, J=13.4, 5.4 Hz, 3H), 7.22 (d, J=8.6 Hz, 1H), 6.83 (t, J=54.9 Hz, 1H), 3.71 (d, J=3.6 Hz, 2H), 1.64 (dt, J=12.7, 6.3 Hz, 1H), 1.26 (dq, J=14.8, 8.3, 6.9 Hz, 2H), 0.98 (s, 3H), 0.75 (t, J=5.9 Hz, 6H); LCMS (ESI) m/e 419.3 [(M+H)$^+$, calcd $C_{20}H_{24}F_5N_2O_2$, 419.2]; LC/MS retention time (method B): $t_R$=2.03 min.

Example 39

(S)-1-(4-(3-chloro-2-fluoropyridin-4-yl)-2-(trifluoromethyl)phenoxy)-2,4-dimethylpentan-2-amine

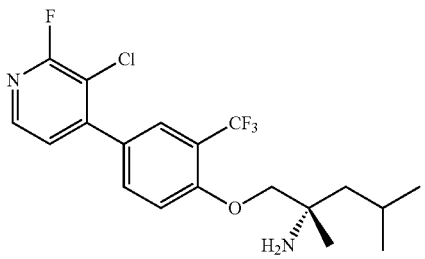 [SMILES: CC(C)C[C@](C)(N)COc1ccc(-c2ccnc(F)c2Cl)cc1C(F)(F)F]

Prepared as described in Example 19. Obtained (S)-1-(4-(3-chloro-2-fluoropyridin-4-yl)-2-(trifluoromethyl)phenoxy)-2,4-dimethylpentan-2-amine (14 mg, 0.035 mmol, 42% yield) as an off-white solid. $^1$H NMR (500 MHz, DMSO-$d_6$) δ 8.25 (d, J=5.1 Hz, 1H), 7.88-7.79 (m, 2H), 7.53 (d, J=5.1 Hz, 1H), 7.40 (d, J=8.5 Hz, 1H), 3.87 (q, J=8.9 Hz, 2H), 1.80 (hept, J=6.5 Hz, 1H), 1.39 (d, J=5.6 Hz, 2H), 1.12 (s, 3H), 0.92 (dd, J=6.7, 2.4 Hz, 6H); $^{19}$F NMR (376 MHz, DMSO-$d_6$) δ −61.18, −71.35; LCMS (ESI) m/e 405.1 [(M+H)$^+$, calcd $C_{19}H_{22}Cl_1F_4N_2O_1$, 405.1]; LC/MS retention time (method B): $t_R$=2.04 min.

Example 40

(S)-1-(4-(5-chloro-2-fluoropyridin-4-yl)-2-(trifluoromethyl)phenoxy)-2,4-dimethylpentan-2-amine

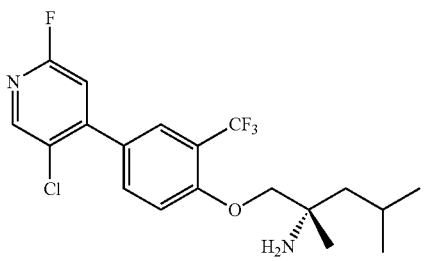 [SMILES: CC(C)C[C@](C)(N)COc1ccc(-c2cc(F)ncc2Cl)cc1C(F)(F)F]

Prepared as described in Example 19. Obtained (S)-1-(4-(5-chloro-2-fluoropyridin-4-yl)-2-(trifluoromethyl)phenoxy)-2,4-dimethylpentan-2-amine (15.2 mg, 0.037 mmol, 43% yield) as an off-white solid. $^1$H NMR (500 MHz, DMSO-$d_6$) δ 8.45 (s, 1H), 7.88-7.80 (m, 2H), 7.46 (d, J=1.9 Hz, 1H), 7.39 (d, J=8.5 Hz, 1H), 3.93-3.82 (m, 2H), 1.80 (dp, J=12.8, 6.5 Hz, 1H), 1.40 (d, J=5.5 Hz, 2H), 1.13 (s, 3H), 0.92 (dd, J=6.6, 2.5 Hz, 6H); $^{19}$F NMR (376 MHz, DMSO-d6) δ −61.16, −71.37; LCMS (ESI) m/e 405.1 [(M+H)$^+$, calcd $C_{19}H_{22}Cl_1F_4N_2O_1$, 405.1]; LC/MS retention time (method B): $t_R$=2.04 min.

Example 41

(S)-1-(4-(2-fluoro-3-methylpyridin-4-yl)-2-(trifluoromethyl)phenoxy)-2,4-dimethylpentan-2-amine

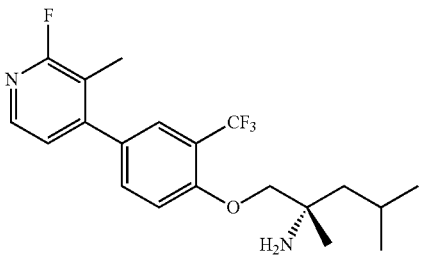 [SMILES: Cc1c(-c2ccc(OC[C@@](C)(N)CC(C)C)c(C(F)(F)F)c2)ccnc1F]

Prepared as described in Example 19. Obtained (S)-1-(4-(2-fluoro-3-methylpyridin-4-yl)-2-(trifluoromethyl)phenoxy)-2,4-dimethylpentan-2-amine (14.1 mg, 0.036 mmol, 42% yield) as an off-white solid. $^1$H NMR (500 MHz, DMSO-$d_6$) δ 8.10 (d, J=5.1 Hz, 1H), 7.72 (dd, J=8.6, 2.3 Hz, 1H), 7.67 (d, J=2.2 Hz, 1H), 7.36 (d, J=8.6 Hz, 1H), 7.29 (d, J=5.1 Hz, 1H), 3.87 (q, J=8.8 Hz, 2H), 2.17 (s, 3H), 1.81 (dp, J=12.7, 6.4 Hz, 1H), 1.46-1.35 (m, 2H), 1.13 (s, 3H), 0.92 (dd, J=6.7, 2.8 Hz, 6H); $^{19}$F NMR (376 MHz, DMSO-d6) δ −61.03, −71.80; LCMS (ESI) m/e 385.2 [(M+H)$^+$, calcd $C_2H_{25}F_4N_2O_1$, 385.2]; LC/MS retention time (method B): $t_R$=1.99 min.

Example 42

(S)-1-(4-(2,3-difluoropyridin-4-yl)-2-(trifluoromethyl)phenoxy)-2,4-dimethylpentan-2-amine

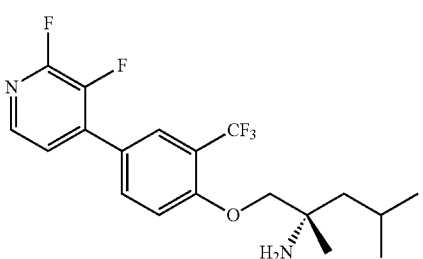

Prepared as described in Example 19. Obtained (S)-1-(4-(2,3-difluoropyridin-4-yl)-2-(trifluoromethyl)phenoxy)-2,4-dimethylpentan-2-amine (7 mg, 0.018 mmol, 21% yield) as an off-white solid. $^1$H NMR (500 MHz, DMSO-$d_6$) δ 8.10 (d, J=5.1 Hz, 1H), 7.99 (d, J=8.7 Hz, 1H), 7.95 (d, J=2.3 Hz, 1H), 7.66 (t, J=5.1 Hz, 1H), 7.43 (d, J=8.8 Hz, 1H), 3.90 (q, J=8.8 Hz, 2H), 1.79 (dq, J=12.8, 6.4 Hz, 1H), 1.40 (d, J=5.5 Hz, 2H), 1.13 (s, 3H), 0.92 (dd, J=6.6, 2.2 Hz, 6H); $^{19}$F NMR (376 MHz, DMSO-d6) δ −61.23, −89.72, −89.79; LCMS (ESI) m/e 389.2 [(M+H)$^+$, calcd $C_{19}H_{22}F_5N_2O_1$, 389.2]; LC/MS retention time (method B): $t_R$=2.01 min.

Example 43

(S)-2,4-dimethyl-1-(4-(pyridin-4-yl)-2-(trifluoromethyl)phenoxy)pentan-2-amine

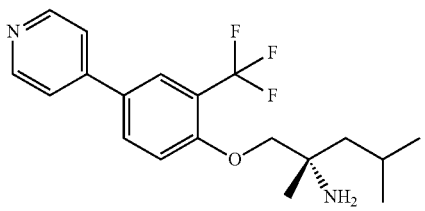 [SMILES: CC(C)C[C@](C)(N)COc1ccc(-c2ccncc2)cc1C(F)(F)F]

Prepared as described in Example 19. A mixture of sodium carbonate (0.068 mL, 0.136 mmol), 1,1'-bis(diphenylphosphino)ferrocene-palladium(II) dichloride dichloromethane complex (3.89 mg, 4.76 µmol), pyridin-4-ylboronic acid (8.36 mg, 0.068 mmol) and (S)-1-(4-bromo-2-(trifluoromethyl)phenoxy)-2,4-dimethylpentan-2-amine (0.0241 g, 0.068 mmol) in dioxane (0.5 mL) (degassed with $N_2$) was heated at 80° C. overnight. The reaction mixture was cooled to rt and diluted with ethyl acetate then washed with water (3×). The ethyl acetate layer was dried ($Na_2SO_4$), filtered and concentrated under reduced pressure. The residue was purified by reverse phase HPLC (acetonitrile/water/10 mM ammonium acetate). Obtained (S)-2,4-dimethyl-1-(4-(pyridin-4-yl)-2-(trifluoromethyl)phenoxy)pentan-2-amine (89 mg, 0.088 mmol, 46% yield) as an off-white solid. $^1$H NMR (500 MHz, DMSO-$d_6$) δ 8.62 (d, J=5.9 Hz, 2H), 8.09 (d, J=9.2 Hz, 1H), 8.01 (s, 1H), 7.75 (d, J=5.5 Hz, 2H), 7.37 (d, J=8.8 Hz, 1H), 3.87 (d, J=7.0 Hz, 2H), 1.84-1.74 (m, 1H), 1.39 (d, J=5.5 Hz, 2H), 1.12 (s, 3H), 0.91 (d, J=6.6 Hz, 6H) LCMS (ESI) m/e 353.2 [(M+H)$^+$, calcd $C_{19}H_{24}F_3N_2O$, 353.2]; LC/MS retention time (method B): $t_R$=1.48 min.

Example 44

(S)-1-(4-(2-fluoropyridin-4-yl)-2-(trifluoromethyl)phenoxy)-2,4-dimethylpentan-2-amine

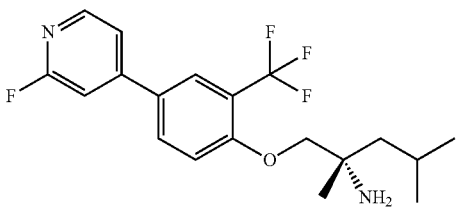 [SMILES: CC(C)C[C@](C)(N)COc1ccc(-c2ccnc(F)c2)cc1C(F)(F)F]

Prepared as described in Example 43. Obtained (S)-1-(4-(2-fluoropyridin-4-yl)-2-(trifluoromethyl)phenoxy)-2,4-dimethylpentan-2-amine (9.3 mg, 0.025 mmol, 36% yield) as an off-white solid. $^1$H NMR (400 MHz, METHANOL-$d_4$) δ 8.27 (d, J=5.4 Hz, 1H), 8.10-8.04 (m, 2H), 7.63 (d, J=5.4 Hz, 1H), 7.45-7.39 (m, 2H), 4.19 (d, J=3.2 Hz, 2H), 1.94 (s, 3H), 1.77 (d, J=5.6 Hz, 2H), 1.71-1.63 (m, 1H), 1.45 (s, 2H), 1.04 (d, J=6.6 Hz, 3H), 1.02 (d, J=6.6 Hz, 3H); LCMS (ESI) m/e 371.2 [(M+H)$^+$, calcd $C_{19}H_{23}F_4N_2O$, 371.2]; LC/MS retention time (method B): $t_R$=1.95 min.

Example 45

(S)-2,4-dimethyl-1-(4-(2-methylpyridin-4-yl)-2-(trifluoromethyl)phenoxy)pentan-2-amine

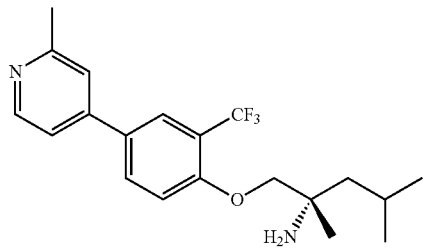 [SMILES: Cc1cc(-c2ccc(OC[C@@](C)(N)CC(C)C)c(C(F)(F)F)c2)ccn1]

Prepared as described in Example 19. Obtained (S)-2,4-dimethyl-1-(4-(2-methylpyridin-4-yl)-2-(trifluoromethyl)phenoxy)pentan-2-amine (16 mg, 0.044 mmol, 50% yield) as an off-white solid. $^1$H NMR (500 MHz, DMSO-$d_6$) δ 8.68 (d, J=5.8 Hz, 1H), 8.26 (dd, J=8.8, 2.6 Hz, 1H), 8.19-8.18 (m, 1H), 8.04 (s, 1H), 7.94 (d, J=5.9 Hz, 1H), 7.51 (d, J=8.8 Hz, 1H), 4.26 (q, J=10.1 Hz, 2H), 2.66 (s, 3H), 1.83 (dq, J=13.0, 6.5 Hz, 1H), 1.74 (dd, J=14.3, 5.5 Hz, 1H), 1.62 (dd, J=14.6, 5.8 Hz, 1H), 1.40 (s, 3H), 0.93 (dd, J=8.6, 6.4 Hz, 6H); 19F NMR (376 MHz, DMSO-d6) δ −60.51, −73.76 (TFA); LCMS (ESI) m/e 367.2 [(M+H)$^+$, calcd $C_{20}H_{26}F_3N_2O_1$, 367.2]; LC/MS retention time (method B): $t_R$=1.51 min.

Example 46

(S)-1-(4-(3-methoxypyridin-4-yl)-2-(trifluoromethyl)phenoxy)-2,4-dimethylpentan-2-amine

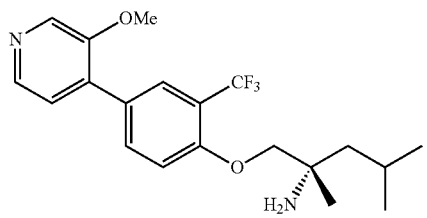 [SMILES: COc1cnccc1-c1ccc(OC[C@@](C)(N)CC(C)C)c(C(F)(F)F)c1]

Prepared as described in Example 19. Obtained (S)-1-(4-(3-methoxypyridin-4-yl)-2-(trifluoromethyl)phenoxy)-2,4-dimethylpentan-2-amine (8.5 mg, 0.021 mmol, 24% yield) as an off-white solid. $^1$H NMR (500 MHz, DMSO-$d_6$) δ 8.47 (s, 1H), 8.28 (d, J=4.8 Hz, 1H), 7.85 (d, J=9.0 Hz, 1H), 7.82 (d, J=2.3 Hz, 1H), 7.41 (d, J=4.8 Hz, 1H), 7.32 (d, J=8.6 Hz, 1H), 3.91 (s, 3H), 3.86 (q, J=8.9 Hz, 2H), 1.80 (hept, J=6.4 Hz, 1H), 1.40 (d, J=5.5 Hz, 2H), 1.13 (s, 3H), 0.92 (dd, J=6.8, 2.5 Hz, 6H); $^{19}$F NMR (376 MHz, DMSO-$d_6$) δ −61.00; LCMS (ESI) m/e 383.2 [(M+H)$^+$, calcd $C_{20}H_{26}F_3N_2O_2$, 383.2]; LC/MS retention time (method B): $t_R$=1.58 min.

Example 47

(S)-1-(4-(3-fluoropyridin-4-yl)-2-(trifluoromethyl)phenoxy)-2,4-dimethylpentan-2-amine

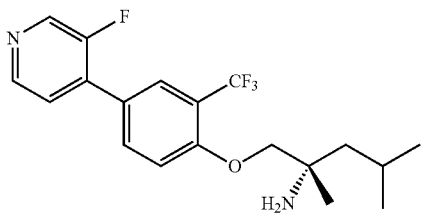 [SMILES: CC(C)C[C@](C)(N)COc1ccc(-c2ccncc2F)cc1C(F)(F)F]

Prepared as described in Example 19. Obtained (S)-1-(4-(3-fluoropyridin-4-yl)-2-(trifluoromethyl)phenoxy)-2,4-dimethylpentan-2-amin (8.9 mg, 0.023 mmol, 25% yield) as an off-white solid. $^1$H NMR (500 MHz, DMSO-d$_6$) δ 8.66 (d, J=2.6 Hz, 1H), 8.51 (d, J=4.9 Hz, 1H), 7.96 (d, J=8.8 Hz, 1H), 7.91 (d, J=2.3 Hz, 1H), 7.70 (dd, J=7.1, 4.9 Hz, 1H), 7.41 (d, J=8.7 Hz, 1H), 3.89 (q, J=8.9 Hz, 2H), 1.80 (dp, J=12.7, 6.4 Hz, 1H), 1.40 (d, J=5.5 Hz, 2H), 1.13 (s, 3H), 0.92 (dd, J=6.6, 2.3 Hz, 6H); $^{19}$F NMR (376 MHz, DMSO-d6) δ −61.17, −133.88; LCMS (ESI) m/e 371.2 [(M+H)$^+$, calcd C$_{19}$H$_{23}$F$_4$N$_2$O$_1$, 371.2]; LC/MS retention time (method B): t$_R$=1.88 min.

Example 48

(S)-2-((2-amino-2,4-dimethylpentyl)oxy)-5-(2-methylpyridin-4-yl)benzonitrile

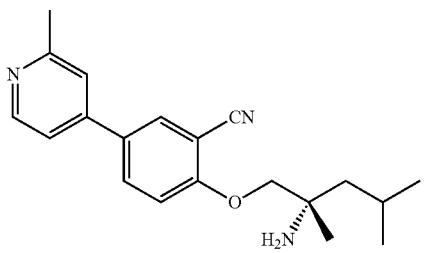 [SMILES: Cc1cc(-c2ccc(OC[C@@](C)(N)CC(C)C)c(C#N)c2)ccn1]

Prepared as described in Example 19. Obtained (S)-2-((2-amino-2,4-dimethylpentyl)oxy)-5-(2-methylpyridin-4-yl)benzonitrile (39.4 mg, 0.116 mmol, 80% yield) as an off-white solid. $^1$H NMR (500 MHz, DMSO-d$_6$) δ 8.49 (d, J=5.2 Hz, 1H), 8.23 (d, J=2.4 Hz, 1H), 8.11 (dd, J=8.9, 2.4 Hz, 1H), 7.64 (s, 1H), 7.54 (dd, J=5.3, 1.9 Hz, 1H), 7.36 (d, J=8.9 Hz, 1H), 3.98-3.87 (m, 2H), 3.58 (s, 2H), 2.52 (s, 3H), 1.82 (dt, J=12.8, 6.4 Hz, 1H), 1.50-1.37 (m, 2H), 1.16 (s, 3H), 0.93 (dd, J=6.6, 3.9 Hz, 6H); LCMS (ESI) m/e 324.1 [(M+H)$^+$, calcd C$_{20}$H$_{26}$N$_3$O$_1$, 324.2]; LC/MS retention time (method B): t$_R$=1.46 min.

Example 49

(S)-1-(2-cyclopropyl-4-(2-methylpyridin-4-yl)phenoxy)-2,4-dimethylpentan-2-amine

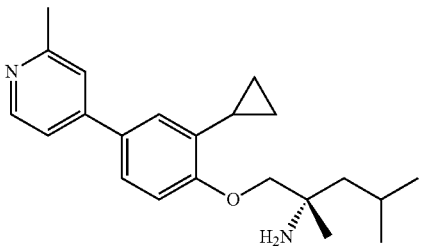 [SMILES: Cc1cc(-c2ccc(OC[C@@](C)(N)CC(C)C)c(C3CC3)c2)ccn1]

Prepared as described in Example 19. Obtained (S)-1-(2-cyclopropyl-4-(2-methylpyridin-4-yl)phenoxy)-2,4-dimethylpentan-2-amine (13.8 mg, 0.040 mmol, 41% yield) as an off-white solid. $^1$H NMR (500 MHz, DMSO-d$_6$) δ 8.42 (d, J=5.3 Hz, 1H), 7.56 (dd, J=8.4, 2.3 Hz, 1H), 7.53 (s, 1H), 7.44 (d, J=5.3 Hz, 1H), 7.25 (d, J=2.3 Hz, 1H), 7.02 (d, J=8.5 Hz, 1H), 3.77 (d, J=2.2 Hz, 2H), 2.22 (ddd, J=13.9, 8.4, 5.3 Hz, 1H), 1.82 (dq, J=12.7, 6.4 Hz, 1H), 1.52-1.39 (m, 2H), 1.17 (s, 3H), 0.93 (t, J=6.5 Hz, 8H), 0.77 (q, J=4.3, 3.5 Hz, 2H). (2-Py-Me was likely buried in DMSO peak of 2.51); LCMS (ESI) m/e 339.1 [(M+H)$^+$, calcd C$_{22}$H$_{31}$N$_2$O$_1$, 339.2]; LC/MS retention time (method B): t$_R$=1.56 min.

Example 50

(S)-1-(2-(difluoromethyl)-4-(2-methylpyridin-4-yl)phenoxy)-2,4-dimethylpentan-2-amine

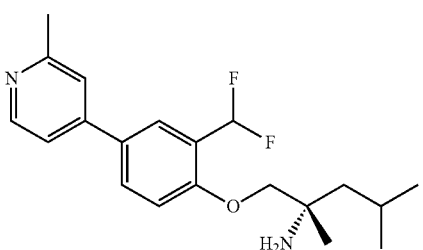

Prepared as described in Example 19. Obtained (S)-1-(2-(difluoromethyl)-4-(2-methylpyridin-4-yl)phenoxy)-2,4-dimethylpentan-2-amine (22 mg, 0.061 mmol, 69% yield) as an off-white solid. $^1$H NMR (500 MHz, DMSO-d$_6$) δ 8.48 (d, J=5.3 Hz, 1H), 7.96 (d, J=8.9 Hz, 1H), 7.92 (d, J=2.4 Hz, 1H), 7.60 (s, 1H), 7.54-7.47 (m, 1H), 7.43-7.16 (m, 2H), 3.87 (s, 2H), 2.53 (s, 3H), 1.80 (dt, J=12.8, 6.4 Hz, 1H), 1.43 (qd, J=14.1, 5.7 Hz, 2H), 1.16 (s, 3H), 0.94 (d, J=6.6 Hz, 3H), 0.91 (d, J=6.7 Hz, 3H); LCMS (ESI) m/e 349.0 [(M+H)$^+$, calcd C$_{20}$H$_{27}$F$_2$N$_2$O$_1$, 349.2]; LC/MS retention time (method B): t$_R$=1.47 min.

Example 51 methyl (6-((2-amino-2,4-dimethylpentyl)oxy)-[3,4'-bipyridin]-2'-yl)carbamate

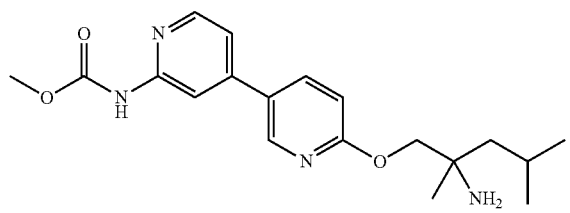 [SMILES: COC(=O)Nc1cc(-c2ccc(OCC(C)(N)CC(C)C)nc2)ccn1]

Prepared as described in Example 29.

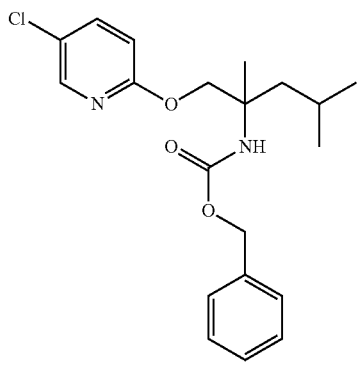 [SMILES: CC(C)CC(C)(COc1ccc(Cl)cn1)NC(=O)OCc1ccccc1]

Part A: Benzyl (1-((5-chloropyridin-2-yl)oxy)-2,4-dimethylpentan-2-yl)carbamate An NMP (0.3 mL) suspension of 5-chloropyridin-2-ol (0.023 g, 0.180 mmol), sodium carbonate (0.019 g, 0.180 mmol) and benzyl 4-isobutyl-4-methyl-1,2,3-oxathiazolidine-3-carboxylate 2,2-dioxide (0.0392 g, 0.120 mmol) was heated to 80° C. overnight. The reaction mixture was cooled to rt and diluted with ethyl acetate and washed with water (3×). The ethyl acetate layer was separated, dried ($Na_2SO_4$), filtered and concentrated under reduced pressure. The residue was purified via silica gel chromatography (0-30% ethyl acetate in hexanes) to afford benzyl (1-((5-chloropyridin-2-yl)oxy)-2,4-dimethylpentan-2-yl)carbamate (0.0387 g, 0.103 mmol, 86% yield) as an off-white solid. $^1$H NMR (400 MHz, CHLOROFORM-d) δ 8.08 (d, J=2.3 Hz, 1H), 7.54 (dd, J=8.8, 2.8 Hz, 1H), 7.37-7.32 (m, 5H), 6.71 (d, J=8.8 Hz, 1H), 5.06 (s, 3H), 4.42 (d, J=10.5 Hz, 1H), 4.26 (d, J=10.8 Hz, 1H), 1.87-1.74 (m, 2H), 1.72-1.63 (m, 1H), 1.43 (s, 3H), 0.96 (dd, J=6.3, 4.8 Hz, 6H); LCMS (ESI) m/e 377.3 [(M+H)$^+$, calcd $C_{20}H_{26}ClN_2O_3$, 377.2]; LC/MS retention time (method A): $t_R$=2.42 min.

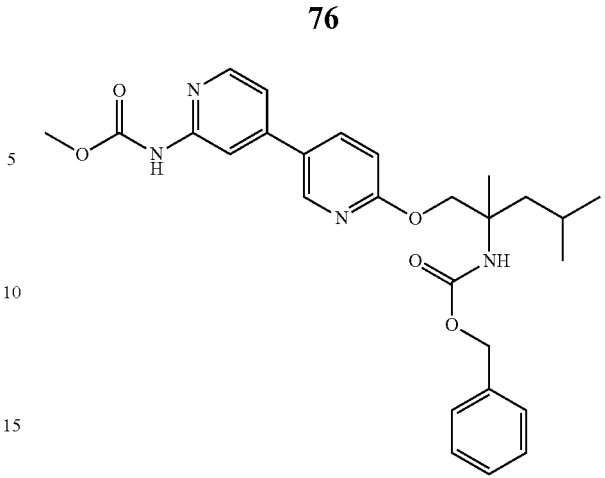

Part B: Cbz methyl (6-((2-amino-2,4-dimethylpentyl)oxy)-[3,4'-bipyridin]-2'-yl)carbamate A mixture of 2$^{nd}$ generation XPHOS precatalyst (1.587 mg, 2.017 μmol), potassium phosphate tribasic (0.403 mL, 0.202 mmol), (2-((methoxycarbonyl)amino)pyridin-4-yl) boronic acid (0.020 g, 0.101 mmol) and benzyl (1-((5-chloropyridin-2-yl)oxy)-2,4-dimethylpentan-2-yl)carbamate (0.038 g, 0.101 mmol) in THF (0.2 mL) was degassed via vacuum/$N_2$ fill cycle three times. The reaction mixture was heated at 70° C. overnight. The reaction was cooled to rt and diluted with ethyl acetate and washed with water (2×) followed by brine. The ethyl acetate layer was separated, dried ($Na_2SO_4$), filtered and concentrated. The product was purified silica gel chromatography (50-100% ethyl acetate in hexanes) to afford Cbz methyl (6-((2-amino-2,4-dimethylpentyl)oxy)-[3,4'-bipyridin]-2'-yl)carbamate (0.011. g, 0.022 mmol, 22% yield) as a white solid. LCMS (ESI) m/e 493.3 [(M+H)$^+$, calcd $C_{27}H_{33}N_4O_5$, 493.3]; LC/MS retention time (method B): $t_R$=2.13 min.

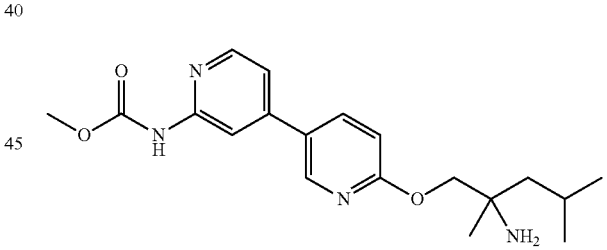

Part C: methyl (6-((2-amino-2,4-dimethylpentyl)oxy)-[3,4'-bipyridin]-2'-yl)carbamate A mixture of Pd/C (5 mg, 4.70 μmol) and Cbz methyl (6-((2-amino-2,4-dimethylpentyl)oxy)-[3,4'-bipyridin]-2'-yl)carbamate (0.011 g, 0.022 mmol) in ethanol (4 mL) was hydrogenated with a $H_2$ balloon at room temperature overnight. The reaction was filtered and washed with DCM. The filtrate was concentrated under reduced pressure and the residue was purified via reverse phase HPLC (acetonitrile/water/10 mM ammonium acetate) to afford methyl (6-((2-amino-2,4-dimethylpentyl)oxy)-[3,4'-bipyridin]-2'-yl)carbamate (6.6 mg, 0.018 mmol, 82% yield) as an off-white solid. $^1$H NMR (600 MHz, DMSO-d$_6$) δ 8.53 (s, 1H), 8.32 (d, J=5.1 Hz, 1H), 8.08 (s, 1H), 8.06 (dd, J=8.6, 2.0 Hz, 1H), 7.38 (d, J=5.1 Hz, 1H), 7.00 (d, J=8.4 Hz, 1H), 4.14-4.00 (m, 2H), 3.70 (s, 3H), 1.89 (s, 3H), 1.80 (dt, J=12.7, 6.1 Hz, 1H), 1.47-1.33 (m, 2H), 0.93 (d, J=6.6 Hz, 3H), 0.91 (d, J=6.6 Hz, 3H); LCMS (ESI) m/e 359.3 [(M+H)+, calcd $C_{19}H_{27}N_4O_3$, 359.2]; LC/MS retention time (method B): $t_R$=1.55 min.

Example 52

(S)-methyl(6-((2-amino-2,4-dimethylpentyl)oxy)-5-methyl-[3,4'-bipyridin]-2'-yl)carbamate

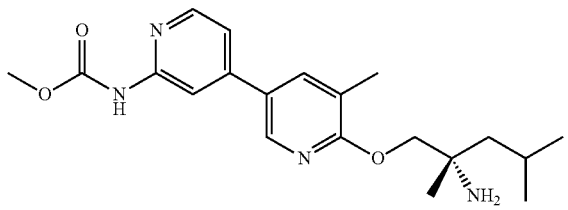 [SMILES: COC(=O)Nc1cc(-c2cnc(OC[C@@](C)(N)CC(C)C)c(C)c2)ccn1]

PREPARED as in Example 51.

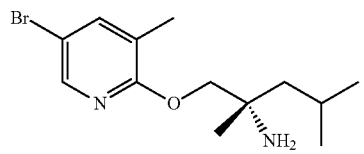 [SMILES: Cc1cc(Br)cnc1OC[C@@](C)(N)CC(C)C]

Part A: (S)-1-((5-bromo-3-methylpyridin-2-yl)oxy)-2,4-dimethylpentan-2-amine

LCMS (ESI) m/e 323.1 [(M+Na)+, calcd $C_{13}H_{21}BrN_2ONa$, 323.1]; LC/MS retention time (method B): $t_R$=1.96 min.

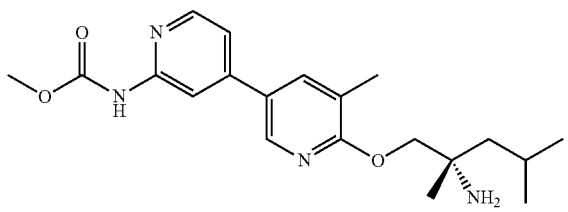 [SMILES: COC(=O)Nc1cc(-c2cnc(OC[C@@](C)(N)CC(C)C)c(C)c2)ccn1]

Part B: (S)-methyl (6-((2-amino-2,4-dimethylpentyl)oxy)-5-methyl-[3,4'-bipyridin]-2'-yl)carbamate A mixture of sodium carbonate (0.149 mL, 0.299 mmol), 1,1'-bis(diphenylphosphino)ferrocene-palladium(II) dichloride dichloromethane complex (6.10 mg, 7.47 μmol), (S)-1-((5-bromo-3-methylpyridin-2-yl)oxy)-2,4-dimethylpentan-2-amine (0.045 g, 0.149 mmol) and (2-((methoxycarbonyl)amino)pyridin-4-yl)boronic acid (0.029 g, 0.149 mmol) in dioxane (0.5 mL) (degassed with $N_2$) was heated at 80° C. for 5 h. The reaction was diluted with ethyl acetate and washed with water (3×). The ethyl acetate layer was dried ($Na_2SO_4$), filtered and concentrated under reduced pressure. The residue was purified by reverse phase HPLC (acetonitrile/water/10 mM ammonium acetate to afford (S)-methyl (6-((2-amino-2,4-dimethylpentyl)oxy)-5-methyl-[3,4'-bipyridin]-2'-yl)carbamate (11.0 mg, 0.073 mmol, 20% yield) as an off-white solid. $^1$H NMR (600 MHz, DMSO-$d_6$) δ 10.25 (br. s., 1H), 8.35 (s, 1H), 8.31 (d, J=5.1 Hz, 1H), 8.08 (s, 1H), 7.91 (s, 1H), 7.36 (d, J=5.1 Hz, 1H), 4.20-4.09 (m, 2H), 2.51 (br. s., 3H), 2.29 (s, 3H), 1.86-1.77 (m, 1H), 1.59-1.39 (m, 2H), 1.20 (d, J=5.1 Hz, 3H), 0.93 (d, J=6.6 Hz, 3H), 0.92 (d, J=6.6 Hz, 3H); LCMS (ESI) m/e 373.4 [(M+H)+, calcd $C_{20}H_{29}N_4O3$ 373.2]; LC/MS retention time (method A): $t_R$=1.89 min.

Example 53

(S)-methyl(6-((2-amino-2,4-dimethylpentyl)oxy)-5-cyano-[3,4'-bipyridin]-2'-yl)carbamate

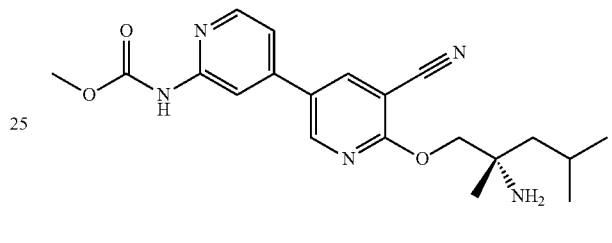

Prepared as in Example 51.

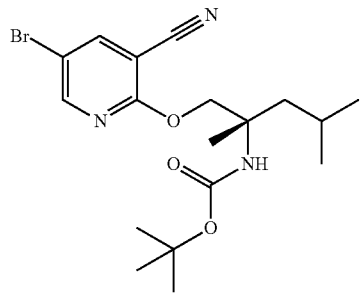 [SMILES: CC(C)C[C@@](C)(COc1ncc(Br)cc1C#N)NC(=O)OC(C)(C)C]

Part A: (S)-tert-butyl (1-((5-bromo-3-cyanopyridin-2-yl)oxy)-2,4-dimethylpentan-2-yl)carbamate A mixture of sodium carbonate (0.246 g, 2.323 mmol), (S)-tert-butyl 4-isobutyl-4-methyl-1,2,3-oxathiazolidine-3-carboxylate 2,2-dioxide (0.3408 g, 1.162 mmol) and 5-bromo-2-hydroxynicotinonitrile (0.277 g, 1.394 mmol) in DMF (4 mL) was heated at 80° C. overnight. The reaction was cooled to rt and diluted with ethyl acetate then washed with NaOH (1N) (2×) and water (1×). The ethyl acetate layer was separated, dried ($Na_2SO_4$), filtered and concentrated under reduced pressure. The product was purified silica gel chromatography (0-25% ethyl acetate in hexanes) to afford (S)-tert-butyl (1-((5-bromo-3-cyanopyridin-2-yl)oxy)-2,4-dimethylpentan-2-yl)carbamate (0.261 g, 0.633 mmol, 55% yield) as a clear oil. LCMS (ESI) m/e 436.1 [(M+Na)+, calcd $C_{18}H_{26}BrN_3O_3Na$, 436.1]; LC/MS retention time (method B): $t_R$=2.38 min.

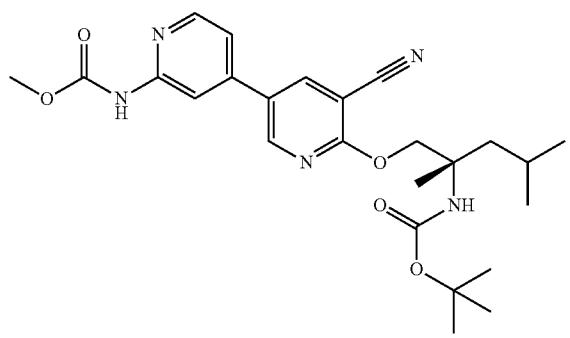 [SMILES: COC(=O)Nc1cc(-c2cnc(OC[C@](C)(CC(C)C)NC(=O)OC(C)(C)C)c(C#N)c2)ccn1]

Part B: Boc-(S)-methyl (6-((2-amino-2,4-dimethylpentyl)oxy)-5-cyano-[3,4'-bipyridin]-2'-yl)carbamate LCMS (ESI) m/e 484.4 [(M+H)$^+$, calcd C$_{25}$H$_{34}$N$_5$O$_5$, 484.3]; LC/MS retention time (method A): t$_R$=2.24 min.

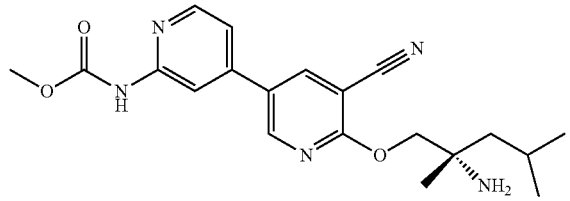 [SMILES: COC(=O)Nc1cc(-c2cnc(OC[C@@](C)(N)CC(C)C)c(C#N)c2)ccn1]

Part C: (S)-methyl(6-((2-amino-2,4-dimethylpentyl)oxy)-5-cyano-[3,4'-bipyridin]-2'-yl)carbamate Obtained (S)-methyl(6-((2-amino-2,4-dimethylpentyl)oxy)-5-cyano-[3,4'-bipyridin]-2'-yl)carbamate (13.3 mg, 0.034 mmol, 36% yield) as a white solid. $^1$H NMR (500 MHz, DMSO-d$_6$) δ 10.36 (s, 1H), 8.81-8.77 (m, 1H), 8.68-8.63 (m, 1H), 8.36 (d, J=5.1 Hz, 1H), 8.09 (s, 1H), 7.43 (d, J=4.0 Hz, 1H), 4.20 (d, J=5.9 Hz, 2H), 3.71 (s, 3H), 3.39 (br. s., 2H), 1.82 (d, J=6.2 Hz, 1H), 1.40 (t, J=5.5 Hz, 2H), 1.14 (s, 3H), 0.95-0.90 (m, 6H); LCMS (ESI) m/e 367.2 [(M-NH$_2$), calcd C$_{20}$H$_{23}$N$_4$O$_3$, 367.2]; LC/MS retention time (method B): t$_R$=1.63 min.

Example 54

(S)-methyl (6-((2-amino-2,4-dimethylpentyl)oxy)-4-methyl-[3,4'-bipyridin]-2'-yl)carbamate

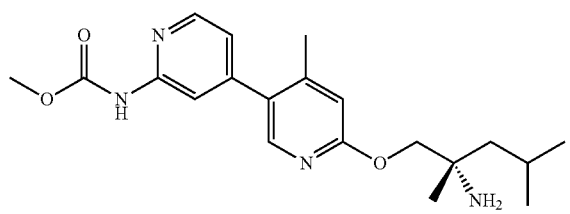 [SMILES: COC(=O)Nc1cc(-c2cnc(OC[C@@](C)(N)CC(C)C)cc2C)ccn1]

Prepared as in Example 51.

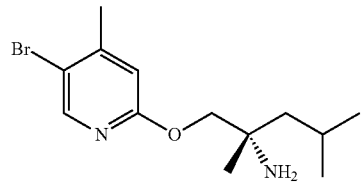 [SMILES: Cc1cc(OC[C@@](C)(N)CC(C)C)ncc1Br]

Part A: (S)-1-((5-bromo-4-methylpyridin-2-yl)oxy)-2,4-dimethylpentan-2-amine

LCMS (ESI) m/e 301.2 [(M+H)$^+$, calcd C$_{13}$H$_{22}$BrN$_2$O, 301.1]; LC/MS retention time (method A): t$_R$=1.77 min.

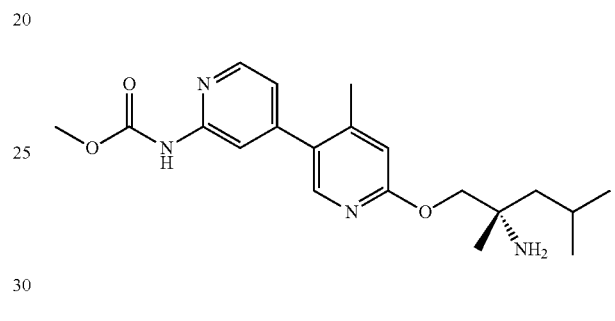

Part B: (S)-methyl (6-((2-amino-2,4-dimethylpentyl)oxy)-4-methyl-[3,4'-bipyridin]-2'-yl)carbamate Obtained (S)-methyl (6-((2-amino-2,4-dimethylpentyl)oxy)-4-methyl-[3,4'-bipyridin]-2'-yl)carbamate (15.3 mg, 0.041 mmol, 32% yield) as an off-white solid. $^1$H NMR (500 MHz, DMSO-d$_6$) δ 8.34-8.30 (m, 1H), 8.00 (s, 1H), 7.81 (s, 1H), 7.11-7.08 (m, 1H), 6.85 (s, 1H), 4.01 (d, J=5.5 Hz, 2H), 3.68 (s, 3H), 2.26 (s, 3H), 1.88 (s, 1H), 1.85-1.77 (m, 1H), 1.37 (s, 2H), 1.10 (s, 3H), 0.93 (m, 6H); LCMS (ESI) m/e 373.3 [(M+H)$^+$, calcd C$_{20}$H$_{29}$N$_4$O$_3$, 373.2]; LC/MS retention time (method B): t$_R$=1.60 min.

Example 55

(S)-methyl (6-((2-amino-2,4-dimethylpentyl)oxy)-5-chloro-[3,4'-bipyridin]-2'-yl)carbamate

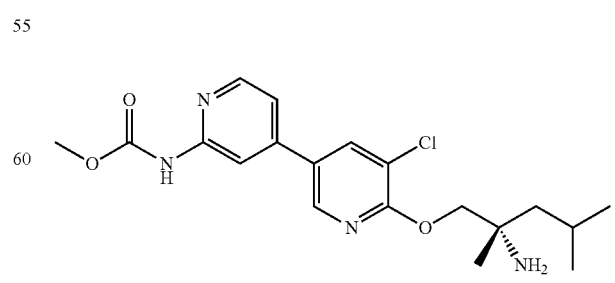

Prepared as in Example 51.

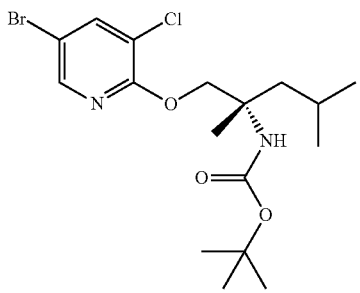 [SMILES: CC(C)C[C@@](C)(COc1ncc(Br)cc1Cl)NC(=O)OC(C)(C)C]

Part A: (S)-tert-butyl (1-((5-bromo-3-chloropyridin-2-yl)oxy)-2,4-dimethylpentan-2-yl)carbamate ¹H NMR (400 MHz, CHLOROFORM-d) δ 8.07 (d, J=2.3 Hz, 1H), 7.76 (d, J=2.3 Hz, 1H), 4.65 (br. s., 1H), 4.48 (d, J=10.3 Hz, 1H), 4.32 (d, J=10.3 Hz, 1H), 1.90-1.75 (m, 2H), 1.67-1.53 (m, 1H), 1.41 (s, 9H), 1.39 (s, 3H), 0.99 (d, J=2.0 Hz, 3H), 0.97 (d, J=2.0 Hz, 3H); LCMS (ESI) m/e 443.1 [(M+Na)⁺, calcd $C_{17}H_{26}BrClN_2O_3Na$, 443.1]; LC/MS retention time (method B): $t_R$=2.55 min.

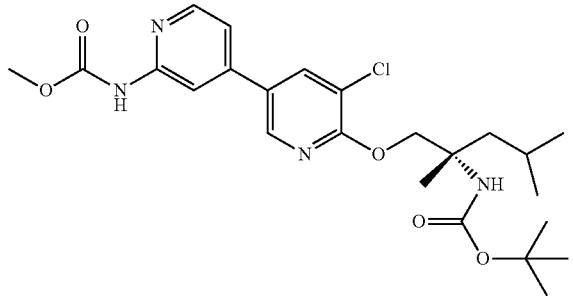 [SMILES: COC(=O)Nc1cc(-c2cnc(OC[C@](C)(CC(C)C)NC(=O)OC(C)(C)C)c(Cl)c2)ccn1]

Part B: Boc-(S)-methyl (6-((2-amino-2,4-dimethylpentyl)oxy)-5-chloro-[3,4'-bipyridin]-2'-yl)carbamate LCMS (ESI) m/e 493.4 [(M+H)⁺, calcd $C_{24}H_{34}ClN_4O_5$, 493.2]; LC/MS retention time (method A): $t_R$=2.38 min.

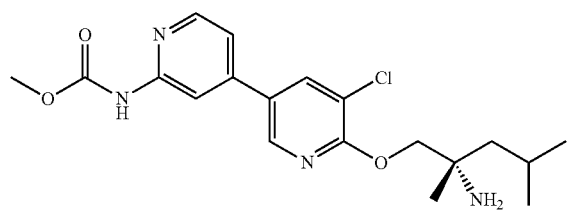 [SMILES: COC(=O)Nc1cc(-c2cnc(OC[C@@](C)(N)CC(C)C)c(Cl)c2)ccn1]

Part C: (S)-methyl (6-((2-amino-2,4-dimethylpentyl)oxy)-5-chloro-[3,4'-bipyridin]-2'-yl)carbamate Obtained (S)-methyl (6-((2-amino-2,4-dimethylpentyl)oxy)-5-chloro-[3,4'-bipyridin]-2'-yl)carbamate (19.6 mg, 0.047 mmol, 85% yield) as an off-white solid. ¹H NMR (500 MHz, DMSO-d₆) δ 8.49 (d, J=2.2 Hz, 1H), 8.34 (d, J=5.1 Hz, 1H), 8.25 (d, J=2.2 Hz, 1H), 8.07 (s, 1H), 7.42 (dd, J=5.1, 1.5 Hz, 1H), 4.22-4.06 (m, 2H), 3.71 (s, 3H), 1.87-1.75 (m, 1H), 1.48-1.34 (m, 2H), 1.14 (s, 3H), 0.93 (d, J=3.7 Hz, 3H), 0.92 (d, J=3.7 Hz, 3H); LCMS (ESI) m/e 393.3 [(M+H)⁺, calcd $C_{19}H_{26}ClN_4O_3$, 393.2]; LC/MS retention time (method A): $t_R$=1.98 min.

Example 56

(S)-methyl (6-((2-amino-2,4-dimethylpentyl)oxy)-5-methoxy-[3,4'-bipyridin]-2'-yl)carbamate

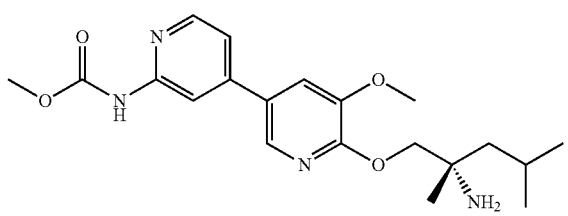 [SMILES: COC(=O)Nc1cc(-c2cnc(OC[C@@](C)(N)CC(C)C)c(OC)c2)ccn1]

Prepared as in Example 51.

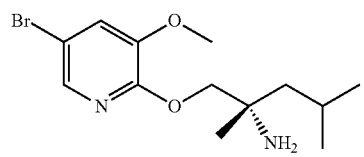 [SMILES: COc1cc(Br)cnc1OC[C@@](C)(N)CC(C)C]

Part A: (S)-1-((5-bromo-3-methoxypyridin-2-yl)oxy)-2,4-dimethylpentan-2-amine

LCMS (ESI) m/e 338.9 [(M+Na)⁺, calcd $C_{13}H_{21}BrN_2O_2Na$, 339.1]; LC/MS retention time (method B): $t_R$=1.87 min.

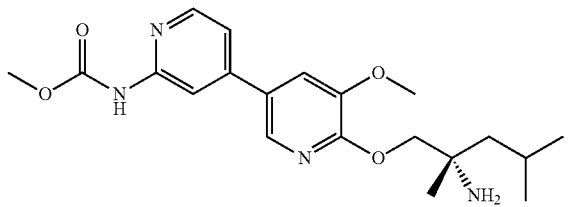 [SMILES: COC(=O)Nc1cc(-c2cnc(OC[C@@](C)(N)CC(C)C)c(OC)c2)ccn1]

Part B: (S)-methyl (6-((2-amino-2,4-dimethylpentyl)oxy)-5-methoxy-[3,4'-bipyridin]-2'-yl)carbamate Obtained (S)-methyl (6-((2-amino-2,4-dimethylpentyl)oxy)-5-methoxy-[3,4'-bipyridin]-2'-yl)carbamate (8.4 mg, 0.021 mmol, 29% yield) as an off-white solid. ¹H NMR (500 MHz, DMSO-d₆) δ 8.32 (d, J=5.1 Hz, 1H), 8.09 (s, 1H), 8.04 (d, J=1.8 Hz, 1H), 7.56 (d, J=1.5 Hz, 1H), 7.41 (d, J=4.0 Hz, 1H), 4.08 (q, J=10.3 Hz, 2H), 3.92 (s, 3H), 3.70 (s, 3H), 3.45 (br. s., 3H), 1.81 (dt, J=13.0, 6.3 Hz, 1H), 1.47-1.31 (m, 2H), 1.12 (s, 3H), 0.92 (m, 6H); LCMS (ESI) m/e 389.1 [(M+H)⁺, calcd $C_{20}H_{29}N_4O_4$, 389.2]; LC/MS retention time (method B): $t_R$=1.64 min.

Example 57

(S)-1-((2'-chloro-5-methyl-[3,4'-bipyridin]-6-yl)oxy)-2,4-dimethylpentan-2-amine

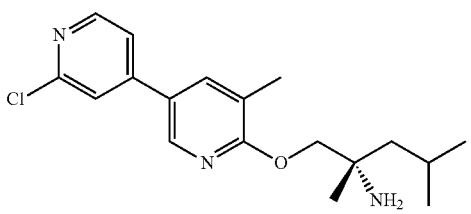 [SMILES: Cc1cc(-c2ccnc(Cl)c2)cnc1OC[C@@](C)(N)CC(C)C]

Prepared as in Example 51. Obtained (S)-1-((2'-chloro-5-methyl-[3,4'-bipyridin]-6-yl)oxy)-2,4-dimethylpentan-2-amine (15 mg, 0.044 mmol, 49% yield) as an off-white solid. $^1$H NMR (600 MHz, DMSO-$d_6$) δ 8.51 (br. s., 1H), 8.44 (d, J=5.1 Hz, 1H), 8.09 (br. s., 1H), 7.87 (s, 1H), 7.76 (d, J=4.0 Hz, 1H), 4.10-4.04 (m, 2H), 2.26 (s, 3H), 1.84-1.75 (m, 1H), 1.40 (t, J=6.2 Hz, 2H), 1.13 (s, 3H), 0.92 (t, J=6.4 Hz, 6H); LCMS (ESI) m/e 334.3 [(M-NH$_2$)+, calcd C$_{18}$H$_{25}$ClN$_3$O, 334.2]; LC/MS retention time (method B): $t_R$=1.94 min.

Example 58

(S)-1-((2'-(difluoromethyl)-5-methyl-[3,4'-bipyridin]-6-yl)oxy)-2,4-dimethylpentan-2-amine

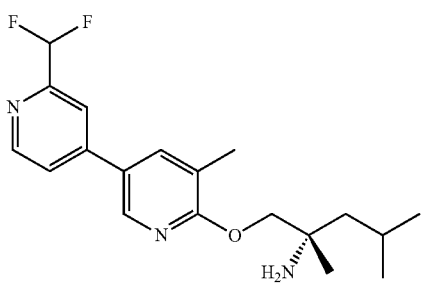 [SMILES: Cc1cc(-c2ccnc(C(F)F)c2)cnc1OC[C@@](C)(N)CC(C)C]

Prepared as in Example 51. Obtained (S)-1-((2'-(difluoromethyl)-5-methyl-[3,4'-bipyridin]-6-yl)oxy)-2,4-dimethylpentan-2-amine (15.1 mg, 0.043 mmol, 81% yield) as an off-white solid. $^1$H NMR (500 MHz, DMSO-$d_6$) δ 8.72 (d, J=5.2 Hz, 1H), 8.53 (d, J=2.5 Hz, 1H), 8.12 (d, J=2.5 Hz, 1H), 8.01 (s, 1H), 7.92 (d, J=5.2 Hz, 1H), 6.99 (t, J=54.9 Hz, 1H), 4.16-4.02 (m, 2H), 2.28 (s, 3H), 1.80 (tt, J=11.5, 5.7 Hz, 1H), 1.49-1.35 (m, 2H), 1.14 (s, 3H), 0.92 (m, 6H); LCMS (ESI) m/e 350.3 [(M+H)$^+$, calcd C$_{19}$H$_{26}$F$_2$N$_3$O, 350.2]; LC/MS retention time (method A): $t_R$=1.80 min.

Example 59

(S)-6-((2-amino-2,4-dimethylpentyl)oxy)-2'-(difluoromethyl)-[3,4'-bipyridine]-5-carbonitrile

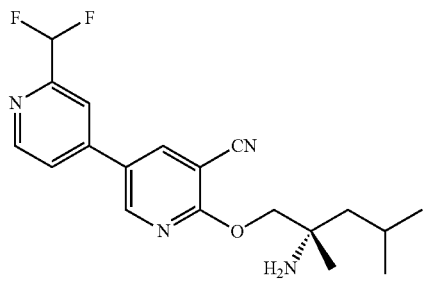 [SMILES: CC(C)C[C@](C)(N)COc1ncc(-c2ccnc(C(F)F)c2)cc1C#N]

Prepared as in Example 51.

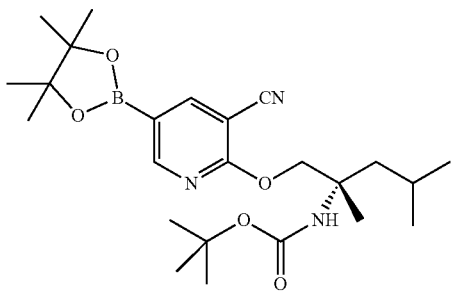 [SMILES: CC(C)C[C@@](C)(COc1ncc(B2OC(C)(C)C(C)(C)O2)cc1C#N)NC(=O)OC(C)(C)C]

Part A: (S)-tert-butyl (1-((3-cyano-5-(4,4,5,5-tetramethyl-1,3,2-dioxaborolan-2-yl)pyridin-2-yl)oxy)-2,4-dimethylpentan-2-yl)carbamate To a 20 mL vial was added (S)-tert-butyl (1-((5-bromo-3-cyanopyridin-2-yl)oxy)-2,4-dimethylpentan-2-yl)carbamate (73 mg, 0.177 mmol), 4,4,4',4',5,5,5',5'-octamethyl-2,2'-bi(1,3,2-dioxaborolane) (54.0 mg, 0.212 mmol), and potassium acetate (52.1 mg, 0.531 mmol) in dioxane (2 mL) with nitrogen bubbling to give a colorless suspension. PdCl$_2$(dppf) (3.89 mg, 5.31 µmol) was added under nitrogen. The vial was sealed and the mixture was heated at 80° C. for 4 h. The reaction mixture was cooled to rt and concentrated under reduced pressure. The crude material was used directly in the next step.

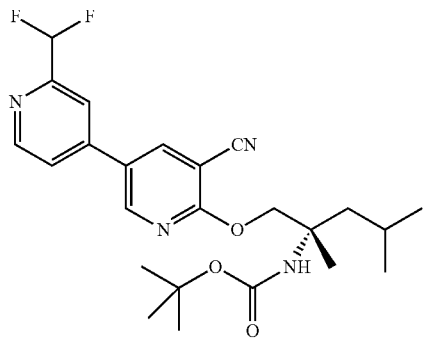 [SMILES: CC(C)C[C@@](C)(COc1ncc(-c2ccnc(C(F)F)c2)cc1C#N)NC(=O)OC(C)(C)C]

Part B: (S)-tert-butyl (1-((5-cyano-2'-(difluoromethyl)-[3,4'-bipyridin]-6-yl)oxy)-2,4-dimethylpentan-2-yl)carbamate The mixture of (S)-tert-butyl (1-((3-cyano-5-(4,4,5,5-tetramethyl-1,3,2-dioxaborolan-2-yl)pyridin-2-yl)oxy)-2,4-dimethylpentan-2-yl)carbamate (0.040 g, 0.088 mmol), 1,1'-bis(diphenylphosphino)ferrocene-palladium(II) dichloromethane complex (5.03 mg, 6.16 μmol), 4-chloro-2-(difluoromethyl)pyridine hydrochloride (0.018 g, 0.088 mmol) and $Na_2CO_3$ (0.176 mL, 0.352 mmol) in dioxane (1 mL) (degassed with $N_2$) was heated at 120° C. for 16 h. The reaction mixture was cooled to rt, diluted with ethyl acetate and washed with water (3×). The ethyl acetate layer was dried ($Na_2SO_4$), filtered and concentrated under reduced pressure. The residue was directly carried onto next reaction. LCMS (ESI) m/e 483.2 [(M+Na)+, calcd $C_{24}H_3F_2N_4Na_1O_3$, 483.2]; LC/MS retention time (method B): $t_R$=2.30 min.

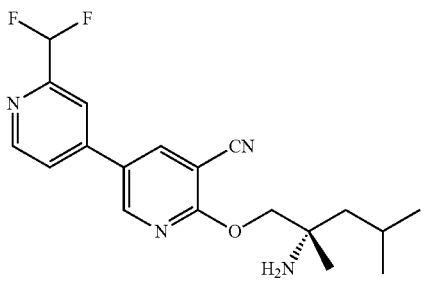 [SMILES: CC(C)C[C@](C)(N)COc1ncc(-c2ccnc(C(F)F)c2)cc1C#N]

Part C: (S)-6-((2-amino-2,4-dimethylpentyl)oxy)-2'-(difluoromethyl)-[3,4'-bipyridine]-5-carbonitrile Prepared using procedure described in Example 51 to afford (S)-6-((2-amino-2,4-dimethylpentyl)oxy)-2'-(difluoromethyl)-[3,4'-bipyridine]-5-carbonitrile (4.7 mg, 0.013 mmol, 15% yield) as an off-white solid. $^1$H NMR (500 MHz, DMSO-$d_6$) δ 9.02 (d, J=2.5 Hz, 1H), 8.95 (d, J=2.6 Hz, 1H), 8.80 (d, J=5.1 Hz, 1H), 8.15 (s, 1H), 8.02 (d, J=5.0 Hz, 1H), 7.01 (t, J=54.8 Hz, 1H), 4.63 (d, J=11.6 Hz, 1H), 4.51 (d, J=11.5 Hz, 1H), 1.86 (dq, J=12.4, 6.2 Hz, 1H), 1.79 (dd, J=14.4, 5.5 Hz, 1H), 1.62 (dd, J=14.3, 5.5 Hz, 1H), 1.41 (s, 3H), 0.98 (dd, J=6.7, 2.2 Hz, 6H); $^{19}$F NMR (376 MHz, DMSO-d6) δ −73.65; LCMS (ESI) m/e 383.3 [(M+Na)+, calcd $C_{19}H_{22}F_2N_4Na_1O_1$, 383.2]; LC/MS retention time (method B): $t_R$=1.77 min.

Example 60

(S)-1-((5-chloro-2'-methyl-[3,4'-bipyridin]-6-yl)oxy)-2,4-dimethylpentan-2-amine

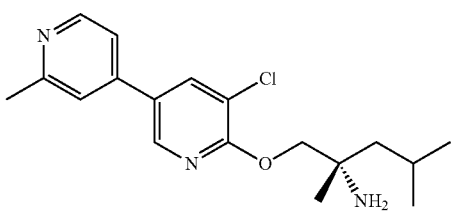 [SMILES: Cc1cc(-c2cnc(OC[C@@](C)(N)CC(C)C)c(Cl)c2)ccn1]

Prepared as in Example 51. Obtained (S)-1-((5-chloro-2'-methyl-[3,4'-bipyridin]-6-yl)oxy)-2,4-dimethylpentan-2-amine (2 mg, 5.99 umol, 31% yield) as an off-white solid. H NMR (500 MHz, DMSO-$d_6$) δ 8.59 (d, J=1.8 Hz, 1H), 8.50 (d, J=5.1 Hz, 1H), 8.39 (d, J=1.8 Hz, 1H), 7.67 (s, 1H), 7.57 (d, J=4.4 Hz, 1H), 4.19-4.10 (m, 2H), 2.53 (s, 3H), 1.86-1.77 (m, 1H), 1.47-1.37 (m, 2H), 1.15 (s, 3H), 0.99-0.88 (m, 6H); LCMS (ESI) m/e 334.3 [(M+H)+, calcd $C_{18}H_{25}ClN_3O$, 334.2]; LC/MS retention time (method A): $t_R$=1.90 min.

Example 61

(S)-1-((2',5-dimethyl-[3,4'-bipyridin]-6-yl)oxy)-2,4-dimethylpentan-2-amine

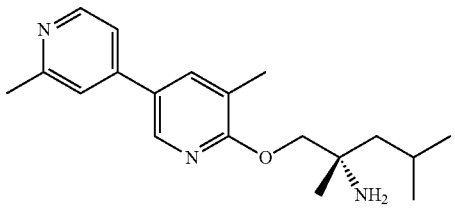 [SMILES: Cc1cc(-c2cnc(OC[C@@](C)(N)CC(C)C)c(C)c2)ccn1]

Prepared as in Example 51. Obtained (S)-1-((5-chloro-2'-methyl-[3,4'-bipyridin]-6-yl)oxy)-2,4-dimethylpentan-2-amine (20.5 mg, 0.065 mmol, 41% yield) as an off-white solid. $^1$H NMR (500 MHz, DMSO-$d_6$) δ 8.47 (d, J=5.1 Hz, 1H), 8.43 (d, J=2.2 Hz, 1H), 8.01 (s, 1H), 7.59 (s, 1H), 7.50 (d, J=5.5 Hz, 1H), 4.11-4.00 (m, 2H), 2.52 (s, 3H), 2.26 (s, 3H), 1.80 (dq, J=12.6, 6.3 Hz, 1H), 1.46-1.35 (m, 2H), 1.13 (s, 3H), 0.93 (d, J=4.8 Hz, 3H), 0.92 (d, J=4.8 Hz, 3H); LCMS (ESI) m/e 297.1 [(M-$NH_2$)+, calcd $C_{19}H_{25}ClN_2O$, 297.2]; LC/MS retention time (method B): $t_R$=1.51 min.

Example 62

(S)-1-((5-methoxy-2'-methyl-[3,4'-bipyridin]-6-yl)oxy)-2,4-dimethylpentan-2-amine

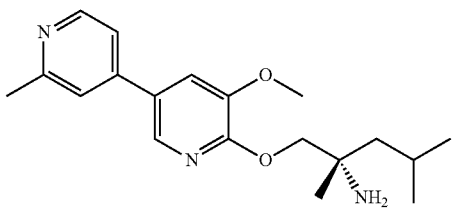 [SMILES: COc1cc(-c2ccnc(C)c2)cnc1OC[C@@](C)(N)CC(C)C]

Prepared as in Example 51. Obtained (S)-1-((5-methoxy-2'-methyl-[3,4'-bipyridin]-6-yl)oxy)-2,4-dimethylpentan-2-amine (20.5 mg, 0.065 mmol, 41% yield) as an off-white solid. $^1$H NMR (500 MHz, DMSO-$d_6$) δ 8.48 (d, J=5.1 Hz, 1H), 8.14 (s, 1H), 7.65 (d, J=4.0 Hz, 2H), 7.55 (d, J=3.7 Hz, 1H), 4.06 (q, J=10.1 Hz, 2H), 3.93 (s, 3H), 2.53 (s, 3H), 1.85-1.70 (m, 1H), 1.42-1.31 (m, 2H), 1.11 (s, 3H), 0.92 (t, J=7.0 Hz, 6H); LCMS (ESI) m/e 330.1 [(M+H)+, calcd $C_{19}H_{28}N_3O_2$, 330.2]; LC/MS retention time (method B): $t_R$=1.42 min.

Example 63 methyl (5-((2-amino-2,4-dimethylpentyl)oxy)-[2,4'-bipyridin]-2'-yl)carbamate

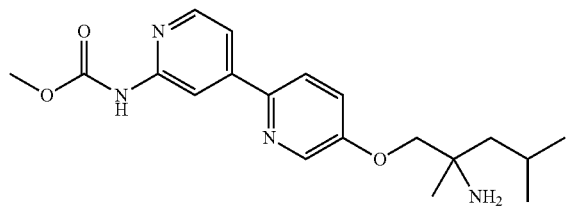

Prepared as in Example 29.

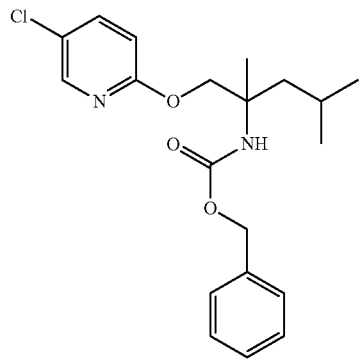 [SMILES: CC(C)CC(C)(COc1ccc(Cl)cn1)NC(=O)OCc1ccccc1]

Part A: Benzyl (1-((5-chloropyridin-2-yl)oxy)-2,4-dimethylpentan-2-yl)carbamate

LCMS (ESI) m/e 377.3 [(M+H)$^+$, calcd C$_{20}$H$_{26}$ClN$_2$O$_3$, 377.2]; LC/MS retention time (method A): t$_R$=2.42 min.

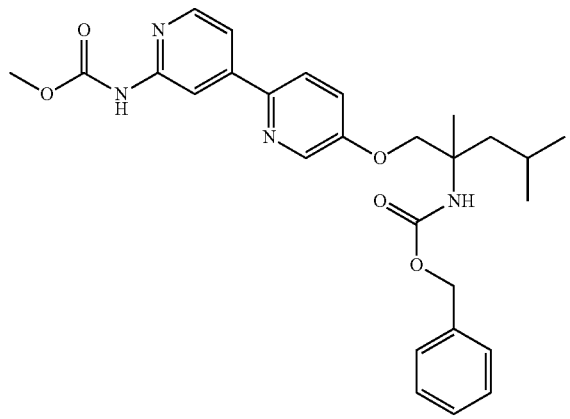 [SMILES: COC(=O)Nc1cc(-c2ccc(OCC(C)(CC(C)C)NC(=O)OCc3ccccc3)cn2)ccn1]

Part B: Cbz methyl (5-((2-amino-2,4-dimethylpentyl)oxy)-[2,4'-bipyridin]-2'-yl)carbamate LCMS (ESI) m/e 493.0 [(M+H)$^+$, calcd C$_{27}$H$_{33}$N$_4$O$_5$, 493.2]; LC/MS retention time (method B): t$_R$=2.15 min.

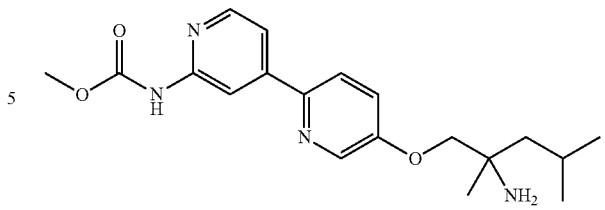

Part C: methyl (5-((2-amino-2,4-dimethylpentyl)oxy)-[2,4'-bipyridin]-2'-yl)carbamate A mixture of Pd/C (4 mg, 3.76 µmol) and Cbz protected methyl (5-((2-amino-2,4-dimethylpentyl)oxy)-[2,4'-bipyridin]-2'-yl)carbamate (0.0123 g, 0.025 mmol) in ethanol (4 mL) was stirred under H$_2$ balloon at room temperature overnight. The reaction mixture was filtered and the flask was rinsed with CH$_2$Cl$_2$. The filter cake was washed with CH$_2$Cl$_2$. The filtrate was concentrated under reduced pressure and the residue was purified by reverse phase HPLC (acetonitrile/water/10 mM ammonium acetate) to afford methyl (5-((2-amino-2,4-dimethylpentyl)oxy)-[2,4'-bipyridin]-2'-yl)carbamate (12.1 mg, 0.032 mmol, 98% yield) as an off-white solid. $^1$H NMR (600 MHz, DMSO-d$_6$) δ 10.14 (br. s., 1H), 8.49 (s, 1H), 8.45 (d, J=2.8 Hz, 1H), 8.32 (d, J=5.1 Hz, 1H), 7.97 (d, J=8.8 Hz, 1H), 7.63 (d, J=5.1 Hz, 1H), 7.54 (dd, J=8.7, 2.8 Hz, 1H), 3.84 (s, 2H), 3.71 (s, 3H), 1.82 (tt, J=12.7, 6.5 Hz, 1H), 1.46-1.35 (m, 2H), 1.14 (s, 3H), 0.95 (d, J=6.8 Hz, 3H), 0.93 (d, J=6.6 Hz, 3H); LCMS (ESI) m/e 359.3 [(M+H)$^+$, calcd C$_{19}$H$_{27}$N$_4$O$_3$, 359.2]; LC/MS retention time (method A): t$_R$=1.48 min.

Example 64

(S)-methyl (5-((2-amino-2,4-dimethylpentyl)oxy)-6-methyl-[2,4'-bipyridin]-2'-yl)carbamate

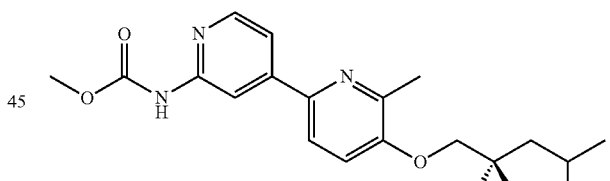

Prepared as in Example 19.

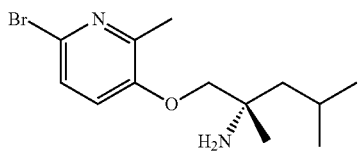 [SMILES: Cc1nc(Br)ccc1OC[C@@](C)(N)CC(C)C]

Part A: (S)-1-((6-bromo-2-methylpyridin-3-yl)oxy)-2,4-dimethylpentan-2-amine

LCMS (ESI) m/e 284.2 [(M-NH$_2$), calcd C$_{13}$H$_{19}$BrNO, 284.1]; LC/MS retention time (method A): t$_R$=1.78 min (SM: t$_R$=1.61 min).

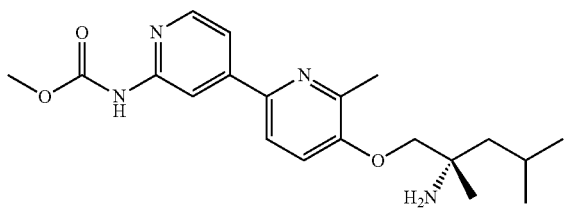 [SMILES: COC(=O)Nc1cc(-c2ccc(OC[C@@](C)(N)CC(C)C)c(C)n2)ccn1]

Part B: (S)-methyl (5-((2-amino-2,4-dimethylpentyl)oxy)-6-methyl-[2,4'-bipyridin]-2'-yl)carbamate Obtained (S)-methyl (5-((2-amino-2,4-dimethylpentyl)oxy)-6-methyl-[2,4'-bipyridin]-2'-yl)carbamate (8.5 mg, 0.022 mmol, 34% yield) as an off-white solid. $^1$H NMR (500 MHz, DMSO-$d_6$) δ 8.48 (s, 1H), 8.30 (d, J=5.3 Hz, 1H), 7.83 (d, J=8.6 Hz, 1H), 7.67-7.60 (m, 1H), 7.43 (d, J=8.6 Hz, 1H), 3.79 (d, J=2.0 Hz, 2H), 3.58 (s, 3H), 2.50 (s, 3H), 1.79 (m, 1H), 1.51-1.34 (m, 2H), 1.16 (s, 3H), 0.93 (t, J=6.4 Hz, 6H); LCMS (ESI) m/e 373.3 [(M+H)$^+$, calcd $C_{20}H_{29}N_4O_3$, 373.2]; LC/MS retention time (method A): $t_R$=1.82 min.

Example 65

(S)-1-((2',6-dimethyl-[2,4'-bipyridin]-5-yl)oxy)-2,4-dimethylpentan-2-amine

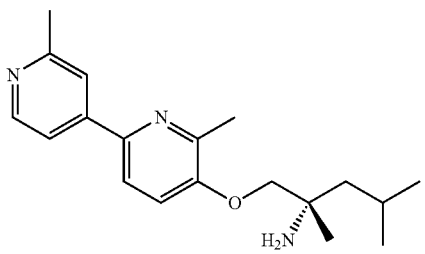 [SMILES: Cc1cc(-c2ccc(OC[C@@](C)(N)CC(C)C)c(C)n2)ccn1]

Prepared as in Example 51. Obtained ((S)-1-((2',6-dimethyl-[2,4'-bipyridin]-5-yl)oxy)-2,4-dimethylpentan-2-amine (7.2 mg, 0.022 mmol, 29% yield) as an off-white solid. $^1$H NMR (500 MHz, DMSO-$d_6$) δ 8.49 (d, J=5.3 Hz, 1H), 7.92 (d, J=8.5 Hz, 1H), 7.87 (s, 1H), 7.78 (d, J=5.3 Hz, 1H), 7.43 (d, J=8.5 Hz, 1H), 3.78 (s, 2H), 2.54 (s, 3H), 2.51 (s, 3H), 1.83 (dt, J=12.8, 6.4 Hz, 1H), 1.42 (t, J=5.2 Hz, 2H), 1.15 (s, 3H), 0.94 (t, J=6.2 Hz, 6H); LCMS (ESI) m/e 314.4 [(M+H)$^+$, calcd $C_{19}H_{28}N_3O$, 314.2]; LC/MS retention time (method A): $t_R$=1.84 min.

Example 66

(S)-methyl (5-((2-amino-2,4-dimethylpentyl)oxy)-6-chloro-[2,4'-bipyridin]-2'-yl)carbamate

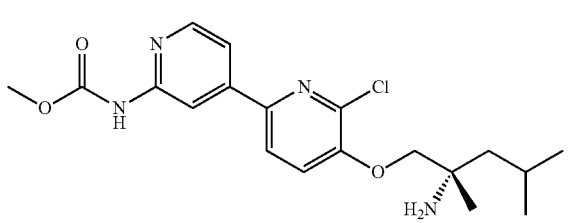 [SMILES: COC(=O)Nc1cc(-c2ccc(OC[C@@](C)(N)CC(C)C)c(Cl)n2)ccn1]

Prepared as in Example 32.

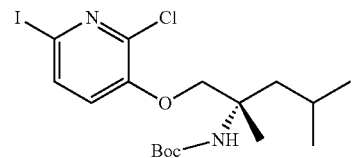 [SMILES: CC(C)C[C@@](C)(COc1ccc(I)nc1Cl)NC(=O)OC(C)(C)C]

Part A: (S)-tert-butyl (1-((2-chloro-6-iodopyridin-3-yl)oxy)-2,4-dimethylpentan-2-yl)carbamate LCMS (ESI) m/e 490.9 [(M+Na)$^+$, calcd $C_{17}H_{26}ClIN_2NaO_3$, 491.1]; LC/MS retention time (method B): $t_R$=2.40 min.

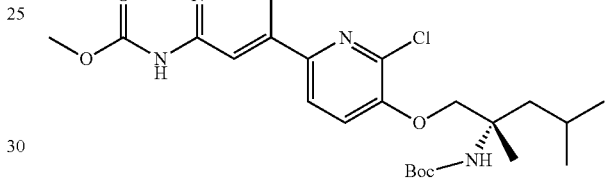

Part B: (S)-methyl (5-((2-Boc-amino-2,4-dimethylpentyl)oxy)-6-chloro-[2,4'-bipyridin]-2'-yl)carbamate LCMS (ESI) m/e 493.0 [(M+H)$^+$, calcd $C_{24}H_{34}ClN_4O_5$, 493.2]; LC/MS retention time (method B): $t_R$=2.19 min.

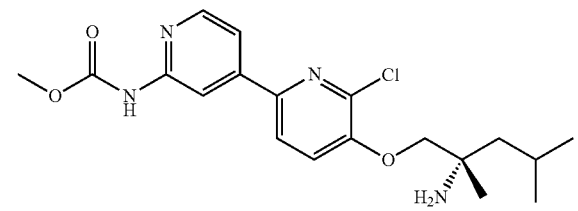 [SMILES: COC(=O)Nc1cc(-c2ccc(OC[C@@](C)(N)CC(C)C)c(Cl)n2)ccn1]

Part C: (S)-methyl(5-((2-amino-2,4-dimethylpentyl)oxy)-6-chloro-[2,4'-bipyridin]-2'-yl)carbamate Obtained(S)-methyl(5-((2-amino-2,4-dimethylpentyl)oxy)-6-chloro-[2,4'-bipyridin]-2'-yl)carbamate (12.6 mg, 0.032 mmol, 69% yield) as an off-white solid. $^1$H NMR (500 MHz, DMSO-$d_6$) δ 8.45 (s, 1H), 8.35 (d, J=5.3 Hz, 1H), 8.04 (d, J=8.4 Hz, 1H), 7.71 (d, J=8.4 Hz, 1H), 7.62 (d, J=5.2 Hz, 1H), 3.93 (s, 2H), 3.71 (s, 3H), 1.81 (dq, J=13.1, 6.5 Hz, 1H), 1.45 (qd, J=14.0, 5.5 Hz, 2H), 1.18 (s, 3H), 0.93 (t, J=6.4 Hz, 6H); LCMS (ESI) m/e 393.0 [(M+H)$^+$, calcd $C_{19}H_{26}Cl_1N_4O_3$, 393.2]; LC/MS retention time (method A): $t_R$=1.66 min.

Example 67

(S)-1-((6-chloro-2'-methyl-[2,4'-bipyridin]-5-yl)oxy)-2,4-dimethylpentan-2-amine

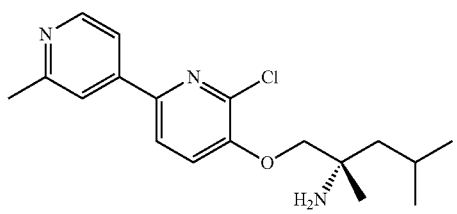 [SMILES: Cc1cc(-c2ccc(OC[C@@](C)(N)CC(C)C)c(Cl)n2)ccn1]

Prepared as in Example 32.

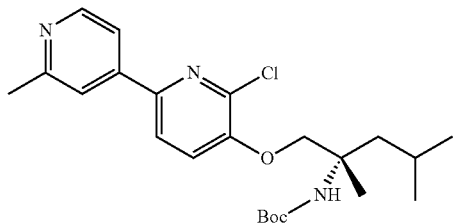 [SMILES: Cc1cc(-c2ccc(OC[C@](C)(CC(C)C)NC(=O)OC(C)(C)C)c(Cl)n2)ccn1]

Part A: (S)-tert-butyl (1-((6-chloro-2'-methyl-[2,4'-bipyridin]-5-yl)oxy)-2,4-dimethylpentan-2-yl)carbamate Synthesis followed previous procedure. LCMS (ESI) m/e 434.0 [(M+H)$^+$, calcd C$_{23}$H$_{33}$Cl$_1$N$_3$O$_3$, 434.2]; LC/MS retention time (method B): t$_R$=1.96 min.

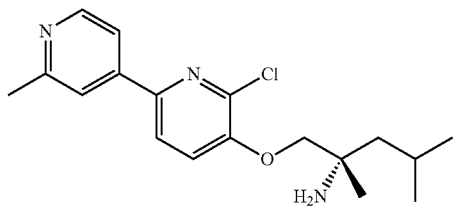 [SMILES: Cc1cc(-c2ccc(OC[C@@](C)(N)CC(C)C)c(Cl)n2)ccn1]

Part B: (S)-1-((6-chloro-2'-methyl-[2,4'-bipyridin]-5-yl)oxy)-2,4-dimethylpentan-2-amine Obtained (S)-1-((6-chloro-2'-methyl-[2,4'-bipyridin]-5-yl)oxy)-2,4-dimethylpentan-2-amine (4.6 mg, 0.013 mmol, 30% yield) as an off-white solid. $^1$H NMR (500 MHz, DMSO-d$_6$) δ 8.53 (d, J=5.2 Hz, 1H), 8.13 (d, J=8.4 Hz, 1H), 7.85 (s, 1H), 7.76 (d, J=5.3 Hz, 1H), 7.72 (d, J=8.5 Hz, 1H), 3.91 (s, 2H), 2.55 (s, 3H), 1.82 (p, J=6.4 Hz, 1H), 1.52-1.38 (m, 2H), 1.17 (s, 3H), 0.94 (t, J=6.3 Hz, 6H); LCMS (ESI) m/e 334.1 [(M+H)$^+$, calcd C$_{18}$H$_{25}$Cl$_1$N$_3$O$_1$, 334.2]; LC/MS retention time (method A): t$_R$=1.48 min.

Example 68

(S)-methyl(5-((2-amino-2,4-dimethylpentyl)oxy)-4-methyl-[2,4'-bipyridin]-2'-yl)carbamate Prepared as in Example 32.

Part A: (S)-tert-butyl (1-((6-chloro-4-methylpyridin-3-yl)oxy)-2,4-dimethylpentan-2-yl)carbamate LCMS (ESI) m/e 357.3 [(M+H)$^+$, calcd CH$_{30}$ClN$_2$O$_3$, 357.2]; LC/MS retention time (method A): t$_R$=2.23 min.

Part B: (S)-tert-butyl (1-((6-chloro-4-methylpyridin-3-yl)oxy)-2,4-dimethylpentan-2-yl)carbamate LCMS (ESI) m/e 357.3 [(M+H)$^+$, calcd CH$_{30}$ClN$_2$O$_3$, 357.2]; LC/MS retention time (method A): t$_R$=2.23 min.

Part C: (S)-1-((6-chloro-4-methylpyridin-3-yl)oxy)-2,4-dimethylpentan-2-amine

LCMS (ESI) m/e 257.0 [(M+H)+, calcd $C_{13}H_{22}ClN_2O$, 257.1]; LC/MS retention time (method B): $t_R$=1.70 min.

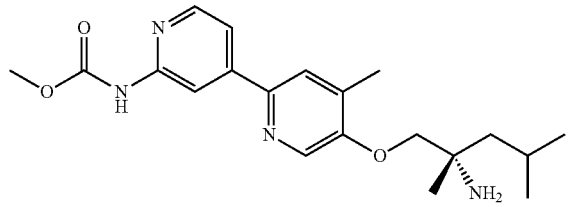 [SMILES: COC(=O)Nc1cc(-c2cc(C)c(OC[C@@](C)(N)CC(C)C)cn2)ccn1]

Part D: (S)-methyl (5-((2-amino-2,4-dimethylpentyl)oxy)-4-methyl-[2,4'-bipyridin]-2'-yl)carbamate Obtained (S)-methyl (5-((2-amino-2,4-dimethylpentyl)oxy)-4-methyl-[2,4'-bipyridin]-2'-yl)carbamate (1.1 mg, 2.92 umol, 5% yield) as an off-white solid. $^1$H NMR (500 MHz, DMSO-$d_6$) δ 8.49 (s, 1H), 8.36 (s, 1H), 8.32 (d, J=5.1 Hz, 1H), 7.87 (s, 1H), 7.63 (d, J=5.5 Hz, 1H), 3.89 (s, 2H), 3.71 (s, 3H), 2.32 (s, 3H), 1.86-1.79 (m, 1H), 1.42 (t, J=5.7 Hz, 2H), 1.15 (s, 3H), 0.93 (t, J=6.6 Hz, 6H); LCMS (ESI) m/e 373.1 [(M+H)+, calcd $C_{20}H_{29}N_4O_3$, 373.2]; LC/MS retention time (method B): $t_R$=1.67 min.

Example 69

(S)-2,4-dimethyl-1-(4-(quinolin-4-yl)-2-(trifluoromethyl)phenoxy)pentan-2-amine

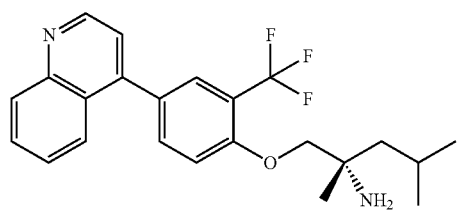 [SMILES: CC(C)C[C@](C)(N)COc1ccc(-c2ccnc3ccccc23)cc1C(F)(F)F]

Prepared as in Example 32. Obtained (S)-2,4-dimethyl-1-(4-(quinolin-4-yl)-2-(trifluoromethyl)phenoxy)pentan-2-amine (50 mg, 0.123 mmol, 17% yield) as a brown solid. $^1$H NMR (400 MHz, CHLOROFORM-d) δ 8.96 (d, J=4.5 Hz, 1H), 8.20 (d, J=8.5 Hz, 1H), 7.87 (dd, J=8.4, 0.9 Hz, 1H), 7.75 (td, J=4.2, 1.4 Hz, 2H), 7.65 (dd, J=8.5, 2.0 Hz, 1H), 7.58-7.52 (m, 1H), 7.33 (d, J=4.5 Hz, 1H), 7.14 (d, J=8.5 Hz, 1H), 3.93-3.86 (m, 2H), 1.82 (d, J=6.5 Hz, 1H), 1.68-1.59 (m, 2H), 1.54 (t, J=5.5 Hz, 2H), 1.28 (s, 3H), 1.06-0.98 (m, 6H); $^{19}$F NMR (376 MHz, CHLOROFORM-d) δ −62.29 (s, 3F); LCMS (ESI) m/e 403.2 [(M+H)+, calcd $C_{23}H_{26}F_3N_2O$, 403.2]; LC/MS retention time (method B): $t_R$=1.73 min.

Example 70

(S)-2,4-dimethyl-1-(2-(trifluoromethyl)-4-(7-(trifluoromethyl)quinolin-4-yl)phenoxy)pentan-2-amine

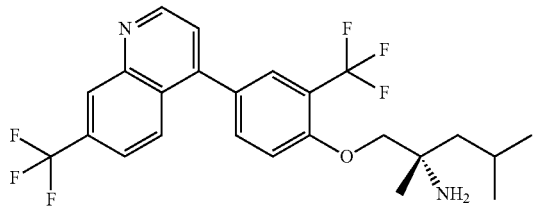 [SMILES: CC(C)C[C@](C)(N)COc1ccc(-c2ccnc3cc(C(F)(F)F)ccc23)cc1C(F)(F)F]

Prepared as in Example 32. A mixture of 2-(dicyclohexylphosphino)-2',4',6'-triisopropylbiphenyl (2.90 mg, 6.09 μmol), potassium acetate (0.090 g, 0.913 mmol), $2^{nd}$ generation Xphos precatalyst (2.395 mg, 3.04 μmol), 4-chloro-8-(trifluoromethyl)quinoline (0.0705 g, 0.304 mmol) and hypodiboric acid (0.041 g, 0.457 mmol) in ethanol (4 mL) was degassed three times via vacuum/$N_2$ fill cycle. The reaction mixture was heated at 80° C. for 3 h. The reaction was cooled to room temperature. (S)-1-(4-bromo-2-(trifluoromethyl)phenoxy)-2,4-dimethylpentan-2-amine (0.026 g, 0.073 mmol) and $2^{nd}$ generation Xphos precatalyst (2.395 mg, 3.04 μmol) in THF (4 mL) was added to the reaction mixture, followed by addition of potassium phosphate tribasic (3 mL, 1.500 mmol) at room temperature. The reaction mixture was underwent vacuum/$N_2$ fill cycle three times before heated at 80° C. overnight. The reaction was cooled to rt then diluted with ethyl acetate and washed with water (3×). The ethyl acetate layer was separated, dried ($Na_2SO_4$), filtered and concentrated under reduced pressure. The crude was purified by reverse phase HPLC (acetonitrile/water/10 mM ammonium acetate to afford (S)-2,4-dimethyl-1-(2-(trifluoromethyl)-4-(7-(trifluoromethyl)quinolin-4-yl)phenoxy)pentan-2-amine (8.9 mg, 0.018 mmol, 5% yield) as an off-white solid. $^1$H NMR (500 MHz, DMSO-$d_6$) δ 9.11 (d, J=4.3 Hz, 1H), 8.46 (s, 1H), 8.08 (d, J=8.5 Hz, 1H), 7.90 (d, J=8.9 Hz, 1H), 7.86 (d, J=8.2 Hz, 1H), 7.83 (s, 1H), 7.70 (d, J=4.3 Hz, 1H), 7.45 (d, J=8.5 Hz, 1H), 3.94-3.87 (m, 2H), 1.82 (d, J=6.1 Hz, 1H), 1.42 (d, J=5.5 Hz, 2H), 1.15 (s, 3H), 0.94 (dd, J=6.4, 2.1 Hz, 6H); LCMS (ESI) m/e 471.3 [(M+H)+, calcd $C_{24}H_{25}F_6N_2O$, 471.2]; LC/MS retention time (method A): $t_R$=2.28 min.

Example 71

(S)-1-(4-(7-fluoroquinolin-4-yl)-2-(trifluoromethyl)phenoxy)-2,4-dimethylpentan-2-amine

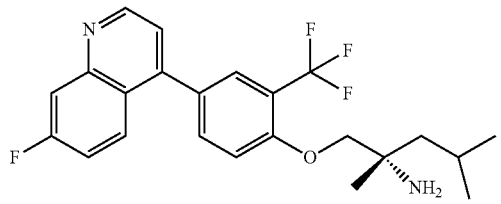 [SMILES: CC(C)C[C@](C)(N)COc1ccc(-c2ccnc3cc(F)ccc23)cc1C(F)(F)F]

Prepared as in Example 32. Obtained (S)-1-(4-(7-fluoroquinolin-4-yl)-2-(trifluoromethyl)phenoxy)-2,4-dimethylpentan-2-amine (4.2 mg, 9.89 umol, 2% yield) as an off-white solid. $^1$H NMR (500 MHz, DMSO-$d_6$) δ 8.96 (d, J=4.0 Hz, 1H), 7.97-7.79 (m, 3H), 7.77 (s, 1H), 7.60-7.53 (m, 1H), 7.50 (d, J=4.0 Hz, 1H), 7.43 (d, J=8.5 Hz, 1H), 3.89 (d, J=7.6 Hz, 2H), 1.81 (d, J=6.4 Hz, 1H), 1.41 (d, J=5.2 Hz, 2H), 1.14 (s, 3H), 0.93 (d, J=4.9 Hz, 6H); LCMS (ESI) m/e 404.2 [(M-NH$_2$)+, calcd C$_{23}$H$_{22}$F$_4$NO, 404.2]; LC/MS retention time (method B): $t_R$=1.88 min.

Example 72

(S)-1-(4-(5,7-difluoroquinolin-4-yl)-2-(trifluoromethyl)phenoxy)-2,4-dimethylpentan-2-amine

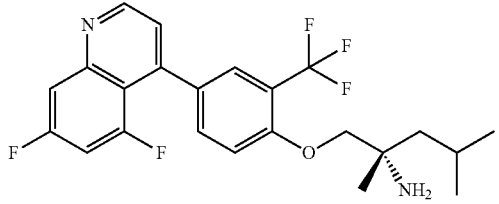

Prepared as in Example 32. Obtained (S)-1-(4-(5,7-difluoroquinolin-4-yl)-2-(trifluoromethyl)phenoxy)-2,4-dimethylpentan-2-amine (17.5 mg, 0.039 mmol, 23% yield) as an off-white solid. $^1$H NMR (500 MHz, DMSO-$d_6$) δ 9.02-8.96 (m, 1H), 7.82-7.76 (m, 1H), 7.73 (br. s., 2H), 7.56 (br. s., 1H), 7.46 (d, J=4.3 Hz, 1H), 7.33 (d, J=8.5 Hz, 1H), 3.88 (d, J=6.4 Hz, 2H), 1.82 (br. s., 1H), 1.42 (d, J=5.2 Hz, 2H), 1.15 (s, 3H), 0.93 (d, J=6.6 Hz, 6H); LCMS (ESI) m/e 439.4 [(M+H)$^+$, calcd C$_{23}$H$_{24}$F$_5$N$_2$O, 439.2]; LC/MS retention time (method A): $t_R$=2.14 min.

Example 73

(S)-1-(4-(6-fluoroquinolin-4-yl)-2-(trifluoromethyl)phenoxy)-2,4-dimethylpentan-2-amine

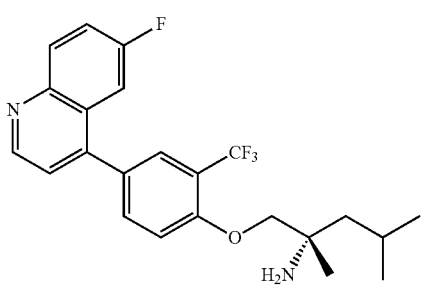

Prepared as in Example 32. Obtained (S)-1-(4-(6-fluoroquinolin-4-yl)-2-(trifluoromethyl)phenoxy)-2,4-dimethylpentan-2-amine (9.6 mg, 0.023 mmol, 22% yield) as an off-white solid. $^1$H NMR (500 MHz, DMSO-$d_6$) δ 8.95 (d, J=4.4 Hz, 1H), 8.21 (dd, J=9.2, 5.5 Hz, 1H), 7.85 (d, J=8.5 Hz, 1H), 7.79 (d, J=2.6 Hz, 1H), 7.75 (td, J=8.9, 2.9 Hz, 1H), 7.57 (d, J=4.4 Hz, 1H), 7.50 (dd, J=10.3, 3.0 Hz, 1H), 7.44 (d, J=8.6 Hz, 1H), 3.92 (q, J=8.9 Hz, 2H), 1.83 (dt, J=13.1, 6.7 Hz, 1H), 1.43 (d, J=5.5 Hz, 2H), 1.16 (s, 3H), 0.94 (dd, J=6.7, 3.2 Hz, 6H); $^{19}$F NMR (376 MHz, DMSO-d6) δ −61.01, −244.69; LCMS (ESI) m/e 421.2 [(M+H)$^+$, calcd C$_{23}$H$_{25}$F$_4$N$_2$O$_1$, 421.2]; LC/MS retention time (method B): $t_R$=1.80 min.

Example 74

(S)-1-(2-cyclopropyl-4-(quinolin-4-yl)phenoxy)-2,4-dimethylpentan-2-amine

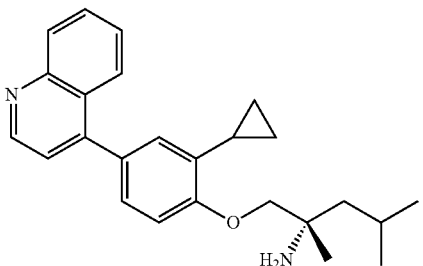

Prepared as in Example 32.

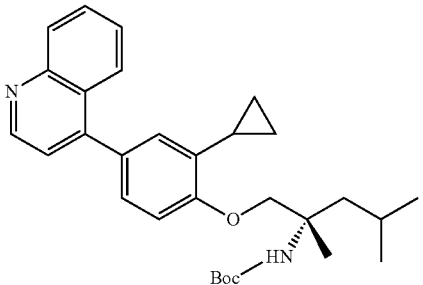 [SMILES: CC(C)C[C@@](C)(COc1ccc(-c2ccnc3ccccc23)cc1C1CC1)NC(=O)OC(C)(C)C]

Part A: (S)-tert-butyl (1-(2-cyclopropyl-4-(quinolin-4-yl)phenoxy)-2,4-dimethylpentan-2-yl)carbamate LCMS (ESI) m/e 475.1 [(M+H)$^+$, calcd C$_3$H$_{39}$N$_2$O$_3$, 475.3]; LC/MS retention time (method B): $t_R$=2.21 min.

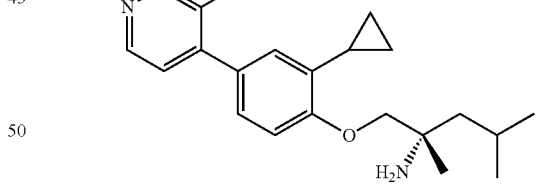

Part B: (S)-1-(2-cyclopropyl-4-(quinolin-4-yl)phenoxy)-2,4-dimethylpentan-2-amine Obtained (12.7 mg, 0.032 mmol, 33% yield) as an off-white solid. $^1$H NMR (500 MHz, DMSO-$d_6$) δ 8.90 (d, J=4.4 Hz, 1H), 8.09 (d, J=8.3 Hz, 1H), 7.90 (d, J=8.5 Hz, 1H), 7.78 (t, J=7.6 Hz, 1H), 7.60 (t, J=7.6 Hz, 1H), 7.42 (d, J=4.4 Hz, 1H), 7.32 (d, J=8.2 Hz, 1H), 7.10 (d, J=8.3 Hz, 1H), 7.03 (s, 1H), 3.82 (s, 2H), 2.27 (p, J=6.9 Hz, 1H), 1.85 (dt, J=12.7, 6.6 Hz, 1H), 1.47 (q, J=8.2, 7.0 Hz, 2H), 1.20 (s, 3H), 0.95 (q, J=7.9, 7.2 Hz, 8H), 0.71 (t, J=4.1 Hz, 2H); LCMS (ESI) m/e 375.1 [(M+H)$^+$, calcd C$_{25}$H$_{31}$N$_2$O$_1$, 375.2]; LC/MS retention time (method B): $t_R$=1.69 min.

Example 75

1-(2-chloro-6-fluoro-4-(quinolin-4-yl)phenoxy)-2,4-dimethylpentan-2-amine

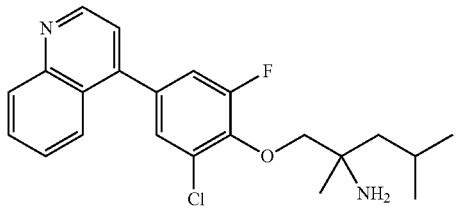 [SMILES: CC(C)CC(C)(N)COc1c(F)cc(-c2ccnc3ccccc23)cc1Cl]

Prepared as in Example 29.

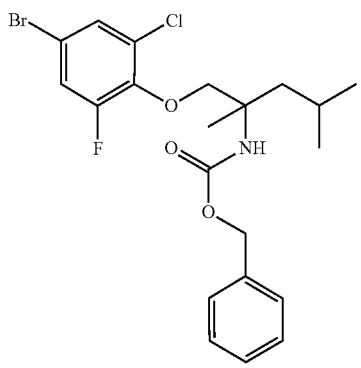 [SMILES: CC(C)CC(C)(COc1c(F)cc(Br)cc1Cl)NC(=O)OCc1ccccc1]

Part A: Benzyl (1-(4-bromo-2-chloro-6-fluorophenoxy)-2,4-dimethylpentan-2-yl)carbamate An NMP (0.3 mL) suspension of 4-bromo-2-chloro-6-fluorophenol (23.00 mg, 0.102 mmol), sodium carbonate (35 mg, 0.330 mmol) and benzyl 4-isobutyl-4-methyl-1,2,3-oxathiazolidine-3-carboxylate 2,2-dioxide (0.0334 g, 0.102 mmol) was heated at 50° C. overnight. The reaction was diluted with ethyl acetate and washed with water (3×). The ethyl acetate layer was separated, dried ($Na_2SO_4$), filtered and concentrated under reduced pressure. The crude material was carried on without further purification. LCMS (ESI) m/e 496.0 [(M+Na)$^+$, calcd $C_2H_{24}ClBrFNO_3Na$, 494.1]; LC/MS retention time (method B): $t_R$=2.59 min.

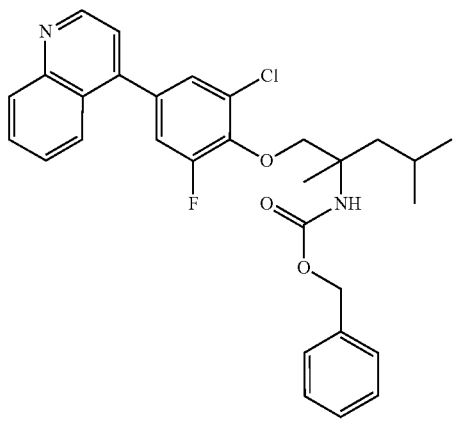 [SMILES: CC(C)CC(C)(COc1c(F)cc(-c2ccnc3ccccc23)cc1Cl)NC(=O)OCc1ccccc1]

Part B: Benzyl (1-(2-chloro-6-fluoro-4-(quinolin-4-yl)phenoxy)-2,4-dimethylpentan-2-yl)carbamate LCMS (ESI) m/e 521.4 [(M+H)$^+$, calcd $C_{30}H_{31}ClFN_2O_3$, 521.2]; LC/MS retention time (method A): $t_R$=2.38 min.

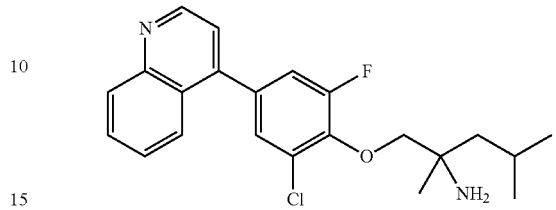

Part C: 1-(2-chloro-6-fluoro-4-(quinolin-4-yl)phenoxy)-2,4-dimethylpentan-2-amine Triethylsilane(0.1 ml, 0.626 mmol) was added to a $CH_2Cl_2$ (0.2 mL) suspension of palladium(II) acetate (2 mg, 8.91 μmol) and triethylamine (0.1 ml, 0.717 mmol) at rt. The reaction turned black. The solution was stirred at room temperature for 10 min before addition of $CH_2Cl_2$ (0.2 mL) solution of benzyl (1-(2-chloro-6-fluoro-4-(quinolin-4-yl)phenoxy)-2,4-dimethylpentan-2-yl)carbamate (0.0441 g, 0.085 mmol) (the flask contain the benzyl (1-(2-chloro-6-fluoro-4-(quinolin-4-yl)phenoxy)-2,4-dimethylpentan-2-yl)carbamate (0.0441 g, 0.085 mmol) was rinsed with $CH_2Cl_2$ (0.2 mL) and added to the reaction mixture). The reaction was stirred at room temperature overnight. The solvent was removed under reduced pressure and the crude material was purified via reverse phase HPLC (acetonitrile/water/10 mM ammonium acetate) to afford 1-(2-chloro-6-fluoro-4-(quinolin-4-yl)phenoxy)-2,4-dimethylpentan-2-amine (8.9 mg, 0.022 mmol, 26% yield.) $^1$H NMR (500 MHz, DMSO-d6) δ 8.96 (d, J=4.4 Hz, 1H), 8.13 (d, J=8.4 Hz, 1H), 7.88 (s, 1H), 7.83 (s, 1H), 7.66 (s, 1H), 7.60-7.50 (m, 3H), 3.98-3.90 (m, 2H), 1.89-1.81 (m, 1H), 1.44 (dd, J=14.9, 5.7 Hz, 2H), 1.18 (s, 3H), 0.97 (dd, J=9.4, 6.8 Hz, 6H); LCMS (ESI) m/e 387.2 [(M+H)$^+$, calcd $C_{22}H_{25}FClN_2O$, 387.2]; LC/MS retention time (method B): $t_R$=1.70 min.

Example 76

(S)-1-((5-(7-fluoroquinolin-4-yl)-3-methylpyridin-2-yl)oxy)-2,4-dimethylpentan-2-amine

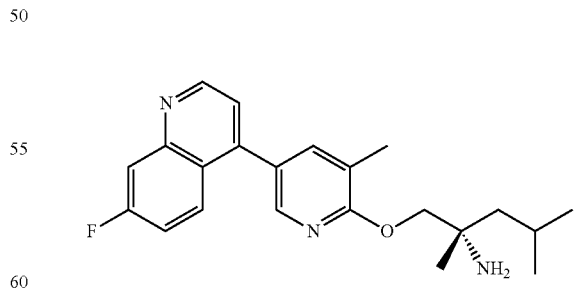

Intermediates prepared as described in Example 19. A mixture of potassium acetate (0.026 g, 0.266 mmol), (S)-1-((5-bromo-3-methylpyridin-2-yl)oxy)-2,4-dimethylpentan-2-amine (0.0267 g, 0.089 mmol), 4,4,4',4',5,5,5',5'-octamethyl-2,2'-bi(1,3,2-dioxaborolane) (0.027 g, 0.106 mmol) in dioxane (1 mL) underwent vacuum/backfill $N_2$ (5×). $PdCl_2$ (dppf) (1.946 mg, 2.66 µmol) was added to the reaction mixture and the reaction was heated at 80° C. overnight. The reaction mixture was cooled to room temperature. PdCl₂ (dppf) (3.26 mg, 4.45 µmol), sodium carbonate (0.089 mL, 0.178 mmol, 2N), 4-chloro-7-fluoroquinoline (16.16 mg, 0.089 mmol) and (S)-2,4-dimethyl-1-((3-methyl-5-(4,4,5,5-tetramethyl-1,3,2-dioxaborolan-2-yl)pyridin-2-yl)oxy)pentan-2-amine (31.0 mg, 0.089 mmol) in dioxane (1.2 mL) were added to the vessel mixture and the mixture was degassed via vacuum/N₂ fill cycle three times. The reaction mixture was heated at 130° C. for 4 h. The reaction was cooled to rt then diluted with ethyl acetate and washed with water (2×) followed by brine. The ethyl acetate layer was separated, dried (Na₂SO₄), filtered and concentrated under reduced pressure. The crude was purified via reverse phase HPLC (acetonitrile/water/10 mM ammonium acetate) to afford (S)-1-((5-(7-fluoroquinolin-4-yl)-3-methylpyridin-2-yl)oxy)-2,4-dimethylpentan-2-amine (15.2 mg, 0.041 mmol, 47% yield) as an off-white solid. $^1$H NMR (500 MHz, DMSO-d₆) δ 8.99-8.95 (m, 1H), 8.20-8.16 (m, 1H), 7.98 (dd, J=9.2, 6.2 Hz, 1H), 7.88-7.83 (m, 1H), 7.81 (s, 1H), 7.59-7.53 (m, 1H), 7.49 (d, J=4.4 Hz, 1H), 4.11 (d, J=4.4 Hz, 2H), 3.46 (br. s., 2H), 1.90 (s, 3H), 1.87-1.79 (m, 1H), 1.45 (t, J=6.2 Hz, 2H), 1.17 (s, 3H), 0.95 (t, J=6.1 Hz, 6H); LCMS (ESI) m/e 386.2 [(M+H)⁺, calcd C₂₂H₂₇FN₃O, 386.2]; LC/MS retention time (method B): $t_R$=1.78 min.

Example 77

(S)-2-((2-amino-2,4-dimethylpentyl)oxy)-5-(5,7-difluoroquinolin-4-yl)nicotinonitrile

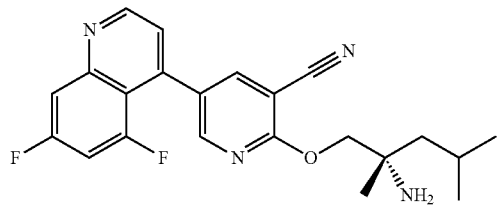 [SMILES: CC(C)C[C@](C)(N)COc1ncc(-c2ccnc3cc(F)cc(F)c23)cc1C#N]

Prepared as in Example 53.

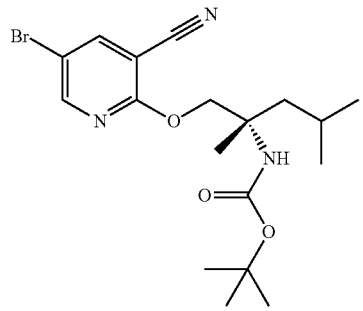 [SMILES: CC(C)C[C@@](C)(COc1ncc(Br)cc1C#N)NC(=O)OC(C)(C)C]

Part A: (S)-tert-butyl (1-((5-bromo-3-cyanopyridin-2-yl)oxy)-2,4-dimethylpentan-2-yl)carbamate LCMS (ESI) m/e 434.1 [(M+Na)⁺, calcd C₁₈H₂₆BrN₃O₃Na, 434.1]; LC/MS retention time (method B): $t_R$=2.38 min.

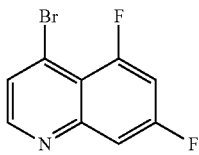 [SMILES: Fc1cc(F)c2c(Br)ccnc2c1]

Part B: 4-bromo-5,7-difluoroquinoline

To a 20 mL microwave tube was added 4-chloro-5,7-difluoroquinoline (0.159 g, 0.795 mmol) and propionitrile (1 mL), followed by TMS-Br (0.206 mL, 1.59 mmol) at room temperature. A precipitate formed. The tube was sealed and heated to 100° C. overnight. The reaction was cooled to room temperature. The crude mixture was poured into iced NaOH (1N, 3 mL) and the tube was washed with water.

The aqueous layer was extracted with diethyl ether (3×). The diethyl ether layers were combined, dried (Na₂SO₄), filtered and concentrated under reduced pressure to give 4-bromo-5,7-difluoroquinoline (14.2 mg, 0.582 mmol, 73% yield) as a yellow solid. LCMS (ESI) m/e 243.8 [(M+Na)⁺, calcd C₉H₅BrNF₂, 244.0]; LC/MS retention time (method B): $t_R$=2.04 min.

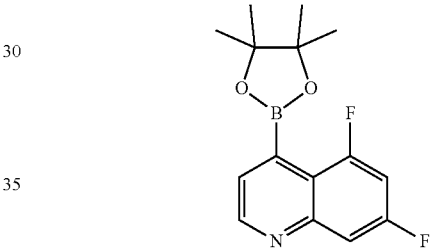

Part C: 5,7-difluoro-4-(4,4,5,5-tetramethyl-1,3,2-dioxaborolan-2-yl)quinoline

A mixture of potassium acetate (0.122 g, 1.242 mmol), 4-bromo-5,7-difluoroquinoline (0.1010 g, 0.414 mmol), 4,4,4',4',5,5,5',5'-octamethyl-2,2'-bi(1,3,2-dioxaborolane) (0.126 g, 0.497 mmol) in dioxane (3 mL) underwent a cycle of vacuum/backfill with nitrogen 5 times. PdCl₂(dppf) (9.09 mg, 0.012 mmol) was added to the reaction mixture at room temperature and the reaction was heated at 80° C. overnight. The crude was used as it is in the next step.

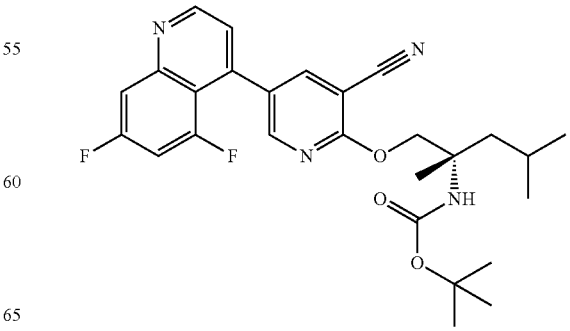

Part D: (S)-tert-butyl (1-((3-cyano-5-(5,7-difluoro-quinolin-4-yl)pyridin-2-yl)oxy)-2,4-dimethylpentan-2-yl)carbamate A mixture of sodium carbonate (0.138 mL, 0.276 mmol), 1,1'-bis(diphenylphosphino)ferrocene-palladium(II) dichloride dichloromethane complex (7.89 mg, 9.66 μmol), 5,7-difluoro-4-(4,4,5,5-tetramethyl-1,3,2-dioxaborolan-2-yl)quinoline (0.040 g, 0.138 mmol) and (S)-tert-butyl (1-((5-bromo-3-cyanopyridin-2-yl)oxy)-2,4-dimethylpentan-2-yl)carbamate (0.057 g, 0.138 mmol) in dioxane (2 mL) (degassed) was heated at 100° C. for 3 h. The reaction was diluted with ethyl acetate and washed with water (3×). The ethyl acetate layer was dried (Na$_2$SO$_4$), filtered and concentrated under reduced pressure. The residue was purified by silica gel chromatography (0-10-25% ethyl acetate in hexanes) to afford (S)-tert-butyl (1-((3-cyano-5-(5,7-difluoroquinolin-4-yl)pyridin-2-yl)oxy)-2,4-dimethylpentan-2-yl)carbamate (0.0372 g, 0.075 mmol, 54% yield) as a brown solid. LCMS (ESI) m/e 519.0 [(M+Na)$^+$, calcd C$_{27}$H$_{30}$F$_2$N$_4$O$_3$Na, 519.2]; LC/MS retention time (method B): t$_R$=2.38 min.

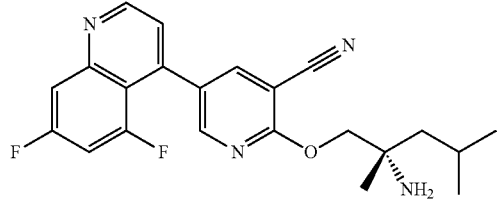 [SMILES: CC(C)C[C@](C)(N)COc1ncc(-c2ccnc3cc(F)cc(F)c23)cc1C#N]

Part E: (S)-2-((2-amino-2,4-dimethylpentyl)oxy)-5-(5,7-difluoroquinolin-4-yl)nicotinonitrile $^1$H NMR (500 MHz, DMSO-d$_6$) δ 9.04 (d, J=4.4 Hz, 1H), 8.59 (s, 1H), 8.54 (br. s., 1H), 7.82 (d, J=9.2 Hz, 1H), 7.70-7.59 (m, 1H), 7.54 (d, J=4.4 Hz, 1H), 4.30-4.17 (m, 2H), 3.44 (br. s., 2H), 1.87-1.79 (m, 1H), 1.50-1.36 (m, 2H), 1.16 (s, 3H), 0.96 (d, J=2.9 Hz, 3H), 0.94 (d, J=2.9 Hz, 3H); LCMS (ESI) m/e 397.2 [(M+H)$^+$, calcd C$_{22}$H$_{23}$F$_2$N$_4$O, 397.2]; LC/MS retention time (method B): t$_R$=2.39 min.

Example 78

(S)-1-((3-chloro-5-(quinolin-4-yl)pyridin-2-yl)oxy)-2,4-dimethylpentan-2-amine

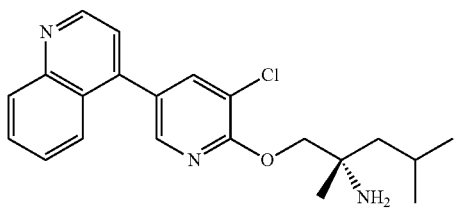

Prepared as in example 77.

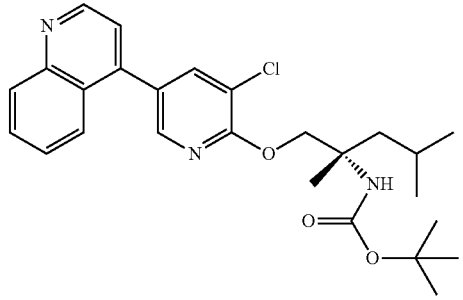 [SMILES: CC(C)C[C@@](C)(COc1ncc(-c2ccnc3ccccc23)cc1Cl)NC(=O)OC(C)(C)C]

Part A: Boc (S)-1-((3-chloro-5-(quinolin-4-yl)pyridin-2-yl)oxy)-2,4-dimethylpentan-2-amine (ESI) m/e 470.4 [(M+H)$^+$, calcd C$_{26}$H$_{33}$ClN$_3$O$_3$, 470.2]; LC/MS retention time (method A): t$_R$=2.45 min.

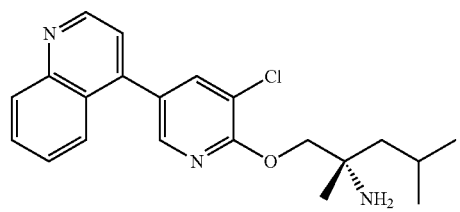 [SMILES: CC(C)C[C@](C)(N)COc1ncc(-c2ccnc3ccccc23)cc1Cl]

Part B: (S)-1-((3-chloro-5-(quinolin-4-yl)pyridin-2-yl)oxy)-2,4-dimethylpentan-2-amine $^1$H NMR (500 MHz, DMSO-d$_6$) δ 8.99 (d, J=4.4 Hz, 1H), 8.36 (d, J=1.8 Hz, 1H), 8.25 (d, J=1.8 Hz, 1H), 7.96 (s, 1H), 7.89-7.80 (m, 2H), 7.67 (t, J=7.5 Hz, 1H), 7.55 (d, J=4.4 Hz, 1H), 4.59-4.42 (m, 2H), 1.94-1.61 (m, 3H), 1.43 (s, 3H), 0.98 (t, J=6.4 Hz, 6H); LCMS (ESI) m/e 370.3 [(M+H)$^+$, calcd C$_{21}$H$_{25}$ClN$_3$O, 370.2]; LC/MS retention time (method A): t$_R$=2.09 min.

Example 79

(S)-1-((3-methoxy-5-(quinolin-4-yl)pyridin-2-yl)oxy)-2,4-dimethylpentan-2-amine

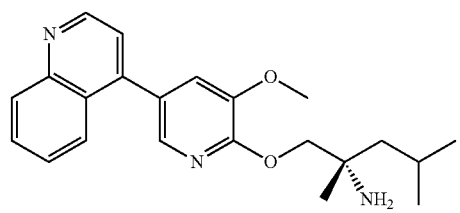 [SMILES: COc1cc(-c2ccnc3ccccc23)cnc1OC[C@@](C)(N)CC(C)C]

Prepared as in Example 77. Obtained (S)-1-((3-methoxy-5-(quinolin-4-yl)pyridin-2-yl)oxy)-2,4-dimethylpentan-2-amine (5.4 mg, 0.014 mmol, 23% yield) as an off-white solid. $^1$H NMR (500 MHz, DMSO-d$_6$) δ 8.96 (d, J=4.4 Hz, 1H), 8.12 (d, J=8.4 Hz, 1H), 7.97 (d, J=8.4 Hz, 1H), 7.86 (d, J=1.5 Hz, 1H), 7.82 (t, J=7.5 Hz, 1H), 7.64 (t, J=7.7 Hz, 1H), 7.53 (d, J=4.4 Hz, 1H), 7.51 (d, J=1.5 Hz, 1H), 4.17-4.06 (m, 2H), 3.60 (br. s., 3H), 1.84 (dt, J=12.8, 6.4 Hz, 1H), 1.47-1.36 (m, 2H), 1.15 (s, 3H), 0.95 (t, J=7.2 Hz, 6H); LCMS (ESI) m/e 366.0 [(M+H)⁺, calcd $C_{22}H_{28}N_3O_2$, 366.2]; LC/MS retention time (method B): $t_R$=1.55 min.

Example 80

(S)-2-((2-amino-2,4-dimethylpentyl)oxy)-5-(1,6-naphthyridin-4-yl)nicotinonitrile

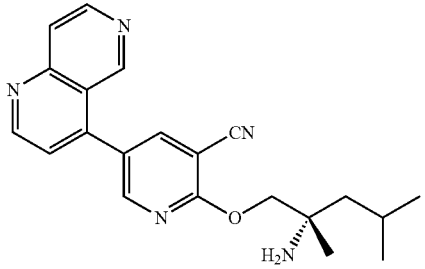

Prepared as in Example 77.

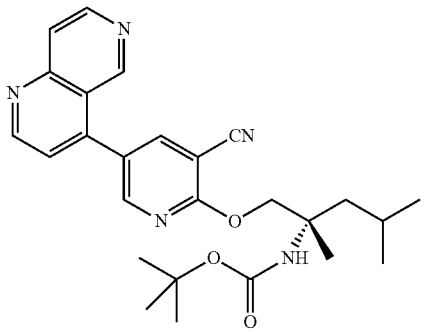 [SMILES: CC(C)C[C@@](C)(COc1ncc(-c2ccnc3ccncc23)cc1C#N)NC(=O)OC(C)(C)C]

Part A: (S)-tert-butyl (1-((3-cyano-5-(1,6-naphthyridin-4-yl)pyridin-2-yl)oxy)-2,4-dimethylpentan-2-yl)carbamate LCMS (ESI) m/e 484.2 [(M+Na)⁺, calcd $C_{26}H_{31}F_2N_5Na_1O_3$, 484.2]; LC/MS retention time (method B): $t_R$=2.14 min.

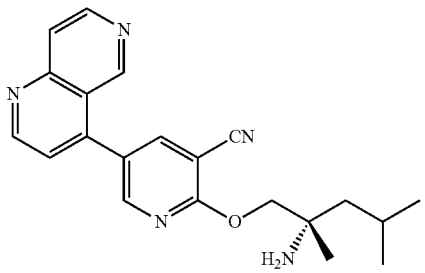 [SMILES: CC(C)C[C@](C)(N)COc1ncc(-c2ccnc3ccncc23)cc1C#N]

Part B: (S)-2-((2-amino-2,4-dimethylpentyl)oxy)-5-(1,6-naphthyridin-4-yl)nicotinonitrile Obtained (S)-2-((2-amino-2,4-dimethylpentyl)oxy)-5-(1,6-naphthyridin-4-yl)nicotinonitrile (22 mg, 0.058 mmol, 66% yield) as an off-white solid. ¹H NMR (500 MHz, DMSO-d₆) δ 9.28 (s, 1H), 9.23 (d, J=4.4 Hz, 1H), 8.84 (d, J=5.7 Hz, 1H), 8.78 (d, J=2.4 Hz, 1H), 8.75 (d, J=2.5 Hz, 1H), 8.04 (d, J=5.8 Hz, 1H), 7.74 (d, J=4.5 Hz, 1H), 4.68 (d, J=11.6 Hz, 1H), 4.56 (d, J=11.5 Hz, 1H), 1.89 (dq, J=12.7, 6.2 Hz, 1H), 1.81 (dd, J=14.4, 5.5 Hz, 1H), 1.64 (dd, J=14.4, 5.6 Hz, 1H), 1.44 (s, 3H), 1.01 (d, J=6.6 Hz, 6H); LCMS (ESI) m/e 362.2 [(M+H)⁺, calcd $C_{21}H_{24}N_5O_1$, 362.2]; LC/MS retention time (method B): $t_R$=1.56 min.

Example 81

(S)-2,4-dimethyl-1-((2-methyl-6-(quinolin-4-yl)pyridin-3-yl)oxy)pentan-2-amine

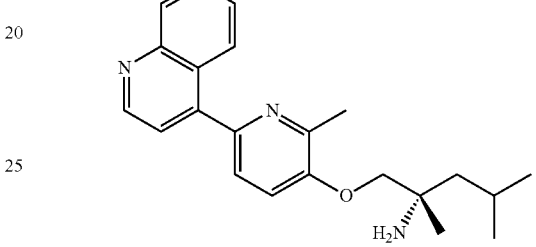

Prepared as in Example 77. Obtained (S)-2,4-dimethyl-1-((2-methyl-6-(quinolin-4-yl)pyridin-3-yl)oxy)pentan-2-amine (10.3 mg, 0.028 mmol, 43% yield) as an off-white solid. ¹H NMR (500 MHz, DMSO-d₆) δ 8.96 (d, J=4.4 Hz, 1H), 8.25 (d, J=8.5 Hz, 1H), 8.10 (d, J=8.5 Hz, 1H), 7.79 (t, J=7.6 Hz, 1H), 7.65-7.56 (m, 3H), 7.51 (d, J=8.4 Hz, 1H), 3.81 (d, J=2.2 Hz, 2H), 2.53 (s, 3H), 1.84 (dq, J=12.6, 6.4 Hz, 1H), 1.50-1.38 (m, 2H), 1.17 (s, 3H), 0.96 (t, J=6.2 Hz, 6H); LCMS (ESI) m/e 350.3 [(M+H)⁺, calcd $C_{22}H_{28}N_3O_1$, 350.2]; LC/MS retention time (method A): $t_R$=1.86 min.

Example 82

(S)-2,4-dimethyl-1-((4-methyl-6-(quinolin-4-yl)pyridin-3-yl)oxy)pentan-2-amine

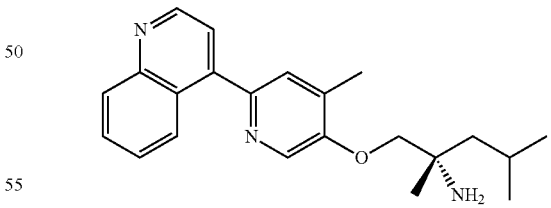

Prepared as in Example 77. Obtained (S)-2,4-dimethyl-1-((4-methyl-6-(quinolin-4-yl)pyridin-3-yl)oxy)pentan-2-amine (11 mg, 0.030 mmol, 39% yield) as an off-white solid. ¹H NMR (500 MHz, DMSO-d₆) δ 8.97 (d, J=4.4 Hz, 1H), 8.44 (s, 1H), 8.25 (d, J=8.8 Hz, 1H), 8.10 (d, J=8.4 Hz, 1H), 7.80 (t, J=7.7 Hz, 1H), 7.67-7.57 (m, 3H), 3.94 (s, 2H), 2.34 (s, 3H), 1.87-1.81 (m, 1H), 1.52-1.40 (m, 2H), 1.18 (s, 3H), 0.96 (t, J=6.8 Hz, 6H); LCMS (ESI) m/e 350.1 [(M+H)⁺, calcd $C_{22}H_{28}N_3O$, 350.2]; LC/MS retention time (method B): $t_R$=1.67 min.

Example 83

(S)-1-((2-chloro-6-(quinolin-4-yl)pyridin-3-yl)oxy)-2,4-dimethylpentan-2-amine

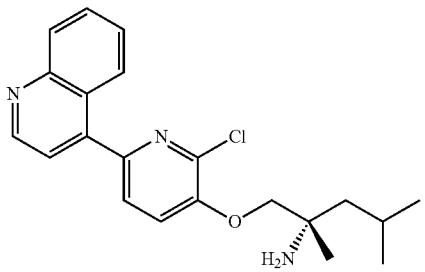

Prepared as in Example 77.

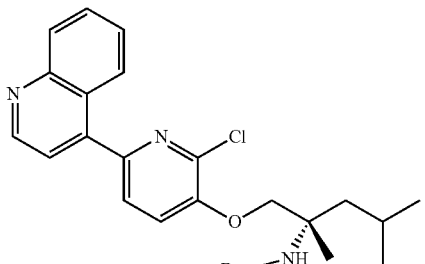

Part A: (S)-tert-butyl (1-((2-chloro-6-(quinolin-4-yl)pyridin-3-yl)oxy)-2,4-dimethylpentan-2-yl)carbamate LCMS (ESI) m/e 470.0 [(M+H)$^+$, calcd $C_{26}H_{33}ClN_3O_3$, 470.2]; LC/MS retention time (method B): $t_R$=2.15 min.

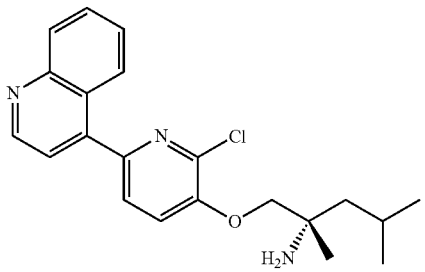 [SMILES: CC(C)C[C@](C)(N)COc1ccc(-c2ccnc3ccccc23)nc1Cl]

Part B: (S)-1-((2-chloro-6-(quinolin-4-yl)pyridin-3-yl)oxy)-2,4-dimethylpentan-2-amine Obtained (6.3 mg, 0.016 mmol, 36% yield) as an off-white solid. $^1$H NMR (500 MHz, DMSO-d$_6$) δ 9.00 (d, J=4.4 Hz, 1H), 8.20 (d, J=8.5 Hz, 1H), 8.13 (d, J=8.4 Hz, 1H), 7.86-7.77 (m, 3H), 7.69-7.60 (m, 2H), 3.97-3.87 (m, 2H), 1.85 (dt, J=12.8, 6.5 Hz, 1H), 1.44 (t, J=4.8 Hz, 2H), 1.17 (s, 3H), 0.96 (t, J=6.0 Hz, 6H); LCMS (ESI) m/e 370.0 [(M+H)$^+$, calcd $C_{21}H_{25}Cl_1N_3O_1$, 370.2]; LC/MS retention time (method B): $t_R$=1.57 min.

Example 84

(S)-1-(4-(1H-pyrrolo[2,3-b]pyridin-4-yl)-2-(trifluoromethyl)phenoxy)-2,4-dimethylpentan-2-amine

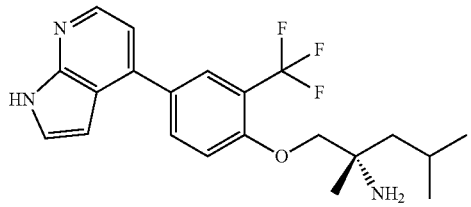 [SMILES: CC(C)C[C@](C)(N)COc1ccc(-c2ccnc3[nH]ccc23)cc1C(F)(F)F]

Prepared as in example 19 to obtain (S)-1-(4-(1H-pyrrolo[2,3-b]pyridin-4-yl)-2-(trifluoromethyl)phenoxy)-2,4-dimethylpentan-2-amine (27 mg, 0.069 mmol, 79% yield) as an off-white solid. $^1$H NMR (400 MHz, CHLOROFORM-d) δ 8.36 (d, J=5.0 Hz, 1H), 8.00 (d, J=2.0 Hz, 1H), 7.89 (dd, J=8.5, 2.0 Hz, 1H), 7.41 (d, J=3.5 Hz, 1H), 7.18-7.08 (m, 2H), 6.68 (d, J=3.5 Hz, 1H), 3.92-3.84 (m, 2H), 1.82-1.77 (m, 1H), 1.60-1.48 (m, 2H), 1.28 (s, 3H), 1.01 (dd, J=9.0, 6.8 Hz, 6H); $^{19}$F NMR (376 MHz, CHLOROFORM-d) δ −62.31 (s, 3F); LCMS (ESI) m/e 392.2 [(M+H)$^+$, calcd $C_{21}H_{25}F_3N_3O$, 392.2]; LC/MS retention time (method B): $t_R$=1.81 min.

Example 85

(S)-1-(4-(1,6-naphthyridin-4-yl)-2-(trifluoromethyl)phenoxy)-2,4-dimethylpentan-2-amine

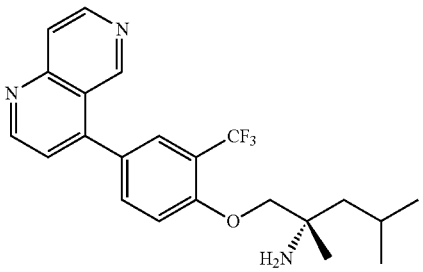

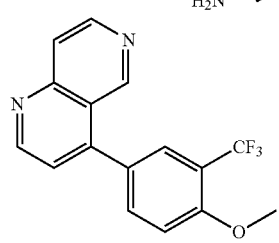

Part A: 4-(4-methoxy-3-(trifluoromethyl)phenyl)-1,6-naphthyridine

To a 20 mL vial was added 4-chloro-1,6-naphthyridine (200 mg, 1.215 mmol), (4-methoxy-3-(trifluoromethyl)phenyl)boronic acid (321 mg, 1.458 mmol), and potassium phosphate tribasic (4.86 mL, 2.430 mmol) in THF (2.5 mL) to give a yellow suspension. After degassing with N$_2$ for 5 min, 2$^{nd}$ generation XPHOS precatalyst (19.12 mg, 0.024 mmol) was added. The mixture was sealed under nitrogen and heated at 40° C. for 2 h. The reaction mixture was cooled to rt and diluted with water and EtOAc. The layers were separated. The organic layer was washed with brine, dried (Na$_2$SO$_4$) and concentrated under reduced pressure. The residue was purified by silica gel chromatography (up to 8% MeOH/CH$_2$Cl$_2$) to afford 4-(4-methoxy-3-(trifluoromethyl)phenyl)-1,6-naphthyridine (369 mg, 1.213 mmol, quantitative yield) as a light yellow solid: $^1$H NMR (400 MHz, Chloroform-d) δ 9.37 (d, J=0.9 Hz, 1H), 9.14 (d, J=4.5 Hz, 1H), 8.83 (d, J=5.9 Hz, 1H), 8.03 (dd, J=6.0, 0.9 Hz, 1H), 7.80 (d, J=2.2 Hz, 1H), 7.73 (dd, J=8.5, 2.2 Hz, 1H), 7.47 (d, J=4.5 Hz, 1H), 7.23 (d, J=8.6 Hz, 1H), 4.05 (s, 3H); $^{19}$F NMR (376 MHz, Chloroform-d) δ −62.63; LCMS (ESI) m/e 305.2 [(M+H)$^+$, calcd C$_{16}$H$_{12}$F$_3$N$_2$O$_1$, 305.1]; LC/MS retention time (method A): $t_R$=1.86 min.

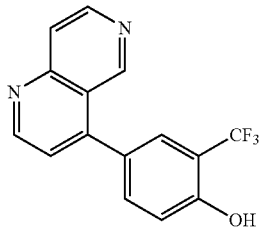 [SMILES: Oc1ccc(-c2ccnc3ccncc23)cc1C(F)(F)F]

Part B: 4-(1,6-naphthyridin-4-yl)-2-(trifluoromethyl)phenol

To a 250 mL round-bottomed flask was added 4-(4-methoxy-3-(trifluoromethyl)phenyl)-1,6-naphthyridine (369 mg, 1.213 mmol) in CH$_2$Cl$_2$ (5 mL) under nitrogen to give a yellow solution. BBr$_3$ (12.13 mL, 12.13 mmol) was slowly added. The mixture was refluxed under nitrogen for 5 h. The reaction was slowly quenched with 1N NaOH to adjust the pH to ~5. EtOAc was added. The layers were separated. The aqueous layer was extracted with EtOAc. The combined organic layers were washed with brine, dried (Na$_2$SO$_4$) and concentrated under reduced pressure. The residue was purified by silica gel chromatography (up to 8% MeOH/CH$_2$Cl$_2$) to afford 4-(1,6-naphthyridin-4-yl)-2-(trifluoromethyl)phenol (124 mg, 0.427 mmol, 35%) as a white solid: $^1$H NMR (400 MHz, Chloroform-d) δ 9.45 (s, 1H), 9.21 (d, J=4.7 Hz, 1H), 8.84 (d, J=6.1 Hz, 1H), 8.16 (d, J=6.1 Hz, 1H), 7.89-7.75 (m, 1H), 7.60 (q, J=3.4 Hz, 2H), 7.34 (d, J=8.4 Hz, 1H); $^{19}$F NMR (376 MHz, Chloroform-d) δ −62.58; LCMS (ESI) m/e 291.2 [(M+H)$^+$, calcd C$_{15}$H$_{10}$F$_3$N$_2$O$_1$, 291.2]; LC/MS retention time (method B): $t_R$=1.59 min.

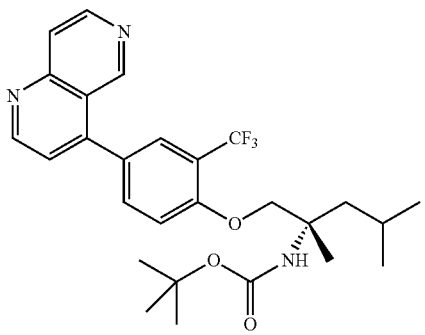 [SMILES: CC(C)C[C@@](C)(COc1ccc(-c2ccnc3ccncc23)cc1C(F)(F)F)NC(=O)OC(C)(C)C]

Part C: (S)-tert-butyl (1-(4-(1,6-naphthyridin-4-yl)-2-(trifluoromethyl)phenoxy)-2,4-dimethylpentan-2-yl)carbamate LCMS (ESI) m/e 526.2 [(M+Na)$^+$, calcd C$_{27}$H$_{32}$F$_3$N$_3$Na$_1$O$_3$, 526.2]; LC/MS retention time (method B): $t_R$=2.31 min.

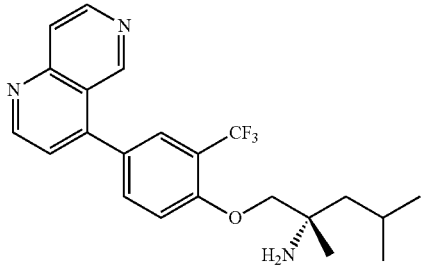

Part D: (S)-1-(4-(1,6-naphthyridin-4-yl)-2-(trifluoromethyl)phenoxy)-2,4-dimethylpentan-2-amine Obtained (35.7 mg, 0.087 mmol, 99% yield) as an off-white solid. $^1$H NMR (500 MHz, DMSO-d6) δ 9.26 (s, 1H), 9.17 (d, J=4.5 Hz, 1H), 8.80 (d, J=5.8 Hz, 1H), 8.01 (d, J=5.9 Hz, 1H), 7.95 (d, J=8.7 Hz, 1H), 7.90 (s, 1H), 7.69 (d, J=4.4 Hz, 1H), 7.47 (d, J=8.6 Hz, 1H), 3.94 (q, J=9.0 Hz, 2H), 1.83 (dq, J=12.9, 6.4 Hz, 1H), 1.44 (dd, J=5.8, 2.6 Hz, 2H), 1.17 (s, 3H), 0.94 (dd, J=6.8, 3.3 Hz, 6H); 19F NMR (376 MHz, DMSO-d6) δ −61.02; LCMS (ESI) m/e 404.2 [(M+H)$^+$, calcd C$_{22}$H$_{25}$F$_3$N$_3$O$_1$, 362.2]; LC/MS retention time (method B): $t_R$=1.79 min.

Example 86

(S)-2-((2-amino-2,4-dimethylpentyl)oxy)-5-(1,6-naphthyridin-4-yl)benzonitrile

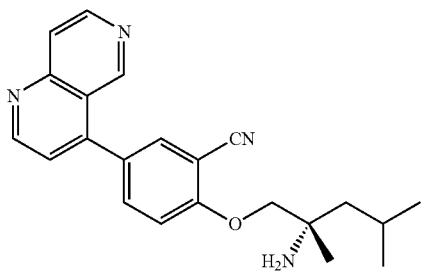

Prepared as in Example 51.

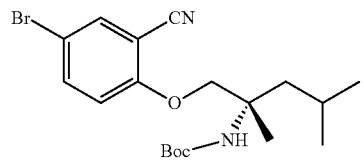 [SMILES: CC(C)C[C@@](C)(COc1ccc(Br)cc1C#N)NC(=O)OC(C)(C)C]

Part A: (S)-tert-butyl (1-(4-bromo-2-cyanophenoxy)-2,4-dimethylpentan-2-yl)carbamate $^1$H NMR (400 MHz, Chloroform-d) δ 7.63 (d, J=2.5 Hz, 1H), 7.58 (dd, J=9.0, 2.5 Hz, 1H), 6.91 (d, J=9.0 Hz, 1H), 4.57 (s, 1H), 4.31 (d, J=9.0 Hz, 1H), 4.09 (d, J=9.0 Hz, 1H), 1.90 (dd, J=14.0, 6.5 Hz, 1H), 1.86-1.75 (m, 1H), 1.47 (dd, J=14.0, 5.0 Hz, 1H), 1.39 (s, 3H), 1.37 (s, 9H), 0.99 (d, J=1.9 Hz, 3H), 0.97 (d, J=1.9 Hz, 3H); LCMS (ESI) m/e 432.9 [(M+Na)$^+$, calcd C$_{19}$H$_{27}$BrN$_2$NaO$_3$, 433.1]; LC/MS retention time (method B): t$_R$=2.38 min.

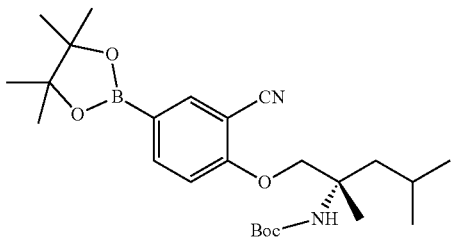 [SMILES: CC(C)C[C@@](C)(COc1ccc(B2OC(C)(C)C(C)(C)O2)cc1C#N)NC(=O)OC(C)(C)C]

Part B: (S)-tert-butyl (1-(2-cyano-4-(4,4,5,5-tetramethyl-1,3,2-dioxaborolan-2-yl)phenoxy)-2,4-dimethylpentan-2-yl)carbamate LCMS (ESI) m/e 481.1 [(M+Na)$^+$, calcd C$_{25}$H$_{39}$BN$_2$NaO$_5$, 481.3]; LC/MS retention time (method B): t$_R$=2.49 min.

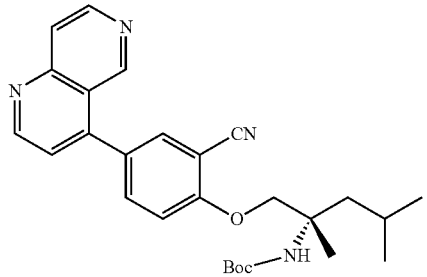 [SMILES: CC(C)C[C@@](C)(COc1ccc(-c2ccnc3ccncc23)cc1C#N)NC(=O)OC(C)(C)C]

Part C: (S)-tert-butyl (1-(2-cyano-4-(1,6-naphthyridin-4-yl)phenoxy)-2,4-dimethylpentan-2-yl)carbamate LCMS (ESI) m/e 483.1 [(M+Na)$^+$, calcd C$_{27}$H$_{32}$N$_4$Na$_1$O$_3$, 483.2]; LC/MS retention time (method B): t$_R$=2.10 min.

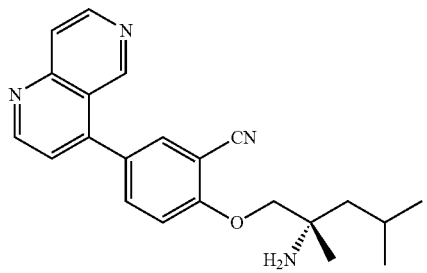

Part D: (S)-2-((2-amino-2,4-dimethylpentyl)oxy)-5-(1,6-naphthyridin-4-yl)benzonitrile Obtained (S)-2-((2-amino-2,4-dimethylpentyl)oxy)-5-(1,6-naphthyridin-4-yl)benzonitrile (6.7 mg, 0.017 mmol, 34% yield) as an off-white solid. $^1$H NMR (500 MHz, DMSO-d$_6$) δ 9.27 (s, 1H), 9.17 (d, J=4.5 Hz, 1H), 8.80 (d, J=5.8 Hz, 1H), 8.11 (d, J=2.2 Hz, 1H), 8.01 (d, J=5.8 Hz, 1H), 7.97 (dd, J=8.7, 2.3 Hz, 1H), 7.67 (d, J=4.5 Hz, 1H), 7.47 (d, J=8.8 Hz, 1H), 4.03-3.92 (m, 2H), 1.85 (dt, J=12.6, 6.3 Hz, 1H), 1.51-1.40 (m, 2H), 1.18 (s, 3H), 0.96 (dd, J=6.7, 4.3 Hz, 6H); LCMS (ESI) m/e 361.0 [(M+H)$^+$, calcd C$_{22}$H$_{25}$N$_4$O$_1$, 361.2]; LC/MS retention time (method B): t$_R$=1.58 min.

Example 87

(S)-2-((2-amino-2,4-dimethylpentyl)oxy)-5-(1,5-naphthyridin-4-yl)benzonitrile

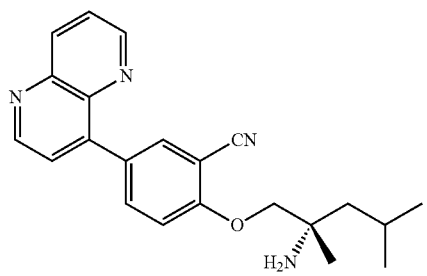 [SMILES: CC(C)C[C@](C)(N)COc1ccc(-c2ccnc3cccnc23)cc1C#N]

Prepared as in Example 51.

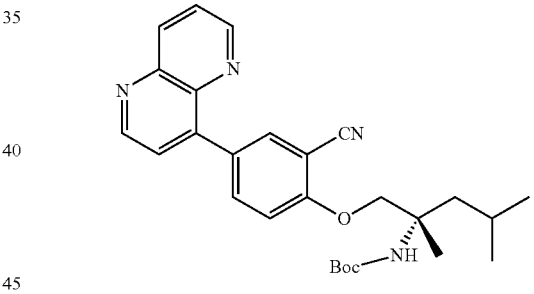

Part A: (S)-tert-butyl (1-(2-cyano-4-(1,5-naphthyridin-4-yl)phenoxy)-2,4-dimethylpentan-2-yl)carbamate LCMS (ESI) m/e 483.1 [(M+Na)$^+$, calcd C$_{27}$H$_{32}$N$_4$Na$_1$O$_3$, 483.2]; LC/MS retention time (method B): t$_R$=2.22 min.

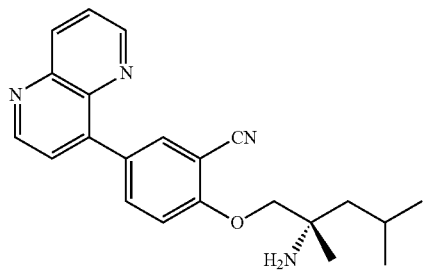

Part B: (S)-2-((2-amino-2,4-dimethylpentyl)oxy)-5-(1,5-naphthyridin-4-yl)benzonitrile Obtained (5.5 mg, 0.015 mmol, 29% yield) as an off-white solid. $^1$H NMR (500 MHz, DMSO-$d_6$) δ 9.06 (t, J=4.6 Hz, 2H), 8.51 (d, J=8.4 Hz, 1H), 8.23 (d, J=2.3 Hz, 1H), 8.18-8.11 (m, 1H), 7.90-7.82 (m, 2H), 7.41 (d, J=8.9 Hz, 1H), 3.65 (s, 2H), 1.84 (dt, J=12.4, 6.5 Hz, 1H), 1.45 (dd, J=5.6, 2.5 Hz, 2H), 1.17 (s, 3H), 0.95 (dd, J=6.7, 3.9 Hz, 6H). (OCH2 was likely buried in a broad peak); LCMS (ESI) m/e 361.0 [(M+H)$^+$, calcd $C_{22}H_{25}N_4O_1$, 361.2]; LC/MS retention time (method B): $t_R$=1.68 min.

Example 88

(S)-1-(4-(7-chloroquinolin-4-yl)-2-(trifluoromethyl)phenoxy)-2,4-dimethylpentan-2-amine

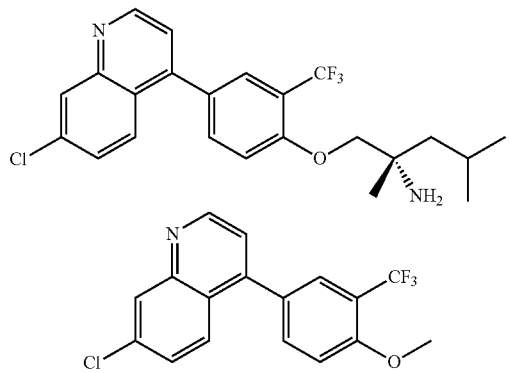

Part A: 7-chloro-4-(4-methoxy-3-(trifluoromethyl)phenyl)quinoline

A mixture of 4,7-dichloroquinoline (810 mg, 4.09 mmol), (4-methoxy-3-(trifluoromethyl)phenyl)boronic acid (900 mg, 4.09 mmol), PdCl$_2$(dppf) (150 mg, 0.205 mmol), cesium carbonate (2000 mg, 6.14 mmol), and 1,4-dioxane (10 mL) were charged to a 20 mL pressure rated vial and a stream of nitrogen was bubbled through for 10 minutes. The vial was sealed, purged of oxygen, and stirred at 90° C. overnight. The resultant mixture was vacuum filtered and the filtrate concentrated under reduced pressure. The reside was purified by silica gel chromatography (5-40% ethyl acetate/hexanes gradient elution) to afford 7-chloro-4-(4-methoxy-3-(trifluoromethyl)phenyl)quinoline (1.04 g, 3.08 mmol, 75% yield) as a white solid. The material was carried on without further purification. LCMS (ESI) m/e 338.1 [(M+H)$^+$, calcd $C_{17}H_2ClF_3NO$, 338.1]; LC/MS retention time (method D): $t_R$=1.13 min.

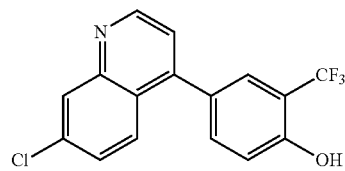 [SMILES: Oc1ccc(-c2ccnc3cc(Cl)ccc23)cc1C(F)(F)F]

Part B: 4-(7-chloroquinolin-4-yl)-2-(trifluoromethyl)phenol

A solution of 7-chloro-4-(4-methoxy-3-(trifluoromethyl)phenyl)quinoline (0.51 g, 1.510 mmol) in dichloromethane (10 mL) 0° C. was treated with BBr$_3$ (3.02 mL, 3.02 mmol). The cooling bath was removed and the reaction solution stirred at ambient temperature overnight. The resultant was cooled to 0° C. and quenched with saturated aqueous sodium bicarbonate. The layers were separated and the aqueous layer was extracted with ethyl acetate (2×10 mL). The combined organics were dried over magnesium sulfate, filtered, and concentrated under reduced pressure to give an orange solid. The crude residue was adsorbed onto silica gel and purified by silica gel chromatography (10-80% ethyl acetate/hexanes) to afford 4-(7-chloroquinolin-4-yl)-2-(trifluoromethyl)phenol (195 mg, 0.271 mmol, 18% yield) as a pale yellow solid. LCMS (ESI) m/e 323.9 [(M+H)$^+$, calcd $C_{16}H_{10}ClF_3NO$, 324.0]; LC/MS retention time (method D): $t_R$=1.00 min.

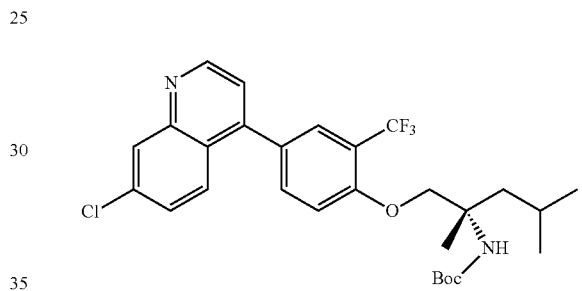

Part C: (S)-tert-butyl (1-(4-(7-chloroquinolin-4-yl)-2-(trifluoromethyl)phenoxy)-2,4-dimethylpentan-2-yl)carbamate A mixture of 4-(7-chloroquinolin-4-yl)-2-(trifluoromethyl)phenol (195 mg, 0.602 mmol), (S)-tert-butyl 4-isobutyl-4-methyl-1,2,3-oxathiazolidine-3-carboxylate 2,2-dioxide (194 mg, 0.663 mmol), cesium carbonate (393 mg, 1.205 mmol), and N,N-dimethylformamide (4 mL) was heated to 80° C. overnight. The resultant mixture was cooled to room temperature and diluted with ethyl acetate (40 mL). The organic layer was washed with brine (3×15 mL), dried over magnesium sulfate, filtered, and concentrated under reduced pressure. The residue was purified by purified by silica gel chromatography to afford (S)-tert-butyl (1-(4-(7-chloroquinolin-4-yl)-2-(trifluoromethyl)phenoxy)-2,4-dimethylpentan-2-yl)carbamate (160 mg, 0.298 mmol, 50% yield as a pale purple oil. LCMS (ESI) m/e 537.4 [(M+H)$^+$, calcd $C_{28}H_{33}ClF_3N_2O_3$, 537.2]; LC/MS retention time (method A): $t_R$=2.60 min; $^1$H NMR (400 MHz, CHLOROFORM-d) δ 8.95 (d, J=4.3 Hz, 1H), 8.19 (d, J=2.3 Hz, 1H), 7.81 (d, J=9.0 Hz, 1H), 7.71 (d, J=2.0 Hz, 1H), 7.62 (dd, J=8.5, 2.0 Hz, 1H), 7.50 (dd, J=8.9, 2.1 Hz, 1H), 7.33 (d, J=4.5 Hz, 1H), 7.20 (d, J=8.5 Hz, 1H), 4.39-4.17 (m, 2H), 2.00-1.79 (m, 3H), 1.44 (s, 3H), 1.42 (s, 9H), 1.03 (d, J=6.5 Hz, 3H), 1.01 (d, J=6.5 Hz, 3H).

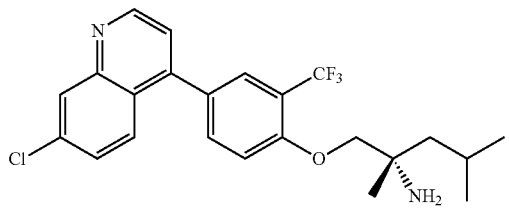 [SMILES: CC(C)C[C@](C)(N)COc1ccc(-c2ccnc3cc(Cl)ccc23)cc1C(F)(F)F]

Part D: (S)-1-(4-(7-chloroquinolin-4-yl)-2-(trifluoromethyl)phenoxy)-2,4-dimethylpentan-2-amine (S)-tert-Butyl (1-(4-(7-chloroquinolin-4-yl)-2-(trifluoromethyl)phenoxy)-2,4-dimethylpentan-2-yl)carbamate (40 mg, 0.074 mmol) was treated with TFA (1 mL, 12.98 mmol) and stirred at ambient temperature for 30 min. The resultant was concentrated under reduced pressure. The residue was purified via preparative LC/MS (Column: XBridge C18, 19×200 mm, 5-am; Mobile Phase A: 5:95 acetonitrile: water with 10-mM ammonium acetate; Mobile Phase B: 95:5 acetonitrile: water with 10-mM ammonium acetate; Gradient: 45-85% B over 15 minutes, then a 5-minute hold at 100% B; Flow: 20 mL/min.). Obtained (S)-1-(4-(7-chloroquinolin-4-yl)-2-(trifluoromethyl)phenoxy)-2,4-dimethylpentan-2-amine carbamate (160 mg, 0.298 mmol, 50% yield) as a colorless solid. LCMS (ESI) m/e 437.2 [(M+H)$^+$, calcd $C_{23}H_{25}ClF_3N_2O$, 437.2]; LC/MS retention time (method D): $t_R$=0.97 min; $^1$H NMR (500 MHz, DMSO-d$_6$) δ 8.98 (d, J=4.4 Hz, 1H), 8.17 (d, J=1.8 Hz, 1H), 7.88 (d, J=9.2 Hz, 1H), 7.83 (d, J=8.8 Hz, 1H), 7.78 (s, 1H), 7.66 (dd, J=9.2, 1.8 Hz, 1H), 7.55 (d, J=4.4 Hz, 1H), 7.44 (d, J=8.4 Hz, 1H), 3.96-3.83 (m, 2H), 1.86-1.77 (m, 1H), 1.41 (d, J=5.5 Hz, 2H), 1.14 (s, 3H), 0.94 (d, J=6.6 Hz, 3H), 0.93 (d, J=6.6 Hz, 3H).

Example 89

(S)-4-(4-((2-amino-2,4-dimethylpentyl)oxy)-3-(trifluoromethyl)phenyl)quinoline-7-carbonitrile

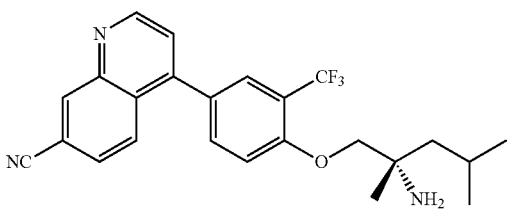

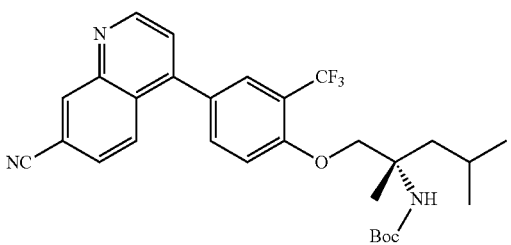

Part A: (S)-tert-butyl (1-(4-(7-cyanoquinolin-4-yl)-2-(trifluoromethyl)phenoxy)-2,4-dimethylpentan-2-yl)carbamate (S)-tert-butyl (1-(4-(7-chloroquinolin-4-yl)-2-(trifluoromethyl)phenoxy)-2,4-dimethylpentan-2-yl)carbamate (84 mg, 0.156 mmol) (prepared as described in Example 88), zinc cyanide (20.20 mg, 0.172 mmol), 1,1'-bis(diphenylphosphino)ferrocene (13.01 mg, 0.023 mmol), Pd2(dba)3 (7.16 mg, 7.82 μmol), N,N-dimethylformamide (1 mL), and water (0.10 mL) were charged to a pressure rated vial and the mixture was sparged with nitrogen for 5 minutes. The vial was sealed, purged of oxygen, and heated under nitrogen at 115° C. overnight. The resultant mixture was cooled to ambient temperature, vacuum filtered, and concentrated under reduced pressure. The residue was purified by silica gel chromatography (10-80% ethyl acetate/hexanes gradient elution) to afford (S)-tert-butyl (1-(4-(7-cyanoquinolin-4-yl)-2-(trifluoromethyl)phenoxy)-2,4-dimethylpentan-2-yl)carbamate (22.5 mg, 0.043 mmol, 27% yield) as a near colorless film. LCMS (ESI) m/e 528.2 [(M+H)$^+$, calcd $C_{29}H_{33}F_3N_3O_3$, 528.3]; LC/MS retention time (method D): $t_R$=1.30 min.

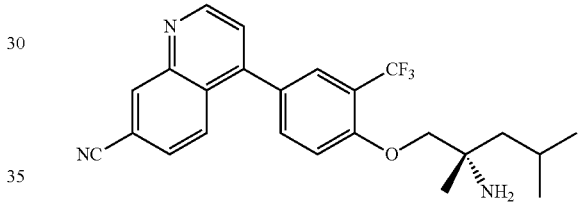

Part B: (S)-4-(4-((2-amino-2,4-dimethylpentyl)oxy)-3-(trifluoromethyl)phenyl)quinoline-7-carbonitrile (S)-tert-Butyl (1-(4-(7-cyanoquinolin-4-yl)-2-(trifluoromethyl)phenoxy)-2,4-dimethylpentan-2-yl)carbamate (22 mg, 0.042 mmol) was treated with TFA (964 μL, 12.51 mmol) and stirred at room temperature for 30 minutes. The resultant was concentrated under reduced pressure. The residue was purified via preparative LC/MS (Column: XBridge C18, 19×200 mm, 5-am; Mobile Phase A: 5:95 acetonitrile: water with 10-mM ammonium acetate; Mobile Phase B: 95:5 acetonitrile: water with 10-mM ammonium acetate; Gradient: 45-85% B over 15 minutes, then a 5-minute hold at 100% B; Flow: 20 mL/min.). Obtained (S)-4-(4-((2-amino-2,4-dimethylpentyl)oxy)-3-(trifluoromethyl)phenyl)quinoline-7-carbonitrile (13.3 mg, 0.031 mmol, 75% yield) as a colorless solid. LCMS (ESI) m/e 428.2 [(M+H)$^+$, calcd $C_{24}H_{25}F_3N_3O$, 428.2]; LC/MS retention time (method D): $t_R$=0.97 min; $^1$H NMR (500 MHz, DMSO-d$_6$) δ 9.11 (d, J=4.4 Hz, 1H), 8.68 (s, 1H), 8.06-7.98 (m, 1H), 7.92 (d, J=8.8 Hz, 1H), 7.84 (d, J=8.8 Hz, 1H), 7.81 (s, 1H), 7.70 (d, J=4.4 Hz, 1H), 7.45 (d, J=8.8 Hz, 1H), 4.00-3.77 (m, 2H), 1.82 (dt, J=12.7, 6.3 Hz, 1H), 1.41 (d, J=5.5 Hz, 2H), 1.14 (s, 3H), 0.94 (d, J=6.5 Hz, 3H), 0.93 (d, J=6.5 Hz, 3H).

Example 90

(S)-2,4-dimethyl-1-(2-methyl-4-(2-methylpyridin-4-yl)phenoxy)pentan-2-amine

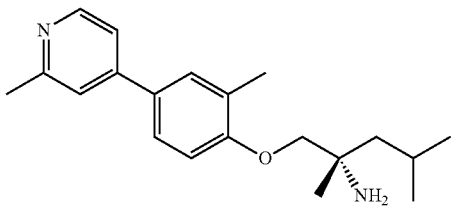

Prepared as described in Example 32 to afford (S)-2,4-dimethyl-1-(2-methyl-4-(2-methylpyridin-4-yl)phenoxy)pentan-2-amine carbonitrile (17 mg, 0.054 mmol, 98% yield for the final step) as a colorless solid. LCMS (ESI) m/e 313.1 [(M+H)$^+$, calcd $C_{20}H_{29}N_2O$, 313.2]; LC/MS retention time (method D): $t_R$=0.65 min; $^1$H NMR (500 MHz, DMSO-d$_6$) δ 8.44 (d, J=5.1 Hz, 1H), 7.67-7.60 (m, 2H), 7.54 (s, 1H), 7.45 (d, J=5.1 Hz, 1H), 7.05 (d, J=8.1 Hz, 1H), 3.88-3.29 (m, 2H), 2.30 (s, 3H), 1.91 (s, 3H), 1.81 (dt, J=12.8, 6.4 Hz, 1H), 1.64-1.55 (m, 1H), 1.53-1.44 (m, 1H), 1.26 (s, 3H), 0.95 (d, J=6.6 Hz, 3H), 0.92 (d, J=6.6 Hz, 3H).

Example 91

(S)-1-(2-fluoro-4-(2-methylpyridin-4-yl)phenoxy)-2,4-dimethylpentan-2-amine

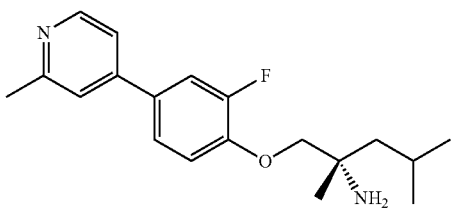 [SMILES: Cc1cc(-c2ccc(OC[C@@](C)(N)CC(C)C)c(F)c2)ccn1]

Prepared as described in Example 32 to afford (S)-1-(2-fluoro-4-(2-methylpyridin-4-yl)phenoxy)-2,4-dimethylpentan-2-amine (12 mg, 0.037 mmol, 96% yield for the final step) as a colorless solid. LCMS (ESI) m/e 317.1 [(M+H)$^+$, calcd $C_{19}H_{26}FN_2O$, 317.2]; LC/MS retention time (method D): $t_R$=0.62 min; H NMR (500 MHz, DMSO-d$_6$) δ 8.57 (d, J=5.5 Hz, 1H), 8.13 (br. s., 2H), 7.87 (d, J=12.5 Hz, 1H), 7.80 (s, 1H), 7.74 (d, J=9.2 Hz, 1H), 7.70 (d, J=5.1 Hz, 1H), 7.42 (t, J=8.6 Hz, 1H), 4.23-4.08 (m, 2H), 2.58 (s, 3H), 1.82 (dt, J=12.7, 6.1 Hz, 1H), 1.77-1.69 (m, 1H), 1.60 (dd, J=14.3, 5.1 Hz, 1H), 1.38 (s, 3H), 0.97 (d, J=6.6 Hz, 3H), 0.93 (d, J=6.2 Hz, 3H).

Example 92

(S)-1-(4-(2-fluoropyridin-4-yl)-2-methylphenoxy)-2,4-dimethylpentan-2-amine

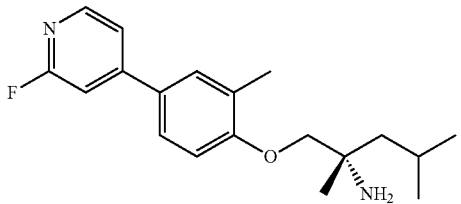

Prepared as described in Example 32 to afford (S)-1-(4-(2-fluoropyridin-4-yl)-2-methylphenoxy)-2,4-dimethylpentan-2-amine (4.8 mg, 0.015 mmol, 90% yield for the final step) as a colorless solid. LCMS (ESI) m/e 317.1 [(M+H)$^+$, calcd $C_{19}H_{26}FN_2O$, 317.2]; LC/MS retention time (method D): $t_R$=0.96 min; $^1$H NMR (500 MHz, DMSO-d$_6$) δ 8.24 (d, J=5.1 Hz, 1H), 7.80-7.69 (m, 2H), 7.66 (d, J=5.1 Hz, 1H), 7.47 (s, 1H), 7.03 (d, J=8.1 Hz, 1H), 3.80-3.38 (m, 2H), 2.28 (s, 3H), 1.86-1.77 (m, 1H), 1.49-1.35 (m, 2H), 1.15 (s, 3H), 0.93 (t, J=6.2 Hz, 6H).

Example 93

(S)-1-(2-fluoro-4-(2-fluoropyridin-4-yl)phenoxy)-2,4-dimethylpentan-2-amine

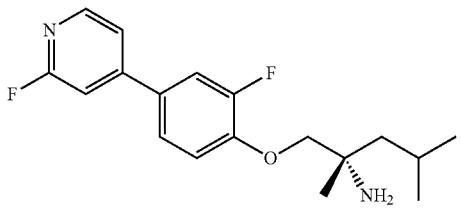 [SMILES: CC(C)C[C@](C)(N)COc1ccc(-c2ccnc(F)c2)cc1F]

Prepared as described in Example 32 to afford (S)-1-(2-fluoro-4-(2-fluoropyridin-4-yl)phenoxy)-2,4-dimethylpentan-2-amine (10.8 mg, 0.034 mmol, 75% yield for the final step) as a colorless solid. LCMS (ESI) m/e 321.1 [(M+H)$^+$, calcd $C_{18}H_{23}F_2N_2O$, 321.2]; LC/MS retention time (method D): $t_R$=0.90 min; $^1$H NMR (500 MHz, DMSO-d$_6$) δ 8.27 (d, J=5.1 Hz, 1H), 7.86 (dd, J=12.7, 2.0 Hz, 1H), 7.72 (d, J=5.9 Hz, 2H), 7.55 (s, 1H), 7.30 (t, J=8.8 Hz, 1H), 3.88-3.75 (m, 2H), 1.81 (dquin, J=12.7, 6.3 Hz, 1H), 1.48-1.31 (m, 2H), 1.13 (s, 3H), 0.93 (t, J=7.2 Hz, 6H).

Example 94

(S)-2-((2-amino-2,4-dimethylpentyl)oxy)-5-(2-fluoropyridin-4-yl)benzonitrile

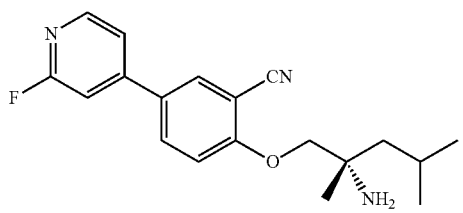 [SMILES: CC(C)C[C@](C)(N)COc1ccc(-c2ccnc(F)c2)cc1C#N]

Prepared as described in Example 32 to afford (S)-2-((2-amino-2,4-dimethylpentyl)oxy)-5-(2-fluoropyridin-4-yl)benzonitrile (16.9 mg, 0.051 mmol, 80% yield for the final step) as a colorless solid. LCMS (ESI) m/e 328.1 [(M+H)$^+$, calcd C$_{19}$H$_{23}$FN$_3$O, 328.2]; LC/MS retention time (method D): t$_R$=0.94 min; $^1$H NMR (500 MHz, DMSO-d$_6$) δ 8.37 (d, J=2.2 Hz, 1H), 8.31 (d, J=5.1 Hz, 1H), 8.22 (dd, J=8.8, 2.2 Hz, 1H), 7.78 (d, J=5.1 Hz, 1H), 7.63 (s, 1H), 7.43 (d, J=9.2 Hz, 1H), 4.12-3.99 (m, 2H), 1.83 (dt, J=12.7, 6.3 Hz, 1H), 1.60-1.43 (m, 2H), 1.24 (s, 3H), 0.95 (t, J=6.4 Hz, 6H).

Example 95

(S)-1-((2'-fluoro-5-methyl-[3,4'-bipyridin]-6-yl)oxy)-2,4-dimethylpentan-2-amine

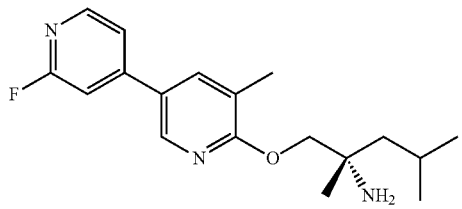 [SMILES: Cc1cc(-c2ccnc(F)c2)cnc1OC[C@@](C)(N)CC(C)C]

Prepared as described in Example 32 to afford (S)-1-((2'-fluoro-5-methyl-[3,4'-bipyridin]-6-yl)oxy)-2,4-dimethylpentan-2-amine (6.5 mg, 0.020 mmol, 57% yield for the final step) as a colorless solid. LCMS (ESI) m/e 318.1 [(M+H)$^+$, calcd C$_{18}$H$_{25}$FN$_3$O, 318.2]; LC/MS retention time (method D): t$_R$=0.95 min; $^1$H NMR (500 MHz, DMSO-d$_6$) δ 8.54 (d, J=2.2 Hz, 1H), 8.29 (d, J=5.1 Hz, 1H), 8.12 (s, 1H), 7.73 (d, J=5.1 Hz, 1H), 7.57 (s, 1H), 4.22-4.08 (m, 2H), 1.91 (s, 3H), 1.81 (dq, J=12.7, 6.2 Hz, 1H), 1.55-1.39 (m, 2H), 1.20 (s, 3H), 0.93 (dd, J=8.8, 6.6 Hz, 6H).

Example 96

(S)-4-(6-((2-amino-2,4-dimethylpentyl)oxy)-5-methylpyridin-3-yl)quinoline-7-carbonitrile

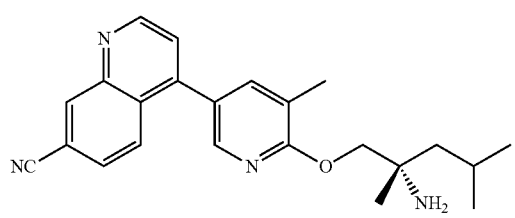 [SMILES: Cc1cc(-c2ccnc3cc(C#N)ccc23)cnc1OC[C@@](C)(N)CC(C)C]

Prepared as described in Example 89 to afford (S)-4-(6-((2-amino-2,4-dimethylpentyl)oxy)-5-methylpyridin-3-yl)quinoline-7-carbonitrile (9.9 mg, 0.026 mmol, 35% yield for the final step) as a colorless solid. LCMS (ESI) m/e 375.1 [(M+H)$^+$, calcd C$_{23}$H$_{27}$N$_4$O, 375.2]; LC/MS retention time (method D): t$_R$=0.94 min; $^1$H NMR (600 MHz, DMSO-d$_6$) δ 9.10 (d, J=4.4 Hz, 1H), 8.68 (s, 1H), 8.18 (s, 1H), 8.07 (d, J=8.8 Hz, 1H), 7.92 (d, J=8.4 Hz, 1H), 7.82 (br. s., 1H), 7.68 (d, J=4.0 Hz, 1H), 4.17-4.05 (m, 2H), 2.29 (s, 3H), 1.90-1.79 (m, 1H), 1.49-1.37 (m, 2H), 1.16 (s, 3H), 0.95 (t, J=6.2 Hz, 6H).

Example 97

(S)-1-((5-fluoro-2'-methyl-[3,4'-bipyridin]-6-yl)oxy)-2,4-dimethylpentan-2-amine

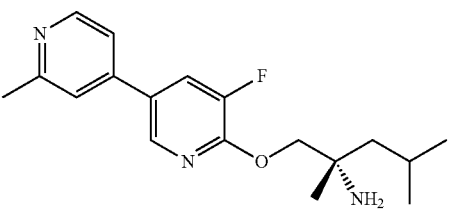 [SMILES: Cc1cc(-c2cnc(OC[C@@](C)(N)CC(C)C)c(F)c2)ccn1]

Prepared as described in Example 32 to afford (S)-1-((5-fluoro-2'-methyl-[3,4'-bipyridin]-6-yl)oxy)-2,4-dimethylpentan-2-amine (4.8 mg, 0.015 mmol, 90% yield for the final step) as a colorless solid. LCMS (ESI) m/e 318.2 [(M+H)$^+$, calcd C$_{18}$H$_{25}$FN$_3$O, 318.2]; LC/MS retention time (method D): t$_R$=0.60 min; $^1$H NMR (500 MHz, DMSO-d$_6$) δ 8.51 (d, J=5.1 Hz, 1H), 8.48 (s, 1H), 8.23 (d, J=11.4 Hz, 1H), 7.66 (s, 1H), 7.57 (d, J=5.1 Hz, 1H), 4.32-4.21 (m, 2H), 1.91 (s, 3H), 1.87-1.77 (m, 1H), 1.57-1.41 (m, 2H), 1.22 (s, 3H), 0.95 (d, J=6.6 Hz, 3H), 0.93 (d, J=6.6 Hz, 3H).

Example 98

(S)-1-((3-fluoro-5-(quinolin-4-yl)pyridin-2-yl)oxy)-2,4-dimethylpentan-2-amine

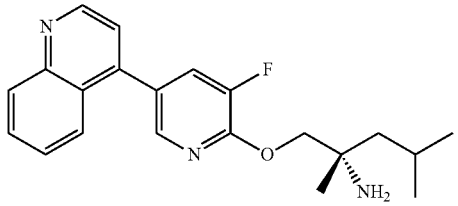 [SMILES: CC(C)C[C@](C)(N)COc1ncc(-c2ccnc3ccccc23)cc1F]

Prepared as described in Example 32 to afford (S)-1-((3-fluoro-5-(quinolin-4-yl)pyridin-2-yl)oxy)-2,4-dimethylpentan-2-amine (8.4 mg, 0.024 mmol, 59% yield for the final step) as a colorless solid. LCMS (ESI) m/e 354.1 [(M+H)$^+$, calcd C$_{21}$H$_{25}$FN$_3$O, 354.2]; LC/MS retention time (method D): t$_R$=0.74 min; $^1$H NMR (500 MHz, DMSO-d$_6$) δ 8.98 (d, J=4.0 Hz, 1H), 8.18 (d, J=1.8 Hz, 1H), 8.14 (d, J=8.4 Hz, 1H), 8.03 (d, J=11.0 Hz, 1H), 7.91 (d, J=8.4 Hz, 1H), 7.84 (t, J=7.5 Hz, 1H), 7.70-7.62 (m, 1H), 7.54 (d, J=4.4 Hz, 1H), 4.27-4.17 (m, 2H), 1.85 (dt, J=12.7, 6.1 Hz, 1H), 1.53-1.38 (m, 2H), 1.19 (s, 3H), 0.96 (t, J=7.0 Hz, 6H).

Example 99

(S)-4-(6-((2-amino-2,4-dimethylpentyl)oxy)-5-fluoropyridin-3-yl)quinoline-7-carbonitrile

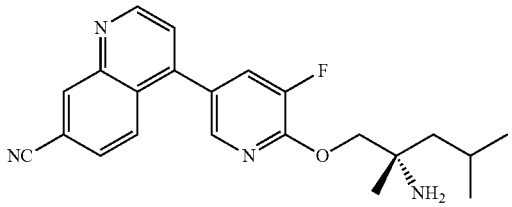 [SMILES: CC(C)C[C@](C)(N)COc1ncc(-c2ccnc3cc(C#N)ccc23)cc1F]

Prepared as described in Example 88 to (S)-4-(6-((2-amino-2,4-dimethylpentyl)oxy)-5-fluoropyridin-3-yl)quinoline-7-carbonitrile (5.6 mg, 0.014 mmol, 62% yield for the final step) as a colorless solid. LCMS (ESI) m/e 379.1 [(M+H)$^+$, calcd C$_{22}$H$_{24}$FN$_4$O, 379.2]; LC/MS retention time (method D): t$_R$=0.91 min; $^1$H NMR (500 MHz, DMSO-d$_6$) δ 9.13 (d, J=4.4 Hz, 1H), 8.70 (s, 1H), 8.19 (d, J=1.8 Hz, 1H), 8.09 (d, J=8.8 Hz, 1H), 8.06-8.01 (m, 1H), 7.98-7.90 (m, 1H), 7.73 (d, J=4.4 Hz, 1H), 4.22-4.10 (m, 2H), 1.85 (dt, J=12.7, 6.3 Hz, 1H), 1.50-1.35 (m, 2H), 1.15 (s, 3H), 0.95 (t, J=6.6 Hz, 6H).

Example 100

(S)-methyl(4-(4-((2-amino-2,4-dimethylpentyl)oxy)-3-cyanophenyl)-3-fluoropyridin-2-yl)carbamate

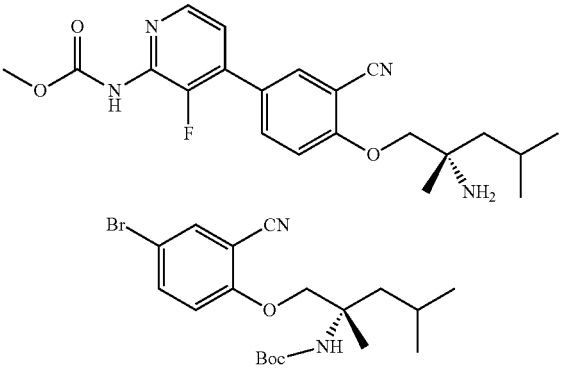

Part A: (S)-tert-butyl (1-(4-bromo-2-cyanophenoxy)-2,4-dimethylpentan-2-yl)carbamate Prepared as in Example 32 Parts A-F to yield (S)-tert-butyl (1-(4-bromo-2-cyanophenoxy)-2,4-dimethylpentan-2-yl)carbamate. LC/MS retention time (method D): t$_R$=1.29 min.

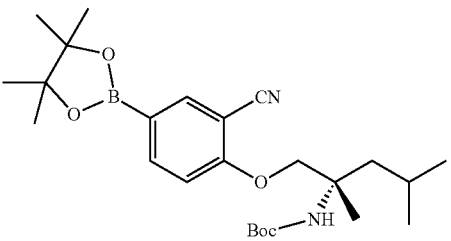 [SMILES: CC(C)C[C@@](C)(COc1ccc(B2OC(C)(C)C(C)(C)O2)cc1C#N)NC(=O)OC(C)(C)C]

Part B: (S)-tert-butyl (1-(2-cyano-4-(4,4,5,5-tetramethyl-1,3,2-dioxaborolan-2-yl)phenoxy)-2,4-dimethylpentan-2-yl)carbamate (S)-tert-butyl (1-(4-bromo-2-cyanophenoxy)-2,4-dimethylpentan-2-yl)carbamate (0.57 g, 1.386 mmol), 4,4,4',4',5,5,5',5'-octamethyl-2,2'-bi(1,3,2-dioxaborolane) (0.422 g, 1.663 mmol), PdCl$_2$(dppf) (0.051 g, 0.069 mmol), potassium acetate (0.408 g, 4.16 mmol), and dioxane (5 mL) were charged to a pressure rated vial. The vial was purged of oxygen and the mixture stirred under nitrogen at 80° C. overnight. The mixture was cooled to ambient temperature, vacuum filtered, and concentrated under reduced pressure. Obtained (S)-tert-butyl (1-(2-cyano-4-(4,4,5,5-tetramethyl-1,3,2-dioxaborolan-2-yl)phenoxy)-2,4-dimethylpentan-2-yl)carbamate (600 mg, 1.30 mmol, 100% crude yield) as a brown oil that was used without further purification. LCMS (ESI) m/e 481.1 [(M+Na)$^+$, calcd C$_{25}$H$_{39}$BN$_2$NaO$_5$, 481.3]; LC/MS retention time (method B): t$_R$=2.49 min.

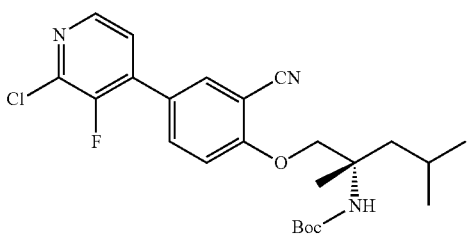 [SMILES: CC(C)C[C@@](C)(COc1ccc(-c2ccnc(Cl)c2F)cc1C#N)NC(=O)OC(C)(C)C]

Part C: (S)-tert-butyl (1-(4-(2-chloro-3-fluoropyridin-4-yl)-2-cyanophenoxy)-2,4-dimethylpentan-2-yl)carbamate A mixture of 2-chloro-3-fluoro-4-iodopyridine (105 mg, 0.408 mmol), (S)-tert-butyl (1-(2-cyano-4-(4,4,5,5-tetramethyl-1,3,2-dioxaborolan-2-yl)phenoxy)-2,4-dimethylpentan-2-yl)carbamate (374 mg, 0.816 mmol), potassium carbonate (169 mg, 1.224 mmol), and Pd(Ph$_3$P)$_4$ (14.14 mg, 0.012 mmol) in toluene (1 mL), water (0.050 mL), and ethanol (0.100 mL) in a pressure rated 1 dram vial was purged of oxygen, and stirred under nitrogen at 80° C. overnight. The mixture was filtered via syringe tip filter and concentrated under reduced pressure. The residue was purified by silica gel chromatography (10-80% ethyl acetate/hexanes gradient elution) to afford (S)-tert-butyl (1-(4-(2-chloro-3-fluoropyridin-4-yl)-2-cyanophenoxy)-2,4-dimethylpentan-2-yl)carbamate (49 mg, 0.106 mmol, 26% yield) as a light yellow film. LCMS (ESI) m/e 462.0 (M+H)$^+$, calcd C$_{23}$H$_{30}$ClFN$_3$O$_3$, 462.2]; LC/MS retention time (method D): $t_R$=1.30 min; $^1$H NMR (400 MHz, CHLOROFORM-d) δ 8.28 (d, J=5.0 Hz, 1H), 7.82 (dd, J=2.0, 1.0 Hz, 1H), 7.77 (dt, J=8.8, 1.9 Hz, 1H), 7.33-7.29 (m, 1H), 7.18 (d, J=9.0 Hz, 1H), 4.59 (s, 1H), 4.45 (d, J=8.8 Hz, 1H), 4.22 (d, J=9.0 Hz, 1H), 2.01-1.92 (m, 1H), 1.91-1.79 (m, 1H), 1.56-1.50 (m, 1H), 1.46 (s, 3H), 1.40 (s, 9H), 1.03 (d, J=6.8 Hz, 6H).

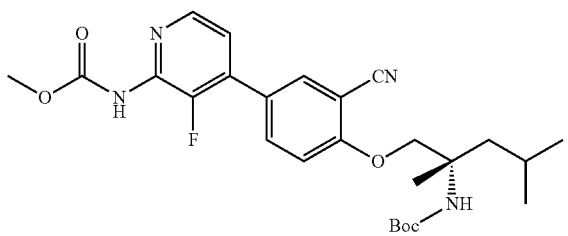 [SMILES: COC(=O)Nc1nccc(-c2ccc(OC[C@](C)(CC(C)C)NC(=O)OC(C)(C)C)c(C#N)c2)c1F]

Part D: (S)-methyl (4-(4-((2-Boc-amino-2,4-dimethylpentyl)oxy)-3-cyanophenyl)-3-fluoropyridin-2-yl)carbamate A solution of (S)-tert-butyl (1-(4-(2-amino-3-fluoropyridin-4-yl)-2-cyanophenoxy)-2,4-dimethylpentan-2-yl)carbamate (40 mg, 0.090 mmol) cooled to 0° C. was added methyl chloroformate (0.035 mL, 0.452 mmol) and pyridine (0.073 mL, 0.904 mmol) followed by DMAP (1.104 mg, 9.04 μmol). The cooling bath was removed and the mixture stirred overnight. The reaction mixture was concentrated under reduced pressure. Obtained (S)-methyl (4-(4-((2-Boc-amino-2,4-dimethylpentyl)oxy)-3-cyanophenyl)-3-fluoropyridin-2-yl)carbamate (20 mg, 0.040 mmol, 44% crude yield) which was used without further purification. LCMS (ESI) m/e 501.1 (M+H)$^+$, calcd C$_{23}$H$_{30}$ClFN$_3$O$_3$, 501.3]; LC/MS retention time (method D): $t_R$=1.17 min.

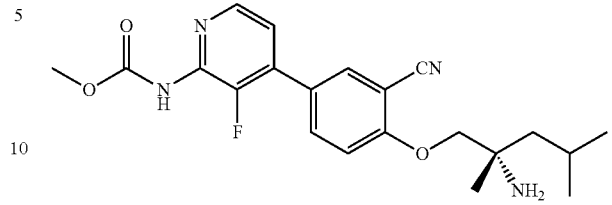

Part E: (S)-methyl (4-(4-((2-amino-2,4-dimethylpentyl)oxy)-3-cyanophenyl)-3-fluoropyridin-2-yl)carbamate (S)-Methyl (4-(4-((2-Boc-amino-2,4-dimethylpentyl)oxy)-3-cyanophenyl)-3-fluoropyridin-2-yl)carbamate (20 mg, 0.040 mmol) and TFA (1 mL, 12.98 mmol) were stored at ambient temperature for 2 hours. The resultant was concentrated under reduced pressure. The residue was purified via preparative LC/MS (Column: XBridge C18, 19×200 mm, 5-am; Mobile Phase A: 5:95 acetonitrile: water with 10-mM ammonium acetate; Mobile Phase B: 95:5 acetonitrile: water with 10-mM ammonium acetate; Gradient: 45-85% B over 15 minutes, then a 5-minute hold at 100% B; Flow: 20 mL/min.). Obtained (S)-methyl (4-(4-((2-amino-2,4-dimethylpentyl)oxy)-3-cyanophenyl)-3-fluoropyridin-2-yl)carbamate (4.1 mg, 10.14 □mol, 25% yield for two steps) as a colorless solid. LCMS (ESI) m/e 401.0 (M+H)$^+$, calcd C$_{21}$H$_{26}$FN$_4$O$_3$, 401.2]; LC/MS retention time (method D): $t_R$=0.82 min; $^1$H NMR (500 MHz, DMSO-d$_6$) δ 8.26 (d, J=4.8 Hz, 1H), 8.05 (s, 1H), 7.95 (d, J=9.5 Hz, 1H), 7.50 (t, J=5.1 Hz, 1H), 7.43 (d, J=8.8 Hz, 1H), 4.13-3.99 (m, 2H), 1.91 (s, 3H), 1.86-1.78 (m, 1H), 1.60-1.44 (m, 2H), 1.24 (s, 3H), 0.94 (t, J=5.9 Hz, 6H).

Example 101

(S)-6-((2-amino-2,4-dimethylpentyl)oxy)-2'-methyl-[3,4'-bipyridine]-5-carbonitrile

Prepared as described in Example 32 to afford (S)-6-((2-amino-2,4-dimethylpentyl)oxy)-2'-methyl-[3,4'-bipyridine]-5-carbonitrile (16 mg, 0.054 mmol, 44% yield for the final step) as a pale yellow oil. LCMS (ESI) m/e 325.1 [(M+H)$^+$, calcd C$_{19}$H$_{25}$N$_4$O, 325.2]; LC/MS retention time (method D): $t_R$=0.58 min; $^1$H NMR (500 MHz, DMSO-d$_6$) δ 9.02 (d, J=2.2 Hz, 1H), 8.92 (d, J=2.6 Hz, 1H), 8.68 (d, J=5.5 Hz, 1H), 8.42 (br. s., 2H), 7.99 (s, 1H), 7.89 (d, J=4.8 Hz, 1H), 4.74-4.47 (m, 2H), 2.64 (s, 3H), 1.89 (dt, J=12.6, 6.4 Hz, 1H), 1.83-1.74 (m, 1H), 1.65 (dd, J=14.3, 5.5 Hz, 1H), 1.43 (s, 3H), 0.98 (d, J=1.8 Hz, 3H), 0.96 (d, J=1.8 Hz, 3H).

Example 102

(S)-2-((2-amino-2,4-dimethylpentyl)oxy)-5-(7-methylquinolin-4-yl)benzonitrile

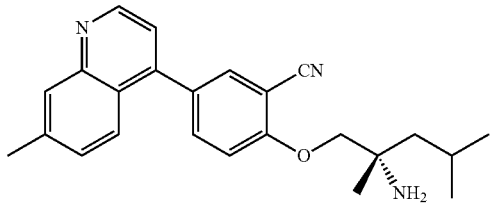 [SMILES: Cc1ccc2c(-c3ccc(OC[C@@](C)(N)CC(C)C)c(C#N)c3)ccnc2c1]

Prepared as described in Example 32 to afford (S)-2-((2-amino-2,4-dimethylpentyl)oxy)-5-(7-methylquinolin-4-yl)benzonitrile (76 mg, 0.195 mmol, 53% yield for the final step) as a colorless film. LCMS (ESI) m/e 374.0 [(M+H)$^+$, calcd $C_{24}H_{28}N_3O$, 374.2]; LC/MS retention time (method D): $t_R$=0.76 min; $^1$H NMR (600 MHz, DMSO-$d_6$) δ 8.90 (d, J=4.0 Hz, 1H), 7.98 (s, 1H), 7.91 (s, 1H), 7.87 (dd, J=8.8, 2.2 Hz, 1H), 7.73 (d, J=8.4 Hz, 1H), 7.48 (dd, J=8.1, 4.8 Hz, 2H), 7.42 (d, J=4.0 Hz, 1H), 4.29-4.09 (m, 2H), 2.55 (s, 3H), 1.86 (dt, J=12.3, 6.3 Hz, 1H), 1.72 (dd, J=13.9, 5.1 Hz, 1H), 1.58 (dd, J=14.1, 5.7 Hz, 1H), 1.35 (s, 3H), 0.97 (t, J=6.2 Hz, 6H).

Example 103

(S)-2-((2-amino-2,4-dimethylpentyl)oxy)-5-(3-fluoro-2-methylpyridin-4-yl)benzonitrile

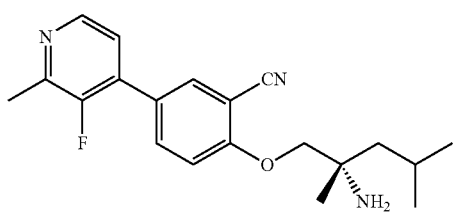 [SMILES: Cc1nccc(-c2ccc(OC[C@@](C)(N)CC(C)C)c(C#N)c2)c1F]

Prepared as described in Example 32 to afford (S)-2-((2-amino-2,4-dimethylpentyl)oxy)-5-(3-fluoro-2-methylpyridin-4-yl)benzonitrile (7.7 mg, 0.022 mmol, 74% yield for the final step) as a colorless film. LCMS (ESI) m/e 342.0 [(M+H)$^+$, calcd $C_{20}H_{25}FN_3O$, 342.2]; LC/MS retention time (method D): $t_R$=0.79 min; $^1$H NMR (600 MHz, DMSO-$d_6$) δ 8.35 (d, J=4.8 Hz, 1H), 8.05 (s, 1H), 7.95 (d, J=8.8 Hz, 1H), 7.48 (br. s., 1H), 7.39 (d, J=8.8 Hz, 1H), 3.96-3.83 (m, 2H), 2.51 (s, 3H), 1.82 (dt, J=12.1, 6.1 Hz, 1H), 1.52-1.37 (m, 2H), 1.15 (s, 3H), 0.93 (t, J=5.0 Hz, 6H).

Example 104

(S)-2-((2-amino-2,4-dimethylpentyl)oxy)-5-(quinolin-4-yl)benzonitrile

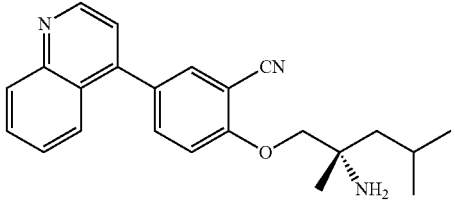 [SMILES: CC(C)C[C@](C)(N)COc1ccc(-c2ccnc3ccccc23)cc1C#N]

Prepared as described in Example 32 to afford (S)-2-((2-amino-2,4-dimethylpentyl)oxy)-5-(quinolin-4-yl)benzonitrile (23 mg, 0.061 mmol, 14% yield for the final step) as a colorless film. LCMS (ESI) m/e 360.0 [(M+H)$^+$, calcd $C_{23}H_{26}N_3O$, 360.2]; LC/MS retention time (method D): $t_R$=0.69 min; $^1$H NMR (600 MHz, DMSO-$d_6$) δ 8.97 (d, J=4.4 Hz, 1H), 8.13 (d, J=8.4 Hz, 1H), 7.99 (s, 1H), 7.90-7.79 (m, 3H), 7.64 (t, J=7.2 Hz, 1H), 7.50 (d, J=4.4 Hz, 1H), 7.47 (d, J=8.8 Hz, 1H), 4.11-3.98 (m, 2H), 1.86 (dquin, J=12.5, 6.4 Hz, 1H), 1.63-1.45 (m, 2H), 1.25 (s, 3H), 0.97 (t, J=6.2 Hz, 6H).

Example 105

(S)-2-((2-amino-2,4-dimethylpentyl)oxy)-5-(5-fluoro-2-methylpyridin-4-yl)benzonitrile

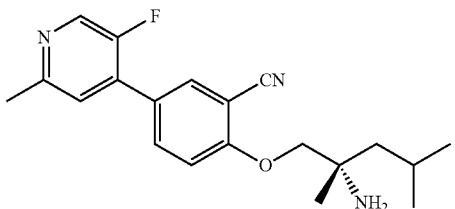

Prepared as described in Example 32 to afford (S)-2-((2-amino-2,4-dimethylpentyl)oxy)-5-(5-fluoro-2-methylpyridin-4-yl)benzonitrile (9.5 mg, 0.026 mmol, 25% yield for the final step) as a pale yellow film. LCMS (ESI) m/e 342.0 [(M+H)$^+$, calcd $C_{20}H_{25}FN_3O$, 342.2]; LC/MS retention time (method D): $t_R$=0.80 min; $^1$H NMR (500 MHz, DMSO-$d_6$) δ 8.50 (d, J=2.6 Hz, 1H), 8.08 (d, J=1.8 Hz, 1H), 7.97 (d, J=8.1 Hz, 1H), 7.56 (d, J=6.6 Hz, 1H), 7.40 (d, J=8.8 Hz, 1H), 3.96-3.85 (m, 2H), 2.52 (s, 3H), 1.86-1.77 (m, 1H), 1.51-1.36 (m, 2H), 1.15 (s, 3H), 0.94 (d, J=3.7 Hz, 3H), 0.93 (d, J=3.7 Hz, 3H).

Example 106

(S)-methyl(4-(4-((2-amino-2,4-dimethylpentyl)oxy)-3-cyanophenyl)-5-fluoropyridin-2-yl)carbamate

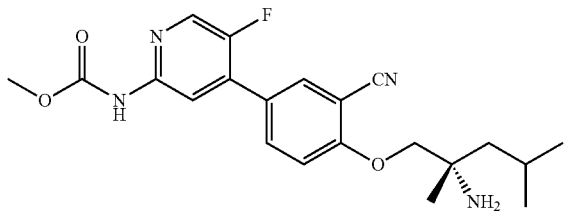 [SMILES: COC(=O)Nc1cc(-c2ccc(OC[C@@](C)(N)CC(C)C)c(C#N)c2)c(F)cn1]

Prepared as described in Example 100 to afford (S)-methyl (4-(4-((2-amino-2,4-dimethylpentyl)oxy)-3-cyanophenyl)-5-fluoropyridin-2-yl)carbamate (20.5 mg, 0.050 mmol, 36% yield for the final step) as a colorless film. LCMS (ESI) m/e 401.0 (M+H)$^+$, calcd $C_{21}H_{26}FN_4O_3$, 401.2]; LC/MS retention time (method D): $t_R$=0.91 min; $^1$H NMR (500 MHz, DMSO-$d_6$) δ 8.38 (s, 1H), 8.02 (s, 1H), 7.97 (d, J=5.9 Hz, 1H), 7.91 (d, J=9.2 Hz, 1H), 7.41 (d, J=8.8 Hz, 1H), 3.96-3.84 (m, 2H), 2.52 (s, 3H), 1.82 (dt, J=12.7, 6.3 Hz, 1H), 1.49-1.34 (m, 2H), 1.15 (s, 3H), 0.94 (d, J=3.7 Hz, 3H), 0.93 (d, J=3.7 Hz, 3H).

Example 107

(S)-1-((6-fluoro-2',4-dimethyl-[2,4'-bipyridin]-5-yl)oxy)-2,4-dimethylpentan-2-amine

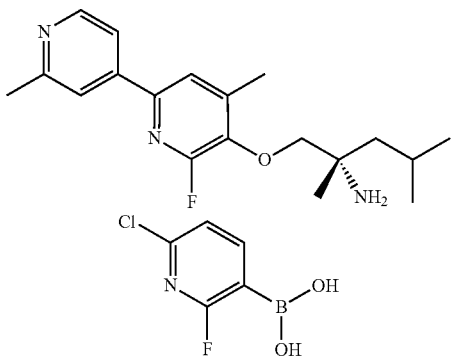

Part A: (6-chloro-2-fluoropyridin-3-yl)boronic acid

A solution of LDA (1M in THF) (8.36 ml, 8.36 mmol) at −78° C. was treated dropwise with a solution of 2-chloro-6-fluoropyridine (1.0 g, 7.60 mmol) in THE (2 mL). The mixture was maintained at −78° C. for 1 h and then treated with a solution of triisopropyl borate (1.765 ml, 7.60 mmol) in THE (1 mL). The reaction mixture was treated with water (4 mL) and concentrated under reduced pressure to afford (6-chloro-2-fluoropyridin-3-yl)boronic acid (1.33 g, 7.60 mmol, 100% crude yield) as a pale orange waxy solid that was used without further purification. LCMS (ESI) m/e 176.0 (M+H)$^+$, calcd $C_5H_5BClFNO_2$, 176.0]; LC/MS retention time (method D): $t_R$=0.71 min.

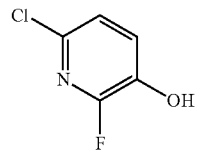

Part B: 6-chloro-2-fluoropyridin-3-ol

A suspension of (6-chloro-2-fluoropyridin-3-yl)boronic acid (1.3 g, 7.41 mmol) in NaOH (4.45 ml, 22.24 mmol) at 0° C. was treated all at once with hydrogen peroxide (0.500 ml, 8.15 mmol). The mixture was stirred at ambient temperature overnight. The resulting solution was quenched with ice water, acidified with 3 N aqueous hydrochloric acid to pH=5, and extracted three times with ethyl acetate. The pooled organics were dried over sodium sulfate and concentrated under reduced pressure to afford 6-chloro-2-fluoropyridin-3-ol (1.08 g, 7.32 mmol, 99% crude yield) as a waxy solid that was used without further purification. LCMS (ESI) m/e 148.0 (M+H)$^+$, calcd $C_5H_4ClFNO$, 148.0]; LC/MS retention time (method D): $t_R$=0.83 min.

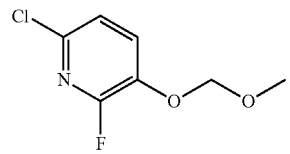

Part C: 6-chloro-2-fluoro-3-(methoxymethoxy)pyridine

A solution of 6-chloro-2-fluoropyridin-3-ol (0.49 g, 3.32 mmol), MOM-Cl (0.277 mL, 3.65 mmol), potassium carbonate (0.551 g, 3.99 mmol) in acetone (20 mL) was stirred at 60° C. for 3 h. The mixture was cooled to ambient temperature and vacuum filtered. The filtrate was concentrated under reduced pressure. The residue was purified by silica gel chromatography (5-30% ethyl acetate/hexanes) to afford 6-chloro-2-fluoro-3-(methoxymethoxy)pyridine (0.24 g, 1.25 mmol, 38% yield for three steps) as a near colorless oil. LCMS (ESI) m/e 192.0 (M+H)$^+$, calcd $C_7H_8ClFNO_2$, 192.0]; LC/MS retention time (method D): $t_R$=1.20 min; $^1$H NMR (400 MHz, CHLOROFORM-d) δ 7.57 (dd, J=9.8, 8.3 Hz, 1H), 7.16 (d, J=8.3 Hz, 1H), 5.24 (s, 2H), 3.56-3.52 (m, 3H).

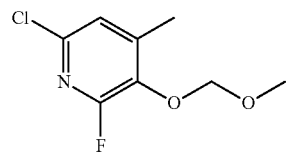

Part D: 6-chloro-2-fluoro-3-(methoxymethoxy)-4-methylpyridine

A solution of 6-chloro-2-fluoro-3-(methoxymethoxy)pyridine (0.24 g, 1.253 mmol) in tetrahydrofuran (9 mL) at −78° C. was treated dropwise with LDA (1.378 mL, 1.378 mmol). The resulting orange solution was maintained at −78° C. for 1 h and then treated dropwise with a solution of methyl iodide (0.094 mL, 1.503 mmol) in THF (0.5 mL). The resulting solution was stirred at −78° C. for 30 min. The resulting solution was warmed to ambient temperature, quenched with saturated aqueous ammonium chloride (5 mL), and stirred overnight. The layers were separated and the aqueous layer was extracted with ethyl acetate. The pooled organics were dried over sodium sulfate and concentrated under reduced pressure. The residue was purified by silica gel chromatography (5-30% ethyl acetate/hexanes) afforded 6-chloro-2-fluoro-3-(methoxymethoxy)-4-methylpyridine (0.22 g, 1.07 mmol, 85% yield) as a colorless oil. LCMS (ESI) m/e 206.1 (M+H)$^+$, calcd $C_8H_{10}ClFNO_2$, 206.0]; LC/MS retention time (method D): $t_R$=1.05 min; $^1$H NMR (400 MHz, CHLOROFORM-d) δ 7.07 (s, 1H), 5.21-5.10 (m, 2H), 3.64-3.54 (m, 3H), 2.37 (d, J=1.0 Hz, 3H).

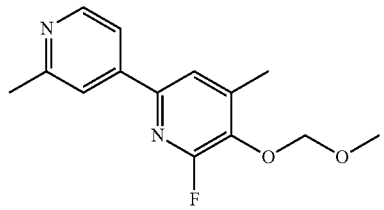

Part E: 6-fluoro-5-(methoxymethoxy)-2',4-dimethyl-2,4'-bipyridine

To a pressure rated vial was added 6-chloro-2-fluoro-3-(methoxymethoxy)-4-methylpyridine (110 mg, 0.535 mmol), (2-methylpyridin-4-yl)boronic acid (81 mg, 0.588 mmol), cesium carbonate (349 mg, 1.070 mmol), toluene (1 mL), and ethanol (0.200 mL). The solution was sparged with a stream of nitrogen for 5 min. Tetrakis(triphenylphosphine)palladium(0) (43.3 mg, 0.037 mmol) was added and the vial was sealed, purged of oxygen, and stirred under nitrogen at 85° C. overnight. The resulting suspension was vacuum filtered and concentrated under reduced pressure. The residue was purified by silica gel chromatography (5-40% ethyl acetate/hexanes gradient elution) to afford 6-fluoro-5-(methoxymethoxy)-2',4-dimethyl-2,4'-bipyridine (40 mg, 0.153 mmol, 29% yield) as a near colorless oil. LCMS (ESI) m/e 263.1 (M+H)$^+$, calcd $C_{14}H_{16}FN_2O_2$, 263.1]; LC/MS retention time (method D): $t_R$=0.80 min; $^1$H NMR (400 MHz, CHLOROFORM-d) δ 8.59 (d, J=5.3 Hz, 1H), 7.73 (s, 1H), 7.61 (dd, J=5.3, 1.3 Hz, 1H), 7.55 (s, 1H), 5.24 (d, J=1.0 Hz, 2H), 3.63 (s, 3H), 2.65 (s, 3H), 2.47 (s, 3H).

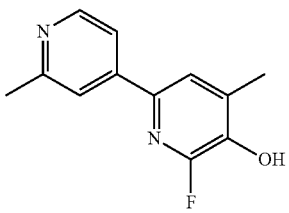 [SMILES: Cc1cc(-c2cc(C)c(O)c(F)n2)ccn1]

Part F: 6-fluoro-2',4-dimethyl-[2,4'-bipyridin]-5-ol

A solution of 6-fluoro-5-(methoxymethoxy)-2',4-dimethyl-2,4'-bipyridine (40 mg, 0.153 mmol) in methanol (5 mL) and HCl (conc.) (0.05 mL, 0.600 mmol) was stirred at 65° C. for 1 h and then concentrated under reduced pressure to afford 6-fluoro-2',4-dimethyl-[2,4'-bipyridin]-5-ol (30 mg, 0.137 mmol, 90% yield) as a pale tan solid. Used without further purification. LCMS (ESI) m/e 219.1 (M+H)$^+$, calcd $C_{12}H_{12}FN_2O$, 219.1]; LC/MS retention time (method D): $t_R$=0.59 min.

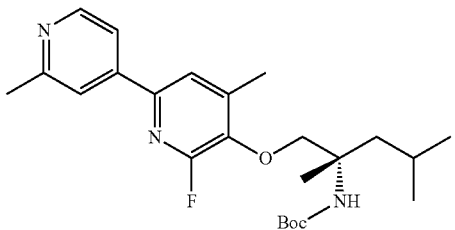 [SMILES: Cc1cc(-c2cc(C)c(OC[C@](C)(CC(C)C)NC(=O)OC(C)(C)C)c(F)n2)ccn1]

Part G: (S)-tert-butyl (1-((6-fluoro-2',4-dimethyl-[2,4'-bipyridin]-5-yl)oxy)-2,4-dimethylpentan-2-yl)carbamate A solution of 6-fluoro-2',4-dimethyl-[2,4'-bipyridin]-5-ol (30 mg, 0.137 mmol), (S)-tert-butyl 4-isobutyl-4-methyl-1,2,3-oxathiazolidine-3-carboxylate 2,2-dioxide (48.4 mg, 0.165 mmol), and cesium carbonate (134 mg, 0.412 mmol) in N,N-dimethylformamide (1 mL) in a pressure rated vial was stirred at 80° C. overnight. The mixture was cooled to ambient temperature and filtered through a syringe tip filter. Obtained (S)-tert-butyl (1-((6-fluoro-2',4-dimethyl-[2,4'-bipyridin]-5-yl)oxy)-2,4-dimethylpentan-2-yl)carbamate (38.6 mg, 0.089 mmol, 65% crude yield) as a colorless oil that was used without further purification. LCMS (ESI) m/e 432.2 (M+H)$^+$, calcd $C_{24}H_{35}FN_3O_3$, 432.3]; LC/MS retention time (method D): $t_R$=1.08 min.

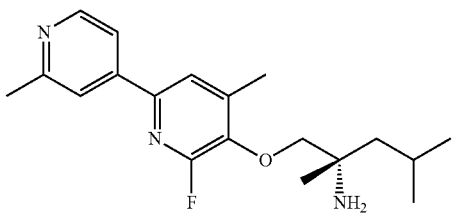 [SMILES: Cc1cc(-c2cc(C)c(OC[C@@](C)(N)CC(C)C)c(F)n2)ccn1]

Part H: (S)-1-((6-fluoro-2',4-dimethyl-[2,4'-bipyridin]-5-yl)oxy)-2,4-dimethylpentan-2-amine A solution of (S)-tert-butyl (1-((6-fluoro-2',4-dimethyl-[2,4'-bipyridin]-5-yl)oxy)-2,4-dimethylpentan-2-yl)carbamate (38 mg, 0.088 mmol) in DMF (1 mL) was treated with TFA (1 mL, 12.98 mmol) and stirred at ambient temperature overnight. The solution was concentrated under reduced pressure. The crude material was purified via preparative LC/MS (Column: XBridge C18, 19×200 mm, 5-μm; Mobile Phase A: 5:95 acetonitrile: water with 10-mM ammonium acetate; Mobile Phase B: 95:5 acetonitrile: water with 10-mM ammonium acetate; Gradient: 20-60% B over 15 minutes, then a 5-minute hold at 100% B; Flow: 20 mL/min). Obtained (S)-1-((6-fluoro-2',4-dimethyl-[2,4'-bipyridin]-5-yl)oxy)-2,4-dimethylpentan-2-amine (20 mg, 0.060 mmol, 68% crude yield) as a colorless oil that was used without further purification. LCMS (ESI) m/e 332.3 (M+H)+, calcd $C_{19}H_{27}FN_3O$, 332.2]; LC/MS retention time (method D): $t_R$=0.64 min; $^1$H NMR (500 MHz, DMSO-$d_6$) δ 8.54 (d, J=5.1 Hz, 1H), 7.99 (s, 1H), 7.83 (s, 1H), 7.74 (d, J=4.4 Hz, 1H), 3.84-3.80 (m, 2H), 2.55 (s, 3H), 2.41 (s, 3H), 1.88-1.75 (m, 1H), 1.49-1.31 (m, 2H), 1.15 (s, 3H), 1.00-0.90 (m, 6H).

Example 108 methyl (5-((3-isobutylazetidin-3-yl)methoxy)-6-methyl-[2,4'-bipyridin]-2'-yl)carbamate

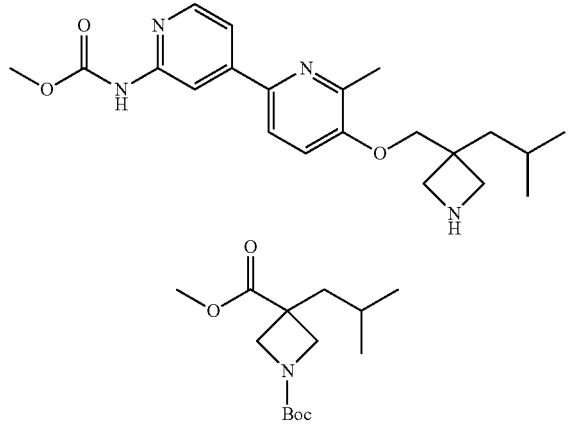

Part A: 1-tert-butyl 3-methyl 3-isobutylazetidine-1,3-dicarboxylate

A solution of 1-tert-butyl 3-methyl azetidine-1,3-dicarboxylate (5.0 g, 23.23 mmol) and 1-iodo-2-methylpropane (21.37 g, 116 mmol) in tetrahydrofuran (100 mL) at −78° C. was treated dropwise with KHMDS (69.7 mL, 34.8 mmol). The solution was stirred at ambient temperature overnight. The resulting suspension was diluted with ethyl acetate (500 mL), washed with 0.5 N aqueous hydrochloric acid (2×100 mL), and brine (1×100 mL), dried over sodium sulfate and concentrated. The residue was purified via silica gel chromatography purification (2-20% ethyl acetate/hexanes gradient elution) to afford 1-tert-butyl 3-methyl 3-isobutylazetidine-1,3-dicarboxylate (3.37 g, 12.42 mmol, 54% yield) as an amber oil. $^1$H NMR (400 MHz, CHLOROFORM-d) δ 4.22 (d, J=8.8 Hz, 2H), 3.82-3.70 (m, 5H), 1.87 (d, J=7.0 Hz, 2H), 1.63-1.51 (m, 1H), 1.45 (s, 9H), 0.89 (d, J=6.8 Hz, 6H).

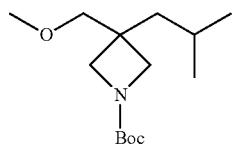 [SMILES: COCC1(CC(C)C)CN(C(=O)OC(C)(C)C)C1]

Part B: tert-butyl 3-isobutyl-3-(methoxymethyl)azetidine-1-carboxylate

A solution of 1-tert-butyl 3-methyl 3-isobutylazetidine-1,3-dicarboxylate (2.51 g, 9.25 mmol) in tetrahydrofuran (40 mL) at ambient temperature was treated with lithium borohydride (0.403 g, 18.50 mmol) and stirred at 70° C. for 3 h. TLC indicated 50% consumption of starting material. The reaction mixture was treated with additional lithium borohydride (0.302 g, 13.97 mmol) and stirred for 1.5 h at 70° C. TLC indicated complete consumption of starting material. The reaction mixture was cooled to 0° C., quenched with 0.1N aqueous hydrochloric acid, and then diluted with ethyl acetate. The layers were separated and the aqueous extracted with ethyl acetate (2×). The pooled organics were dried over sodium sulfate, filtered, and concentrated under reduced pressure. The residue was purified by silica gel chromatography (10-80% ethyl acetate/hexanes gradient elution) to afford tert-butyl 3-isobutyl-3-(methoxymethyl)azetidine-1-carboxylate (2.07 g, 8.51 mmol, 92% yield) as a colorless oil. $^1$H NMR (400 MHz, CHLOROFORM-d) δ 3.81-3.70 (m, 4H), 3.64 (d, J=8.5 Hz, 2H), 1.74 (tt, J=13.5, 6.7 Hz, 2H), 1.60 (d, J=7.0 Hz, 2H), 1.46 (s, 9H), 0.91 (d, J=6.5 Hz, 6H).

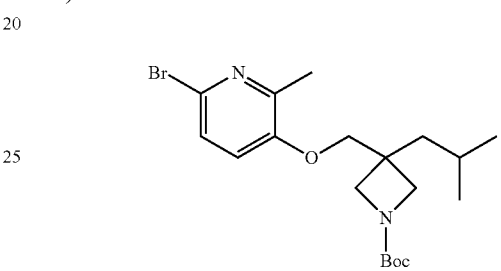

Part C: tert-butyl 3-(((6-bromo-2-methylpyridin-3-yl)oxy)methyl)-3-isobutylazetidine-1-carboxylate A solution of tert-butyl 3-(hydroxymethyl)-3-isobutylazetidine-1-carboxylate (0.582 g, 2.392 mmol) in tetrahydrofuran (4 mL) was charged to a pressure rated vial and treated dropwise with KOtBu (1M in THF) (2.392 mL, 2.392 mmol). After 5 minutes, 6-bromo-3-fluoro-2-methylpyridine (0.50 g, 2.63 mmol) in THF (2 mL) was added all at once. The vial was sealed and heated to 80° C. overnight. The mixture was partitioned between ethyl acetate and brine. The layers were separated and the aqueous extracted with ethyl acetate (2×). The pooled organics were dried over sodium sulfate and concentrated under reduced pressure. The residue was purified via silica gel chromatography to afford tert-butyl 3-(((6-bromo-2-methylpyridin-3-yl)oxy)methyl)-3-isobutylazetidine-1-carboxylate (50 mg, 0.121 mmol, 5% yield) as a near colorless oil. LCMS (ESI) m/e 313.0 (M-Boc+H)+, calcd $C_{14}H_{22}BrN_2O$, 313.1]; LC/MS retention time (method D): $t_R$=0.92 min.

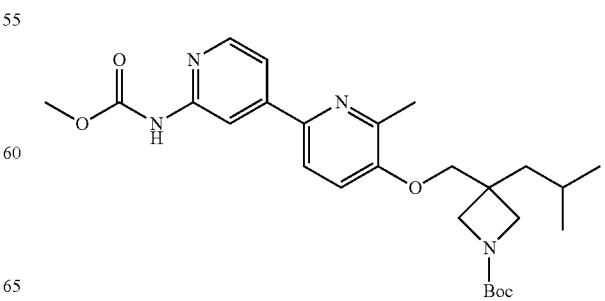

Part D: tert-butyl 3-isobutyl-3-(((2'-((methoxycarbonyl)amino)-6-methyl-[2,4'-bipyridin]-5-yl)oxy)methyl)azetidine-1-carboxylate A solution of (2-((methoxycarbonyl)amino)pyridin-4-yl) boronic acid (50 mg, 0.255 mmol), tert-butyl 3-(((6-bromo-2-methylpyridin-3-yl)oxy)methyl)-3-isobutylazetidine-1-carboxylate (70.3 mg, 0.170 mmol), Pd(Ph$_3$P)$_4$ (13.76 mg, 0.012 mmol), and cesium carbonate (111 mg, 0.340 mmol) in toluene (1 mL), and ethanol (0.1 mL) was charged to a pressure rated vial and sparged with a stream of nitrogen for 5 min. The vial was sealed, purged of oxygen, and stirred under nitrogen at 80° C. overnight. The mixture was cooled to ambient temperature and concentrated under reduced pressure. The residue was purified by silica gel chromatography (10-80% ethyl acetate/hexanes gradient elution) to afford tert-butyl 3-isobutyl-3-(((2'-((methoxycarbonyl)amino)-6-methyl-[2,4'-bipyridin]-5-yl)oxy)methyl)azetidine-1-carboxylate (29 mg, 0.060 mmol, 35% yield) as a pale yellow film. LCMS (ESI) m/e 485.1 (M+H)$^+$, calcd C$_{26}$H$_{37}$N$_4$O$_5$, 485.3]; LC/MS retention time (method D): t$_R$=1.14 min.

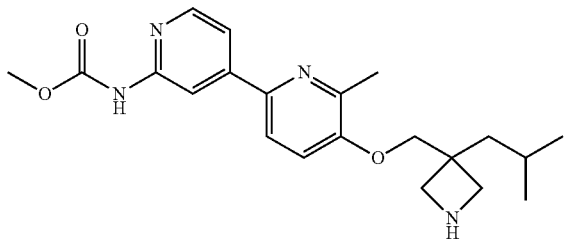 [SMILES: COC(=O)Nc1cc(-c2ccc(OCC3(CC(C)C)CNC3)c(C)n2)ccn1]

Part D: methyl (5-((3-isobutylazetidin-3-yl)methoxy)-6-methyl-[2,4'-bipyridin]-2'-yl)carbamate Tert-butyl 3-isobutyl-3-(((2'-((methoxycarbonyl)amino)-6-methyl-[2,4'-bipyridin]-5-yl)oxy)methyl)azetidine-1-carboxylate (29 mg, 0.060 mmol) and TFA (1 mL, 12.98 mmol) were stirred at ambient temperature for 3 h. The solution was concentrated under reduced pressure. The crude material was purified via preparative HPLC (Column: XBridge C18, 19×200 mm, 5-am; Mobile Phase A: 5:95 methanol: water with 10-mM ammonium acetate; Mobile Phase B: 95:5 methanol: water with 10-mM ammonium acetate; Gradient: 40-80% B over 40 minutes, then a 5-minute hold at 100% B; Flow: 20 mL/min). Obtained methyl (5-((3-isobutylazetidin-3-yl)methoxy)-6-methyl-[2,4'-bipyridin]-2'-yl)carbamate (11.5 mg, 0.030 mmol, 50% yield) as a colorless film. LCMS (ESI) m/e 385.1 (M+H)$^+$, calcd C$_{21}$H$_{29}$N$_4$O$_3$, 385.3]; LC/MS retention time (method D): t$_R$=0.76 min; $^1$H NMR (500 MHz, DMSO-d$_6$) δ 8.49 (s, 1H), 8.31 (d, J=5.1 Hz, 1H), 7.86 (d, J=8.4 Hz, 1H), 7.64 (d, J=4.4 Hz, 1H), 7.56 (d, J=8.4 Hz, 1H), 4.27 (s, 2H), 3.54-3.38 (m, 4H), 2.46 (s, 3H), 1.86 (m, 3H), 1.73-1.59 (m, 3H), 0.86 (d, J=5.9 Hz, 6H).

Example 109

(S)-2-((2-amino-4-methylpentyl)oxy)-5-(6-methylpyridazin-4-yl)benzonitrile

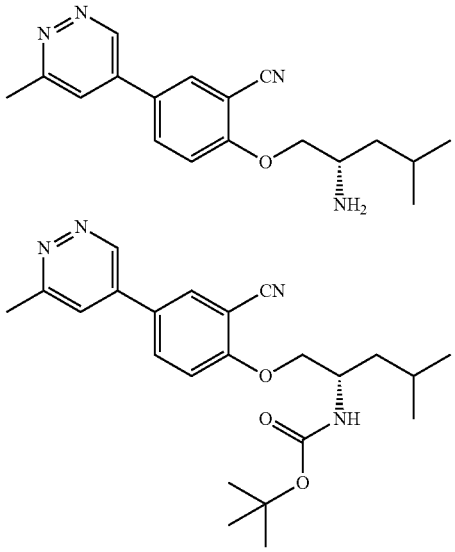

Part A: (S)-tert-butyl (1-(2-cyano-4-(6-methylpyridazin-4-yl)phenoxy)-4-methylpentan-2-yl)carbamate To a 2 mL vial was added (6-methylpyridazin-4-yl)boronic acid (20.56 mg, 0.149 mmol), (S)-tert-butyl (1-(4-bromo-2-cyanophenoxy)-4-methylpentan-2-yl)carbamate (42.3 mg, 0.106 mmol), and Na$_2$CO$_3$ (0.160 mL, 0.319 mmol) in dioxane (0.5 mL) to give a colorless suspension under nitrogen. 1,1'-bis(diphenylphosphino)ferrocenepalladium(II) dichloride, toluene (4.38 mg, 5.32 µmol) was added under nitrogen. The vial was sealed and heated at 100° C. (bath: 108° C.) for 2 h. The mixture was diluted with EtOAc, dried with Na$_2$SO$_4$, and passed through a plug of Na$_2$SO$_4$. The organic solution was concentrated to afford the desired product (70 mg, 100% crude yield) as a tan oil, which was directly used in the next step. LCMS (ESI) m/e 411.2 [(M+H)$^+$, calcd C$_{23}$H$_{31}$N$_4$O$_3$, 411.2].

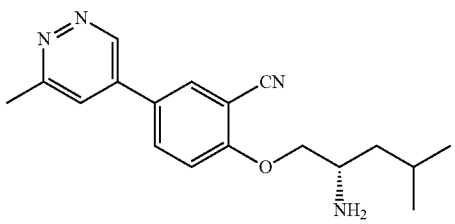 [SMILES: Cc1cc(-c2ccc(OC[C@@H](N)CC(C)C)c(C#N)c2)cnn1]

Part B: (S)-2-((2-amino-4-methylpentyl)oxy)-5-(6-methylpyridazin-4-yl)benzonitrile Prepared as previously described in Example 7, Part B to afford (S)-2-((2-amino-4-methylpentyl)oxy)-5-(6-methylpyridazin-4-yl)benzonitrile (20.8 mg, 63% for 2 steps) as a colorless solid. ¹H NMR (500 MHz, DMSO-d₆) δ 9.51 (d, J=2.4 Hz, 1H), 8.40 (d, J=2.4 Hz, 1H), 8.24 (dd, J=8.9, 2.5 Hz, 1H), 7.96 (d, J=2.4 Hz, 1H), 7.44 (d, J=9.0 Hz, 1H), 4.11 (dd, J=9.7, 5.1 Hz, 1H), 4.04 (dd, J=9.6, 6.3 Hz, 1H), 3.17 (t, J=6.6 Hz, 1H), 2.67 (s, 3H), 1.84 (p, J=6.6 Hz, 1H), 1.38 (ddd, J=13.5, 8.3, 5.0 Hz, 1H), 1.30 (dq, J=13.9, 7.0, 6.4 Hz, 1H), 0.93 (d, J=6.6 Hz, 3H), 0.89 (d, J=6.6 Hz, 3H); LCMS (ESI) m/e 311.2 [(M+H)⁺, calcd $C_{18}H_{23}N_4O$, 311.2]; LC/MS retention time (method B): $t_R$=1.46 min.

Example 110

(S)-1-(2-(isoxazol-5-yl)-4-(quinolin-4-yl)phenoxy)-4-methylpentan-2-amine

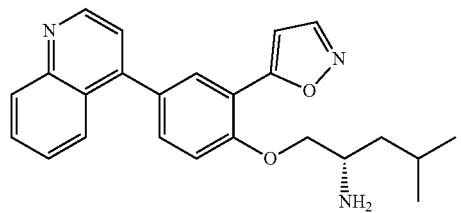

Part A: (S)-tert-butyl (1-(4-bromo-2-(isoxazol-5-yl)phenoxy)-4-methylpentan-2-yl)carbamate To a 15 mL vial was added (S)-tert-butyl (1-hydroxy-4-methylpentan-2-yl)carbamate (204 mg, 0.939 mmol), Ph₃P (320 mg, 1.220 mmol), and 4-bromo-2-(isoxazol-5-yl)phenol (225 mg, 0.939 mmol) in tetrahydrofuran (3 mL) to give a tan solution. DIAD (0.256 mL, 1.314 mmol) was added at rt. The resultant clear tan solution was stirred at rt overnight for 18 h. The solution was concentrated to a dense oil and was directly purified by silica gel chromatography (up to 40% EtOAc/hexane) to afford (S)-tert-butyl (1-(4-bromo-2-(isoxazol-5-yl)phenoxy)-4-methylpentan-2-yl)carbamate (319 mg, 77%) as a white solid: ¹H NMR (400 MHz, Chloroform-d) δ 8.31 (s, 1H), 8.09 (d, J=2.4 Hz, 1H), 7.46 (dd, J=9.1, 2.6 Hz, 1H), 6.88 (d, J=9.0 Hz, 2H), 4.60 (d, J=8.9 Hz, 1H), 4.19 (d, J=7.0 Hz, 1H), 4.02 (qd, J=9.2, 5.2 Hz, 2H), 1.75 (dq, J=13.6, 6.7 Hz, 1H), 1.46 (d, J=12.0 Hz, 11H), 0.98 (d, J=6.6 Hz, 6H).

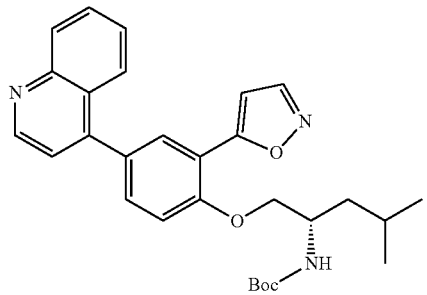 [SMILES: CC(C)C[C@@H](COc1ccc(-c2ccnc3ccccc23)cc1-c1ccno1)NC(=O)OC(C)(C)C]

Part B: (S)-tert-butyl (1-(2-(isoxazol-5-yl)-4-(quinolin-4-yl)phenoxy)-4-methylpentan-2-yl)carbamate Prepared as previously described in Example 109 to afford (S)-tert-butyl (1-(2-(isoxazol-5-yl)-4-(quinolin-4-yl)phenoxy)-4-methylpentan-2-yl)carbamate. LCMS (ESI) m/e 488.4 [(M+H)⁺, calcd $C_{29}H_{34}N_3O_4$, 488.2]; LC/MS retention time (method A): $t_R$=2.27 min.

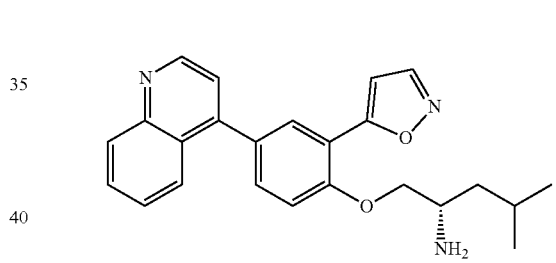

Part C: (S)-1-(2-(isoxazol-5-yl)-4-(quinolin-4-yl)phenoxy)-4-methylpentan-2-amine Prepared as previously described in Example 7, Part B to afford (S)-1-(2-(isoxazol-5-yl)-4-(quinolin-4-yl)phenoxy)-4-methylpentan-2-amine (12.9 mg, 44% for two steps): ¹H NMR (500 MHz, DMSO-d₆) δ 8.97 (d, J=4.4 Hz, 1H), 8.72 (d, J=1.8 Hz, 1H), 8.14 (d, J=8.5 Hz, 1H), 8.02 (d, J=2.3 Hz, 1H), 7.95 (d, J=8.5 Hz, 1H), 7.82 (t, J=7.6 Hz, 1H), 7.70 (dd, J=8.5, 2.3 Hz, 1H), 7.64 (t, J=7.6 Hz, 1H), 7.54 (d, J=4.4 Hz, 1H), 7.45 (d, J=8.6 Hz, 1H), 7.06 (d, J=1.9 Hz, 1H), 4.13 (dd, J=9.4, 4.9 Hz, 1H), 4.05 (dd, J=9.4, 6.2 Hz, 1H), 3.25 (dq, J=10.4, 5.6 Hz, 1H), 1.85 (dt, J=13.4, 7.5 Hz, 1H), 1.41 (ddd, J=13.4, 8.4, 4.7 Hz, 1H), 1.32 (ddd, J=13.8, 8.7, 5.6 Hz, 1H), 0.93 (dd, J=9.2, 6.6 Hz, 6H); LCMS (ESI) m/e 388.1 [(M+H)⁺, calcd $C_{24}H_{26}N_3O_2$, 388.2]; LC/MS retention time (method B): $t_R$=1.59 min.

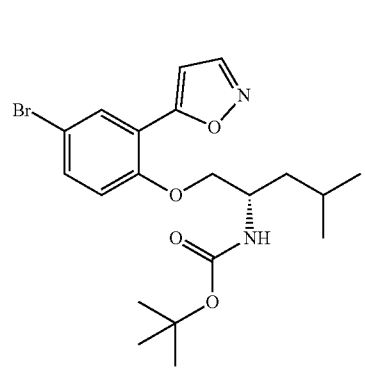

Example 111

(S)-4-(4-((2-amino-2,4-dimethylpentyl)oxy)-3-(trifluoromethyl)phenyl)-2-methylnicotinic acid

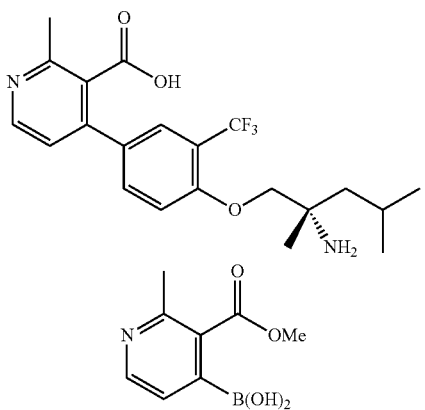

Part A: (3-(methoxycarbonyl)-2-methylpyridin-4-yl)boronic acid

To a vial was added methyl 4-chloro-2-methylnicotinate (52 mg, 0.280 mmol), hypodiboric acid (37.7 mg, 0.420 mmol), 2-(dicyclohexylphosphino))-2',4',6'-triisopropylbiphenyl (2.67 mg, 5.60 µmol), Xphos precatalyst (2.204 mg, 2.80 µmol) and potassium acetate (82 mg, 0.840 mmol) in ethanol (2.6 mL) to give a tan suspension (degassed before adding reagents). The vial was capped and heated at 80° C. for 1 h. LCMS showed conversion of the starting material to a new polar peak but with no parent ion. The mixture was directly used in the next step.

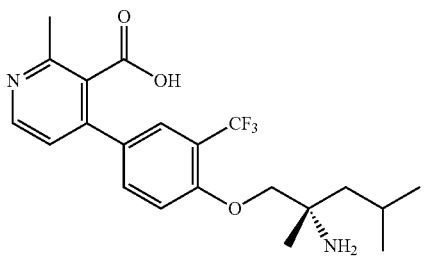 [SMILES: Cc1nccc(-c2ccc(OC[C@@](C)(N)CC(C)C)c(C(F)(F)F)c2)c1C(=O)O]

Part B: (S)-4-(4-((2-amino-2,4-dimethylpentyl)oxy)-3-(trifluoromethyl)phenyl)-2-methylnicotinic acid To a 20 mL vial was added (3-(methoxycarbonyl)-2-methylpyridin-4-yl)boronic acid (48.9 mg, 0.251 mmol) (previous reaction vessel) was added potassium phosphate tribasic (2.2 mL, 1.100 mmol). After degassing for 5 min, Xphos precatalyst (4.5 mg, 5.72 µmol) and (S)-1-(4-bromo-2-(trifluoromethyl)phenoxy)-2,4-dimethylpentan-2-amine (33 mg, 0.084 mmol) and tetrahydrofuran (2.2 mL) were added. The vial was sealed and heated at 80° C. overnight for 18 h. Volatiles were blown off. The residue was partitioned between EtOAc and water. The organic layer was dried, filtered and concentrated. The residue was dissolved in MeOH and purified by prep-HPLC to afford (S)-4-(4-((2-amino-2,4-dimethylpentyl)oxy)-3-(trifluoromethyl)phenyl)-2-methylnicotinic acid (18.8 mg, 53%): $^1$H NMR (600 MHz, DMSO-$d_6$) δ 8.27 (d, J=5.1 Hz, 1H), 7.88 (s, 1H), 7.83 (d, J=8.6 Hz, 1H), 7.08 (d, J=5.2 Hz, 1H), 6.96 (d, J=8.6 Hz, 1H), 3.99-3.92 (m, 2H), 2.47 (s, 3H), 1.88-1.72 (m, 1H), 1.60-1.45 (m, 2H), 1.24 (s, 3H), 0.89 (d, J=6.5 Hz, 6H); LCMS (ESI) m/e 433.2 [(M+Na)$^+$, calcd $C_{21}H_{25}F_3N_2O_3Na$, 433.2]; LC/MS retention time (method C): $t_R$=2.60 min.

Example 112

(S)-methyl(4-(4-((2-amino-2,4-dimethylpentyl)oxy)-3-((dimethylamino)methyl)phenyl)pyridin-2-yl)carbamate

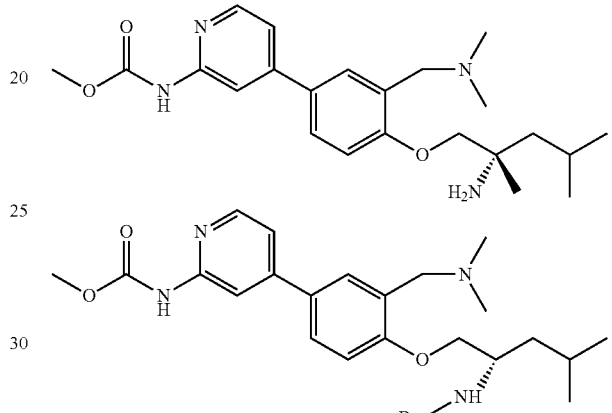

Part A: (S)-methyl (4-(4-((2-Boc-amino-2,4-dimethylpentyl)oxy)-3-((dimethylamino)methyl)phenyl)pyridin-2-yl)carbamate To a 2 mL vial was added crude aldehyde (prepared as described in Example 32 (10.68 mg, 0.022 mmol) in CH$_2$Cl$_2$ (0.5 mL) to give a tan solution. Dimethylamine (0.110 mL, 0.220 mmol) (2.0 M in THF, excess) was added, followed by sodium triacetoxyborohydride (0.019 g, 0.088 mmol). The mixture was stirred at rt overnight for 16 h. LCMS showed complete conversion to the desired product (M+H=515.2). The mixture was partitioned between water and EtOAc. The layers were separated. The organic layer was washed with brine, dried and concentrated. The tan residue was directly carried onto next reaction.

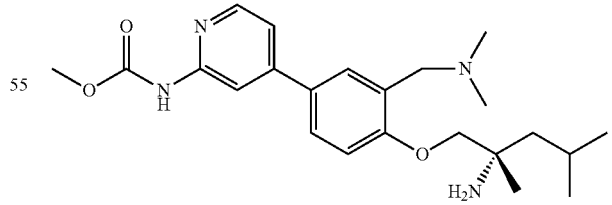

Part B: (S)-methyl (4-(4-((2-amino-2,4-dimethylpentyl)oxy)-3-((dimethylamino)methyl)phenyl)pyridin-2-yl)carbamate Prepared as previously described in Example 7, Part B to afford (S)-methyl (4-(4-((2-amino-2,4-dimethylpentyl)oxy)-

3-((dimethylamino)methyl)phenyl)pyridin-2-yl)carbamate (5.5 mg, 60% for three steps): $^1$H NMR (500 MHz, DMSO-$d_6$) δ 8.28 (d, J=5.3 Hz, 1H), 8.10 (s, 1H), 7.64 (d, J=6.8 Hz, 2H), 7.32 (d, J=5.4 Hz, 1H), 7.12 (d, J=8.8 Hz, 1H), 3.83 (s, 2H), 3.70 (s, 3H), 3.51 (s, 2H), 2.20 (s, 6H), 1.81 (dt, J=12.6, 6.4 Hz, 1H), 1.46 (qd, J=14.0, 5.6 Hz, 2H), 1.19 (s, 3H), 0.94 (t, J=6.1 Hz, 6H); LCMS (ESI) m/e 415.1 [(M+H)$^+$, calcd $C_{23}H_{35}N_4O_3$, 415.3]; LC/MS retention time (method B): $t_R$=1.43 min.

Example 113

(S)-methyl(4-(4-((2-amino-2,4-dimethylpentyl)oxy)-3-(methylsulfonyl)phenyl)pyridin-2-yl)carbamate

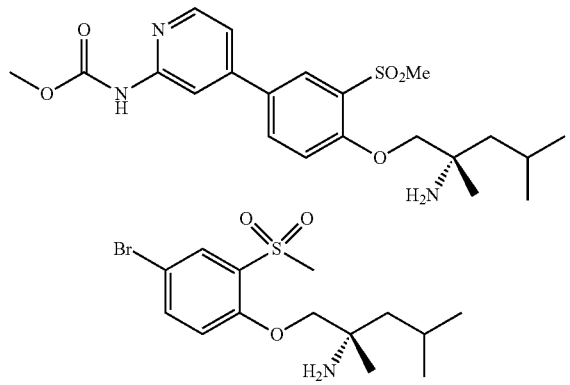

Part A: (S)-1-(4-bromo-2-(methylsulfonyl)phenoxy)-2,4-dimethylpentan-2-amine

To a 5 mL vial was added (S)-2-amino-2,4-dimethylpentan-1-ol (120 mg, 0.915 mmol) in tetrahydrofuran (1.2 mL) to give a colorless solution. Potassium tert-butoxide (1.097 mL, 1.097 mmol) (1.0 M in THF) was added dropwise under nitrogen. After 5 min, 4-bromo-1-fluoro-2-(methylsulfonyl) benzene (243 mg, 0.960 mmol) was added in one portion. The bottle was sealed and the mixture was stirred at 70° C. for 18 h. The mixture was partitioned between water and EtOAc. The layers were separated. The aqueous layer was extracted with EtOAc. The combined organic solution was washed with brine, dried and concentrated to a red oil (313 mg, 94%): $^1$H NMR (400 MHz, Chloroform-d) δ 8.10 (d, J=2.6 Hz, 1H), 7.69 (dd, J=8.8, 2.5 Hz, 1H), 6.94 (d, J=8.8 Hz, 1H), 3.90 (q, J=8.5 Hz, 2H), 3.24 (s, 3H), 1.90-1.75 (m, 1H), 1.52 (dd, J=5.7, 3.5 Hz, 2H), 1.28 (s, 3H), 1.01 (dd, J=10.6, 6.7 Hz, 6H); LCMS (ESI) m/e 363.9 [(M+H)$^+$, calcd C14H23BrNO$_3$S, 364.1]; LC/MS retention time (method B): $t_R$=1.64 min.

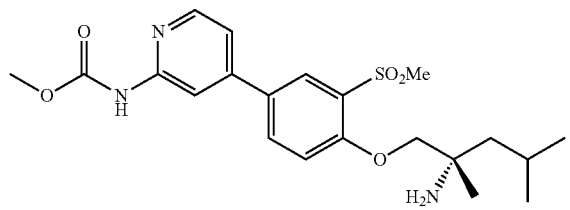 [SMILES: COC(=O)Nc1cc(-c2ccc(OC[C@@](C)(N)CC(C)C)c(S(C)(=O)=O)c2)ccn1]

Part B: (S)-methyl (4-(4-((2-amino-2,4-dimethylpentyl)oxy)-3-(methylsulfonyl)phenyl)pyridin-2-yl) carbamate Prepared as previously described in Example 109 to afford (S)-methyl (4-(4-((2-amino-2,4-dimethylpentyl)oxy)-3-(methylsulfonyl)phenyl)pyridin-2-yl)carbamate (25.6 mg, 75%): $^1$H NMR (500 MHz, DMSO-$d_6$) δ 8.34 (d, J=5.2 Hz, 1H), 8.14 (s, 1H), 8.12-8.03 (m, 2H), 7.45 (d, J=8.6 Hz, 1H), 7.38 (d, J=5.3 Hz, 1H), 3.97 (s, 2H), 3.71 (s, 3H), 3.42 (s, 3H), 1.83 (dt, J=12.2, 6.2 Hz, 1H), 1.49-1.37 (m, 2H), 1.17 (s, 3H), 0.94 (dd, J=8.7, 6.6 Hz, 6H); LCMS (ESI) m/e 436.0 [(M+H)$^+$, calcd $C_{21}H_3N_3O_5S$, 436.2]; LC/MS retention time (method B): $t_R$=1.52 min.

Example 114

(S)-2,4-dimethyl-1-(4-(2-methylpyridin-4-yl)-2-(methylsulfonyl)phenoxy)pentan-2-amine

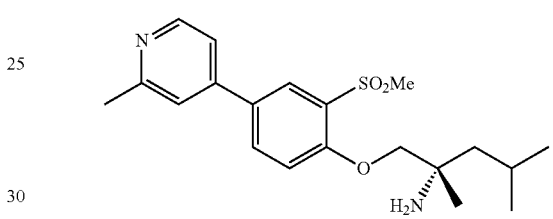

Prepared as described in Example 113 to afford (S)-2,4-dimethyl-1-(4-(2-methylpyridin-4-yl)-2-(methylsulfonyl) phenoxy)pentan-2-amine (19 mg, 0.049 mmol, 83%): $^1$H NMR (500 MHz, DMSO-$d_6$) δ 8.51 (d, J=5.3 Hz, 1H), 8.17-8.10 (m, 2H), 7.59 (s, 1H), 7.52-7.46 (m, 1H), 7.43 (d, J=9.2 Hz, 1H), 3.97 (s, 2H), 3.55 (s, 3H), 2.55 (s, 3H), 1.83 (dt, J=13.0, 6.3 Hz, 1H), 1.50-1.37 (m, 2H), 1.17 (s, 3H), 0.94 (dd, J=8.8, 6.5 Hz, 6H); LCMS (ESI) m/e 377.0 [(M+H)$^+$, calcd $C_{20}H_{29}N_2O_3S$, 377.2]; LC/MS retention time (method B): $t_R$=1.32 min.

Example 115

(S)-2,4-dimethyl-1-(2-(methylsulfonyl)-4-(quinolin-4-yl)phenoxy)pentan-2-amine

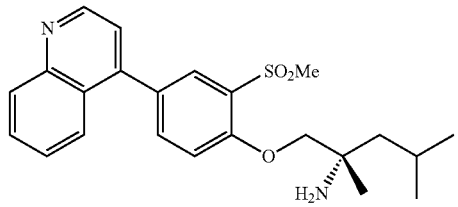 [SMILES: CC(C)C[C@](C)(N)COc1ccc(-c2ccnc3ccccc23)cc1S(C)(=O)=O]

Prepared as described in Example 113 to afford (S)-2,4-dimethyl-1-(2-(methylsulfonyl)-4-(quinolin-4-yl)phenoxy) pentan-2-amine (12.2 mg, 0.029 mmol, 58%): $^1$H NMR (500 MHz, DMSO-$d_6$) δ 8.97 (d, J=4.4 Hz, 1H), 8.14 (d, J=8.3 Hz, 1H), 7.95-7.87 (m, 3H), 7.83 (t, J=7.7 Hz, 1H), 7.65 (t, J=7.7 Hz, 1H), 7.55-7.47 (m, 2H), 4.01 (s, 2H), 3.49 (s, 3H), 1.85 (dt, J=12.9, 6.5 Hz, 1H), 1.53-1.39 (m, 2H), 1.19 (s, 3H), 0.97 (dd, J=8.4, 6.6 Hz, 6H); LCMS (ESI) m/e 413.0

[(M+H)+, calcd C23H29N2O3S, 413.2]; LC/MS retention time (method B): $t_R$=1.41 min.

Example 116

(S)-1-(2-(difluoromethyl)-4-(6-fluoroquinolin-4-yl)phenoxy)-2,4-dimethylpentan-2-amine

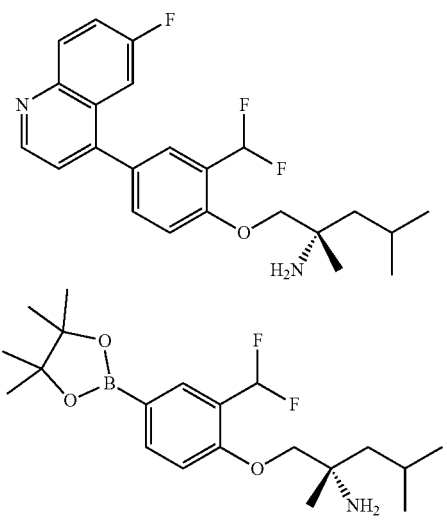

Part A: (S)-1-(2-(difluoromethyl)-4-(4,4,5,5-tetramethyl-1,3,2-dioxaborolan-2-yl)phenoxy)-2,4-dimethylpentan-2-amine To a 5 mL vial was added (S)-1-(4-bromo-2-(difluoromethyl)phenoxy)-2,4-dimethylpentan-2-amine (16.2 mg, 0.048 mmol), 4,4,4',4',5,5,5',5'-octamethyl-2,2'-bi(1,3,2-dioxaborolane) (14.68 mg, 0.058 mmol), and potassium acetate (14.19 mg, 0.145 mmol) in dioxane (0.5 mL) to give a colorless suspension with nitrogen bubbling. PdCl2(dppf) (1.058 mg, 1.446 μmol) was added under nitrogen. The vial was sealed and the mixture was heated at 80° C. for 4 h. LCMS showed most starting material was gone and several peaks. It was used directly in the next step.

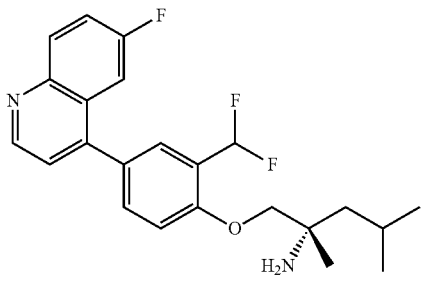

Part B: (S)-1-(2-(difluoromethyl)-4-(6-fluoroquinolin-4-yl)phenoxy)-2,4-dimethylpentan-2-amine The mixture of (S)-1-(2-(difluoromethyl)-4-(4,4,5,5-tetramethyl-1,3,2-dioxaborolan-2-yl)phenoxy)-2,4-dimethylpentan-2-amine (18.40 mg, 0.048 mmol), 1,1'-bis(diphenylphosphino)ferrocenepalladium(II) dichloride, dichloromethane complex (2.74 mg, 3.36 μmol), Na2CO3 (0.096 mL, 0.192 mmol) and 4-chloro-6-fluoroquinoline (8.72 mg, 0.048 mmol) in dioxane (0.5 mL) (degassed) (previous vial) was heated at 120° C. for 16 h. The reaction mixture was diluted with ethyl acetate and dried (Na2SO4), filtered and concentrated. The residue was dissolved in MeOH and purified by prep-HPLC to afford (S)-1-(2-(difluoromethyl)-4-(6-fluoroquinolin-4-yl)phenoxy)-2,4-dimethylpentan-2-amine (6.7 mg, 35% for two steps): 1H NMR (500 MHz, DMSO-d6) δ 8.95 (d, J=4.5 Hz, 1H), 8.20 (dd, J=9.2, 5.7 Hz, 1H), 7.74 (ddd, J=13.0, 8.0, 3.4 Hz, 2H), 7.68 (d, J=2.3 Hz, 1H), 7.54 (d, J=4.4 Hz, 1H), 7.50 (dd, J=10.3, 2.9 Hz, 1H), 7.44-7.17 (m, 2H), 3.61 (s, 2H), 1.82 (dq, J=12.8, 6.4 Hz, 1H), 1.50-1.37 (m, 2H), 1.16 (s, 3H), 0.95 (dd, J=10.2, 6.6 Hz, 6H); LCMS (ESI) m/e 403.0 [(M+H)+, calcd C23H26F3N2O, 403.2]; LC/MS retention time (method B): $t_R$=1.78 min.

Example 117

(S)-methyl (5-((2-amino-2,4-dimethylpentyl)oxy)-6-(difluoromethyl)-[2,4'-bipyridin]-2'-yl)carbamate

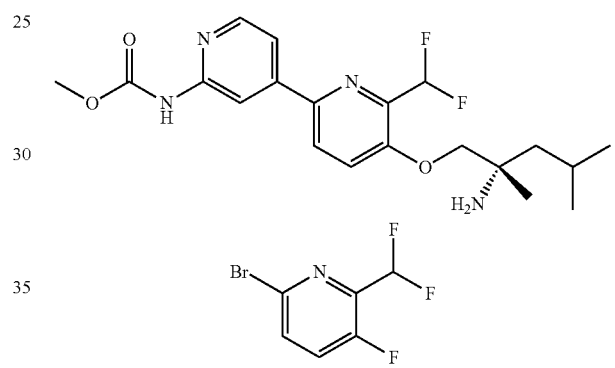

Part A: 6-bromo-2-(difluoromethyl)-3-fluoropyridine

To a 100 mL round-bottomed flask was added 6-bromo-3-fluoropicolinaldehyde (459.8 mg, 2.254 mmol) in CH2Cl2 (10 mL) to give a tan solution. After cooling to −20° C., DAST (0.596 mL, 4.51 mmol) was added dropwise under nitrogen. The mixture was gradually warmed up to rt. The mixture was stirred at rt for 3 h. TLC (3/1 hexane/EtOAc) showed complete conversion to a less polar spot. The reaction was slowly quenched by saturated NaHCO3 solution and diluted with ether. The layers were separated. The organic layer was washed with water, brine, dried and concentrated to 6-bromo-2-(difluoromethyl)-3-fluoropyridine (509 mg, 100%) as a tan solid: 1H NMR (400 MHz, Chloroform-d) δ 7.65 (ddt, J=8.6, 3.5, 1.0 Hz, 1H), 7.46 (t, J=8.7 Hz, 1H), 6.73 (t, J=53.4 Hz, 1H); 19F NMR (376 MHz, Chloroform-d) δ −116.97, −127.89.

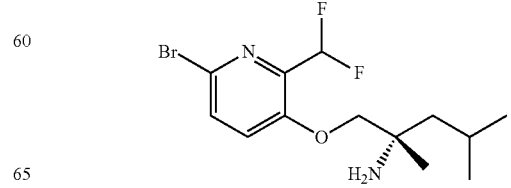

Part B: (S)-1-((6-bromo-2-(difluoromethyl)pyridin-3-yl)oxy)-2,4-dimethylpentan-2-amine To a 5 mL pressure bottle was added (S)-2-amino-2,4-dimethylpentan-1-ol (140 mg, 1.067 mmol) in tetrahydrofuran (1.3 mL) to give a colorless solution. Potassium tert-butoxide (1.280 mL, 1.280 mmol) (1.0 M in THF) was added dropwise under nitrogen. After 5 min, 6-bromo-2-(difluoromethyl)-3-fluoropyridine (241 mg, 1.067 mmol) was added in one portion. The bottle was sealed and the mixture was stirred at 80° C. for 18 h. The mixture was partitioned between water and EtOAc. The layers were separated. The aqueous layer was extracted with EtOAc. The combined organic solution was washed with brine, dried and concentrated to a tan oil (338 mg, 94%): $^1$H NMR (400 MHz, Chloroform-d) δ 7.54 (dt, J=9.0, 1.1 Hz, 1H), 7.22 (d, J=8.8 Hz, 1H), 6.74 (t, J=53.9 Hz, 1H), 3.79 (d, J=1.7 Hz, 2H), 1.80 (dtd, J=13.3, 6.7, 1.1 Hz, 1H), 1.54 (s, 2H), 1.52-1.47 (m, 2H), 1.25 (s, 3H), 1.00 (dd, J=8.3, 6.6 Hz, 6H); $^{19}$F NMR (376 MHz, Chloroform-d) 6-117.98; LCMS (ESI) m/e 336.9 [(M+H)$^+$, calcd C$_{13}$H$_{20}$BrF$_2$N$_2$O, 337.1]; LC/MS retention time (method B): $t_R$=1.67 min.

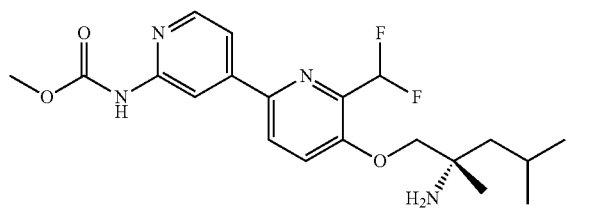 [SMILES: COC(=O)Nc1cc(-c2ccc(OC[C@@](C)(N)CC(C)C)c(C(F)F)n2)ccn1]

Part C: (S)-methyl(5-((2-amino-2,4-dimethylpentyl)oxy)-6-(difluoromethyl)-[2,4'-bipyridin]-2'-yl)carbamate To a 2 mL vial was added (S)-1-((6-bromo-2-(difluoromethyl)pyridin-3-yl)oxy)-2,4-dimethylpentan-2-amine (28.4 mg, 0.084 mmol), (2-((methoxycarbonyl)amino)pyridin-4-yl)boronic acid (41.3 mg, 0.211 mmol), and Na$_2$CO$_3$ (0.126 mL, 0.253 mmol) in dioxane (0.6 mL) to give a colorless suspension under nitrogen. 1,1'-bis(diphenylphosphino)ferrocenepalladium(II) dichloride, toluene (3.46 mg, 4.21 μmol) was added under nitrogen. The vial was sealed and heated at 100° C. (bath temp: 110° C.) for 3 h. The mixture was diluted with EtOAc and passed through a plug of Na$_2$SO$_4$. The organic solution was concentrated. The residue was purified twice by prep-HPLC to afford (S)-methyl (5-((2-amino-2,4-dimethylpentyl)oxy)-6-(difluoromethyl)-[2,4'-bipyridin]-2'-yl)carbamate (12.6 mg, 37%): $^1$H NMR (500 MHz, DMSO-d$_6$) δ 8.50 (s, 1H), 8.36 (d, J=5.2 Hz, 1H), 8.17 (d, J=8.8 Hz, 1H), 7.78 (d, J=8.8 Hz, 1H), 7.67 (dd, J=5.1, 1.7 Hz, 1H), 7.22 (t, J=53.6 Hz, 1H), 3.88 (s, 2H), 3.52 (s, 3H), 1.86-1.73 (m, 1H), 1.47-1.33 (m, 2H), 1.13 (s, 3H), 0.93 (dd, J=10.0, 6.6 Hz, 6H); LCMS (ESI) m/e 409.0 (M+H)$^+$, calcd C$_{20}$H$_{27}$F$_2$N$_4$O$_3$, 409.2]; LC/MS retention time (method B): $t_R$=1.66 min.

Example 118

(S)-1-((2-(difluoromethyl)-6-(quinolin-4-yl)pyridin-3-yl)oxy)-2,4-dimethylpentan-2-amine

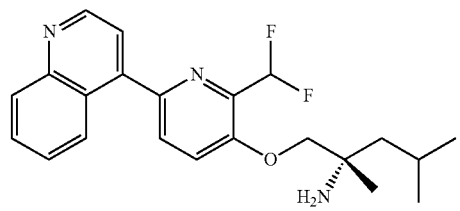 [SMILES: CC(C)C[C@](C)(N)COc1ccc(-c2ccnc3ccccc23)nc1C(F)F]

Prepared as described in Example 117 to afford (S)-1-((2-(difluoromethyl)-6-(quinolin-4-yl)pyridin-3-yl)oxy)-2,4-dimethylpentan-2-amine (10.6 mg, 0.027 mmol, 60% yield for three steps): $^1$H NMR (500 MHz, DMSO-d$_6$) δ 9.01 (d, J=4.4 Hz, 1H), 8.21 (d, J=8.5 Hz, 1H), 8.13 (d, J=8.4 Hz, 1H), 7.97 (d, J=8.7 Hz, 1H), 7.87 (d, J=8.7 Hz, 1H), 7.82 (t, J=7.7 Hz, 1H), 7.64 (dd, J=9.5, 6.0 Hz, 2H), 7.28 (t, J=53.6 Hz, 1H), 3.53 (s, 2H), 1.83 (dt, J=13.2, 6.6 Hz, 1H), 1.50-1.37 (m, 2H), 1.16 (s, 3H), 0.95 (dd, J=10.0, 6.7 Hz, 6H); LCMS (ESI) m/e 386.0 [(M+H)$^+$, calcd C$_{22}$H$_{26}$F$_2$N$_3$O, 386.2]; LC/MS retention time (method B): $t_R$=1.54 min.

Example 119

(S)-1-((6-(difluoromethyl)-2'-methyl-[2,4'-bipyridin]-5-yl)oxy)-2,4-dimethylpentan-2-amine

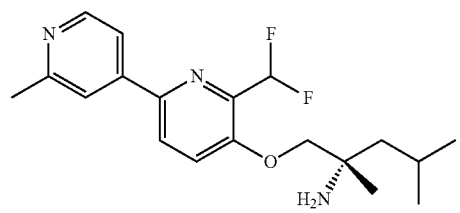

Prepared as described in Example 117 to afford (S)-1-((6-(difluoromethyl)-2'-methyl-[2,4'-bipyridin]-5-yl)oxy)-2,4-dimethylpentan-2-amine (18.3 mg, 0.051 mmol, 92% yield for three steps): $^1$H NMR (500 MHz, DMSO-d$_6$) δ 8.54 (d, J=5.2 Hz, 1H), 8.26 (d, J=8.8 Hz, 1H), 7.90 (s, 1H), 7.82 (d, J=5.3 Hz, 1H), 7.78 (d, J=8.8 Hz, 1H), 7.23 (t, J=53.6 Hz, 1H), 3.89 (s, 2H), 2.56 (s, 3H), 1.81 (dq, J=12.8, 6.5 Hz, 1H), 1.50-1.34 (m, 2H), 1.14 (s, 3H), 0.92 (dd, J=10.5, 6.6 Hz, 6H); LCMS (ESI) m/e 350.0 [(M+H)$^+$, calcd C$_{19}$H$_{26}$F$_2$N$_3$O, 350.2]; LC/MS retention time (method B): $t_R$=1.45 min.

Example 120

(S)-methyl (5-((2-amino-2,4-dimethylpentyl)oxy)-4-(difluoromethyl)-[2,4'-bipyridin]-2'-yl)carbamate

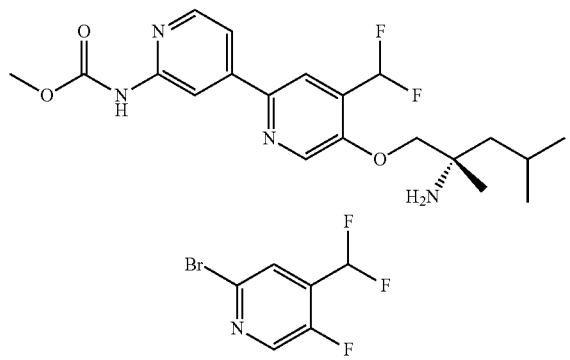

Part A: 2-bromo-4-(difluoromethyl)-5-fluoropyridine

To a 100 mL round-bottomed flask was added 2-bromo-5-fluoroisonicotinaldehyde (605 mg, 2.97 mmol) in $CH_2Cl_2$ (12 mL) to give a tan solution. After cooling to −20° C., DAST (0.705 mL, 5.34 mmol) was added dropwise under nitrogen. The mixture was gradually warmed up to rt. The mixture was stirred at rt for 3 h. TLC (3/1 hexane/EtOAc) showed complete conversion to a less polar spot. The reaction was slowly quenched by saturated NaHCO3 solution and diluted with ether. The layers were separated. The organic layer was washed with water, brine, dried and concentrated to afford 2-bromo-4-(difluoromethyl)-5-fluoropyridine (639 mg, 95%) as a tan oil: $^1$H NMR (400 MHz, Chloroform-d) δ 8.39 (q, J=1.2 Hz, 1H), 7.77-7.68 (m, 1H), 6.86 (t, J=54.0 Hz, 1H); $^{19}$F NMR (376 MHz, Chloroform-d) δ −117.92, −135.51.

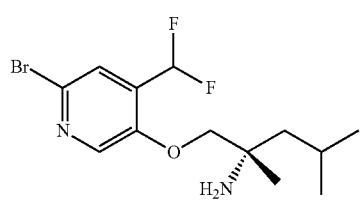 [SMILES: CC(C)C[C@](C)(N)COc1cnc(Br)cc1C(F)F]

Part B: (S)-1-((6-bromo-4-(difluoromethyl)pyridin-3-yl)oxy)-2,4-dimethylpentan-2-amine To a 20 mL pressure bottle was added (S)-2-amino-2,4-dimethylpentan-1-ol (146 mg, 1.113 mmol) and 2-bromo-4-(difluoromethyl)-5-fluoropyridine (251 mg, 1.113 mmol) in tetrahydrofuran (1.5 mL) to give a tan solution. Potassium tert-butoxide (1.335 mL, 1.335 mmol) (1.0 M in THF) was added dropwise under nitrogen. After 5 min stirring at rt, the bottle was sealed and the mixture was stirred at 80° C. for 18 h. The mixture was partitioned between water and EtOAc. The layers were separated. The aqueous layer was extracted with EtOAc. The combined organic solution was washed with brine, dried and concentrated to a tan oil (361 mg, 96%): $^1$H NMR (400 MHz, Chloroform-d) δ 8.13 (s, 1H), 7.62 (s, 1H), 6.85 (t, J=54.4 Hz, 1H), 3.87 (s, 2H), 1.80 (dtd, J=13.2, 6.7, 1.0 Hz, 1H), 1.61-1.50 (m, 2H), 1.50-1.47 (m, 2H), 1.24 (s, 3H), 1.00 (dd, J=7.4, 6.7 Hz, 6H); $^{19}$F NMR (376 MHz, Chloroform-d) δ −119.58; LCMS (ESI) m/e 336.9 [(M+H)$^+$, calcd $C_{13}H_{20}BrF_2N_2O$, 337.1]; LC/MS retention time (method B): $t_R$=1.79 min.

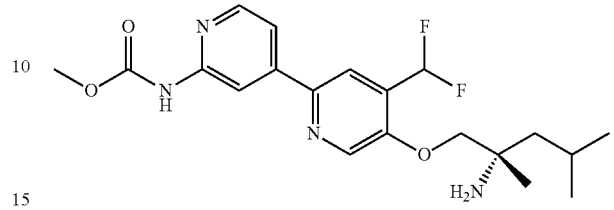

Part C: (S)-methyl (5-((2-amino-2,4-dimethylpentyl)oxy)-4-(difluoromethyl)-[2,4'-bipyridin]-2'-yl)carbamate Prepared as described in Example 117 to afford (S)-methyl (5-((2-amino-2,4-dimethylpentyl)oxy)-4-(difluoromethyl)-[2,4'-bipyridin]-2'-yl)carbamate (2.5 mg, 0.006 mmol, 6% yield for three steps): $^1$H NMR (500 MHz, DMSO-$d_6$) δ 8.71 (s, 1H), 8.53 (s, 1H), 8.36 (d, J=5.2 Hz, 1H), 8.08 (s, 1H), 7.71 (d, J=5.2 Hz, 1H), 7.48 (t, J=53.9 Hz, 1H), 4.12 (s, 2H), 3.71 (s, 3H), 1.82 (dt, J=12.9, 6.4 Hz, 1H), 1.53 (dd, J=14.2, 5.3 Hz, 1H), 1.46 (dd, J=14.2, 5.8 Hz, 1H), 1.22 (s, 3H), 0.95 (d, J=6.6 Hz, 3H), 0.91 (d, J=6.6 Hz, 3H); LCMS (ESI) m/e 408.9 (M+H)$^+$, calcd $C_{20}H_{27}F_2N_4O_3$, 409.2]; LC/MS retention time (method B): $t_R$=1.66 min.

Example 121

(S)-1-((4-(difluoromethyl)-6-(quinolin-4-yl)pyridin-3-yl)oxy)-2,4-dimethylpentan-2-amine

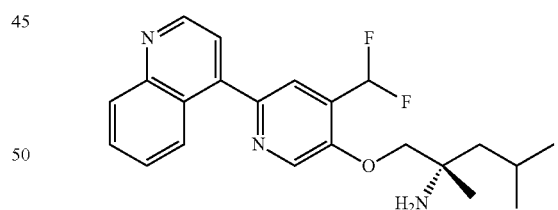

Prepared as described in Example 117 to afford (S)-1-((4-(difluoromethyl)-6-(quinolin-4-yl)pyridin-3-yl)oxy)-2,4-dimethylpentan-2-amine (11.7 mg, 0.030 mmol, 69% yield for three steps): $^1$H NMR (500 MHz, DMSO-$d_6$) δ 9.00 (d, J=4.4 Hz, 1H), 8.78 (s, 1H), 8.18 (d, J=8.5 Hz, 1H), 8.13 (d, J=8.5 Hz, 1H), 7.88 (s, 1H), 7.82 (t, J=7.6 Hz, 1H), 7.69-7.60 (m, 2H), 7.39 (t, J=53.8 Hz, 1H), 4.06 (s, 2H), 1.84 (dt, J=12.9, 6.3 Hz, 1H), 1.51-1.37 (m, 2H), 1.17 (s, 3H), 0.96 (dd, J=11.7, 6.7 Hz, 6H); LCMS (ESI) m/e 386.0 [(M+H)$^+$, calcd $C_{22}H_{26}F_2N_3O$, 386.2]; LC/MS retention time (method B): $t_R$=1.58 min.

Example 122

(S)-1-((4-(difluoromethyl)-2'-methyl-[2,4'-bipyridin]-5-yl)oxy)-2,4-dimethylpentan-2-amine

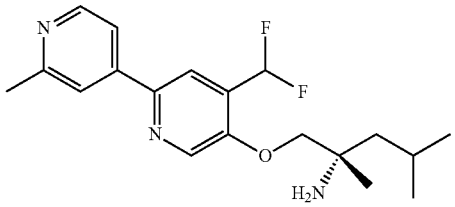

Prepared as described in Example 117 to afford (S)-1-((4-(difluoromethyl)-2'-methyl-[2,4'-bipyridin]-5-yl)oxy)-2,4-dimethylpentan-2-amine (13.6 mg, 0.039 mmol, 74% yield for three steps): $^1$H NMR (500 MHz, DMSO-d$_6$) δ 8.68 (s, 1H), 8.54 (d, J=5.3 Hz, 1H), 8.19 (s, 1H), 7.94 (s, 1H), 7.84 (d, J=5.2 Hz, 1H), 7.39 (t, J=53.9 Hz, 1H), 4.06 (s, 2H), 2.56 (s, 3H), 1.81 (dt, J=12.8, 6.4 Hz, 1H), 1.45 (qd, J=14.2, 5.7 Hz, 2H), 1.18 (s, 3H), 0.94 (d, J=6.6 Hz, 3H), 0.91 (d, J=6.6 Hz, 3H); LCMS (ESI) m/e 350.0 [(M+H)$^+$, calcd C$_{19}$H$_{26}$F$_2$N$_3$O, 350.2]; LC/MS retention time (method B): $t_R$=1.46 min.

Example 123

(S)-1-((2',6-bis(difluoromethyl)-[2,4'-bipyridin]-5-yl)oxy)-2,4-dimethylpentan-2-amine

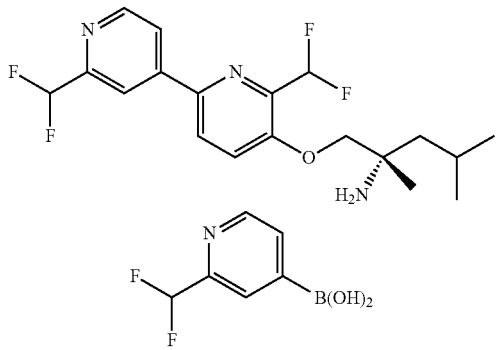

Part A: (2-(difluoromethyl)pyridin-4-yl)boronic acid

To a 20 mL vial was added 4-chloro-2-(difluoromethyl)pyridine hydrochloride (180 mg, 0.900 mmol), hypodiboric acid (121 mg, 1.350 mmol), 2-(dicyclohexylphosphino))-2', 4',6'-triisopropylbiphenyl (8.58 mg, 0.018 mmol), Xphos precatalyst (7.08 mg, 9.00 μmol) and potassium acetate (265 mg, 2.70 mmol) in ethanol (8.5 mL) to give a tan suspension (degassed before adding agents). The bottle was capped and heated at 80° C. for 1.5 h. LCMS showed the consumption of the starting material and formation of a new spot: (2-(difluoromethyl)pyridin-4-yl)boronic acid. The mixture was divided into parts and directly used in the next step of different reactions.

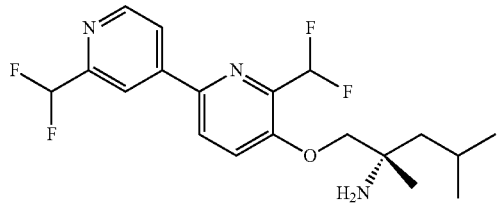 [SMILES: CC(C)C[C@](C)(N)COc1ccc(-c2ccnc(C(F)F)c2)nc1C(F)F]

Part B: (S)-1-((2',6-bis(difluoromethyl)-[2,4'-bipyridin]-5-yl)oxy)-2,4-dimethylpentan-2-amine To a 5 mL vial was added (2-(difluoromethyl)pyridin-4-yl)boronic acid (25.9 mg, 0.15 mmol) was added potassium phosphate tribasic (1 mL, 0.500 mmol). After degassing for 5 min, Xphos precatalyst (4 mg, 5.08 μmol) and (S)-1-((6-bromo-2-(difluoromethyl)pyridin-3-yl)oxy)-2,4-dimethylpentan-2-amine (26.5 mg, 0.079 mmol) and tetrahydrofuran (1 mL) were added. The vial was sealed and heated at 80° C. overnight for 18 h. Volatiles were blown off. The residue was partitioned between EtOAc and water. The organic layer was dried, filtered and concentrated. The residue was dissolved in MeOH and purified by prep-HPLC to afford (S)-1-((2',6-bis(difluoromethyl)-[2,4'-bipyridin]-5-yl)oxy)-2,4-dimethylpentan-2-amine (29.8 mg, 98%) as a colorless solid. $^1$H NMR (500 MHz, DMSO-d6) δ 8.79 (d, J=5.2 Hz, 1H), 8.40 (d, J=8.8 Hz, 1H), 8.32 (s, 1H), 8.21 (d, J=5.1 Hz, 1H), 7.82 (d, J=8.9 Hz, 1H), 7.31 (t, J=53.5 Hz, 1H), 7.04 (t, J=54.9 Hz, 1H), 3.96 (s, 2H), 3.46 (s, 2H), 1.80 (dp, J=12.5, 6.7, 6.3 Hz, 1H), 1.45 (qd, J=14.1, 5.6 Hz, 2H), 1.17 (s, 3H), 0.92 (dd, J=13.6, 6.6 Hz, 6H); $^{19}$F NMR (376 MHz, DMSO-d$_6$) δ −115.43 (d, J=55.2 Hz), −117.78−−119.55 (m); LCMS (ESI) m/e 386.0 [(M+H)$^+$, calcd C$_{19}$H$_{24}$F$_4$N$_3$O, 386.2]; LC/MS retention time (method B): $t_R$=1.85 min.

Example 124

(S)-1-((2',4-bis(difluoromethyl)-[2,4'-bipyridin]-5-yl)oxy)-2,4-dimethylpentan-2-amine

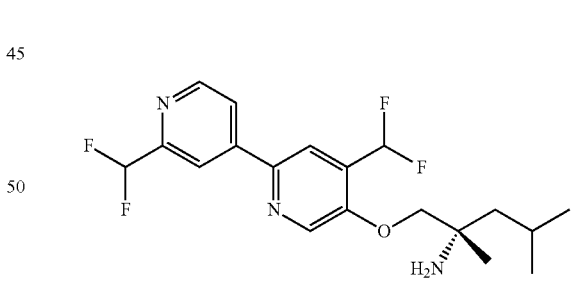

Prepared as described in Example 123 to afford (S)-1-((2',4-bis(difluoromethyl)-[2,4'-bipyridin]-5-yl)oxy)-2,4-dimethylpentan-2-amine (25.9 mg, 0.067 mmol, 77% yield) as a colorless solid. $^1$H NMR (500 MHz, DMSO-d$_6$) δ 8.79 (d, J=5.2 Hz, 1H), 8.71 (s, 1H), 8.36 (s, 1H), 8.32 (s, 1H), 8.25 (d, J=5.1 Hz, 1H), 7.35 (t, J=53.9 Hz, 1H), 7.04 (t, J=54.9 Hz, 1H), 4.03 (s, 2H), 1.81 (dt, J=12.8, 6.4 Hz, 1H), 1.48-1.33 (m, 2H), 1.14 (s, 3H), 0.93 (dd, J=12.3, 6.6 Hz, 6H); $^{19}$F NMR (376 MHz, DMSO-d$_6$) δ −115.44 (d, J=54.7 Hz), −116.34−−119.67 (m); LCMS (ESI) m/e 386.0 [(M+H)$^+$, calcd C$_{19}$H$_{24}$F$_4$N$_3$O, 386.2]; LC/MS retention time (method B): $t_R$=1.83 min.

Example 125

(S)-1-((2'-(difluoromethyl)-4-methyl-[2,4'-bipyridin]-5-yl)oxy)-2,4-dimethylpentan-2-amine

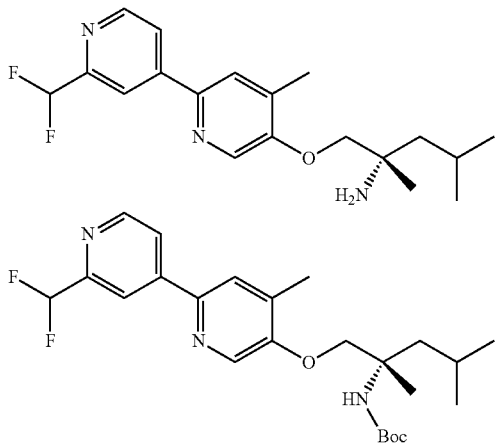

Part A: (S)-tert-butyl (1-((2'-(difluoromethyl)-4-methyl-[2,4'-bipyridin]-5-yl)oxy)-2,4-dimethylpentan-2-yl)carbamate Prepared as described in Example 123 to afford (S)-tert-butyl (1-((2'-(difluoromethyl)-4-methyl-[2,4'-bipyridin]-5-yl)oxy)-2,4-dimethylpentan-2-yl)carbamate (38.5 mg, 0.086 mmol, 80% yield) as a colorless solid. $^1$H NMR (400 MHz, Chloroform-d) δ 8.71 (d, J=5.2 Hz, 1H), 8.31 (s, 1H), 8.18 (d, J=1.7 Hz, 1H), 7.98 (dd, J=5.2, 1.7 Hz, 1H), 7.66 (s, 1H), 6.72 (t, J=55.5 Hz, 1H), 4.63 (s, 1H), 4.32 (d, J=8.7 Hz, 1H), 4.14 (d, J=8.8 Hz, 1H), 2.36 (s, 3H), 1.96-1.77 (m, 2H), 1.65-1.54 (m, 1H), 1.44 (s, 3H), 1.42 (s, 9H), 1.01 (dd, J=6.6, 3.5 Hz, 6H); $^{19}$F NMR (376 MHz, Chloroform-d) δ −115.81; LCMS (ESI) m/e 450.1 [(M+H)$^+$, calcd C$_{24}$H$_{34}$F$_2$N$_3$O$_3$, 450.2]; LC/MS retention time (method B): t$_R$=2.31 min.

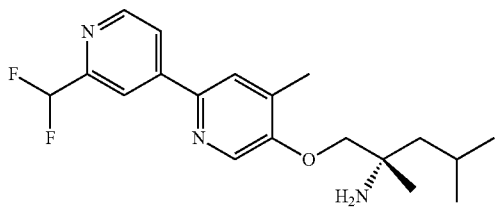 [SMILES: Cc1cc(-c2ccnc(C(F)F)c2)ncc1OC[C@@](C)(N)CC(C)C]

Part B: (S)-1-((2'-(difluoromethyl)-4-methyl-[2,4'-bipyridin]-5-yl)oxy)-2,4-dimethylpentan-2-amine Prepared as previously described in Example 7, Part B (34.9 mg, 100%): $^1$H NMR (500 MHz, DMSO-d$_6$) δ 8.76 (d, J=5.1 Hz, 1H), 8.42 (s, 1H), 8.31 (s, 1H), 8.22-8.15 (m, 1H), 8.12 (s, 1H), 7.03 (t, J=55.0 Hz, 1H), 4.13-4.00 (m, 2H), 2.36 (s, 3H), 1.83 (dp, J=12.7, 6.5 Hz, 1H), 1.60 (dd, J=14.1, 5.5 Hz, 1H), 1.52 (dd, J=14.1, 5.6 Hz, 1H), 1.27 (s, 3H), 0.95 (d, J=6.6 Hz, 3H), 0.92 (d, J=6.6 Hz, 3H); $^{19}$F NMR (376 MHz, DMSO-d6) δ −115.37 (d, J=54.8 Hz); LCMS (ESI) m/e 350.0 [(M+H)$^+$, calcd C$_{19}$H$_{26}$F$_2$N$_3$O, 350.2]; LC/MS retention time (method B): t$_R$=1.80 min.

Example 126

(S)-1-(2-cyclopropyl-4-(2-(difluoromethyl)pyridin-4-yl)phenoxy)-2,4-dimethylpentan-2-amine

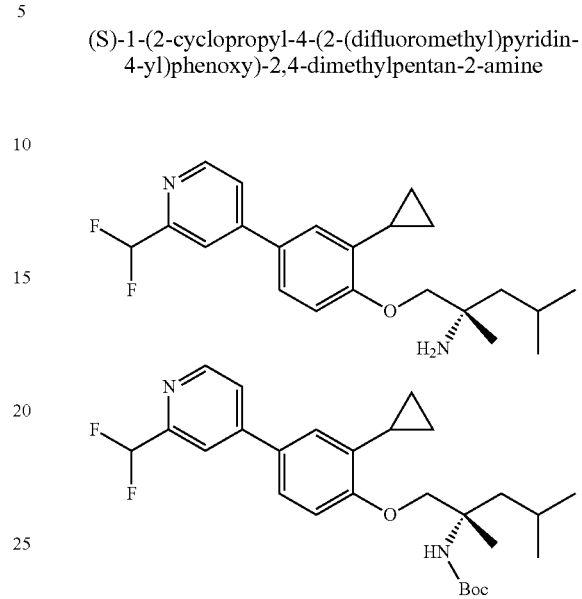

Part A: (S)-tert-butyl (1-(2-cyclopropyl-4-(2-(difluoromethyl)pyridin-4-yl)phenoxy)-2,4-dimethylpentan-2-yl)carbamate Prepared as described in Example 123 to afford (S)-tert-butyl (1-(2-cyclopropyl-4-(2-(difluoromethyl)pyridin-4-yl)phenoxy)-2,4-dimethylpentan-2-yl)carbamate (31.4 mg, 0.066 mmol, 79% yield) as a colorless solid. $^1$H NMR (400 MHz, Chloroform-d) δ 8.65 (d, J=5.1 Hz, 1H), 7.79 (d, J=1.7 Hz, 1H), 7.56 (dd, J=5.2, 1.8 Hz, 1H), 7.47 (dd, J=8.4, 2.4 Hz, 1H), 7.23 (d, J=2.3 Hz, 1H), 6.97 (d, J=8.4 Hz, 1H), 6.71 (t, J=55.5 Hz, 1H), 4.73 (s, 1H), 4.21 (d, J=8.8 Hz, 1H), 4.05 (d, J=8.8 Hz, 1H), 2.19 (tt, J=8.6, 5.4 Hz, 1H), 1.87 (ddt, J=13.1, 11.4, 6.8 Hz, 2H), 1.72-1.62 (m, 1H), 1.47 (s, 3H), 1.43 (s, 9H), 1.01 (dt, J=5.5, 2.7 Hz, 8H), 0.74 (td, J=5.7, 4.0 Hz, 2H); $^{19}$F NMR (376 MHz, Chloroform-d) δ −115.77; LCMS (ESI) m/e 475.0 [(M+H)$^+$, calcd C$_{27}$H$_{37}$F$_2$N$_2$O$_3$, 475.3]; LC/MS retention time (method B): t$_R$=2.48 min.

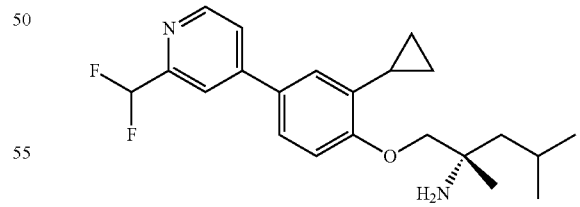

Part B: (S)-1-(2-cyclopropyl-4-(2-(difluoromethyl)pyridin-4-yl)phenoxy)-2,4-dimethylpentan-2-amine Prepared as previously described in Example 7, Part B (25.8 mg, 100%) as a colorless solid. $^1$H NMR (500 MHz, DMSO-d$_6$) δ 8.66 (d, J=5.3 Hz, 1H), 7.94 (s, 1H), 7.86 (d, J=5.3 Hz, 1H), 7.66 (dd, J=8.6, 2.3 Hz, 1H), 7.32 (d, J=2.4 Hz, 1H), 7.11-6.84 (m, 2H), 3.90-3.79 (m, 2H), 2.26 (td, J=8.5, 4.2 Hz, 1H), 1.82 (hept, J=6.4 Hz, 1H), 1.50 (qd, J=14.1, 5.6 Hz, 2H), 1.21 (s, 3H), 0.98-0.88 (m, 8H), 0.86-0.73 (m, 2H); $^{19}$F NMR (376 MHz, DMSO-d6) δ −115.05 (d, J=54.9 Hz); LCMS (ESI) m/e 375.0 [(M+H)$^+$, calcd $C_{22}H_{29}F_2N_2O$, 375.2]; LC/MS retention time (method B): $t_R$=1.97 min.

Example 127

(S)-1-((2-(difluoromethyl)-6-(6-fluoroquinolin-4-yl)pyridin-3-yl)oxy)-2,4-dimethylpentan-2-amine

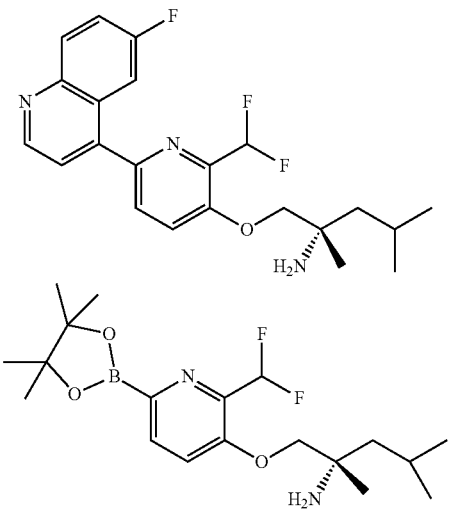

Part A: (S)-1-((2-(difluoromethyl)-6-(4,4,5,5-tetramethyl-1,3,2-dioxaborolan-2-yl)pyridin-3-yl)oxy)-2,4-dimethylpentan-2-amine To a 5 mL vial was added (S)-1-((6-bromo-2-(difluoromethyl)pyridin-3-yl)oxy)-2,4-dimethylpentan-2-amine (79.5 mg, 0.236 mmol), 4,4,4',4',5,5,5',5'-octamethyl-2,2'-bi(1,3,2-dioxaborolane) (71.8 mg, 0.283 mmol), and potassium acetate (69.4 mg, 0.707 mmol) in dioxane (2.4 mL) to give a colorless suspension with nitrogen bubbling. PdCl$_2$(dppf) (5.18 mg, 7.07 µmol) was added under nitrogen. The vial was sealed and the mixture was heated at 80° C. for 20 h. LC/MS showed complete conversion to a new peak. It was divided into parts and used directly in the next step. LC/MS retention time (method B): $t_R$=1.52 min.

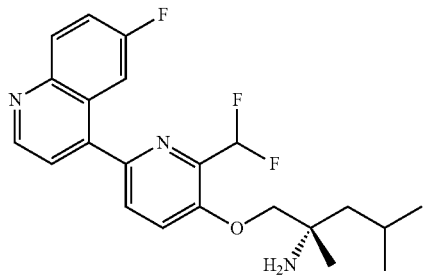 [SMILES: CC(C)C[C@](C)(N)COc1ccc(-c2ccnc3ccc(F)cc23)nc1C(F)F]

Part B: (S)-1-((2-(difluoromethyl)-6-(6-fluoroquinolin-4-yl)pyridin-3-yl)oxy)-2,4-dimethylpentan-2-amine Prepared as previously described in Example 116 to afford (S)-1-((2-(difluoromethyl)-6-(6-fluoroquinolin-4-yl)pyridin-3-yl)oxy)-2,4-dimethylpentan-2-amine (5.3 mg, 16% for 2 steps) as a colorless solid. $^1$H NMR (400 MHz, CHLOROFORM-d) δ 8.97 (d, J=4.5 Hz, 1H), 8.19 (dd, J=9.3, 5.5 Hz, 1H), 7.85 (dd, J=10.4, 2.9 Hz, 1H), 7.73 (d, J=8.5 Hz, 1H), 7.59-7.43 (m, 3H), 7.09-6.72 (t, J=54.0 Hz, 1H), 4.01-3.84 (m, 2H), 1.91-1.78 (m, 1H), 1.61-1.49 (m, 2H), 1.31 (s, 3H), 1.03 (app t, J=7.0 Hz, 6H), two exchangeable protons not observed; LCMS (ESI) m/e 404.0 [(M+H)$^+$, calcd $C_{22}H_{25}F_3N_3O$, 404.2]; LC/MS retention time (method B): $t_R$=1.81 min.

Example 128

(S)-1-((2-(difluoromethyl)-6-(7-fluoroquinolin-4-yl)pyridin-3-yl)oxy)-2,4-dimethylpentan-2-amine

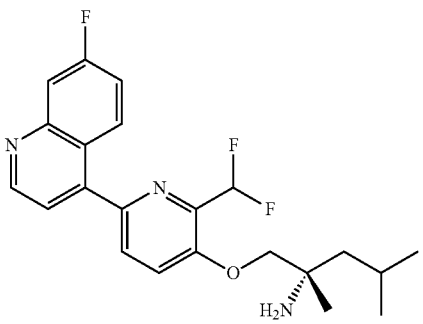 [SMILES: CC(C)C[C@](C)(N)COc1ccc(-c2ccnc3cc(F)ccc23)nc1C(F)F]

Prepared as previously described in Example 116 to afford (S)-1-((2-(difluoromethyl)-6-(7-fluoroquinolin-4-yl)pyridin-3-yl)oxy)-2,4-dimethylpentan-2-amine (11.1 mg, 35% for 2 steps) as a colorless solid. $^1$H NMR (400 MHz, CHLOROFORM-d) δ 8.98 (d, J=4.5 Hz, 1H), 8.21 (dd, J=9.3, 6.0 Hz, 1H), 7.81 (dd, J=9.9, 2.6 Hz, 1H), 7.72 (d, J=8.5 Hz, 1H), 7.50 (d, J=8.8 Hz, 1H), 7.45 (d, J=4.5 Hz, 1H), 7.35 (ddd, J=9.3, 8.0, 2.8 Hz, 1H), 6.98 (t, J=55.0 Hz, 1H), 3.98 (s, 2H), 1.85 (tt, J=12.7, 6.4 Hz, 1H), 1.68-1.56 (m, 2H), 1.36 (s, 3H), 1.03 (d, J=6.8 Hz, 3H), 1.01 (d, J=6.8 Hz, 3H), two exchangeable protons not observed; LCMS (ESI) m/e 404.0 [(M+H)$^+$, calcd $C_{22}H_{25}F_3N_3O$, 404.2]; LC/MS retention time (method B): $t_R$=1.68 min.

Example 129

(S)-1-((2-(difluoromethyl)-6-(5,7-difluoroquinolin-4-yl)pyridin-3-yl)oxy)-2,4-dimethylpentan-2-amine

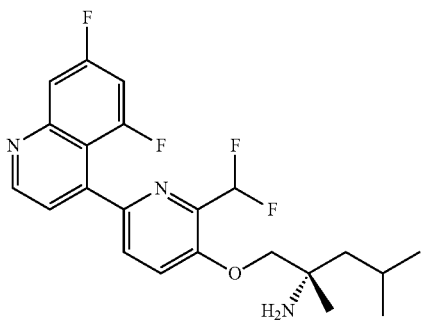 [SMILES: CC(C)C[C@](C)(N)COc1ccc(-c2ccnc3cc(F)cc(F)c23)nc1C(F)F]

Prepared as previously described in Example 16 to afford (S)-1-((2-(difluoromethyl)-6-(5,7-difluoroquinolin-4-yl)pyridin-3-yl)oxy)-2,4-dimethylpentan-2-amine (25.9 mg, 75% for 2 steps) as a colorless solid. $^1$H NMR (600 MHz, DMSO-$d_6$) δ 9.13-9.02 (m, 1H), 7.93-7.73 (m, 3H), 7.56 (dt, J=23.8, 6.1 Hz, 2H), 7.38-7.09 (m, 1H), 3.95 (d, J=22.2 Hz, 2H), 1.84 (dt, J=18.4, 6.3 Hz, 1H), 1.45 (dtd, J=23.9, 14.0, 11.7, 5.4 Hz, 2H), 1.27-1.14 (m, 3H), 0.96 (ddd, J=23.9, 13.5, 6.6 Hz, 6H); LCMS (ESI) m/e 421.9 [(M+H)$^+$, calcd $C_{22}H_{24}F_4N_3O$, 422.2]; LC/MS retention time (method B): $t_R$=1.82 min.

Example 130

(S)-1-((4-(difluoromethyl)-6-(5,7-difluoroquinolin-4-yl)pyridin-3-yl)oxy)-2,4-dimethylpentan-2-amine

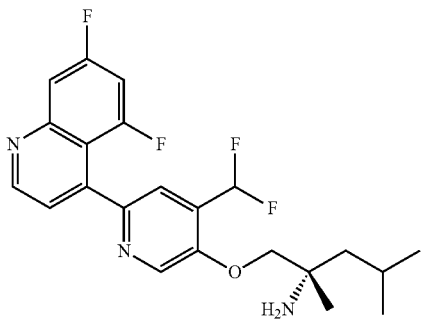 [SMILES: CC(C)C[C@](C)(N)COc1cnc(-c2ccnc3cc(F)cc(F)c23)cc1C(F)F]

Part A: 5,7-difluoro-4-(4,4,5,5-tetramethyl-1,3,2-dioxaborolan-2-yl)quinoline

Prepared as previously described in Example 127. Obtained 5,7-difluoro-4-(4,4,5,5-tetramethyl-1,3,2-dioxaborolan-2-yl)quinoline which was divided into parts and used directly in the next step. LC/MS retention time (method A): $t_R$=1.93 min.

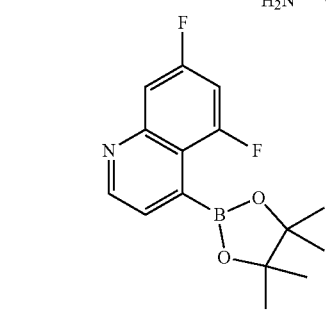

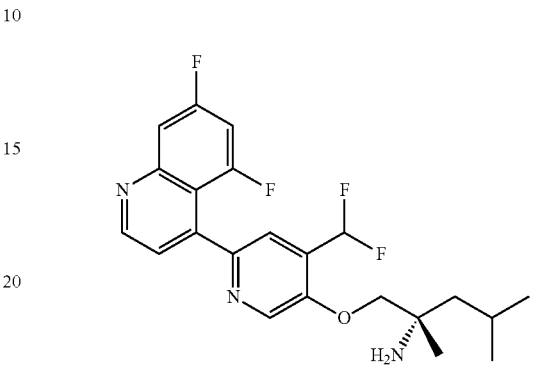

Part B: (S)-1-((4-(difluoromethyl)-6-(5,7-difluoroquinolin-4-yl)pyridin-3-yl)oxy)-2,4-dimethylpentan-2-amine Prepared as previously described in Example 16 to afford (S)-1-((4-(difluoromethyl)-6-(5,7-difluoroquinolin-4-yl)pyridin-3-yl)oxy)-2,4-dimethylpentan-2-amine (14.7 mg, 49% for 2 steps) as a colorless solid. $^1$H NMR (600 MHz, DMSO-$d_6$) δ 9.04 (d, J=4.7 Hz, 1H), 8.62 (d, J=5.7 Hz, 1H), 7.80 (d, J=9.6 Hz, 1H), 7.75 (d, J=6.5 Hz, 1H), 7.56 (qd, J=8.5, 7.9, 4.9 Hz, 2H), 7.36 (t, J=53.9 Hz, 1H), 4.01 (s, 2H), 1.82 (q, J=6.5 Hz, 1H), 1.43 (qd, J=14.0, 5.9 Hz, 2H), 1.16 (s, 3H), 0.94 (dd, J=14.6, 6.7 Hz, 6H); $^{19}$F NMR (376 MHz, DMSO-$d_6$)δ −102.43 (d, J=9.6 Hz), −107.91 (d, J=9.0 Hz), −116.03−−119.87 (m); LCMS (ESI) m/e 422.0 [(M+H)$^+$, calcd $C_{22}H_{24}F_4N_3O$, 422.2]; LC/MS retention time (method B): $t_R$=1.88 min.

Example 131

(S)-1-((4-(difluoromethyl)-6-(7-fluoroquinolin-4-yl)pyridin-3-yl)oxy)-2,4-dimethylpentan-2-amine

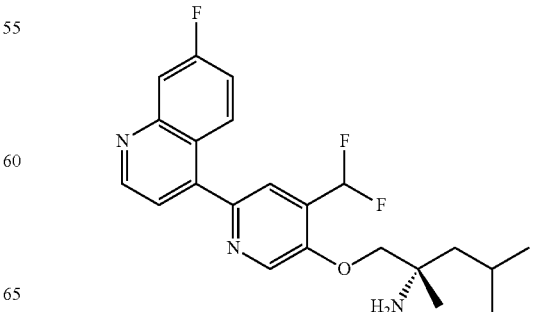

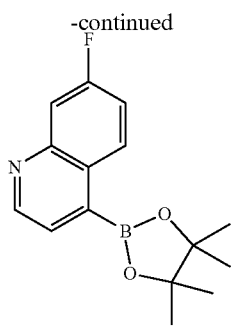

Part A: 7-fluoro-4-(4,4,5,5-tetramethyl-1,3,2-dioxaborolan-2-yl)quinoline

Prepared as previously described in Example 127. Obtained 7-fluoro-4-(4,4,5,5-tetramethyl-1,3,2-dioxaborolan-2-yl)quinoline which was divided into parts and used directly in the next step. LC/MS retention time (method A): $t_R$=1.19 min.

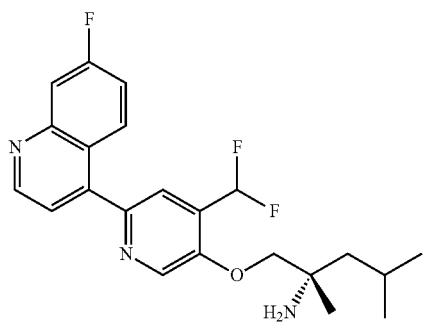 [SMILES: CC(C)C[C@](C)(N)COc1cnc(-c2ccnc3cc(F)ccc23)cc1C(F)F]

Part B: (S)-1-((4-(difluoromethyl)-6-(7-fluoroquinolin-4-yl)pyridin-3-yl)oxy)-2,4-dimethylpentan-2-amine Prepared as previously described in Example 16 to afford (S)-1-((4-(difluoromethyl)-6-(7-fluoroquinolin-4-yl)pyridin-3-yl)oxy)-2,4-dimethylpentan-2-amine (11.1 mg, 39% for 2 steps) as a colorless solid. $^1$H NMR (600 MHz, DMSO-$d_6$) δ 9.02 (d, J=4.3 Hz, 1H), 8.77 (s, 1H), 8.30 (ddd, J=9.0, 6.3, 2.4 Hz, 1H), 7.90 (s, 1H), 7.86 (dd, J=10.2, 2.7 Hz, 1H), 7.67 (d, J=4.3 Hz, 1H), 7.58 (td, J=8.8, 2.7 Hz, 1H), 7.37 (t, J=53.9 Hz, 1H), 4.05 (s, 2H), 1.83 (p, J=6.5 Hz, 1H), 1.43 (qd, J=14.0, 5.4 Hz, 2H), 1.16 (s, 3H), 0.95 (ddd, J=13.9, 6.8, 2.1 Hz, 6H); $^{19}$F NMR (376 MHz, DMSO-$d_6$) δ −110.25, −115.90−−119.14 (m); LCMS (ESI) m/e 404.0 [(M+H)$^+$, calcd $C_{22}H_{25}F_3N_3O$, 404.2]; LC/MS retention time (method B): $t_R$=1.78 min.

Example 132

(S)-1-((4-(difluoromethyl)-6-(6-fluoroquinolin-4-yl)pyridin-3-yl)oxy)-2,4-dimethylpentan-2-amine

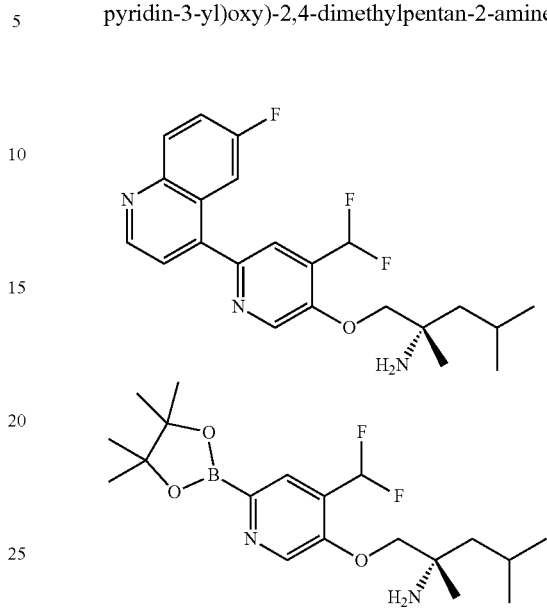

Part A: (S)-1-((4-(difluoromethyl)-6-(4,4,5,5-tetramethyl-1,3,2-dioxaborolan-2-yl)pyridin-3-yl)oxy)-2,4-dimethylpentan-2-amine To a 5 mL vial was added (S)-1-((6-bromo-4-(difluoromethyl)pyridin-3-yl)oxy)-2,4-dimethylpentan-2-amine (82.5 mg, 0.245 mmol), 4,4,4',4',5,5,5',5'-octamethyl-2,2'-bi(1,3,2-dioxaborolane) (74.6 mg, 0.294 mmol), and potassium acetate (72.0 mg, 0.734 mmol) in dioxane (2.4 mL) to give a colorless suspension with nitrogen bubbling. PdCl$_2$(dppf) (5.37 mg, 7.34 µmol) was added under nitrogen. The vial was sealed and the mixture was heated at 80° C. for 20 h. LCMS showed mainly the starting material (dark red color mixture). The temperature was raised to 100° C. After 4 h, LCMS showed a little better conversion. The reaction continued for another 16 h at 100° C. LCMS showed better conversion but there was still some starting material left. The temperature was raised to 110° C. and the reaction continued for 5 h. LCMS showed only a little starting material left. The reaction continued at 110° C. for another 5 h. After cooling down, the reaction mixture was divided into parts and used directly in the next step.

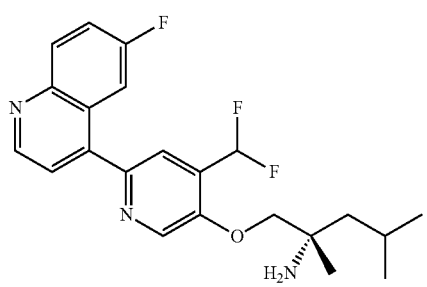 [SMILES: CC(C)C[C@](C)(N)COc1cnc(-c2ccnc3ccc(F)cc23)cc1C(F)F]

Part B: (S)-1-((4-(difluoromethyl)-6-(6-fluoroquinolin-4-yl)pyridin-3-yl)oxy)-2,4-dimethylpentan-2-amine Prepared as previously described in Example 116 to afford (S)-1-((4-(difluoromethyl)-6-(6-fluoroquinolin-4-yl)pyridin-3-yl)oxy)-2,4-dimethylpentan-2-amine (1.6 mg, 5% for 2 steps) as a colorless solid. $^1$H NMR (600 MHz, DMSO-$d_6$) δ 8.99 (d, J=4.4 Hz, 1H), 8.80 (s, 1H), 8.20 (dd, J=9.3, 5.6 Hz, 1H), 8.01 (dd, J=11.0, 2.9 Hz, 1H), 7.94 (s, 1H), 7.79-7.70 (m, 2H), 7.40 (t, J=53.9 Hz, 1H), 4.09 (s, 2H), 1.84 (dt, J=12.8, 6.5 Hz, 1H), 1.46 (qd, J=14.0, 5.6 Hz, 2H), 1.19 (s, 3H), 0.97 (d, J=6.6 Hz, 3H), 0.94 (d, J=6.6 Hz, 3H); $^{19}$F NMR (376 MHz, DMSO-$d_6$) δ −112.45, −118.42 (dd, J=134.0, 57.0 Hz); LCMS (ESI) m/e 404.0 [(M+H)$^+$, calcd $C_{22}H_{25}F_3N_3O$, 404.2]; LC/MS retention time (method B): $t_R$=1.79 min.

Example 133

((S)-1-((4-(difluoromethyl)-6-(6-(trifluoromethyl)quinolin-4-yl)pyridin-3-yl)oxy)-2,4-dimethylpentan-2-amine

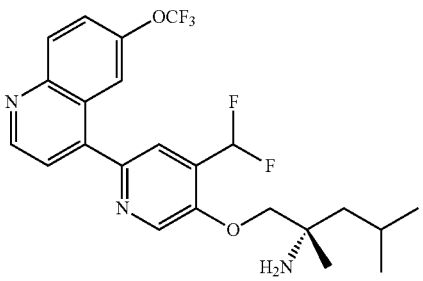 [SMILES: CC(C)C[C@](C)(N)COc1cnc(-c2ccnc3ccc(OC(F)(F)F)cc23)cc1C(F)F]

Prepared as previously described in Example 132 to afford ((S)-1-((4-(difluoromethyl)-6-(6-(trifluoromethyl)quinolin-4-yl)pyridin-3-yl)oxy)-2,4-dimethylpentan-2-amine (2.1 mg, 6% for 2 steps) as a colorless solid. $^1$H NMR (600 MHz, DMSO-$d_6$) δ 9.17 (d, J=4.4 Hz, 1H), 8.85 (s, 1H), 8.75 (s, 1H), 8.34 (d, J=8.8 Hz, 1H), 8.08 (dd, J=8.8, 2.1 Hz, 1H), 8.02 (s, 1H), 7.88 (d, J=4.3 Hz, 1H), 7.43 (t, J=53.9 Hz, 1H), 4.13 (d, J=3.0 Hz, 2H), 1.84 (p, J=6.2 Hz, 1H), 1.57-1.41 (m, 2H), 1.21 (s, 3H), 0.97 (d, J=6.6 Hz, 3H), 0.94 (d, J=6.5 Hz, 3H); LCMS (ESI) m/e 454.0 [(M+H)$^+$, calcd $C_{23}H_{25}F_5N_3O$, 454.2]; LC/MS retention time (method B): $t_R$=2.02 min.

Example 134

(S)-1-((4-(difluoromethyl)-6-(6-(trifluoromethoxy)quinolin-4-yl)pyridin-3-yl)oxy)-2,4-dimethylpentan-2-amine

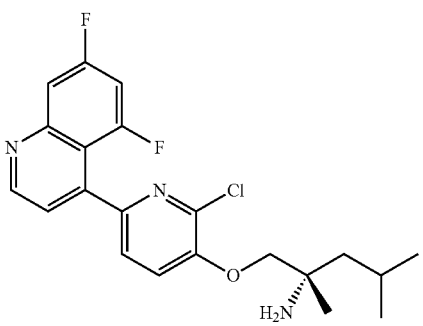 [SMILES: CC(C)C[C@](C)(N)COc1ccc(-c2ccnc3cc(F)cc(F)c23)nc1Cl]

Prepared as previously described in Example 132 to afford (S)-1-((4-(difluoromethyl)-6-(6-(trifluoromethoxy)quinolin-4-yl)pyridin-3-yl)oxy)-2,4-dimethylpentan-2-amine (1.5 mg, 4% for 2 steps) as a colorless solid. $^1$H NMR (600 MHz, DMSO-$d_6$) δ 9.07 (d, J=4.4 Hz, 1H), 8.80 (s, 1H), 8.29 (s, 1H), 8.27 (d, J=9.2 Hz, 1H), 7.97 (s, 1H), 7.83 (dd, J=8.7, 3.2 Hz, 2H), 7.38 (t, J=53.9 Hz, 1H), 4.06 (s, 2H), 1.84 (dt, J=12.7, 6.3 Hz, 1H), 1.42 (qd, J=14.0, 5.6 Hz, 2H), 1.16 (s, 3H), 0.96 (d, J=6.5 Hz, 3H), 0.94 (d, J=6.6 Hz, 3H); LCMS (ESI) m/e 470.0 [(M+H)$^+$, calcd $C_{23}H_{25}F_5N_3O_2$, 470.2]; LC/MS retention time (method B): $t_R$=2.00 min.

Example 135

(S)-1-((2-chloro-6-(5,7-difluoroquinolin-4-yl)pyridin-3-yl)oxy)-2,4-dimethylpentan-2-amine

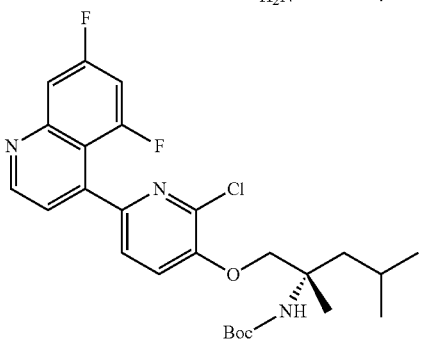

Part A: (S)-tert-butyl (1-((2-chloro-6-(5,7-difluoro-quinolin-4-yl)pyridin-3-yl)oxy)-2,4-dimethylpentan-2-yl)carbamate Prepared as previously described in Example 66. The intermediates were as described in Example 66 and Example 130 to afford (S)-tert-butyl (1-((2-chloro-6-(5,7-difluoroquinolin-4-yl)pyridin-3-yl)oxy)-2,4-dimethylpentan-2-yl)carbamate (12.1 mg, 34%) as a colorless solid. $^1$H NMR (400 MHz, Chloroform-d) δ 8.97 (d, J=4.4 Hz, 1H), 7.68 (ddd, J=9.5, 2.6, 1.5 Hz, 1H), 7.42-7.32 (m, 3H), 7.05 (ddd, J=11.5, 8.8, 2.6 Hz, 1H), 4.64 (s, 1H), 4.37 (d, J=8.9 Hz, 1H), 4.18 (d, J=8.9 Hz, 1H), 1.96 (dd, J=13.9, 6.4 Hz, 1H), 1.87 (ddd, J=13.1, 6.5, 4.9 Hz, 1H), 1.58 (dd, J=13.9, 4.9 Hz, 1H), 1.47 (s, 3H), 1.42 (s, 9H), 1.04 (s, 3H), 1.02 (s, 3H); $^{19}$F NMR (376 MHz, Chloroform-d) δ −102.47, −107.56; LCMS (ESI) m/e 506.0 [(M+H)$^+$, calcd $C_{26}H_{31}ClF_2N_3O_3$, 506.2]; LC/MS retention time (method B): $t_R$=2.36 min.

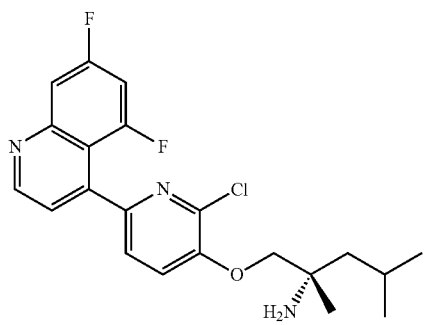

Part B: (S)-1-((2-chloro-6-(5,7-difluoroquinolin-4-yl)pyridin-3-yl)oxy)-2,4-dimethylpentan-2-amine Prepared as previously described in Example 7, Part B to afford (S)-1-((2-chloro-6-(5,7-difluoroquinolin-4-yl)pyridin-3-yl)oxy)-2,4-dimethylpentan-2-amine (10.6 mg, 100%) as a colorless solid. $^1$H NMR (400 MHz, CHLOROFORM-d) δ 8.97 (d, J=4.3 Hz, 1H), 7.77-7.62 (m, 1H), 7.40 (d, J=4.3 Hz, 1H), 7.38-7.34 (m, 1H), 7.33-7.28 (m, 1H), 7.05 (ddd, J=11.6, 8.8, 2.6 Hz, 1H), 3.93-3.84 (m, 2H), 1.92-1.73 (m, 1H), 1.66-1.50 (m, 2H), 1.32 (s, 3H), 1.04 (d, J=6.8 Hz, 3H), 1.02 (d, J=6.5 Hz, 3H), two exchangeable protons not observed; $^{19}$F NMR (376 MHz, DMSO-d6) δ −101.38--103.03 (m), −105.03--107.99 (m); LCMS (ESI) m/e 405.9 [(M+H)$^+$, calcd $C_{21}H_{23}ClF_2N_3O$, 406.1]; LC/MS retention time (method B): $t_R$=1.84 min.

Example 136

(S)-1-((2-chloro-6-(7-fluoroquinolin-4-yl)pyridin-3-yl)oxy)-2,4-dimethylpentan-2-amine

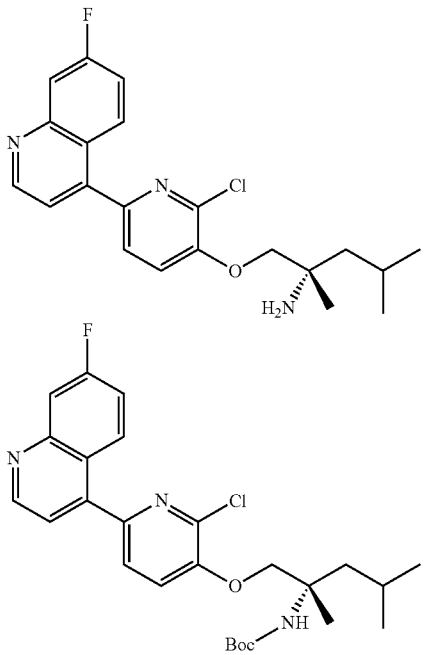

Part A: (S)-tert-butyl (1-((2-chloro-6-(7-fluoroquinolin-4-yl)pyridin-3-yl)oxy)-2,4-dimethylpentan-2-yl)carbamate Prepared as previously described in Example 66. The intermediates were as described in Example 66 and Example 131 to afford (S)-tert-butyl (1-((2-chloro-6-(7-fluoroquinolin-4-yl)pyridin-3-yl)oxy)-2,4-dimethylpentan-2-yl)carbamate (12.4 mg, 36%) as a colorless solid. $^1$H NMR (400 MHz, Chloroform-d) δ 8.98 (d, J=4.5 Hz, 1H), 8.24 (dd, J=9.4, 6.1 Hz, 1H), 7.81 (dd, J=9.9, 2.6 Hz, 1H), 7.53 (d, J=8.2 Hz, 1H), 7.49-7.43 (m, 2H), 7.37 (ddd, J=9.3, 8.0, 2.7 Hz, 1H), 4.64 (s, 1H), 4.41 (d, J=9.0 Hz, 1H), 4.21 (d, J=9.0 Hz, 1H), 2.01-1.82 (m, 2H), 1.58 (dd, J=13.9, 5.0 Hz, 1H), 1.48 (s, 3H), 1.42 (s, 9H), 1.05 (s, 3H), 1.03 (s, 3H); $^{19}$F NMR (376 MHz, Chloroform-d) δ −109.85; LCMS (ESI) m/e 488.0 [(M+H)$^+$, calcd $C_{26}H_{32}ClFN_3O_3$, 488.2]; LC/MS retention time (method B): $t_R$=2.28 min.

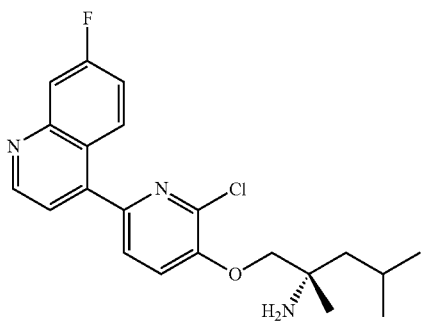

Part B: (S)-1-((2-chloro-6-(7-fluoroquinolin-4-yl)pyridin-3-yl)oxy)-2,4-dimethylpentan-2-amine Prepared as previously described in Example 7, Part B to afford (S)-1-((2-chloro-6-(7-fluoroquinolin-4-yl)pyridin-3-yl)oxy)-2,4-dimethylpentan-2-amine (11.1 mg, 100%) as a colorless solid. $^1$H NMR (600 MHz, DMSO-$d_6$) δ 9.01 (d, J=4.4 Hz, 1H), 8.32 (dd, J=9.4, 6.1 Hz, 1H), 7.88-7.77 (m, 3H), 7.63 (d, J=4.2 Hz, 1H), 7.60 (td, J=8.8, 2.7 Hz, 1H), 3.98-3.89 (m, 2H), 1.85 (dq, J=12.8, 6.4 Hz, 1H), 1.50-1.40 (m, 2H), 1.18 (s, 3H), 0.95 (dd, J=7.5, 5.4 Hz, 6H); 19F NMR (376 MHz, DMSO-d6) δ −110.18; LCMS (ESI) m/e 388.0 [(M+H)$^+$, calcd $C_{21}H_{24}ClFN_3O$, 388.2]; LC/MS retention time (method B): $t_R$=1.76 min.

Example 137

(S)-1-((6-(7-fluoroquinolin-4-yl)-2-methylpyridin-3-yl)oxy)-2,4-dimethylpentan-2-amine

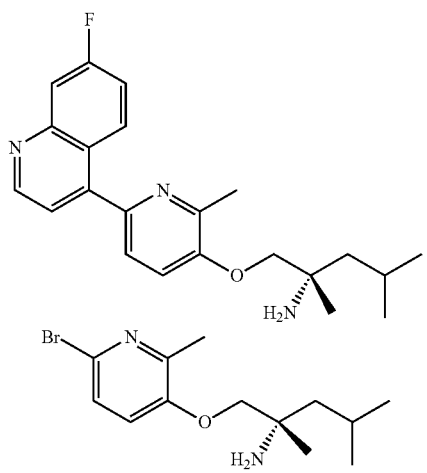

Part A: (S)-1-((6-bromo-2-methylpyridin-3-yl)oxy)-2,4-dimethylpentan-2-amine

To a 20 mL pressure bottle was added (S)-2-amino-2,4-dimethylpentan-1-ol (214.8 mg, 1.637 mmol) in tetrahydrofuran (2.2 mL) to give a colorless solution. Potassium tert-butoxide (2.128 mL, 2.128 mmol) (1.0 M in THF) was added dropwise under nitrogen. After 5 min, 6-bromo-3-fluoro-2-methylpyridine (311 mg, 1.637 mmol) was added in one portion. The bottle was sealed and the mixture was stirred at 80° C. for 20 h. The mixture was partitioned between water and EtOAc. The layers were separated. The aqueous layer was extracted with EtOAc. The combined organic solution was washed with brine, dried and concentrated to a tan oil. It was purified by silica gel chromatography up to 10% MeOH (2N NH$_3$) in CH$_2$Cl$_2$ to afford (S)-1-((6-bromo-2-methylpyridin-3-yl)oxy)-2,4-dimethylpentan-2-amine (220 mg, 45% with one unknown impurity-likely substitution at Br). LCMS (ESI) m/e 283.9 [(M-NH$_2$)+, calcd $C_{13}H_{19}BrNO$, 284.1]; LC/MS retention time (method B): $t_R$=1.70 min (impurity: 1.81 min).

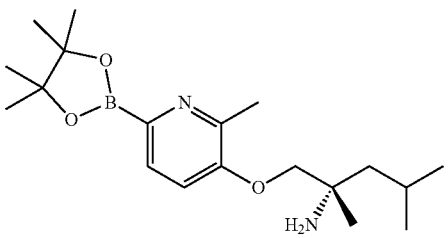 [SMILES: Cc1nc(B2OC(C)(C)C(C)(C)O2)ccc1OC[C@@](C)(N)CC(C)C]

Part B: (S)-2,4-dimethyl-1-((2-methyl-6-(4,4,5,5-tetramethyl-1,3,2-dioxaborolan-2-yl)pyridin-3-yl)oxy)pentan-2-amine To a 5 mL vial was added (S)-1-((6-bromo-2-methylpyridin-3-yl)oxy)-2,4-dimethylpentan-2-amine (89.5 mg, 0.267 mmol), 4,4,4',4',5,5,5',5'-octamethyl-2,2'-bi(1,3,2-dioxaborolane) (81 mg, 0.321 mmol), and potassium acetate (79 mg, 0.802 mmol) in dioxane (2.8 mL) to give a colorless suspension with nitrogen bubbling. PdCl$_2$(dppf) (5.87 mg, 8.02 μmol) was added under nitrogen. The vial was sealed and the mixture was heated at 80° C. for 18 h. LCMS showed there was substantial amount of starting material. The reaction mixture was heated at 100° C. for 4 h. LCMS showed the majority of starting material was gone (the side product from previous reaction remained). It was divided into parts and used directly in the next step.

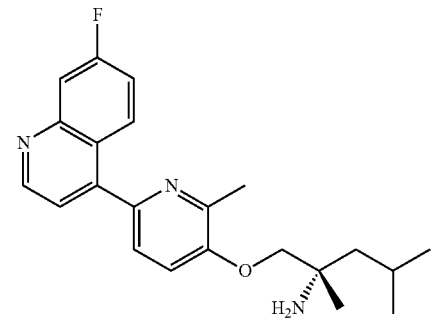 [SMILES: Cc1nc(-c2ccnc3cc(F)ccc23)ccc1OC[C@@](C)(N)CC(C)C]

Part C: (S)-1-((6-(7-fluoroquinolin-4-yl)-2-methylpyridin-3-yl)oxy)-2,4-dimethylpentan-2-amine Prepared as previously described in Example 132 to afford (S)-1-((6-(7-fluoroquinolin-4-yl)-2-methylpyridin-3-yl)oxy)-2,4-dimethylpentan-2-amine (1.0 mg, 3%) as a colorless solid. $^1$H NMR (500 MHz, DMSO-$d_6$) δ 8.99 (d, J=4.5 Hz, 1H), 8.37 (dd, J=9.3, 6.4 Hz, 1H), 7.84 (dd, J=10.4, 2.7 Hz, 1H), 7.65 (d, J=8.4 Hz, 1H), 7.62-7.54 (m, 3H), 3.98 (s, 2H), 2.57 (s, 3H), 1.90-1.80 (m, 1H), 1.61 (d, J=5.3 Hz, 1H), 1.53 (dd, J=14.0, 5.5 Hz, 1H), 1.30 (s, 3H), 0.98 (d, J=6.6 Hz, 3H), 0.96 (d, J=6.7 Hz, 3H). LCMS (ESI) m/e 368.2 [(M+H)$^+$, calcd $C_{22}H_{27}FN_3O$, 368.2].

Example 138

(S)-1-((6-(6-fluoroquinolin-4-yl)-2-methylpyridin-3-yl)oxy)-2,4-dimethylpentan-2-amine

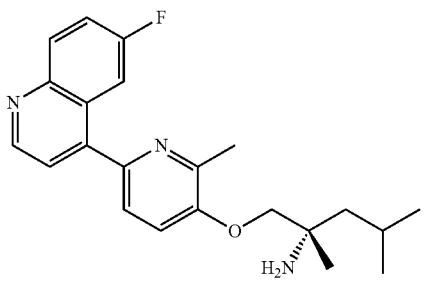 [SMILES: Cc1nc(-c2ccnc3ccc(F)cc23)ccc1OC[C@@](C)(N)CC(C)C]

Prepared as previously described in Example 132 with intermediate from Example 137 to afford (S)-1-((6-(6-fluoroquinolin-4-yl)-2-methylpyridin-3-yl)oxy)-2,4-dimethylpentan-2-amine (1.5 mg, 3%, 64% purity by analytical HPLC): $^1$H NMR (500 MHz, DMSO-$d_6$) δ 8.96 (d, J=4.4 Hz, 1H), 8.17 (dd, J=9.4, 5.7 Hz, 1H), 8.07 (dd, J=10.8, 2.8 Hz, 1H), 7.78-7.51 (m, 5H), 6.70 (dd, J=8.8, 2.6 Hz, 1H), 3.93-3.77 (m, 2H), 2.55 (s, 3H), 1.87-1.72 (m, 1H), 1.58-1.30 (m, 2H), 1.15 (s, 3H), 1.00-0.83 (m, 6H) LCMS (ESI) m/e 368.2 [(M+H)$^+$, calcd $C_{22}H_{27}FN_3O$, 368.2].

Example 139

(S)-1-((2-(difluoromethyl)-6-(2-methylpyrimidin-4-yl)pyridin-3-yl)oxy)-2,4-dimethylpentan-2-amine

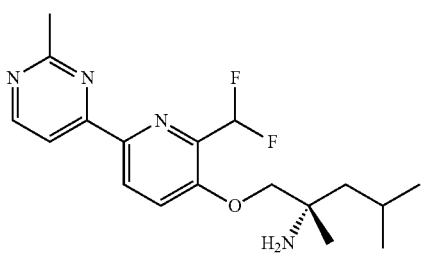

Prepared as previously described in Example 127 with intermediate as described in Example 127 and 4-bromo-2-methylpyrimidine to afford (S)-1-((2-(difluoromethyl)-6-(2-methylpyrimidin-4-yl)pyridin-3-yl)oxy)-2,4-dimethylpentan-2-amine (15.9 mg, 45%): $^1$H NMR (500 MHz, DMSO-$d_6$) δ 8.82 (d, J=5.2 Hz, 1H), 8.57 (d, J=8.9 Hz, 1H), 8.07 (d, J=5.3 Hz, 1H), 7.83 (d, J=8.9 Hz, 1H), 7.26 (t, J=53.6 Hz, 1H), 3.92 (s, 2H), 2.71 (s, 3H), 1.81 (dd, J=12.9, 6.6 Hz, 1H), 1.47-1.36 (m, 2H), 1.15 (s, 3H), 0.93 (dd, J=11.0, 6.8 Hz, 6H); LCMS (ESI) m/e 373.1 [(M+Na)$^+$, calcd $C_{18}H_{24}F_2N_4NaO$, 373.2]; LC/MS retention time (method B): $t_R$=1.73 min.

Example 140

(S)-1-((2-(difluoromethyl)-6-(6-methylpyrimidin-4-yl)pyridin-3-yl)oxy)-2,4-dimethylpentan-2-amine

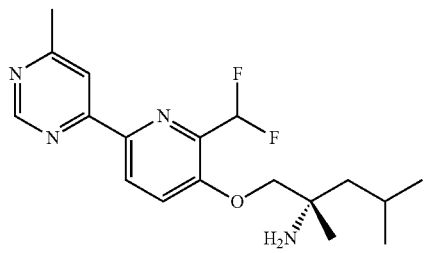

Prepared as previously described in Example 127 with intermediate as described in Example 127 and 4-bromo-6-methylpyrimidine to afford (S)-1-((2-(difluoromethyl)-6-(6-methylpyrimidin-4-yl)pyridin-3-yl)oxy)-2,4-dimethylpentan-2-amine (3.5 mg, 6.8%): $^1$H NMR (400 MHz, CHLOROFORM-d) δ 9.11 (d, J=1.3 Hz, 1H), 8.58 (d, J=8.8 Hz, 1H), 8.21 (s, 1H), 7.43 (d, J=8.8 Hz, 1H), 7.10-6.72 (t, J=53.0 Hz, 1H), 3.96 (s, 2H), 2.63 (s, 3H), 1.88-1.75 (m, 1H), 1.66-1.52 (m, 2H), 1.26 (s, 3H), 1.01 (d, J=6.5 Hz, 3H), 0.98 (d, J=6.8 Hz, 3H), two exchangeable protons not observed; LCMS (ESI) m/e 334.1 [(M-NH$_2$)+, calcd $C_{18}H_{22}F_2N_3O$, 334.2]; LC/MS retention time (method B): $t_R$=1.78 min.

Example 141

(S)-1-((4-(difluoromethyl)-2'-ethyl-[2,4'-bipyridin]-5-yl)oxy)-2,4-dimethylpentan-2-amine

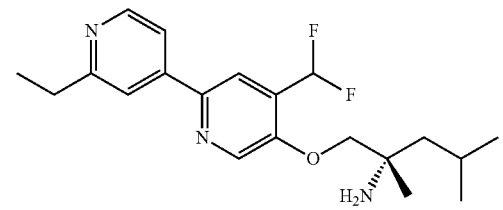 [SMILES: CCc1cc(-c2cc(C(F)F)c(OC[C@@](C)(N)CC(C)C)cn2)ccn1]

Prepared as previously described in Example 117 with intermediate as described in Example 120 and (2-ethylpyridin-4-yl)boronic acid to afford (S)-1-((4-(difluoromethyl)-2'-ethyl-[2,4'-bipyridin]-5-yl)oxy)-2,4-dimethylpentan-2-amine (8.0 mg, 39%): $^1$H NMR (500 MHz, DMSO-$d_6$) δ 8.67 (s, 1H), 8.57 (d, J=5.2 Hz, 1H), 8.20 (s, 1H), 7.93 (s, 1H), 7.85 (dd, J=5.2, 1.6 Hz, 1H), 7.34 (t, J=53.9 Hz, 1H), 4.01 (s, 2H), 2.84 (q, J=7.6 Hz, 2H), 1.80 (dq, J=12.5, 6.2 Hz, 1H), 1.47-1.35 (m, 2H), 1.28 (t, J=7.6 Hz, 3H), 1.14 (s, 3H), 0.93 (dd, J=12.6, 6.6 Hz, 6H); LCMS (ESI) m/e 364.2 [(M+H)$^+$, calcd $C_{2}H_{28}F_2N_3O$, 364.2]; LC/MS retention time (method B): $t_R$=1.54 min.

Example 142

(S)-1-((2'-chloro-4-(difluoromethyl)-3'-fluoro-[2,4'-bipyridin]-5-yl)oxy)-2,4-dimethylpentan-2-amine

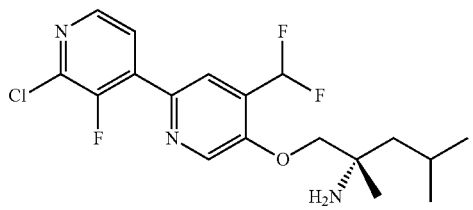

Prepared as previously described in Example 117 with intermediate as described in Example 120 and (2-chloro-3-fluoro-pyridin-4-yl)boronic acid to afford (5)-1-((2'-chloro-4-(difluoromethyl)-3'-fluoro-[2,4'-bipyridin]-5-yl)oxy)-2,4-dimethylpentan-2-amine (10.8 mg, 13%): $^1$H NMR (500 MHz, DMSO-$d_6$) δ 8.76 (s, 1H), 8.38 (d, J=5.0 Hz, 1H), 8.05 (s, 1H), 7.97 (t, J=5.3 Hz, 1H), 7.37 (t, J=53.9 Hz, 1H), 4.03 (s, 2H), 1.81 (dt, J=12.8, 6.4 Hz, 1H), 1.45-1.35 (m, 2H), 1.14 (s, 3H), 0.93 (dd, J=12.4, 6.7 Hz, 7H); LCMS (ESI) m/e 371.1 [(M-NH$_2$)+, calcd $C_{18}H_{19}ClF_3N_2O$, 371.1]; LC/MS retention time (method B): $t_R$=1.98 min.

Example 143

(S)-1-((2'-chloro-4-(difluoromethyl)-5'-fluoro-[2,4'-bipyridin]-5-yl)oxy)-2,4-dimethylpentan-2-amine

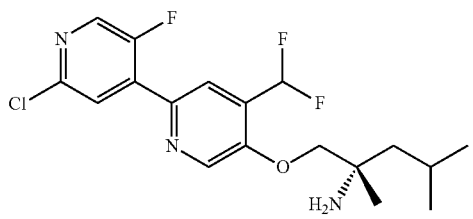 [SMILES: CC(C)C[C@](C)(N)COc1cnc(-c2cc(Cl)ncc2F)cc1C(F)F]

Prepared as previously described in Example 117 with intermediate as described in Example 120 and (2-chloro-5-fluoro-pyridin-4-yl)boronic acid to afford (S)-1-((2'-chloro-4-(difluoromethyl)-5'-fluoro-[2,4'-bipyridin]-5-yl)oxy)-2,4-dimethylpentan-2-amine (9.6 mg, 11%): $^1$H NMR (500 MHz, DMSO-$d_6$) δ 8.76 (s, 1H), 8.61 (d, J=2.6 Hz, 1H), 8.05 (s, 1H), 8.02 (d, J=5.5 Hz, 1H), 7.37 (t, J=53.9 Hz, 1H), 4.04 (s, 2H), 1.81 (dt, J=12.6, 6.4 Hz, 1H), 1.46-1.35 (m, 2H), 1.14 (s, 3H), 0.93 (dd, J=12.8, 6.6 Hz, 6H); LCMS (ESI) m/e 371.1 [(M-NH$_2$)+, calcd $C_{18}H_{19}ClF_3N_2O$, 371.1]; LC/MS retention time (method B): $t_R$=1.97 min.

Example 144

(S)-2,4-dimethyl-1-((2'-methyl-4-(trifluoromethyl)-[2,4'-bipyridin]-5-yl)oxy)pentan-2-amine

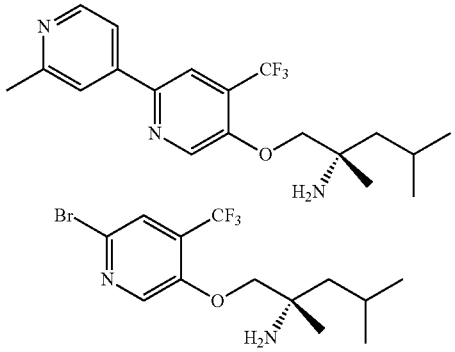

Part A: (S)-1-((6-bromo-4-(difluoromethyl)pyridin-3-yl)oxy)-2,4-dimethylpentan-2-amine To a 20 mL pressure vial was added (S)-2-amino-2,4-dimethylpentan-1-ol (323 mg, 2.462 mmol) and 2-bromo-5-fluoro-4-(trifluoromethyl)pyridine (601 mg, 2.462 mmol) in tetrahydrofuran (3.3 mL) to give a tan solution. Potassium tert-butoxide (2.95 mL, 2.95 mmol) (1.0 M in THF) was added dropwise under nitrogen. After 5 min stirring at rt, the vial was sealed and the mixture was stirred at 80° C. for 18 h. The mixture was partitioned between water and EtOAc. The layers were separated. The aqueous layer was extracted with EtOAc. The combined organic solution was washed with brine, dried and concentrated to a tan oil. The crude was purified by silica gel chromatography up to 10% MeOH/CH$_2$Cl$_2$ to afford (S)-1-((6-bromo-4-(difluoromethyl)pyridin-3-yl)oxy)-2,4-dimethylpentan-2-amine (0.42 g, 48%) as a tan oil: $^1$H NMR (400 MHz, Chloroform-d) δ 8.19 (s, 1H), 7.64 (s, 1H), 3.95-3.86 (m, 2H), 1.80 (dt, J=12.8, 6.4 Hz, 1H), 1.65 (s, 2H), 1.50 (dd, J=5.7, 4.0 Hz, 2H), 1.25 (s, 3H), 0.99 (dd, J=9.1, 6.6 Hz, 6H); $^9$F NMR (376 MHz, Chloroform-d) δ −64.37; LCMS (ESI) m/e 338.0 [(M+H)+, calcd $C_{13}H_{16}BrF_3NO$, 338.1]; LC/MS retention time (method B): $t_R$=1.88 min.

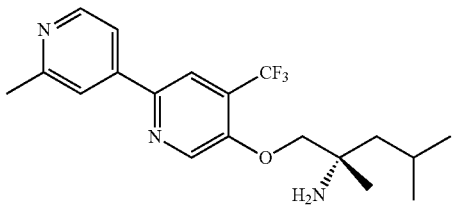

Part B: (S)-2,4-dimethyl-1-((2'-methyl-4-(trifluoromethyl)-[2,4'-bipyridin]-5-yl)oxy)pentan-2-amine Prepared as described in Example 117 to afford (S)-2,4-dimethyl-1-((2'-methyl-4-(trifluoromethyl)-[2,4'-bipyridin]-5-yl)oxy)pentan-2-amine (25.2 mg, 0.066 mmol, 61% yield): $^1$H NMR (500 MHz, DMSO-$d_6$) δ 8.79 (s, 1H), 8.55 (d, J=5.2 Hz, 1H), 8.28 (s, 1H), 7.96 (s, 1H), 7.87 (d, J=5.4

Hz, 1H), 4.05 (d, J=5.5 Hz, 2H), 2.56 (s, 3H), 1.81 (dt, J=12.6, 6.3 Hz, 1H), 1.45-1.33 (m, 2H), 1.12 (s, 3H), 0.92 (dd, J=6.6, 3.0 Hz, 6H); LCMS (ESI) m/e 368.2 (M+H)+, calcd $C_{19}H_{25}F_3N_3O$, 368.2]; LC/MS retention time (method B): $t_R$=1.48 min.

Example 145

(S)-2,4-dimethyl-1-((6-(quinolin-4-yl)-4-(trifluoromethyl)pyridin-3-yl)oxy)pentan-2-amine

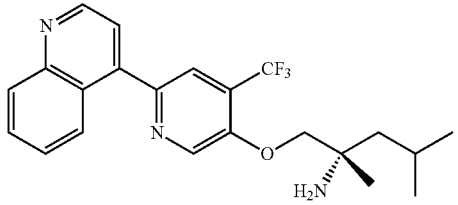 [SMILES: CC(C)C[C@](C)(N)COc1cnc(-c2ccnc3ccccc23)cc1C(F)(F)F]

Prepared as described in Example 117 to afford (S)-2,4-dimethyl-1-((6-(quinolin-4-yl)-4-(trifluoromethyl)pyridin-3-yl)oxy)pentan-2-amine (16.2 mg, 0.038 mmol, 58% yield): $^1$H NMR (500 MHz, DMSO-$d_6$) δ 9.01 (d, J=4.6 Hz, 1H), 8.92 (s, 1H), 8.17 (d, J=8.3 Hz, 1H), 8.13 (d, J=8.5 Hz, 1H), 8.03 (s, 1H), 7.82 (t, J=7.6 Hz, 1H), 7.70 (d, J=4.4 Hz, 1H), 7.64 (t, J=7.7 Hz, 1H), 4.20 (d, J=3.9 Hz, 2H), 1.84 (d, J=10.3 Hz, 1H), 1.50 (qd, J=14.1, 5.5 Hz, 2H), 1.23 (s, 3H), 0.95 (t, J=6.1 Hz, 6H); LCMS (ESI) m/e 404.2 (M+H)+, calcd $C_{22}H_{25}F_3N_3O$, 404.2]; LC/MS retention time (method B): $t_R$=1.71 min.

Example 146

(S)-methyl (5-((2-amino-2,4-dimethylpentyl)oxy)-4-(trifluoromethyl)-[2,4'-bipyridin]-2'-yl)carbamate

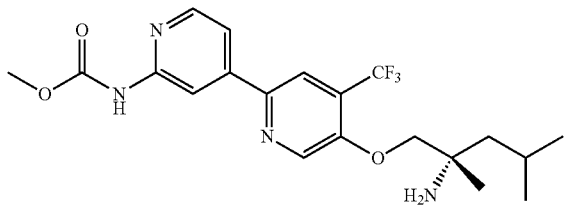 [SMILES: COC(=O)Nc1cc(-c2cc(C(F)(F)F)c(OC[C@@](C)(N)CC(C)C)cn2)ccn1]

Prepared as described in Example 117 to afford (S)-methyl (5-((2-amino-2,4-dimethylpentyl)oxy)-4-(trifluoromethyl)-[2,4'-bipyridin]-2'-yl)carbamate (4.4 mg, 0.010 mmol, 18% yield): $^1$H NMR (500 MHz, DMSO-$d_6$) δ 10.31 (s, 1H), 8.82 (s, 1H), 8.55 (s, 1H), 8.37 (d, J=5.5 Hz, 1H), 8.18 (s, 1H), 7.74 (d, J=5.4 Hz, 1H), 4.12-3.99 (m, 2H), 3.71 (s, 3H–under solvent peak), 1.81 (dt, J=13.2, 6.6 Hz, 1H), 1.39 (d, J=5.6 Hz, 2H), 1.12 (s, 3H), 0.92 (dd, J=6.6, 2.9 Hz, 6H); LCMS (ESI) m/e 449.2 (M+Na)+, calcd $C_{20}H_{25}F_3N_4NaO_3$, 449.2]; LC/MS retention time (method B): $t_R$=1.79 min.

Example 147

(S)-1-((2'-chloro-4-(difluoromethyl)-[2,4'-bipyridin]-5-yl)oxy)-2,4-dimethylpentan-2-amine

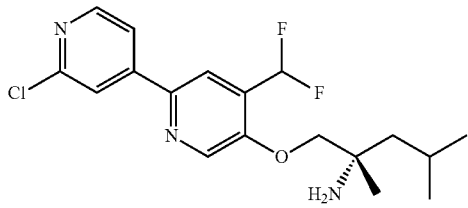 [SMILES: CC(C)C[C@](C)(N)COc1cnc(-c2ccnc(Cl)c2)cc1C(F)F]

Prepared as previously described in Example 117 with intermediate as described in Example 120 and (2-chloropyridin-4-yl)boronic acid to afford (S)-1-((2'-chloro-4-(difluoromethyl)-[2,4'-bipyridin]-5-yl)oxy)-2,4-dimethylpentan-2-amine (13.5 mg, 53%): $^1$H NMR (500 MHz, DMSO-$d_6$) δ 8.69 (s, 1H), 8.51 (d, J=5.2 Hz, 1H), 8.30 (s, 1H), 8.17 (s, 1H), 8.09 (d, J=5.3 Hz, 1H), 7.33 (t, J=53.8 Hz, 1H), 4.03 (s, 2H), 1.80 (p, J=6.2 Hz, 1H), 1.41 (qd, J=14.0, 5.5 Hz, 2H), 1.14 (s, 3H), 0.92 (dd, J=13.2, 6.6 Hz, 6H); LCMS (ESI) m/e 370.1 [(M+H)+, calcd $C_{18}H_{23}ClF_2N_3O$, 370.1]; LC/MS retention time (method B): $t_R$=1.91 min.

Example 148

(S)-1-((4-(difluoromethyl)-5'-fluoro-2'-methyl-[2,4'-bipyridin]-5-yl)oxy)-2,4-dimethylpentan-2-amine

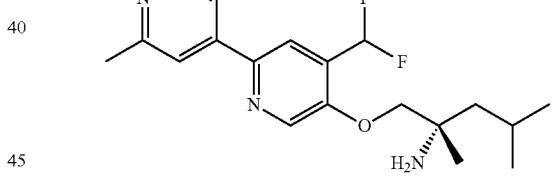

To a 2 mL vial was added (S)-1-((2'-chloro-4-(difluoromethyl)-5'-fluoro-[2,4'-bipyridin]-5-yl)oxy)-2,4-dimethylpentan-2-amine (Example 143) (7.42 mg, 0.019 mmol), 2,4,6-trimethyl-1,3,5,2,4,6-trioxatriborinane (2.402 mg, 0.019 mmol), and $Cs_2CO_3$ (9.35 mg, 0.029 mmol) in dioxane (0.2 mL) and water (0.1 mL) to give a colorless suspension under nitrogen (degassed for 5 min). 1,1'-Bis(diphenylphosphino)ferrocenepalladium(II) dichloride, toluene (0.787 mg, 0.957 μmol) was added under nitrogen. The vial was sealed and heated at 100° C. for 20 h. The mixture was dried, and diluted with MeOH, filtered and purified by prep-HPLC to afford (S)-1-((4-(difluoromethyl)-5'-fluoro-2'-methyl-[2,4'-bipyridin]-5-yl)oxy)-2,4-dimethylpentan-2-amine (1.8 mg, 26%): $^1$H NMR (500 MHz, DMSO-$d_6$) δ 8.73 (s, 1H), 8.54 (d, J=2.9 Hz, 1H), 7.99 (s, 1H), 7.80 (d, J=6.5 Hz, 1H), 7.38 (t, J=53.9 Hz, 1H), 4.12-4.02 (m, 2H), 2.54 (s, 3H), 1.79 (dq, J=12.6, 6.2 Hz, 1H), 1.44 (qd, J=14.0, 5.6 Hz, 2H), 1.17 (s, 3H), 0.94 (d, J=6.6 Hz, 3H), 0.91 (d, J=6.6 Hz, 3H); LCMS (ESI) m/e 351.1 [(M-NH$_2$)+, calcd $C_{19}H_{22}F_3N_2O$, 351.2]; LC/MS retention time (method B): $t_R$=1.81 min.

Example 149

(S)-1-((4-(difluoromethyl)-3'-fluoro-2'-methyl-[2,4'-bipyridin]-5-yl)oxy)-2,4-dimethylpentan-2-amine

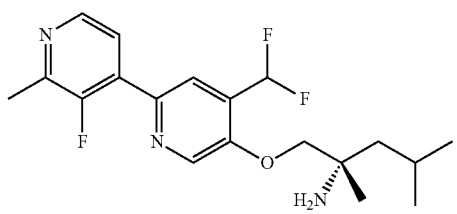 [SMILES: Cc1nccc(-c2cc(C(F)F)c(OC[C@@](C)(N)CC(C)C)cn2)c1F]

Prepared as previously described in Example 148 with Example 142 as the starting material to afford (S)-1-((4-(difluoromethyl)-3'-fluoro-2'-methyl-[2,4'-bipyridin]-5-yl)oxy)-2,4-dimethylpentan-2-amine (2.0 mg, 25%): $^1$H NMR (500 MHz, DMSO-$d_6$) δ 8.74 (s, 1H), 8.39 (d, J=5.1 Hz, 1H), 8.01 (s, 1H), 7.77 (t, J=5.5 Hz, 1H), 7.38 (t, J=53.9 Hz, 1H), 4.06 (d, J=3.0 Hz, 2H), 2.54 (d, J=3.4 Hz, 3H), 1.86-1.76 (m, 1H), 1.50-1.37 (m, 2H), 1.17 (s, 3H), 0.95 (d, J=6.6 Hz, 3H), 0.92 (d, J=6.7 Hz, 3H); LCMS (ESI) m/e 351.1 [(M-NH$_2$)+, calcd C$_{19}$H$_{22}$F$_3$N$_2$O, 351.2]; LC/MS retention time (method B): $t_R$=1.78 min.

Example 150

(S)-1-((4-(difluoromethyl)-6-(2-methylpyrimidin-4-yl)pyridin-3-yl)oxy)-2,4-dimethylpentan-2-amine

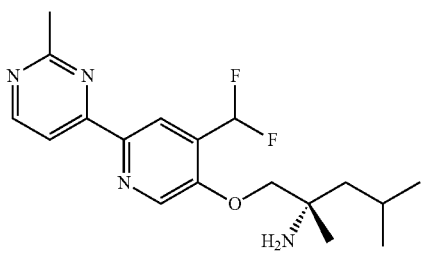 [SMILES: Cc1nccc(-c2cc(C(F)F)c(OC[C@@](C)(N)CC(C)C)cn2)n1]

Prepared as previously described in Example 132 to afford (S)-1-((4-(difluoromethyl)-6-(2-methylpyrimidin-4-yl)pyridin-3-yl)oxy)-2,4-dimethylpentan-2-amine (0.8 mg, 2.3% for 2 steps) as a colorless solid. $^1$H NMR (500 MHz, DMSO-$d_6$) δ 8.83 (d, J=5.2 Hz, 1H), 8.71 (s, 1H), 8.53 (s, 1H), 8.10 (d, J=5.2 Hz, 1H), 7.41 (s, 1H), 4.08 (d, J=2.2 Hz, 2H), 2.72 (s, 3H), 1.81 (dt, J=12.9, 6.5 Hz, 1H), 1.44 (qd, J=14.0, 5.5 Hz, 2H), 1.17 (s, 3H), 0.95 (d, J=6.6 Hz, 3H), 0.92 (d, J=6.7 Hz, 3H); LCMS (ESI) m/e 334.1 [(M-NH$_2$)+, calcd C$_{18}$H$_{22}$F$_2$N$_3$O, 334.2]; LC/MS retention time (method B): $t_R$=1.83 min.

Example 152

(S)-1-(2-(difluoromethyl)-4-(2-methylpyrimidin-4-yl)phenoxy)-2,4-dimethylpentan-2-amine

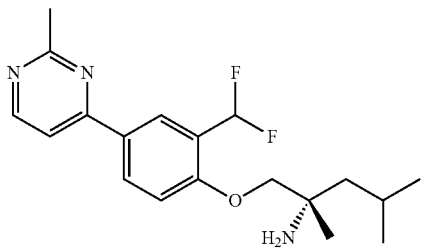 [SMILES: Cc1nccc(-c2ccc(OC[C@@](C)(N)CC(C)C)c(C(F)F)c2)n1]

Prepared as previously described in Example 116 with 4-bromo-2-methylpyrimidine to afford (S)-1-(2-(difluoromethyl)-4-(2-methylpyrimidin-4-yl)phenoxy)-2,4-dimethylpentan-2-amine (32.2 mg, 56% for 2 steps) as a colorless solid. $^1$H NMR (500 MHz, DMSO-$d_6$) δ 8.72 (d, J=5.4 Hz, 1H), 8.38 (d, J=2.2 Hz, 1H), 8.35 (dd, J=8.8, 2.3 Hz, 1H), 7.89 (d, J=5.4 Hz, 1H), 7.43-7.16 (m, 2H), 3.87 (s, 2H), 2.68 (s, 3H), 1.80 (dp, J=12.8, 6.3 Hz, 1H), 1.48-1.35 (m, 2H), 1.14 (s, 3H), 0.93 (d, J=6.6 Hz, 3H), 0.91 (d, J=6.7 Hz, 3H); LCMS (ESI) m/e 333.2 [(M-NH$_2$)+, calcd C$_{19}$H$_{23}$F$_2$N$_2$O, 333.2]; LC/MS retention time (method B): $t_R$=1.85 min.

Example 153

(S)-5-((2-amino-2,4-dimethylpentyl)oxy)-3'-fluoro-6-methyl-[2,4'-bipyridin]-2'-amine

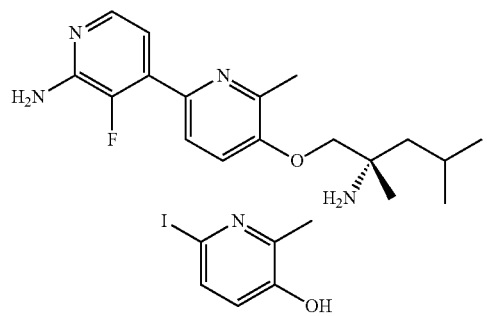

Part A: 6-iodo-2-methylpyridin-3-ol

To a 500 mL round-bottomed flask was added 2-methylpyridin-3-ol (4.0 g, 36.7 mmol) and Na$_2$CO$_3$ (7.8 g, 73.6 mmol) in water (100 mL) to give a slightly tan solution/suspension. I$_2$ (9.6 g, 37.8 mmol) was added in one portion. The mixture was stirred at rt for 3 h. There were noticeable I$_2$ left. The mixture was stirred overnight and there was still I$_2$ left. The reaction mixture was heated at 42° C. (bath temp) for 5 h (most I$_2$ disappeared). The reaction was slowly neutralized with 1N HCl (150 mL) to pH-5. Precipitate was collected by filtration, rinsed with water, aqueous sodium bisulfite solution, and dried under vacuum to yield a yellowish gray powder (7 g). The solids were purified by silica gel chromatography up to 30% EtOAc/hexane to afford 6-iodo-2-methylpyridin-3-ol (4.58 g, 53%) as a light yellow solid: ¹H NMR (400 MHz, Chloroform-d) δ 7.42 (dd, J=8.3, 0.7 Hz, 1H), 6.81 (d, J=8.3 Hz, 1H), 2.48 (s, 3H); LCMS (ESI) m/e 235.8 [(M+H)⁺, calcd C₆H₇INO, 236.0]; LC/MS retention time (method B): $t_R$=1.14 min.

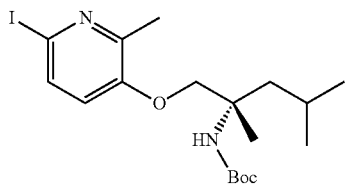 [SMILES: Cc1nc(I)ccc1OC[C@](C)(CC(C)C)NC(=O)OC(C)(C)C]

Part B: (S)-tert-butyl (1-((6-iodo-2-methylpyridin-3-yl)oxy)-2,4-dimethylpentan-2 yl)carbamate Prepared as previously described in Example 32 to afford (S)-tert-butyl (1-((6-iodo-2-methylpyridin-3-yl)oxy)-2,4-dimethylpentan-2 yl)carbamate (528 mg, 100%) as a tan oil: ¹H NMR (400 MHz, Chloroform-d) δ 7.46 (d, J=8.4 Hz, 1H), 6.83 (d, J=8.4 Hz, 1H), 4.53 (s, 1H), 4.14 (d, J=8.9 Hz, 1H), 3.96 (d, J=8.9 Hz, 1H), 2.46 (s, 3H), 1.83 (tdt, J=13.2, 11.6, 6.5 Hz, 2H), 1.53 (d, J=4.7 Hz, 1H), 1.40 (s, 9H), 1.39 (s, 3H), 1.00 (d, J=3.0 Hz, 3H), 0.98 (d, J=3.0 Hz, 3H); LCMS (ESI) m/e 448.9 [(M+H)⁺, calcd C₁₈H₃₁IN₂O₃, 449.1]; LC/MS retention time (method B): $t_R$=2.38 min.

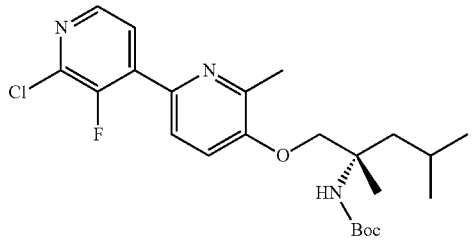 [SMILES: Cc1nc(-c2ccnc(Cl)c2F)ccc1OC[C@](C)(CC(C)C)NC(=O)OC(C)(C)C]

Part C: (S)-tert-butyl(1-((2'-chloro-3'-fluoro-6-methyl-[2,4'-bipyridin]-5-yl)oxy)-2,4-dimethylpentan-2-yl)carbamate Prepared as previously described in Example 66 to afford (S)-tert-butyl (1-((2'-chloro-3'-fluoro-6-methyl-[2,4'-bipyridin]-5-yl)oxy)-2,4-dimethylpentan-2-yl)carbamate (18.9 mg, 17%): LCMS (ESI) m/e 452.2 [(M+H)⁺, calcd C₂₃H₃₂ClFN₃O₃, 452.2]; LC/MS retention time (method B): $t_R$=2.46 min.

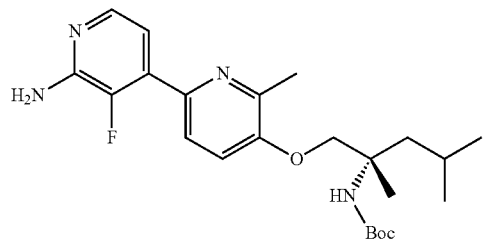 [SMILES: Cc1nc(-c2ccnc(N)c2F)ccc1OC[C@](C)(CC(C)C)NC(=O)OC(C)(C)C]

Part D: (S)-tert-butyl (1-((2'-amino-3'-fluoro-6-methyl-[2,4'-bipyridin]-5-yl)oxy)-2,4-dimethylpentan-2-yl)carbamate To a 20 mL pressure vial was added (S)-tert-butyl (1-((2'-chloro-3'-fluoro-6-methyl-[2,4'-bipyridin]-5-yl)oxy)-2,4-dimethylpentan-2-yl)carbamate (18.9 mg, 0.042 mmol), and methyl carbamate (4.39 mg, 0.059 mmol) in 1,4-dioxane (0.4 mL) to give a colorless solution. While degassing, PdOAc₂ (0.939 mg, 4.18 μmol), XANTPHOS (4.84 mg, 8.36 μmol), Cs₂CO₃ (20.44 mg, 0.063 mmol) were added.

The vial was sealed under nitrogen and heated at 90° C. for 20 h. LCMS showed partial conversion but the carbamate was completely hydrolyzed. The mixture was diluted with EtOAc, dried, filtered, and concentrated. The residue (containing a mixture of the starting material chloride and the hydrolyzed amine product) was directly used in the next step. The amine: LCMS (ESI) m/e 433.3 (M+H)⁺, calcd C₂₃H₃₄FN₄O₃, 433.3]; LC/MS retention time (method B): $t_R$=1.99 min; The chloride: LCMS (ESI) m/e 452.1 [(M+H)⁺, calcd C₂₃H₃₂ClFN₃O₃, 452.2]; LC/MS retention time (method B): $t_R$=2.48 min.

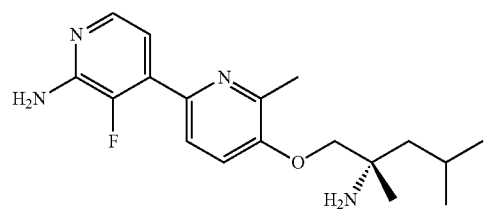 [SMILES: Cc1nc(-c2ccnc(N)c2F)ccc1OC[C@@](C)(N)CC(C)C]

Part E: (S)-5-((2-amino-2,4-dimethylpentyl)oxy)-3'-fluoro-6-methyl-[2,4'-bipyridin]-2'-amine Prepared as previously described in Example 7, Part B to afford a mixture of the amine and chloride. The mixture was purified by prep-HPLC to afford (S)-5-((2-amino-2,4-dimethylpentyl)oxy)-3'-fluoro-6-methyl-[2,4'-bipyridin]-2'-amine (4.3 mg, 31% for 2 steps): ¹H NMR (500 MHz, DMSO-d₆) δ 7.79 (d, J=5.3 Hz, 1H), 7.69 (d, J=8.5 Hz, 1H), 7.45 (d, J=8.5 Hz, 1H), 7.02 (t, J=5.2 Hz, 1H), 6.22 (s, 2H), 3.86 (s, 2H), 2.50 (s, 3H), 1.81 (dq, J=12.8, 6.5 Hz, 1H), 1.56-1.42 (m, 2H), 1.21 (s, 3H), 0.94 (dd, J=10.3, 6.7 Hz, 6H); LCMS (ESI) m/e 333.2 [(M+H)⁺, calcd C₁₈H₂₆FN₄O, 333.2]; LC/MS retention time (method B): $t_R$=1.48 min.

Example 154

(S)-1-((2'-chloro-3'-fluoro-6-methyl-[2,4'-bipyridin]-5-yl)oxy)-2,4-dimethylpentan-2-amine

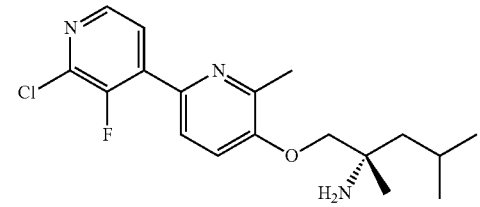

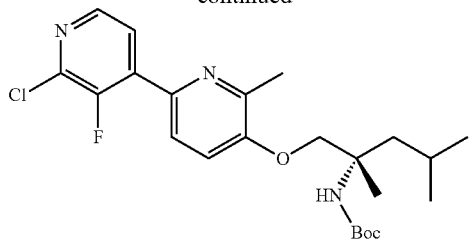

Part A: (S)-tert-butyl (1-((2'-amino-3'-fluoro-6-methyl-[2,4'-bipyridin]-5-yl)oxy)-2,4-dimethylpentan-2-yl)carbamate Obtained as a mixture with the amine from Example 153, Part D. LCMS (ESI) m/e 452.1 [(M+H)$^+$, calcd $C_{23}H_{32}ClFN_3O_3$, 452.2]; LC/MS retention time (method B): $t_R$=2.48 min.

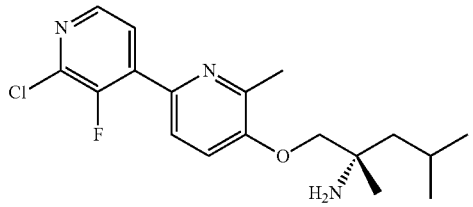 [SMILES: Cc1nc(-c2ccnc(Cl)c2F)ccc1OC[C@@](C)(N)CC(C)C]

Part B: (S)-1-((2'-chloro-3'-fluoro-6-methyl-[2,4'-bipyridin]-5-yl)oxy)-2,4-dimethylpentan-2-amine The crude mixture from Example 153, Part D was deprotected as previously described in Example 7, Part B to afford a mixture of the amine and chloride. The mixture was separated and purified by prep-HPLC to afford (S)-1-((2'-chloro-3'-fluoro-6-methyl-[2,4'-bipyridin]-5-yl)oxy)-2,4-dimethylpentan-2-amine: (2.6 mg, 17% for 2 steps): $^1$H NMR (500 MHz, DMSO-d$_6$) δ 8.33 (d, J=5.0 Hz, 1H), 7.99 (t, J=5.3 Hz, 1H), 7.82 (d, J=8.3 Hz, 1H), 7.49 (d, J=8.6 Hz, 1H), 3.83 (s, 2H), 2.51 (s, 3H–OCH3 protons under DMSO peak–predicted shift=2.47 ppm), 1.82 (p, J=6.2 Hz, 1H), 1.53-1.38 (m, 2H), 1.18 (s, 3H), 0.94 (t, J=7.2 Hz, 6H); LCMS (ESI) m/e 335.1 [(M-NH$_2$)+, calcd $C_{18}H_{21}ClFN_2O$, 335.1]; LC/MS retention time (method B): $t_R$=1.91 min.

Example 155

(S)-methyl (5-((2-amino-2,4-dimethylpentyl)oxy)-5'-fluoro-6-methyl-[2,4'-bipyridin]-2'-yl)carbamate

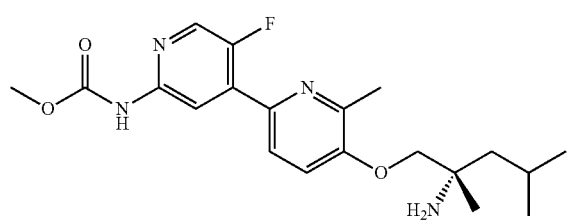 [SMILES: COC(=O)Nc1cc(-c2ccc(OC[C@@](C)(N)CC(C)C)c(C)n2)c(F)cn1]

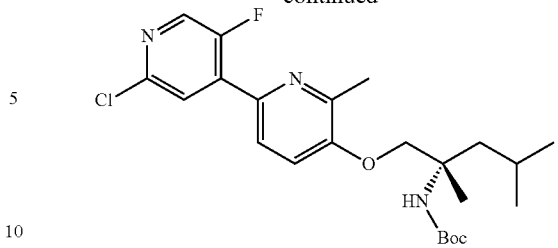

Part A: (S)-tert-butyl (1-((2'-chloro-5'-fluoro-6-methyl-[2,4'-bipyridin]-5-yl)oxy)-2,4-dimethylpentan-2-yl)carbamate Prepared as previously described in Example 66 with intermediate from Example 153 and (2-chloro-5-fluoro-pyridin-4-yl)boronic acid to afford (S)-tert-butyl (1-((2'-chloro-5'-fluoro-6-methyl-[2,4'-bipyridin]-5-yl)oxy)-2,4-dimethylpentan-2-yl)carbamate (13.4 mg, 13%): LCMS (ESI) m/e 452.1 [(M+H)$^+$, calcd $C_{23}H_{32}ClFN_3O_3$, 452.2]; LC/MS retention time (method B): $t_R$=2.49 min.

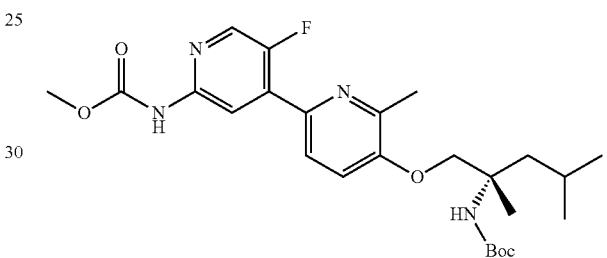

Part B: (S)-methyl (5-((2-Boc-amino-2,4-dimethylpentyl)oxy)-5'-fluoro-6-methyl-[2,4'-bipyridin]-2'-yl)carbamate Prepared as previously described in Example 153 to afford (S)-methyl (5-((2-Boc-amino-2,4-dimethylpentyl)oxy)-5'-fluoro-6-methyl-[2,4'-bipyridin]-2'-yl)carbamate (no carbamate hydrolysis observed) contaminated with left over starting material ((S)-tert-butyl (1-((2'-chloro-5'-fluoro-6-methyl-[2,4'-bipyridin]-5-yl)oxy)-2,4-dimethylpentan-2-yl)carbamate). The crude mixture was carried on without further purification. Carbamate: LCMS (ESI) m/e 491.2 (M+H)$^+$, calcd $C_{25}H_{36}FN_4O_5$, 491.3]; LC/MS retention time (method B): $t_R$=2.30 min.

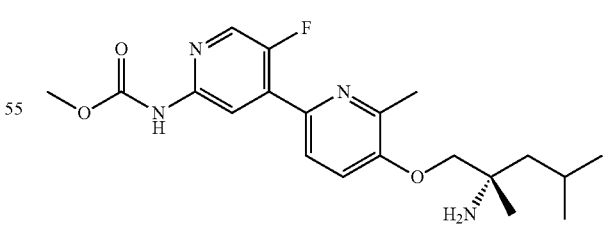

Part C: (S)-methyl (5-((2-amino-2,4-dimethylpentyl)oxy)-5'-fluoro-6-methyl-[2,4'-bipyridin]-2'-yl)carbamate Prepared as previously described in Example 7, Part B. The crude mixture was separated and purified by prep- HPLC to afford (S)-methyl (5-((2-amino-2,4-dimethylpentyl)oxy)-5'-fluoro-6-methyl-[2,4'-bipyridin]-2'-yl)carbamate (0.3 mg, 2.5% for 2 steps) as a colorless solid. $^1$H NMR (400 MHz, Methanol-d$_4$) δ 8.45 (d, J=5.9 Hz, 1H), 8.21 (d, J=2.7 Hz, 1H), 7.79-7.73 (m, 1H), 7.46 (d, J=8.6 Hz, 1H), 4.07-3.96 (m, 2H), 3.80 (s, 3H), 2.61 (s, 3H), 1.87 (dt, J=12.5, 6.4 Hz, 1H), 1.73 (dd, J=14.3, 5.6 Hz, 1H), 1.62 (dd, J=14.2, 5.5 Hz, 1H), 1.39 (s, 3H), 1.04 (dd, J=10.9, 6.6 Hz, 6H); LCMS (ESI) m/e 391.4 [(M+H)$^+$, calcd C$_{20}$H$_{28}$FN$_4$O$_3$, 391.2].

Example 156

(S)-1-((2'-chloro-5'-fluoro-6-methyl-[2,4'-bipyridin]-5-yl)oxy)-2,4-dimethylpentan-2-amine

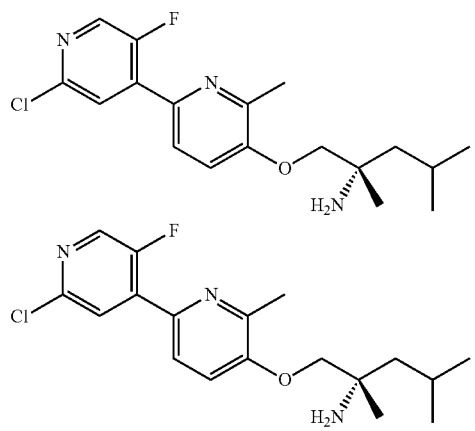

Part C: (S)-1-((2'-chloro-5'-fluoro-6-methyl-[2,4'-bipyridin]-5-yl)oxy)-2,4-dimethylpentan-2-amine Recovered from mixture obtained in Example 155, Part C. The mixture was separated and purified by prep-HPLC to afford (S)-1-((2'-chloro-5'-fluoro-6-methyl-[2,4'-bipyridin]-5-yl)oxy)-2,4-dimethylpentan-2-amine (5.2 mg, 49% for 2 steps) as a colorless solid. $^1$H NMR (500 MHz, DMSO-d$_6$) δ 8.54 (d, J=2.6 Hz, 1H), 8.03 (d, J=5.5 Hz, 1H), 7.83 (d, J=8.4 Hz, 1H), 7.48 (d, J=8.6 Hz, 1H), 3.81 (s, 2H), 2.51 (s, 3H–OCH3 protons under DMSO peak–predicted shift=2.47 ppm), 1.81 (dq, J=12.6, 6.5 Hz, 1H), 1.49-1.36 (m, 2H), 1.16 (s, 3H), 0.93 (t, J=6.3 Hz, 6H); LCMS (ESI) m/e 335.1 [(M-NH$_2$)+, calcd C$_{18}$H$_{21}$ClFN$_2$O, 335.1]; LC/MS retention time (method B): t$_R$=1.93 min.

Example 157

(S)-methyl (5-((2-amino-2,4-dimethylpentyl)oxy)-3'-fluoro-6-methyl-[2,4'-bipyridin]-2'-yl)carbamate

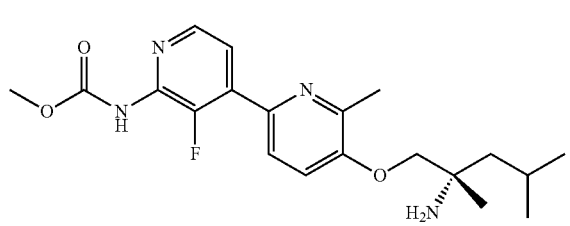

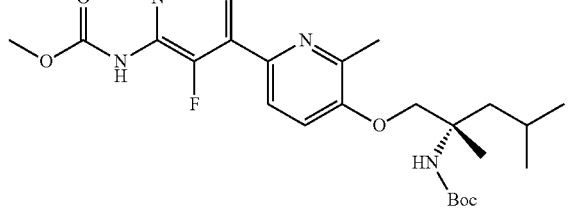

Part A: (S)-methyl (5-((2-Boc-amino-2,4-dimethylpentyl)oxy)-3'-fluoro-6-methyl-[2,4'-bipyridin]-2'-yl)carbamate Prepared as previously described in Example 153 with reaction running at 80° C. for 30 h resulting in the carbamate after prep-HPLC purification (7.1 mg, 19%): LCMS (ESI) m/e 491.4 (M+H)$^+$, calcd C$_{25}$H$_{36}$FN$_4$O$_5$, 491.3]; LC/MS retention time (method A): t$_R$=1.99 min.

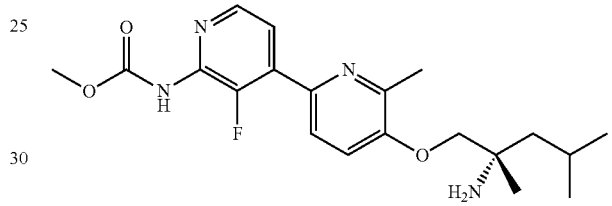

Part B: (S)-methyl (5-((2-amino-2,4-dimethylpentyl)oxy)-3'-fluoro-6-methyl-[2,4'-bipyridin]-2'-yl)carbamate Prepared as previously described in Example 7, Part B to afford (S)-methyl (5-((2-amino-2,4-dimethylpentyl)oxy)-3'-fluoro-6-methyl-[2,4'-bipyridin]-2'-yl)carbamate (5.2 mg, 90%): $^1$H NMR (500 MHz, DMSO-d$_6$) δ 8.25 (d, J=5.1 Hz, 1H), 7.79 (t, J=5.2 Hz, 1H), 7.74 (d, J=8.4 Hz, 1H), 7.46 (d, J=8.7 Hz, 1H), 3.80 (s, 2H), 3.68 (s, 3H), 2.50 (s, 3H), 1.81 (dt, J=12.5, 6.5 Hz, 1H), 1.48-1.38 (m, 2H), 1.15 (s, 3H), 0.93 (t, J=6.3 Hz, 6H); LCMS (ESI) m/e 413.1 [(M+Na)$^+$, calcd C$_{20}$H$_{27}$FN$_4$NaO$_3$, 413.2]; LC/MS retention time (method B): t$_R$=1.66 min.

Example 158

(S)-1-((2'-chloro-6-(difluoromethyl)-[2,4'-bipyridin]-5-yl)oxy)-2,4-dimethylpentan-2-amine

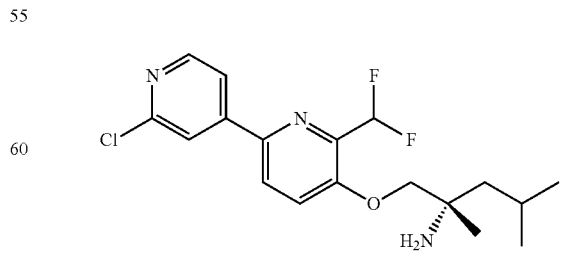

Prepared as described in Example 117 with (2-chloropyridin-4-yl)boronic acid to afford (S)-1-((2'-chloro-6-(difluoromethyl)-[2,4'-bipyridin]-5-yl)oxy)-2,4-dimethylpentan-2-amine (26.3 mg, 0.068 mmol, 49%): $^1$H NMR (500 MHz, DMSO-$d_6$) δ 8.52 (d, J=5.2 Hz, 1H), 8.37 (d, J=8.8 Hz, 1H), 8.13 (s, 1H), 8.07 (d, J=5.2 Hz, 1H), 7.81 (d, J=8.8 Hz, 1H), 7.27 (t, J=53.6 Hz, 1H), 3.94 (s, 2H), 1.79 (dt, J=12.6, 6.4 Hz, 1H), 1.43 (qd, J=14.1, 5.6 Hz, 2H), 1.16 (s, 3H), 0.92 (dd, J=12.8, 6.6 Hz, 6H); LCMS (ESI) m/e 370.1 [(M+H)$^+$, calcd $C_{19}H_{26}F_2N_3O$, 370.1]; LC/MS retention time (method B): $t_R$=1.91 min.

Example 159

(S)-1-((2'-chloro-6-(difluoromethyl)-3'-fluoro-[2,4'-bipyridin]-5-yl)oxy)-2,4-dimethylpentan-2-amine

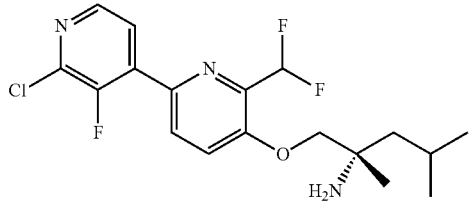 [SMILES: CC(C)C[C@](C)(N)COc1ccc(-c2ccnc(Cl)c2F)nc1C(F)F]

Prepared as described in Example 117 with (2-chloro-3-fluoropyridin-4-yl)boronic acid to afford (S)-1-((2'-chloro-6-(difluoromethyl)-3'-fluoro-[2,4'-bipyridin]-5-yl)oxy)-2,4-dimethylpentan-2-amine (25 mg, 0.064 mmol, 9.6%): $^1$H NMR (500 MHz, DMSO-$d_6$) δ 8.38 (dd, J=5.3, 2.4 Hz, 1H), 8.12 (d, J=8.9 Hz, 1H), 7.96 (td, J=5.3, 2.2 Hz, 1H), 7.83 (d, J=8.8 Hz, 1H), 7.25 (t, J=53.5 Hz, 1H), 3.91 (d, J=2.0 Hz, 2H), 1.86-1.75 (m, 1H), 1.40 (t, J=6.2 Hz, 2H), 1.14 (d, J=2.2 Hz, 3H), 0.92 (ddd, J=9.7, 6.8, 2.3 Hz, 6H); LCMS (ESI) m/e 388.1 [(M+H)$^+$, calcd $C_{18}H_{22}ClF_3N_3O$, 388.1]; LC/MS retention time (method B): $t_R$=1.94 min.

Example 160

(S)-1-((6-(difluoromethyl)-3'-fluoro-2'-methyl-[2,4'-bipyridin]-5-yl)oxy)-2,4-dimethylpentan-2-amine

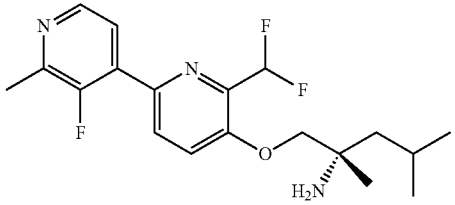 [SMILES: Cc1nccc(-c2ccc(OC[C@@](C)(N)CC(C)C)c(C(F)F)n2)c1F]

Prepared as described in Example 148 to afford (S)-1-((6-(difluoromethyl)-3'-fluoro-2'-methyl-[2,4'-bipyridin]-5-yl)oxy)-2,4-dimethylpentan-2-amine (12.8 mg, 0.033 mmol, 55%): $^1$H NMR (500 MHz, DMSO-$d_6$) δ 8.39 (d, J=5.0 Hz, 1H), 8.07 (d, J=8.8 Hz, 1H), 7.80 (d, J=8.9 Hz, 1H), 7.75 (t, J=5.5 Hz, 1H), 7.24 (t, J=53.5 Hz, 1H), 3.92 (s, 2H), 2.54 (d, J=3.3 Hz, 3H), 1.80 (dt, J=12.6, 6.3 Hz, 1H), 1.50-1.36 (m, 2H), 1.15 (s, 3H), 0.92 (dd, J=11.5, 6.6 Hz, 6H); LCMS (ESI) m/e 368.2 [(M+H)$^+$, calcd $C_{19}H_{25}F_3N_3O$, 368.2]; LC/MS retention time (method B): $t_R$=1.72 min.

Example 161

((S)-1-((6-chloro-2'-(difluoromethyl)-[2,4'-bipyridin]-5-yl)oxy)-2,4-dimethylpentan-2-amine

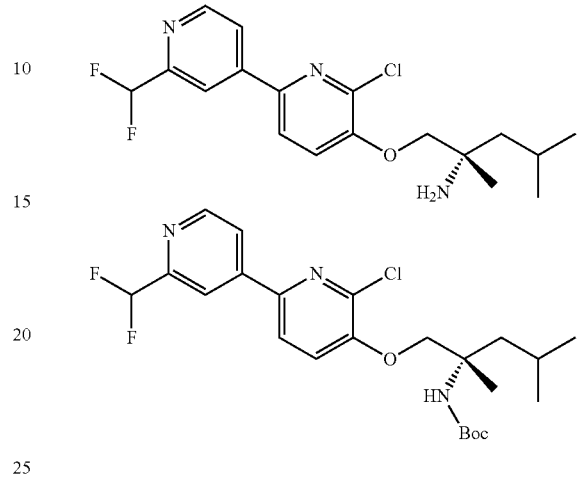

Part A: (S)-tert-butyl (1-((6-chloro-2'-(difluoromethyl)-[2,4'-bipyridin]-5-yl)oxy)-2,4-dimethylpentan-2-yl)carbamate Prepared as previously described in Example 66 with intermediates iodide as described in Example 66 and (2-(difluoromethyl)pyridin-4-yl)boronic acid as described in Example 123 (concentrated to dryness and used as is) to afford (S)-tert-butyl (1-((6-chloro-2'-(difluoromethyl)-[2,4'-bipyridin]-5-yl)oxy)-2,4-dimethylpentan-2-yl)carbamate (70 mg, 19%): $^1$H NMR (400 MHz, Chloroform-d) δ 8.74 (d, J=5.2 Hz, 1H), 8.18 (d, J=1.7 Hz, 1H), 8.04-7.97 (m, 1H), 7.77 (d, J=8.4 Hz, 1H), 7.38 (d, J=8.5 Hz, 1H), 6.73 (t, J=55.5 Hz, 1H), 4.59 (s, 1H), 4.38 (d, J=8.9 Hz, 1H), 4.18 (d, J=8.8 Hz, 1H), 1.99-1.81 (m, 2H), 1.57-1.52 (m, 1H), 1.46 (s, 3H), 1.40 (s, 9H), 1.03 (d, J=6.6 Hz, 6H); $^{19}$F NMR (376 MHz, Chloroform-d) δ −115.83; LCMS (ESI) m/e 470.2 (M+H)$^+$, calcd $C_{23}H_{31}ClF_2N_3O_3$, 470.2]; LC/MS retention time (method A): $t_R$=2.50 min.

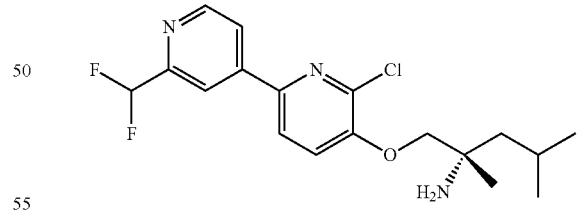

Part B: ((S)-1-((6-chloro-2'-(difluoromethyl)-[2,4'-bipyridin]-5-yl)oxy)-2,4-dimethylpentan-2-amine Prepared as previously described in Example 7, Part B to afford ((S)-1-((6-chloro-2'-(difluoromethyl)-[2,4'-bipyridin]-5-yl)oxy)-2,4-dimethylpentan-2-amine (40.6 mg, 74%): $^1$H NMR (500 MHz, DMSO-$d_6$) δ 8.77 (d, J=5.1 Hz, 1H), 8.22 (d, J=8.1 Hz, 2H), 8.13 (d, J=5.2 Hz, 1H), 7.72 (d, J=8.4 Hz, 1H), 7.01 (t, J=55.0 Hz, 1H), 3.92 (s, 2H), 1.79 (dt, J=12.5, 6.6 Hz, 1H), 1.44 (qd, J=14.1, 5.5 Hz, 2H), 1.16 (s, 3H), 0.91 (t, J=6.2 Hz, 6H); $^{19}$F NMR (376 MHz, DMSO-d6) δ −115.46 (d, J=55.0 Hz); LCMS (ESI) m/e 392.1 [(M+Na)$^+$, calcd $C_{18}H_{22}ClF_2N_3NaO$, 392.1]; LC/MS retention time (method B): $t_R$=1.94 min.

Example 162

(S)-1-((4-(difluoromethyl)-6-(6-methylpyridazin-4-yl)pyridin-3-yl)oxy)-2,4-dimethylpentan-2-amine

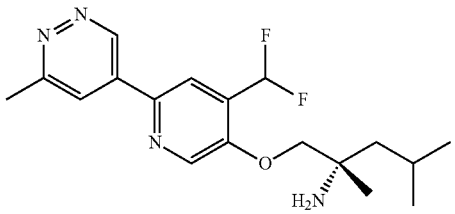 [SMILES: Cc1cc(-c2cc(C(F)F)c(OC[C@@](C)(N)CC(C)C)cn2)cnn1]

Prepared as described in Example 117 with 3-methyl-5-(4,4,5,5-tetramethyl-1,3,2-dioxaborolan-2-yl)pyridazine to afford (S)-1-((4-(difluoromethyl)-6-(6-methylpyridazin-4-yl)pyridin-3-yl)oxy)-2,4-dimethylpentan-2-amine (23.6 mg, 0.066 mmol, 48%): $^1$H NMR (500 MHz, DMSO-d$_6$) δ 9.72 (d, J=2.1 Hz, 1H), 8.72 (s, 1H), 8.34 (s, 1H), 8.19 (d, J=2.0 Hz, 1H), 7.35 (t, J=54.0 Hz, 1H), 4.04 (s, 2H), 2.71 (s, 3H), 1.85-1.74 (m, 1H), 1.42 (qd, J=13.7, 5.3 Hz, 2H), 1.15 (s, 3H), 0.92 (dd, J=13.3, 6.7 Hz, 6H); LCMS (ESI) m/e 373.2 [(M+Na)$^+$, calcd $C_{18}H_{24}F_2N_4NaO$, 373.2]; LC/MS retention time (method B): $t_R$=1.59 min.

Example 163

(S)-1-((2-(difluoromethyl)-6-(6-methylpyridazin-4-yl)pyridin-3-yl)oxy)-2,4-dimethylpentan-2-amine

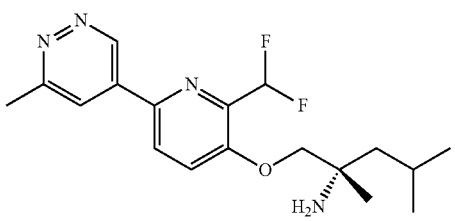 [SMILES: Cc1cc(-c2ccc(OC[C@@](C)(N)CC(C)C)c(C(F)F)n2)cnn1]

Prepared as described in Example 117 with 3-methyl-5-(4,4,5,5-tetramethyl-1,3,2-dioxaborolan-2-yl)pyridazine to afford (S)-1-((2-(difluoromethyl)-6-(6-methylpyridazin-4-yl)pyridin-3-yl)oxy)-2,4-dimethylpentan-2-amine (37.2 mg, 0.105 mmol, 85%): $^1$H NMR (500 MHz, DMSO-d$_6$) δ 9.71 (d, J=2.1 Hz, 1H), 8.40 (d, J=8.8 Hz, 1H), 8.13 (d, J=2.1 Hz, 1H), 7.84 (d, J=8.9 Hz, 1H), 7.24 (t, J=53.6 Hz, 1H), 3.91 (s, 2H), 2.71 (s, 3H), 1.80 (dt, J=13.2, 6.3 Hz, 1H), 1.46-1.34 (m, 2H), 1.13 (s, 3H), 0.92 (dd, J=10.5, 6.6 Hz, 6H); LCMS (ESI) m/e 373.2 [(M+Na)$^+$, calcd $C_{18}H_{24}F_2N_4NaO$, 373.2]; LC/MS retention time (method B): $t_R$=1.62 min.

Example 164

(R)-2,4-dimethyl-1-((2'-methyl-4-(trifluoromethyl)-[2,4'-bipyridin]-5-yl)oxy)pentan-2-amine

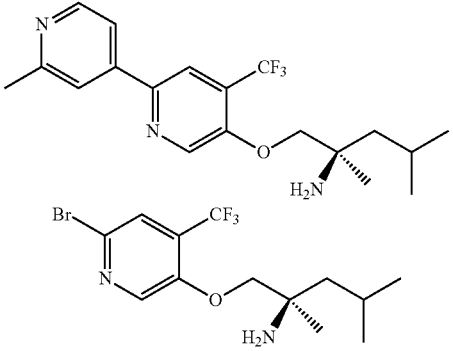

Part A: (R)-1-((6-bromo-4-(difluoromethyl)pyridin-3-yl)oxy)-2,4-dimethylpentan-2-amine Prepared as previously described in Example 144 with R-enantiomer of the amino alcohol to afford (R)-1-((6-bromo-4-(difluoromethyl)pyridin-3-yl)oxy)-2,4-dimethylpentan-2-amine (0.58 g, 97%) as a tan oil: $^1$H NMR (400 MHz, Chloroform-d) δ 8.19 (s, 1H), 7.64 (s, 1H), 3.97-3.83 (m, 2H), 1.85-1.73 (m, 1H), 1.49 (dd, J=5.7, 4.0 Hz, 2H), 1.24 (s, 3H), 0.99 (dd, J=9.3, 6.6 Hz, 6H); $^{19}$F NMR (376 MHz, Chloroform-d) δ −64.39; LCMS (ESI) m/e 338.0 [(M+H)$^+$, calcd $C_{13}H_{16}BrF_3NO$, 338.1]; LC/MS retention time (method B): $t_R$=1.87 min.

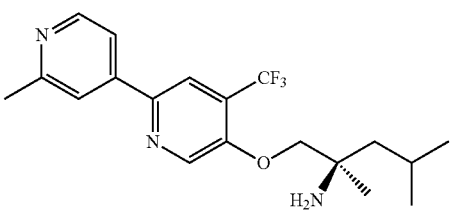 [SMILES: Cc1cc(-c2cc(C(F)(F)F)c(OC[C@](C)(N)CC(C)C)cn2)ccn1]

Part B: (R)-2,4-dimethyl-1-((2'-methyl-4-(trifluoromethyl)-[2,4'-bipyridin]-5-yl)oxy)pentan-2-amine Prepared as described in Example 144 to afford (R)-2,4-dimethyl-1-((2'-methyl-4-(trifluoromethyl)-[2,4'-bipyridin]-5-yl)oxy)pentan-2-amine (7.6 mg, 0.020 mmol, 23% yield): $^1$H NMR (500 MHz, DMSO-d$_6$) δ 8.79 (s, 1H), 8.55 (d, J=5.2 Hz, 1H), 8.29 (s, 1H), 7.97 (s, 1H), 7.88 (d, J=5.2 Hz, 1H), 4.11-4.02 (m, 2H), 2.56 (s, 3H), 1.81 (dt, J=12.9, 6.5 Hz, 1H), 1.40 (dd, J=5.6, 2.8 Hz, 2H), 1.13 (s, 3H), 0.92 (dd, J=6.6, 3.2 Hz, 6H); LCMS (ESI) m/e 368.2 (M+H)$^+$, calcd $C_{19}H_{25}F_3N_3O$, 368.2]; LC/MS retention time (method B): $t_R$=1.44 min.

Example 165

(R)-2,4-dimethyl-1-((6-(quinolin-4-yl)-4-(trifluoromethyl)pyridin-3-yl)oxy)pentan-2-amine

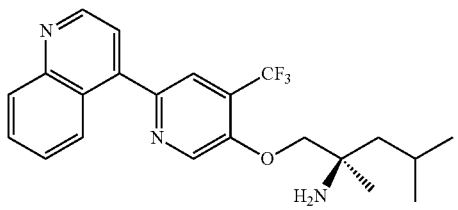 [SMILES: CC(C)C[C@@](C)(N)COc1cnc(-c2ccnc3ccccc23)cc1C(F)(F)F]

Prepared as described in Example 144 to afford (R)-2,4-dimethyl-1-((6-(quinolin-4-yl)-4-(trifluoromethyl)pyridin-3-yl)oxy)pentan-2-amine (14.9 mg, 0.037 mmol, 45% yield): $^1$H NMR (500 MHz, DMSO-$d_6$) δ 9.01 (d, J=4.4 Hz, 1H), 8.90 (s, 1H), 8.18 (d, J=8.5 Hz, 1H), 8.13 (d, J=8.5 Hz, 1H), 8.02 (s, 1H), 7.82 (t, J=7.6 Hz, 1H), 7.70 (d, J=4.4 Hz, 1H), 7.64 (t, J=7.7 Hz, 1H), 4.15-4.05 (m, 2H), 1.83 (dq, J=12.6, 6.3 Hz, 1H), 1.42 (dd, J=5.7, 2.0 Hz, 2H), 1.16 (s, 3H), 0.95 (dd, J=6.6, 3.5 Hz, 6H); LCMS (ESI) m/e 404.2 (M+H)$^+$, calcd $C_{22}H_{25}F_3N_3O$, 404.2]; LC/MS retention time (method B): $t_R$=1.66 min.

Example 166

(R)-methyl (5-((2-amino-2,4-dimethylpentyl)oxy)-4-(trifluoromethyl)-[2,4'-bipyridin]-2'-yl)carbamate

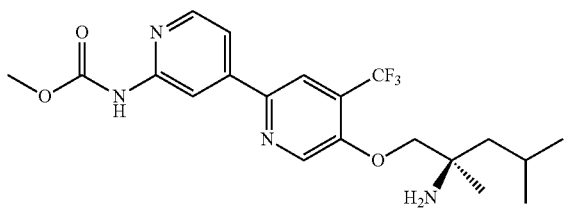 [SMILES: COC(=O)Nc1cc(-c2cc(C(F)(F)F)c(OC[C@](C)(N)CC(C)C)cn2)ccn1]

Prepared as described in Example 144 to afford (R)-methyl (5-((2-amino-2,4-dimethylpentyl)oxy)-4-(trifluoromethyl)-[2,4'-bipyridin]-2'-yl)carbamate (7.8 mg, 0.018 mmol, 35% yield): $^1$H NMR (500 MHz, DMSO-$d_6$) δ 8.81 (s, 1H), 8.54 (s, 1H), 8.37 (d, J=5.2 Hz, 1H), 8.18 (s, 1H), 7.74 (dd, J=5.3, 1.6 Hz, 1H), 4.10-4.00 (m, 2H), 3.71 (s, 3H), 1.81 (hept, J=6.1 Hz, 1H), 1.41-1.34 (m, 2H), 1.12 (s, 3H), 0.92 (dd, J=6.8, 2.7 Hz, 6H); LCMS (ESI) m/e 449.1 (M+Na)$^+$, calcd $C_{20}H_{25}F_3N_4NaO_3$, 449.2]; LC/MS retention time (method B): $t_R$=1.72 min.

Example 167

(R)-1-((2'-chloro-4-(difluoromethyl)-3'-fluoro-[2,4'-bipyridin]-5-yl)oxy)-2,4-dimethylpentan-2-amine

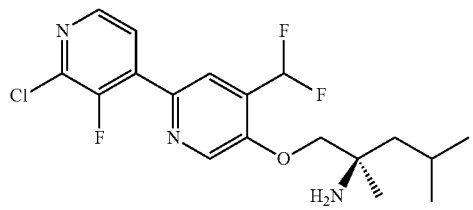 [SMILES: CC(C)C[C@@](C)(N)COc1cnc(-c2ccnc(Cl)c2F)cc1C(F)F]

Part A: (R)-1-((6-bromo-4-(difluoromethyl)pyridin-3-yl)oxy)-2,4-dimethylpentan-2-amine

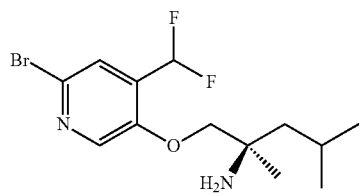

Prepared as previously described in Example 142 with R-enantiomer of the amino alcohol to afford (R)-1-((6-bromo-4-(difluoromethyl)pyridin-3-yl)oxy)-2,4-dimethylpentan-2-amine (740 mg, 95%): LCMS (ESI) m/e 336.9 [(M+H)$^+$, calcd $C_{13}H_{20}BrF_2N_2O$, 337.1]; LC/MS retention time (method B): $t_R$=1.83 min. The material was used as is.

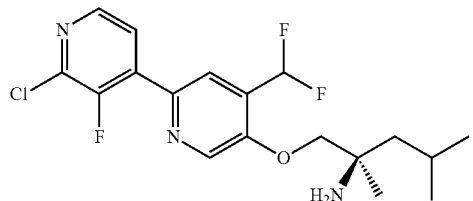

Prepared as previously described in Example 142 with intermediate as described above and (2-chloro-3-fluoropyridin-4-yl)boronic acid (6.7 mg, 11%): $^1$H NMR (500 MHz, DMSO-$d_6$) δ 8.76 (s, 1H), 8.38 (d, J=5.0 Hz, 1H), 8.06 (s, 1H), 7.97 (t, J=5.4 Hz, 1H), 7.38 (t, J=53.9 Hz, 1H), 4.05 (s, 2H), 1.81 (dt, J=12.9, 6.4 Hz, 1H), 1.42 (tt, J=14.1, 6.8 Hz, 2H), 1.15 (d, J=3.5 Hz, 3H), 0.94 (d, J=6.6 Hz, 3H), 0.91 (d, J=6.6 Hz, 3H); LCMS (ESI) m/e 371.1 [(M-NH$_2$)+, calcd $C_{18}H_{19}ClF_3N_2O$, 371.1]; LC/MS retention time (method B): $t_R$=2.02 min.

Example 168

(R)-1-((2'-chloro-4-(difluoromethyl)-5'-fluoro-[2,4'-bipyridin]-5-yl)oxy)-2,4-dimethylpentan-2-amine

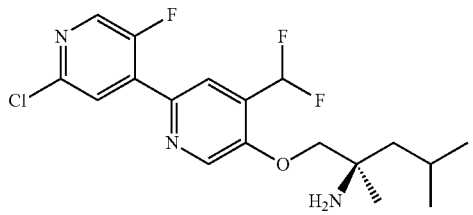 [SMILES: CC(C)C[C@@](C)(N)COc1cnc(-c2cc(Cl)ncc2F)cc1C(F)F]

Prepared as previously described in Example 142 with intermediate as described in Example 167 and (2-chloro-5-fluoro-pyridin-4-yl)boronic acid to afford (R)-1-((2'-chloro-4-(difluoromethyl)-5'-fluoro-[2,4'-bipyridin]-5-yl)oxy)-2,4-dimethylpentan-2-amine (14 mg, 20%): $^1$H NMR (500 MHz, DMSO-d$_6$) δ 8.75 (s, 1H), 8.60 (d, J=2.3 Hz, 1H), 8.05 (s, 1H), 8.02 (d, J=5.5 Hz, 1H), 7.36 (t, J=53.9 Hz, 1H), 4.04 (s, 2H), 1.81 (hept, J=6.4 Hz, 1H), 1.48-1.35 (m, 2H), 1.14 (d, J=3.3 Hz, 3H), 0.93 (dd, J=12.6, 6.6 Hz, 6H); LCMS (ESI) m/e 371.1 [(M-NH$_2$)+, calcd C$_{18}$H$_{19}$ClF$_3$N$_2$O, 371.1]; LC/MS retention time (method B): t$_R$=1.98 min.

Example 169

(R)-1-((2'-chloro-4-(difluoromethyl)-[2,4'-bipyridin]-5-yl)oxy)-2,4-dimethylpentan-2-amine

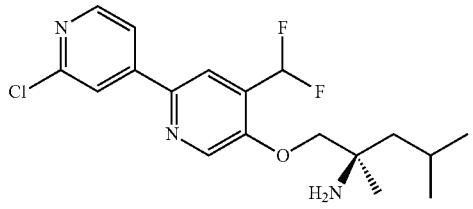 [SMILES: CC(C)C[C@@](C)(N)COc1cnc(-c2ccnc(Cl)c2)cc1C(F)F]

Prepared as previously described in Example 142 with intermediate as described in Example 167 and (2-chloro-pyridin-4-yl)boronic acid to afford (R)-1-((2'-chloro-4-(difluoromethyl)-[2,4'-bipyridin]-5-yl)oxy)-2,4-dimethylpentan-2-amine (10.2 mg, 49%): $^1$H NMR (500 MHz, DMSO-d$_6$) δ 8.70 (s, 1H), 8.51 (d, J=5.3 Hz, 1H), 8.31 (s, 1H), 8.18 (s, 1H), 8.11 (d, J=5.3 Hz, 1H), 7.33 (t, J=53.9 Hz, 1H), 4.02 (s, 2H), 1.80 (q, J=6.3 Hz, 1H), 1.40 (tt, J=14.0, 7.4 Hz, 2H), 1.14 (s, 3H), 0.93 (dd, J=12.5, 6.6 Hz, 6H); LCMS (ESI) m/e 353.1 [(M-NH$_2$)+, calcd C$_{18}$H$_{20}$ClF$_2$N$_2$O, 353.1]; LC/MS retention time (method B): t$_R$=1.90 min.

Example 170

(R)-1-((4-(difluoromethyl)-2'-ethyl-[2,4'-bipyridin]-5-yl)oxy)-2,4-dimethylpentan-2-amine

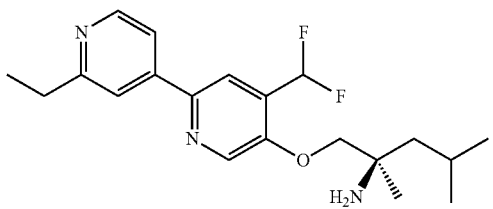 [SMILES: CCc1cc(-c2cc(C(F)F)c(OC[C@](C)(N)CC(C)C)cn2)ccn1]

Prepared as previously described in Example 141 with intermediate as described in Example 167 and (2-ethylpyridin-4-yl)boronic acid to afford (R)-1-((4-(difluoromethyl)-2'-ethyl-[2,4'-bipyridin]-5-yl)oxy)-2,4-dimethylpentan-2-amine (12.3 mg, 60%): $^1$H NMR (500 MHz, DMSO-d$_6$) δ 8.68 (s, 1H), 8.57 (d, J=5.3 Hz, 1H), 8.20 (s, 1H), 7.94 (s, 1H), 7.88-7.84 (m, 1H), 7.35 (t, J=53.9 Hz, 1H), 4.02 (s, 2H), 2.84 (q, J=7.6 Hz, 2H), 1.81 (dt, J=12.7, 6.5 Hz, 1H), 1.42 (qd, J=14.0, 5.5 Hz, 2H), 1.29 (t, J=7.6 Hz, 3H), 1.15 (s, 3H), 0.93 (dd, J=13.5, 6.6 Hz, 6H); LCMS (ESI) m/e 364.2 [(M+H)$^+$, calcd C$_2$H$_{28}$F$_2$N$_3$O, 364.2]; LC/MS retention time (method B): t$_R$=1.48 min.

Example 171

(R)-1-((4-(difluoromethyl)-5'-fluoro-2'-methyl-[2,4'-bipyridin]-5-yl)oxy)-2,4-dimethylpentan-2-amine

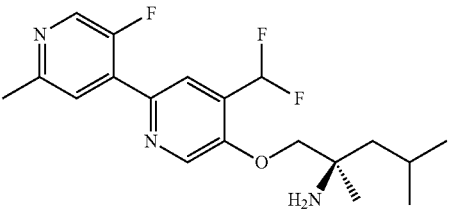 [SMILES: Cc1cc(-c2cc(C(F)F)c(OC[C@](C)(N)CC(C)C)cn2)c(F)cn1]

Prepared as previously described in Example 148 with Example 168 to afford (R)-1-((4-(difluoromethyl)-5'-fluoro-2'-methyl-[2,4'-bipyridin]-5-yl)oxy)-2,4-dimethylpentan-2-amine (1.2 mg, 10%): $^1$H NMR (500 MHz, DMSO-d$_6$) δ 8.74 (s, 1H), 8.55 (d, J=2.9 Hz, 1H), 7.99 (s, 1H), 7.81 (d, J=6.5 Hz, 1H), 7.40 (t, J=53.8 Hz, 1H), 4.15-4.05 (m, 2H), 2.54 (s, 3H), 1.81 (dt, J=12.8, 6.3 Hz, 1H), 1.54-1.39 (m, 2H), 1.19 (s, 3H), 0.95 (d, J=6.6 Hz, 3H), 0.92 (d, J=6.6 Hz, 3H); LCMS (ESI) m/e 351.1 [(M-NH$_2$)+, calcd C$_{19}$H$_{22}$F$_3$N$_2$O, 351.2]; LC/MS retention time (method B): t$_R$=1.80 min.

Example 172

(R)-1-((4-(difluoromethyl)-3'-fluoro-2'-methyl-[2,4'-bipyridin]-5-yl)oxy)-2,4-dimethylpentan-2-amine

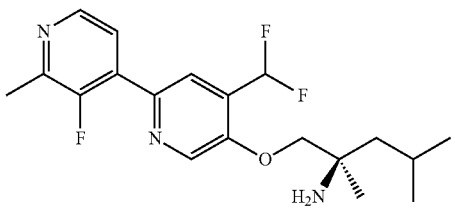 [SMILES: Cc1nccc(-c2cc(C(F)F)c(OC[C@](C)(N)CC(C)C)cn2)c1F]

Prepared as previously described in Example 148 with Example 167 as the starting material to afford (R)-1-((4-(difluoromethyl)-3'-fluoro-2'-methyl-[2,4'-bipyridin]-5-yl)oxy)-2,4-dimethylpentan-2-amine (1.1 mg, 24%): $^1$H NMR (500 MHz, DMSO-d$_6$) δ 8.76 (s, 1H), 8.40 (d, J=5.0 Hz, 1H), 8.02 (s, 1H), 7.77 (t, J=5.5 Hz, 1H), 7.43 (t, J=53.9 Hz, 1H), 4.13 (q, J=9.5 Hz, 2H), 2.54 (d, J=3.3 Hz, 3H), 1.81 (dt, J=12.9, 6.4 Hz, 1H), 1.57-1.41 (m, 2H), 1.22 (s, 3H), 0.95 (d, J=6.6 Hz, 3H), 0.92 (d, J=6.6 Hz, 3H); LCMS (ESI) m/e 351.1 [(M-NH$_2$)+, calcd C$_{19}$H$_{22}$F$_3$N$_2$O, 351.2]; LC/MS retention time (method B): t$_R$=1.79 min.

Example 173

(R)-methyl (5-((2-amino-2,4-dimethylpentyl)oxy)-6-methyl-[2,4'-bipyridin]-2'-yl)carbamate

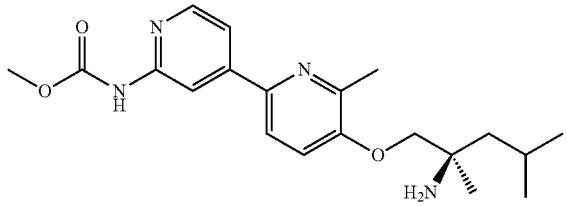 [SMILES: COC(=O)Nc1cc(-c2ccc(OC[C@](C)(N)CC(C)C)c(C)n2)ccn1]

Prepared as previously described in Example 164 using the R-enantiomer of the amino alcohol to afford (R)-methyl (5-((2-amino-2,4-dimethylpentyl)oxy)-6-methyl-[2,4'-bipyridin]-2'-yl)carbamate (26 mg, 0.050 mmol, 26%) as a pale yellow film. $^1$H NMR (400 MHz, MeOH-d$_4$) δ 8.36 (d, J=6.5 Hz, 1H), 8.24 (d, J=1.3 Hz, 1H), 8.05 (m, 2H), 7.58 (d, J=8.5 Hz, 1H), 4.25 (m, 2H), 3.94 (s, 3H), 3.38 (s, 2H), 2.66 (s, 3H), 1.95-1.85 (m, 2H), 1.81-1.71 (m, 1H), 1.55 (s, 3H), 1.09 (d, J=6.5 Hz, 3H), 1.04 (d, J=6.4 Hz, 3H); LCMS (ESI) m/e 373.4 (M+H)$^+$, calcd C$_{20}$H$_{29}$N$_4$O$_3$, 373.2]; LC/MS retention time (method D): t$_R$=1.81 min.

Example 174

(R)-1-((2',6-bis(difluoromethyl)-[2,4'-bipyridin]-5-yl)oxy)-2,4-dimethylpentan-2-amine

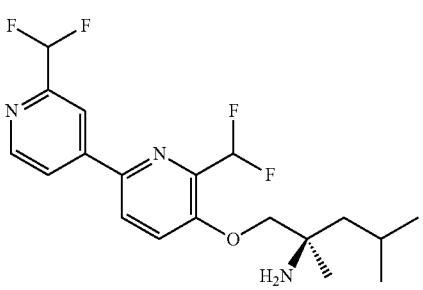 [SMILES: CC(C)C[C@@](C)(N)COc1ccc(-c2ccnc(C(F)F)c2)nc1C(F)F]

Prepared as previously described in Example 123 using the R-enantiomer of the amino alcohol to afford (R)-1-((2',6-bis(difluoromethyl)-[2,4'-bipyridin]-5-yl)oxy)-2,4-dimethylpentan-2-amine (6.6 mg, 0.017 mmol, 15%) as a film. $^1$H NMR (500 MHz, DMSO-d$_6$) δ 8.79 (d, J=5.1 Hz, 1H), 8.40 (d, J=8.8 Hz, 1H), 8.33 (s, 1H), 8.22 (d, J=5.1 Hz, 1H), 7.82 (d, J=8.8 Hz, 1H), 7.25 (t, J=53.5 Hz, 1H), 7.05 (t, J=54.9 Hz, 1H), 3.91 (s, 2H), 3.36 (m 2H), 1.81 (m, 1H), 1.40 (m, 2H), 1.13 (s, 3H) 0.94 (d, J=6.5 Hz, 3H), 0.92 (d, J=6.4 Hz, 3H); LCMS (ESI) m/e 386.4 (M+H)$^+$, calcd C$_{19}$H$_{24}$F$_4$N$_3$O, 386.2]; LC/MS retention time (method D): t$_R$=2.62 min.

Example 175

(R)-1-((2',4-bis(difluoromethyl)-[2,4'-bipyridin]-5-yl)oxy)-2,4-dimethylpentan-2-amine

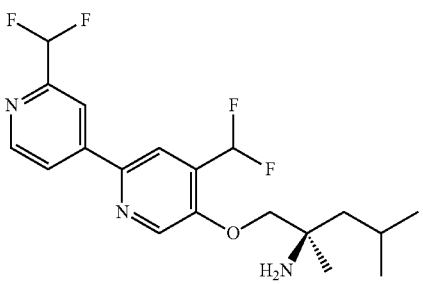 [SMILES: CC(C)C[C@@](C)(N)COc1cnc(-c2ccnc(C(F)F)c2)cc1C(F)F]

Prepared as previously described in Example 124 using the R-enantiomer of the amino alcohol to afford (R)-1-((2',4-bis(difluoromethyl)-[2,4'-bipyridin]-5-yl)oxy)-2,4-dimethylpentan-2-amine (9.3 mg, 0.024 mmol, 21%) as a film. $^1$H NMR (500 MHz, DMSO-d$_6$) δ 8.79 (d, J=5.1 Hz, 1H), 8.71 (s, 1H), 8.37 (s, 1H), 8.32 (s, 1H), 8.25 (d, J=4.8 Hz, 1H), 7.33 (t, J=53.5 Hz, 1H), 7.04 (t, J=54.9 Hz, 1H), 4.01 (s, 2H), 3.32 (m, 2H), 1.81 (m, 1H), 1.40 (m, 2H), 1.13 (s, 3H) 0.94 (d, J=6.5 Hz, 3H), 0.92 (d, J=6.4 Hz, 3H); LCMS (ESI) m/e 386.4 (M+H)$^+$, calcd C$_{19}$H$_{24}$F$_4$N$_3$O, 386.2]; LC/MS retention time (method D): t$_R$=2.66 min.

Example 176

(S)-1-((4-(difluoromethyl)-6-(quinolin-4-yl)pyridin-3-yl)oxy)-2,4-dimethylpentan-2-ol

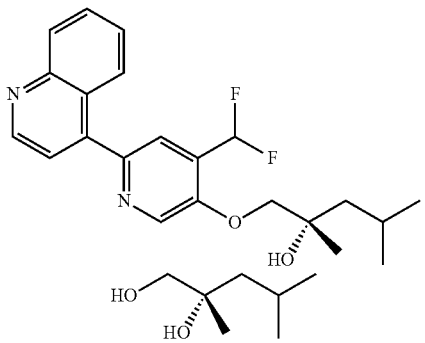

Part A: (S)-2,4-dimethylpentane-1,2-diol

To a 500 mL round-bottomed flask was added AD-MIX-ALPHA (3.60 g, 2.60 mmol) in BuOH (13 mL) and water (13 mL) to give a yellow solution under vigorously stirring. The resulting mixture was stirred at rt for 30 min and then cooled to 0° C. A precipitate appeared and 2,4-dimethylpent-1-ene (0.364 mL, 2.60 mmol) was added in one portion. The resulting mixture was stirred vigorously at 0° C. for 6 h and 3.86 g (30.6 mmol) of sodium sulfite was added. The mixture was allowed to warm to rt and was stirred for 30 min. $CH_2Cl_2$ (40 mL) and water (80 mL) was then added successively and the layers were separated. The aqueous layer was extracted twice with $CH_2Cl_2$. The combined organic phase was dried, filtered, and concentrated to afford (S)-2,4-dimethylpentane-1,2-diol (308 mg, 90%) as a colorless oil: $^1$H NMR (400 MHz, Chloroform-d) δ 3.52-3.38 (m, 2H), 1.85-1.79 (m, 1H), 1.42 (dd, J=6.0, 2.0 Hz, 2H), 1.22 (s, 3H), 0.99 (dd, J=11.7, 6.6 Hz, 6H). Reference: S. J. Leiris et al. *Bioorg. Med. Chem.* 2010, 18, 3481-3493.

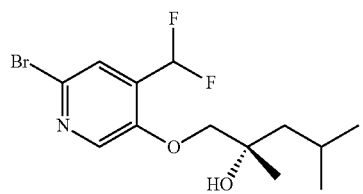 [SMILES: CC(C)C[C@](C)(O)COc1cnc(Br)cc1C(F)F]

Part B: (S)-1-((6-bromo-4-(difluoromethyl)pyridin-3-yl)oxy)-2,4-dimethylpentan-2-ol To a 20 mL pressure bottle was added (S)-2,4-dimethylpentane-1,2-diol (125 mg, 0.946 mmol) and 2-bromo-4-(difluoromethyl)-5-fluoropyridine (214 mg, 0.946 mmol) in tetrahydrofuran (1.3 mL) to give a tan solution. Potassium tert-butoxide (1.229 mL, 1.229 mmol) (1.0 M in THF) was added dropwise under nitrogen. After 5 min stirring at rt, the bottle was sealed and the mixture was stirred at 80° C. for 18 h. The mixture was partitioned between water and EtOAc. The layers were separated. The aqueous layer was extracted with EtOAc. The combined organic solution was washed with brine, dried and concentrated to afford (S)-1-((6-bromo-4-(difluoromethyl)pyridin-3-yl)oxy)-2,4-dimethylpentan-2-ol (300 mg, 94%) as a tan oil. The material was used as is. LCMS (ESI) m/e 338.0 [(M+H)$^+$, calcd $C_{13}H_{19}BrF_2NO_2$, 338.0]; LC/MS retention time (method B): $t_R$=2.30 min.

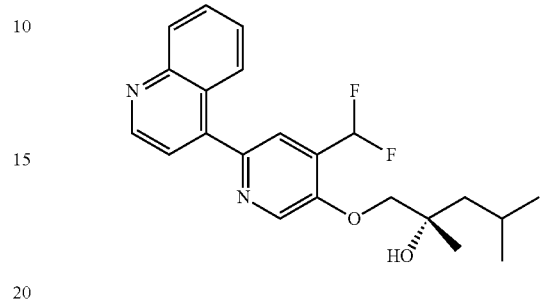

Part C: (S)-1-((4-(difluoromethyl)-6-(quinolin-4-yl)pyridin-3-yl)oxy)-2,4-dimethylpentan-2-ol Prepared as previously described in Example 117 to afford (S)-1-((4-(difluoromethyl)-6-(quinolin-4-yl)pyridin-3-yl)oxy)-2,4-dimethylpentan-2-ol (3.6 mg, 14%): $^1$H NMR (500 MHz, DMSO-d$_6$) δ 9.00 (d, J=4.4 Hz, 1H), 8.80 (s, 1H), 8.18 (d, J=8.4 Hz, 1H), 8.13 (d, J=8.4 Hz, 1H), 7.87 (s, 1H), 7.82 (t, J=7.7 Hz, 1H), 7.69-7.61 (m, 2H), 7.35 (s, 1H), 4.09 (q, J=9.2 Hz, 2H), 1.86 (dt, J=12.7, 6.5 Hz, 1H), 1.50 (d, J=5.9 Hz, 2H), 1.27 (s, 3H), 0.96 (d, J=6.5 Hz, 6H); LCMS (ESI) m/e 387.1 [(M+H)$^+$, calcd $C_{22}H_{25}F_2N_2O_2$, 387.2]; LC/MS retention time (method B): $t_R$=2.06 min.

Example 177

(S)-methyl(4-(difluoromethyl)-5-((2-hydroxy-2,4-dimethylpentyl)oxy)-[2,4'-bipyridin]-2'-yl)carbamate

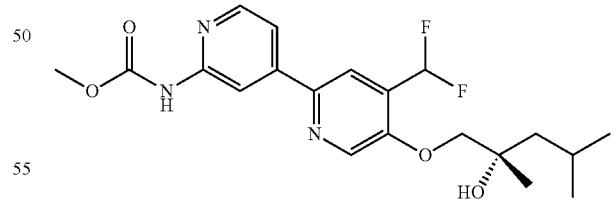

Prepared as previously described in Example 117 with intermediate from Example 176 (1.8 mg, 6.5%): $^1$H NMR (500 MHz, DMSO-d$_6$) δ 8.71 (s, 1H), 8.53 (s, 1H), 8.36 (d, J=5.4 Hz, 1H), 8.07 (s, 1H), 7.77-7.67 (m, 1H), 7.31 (s, 1H), 4.05 (q, J=9.3 Hz, 2H), 3.71 (s, 3H), 1.83 (dt, J=12.6, 6.3 Hz, 1H), 1.47 (d, J=5.9 Hz, 2H), 1.24 (s, 3H), 0.94 (d, J=6.6 Hz, 6H); LCMS (ESI) m/e 410.1 [(M+H)$^+$, calcd $C_{20}H_{26}F_2N_3O_4$, 410.2]; LC/MS retention time (method B): $t_R$=2.07 min.

Example 178

(S)-1-((4-(difluoromethyl)-2'-methyl-[2,4'-bipyridin]-5-yl)oxy)-2,4-dimethylpentan-2-ol

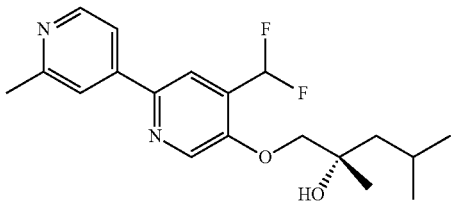 [SMILES: Cc1cc(-c2cc(C(F)F)c(OC[C@@](C)(O)CC(C)C)cn2)ccn1]

Prepared as previously described in Example 117 with intermediate from Example 176 to afford (S)-1-((4-(difluoromethyl)-2'-methyl-[2,4'-bipyridin]-5-yl)oxy)-2,4-dimethylpentan-2-ol (2.2 mg, 7.2%): $^1$H NMR (500 MHz, DMSO-$d_6$) δ 8.69 (s, 1H), 8.54 (d, J=5.3 Hz, 1H), 8.17 (s, 1H), 7.94 (s, 1H), 7.84 (d, J=5.7 Hz, 1H), 7.30 (t, J=54.1 Hz, 1H), 4.04 (q, J=9.2 Hz, 2H), 2.56 (s, 3H), 1.83 (dt, J=12.8, 6.4 Hz, 1H), 1.46 (d, J=5.9 Hz, 2H), 1.24 (s, 3H), 0.94 (dd, J=6.7, 1.6 Hz, 6H); LCMS (ESI) m/e 351.1 [(M+H)$^+$, calcd $C_{19}H_{25}F_2N_2O_2$, 351.2]; LC/MS retention time (method B): $t_R$=1.91 min.

Example 179

(S)-methyl (5-((2-amino-2-(fluoromethyl)-4-methylpentyl)oxy)-6-(difluoromethyl)-[2,4'-bipyridin]-2'-yl)carbamate

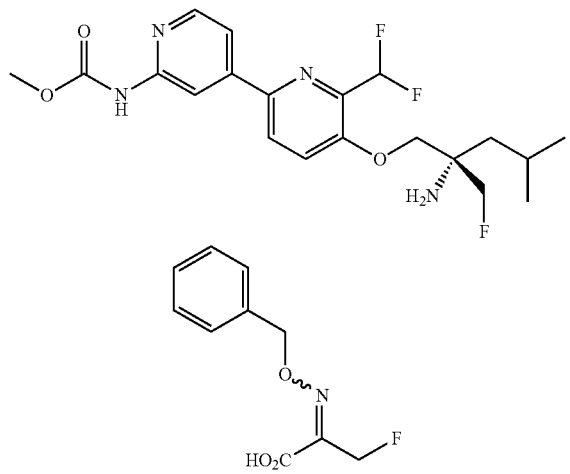

Part A:
(E/Z)-2-((benzyloxy)imino)-3-fluoropropanoic acid

To a 250 mL round-bottomed flask was added O-benzylhydroxylamine (1.5338 g, 12.45 mmol) and sodium 3-fluoro-2-oxopropanoate (1.595 g, 12.45 mmol) in ethanol (36 mL) to give a white suspension. The mixture was heated at 80° C. for 15 h. The ethanol was stripped off. The off-white solid was dissolved in EtOAc and 15 mL 1N HCl. The layer was separated. The aqueous layer was extracted three time with EtOAc. The combined organic solution was dried and concentrated to afford (E/Z)-2-((benzyloxy)imino)-3-fluoropropanoic acid (2.51 g, 96%) as a tan solid. LCMS indicated likely E/Z isomers (about ¼ ratio). The material was used as is.

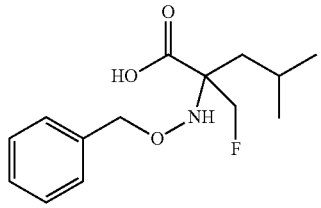 [SMILES: CC(C)CC(CF)(NOCc1ccccc1)C(=O)O]

Part B: 2-((benzyloxy)amino)-2-(fluoromethyl)-4-methylpent-4-enoic acid

To a 250 mL round-bottomed flask was added (E/Z)-2-((benzyloxy)imino)-3-fluoropropanoic acid (2.32 g, 10.99 mmol) and 3-bromo-2-methylpropene (4.43 mL, 43.9 mmol) in THF (10.00 mL) and aqueous NH$_4$Cl (50 mL) to give a tan solution. Zinc (3.59 g, 54.9 mmol) was added portionwise. The mixture was stirred at rt for 30 min. The mixture was diluted with water and EtOAc. The layers were separated. The aqueous layer was extracted twice with EtOAc. The combined organic layers were washed with brine, dried and concentrated to a dense semi-solid. First silica gel chromatography up to 50% EtOAc/hexane did not purify the desired product and the 2nd silica gel chromatography up to 10% MeOH/CH$_2$Cl$_2$ (Rf~0.3) afforded 2-((benzyloxy)amino)-2-(fluoromethyl)-4-methylpent-4-enoic acid (2.33 g, 76%) as a white solid: $^1$H NMR (400 MHz, Chloroform-d) δ 7.44-7.31 (m, 5H), 6.94 (s, 1H), 4.98 (p, J=1.6 Hz, 1H), 4.88 (d, J=2.3 Hz, 1H), 4.87-4.61 (m, 4H), 2.40 (d, J=1.2 Hz, 2H), 1.77 (s, 3H); $^{19}$F NMR (376 MHz, Chloroform-d) δ −233.34; LCMS (ESI) m/e 290.1 [(M+Na)$^+$, calcd $C_{14}H_{18}FNNaO_3$, 290.1]; LC/MS retention time (method B): $t_R$=2.04 min.

The racmeic compound (2 g) was separated by chiral super critical fluid chromatography (Column: ChiralPak AD-H, 30×250 mm, 5 μm); Mobile Phase: 10% EtOH/90% CO$_2$ to give the two enantiomers.

Analytical super critical fluid chromatography conditions: Column: ChiralPak AD-H, 4.6×250 mm, 5 μm; BPR pressure: 100 bars; Temperature: 35° C.; Flow rate: 2.0 mL/min; Mobile Phase: 20% EtOH/80% CO$_2$; Detector Wavelength: UV 205 nm.

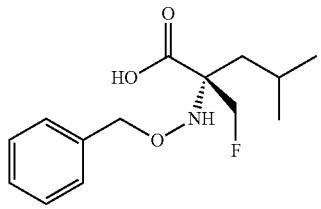 [SMILES: CC(C)C[C@](CF)(NOCc1ccccc1)C(=O)O]

Enantiomer 1 (0.9 g, 90% recovery, e.e. %>99.9%, $α_D$=+7.87° (CHCl$_3$, 3.05 mg/ml)): (S)-benzyl 4-methyl-4-(2-methylallyl)-1,2,3-oxathiazolidine-3-carboxylate 2,2-dioxide HPLC retention time=3.00 min.

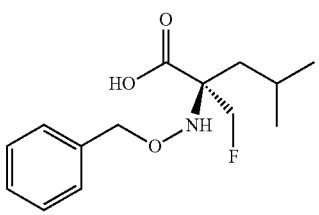 [SMILES: CC(C)C[C@@](CF)(NOCc1ccccc1)C(=O)O]

Enantiomer 2 (0.9 g, 90% recovery, e.e. %=92.6%, α$_D$=−9.20° (CHCl$_3$, 3.15 mg/ml)): (R)-benzyl 4-methyl-4-(2-methylallyl)-1,2,3-oxathiazolidine-3-carboxylate 2,2-dioxide HPLC retention time=3.52 min.

The absolute structures were assigned based on the comparison of the optical rotations of the free amino alcohol below with the des-F analogs, and were further proved by the biology data of the final examples (analogs made from the S-enantiomer (1) were more potent than analogs made from the R-enantiomer (2) as was seen with the other examples).

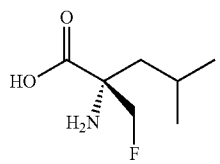

Part C:
(S)-2-amino-2-(fluoromethyl)-4-methylpentanoic acid

To a 1 L round-bottomed flask was added (S)-2-((benzyloxy)amino)-2-(fluoromethyl)-4-methylpent-4-enoic acid (0.89 g, 3.33 mmol) in MeOH (30 mL) to give a colorless solution. Pd—C (0.709 g, 0.666 mmol) was added. The mixture was stirred under hydrogen (balloon) for 16 h. LCMS showed complete disappearance of starting material. The mixture was filtered and rinsed with MeOH. The filtered clear solution was concentrated to afford (S)-2-amino-2-(fluoromethyl)-4-methylpentanoic acid (510 mg, 94%) as a white solid: $^1$H NMR (400 MHz, Methanol-d4) δ 4.62 (ddd, J=62.0, 47.4, 10.0 Hz, 2H), 1.94-1.66 (m, 3H), 1.01 (dd, J=6.3, 3.9 Hz, 6H); $^{19}$F NMR (376 MHz, Methanol-d4) δ −229.19; α$_D$=+21.61° (MeOH, 2.85 mg/mL).

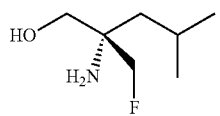

Part D: (S)-2-amino-2-(fluoromethyl)-4-methylpentan-1-ol

To a 250 mL round-bottomed flask was added (S)-2-amino-2-(fluoromethyl)-4-methylpentanoic acid (496 mg, 3.04 mmol) in tetrahydrofuran (15 mL) to give a colorless solution. BH$_3$.THF (12.16 mL, 12.16 mmol) was added under nitrogen. The mixture was stirred at rt over the weekend for 66 h. TLC showed (10% MeOH/CH2Cl$_2$, I$_2$ stain) a new peak above the baseline. The reaction was quenched with MeOH. Volatiles were removed. The residue was treated with 30 mL 1N HCl and heated at 50° C. for 1 h. After cooling down, the mixture was then basified with 40 mL 1N NaOH and extracted three times with CH$_2$Cl$_2$. The combined organic solution was dried and concentrated to give (S)-2-amino-2-(fluoromethyl)-4-methylpentan-1-ol (377 mg, 83%) as a colorless oil: $^1$H NMR (400 MHz, Chloroform-d) δ 4.31 (dd, J=47.7, 0.9 Hz, 2H), 3.53 (dd, J=10.8, 1.3 Hz, 1H), 3.42 (dd, J=10.8, 3.0 Hz, 1H), 1.79 (m, 4H), 1.44-1.32 (m, 2H), 1.00 (d, J=1.8 Hz, 3H), 0.99 (d, J=1.8 Hz, 3H); $^9$F NMR (376 MHz, Chloroform-d) δ −227.90; α$_D$=−1.00° (CHCl$_3$, 2.40 mg/mL).

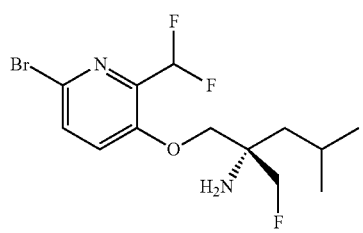 [SMILES: CC(C)C[C@@](N)(CF)COc1ccc(Br)nc1C(F)F]

Part E: (S)-1-((6-bromo-2-(difluoromethyl)pyridin-3-yl)oxy)-2-(fluoromethyl)-4-methylpentan-2-amine To a 2 mL pressure bottle was added (S)-2-amino-2-(fluoromethyl)-4-methylpentan-1-ol (65.7 mg, 0.440 mmol) and 6-bromo-2-(difluoromethyl)-3-fluoropyridine (100 mg, 0.440 mmol) in tetrahydrofuran (0.6 mL) to give a colorless solution. Potassium tert-butoxide (0.528 mL, 0.528 mmol) (1.0 M in THF) was added under nitrogen. The bottle was sealed and the mixture was stirred at 70° C. for 16 h. The mixture was partitioned between water and EtOAc. The layers were separated. The aqueous layer was extracted with EtOAc. The combined organic solution was washed with brine, dried and concentrated to a tan oil (140 mg, 90%): $^1$H NMR (400 MHz, Chloroform-d) δ 7.56 (dt, J=8.7, 1.0 Hz, 1H), 7.26 (d, J=8.8 Hz, 1H), 6.68 (t, J=53.8 Hz, 1H), 4.50-4.25 (m, 2H), 3.93 (ddd, J=32.5, 8.5, 1.8 Hz, 2H), 1.87 (dq, J=12.7, 6.3 Hz, 1H), 1.52-1.44 (m, 2H), 1.03 (d, J=6.7 Hz, 3H), 1.00 (d, J=6.7 Hz, 3H); $^{19}$F NMR (376 MHz, Chloroform-d) δ −117.34, −225.58; LCMS (ESI) m/e 355.1 [(M+H)$^+$, calcd C$_{13}$H$_9$BrF$_3$N$_2$O, 355.1]; LC/MS retention time (method B): t$_R$=1.69 min.

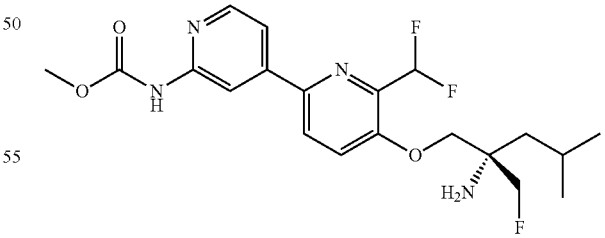

Part F. (S)-methyl(5-((2-amino-2-(fluoromethyl)-4-methylpentyl)oxy)-6-(difluoromethyl)-[2,4'-bipyridin]-2'-yl)carbamate Prepared as previously described for Example 117 but at 80° C. for 5 h to afford the titled product (9.7 mg, 36%): $^1$H NMR (500 MHz, DMSO-d$_6$) δ 8.50 (s, 1H), 8.36 (d, J=5.2

Hz, 1H), 8.18 (d, J=8.8 Hz, 1H), 7.83 (d, J=8.8 Hz, 1H), 7.67 (d, J=5.3 Hz, 1H), 7.23 (t, J=53.5 Hz, 1H), 4.33 (dq, J=47.8, 8.9 Hz, 2H), 4.07-3.92 (m, 2H), 3.71 (s, 3H), 1.89 (dd, J=12.7, 6.5 Hz, 1H), 1.50-1.31 (m, 2H), 0.96 (d, J=6.6 Hz, 3H), 0.93 (d, J=6.6 Hz, 3H); LCMS (ESI) m/e 427.3 [(M+H)+, calcd $C_{20}H_{26}F_3N_4O_3$, 427.2]; LC/MS retention time (method B): $t_R$=1.66 min.

Example 180

(R)-methyl (5-((2-amino-2-(fluoromethyl)-4-methylpentyl)oxy)-6-(difluoromethyl)-[2,4'-bipyridin]-2'-yl)carbamate

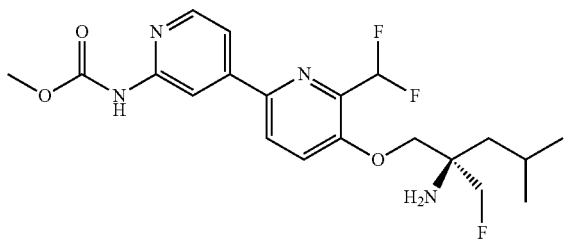 [SMILES: COC(=O)Nc1cc(-c2ccc(OC[C@@](N)(CF)CC(C)C)c(C(F)F)n2)ccn1]

Part A: (R)-2-amino-2-(fluoromethyl)-4-methylpentanoic acid

Prepared as previously described in Example 179, Part C to afford (R)-2-amino-2-(fluoromethyl)-4-methylpentanoic acid (512 mg, 94%) as a white solid: 1H NMR (400 MHz, Methanol-$d_4$) δ 4.62 (ddd, J=62.0, 47.4, 10.0 Hz, 2H), 1.94-1.66 (m, 3H), 1.01 (dd, J=6.3, 3.9 Hz, 6H); 19F NMR (376 MHz, Methanol-d4) δ -229.19; $α_D$=-20.29° (MeOH, 2.70 mg/mL).

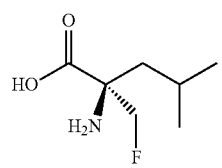

Part B: (R)-2-amino-2-(fluoromethyl)-4-methylpentan-1-ol

Prepared as previously described in Example 179, Part D to afford (R)-2-amino-2-(fluoromethyl)-4-methylpentan-1-ol (362 mg, 80%) as a colorless oil: 1H NMR (400 MHz, Methanol-$d_4$) δ 4.31 (d, J=47.7 Hz, 2H), 3.53 (dd, J=10.8, 1.3 Hz, 1H), 3.42 (dd, J=10.8, 3.0 Hz, 1H), 1.79 (tt, J=12.8, 6.4 Hz, 4H), 1.38 (td, J=5.6, 1.8 Hz, 2H), 1.00 (d, J=1.8 Hz, 3H), 0.99 (d, J=1.9 Hz, 3H); 19F NMR (376 MHz, Chloroform-d) δ -227.87; $α_D$=+1.110 (CHCl3, 2.70 mg/mL).

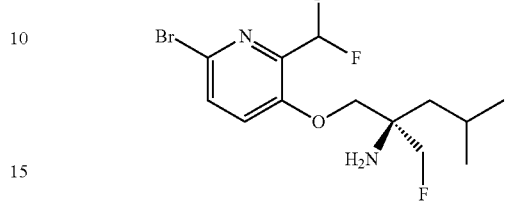

Part C: (R)-1-((6-bromo-2-(difluoromethyl)pyridin-3-yl)oxy)-2-(fluoromethyl)-4-methylpentan-2-amine Prepared as previously described in Example 179, Part E to afford (R)-1-((6-bromo-2-(difluoromethyl)pyridin-3-yl)oxy)-2-(fluoromethyl)-4-methylpentan-2-amine (145 mg, 96%) as a colorless oil: 1H NMR (400 MHz, Methanol-$d_4$) δ 7.56 (dt, J=8.6, 1.0 Hz, 1H), 7.26 (d, J=8.7 Hz, 1H), 6.69 (t, J=53.8 Hz, 1H), 4.49-4.26 (m, 2H), 3.93 (ddd, J=32.8, 8.6, 1.8 Hz, 2H), 1.88 (dp, J=12.8, 6.4 Hz, 1H), 1.56-1.41 (m, 4H), 1.03 (d, J=6.6 Hz, 3H), 1.00 (d, J=6.6 Hz, 3H); 19F NMR (376 MHz, Chloroform-d) δ -117.50, -225.55; LCMS (ESI) m/e 355.1 [(M+H)+, calcd $C_{13}H_9BrF_3N_2O$, 355.1]; LC/MS retention time (method B): $t_R$=1.68 min.

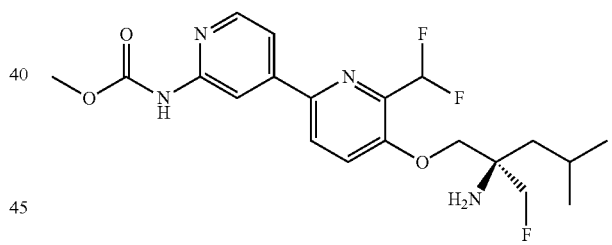

Part D: (R)-methyl (5-((2-amino-2-(fluoromethyl)-4-methylpentyl)oxy)-6-(difluoromethyl)-[2,4'-bipyridin]-2'-yl)carbamate Prepared as previously described In Example 179 to afford (R)-methyl (5-((2-amino-2-(fluoromethyl)-4-methylpentyl)oxy)-6-(difluoromethyl)-[2,4'-bipyridin]-2'-yl)carbamate (8.8 mg, 33%): 1H NMR (500 MHz, DMSO-$d_6$) δ 8.50 (s, 1H), 8.36 (d, J=5.4 Hz, 1H), 8.18 (d, J=8.7 Hz, 1H), 7.83 (d, J=8.8 Hz, 1H), 7.67 (d, J=5.2 Hz, 1H), 7.23 (t, J=53.5 Hz, 1H), 4.33 (dq, J=47.7, 9.0 Hz, 2H), 4.11-3.93 (m, 2H), 3.71 (s, 3H), 1.89 (p, J=6.4 Hz, 1H), 1.50-1.32 (m, 2H), 0.96 (d, J=6.7 Hz, 3H), 0.93 (d, J=6.6 Hz, 3H); LCMS (ESI) m/e 427.3 [(M+H)+, calcd $C_2H_{26}F_3N_4O_3$, 427.2]; LC/MS retention time (method B): $t_R$=1.62 min.

Example 181

(S)-methyl (5-((2-amino-2-(fluoromethyl)-4-methylpentyl)oxy)-4-(difluoromethyl)-[2,4'-bipyridin]-2'-yl)carbamate

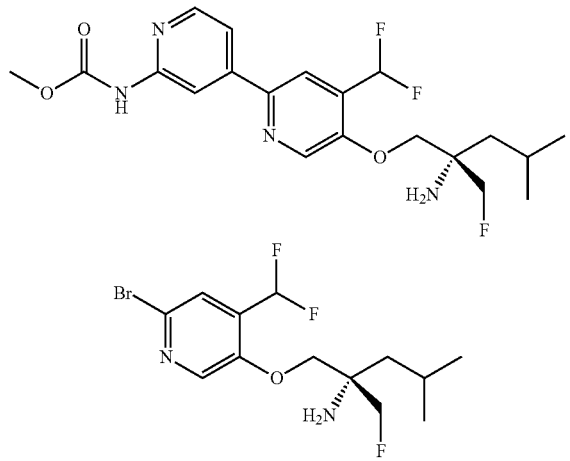

Part A: (S)-1-((6-bromo-4-(difluoromethyl)pyridin-3-yl)oxy)-2-(fluoromethyl)-4-methylpentan-2-amine Prepared as previously described in Example 19 to afford (S)-1-((6-bromo-4-(difluoromethyl)pyridin-3-yl)oxy)-2-(fluoromethyl)-4-methylpentan-2-amine (157 mg, 98%) as a tan oil: $^1$H NMR (400 MHz, Methanol-$d_4$) δ 8.16 (s, 1H), 7.62 (s, 1H), 6.80 (t, J=54.4 Hz, 1H), 4.35 (ddd, J=47.4, 36.8, 9.0 Hz, 2H), 4.01 (qd, J=8.7, 1.7 Hz, 2H), 1.87 (dp, J=12.9, 6.4 Hz, 1H), 1.48-1.43 (m, 2H), 1.03 (d, J=6.6 Hz, 3H), 1.00 (d, J=6.6 Hz, 3H); $^{19}$F NMR (376 MHz, Chloroform-d) δ −119.66, −226.04; LCMS (ESI) m/e 355.1 [(M+H)$^+$, calcd $C_{13}H_{19}BrF_3N_2O$, 355.1]; LC/MS retention time (method B): $t_R$=1.78 min.

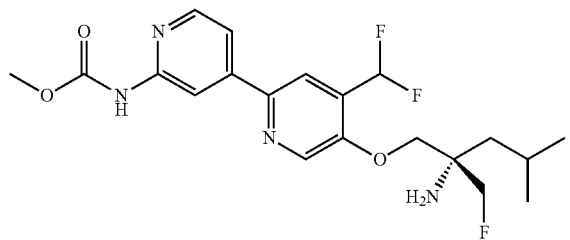 [SMILES: COC(=O)Nc1cc(-c2cc(C(F)F)c(OC[C@](N)(CF)CC(C)C)cn2)ccn1]

Part B: (S)-methyl (5-((2-amino-2-(fluoromethyl)-4-methylpentyl)oxy)-4-(difluoromethyl)-[2,4'-bipyridin]-2'-yl)carbamate Prepared as previously described for Example 179 to afford the titled product (4.0 mg, 17%): $^1$H NMR (500 MHz, DMSO-$d_6$) δ 8.73 (s, 1H), 8.53 (s, 1H), 8.36 (d, J=5.2 Hz, 1H), 8.08 (s, 1H), 7.70 (d, J=5.3 Hz, 1H), 7.35 (t, J=53.9 Hz, 1H), 4.45-4.23 (m, 2H), 4.20-4.05 (m, 2H), 3.71 (s, 3H), 1.90 (p, J=6.5 Hz, 1H), 1.40 (qd, J=13.9, 5.7 Hz, 2H), 0.96 (d, J=6.6 Hz, 3H), 0.94 (d, J=6.6 Hz, 3H); LCMS (ESI) m/e 427.3 [(M+H)$^+$, calcd $C_2H_{26}F_3N_4O_3$, 427.2]; LC/MS retention time (method B): $t_R$=1.67 min.

Example 182

(R)-methyl (5-((2-amino-2-(fluoromethyl)-4-methylpentyl)oxy)-4-(difluoromethyl)-[2,4'-bipyridin]-2'-yl)carbamate

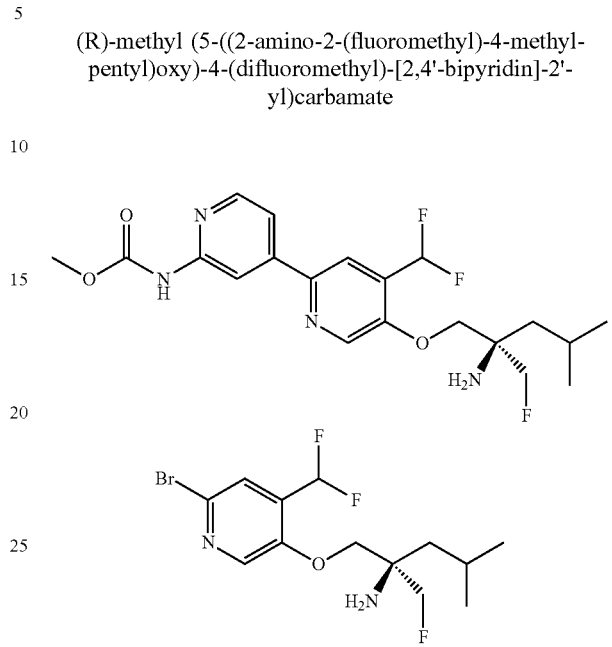

Part A: (R)-1-((6-bromo-4-(difluoromethyl)pyridin-3-yl)oxy)-2-(fluoromethyl)-4-methylpentan-2-amine Prepared as previously described in Example 19 to afford (R)-1-((6-bromo-4-(difluoromethyl)pyridin-3-yl)oxy)-2-(fluoromethyl)-4-methylpentan-2-amine (163 mg, 100%) as a tan oil: $^1$H NMR (400 MHz, Methanol-$d_4$) δ 8.17 (s, 1H), 7.62 (s, 1H), 6.80 (t, J=54.4 Hz, 1H), 4.35 (ddd, J=47.5, 36.9, 9.0 Hz, 2H), 4.01 (qd, J=8.7, 1.7 Hz, 2H), 1.87 (dp, J=12.8, 6.4 Hz, 1H), 1.54-1.43 (m, 4H), 1.03 (d, J=6.6 Hz, 3H), 1.00 (d, J=6.6 Hz, 3H); $^{19}$F NMR (376 MHz, Chloroform-d) δ −119.62, −226.06; LCMS (ESI) m/e 355.1 [(M+H)$^+$, calcd $C_{13}H_9BrF_3N_2O$, 355.1]; LC/MS retention time (method B): $t_R$=1.79 min.

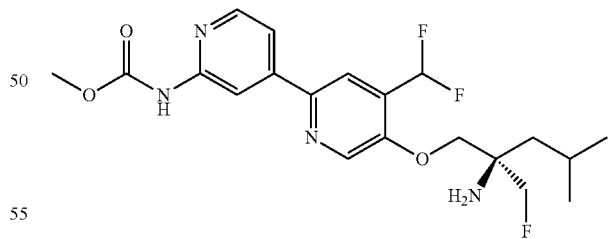

Part B: (R)-methyl (5-((2-amino-2-(fluoromethyl)-4-methylpentyl)oxy)-4-(difluoromethyl)-[2,4'-bipyridin]-2'-yl)carbamate Prepared as previously described for Example 179 to afford (R)-methyl (5-((2-amino-2-(fluoromethyl)-4-methylpentyl)oxy)-4-(difluoromethyl)-[2,4'-bipyridin]-2'-yl)carbamate (3.4 mg, 13%): $^1$H NMR (500 MHz, DMSO-$d_6$) δ 8.73 (s, 1H), 8.53 (s, 1H), 8.36 (d, J=5.2 Hz, 1H), 8.08 (s, 1H), 7.70 (d, J=5.3 Hz, 1H), 7.35 (t, J=53.9 Hz, 1H), 4.43-4.24 (m, 2H), 4.20-4.04 (m, 2H), 3.71 (s, 3H), 1.90 (dt, J=12.6, 6.2 Hz, 1H), 1.40 (qd, J=14.4, 5.7 Hz, 2H), 0.96 (d, J=6.6 Hz, 3H), 0.94 (d, J=6.7 Hz, 3H); LCMS (ESI) m/e 427.3 [(M+H)$^+$, calcd C$_2$H$_{26}$F$_3$N$_4$O$_3$, 427.2]; LC/MS retention time (method B): t$_R$=1.65 min.

Example 183

(S)-1-((2',6-bis(difluoromethyl)-[2,4'-bipyridin]-5-yl)oxy)-2-(fluoromethyl)-4-methylpentan-2-amine

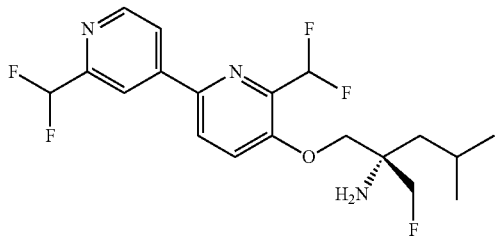 [SMILES: CC(C)C[C@@](N)(CF)COc1ccc(-c2ccnc(C(F)F)c2)nc1C(F)F]

Prepared as previously described for Example 179 but for 3 h to afford (S)-1-((2',6-bis(difluoromethyl)-[2,4'-bipyridin]-5-yl)oxy)-2-(fluoromethyl)-4-methylpentan-2-amine (10 mg, 28%): $^1$H NMR (500 MHz, DMSO-d$_6$) δ 8.80 (d, J=5.1 Hz, 1H), 8.41 (d, J=8.8 Hz, 1H), 8.33 (s, 1H), 8.22 (d, J=5.2 Hz, 1H), 7.88 (d, J=8.9 Hz, 1H), 7.39-7.14 (m, 1H), 7.00 (d, J=54.8 Hz, 1H), 4.43-4.23 (m, 2H), 4.10-3.96 (m, 2H), 1.90 (dt, J=12.8, 6.4 Hz, 1H), 1.49-1.32 (m, 2H), 0.96 (d, J=6.6 Hz, 3H), 0.93 (d, J=6.5 Hz, 3H); LCMS (ESI) m/e 404.3 [(M+H)$^+$, calcd C$_{19}$H$_{23}$F$_5$N$_3$O, 404.2]; LC/MS retention time (method B): t$_R$=1.90 min.

Example 184

(S)-1-((2',4-bis(difluoromethyl)-[2,4'-bipyridin]-5-yl)oxy)-2-(fluoromethyl)-4-methylpentan-2-amine

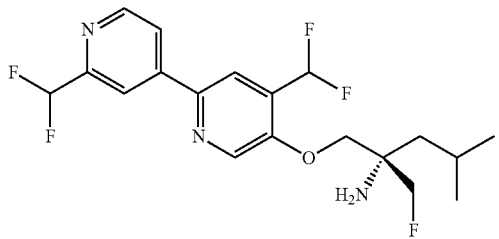 [SMILES: CC(C)C[C@@](N)(CF)COc1cnc(-c2ccnc(C(F)F)c2)cc1C(F)F]

Prepared as previously described for Example 179 but for 3 h to afford (S)-1-((2',4-bis(difluoromethyl)-[2,4'-bipyridin]-5-yl)oxy)-2-(fluoromethyl)-4-methylpentan-2-amine (15.1 mg, 45%): $^1$H NMR (500 MHz, DMSO-d$_6$) δ 8.79 (d, J=5.3 Hz, 1H), 8.76 (s, 1H), 8.37 (s, 1H), 8.33 (s, 1H), 8.26 (d, J=5.2 Hz, 1H), 7.35 (t, J=53.8 Hz, 1H), 7.05 (t, J=54.9 Hz, 1H), 4.43-4.25 (m, 2H), 4.21-4.04 (m, 2H), 1.90 (dt, J=12.8, 6.4 Hz, 1H), 1.48-1.33 (m, 2H), 0.96 (d, J=6.6 Hz, 3H), 0.94 (d, J=6.6 Hz, 3H); LCMS (ESI) m/e 404.3 [(M+H)$^+$, calcd C$_{19}$H$_{23}$F$_5$N$_3$O, 404.2]; LC/MS retention time (method B): t$_R$=1.86 min.

Example 185

(R)-1-((2',6-bis(difluoromethyl)-[2,4'-bipyridin]-5-yl)oxy)-2-(fluoromethyl)-4-methylpentan-2-amine

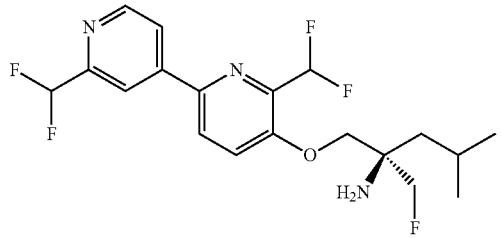 [SMILES: CC(C)C[C@](N)(CF)COc1ccc(-c2ccnc(C(F)F)c2)nc1C(F)F]

Prepared as previously described for Example 179 but for 3 h to afford (R)-1-((2',6-bis(difluoromethyl)-[2,4'-bipyridin]-5-yl)oxy)-2-(fluoromethyl)-4-methylpentan-2-amine (10 mg, 28%): $^1$H NMR (500 MHz, DMSO-d$_6$) δ 8.80 (d, J=5.1 Hz, 1H), 8.41 (d, J=8.8 Hz, 1H), 8.33 (s, 1H), 8.22 (d, J=5.2 Hz, 1H), 7.87 (d, J=8.8 Hz, 1H), 7.40-7.15 (m, 1H), 6.99 (d, J=54.9 Hz, 1H), 4.44-4.23 (m, 2H), 4.11-3.95 (m, 2H), 1.90 (dt, J=12.7, 6.3 Hz, 1H), 1.49-1.32 (m, 2H), 0.96 (d, J=6.7 Hz, 3H), 0.93 (d, J=6.6 Hz, 3H); LCMS (ESI) m/e 404.3 [(M+H)$^+$, calcd C$_{19}$H$_{23}$F$_5$N$_3$O, 404.2]; LC/MS retention time (method B): t$_R$=1.87 min.

Example 186

(R)-1-((2',4-bis(difluoromethyl)-[2,4'-bipyridin]-5-yl)oxy)-2-(fluoromethyl)-4-methylpentan-2-amine

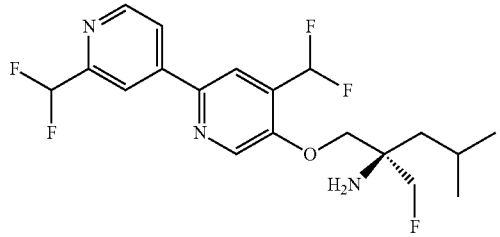 [SMILES: CC(C)C[C@](N)(CF)COc1cnc(-c2ccnc(C(F)F)c2)cc1C(F)F]

Prepared as previously described for Example 179 to afford (R)-1-((2',4-bis(difluoromethyl)-[2,4'-bipyridin]-5-yl)oxy)-2-(fluoromethyl)-4-methylpentan-2-amine (7.7 mg, 16%): $^1$H NMR (500 MHz, DMSO-d$_6$) δ 8.79 (d, J=5.1 Hz, 1H), 8.76 (s, 1H), 8.37 (s, 1H), 8.33 (s, 1H), 8.26 (d, J=5.3 Hz, 1H), 7.35 (t, J=53.8 Hz, 1H), 7.05 (t, J=54.8 Hz, 1H), 4.45-4.24 (m, 2H), 4.21-4.03 (m, 2H), 1.90 (p, J=6.4 Hz, 1H), 1.50-1.33 (m, 2H), 0.97 (d, J=6.6 Hz, 3H), 0.94 (d, J=6.6 Hz, 3H); LCMS (ESI) m/e 404.3 [(M+H)$^+$, calcd C$_{19}$H$_{23}$F$_5$N$_3$O, 404.2]; LC/MS retention time (method B): t$_R$=1.87 min.

Example 187

(S)-1-((4-(difluoromethyl)-2'-methyl-[2,4'-bipyridin]-5-yl)oxy)-2-(fluoromethyl)-4-methylpentan-2-amine

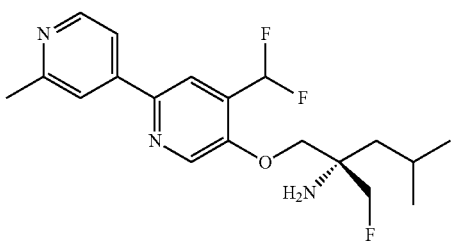 [SMILES: Cc1cc(-c2cc(C(F)F)c(OC[C@](N)(CF)CC(C)C)cn2)ccn1]

Prepared as previously described for Example 179 to afford (S)-1-((4-(difluoromethyl)-2'-methyl-[2,4'-bipyridin]-5-yl)oxy)-2-(fluoromethyl)-4-methylpentan-2-amine (16.8 mg, 50%): $^1$H NMR (500 MHz, DMSO-$d_6$) δ 8.71 (s, 1H), 8.54 (d, J=5.4 Hz, 1H), 8.19 (s, 1H), 7.94 (s, 1H), 7.84 (d, J=5.2 Hz, 1H), 7.34 (t, J=53.9 Hz, 1H), 4.42-4.25 (m, 2H), 4.18-4.03 (m, 2H), 2.56 (s, 3H), 1.90 (dt, J=13.1, 6.5 Hz, 1H), 1.40 (qd, J=14.3, 5.7 Hz, 2H), 0.96 (d, J=6.6 Hz, 3H), 0.94 (d, J=6.7 Hz, 3H); LCMS (ESI) m/e 368.3 [(M+H)$^+$, calcd $C_{19}H_{25}F_3N_3O$, 368.2]; LC/MS retention time (method B): $t_R$=1.39 min.

Example 188

(R)-1-((4-(difluoromethyl)-2'-methyl-[2,4'-bipyridin]-5-yl)oxy)-2-(fluoromethyl)-4-methylpentan-2-amine

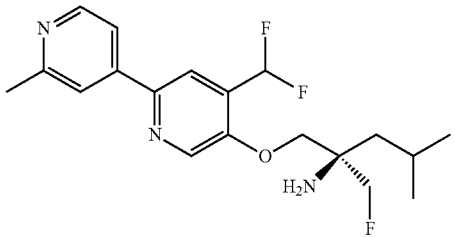 [SMILES: Cc1cc(-c2cc(C(F)F)c(OC[C@@](N)(CF)CC(C)C)cn2)ccn1]

Prepared as previously described for Example 179 to afford (R)-1-((4-(difluoromethyl)-2'-methyl-[2,4'-bipyridin]-5-yl)oxy)-2-(fluoromethyl)-4-methylpentan-2-amine (20.5 mg, 59%): $^1$H NMR (500 MHz, DMSO-$d_6$) δ 8.71 (s, 1H), 8.54 (d, J=5.4 Hz, 1H), 8.19 (s, 1H), 7.94 (s, 1H), 7.84 (d, J=5.2 Hz, 1H), 7.34 (t, J=53.9 Hz, 1H), 4.44-4.24 (m, 2H), 4.18-4.02 (m, 2H), 2.56 (s, 3H), 1.90 (dt, J=12.9, 6.3 Hz, 1H), 1.40 (qd, J=14.2, 5.8 Hz, 2H), 0.96 (d, J=6.6 Hz, 3H), 0.94 (d, J=6.7 Hz, 3H); LCMS (ESI) m/e 368.3 [(M+H)$^+$, calcd $C_{19}H_{25}F_3N_3O$, 368.2]; LC/MS retention time (method B): $t_R$=1.47 min.

Example 189

(S)—N-(4-(4-((2-amino-4-methylpentyl)oxy)-3-fluorophenyl)pyridin-2-yl)acetamide

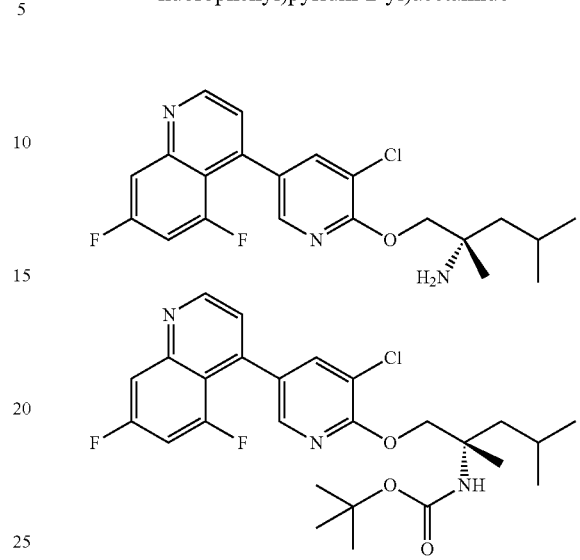

Part A: (S)-tert-butyl(1-((3-chloro-5-(5,7-difluoroquinolin-4-yl)pyridin-2-yl)oxy)-2,4-dimethylpentan-2-yl)carbamate Prepared as described in Example 77. Obtained (S)-tert-butyl (1-((3-chloro-5-(5,7-difluoroquinolin-4-yl)pyridin-2-yl)oxy)-2,4-dimethylpentan-2-yl)carbamate (33.4 mg, 48%). LCMS (ESI) m/e 506.0 [(M+H)$^+$, calcd $C_{26}H_{31}F_2N_3Cl_1O_3$, 506.2]; LC/MS retention time (method B): $t_R$=2.48 min.

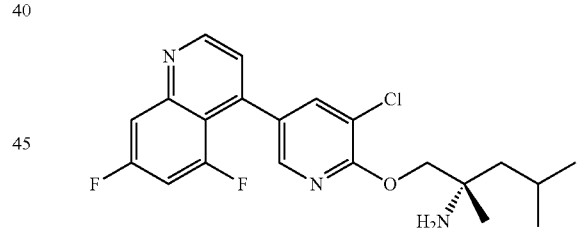

Part B: (S)—N-(4-(4-((2-amino-4-methylpentyl)oxy)-3-fluorophenyl)pyridin-2-yl)acetamide TFA deprotection was carried out as described in Example 32. Obtained (S)—N-(4-(4-((2-amino-4-methylpentyl)oxy)-3-fluorophenyl)pyridin-2-yl)acetamide (27 mg, 100%) as a colorless solid. $^1$H NMR (500 MHz, DMSO-$d_6$) δ 10.53 (s, 1H), 8.33 (d, J=4.9 Hz, 2H), 7.61 (dd, J=12.5, 2.2 Hz, 1H), 7.52 (dd, J=8.5, 2.2 Hz, 1H), 7.43-7.37 (m, 1H), 7.32 (t, J=8.7 Hz, 1H), 3.97 (dd, J=9.5, 4.9 Hz, 1H), 3.90 (dd, J=9.5, 6.5 Hz, 1H), 3.12 (dt, J=11.9, 5.4 Hz, 1H), 2.12 (s, 3H), 1.81 (dq, J=13.0, 6.5 Hz, 1H), 1.33 (ddd, J=13.5, 8.5, 5.0 Hz, 1H), 1.26 (ddd, J=13.5, 8.5, 5.5 Hz, 1H), 0.92 (d, J=6.6 Hz, 3H), 0.88 (d, J=6.5 Hz, 3H); LCMS (ESI) m/e 406.0 [(M+H)$^+$, calcd $C_{21}H_{23}F_2N_3Cl_1O_1$, 406.1]; LC/MS retention time (method B): $t_R$=2.03 min.

Example 190

(S)-1-((3-chloro-5-(7-fluoroquinolin-4-yl)pyridin-2-yl)oxy)-2,4-dimethylpentan-2-amine

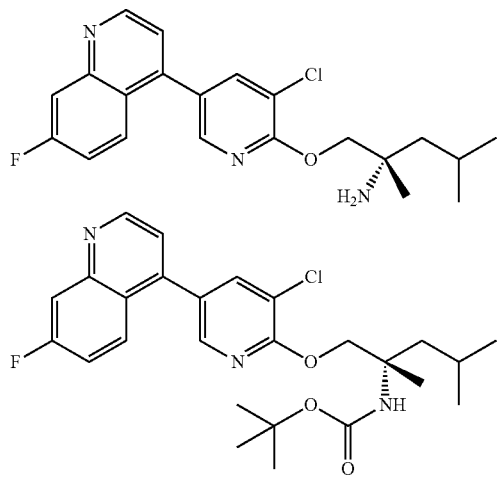

Part A: (S)-tert-butyl (1-((3-chloro-5-(7-fluoroquinolin-4-yl)pyridin-2-yl)oxy)-2,4-dimethylpentan-2-yl)carbamate Intermediate 7-fluoro-4-(4,4,5,5-tetramethyl-1,3,2-dioxaborolan-2-yl)quinoline was prepared as described in Example 77, Part C. Suzuki coupling was performed as described in Example 77, Part D. Obtained (S)-tert-butyl (1-((3-chloro-5-(7-fluoroquinolin-4-yl)pyridin-2-yl)oxy)-2,4-dimethylpentan-2-yl)carbamate (10.6 mg, 76% yield). $^1$H NMR (400 MHz, CHLOROFORM-d) δ 8.97 (d, J=4.3 Hz, 1H), 8.18 (d, J=2.0 Hz, 1H), 7.91-7.80 (m, 3H), 7.37 (ddd, J=9.3, 8.0, 2.5 Hz, 1H), 7.30 (d, J=4.0 Hz, 1H), 4.63 (d, J=10.5 Hz, 1H), 4.47 (d, J=10.5 Hz, 1H), 1.93-1.83 (m, 2H), 1.68 (d, J=8.8 Hz, 1H), 1.46 (s, 3H), 1.44 (s, 9H), 1.02 (m, 6H). $^{19}$F NMR (376 MHz, CHLOROFORM-d) δ −109.18 (s, 1F). LCMS (ESI) m/e 488.0 [(M+H)$^+$, calcd $C_{26}H_{32}F_1N_3Cl_1O_3$, 488.2]; LC/MS retention time (method B): $t_R$=2.39 min.

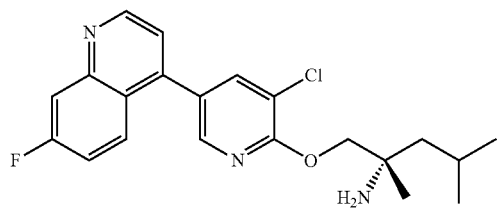 [SMILES: CC(C)C[C@](C)(N)COc1ncc(-c2ccnc3cc(F)ccc23)cc1Cl]

Part B: (S)-1-((3-chloro-5-(7-fluoroquinolin-4-yl)pyridin-2-yl)oxy)-2,4-dimethylpentan-2-amine TFA deprotection was performed as described in Example 32. Obtained (S)-1-((3-chloro-5-(7-fluoroquinolin-4-yl)pyridin-2-yl)oxy)-2,4-dimethylpentan-2-amine (4.4 mg, 50% yield). $^1$H NMR (600 MHz, DMSO-d$_6$) δ 9.06-8.97 (m, 1H), 8.38-8.29 (m, 1H), 8.25-8.16 (m, 1H), 8.04-7.83 (m, 2H), 7.65-7.51 (m, 2H), 4.27-4.13 (m, 2H), 1.95-1.79 (m, 1H), 1.56-1.40 (m, 2H), 1.26-1.16 (m, 3H), 1.03-0.91 (m, 6H). LCMS (ESI) me 409.9 [(M+Na), calcd $C_2H_{23}F_1N_3Cl_1O_1Na_1$, 410.1]; LC/MS retention time (method B): $t_R$=1.85 min.

Example 191

(S)-1-((3-chloro-5-(6-fluoroquinolin-4-yl)pyridin-2-yl)oxy)-2,4-dimethylpentan-2-amine

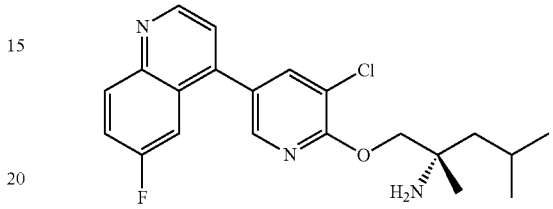

Prepared as described in Example 191 to afford (S)-1-((3-chloro-5-(6-fluoroquinolin-4-yl)pyridin-2-yl)oxy)-2,4-dimethylpentan-2-amine (9.4 mg, 0.024 mmol, 50% yield for the final step) as a colorless solid. $^1$H NMR (600 MHz, DMSO-d$_6$) δ 9.06-8.97 (m, 1H), 8.38-8.29 (m, 1H), 8.25-8.16 (m, 1H), 8.04-7.83 (m, 2H), 7.65-7.51 (m, 2H), 4.27-4.13 (m, 2H), 1.95-1.79 (m, 1H), 1.56-1.40 (m, 2H), 1.26-1.16 (m, 3H), 1.03-0.91 (m, 6H), two exchangeable protons not observed; LCMS (ESI) m/e 388.1 [(M+H)$^+$, calcd $C_{21}H_{24}FN_3ClO$, 388.2]; LC/MS retention time (method E): $t_R$=1.82 min.

Example 192

(S)-1-((3-chloro-5-(2-methylpyrimidin-4-yl)pyridin-2-yl)oxy)-2,4-dimethylpentan-2-amine

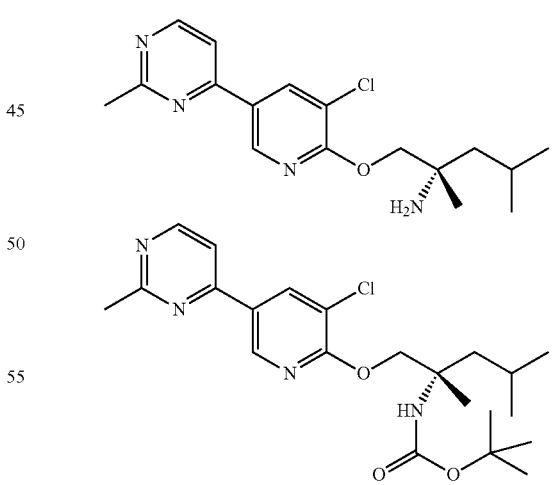

Part A: (S)-tert-butyl (1-((3-chloro-5-(2-methylpyrimidin-4-yl)pyridin-2-yl)oxy)-2,4-dimethylpentan-2-yl)carbamate Intermediate (S)-tert-butyl (1-((3-chloro-5-(4,4,5,5-tetramethyl-1,3,2-dioxaborolan-2-yl)pyridin-2-yl)oxy)-2,4- dimethylpentan-2-yl)carbamate was prepared as described in Example 77, Part C. Suzuki coupling was performed as described in Example 77, Part D. (Crude was carried on next step). LCMS (ESI) m/e 457.1 [(M+Na)$^+$, calcd C$_{23}$H$_{31}$N$_4$ClO$_3$Na, 457.2]; LC/MS retention time (method B): $t_R$=2.41 min.

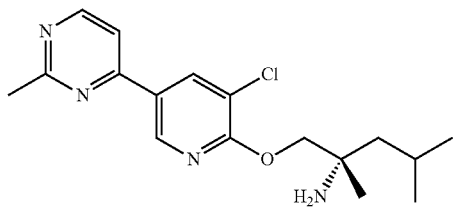 [SMILES: Cc1nccc(-c2cnc(OC[C@@](C)(N)CC(C)C)c(Cl)c2)n1]

Part B: (S)-1-((3-chloro-5-(2-methylpyrimidin-4-yl)pyridin-2-yl)oxy)-2,4-dimethylpentan-2-amine TFA deprotection was performed as described in Example 32 to obtain (S)-1-((3-chloro-5-(2-methylpyrimidin-4-yl)pyridin-2-yl)oxy)-2,4-dimethylpentan-2-amine 10.1 mg, 0.030 mmol, 51% yield in two steps). $^1$H NMR (500 MHz, DMSO-d$_6$) δ 8.94 (d, J=2.2 Hz, 1H), 8.76 (d, J=5.5 Hz, 1H), 8.63 (d, J=1.8 Hz, 1H), 7.95 (d, J=5.5 Hz, 1H), 4.22-4.14 (m, 2H), 2.68 (s, 3H), 1.85-1.78 (m, 1H), 1.42 (dd, J=9.0, 5.3 Hz, 2H), 1.15 (s, 3H), 0.92 (m, 6H); LCMS (ESI) m/e 318.1 [(M-NH$_2$)+, calcd C$_{17}$H$_2$N$_3$C10, 318.1]; LC/MS retention time (method B): $t_R$=1.83 min.

Example 193

(S)-1-((2'-chloro-5-(difluoromethyl)-[3,4'-bipyridin]-6-yl)oxy)-2,4-dimethylpentan-2-amine

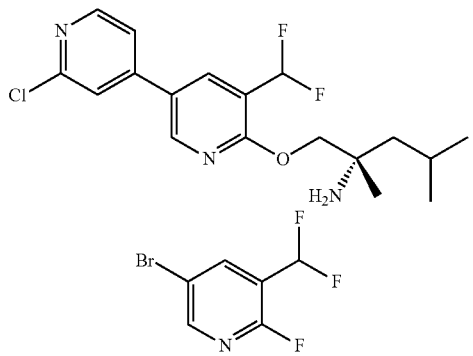

Part A:
5-Bromo-3-(difluoromethyl)-2-fluoropyridine

To a solution of 5-bromo-2-fluoronicotinaldehyde (0.8212 g, 4.03 mmol) in CH$_2$Cl$_2$ (15 mL) at 0° C. was added DAST (1.064 mL, 8.05 mmol). The reaction was stirred at 0° C. for 1 h then warmed to room temperature. The stirring was continued for 3 h. The reaction was poured into an ice cold 1N NaOH solution. The organic layer was separated and the aqueous layer was extracted DCM (2×). The DCM layers were combined, dried (Na$_2$SO$_4$), filtered and concentrated under reduced pressure to give crude 5-bromo-3-(difluoromethyl)-2-fluoropyridine (0.81 g, 3.58 mmol, 89% yield) as a brown solid. $^1$H NMR (400 MHz, CHLOROFORM-d) δ 8.43-8.38 (m, 1H), 8.18-8.13 (m, 1H), 6.82 (t, J=52.0 Hz, 1H); $^{19}$F NMR (376 MHz, CHLOROFORM-d) δ −74.33 (br. s., 1F), −115.87 (s, 2F); LCMS (ESI) m/e 205.9 [(M-F)$^+$, calcd C$_6$H$_3$BrNF$_2$, 205.9]; LC/MS retention time (method B): $t_R$=1.88 min.

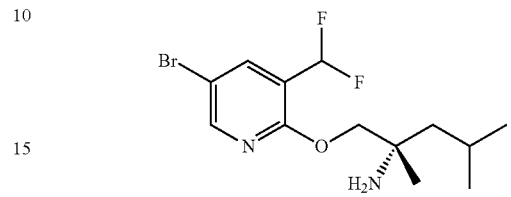

Part B: (S)-1-((5-bromo-3-(difluoromethyl)pyridin-2-yl)oxy)-2,4-dimethylpentan-2-amine To (S)-2-amino-2,4-dimethylpentan-1-ol (0.3359 g, 2.56 mmol) and 5-bromo-3-(difluoromethyl)-2-fluoropyridine (0.579 g, 2.56 mmol) in THF (5 mL) at room temperature was added potassium tert-butoxide (3.07 mL, 3.07 mmol). The reaction was stirred at room temperature overnight. The reaction was quenched by addition of water and the crude solution was diluted with ethyl acetate. The ethyl acetate layer was separated and washed with water (3×), dried (Na$_2$SO$_4$), filtered and concentrated under reduced pressure. The product was purified by silica gel chromatography (eluted with 0-10% methanol in CH$_2$Cl$_2$) to obtain (S)-1-((5-bromo-3-(difluoromethyl)pyridin-2-yl)oxy)-2,4-dimethylpentan-2-amine (0.63 g, 0.923 mmol, 73% yield) as a yellow liquid. $^1$H NMR (400 MHz, CHLOROFORM-d) δ 8.31-8.27 (m, 1H), 7.96-7.93 (m, 1H), 6.97-6.64 (m, 1H), 4.15 (s, 2H), 1.85-1.74 (m, 1H), 1.45 (t, J=5.8 Hz, 2H), 1.20 (s, 3H), 0.98 (m, 6H). $^{19}$F NMR (376 MHz, CHLOROFORM-d) δ −117.61 (s, 2F); LCMS (ESI) m/e 320.1 [(M-NH$_2$)+, calcd C$_{13}$H$_{17}$BrNF$_2$O, 320.1]; LC/MS retention time (method B): $t_R$=1.99 min.

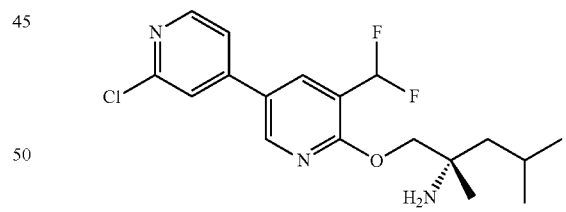

Part C: (S)-1-((2'-chloro-5-(difluoromethyl)-[3,4'-bipyridin]-6-yl)oxy)-2,4-dimethylpentan-2-amine A mixture of 2N sodium carbonate solution (0.050 ml, 0.099 mmol), 1,1'-bis(diphenylphosphine)ferrocene-palladium(II)dichloride dichoromethane complex (2.022 mg, 2.476 μmol), 2-chloro-4-(4,4,5,5-tetramethyl-1,3,2-dioxaborolan-2-yl)pyridine (0.018 g, 0.074 mmol) and (S)-1-((5-bromo-3-(difluoromethyl)pyridin-2-yl)oxy)-2,4-dimethylpentan-2-amine (0.0167 g, 0.050 mmol) in dioxane (0.8 mL) (degassed) was heated at 80° C. for 2 h. The reaction was filtered through celite and purified by reverse phase Prep HPLC. Obtained (S)-1-((2'-chloro-5-(difluoromethyl)-[3,4'- bipyridin]-6-yl)oxy)-2,4-dimethylpentan-2-amine (13.1 mg, 0.035 mmol, 72% yield) as an off-white solid. $^1$H NMR (500 MHz, DMSO-d$_6$) δ 8.83 (s, 1H), 8.48 (d, J=5.1 Hz, 1H), 8.43 (s, 1H), 7.98 (s, 1H), 7.84 (d, J=4.8 Hz, 1H), 7.27 (t, J=55.0 Hz, 1H), 4.22-4.14 (m, 2H), 1.83-1.73 (m, 1H), 1.48-1.37 (m, 2H), 1.15 (s, 3H), 0.91 (m, 6H). LCMS (ESI) m/e 353.1 [(M-NH$_2$), calcd C$_{18}$H$_{20}$N$_2$ClF$_2$O, 353.1]; LC/MS retention time (method B): $t_R$=1.96 min.

Example 194

(S)-1-((5-(difluoromethyl)-2'-methyl-[3,4'-bipyridin]-6-yl)oxy)-2,4-dimethylpentan-2-amine

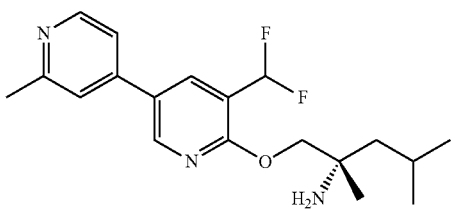 [SMILES: Cc1cc(-c2cnc(OC[C@@](C)(N)CC(C)C)c(C(F)F)c2)ccn1]

Prepared as described in Example 193 to afford (S)-1-((5-(difluoromethyl)-2'-methyl-[3,4'-bipyridin]-6-yl)oxy)-2,4-dimethylpentan-2-amine (9.2 mg, 0.026 mmol, 45% yield for the final step) as a colorless solid. $^1$H NMR (500 MHz, DMSO-d$_6$) δ 8.76 (s, 1H), 8.50 (d, J=5.2 Hz, 1H), 8.33 (s, 1H), 7.66 (s, 1H), 7.57 (d, J=4.9 Hz, 1H), 7.45-7.11 (m, 1H), 4.24-4.11 (m, 2H), 2.53 (s, 3H), 1.82-1.72 (m, 1H), 1.44 (qd, J=13.9, 5.5 Hz, 2H), 1.16 (s, 3H), 0.92 (d, J=6.7 Hz, 3H), 0.89 (d, J=6.4 Hz, 3H) two exchangeable protons not observed; LCMS (ESI) m/e 350.0 [(M+H)$^+$, calcd C$_{19}$H$_{26}$F$_2$N$_3$O, 350.2]; LC/MS retention time (method E): $t_R$=2.62 min.

Example 195

(S)-1-((3-(difluoromethyl)-5-(7-fluoroquinolin-4-yl)pyridin-2-yl)oxy)-2,4-dimethylpentan-2-amine

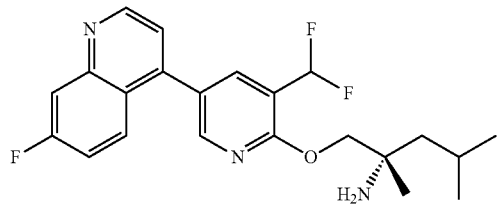 [SMILES: CC(C)C[C@](C)(N)COc1ncc(-c2ccnc3cc(F)ccc23)cc1C(F)F]

Part A: (S)-1-((3-(difluoromethyl)-5-(7-fluoroquinolin-4-yl)pyridin-2-yl)oxy)-2,4-dimethylpentan-2-amine Intermediate 7-fluoro-4-(4,4,5,5-tetramethyl-1,3,2-dioxaborolan-2-yl)quinoline was prepared as described in Example 77, Part C. Final product was prepared as described in Example 193 to obtain (S)-1-((3-(difluoromethyl)-5-(7-fluoroquinolin-4-yl)pyridin-2-yl)oxy)-2,4-dimethylpentan-2-amine (13.9 mg, 0.034 mmol, 34% yield). $^1$H NMR (500 MHz, DMSO-d$_6$) δ 9.00 (d, J=4.4 Hz, 1H), 8.51 (s, 1H), 8.15 (s, 1H), 7.97-7.85 (m, 2H), 7.59 (td, J=8.8, 2.6 Hz, 1H), 7.56 (d, J=4.4 Hz, 1H), 7.28 (t, J=55.0 Hz, 1H), 4.18 (s, 2H), 1.86-1.76 (m, 1H), 1.48-1.36 (m, 2H), 1.15 (s, 3H), 0.94 (m, 6H); LCMS (ESI) m/e 387.1 [(M-NH$_2$)+, calcd C$_{22}$H$_{22}$N$_2$F$_3$O, 387.2]; LC/MS retention time (method B): $t_R$=1.86 min.

Example 196

(S)-methyl(6-((2-amino-2,4-dimethylpentyl)oxy)-5-(difluoromethyl)-[3,4'-bipyridin]-2'-yl)carbamate

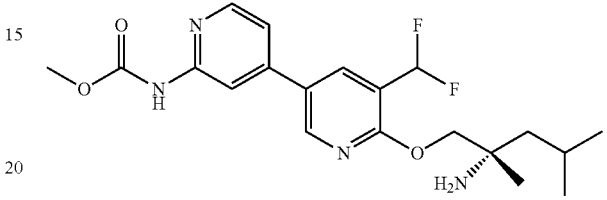

Prepared as described in Example 193. Obtained (S)-methyl (6-((2-amino-2,4-dimethylpentyl)oxy)-5-(difluoromethyl)-[3,4'-bipyridin]-2'-yl)carbamate (8.0 mg, 0.018 mmol, 40% yield). $^1$H NMR (400 MHz, CHLOROFORM-d) δ 8.56 (br. s., 1H), 8.34 (d, J=4.8 Hz, 1H), 8.24 (br. s., 1H), 8.13 (br. s., 2H), 7.19 (d, J=3.8 Hz, 1H), 7.11-6.73 (m, 1H), 4.26 (br. s., 2H), 3.85 (s, 3H), 1.77 (m 1H), 1.50 (br. s., 2H), 1.25 (br. s., 3H), 1.00 (t, J=7.4 Hz, 6H), two exchangeable protons not observed; LCMS (ESI) m/e 431.1 [(M+Na)$^+$, calcd C$_{20}$H$_{26}$N$_4$F$_2$O$_3$Na, 431.2]; LC/MS retention time (method B): $t_R$=1.78 min.

Example 197

(S)-1-((5-(7-chloroquinolin-4-yl)-3-(difluoromethyl)pyridin-2-yl)oxy)-2,4-dimethylpentan-2-amine

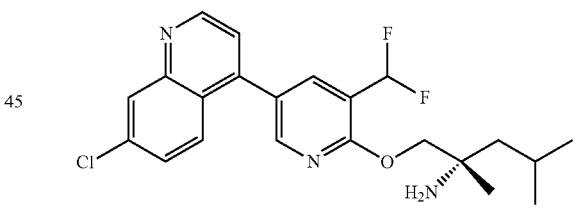

Intermediate (S)-1-((3-(difluoromethyl)-5-(4,4,5,5-tetramethyl-1,3,2-dioxaborolan-2-yl)pyridin-2-yl)oxy)-2,4-dimethylpentan-2-amine was prepared as described in Example 77, Part C. Intermediate 4-bromo-7-chloroquinoline was prepared as described in Example 77, Part B. Suzuki reaction was performed as described in Example 193. Obtained (S)-1-((5-(7-chloroquinolin-4-yl)-3-(difluoromethyl)pyridin-2-yl)oxy)-2,4-dimethylpentan-2-amine (7.8 mg, 0.019 mmol, 34% yield). $^1$H NMR (500 MHz, DMSO-d$_6$) δ 9.02 (d, J=4.6 Hz, 1H), 8.53 (s, 1H), 8.20 (d, J=1.8 Hz, 1H), 8.16 (s, 1H), 7.88 (d, J=9.2 Hz, 1H), 7.69 (dd, J=9.0, 2.0 Hz, 1H), 7.61 (d, J=4.3 Hz, 1H), 7.29 (t, J=55.0 Hz, 1H), 4.22-4.16 (m, 2H), 1.83 (dt, J=12.5, 6.3 Hz, 1H), 1.49-1.38 (m, 2H), 1.17 (s, 3H), 0.97-0.92 (m, 6H), two exchangeable protons not observed; LCMS (ESI) m/e 442.0 [(M+Na)$^+$, calcd C$_{22}$H$_{24}$ClN$_3$F$_2$ONa, 442.2]; LC/MS retention time (method B): $t_R$=2.09 min.

Example 198

(S)-1-((3-(difluoromethyl)-5-(2-methylpyrimidin-4-yl)pyridin-2-yl)oxy)-2,4-dimethylpentan-2-amine

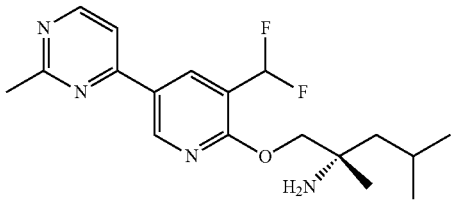 [SMILES: Cc1nccc(-c2cnc(OC[C@@](C)(N)CC(C)C)c(C(F)F)c2)n1]

Intermediate (5)-1-((3-(difluoromethyl)-5-(4,4,5,5-tetramethyl-1,3,2-dioxaborolan-2-yl)pyridin-2-yl)oxy)-2,4-dimethylpentan-2-amine was prepared as described in Example 77, Part C. Suzuki reaction was performed as described in Example 193. Obtained (S)-1-((3-(difluoromethyl)-5-(2-methylpyrimidin-4-yl)pyridin-2-yl)oxy)-2,4-dimethylpentan-2-amine (7.7 mg, 0.036 mmol, 37% yield). $^1$H NMR (500 MHz, DMSO-$d_6$) δ 9.13 (s, 1H), 8.78 (d, J=5.2 Hz, 1H), 8.69 (s, 1H), 7.99 (d, J=5.2 Hz, 1H), 7.29 (t, J=55.0 Hz, 1H), 4.19 (d, J=1.8 Hz, 2H), 2.70 (s, 3H), 1.85-1.76 (m, 1H), 1.46-1.36 (m, 2H), 1.14 (s, 3H), 0.92 (m, 6H); LCMS (ESI) m/e 334.1 [(M-NH$_2$)+, calcd $C_{18}H_{22}N_3F_2O$, 334.2]; LC/MS retention time (method B): $t_R$=1.91 min.

Example 199

(S)-1-((2',5-bis(difluoromethyl)-[3,4'-bipyridin]-6-yl)oxy)-2,4-dimethylpentan-2-amine

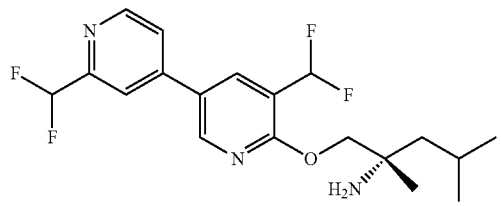 [SMILES: CC(C)C[C@](C)(N)COc1ncc(-c2ccnc(C(F)F)c2)cc1C(F)F]

Intermediate (S)-1-((3-(difluoromethyl)-5-(4,4,5,5-tetramethyl-1,3,2-dioxaborolan-2-yl)pyridin-2-yl)oxy)-2,4-dimethylpentan-2-amine was prepared as described in Example 77, Part C. Suzuki reaction was performed as described in Example 193. Obtained (S)-1-((2',5-bis(difluoromethyl)-[3,4'-bipyridin]-6-yl)oxy)-2,4-dimethylpentan-2-amine (9.2 mg, 0.023 mmol, 39% yield). $^1$H NMR (500 MHz, DMSO-d6) δ 8.86 (s, 1H), 8.77 (d, J=5.2 Hz, 1H), 8.45 (s, 1H), 8.10 (s, 1H), 8.00 (d, J=4.6 Hz, 1H), 7.26 (t, J=55.0 Hz, 1H), 7.02 (t, J=55.0 Hz, 1H), 4.18 (d, J=1.8 Hz, 2H), 1.85-1.75 (m, 1H), 1.48-1.36 (m, 2H), 1.15 (s, 3H), 0.94 (d, J=6.7 Hz, 3H), 0.92 (d, J=6.7 Hz, 3H), two exchangeable protons not observed; LCMS (ESI) m/e 369.1 [(M-NH$_2$)+, calcd $C_{19}H_{24}N_2F_4O$, 369.2]; LC/MS retention time (method B): $t_R$=1.91 min.

Example 200

(S)-1-((3-(difluoromethyl)-5-(6-fluoroquinolin-4-yl)pyridin-2-yl)oxy)-2,4-dimethylpentan-2-amine

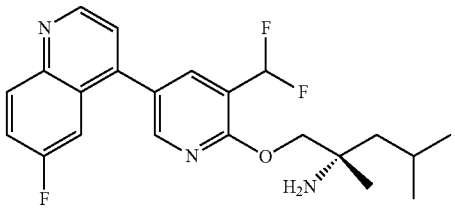 [SMILES: CC(C)C[C@](C)(N)COc1ncc(-c2ccnc3ccc(F)cc23)cc1C(F)F]

Intermediate 6-fluoro-4-(4,4,5,5-tetramethyl-1,3,2-dioxaborolan-2-yl)quinoline was prepared as described in Example 77, Part B and C. Suzuki reaction was performed as described in Example 193. Obtained (S)-1-((3-(difluoromethyl)-5-(6-fluoroquinolin-4-yl)pyridin-2-yl)oxy)-2,4-dimethylpentan-2-amine (27.2 mg, 0.067 mmol, 39% yield). $^1$H NMR (500 MHz, DMSO-d6) δ 8.97 (d, J=4.4 Hz, 1H), 8.52 (s, 1H), 8.22 (dd, J=9.2, 5.9 Hz, 1H), 8.16 (s, 1H), 7.81-7.72 (m, 1H), 7.61 (d, J=4.4 Hz, 1H), 7.51 (dd, J=10.1, 2.8 Hz, 1H), 7.28 (t, J=55.0 Hz, 1H), 4.19 (s, 2H), 1.86-1.77 (m, 1H), 1.49-1.37 (m, 2H), 1.16 (s, 3H), 0.94 (m, 6H), two exchangeable protons not observed; LCMS (ESI) m/e 426.2 [(M+Na)$^+$, calcd $C_{22}H_{24}N_3F_3ONa$, 426.2]; LC/MS retention time (method B): $t_R$=1.93 min.

Example 201

(S)-1-((3-(difluoromethyl)-5-(5,7-difluoroquinolin-4-yl)pyridin-2-yl)oxy)-2,4-dimethylpentan-2-amine

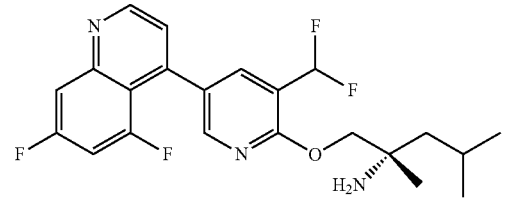 [SMILES: CC(C)C[C@](C)(N)COc1ncc(-c2ccnc3cc(F)cc(F)c23)cc1C(F)F]

Intermediate(S)-tert-butyl(1-((3-chloro-5-(5,7-difluoroquinolin-4-yl)pyridin-2-yl)oxy)-2,4-dimethylpentan-2-yl)carbamate was prepared in Example 189. Suzuki reaction was performed as described in Example 193. Obtained (S)-1-((3-(difluoromethyl)-5-(5,7-difluoroquinolin-4-yl)pyridin-2-yl)oxy)-2,4-dimethylpentan-2-amine (13.0 mg, 0.031 mmol, 37% yield). $^1$H NMR (500 MHz, DMSO-$d_6$) δ 9.02 (d, J=4.4 Hz, 1H), 8.43 (s, 1H), 8.10 (br. s., 1H), 7.80 (d, J=8.4 Hz, 1H), 7.63-7.55 (m, 1H), 7.51 (d, J=4.4 Hz, 1H), 7.25 (t, J=55.0 Hz, 1H), 4.16 (s, 2H), 1.81 (dt, J=12.5, 6.2 Hz, 1H), 1.41 (t, J=6.4 Hz, 2H), 1.14 (s, 3H), 0.93 (m, 6H), two exchangeable protons not observed; LCMS (ESI) m/e 405.7 [(M-NH$_2$)+, calcd $C_{22}H_2N_2F_4O$, 405.2]; LC/MS retention time (method B): $t_R$=2.02 min.

Example 202

(S)-1-((3-(difluoromethyl)-5-(7-(trifluoromethyl)
quinolin-4-yl)pyridin-2-yl)oxy)-2,4-dimethylpentan-
2-amine

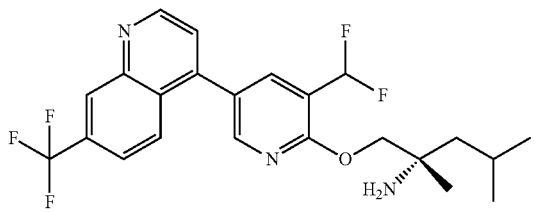 [SMILES: CC(C)C[C@](C)(N)COc1ncc(-c2ccnc3cc(C(F)(F)F)ccc23)cc1C(F)F]

Intermediate 4-(4,4,5,5-tetramethyl-1,3,2-dioxaborolan-2-yl)-7-(trifluoromethyl)quinoline was prepared as described in Example 77, Part C. Suzuki reaction was performed as described in Example 193. Obtained (S)-1-((3-(difluoromethyl)-5-(7-(trifluoromethyl)quinolin-4-yl)pyridin-2-yl)oxy)-2,4-dimethylpentan-2-amine (25.3 mg, 0.055 mmol, 37% yield). $^1$H NMR (500 MHz, DMSO-d$_6$) δ 9.14 (d, J=4.4 Hz, 1H), 8.56 (s, 1H), 8.48 (s, 1H), 8.20 (s, 1H), 8.08 (d, J=8.8 Hz, 1H), 7.92 (d, J=8.8 Hz, 1H), 7.75 (d, J=4.4 Hz, 1H), 7.29 (t, J=55.0 Hz, 1H), 4.20 (s, 2H), 1.87-1.79 (m, 1H), 1.49-1.38 (m, 2H), 1.16 (s, 3H), 0.95 (m, 6H), two exchangeable protons not observed; LCMS (ESI) m/e 437.1 [(M-NH$_2$), calcd C$_{23}$H$_{22}$N$_2$F$_5$O, 437.2]; LC/MS retention time (method B): t$_R$=2.13 min.

Example 203

(S)-1-((5-(difluoromethyl)-2',3'-dimethyl-[3,4'-bi-
pyridin]-6-yl)oxy)-2,4-dimethylpentan-2-amine

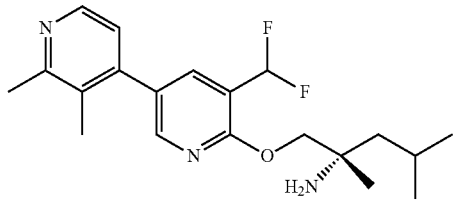 [SMILES: Cc1nccc(-c2cnc(OC[C@@](C)(N)CC(C)C)c(C(F)F)c2)c1C]

Intermediate 2,3-dimethyl-4-(4,4,5,5-tetramethyl-1,3,2-dioxaborolan-2-yl)pyridine was prepared as described in Example 77, Part C. Suzuki reaction was performed as described in Example 193. Obtained (S)-1-((5-(difluoromethyl)-2',3'-dimethyl-[3,4'-bipyridin]-6-yl)oxy)-2,4-dimethylpentan-2-amine (20.4 mg, 0.056 mmol, 26% yield). $^1$H NMR (500 MHz, DMSO-d$_6$) δ 8.32 (d, J=4.0 Hz, 2H), 7.95 (s, 1H), 7.38-7.11 (m, 2H), 4.15 (s, 2H), 2.52 (br. s., 3H), 2.17 (s, 3H), 1.84-1.75 (m, 1H), 1.42 (dd, J=10.5, 5.3 Hz, 2H), 1.15 (s, 3H), 0.93 (m, 6H), two exchangeable protons not observed; LCMS (ESI) m/e 347.1 [(M-NH$_2$)+, calcd C$_{20}$H$_{25}$N$_2$F$_2$O, 347.2]; LC/MS retention time (method B): t$_R$=1.48 min.

Example 204

(S)-1-((3-(difluoromethyl)-5-(quinolin-4-yl)pyridin-
2-yl)oxy)-2,4-dimethylpentan-2-amine

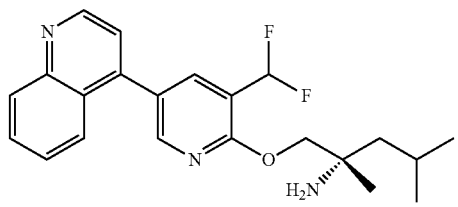 [SMILES: CC(C)C[C@](C)(N)COc1ncc(-c2ccnc3ccccc23)cc1C(F)F]

Suzuki reaction was performed as described in Example 193. Obtained (S)-1-((3-(difluoromethyl)-5-(quinolin-4-yl)pyridin-2-yl)oxy)-2,4-dimethylpentan-2-amine (17.4 mg, 0.045 mmol 66% yield). $^1$H NMR (500 MHz, DMSO-d$_6$) δ 9.05 (d, J=4.0 Hz, 1H), 8.57 (br. s., 1H), 8.34 (br. s., 2H), 8.21 (br. s., 1H), 8.18 (d, J=8.5 Hz, 1H), 7.89 (t, J=7.5 Hz, 1H), 7.85 (d, J=8.5 Hz, 1H), 7.70 (t, J=7.5 Hz, 1H), 7.65 (d, J=4.3 Hz, 1H), 7.63-7.40 (m, 1H), 4.64-4.39 (m, 2H), 1.89-1.73 (m, 2H), 1.65 (dd, J=13.7, 4.6 Hz, 1H), 1.42 (s, 3H), 0.97 (d, J=6.4 Hz, 3H), 0.93 (d, J=6.1 Hz, 3H); LCMS (ESI) m/e 386.1 [(M+H)$^+$, calcd C$_{22}$H$_{26}$N$_3$F$_2$O, 386.2]; LC/MS retention time (method B): t$_R$=1.68 min.

Example 205

(S)-1-((3-(difluoromethyl)-5-(7-methylquinolin-4-yl)
pyridin-2-yl)oxy)-2,4-dimethylpentan-2-amine

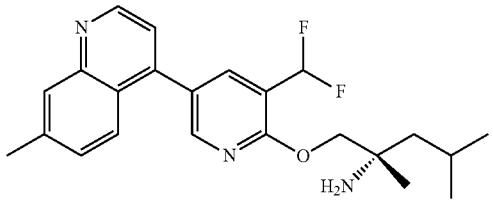 [SMILES: Cc1ccc2c(-c3cnc(OC[C@@](C)(N)CC(C)C)c(C(F)F)c3)ccnc2c1]

A mixture of 2N sodium carbonate solution (0.146 mL, 0.291 mmol), (5)-1-((5-(7-chloroquinolin-4-yl)-3-(difluoromethyl)pyridin-2-yl)oxy)-2,4-dimethylpentan-2-amine (0.0611 g, 0.146 mmol) (Example 197),2,4,6-trimethyl-1,3,5,2,4,6-trioxatriborinane (0.018 g, 0.146 mmol) and 1,1'-bis (diphenylphosphine)ferrocene-palladium(II)dichloride dichoromethane complex (5.94 mg, 7.28 μmol) in dioxane (1 mL) (degassed) was heated at 110° C. for 3 h. The reaction was diluted with ethyl acetate and washed with water three times. The ethyl acetate layer was separated, dried (Na$_2$SO$_4$), filtered and concentrated under reduced pressure. The product was purified by reverse phase Prep HPLC to afford (S)-1-((3-(difluoromethyl)-5-(7-methylquinolin-4-yl)pyridin-2-yl)oxy)-2,4-dimethylpentan-2-amine (1.1 mg, 2.5 □mol, 2% yield). $^1$H NMR (500 MHz, DMSO-d$_6$) δ 8.93 (d, J=4.4 Hz, 1H), 8.51 (s, 1H), 8.13 (s, 1H), 7.93 (s, 1H), 7.73 (d, J=8.8 Hz, 1H), 7.53-7.47 (m, 2H), 7.32 (t, J=55.0 Hz, 1H), 2.56 (s, 3H), 1.87-1.79 (m, 1H), 1.54-1.41 (m, 2H), 1.20 (s, 3H), 0.95 (m, 6H). (NMR water suppression also suppressed OCH$_2$ ether signal); LCMS (ESI) m/e 400.2 [(M+H)$^+$, calcd C$_{23}$H$_{28}$N$_3$F$_2$O, 400.2]; LC/MS retention time (method B): t$_R$=1.72 min.

Example 206

(S)-methyl(5-((2-amino-2,4-dimethylpentyl)oxy)-4-methoxy-[2,4'-bipyridin]-2'-yl)carbamate

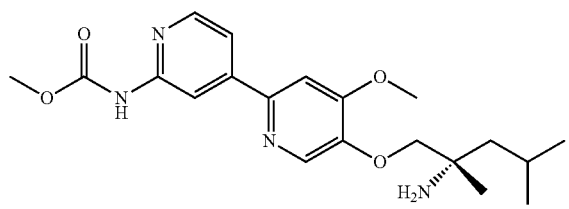

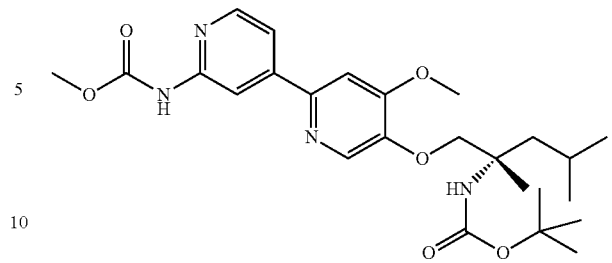

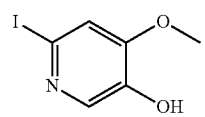

Part A: 6-Iodo-4-methoxypyridin-3-ol n-BuLi (0.319 mL, 0.797 mmol) was added to the THF (4 mL) solution of 2,6-diiodo-4-methoxypyridin-3-yl diethylcarbamate (0.316 g, 0.664 mmol) (Ref: *J. Org. Chem.* 2002, 67, 3272-3276) at −78° C. After stirring at −78° C. for 20 min, the reaction was quenched by addition of NH$_4$Cl (sat.). The reaction was warmed to room temperature and stirred for another 30 min. The volatiles were removed under reduced pressure and the crude material was partitioned between ethyl acetate and water. The ethyl acetate layer was separated, dried (Na$_2$SO$_4$), filtered and concentrated under reduced pressure. The residue was purified via silica gel chromatography (eluted with 0-25% ethyl acetate in hexanes) to give 6-iodo-4-methoxypyridin-3-ol (0.033 g, 0.131 mmol, 20% yield). $^1$H NMR (400 MHz, CHLOROFORM-d) δ 7.95 (s, 1H), 7.14 (s, 1H), 3.92 (s, 3H), one exchangeable proton was not observed; LCMS (ESI) m/e 251.9 [(M+H)$^+$, calcd C$_6$H$_7$INO$_2$, 252.0]; LC/MS retention time (method B): t$_R$=0.85 min.

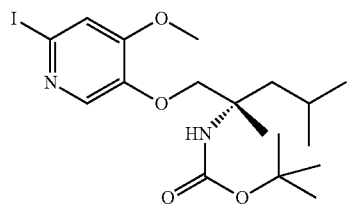 [SMILES: COc1cc(I)ncc1OC[C@](C)(CC(C)C)NC(=O)OC(C)(C)C]

Part B: (S)-tert-butyl (1-((6-iodo-4-methoxypyridin-3-yl)oxy)-2,4-dimethylpentan-2-yl)carbamate Preparation was described as Example 53, Part A. The crude material was carried on without further purification. LCMS (ESI) m/e 465.0 [(M+H)$^+$, calcd C$_{18}$H$_3$IN$_2$O$_4$, 465.1]; LC/MS retention time (method B): t$_R$=2.24 min.

Part C: Boc protected (S)-methyl (5-((2-amino-2,4-dimethylpentyl)oxy)-4-methoxy-[2,4'-bipyridin]-2'-yl)carbamate Suzuki reaction was performed as described in Example 193. Obtained Boc protected (S)-methyl (5-((2-amino-2,4-dimethylpentyl)oxy)-4-methoxy-[2,4'-bipyridin]-2'-yl)carbamate (2.3 mg, 4.71 μmol, 22% yield for two steps). LCMS (ESI) m/e 489.3 [(M+H)$^+$, calcd C$_{25}$H$_{37}$N$_4$O$_6$, 489.2]; LC/MS retention time (method B): t$_R$=2.14 min.

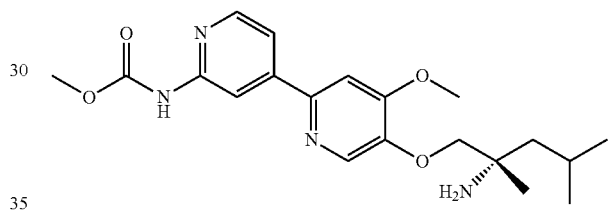

Part D: (S)-methyl (5-((2-amino-2,4-dimethylpentyl)oxy)-4-methoxy-[2,4'-bipyridin]-2'-yl)carbamate TFA deprotection was performed as described in Example 32. Obtained (S)-methyl (5-((2-amino-2,4-dimethylpentyl)oxy)-4-methoxy-[2,4'-bipyridin]-2'-yl)carbamate (1.2 mg, 3.09 μmol, 66% yield). $^1$H NMR (500 MHz, DMSO-d$_6$) δ 8.51 (s, 1H), 8.34 (d, J=5.1 Hz, 1H), 8.31 (s, 1H), 7.69 (d, J=5.1 Hz, 1H), 7.59 (s, 1H), 3.99 (s, 3H), 3.83 (s, 2H), 3.70 (s, 3H), 3.41 (br. s., 2H), 1.85-1.75 (m, 1H), 1.39 (dd, J=9.0, 5.7 Hz, 2H), 1.12 (s, 3H), 0.93 (m, 6H), one exchangeable proton not observed. LCMS (ESI) m/e 389.3 [(M+H)$^+$, calcd C$_{20}$H$_{29}$N$_4$O$_4$, 389.2]; LC/MS retention time (method B): t$_R$=1.56 min.

Example 207

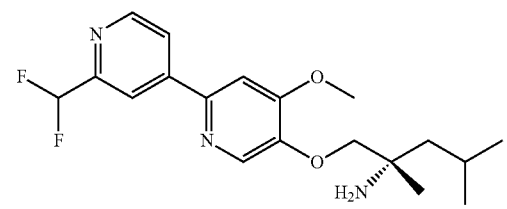 [SMILES: COc1cc(-c2ccnc(C(F)F)c2)ncc1OC[C@@](C)(N)CC(C)C]

-continued

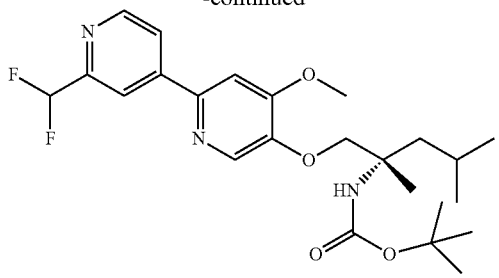

Part A: (S)-tert-butyl (1-((2'-(difluoromethyl)-4-methoxy-[2,4'-bipyridin]-5-yl)oxy)-2,4-dimethylpentan-2-yl)carbamate Suzuki reaction was performed as described in Example 193 to afford (S)-tert-butyl (1-((2'-(difluoromethyl)-4-methoxy-[2,4'-bipyridin]-5-yl)oxy)-2,4-dimethylpentan-2-yl)carbamate (12.9 mg, 0.028 mmol, 13% yield). LCMS (ESI) m/e 466.2 [(M+H)$^+$, calcd C$_{24}$H$_{34}$F$_2$N$_3$O$_4$, 466.2]; LC/MS retention time (method B): t$_R$=2.65 min.

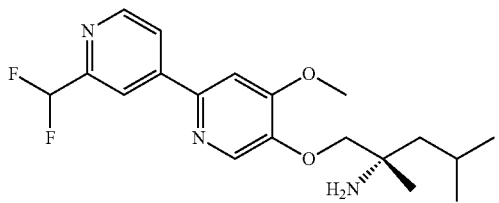

Part B: (S)-1-((2'-(difluoromethyl)-4-methoxy-[2,4'-bipyridin]-5-yl)oxy)-2,4-dimethylpentan-2-amine TFA deprotection was performed as described in Example 32. Obtained (S)-1-((2'-(difluoromethyl)-4-methoxy-[2,4'-bipyridin]-5-yl)oxy)-2,4-dimethylpentan-2-amine (5.0 mg, 0.014 mmol, 53% yield). $^1$H NMR (500 MHz, DMSO-d$_6$) δ 8.78 (d, J=4.8 Hz, 1H), 8.38 (s, 2H), 8.26 (d, J=4.8 Hz, 1H), 7.84 (s, 1H), 7.03 (t, J=1.0 Hz, 1H), 4.03 (s, 3H), 3.96 (s, 2H), 1.85-1.75 (m, 1H), 1.56-1.42 (m, 2H), 1.21 (s, 3H), 0.94 (m, 6H), two exchangeable protons not observed. LCMS (ESI) m/e 366.2 [(M+H)$^+$, calcd C$_{19}$H$_{26}$F$_2$N$_3$O$_2$, 366.2]; LC/MS retention time (method B): t$_R$=1.70 min.

Example 208

(S)-methyl (4-(4-((2-amino-2,4-dimethylpentyl)oxy)naphthalen-1-yl)pyridin-2-yl)carbamate

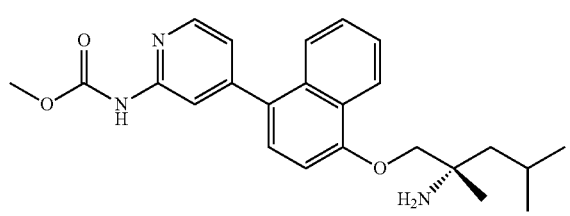 [SMILES: COC(=O)Nc1cc(-c2ccc(OC[C@@](C)(N)CC(C)C)c3ccccc23)ccn1]

-continued

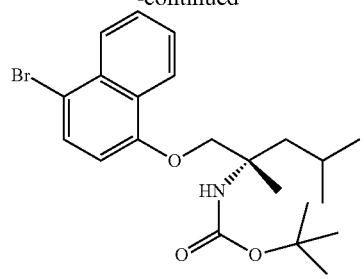

Part A: (S)-tert-butyl (1-((4-bromonaphthalen-1-yl)oxy)-2,4-dimethylpentan-2-yl)carbamate Prepared as described in Example 53, Part A. Obtained (S)-tert-butyl (1-((4-bromonaphthalen-1-yl)oxy)-2,4-dimethylpentan-2-yl)carbamate (37 mg, 0.085 mmol, 19% yield). $^1$H NMR (400 MHz, CHLOROFORM-d) δ 8.29 (dd, J=7.8, 0.8 Hz, 1H), 8.18 (d, J=8.0 Hz, 1H), 7.67-7.35 (m, 3H), 6.73 (d, J=8.3 Hz, 1H), 4.28 (d, J=9.0 Hz, 1H), 4.13 (d, J=9.0 Hz, 1H), 1.86 (d, J=6.5 Hz, 2H), 1.69 (dd, J=13.9, 5.1 Hz, 1H), 1.51 (s, 3H), 1.42-1.38 (m, 9H), 1.01 (m, 6H); LCMS (ESI) m/e 458.1, 460.1 Br pattern [(M+Na)$^+$, calcd C$_{22}$H$_{30}$BrNNaO$_3$, 458.1]; LC/MS retention time (method B): t$_R$=2.60 min.

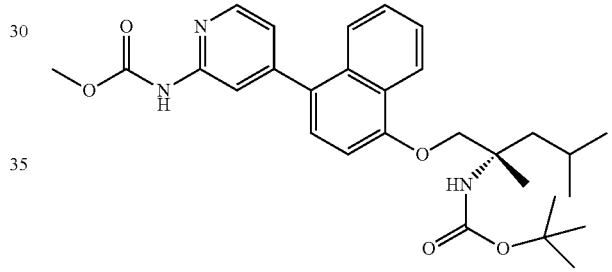

Part B: Boc protected (S)-methyl (4-(4-((2-amino-2,4-dimethylpentyl)oxy)naphthalen-1-yl)pyridin-2-yl)carbamate Prepared as described in Example 77, Part D. Obtained Boc protected (S)-methyl (4-(4-((2-amino-2,4-dimethylpentyl)oxy)naphthalen-1-yl)pyridin-2-yl)carbamate (12.0 mg, 0.024 mmol, 69% yield). $^1$H NMR (400 MHz, CHLOROFORM-d) δ 8.37 (d, J=5.8 Hz, 2H), 8.16 (s, 1H), 7.94-7.90 (m, 1H), 7.58-7.49 (m, 2H), 7.38 (d, J=8.0 Hz, 1H), 7.15 (dd, J=5.1, 1.4 Hz, 1H), 6.91 (d, J=8.0 Hz, 1H), 4.33 (d, J=9.0 Hz, 1H), 4.22-4.17 (m, 1H), 3.82 (s, 3H), 1.94-1.83 (m, 1H), 1.73 (br. s., 2H), 1.42 (s, 9H), 1.52 (s, 3H), 1.03 (m, 6H), two exchangeable protons not observed. LCMS (ESI) m/e 508.2 [(M+H)$^+$, calcd C$_{29}$H$_{38}$N$_3$O$_5$, 508.3]; LC/MS retention time (method B): t$_R$=2.30 min.

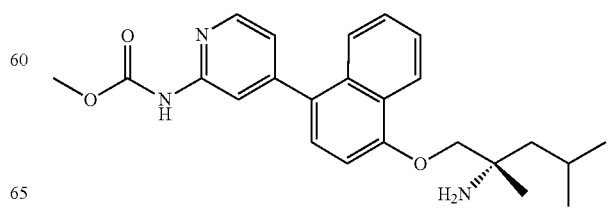

Part C: (S)-methyl(4-(4-((2-amino-2,4-dimethylpentyl)oxy)naphthalen-1-yl)pyridin-2-yl)carbamate TFA deprotection was performed as described in Example 32. Obtained (S)-methyl (4-(4-((2-amino-2,4-dimethylpentyl)oxy)naphthalen-1-yl)pyridin-2-yl)carbamate (9.2 mg, 0.022 mmol, 95% yield). $^1$H NMR (500 MHz, DMSO-$d_6$) δ 8.40 (d, J=7.7 Hz, 1H), 8.37 (d, J=4.8 Hz, 1H), 7.95 (s, 1H), 7.85 (d, J=8.4 Hz, 1H), 7.59 (t, J=8.4 Hz, 2H), 7.42 (d, J=7.7 Hz, 1H), 7.16 (d, J=5.1 Hz, 1H), 7.06 (d, J=8.1 Hz, 1H), 3.94 (s, 2H), 3.67 (s, 3H), 1.86 (d, J=6.6 Hz, 1H), 1.54 (dd, J=9.7, 5.7 Hz, 2H), 1.25 (s, 3H), 0.94 (m, 6H), three exchangeable protons not observed. LCMS (ESI) m/e 408.2 [(M+H)$^+$, calcd $C_{24}H_{30}N_3O_3$, 408.2]; LC/MS retention time (method B): $t_R$=1.78 min.

Example 209

(S)-2,4-dimethyl-1-((4-(quinolin-4-yl)naphthalen-1-yl)oxy)pentan-2-amine

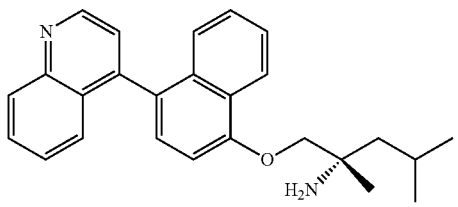

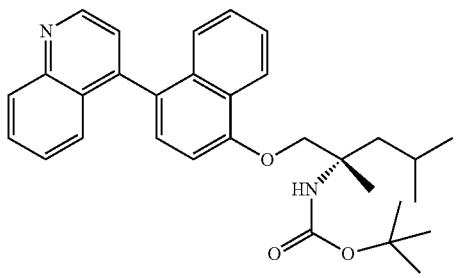

Part A: (S)-tert-butyl (2,4-dimethyl-1-((4-(quinolin-4-yl)naphthalen-1-yl)oxy)pentan-2-yl)carbamate Prepared as described in Example 77, Part D. Obtained (S)-tert-butyl (2,4-dimethyl-1-((4-(quinolin-4-yl)naphthalen-1-yl)oxy)pentan-2-yl)carbamate (8.0 mg, 0.014 mmol, 40% yield). $^1$H NMR (400 MHz, CHLOROFORM-d) δ 9.03 (d, J=4.3 Hz, 1H), 8.41 (d, J=8.5 Hz, 1H), 8.23 (d, J=8.5 Hz, 1H), 7.73 (ddd, J=8.4, 6.9, 1.5 Hz, 1H), 7.56-7.48 (m, 2H), 7.43 (d, J=4.3 Hz, 1H), 7.41-7.33 (m, 4H), 6.99 (d, J=7.8 Hz, 1H), 4.39 (dd, J=8.4, 4.6 Hz, 1H), 4.25 (d, J=6.5 Hz, 1H), 1.97-1.88 (m, 1H), 1.81-1.72 (m, 2H), 1.57 (s, 3H), 1.43 (s, 9H), 1.08-1.03 (m, 6H), one exchangeable proton not observed; LCMS (ESI) m/e 485.2 [(M+H)$^+$, calcd $C_{31}H_{37}N_2O_3$, 485.3]; LC/MS retention time (method B): $t_R$=2.26 min.

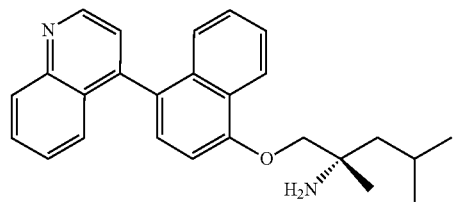 [SMILES: CC(C)C[C@](C)(N)COc1ccc(-c2ccnc3ccccc23)c2ccccc12]

Part B: (S)-2,4-dimethyl-1-((4-(quinolin-4-yl)naphthalen-1-yl)oxy)pentan-2-amine TFA deprotection was performed as described in Example 32. Obtained (S)-2,4-dimethyl-1-((4-(quinolin-4-yl)naphthalen-1-yl)oxy)pentan-2-amine (6.3 mg, 0.016 mmol, 98% yield). $^1$H NMR (500 MHz, DMSO-$d_6$) δ 9.03 (d, J=4.4 Hz, 1H), 8.44 (d, J=6.2 Hz, 1H), 8.15 (d, J=8.4 Hz, 1H), 7.78 (t, J=7.5 Hz, 1H), 7.58 (t, J=7.5 Hz, 1H), 7.52 (d, J=4.0 Hz, 1H), 7.48-7.43 (m, 2H), 7.43-7.39 (m, 1H), 7.35 (d, J=8.4 Hz, 1H), 7.20 (d, J=8.4 Hz, 1H), 7.13 (d, J=7.7 Hz, 1H), 4.00 (s, 2H), 1.90-1.85 (m, 1H), 1.65-1.50 (m, 2H), 1.29 (s, 3H), 1.01-0.94 (m, 6H), two exchangeable protons not observed; LCMS (ESI) m/e 385.2 [(M+H)$^+$, calcd $C_{26}H_{29}N_2O$, 385.2]; LC/MS retention time (method B): $t_R$=1.70 min.

Example 210

(S)-methyl (4-(5-((2-amino-2,4-dimethylpentyl)oxy)pyrimidin-2-yl)pyridin-2-yl)carbamate

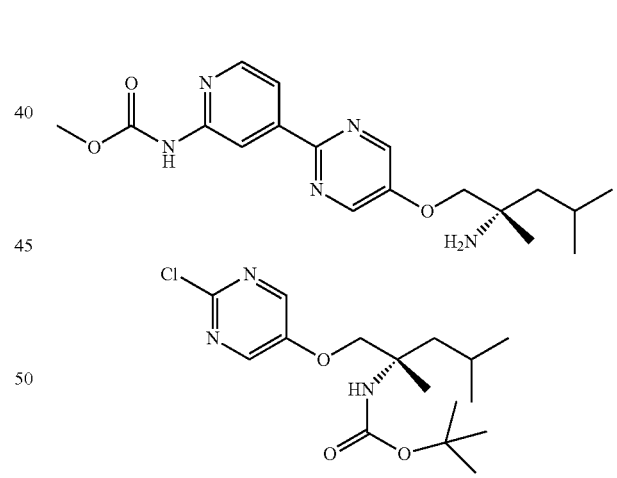

Part A: (S)-tert-butyl (1-((2-chloropyrimidin-5-yl)oxy)-2,4-dimethylpentan-2-yl)carbamate Prepared as described in Example 53, Part A. Obtained (S)-tert-butyl (1-((2-chloropyrimidin-5-yl)oxy)-2,4-dimethylpentan-2-yl)carbamate (25.0 mg, 0.073 mmol, 49% yield). $^1$H NMR (400 MHz, CHLOROFORM-d) δ 8.32 (s, 2H), 4.50 (s, 1H), 4.30 (d, J=8.5 Hz, 1H), 4.06 (d, J=8.8 Hz, 1H), 1.93-1.74 (m, 2H), 1.44 (dd, J=13.9, 4.9 Hz, 1H), 1.39 (s, 9H), 1.36 (s, 3H), 0.99 (dd, J=6.5, 4.5 Hz, 6H).

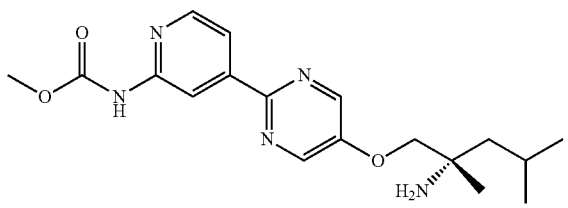 [SMILES: COC(=O)Nc1cc(-c2ncc(OC[C@@](C)(N)CC(C)C)cn2)ccn1]

Part B: (S)-methyl (4-(5-((2-amino-2,4-dimethyl-pentyl)oxy)pyrimidin-2-yl)pyridin-2-yl)carbamate A mixture of 2N sodium carbonate solution (0.073 mL, 0.145 mmol), 1,1'-bis(diphenylphosphine)ferrocene-palladium(II)dichloride dichloromethane complex (2.97 mg, 3.64 μmol), (S)-tert-butyl (1-((2-chloropyrimidin-5-yl)oxy)-2,4-dimethylpentan-2-yl)carbamate and (2-((methoxycarbonyl)amino)pyridin-4-yl)boronic acid (0.025 g, 0.128 mmol) in dioxane (1 mL) (degassed) was heated at 120° C. for 4 h. The reaction was diluted with ethyl acetate and washed with water three times. The ethyl acetate layer was dried ($Na_2SO_4$), filtered and concentrated under reduced pressure. The crude material was diluted with DCM (3 mL) and TFA (2 mL, 26.0 mmol) was added at room temperature. The mixture was stirred for 0.5 h at room temperature. The solvent was removed under reduced pressure and the crude was purified by reverse phase Prep HPLC. Obtained (S)-methyl (4-(5-((2-amino-2,4-dimethylpentyl)oxy)pyrimidin-2-yl)pyridin-2-yl)carbamate (1.9 mg, 5.07 μmol, 7% yield). $^1$H NMR (500 MHz, DMSO-$d_6$) δ 8.76 (s, 1H), 8.73 (s, 2H), 8.39 (d, J=5.5 Hz, 1H), 7.86 (d, J=5.1 Hz, 1H), 3.96 (s, 2H), 3.71 (s, 3H), 1.86-1.78 (m, 1H), 1.46-1.36 (m, 2H), 1.15 (s, 3H), 0.94 (m, 6H), three exchangeable protons not observed. LCMS (ESI) m/e 360.1 [(M+H)$^+$, calcd $C_{18}H_{26}N_5O_3$, 360.4]; LC/MS retention time (method B): $t_R$=1.55 min.

Example 211

(S)-methyl(4-(2-((2-amino-2,4-dimethylpentyl)oxy)pyrimidin-5-yl)pyridin-2-yl)carbamate

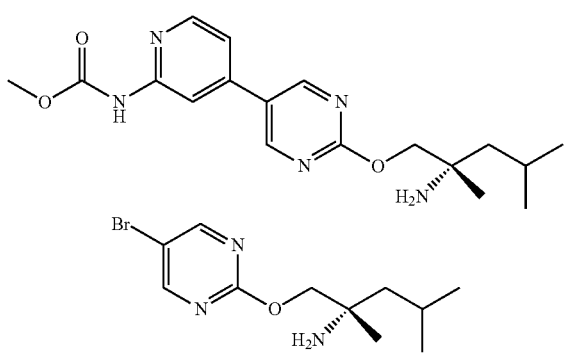

Part A: (S)-1-((5-bromopyrimidin-2-yl)oxy)-2,4-dimethylpentan-2-amine

Potassium tert-butoxide (0.242 mL, 0.242 mmol) was added to a solution of (S)-2-amino-2,4-dimethylpentan-1-ol (0.0265 g, 0.202 mmol) in THF (0.8 mL) at room temperature. After 5 min, 5-bromo-2-chloropyrimidine (0.047 g, 0.242 mmol) was added to the reaction mixture. The reaction was stirred at room temperature overnight. The reaction was quenched by adding water. The volatiles were removed under reduced pressure. The residue was diluted with ethyl acetate and water. The ethyl acetate layer was separated and the aqueous layer was extracted with ethyl acetate. The ethyl acetate layers were combined, dried ($Na_2SO_4$), filtered and concentrated under reduced pressure. The residue was purified via silica gel chromatography (eluted with methanol in DCM from 0 to 10%). Obtained (S)-1-((5-bromopyrimidin-2-yl)oxy)-2,4-dimethylpentan-2-amine (0.014 g, 0.050 mmol, 25% yield). $^1$H NMR (400 MHz, CHLOROFORM-d) δ 8.53 (s, 2H), 4.11 (d, J=2.8 Hz, 2H), 1.87-1.75 (m, 1H), 1.66-1.56 (m, 2H), 1.48 (dd, J=5.6, 3.9 Hz, 2H), 1.22 (s, 3H), 0.98 (m, 6H). LCMS (ESI) m/e 310.1 [(M+Na)$^+$, calcd $C_{11}H_{18}BrN_3ONa$, 310.1]; LC/MS retention time (method B): $t_R$=1.67 min.

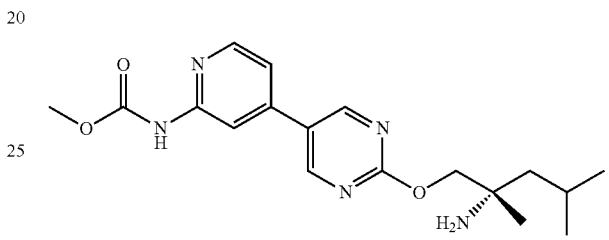

Part B: (S)-methyl (4-(2-((2-amino-2,4-dimethyl-pentyl)oxy)pyrimidin-5-yl)pyridin-2-yl)carbamate Suzuki reaction was performed as described in Example 193. Obtained (S)-methyl (4-(2-((2-amino-2,4-dimethylpentyl)oxy)pyrimidin-5-yl)pyridin-2-yl)carbamate (8.4 mg, 0.023 mmol, 47% yield). $^1$H NMR (400 MHz, CHLOROFORM-d) δ 8.60 (s, 2H), 8.49 (s, 1H), 8.31 (dd, J=5.3, 0.5 Hz, 1H), 8.18 (s, 1H), 7.11 (dd, J=5.4, 1.6 Hz, 1H), 3.85 (s, 3H), 3.84-3.69 (m, 2H), 2.00-1.92 (m, 1H), 1.91-1.78 (m, 1H), 1.56 (dd, J=14.3, 5.0 Hz, 1H), 1.36 (s, 3H), 1.02 (d, J=6.5 Hz, 3H), 0.92 (d, J=6.5 Hz, 3H), two exchangeable protons not observed; LCMS (ESI) m/e 359.9 [(M+H)$^+$, calcd $C_{18}H_{26}N_5O_3$, 360.2]; LC/MS retention time (method B): $t_R$=1.76 min.

Example 212

(S)-2,4-dimethyl-1-((2',4,6-trimethyl-[2,4'-bipyridin]-5-yl)oxy)pentan-2-amine

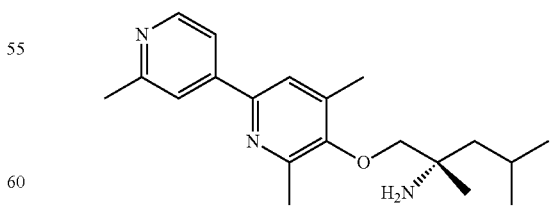

Suzuki reaction was performed as described in Example 193. Obtained (S)-2,4-dimethyl-1-((2',4,6-trimethyl-[2,4'-bipyridin]-5-yl)oxy)pentan-2-amine (10.3 mg, 0.031 mmol, 57% yield). $^1$H NMR (400 MHz, CHLOROFORM-d) δ 8.57 (d, J=5.3 Hz, 1H), 7.75 (s, 1H), 7.62 (dd, J=5.1, 1.4 Hz, 1H), 7.46 (s, 1H), 3.66-3.55 (m, 2H), 2.64 (s, 3H), 2.60 (s, 3H), 2.39 (s, 3H), 2.08 (br. S, 2H); 1.88 (tt, J=12.7, 6.4 Hz, 1H), 1.54 (d, J=5.8 Hz, 2H), 1.34 (s, 3H), 1.04 (d, J=6.5 Hz, 3H), 1.02 (d, J=6.8 Hz, 3H); LCMS (ESI) m/e 328.1 [(M+H)+, calcd $C_{20}H_{30}N_3O$, 328.2]; LC/MS retention time (method B): $t_R$=1.44 min.

Example 213

(S)-methyl(5-((2-amino-2,4-dimethylpentyl)oxy)-4,6-dimethyl-[2,4'-bipyridin]-2'-yl)carbamate

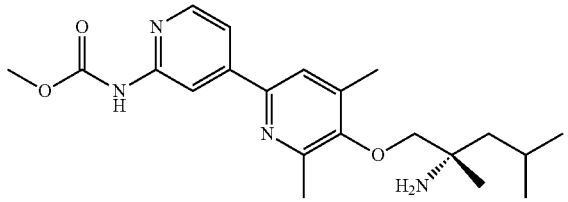 [SMILES: COC(=O)Nc1cc(-c2cc(C)c(OC[C@@](C)(N)CC(C)C)c(C)n2)ccn1]

Suzuki reaction was performed as described in Example 193. Obtained (S)-methyl (5-((2-amino-2,4-dimethylpentyl)oxy)-4,6-dimethyl-[2,4'-bipyridin]-2'-yl)carbamate (8.0 mg, 0.021 mmol, 38% yield). $^1$H NMR (400 MHz, CHLOROFORM-d) δ 8.52 (br. s, 2H), 8.33-8.17 (m, 1H), 7.68 (dd, J=5.3, 1.5 Hz, 1H), 7.53 (s, 1H), 3.85 (s, 3H), 3.65-3.52 (m, 2H), 2.60 (s, 3H), 2.56 (br.s, 2H), 2.38 (s, 3H), 1.88 (dquin, J=12.7, 6.4 Hz, 1H), 1.54 (d, J=5.3 Hz, 2H), 1.34 (s, 3H), 1.04 (d, J=6.8 Hz, 3H), 1.02 (d, J=6.5 Hz, 3H); LCMS (ESI) m/e 387.1 [(M+H)+, calcd $C_{21}H_{31}N_4O_3$, 387.2]; LC/MS retention time (method B): $t_R$=1.54 min.

Example 214

(S)-2,4-dimethyl-1-(4-(quinazolin-4-yl)-2-(trifluoromethyl)phenoxy)pentan-2-amine

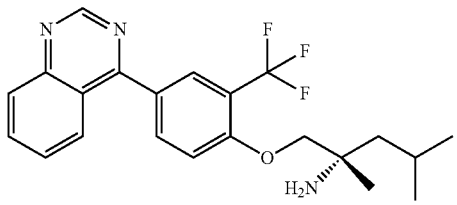 [SMILES: CC(C)C[C@](C)(N)COc1ccc(-c2ncnc3ccccc23)cc1C(F)(F)F]

Prepared as described in Example 19. Obtained (S)-2,4-dimethyl-1-(4-(quinazolin-4-yl)-2-(trifluoromethyl)phenoxy)pentan-2-amine (8.5 mg, 0.020 mmol, 19% yield). $^1$H NMR (500 MHz, DMSO-d$_6$) δ 9.34 (s, 1H), 8.17-8.03 (m, 5H), 7.79 (t, J=7.5 Hz, 1H), 7.47 (d, J=8.4 Hz, 1H), 3.94 (d, J=7.3 Hz, 2H), 1.85-1.76 (m, 1H), 1.43 (m, 2H), 1.16 (s, 3H), 0.97-0.89 (m, 6H), two exchangeable protons not observed; LCMS (ESI) m/e 404.2 [(M+H)+, calcd $C_{22}H_{25}F_3N_3O$, 404.4]; LC/MS retention time (method B): $t_R$=2.01 min.

Example 215

(S)-1-(4-(3,6-dihydro-2H-pyran-4-yl)-2-(trifluoromethyl)phenoxy)-2,4-dimethylpentan-2-amine

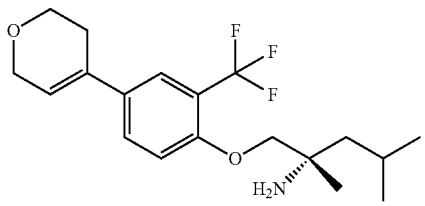

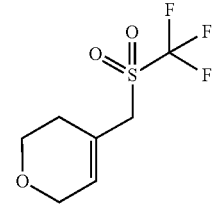

Part A: 3,6-Dihydro-2H-pyran-4-yl trifluoromethanesulfonate

KHMDS (6.66 mL, 3.33 mmol) was added to the THF (7 mL) solution of dihydro-2H-pyran-4(3H)-one (0.2224 g, 2.221 mmol) and 1,1,1-trifluoro-N-phenyl-N-((trifluoromethyl)sulfonyl)methanesulfonamide (0.952 g, 2.67 mmol) at −78° C. The reaction was stirred for 30 min. The reaction was diluted with diethyl ether and washed with water (3×). The diethyl ether layer was separated, dried (Na$_2$SO$_4$), filtered and concentrated. The crude material was carried on without further purification.

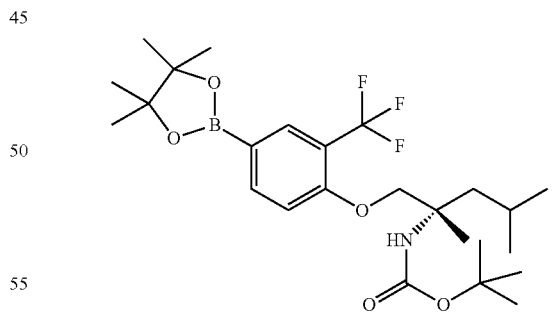

Part B: (S)-tert-butyl (2,4-dimethyl-1-(4-(4,4,5,5-tetramethyl-1,3,2-dioxaborolan-2-yl)-2-(trifluoromethyl)phenoxy)pentan-2-yl)carbamate Prepared as described in Example 77, Part C. The crude material was carried on without further purification. LCMS (ESI) m/e 523.2 [(M+Na)+, calcd $C_{25}H_{39}BF_3NO_5Na$, 524.3]; LC/MS retention time (method B): $t_R$=2.61 min.

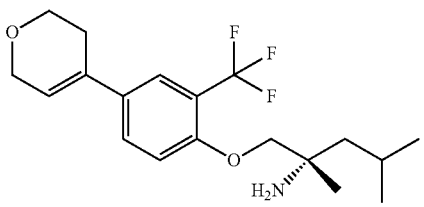 [SMILES: CC(C)C[C@](C)(N)COc1ccc(C2=CCOCC2)cc1C(F)(F)F]

Part C: (S)-1-(4-(3,6-dihydro-2H-pyran-4-yl)-2-(trifluoromethyl)phenoxy)-2,4-dimethylpentan-2-amine A mixture of 2N sodium carbonate solution (0.106 mL, 0.212 mmol), 1,1'-bis(diphenylphosphine)ferrocene-palladium(II)dichloride dichloromethane complex (6.06 mg, 7.42 μmol), 3,6-dihydro-2H-pyran-4-yl trifluoromethanesulfonate (98 mg, 0.424 mmol) and (S)-tert-butyl (2,4-dimethyl-1-(4-(4,4,5,5-tetramethyl-1,3,2-dioxaborolan-2-yl)-2-(trifluoromethyl)phenoxy)pentan-2-yl)carbamate (53.1 mg, 0.106 mmol) in dioxane (2 mL) (degassed) was heated at 120° C. for 5 h. The reaction was diluted with ethyl acetate and washed with water three times. The ethyl acetate layer was dried ($Na_2SO_4$), filtered and concentrated under reduced pressure. The residue was diluted with DCM (3 mL) and TFA (2 mL, 26.0 mmol) was added at room temperature. The reaction was stirred at room temperature for 0.5 h. The solvent was removed under reduced pressure and the residue was purified by reverse phase Prep HPLC to give (S)-1-(4-(3,6-dihydro-2H-pyran-4-yl)-2-(trifluoromethyl)phenoxy)-2,4-dimethylpentan-2-amine (2.7 mg, 0.213 mmol, 7% yield over three steps). $^1$H NMR (500 MHz, DMSO-$d_6$) δ 7.69 (d, J=8.4 Hz, 1H), 7.61 (s, 1H), 7.20 (d, J=8.4 Hz, 1H), 6.24 (m, 1H), 4.21 (d, J=2.6 Hz, 2H), 3.83-3.79 (m, 4H), 2.42 (br. s., 2H), 1.80-1.72 (m, 1H), 1.42-1.37 (m, 2H), 1.12 (s, 3H), 0.89 (m, 6H), two exchangeable protons not observed; LCMS (ESI) m/e 358.3 [(M+H)$^+$, calcd $C_{19}H_{27}F_3NO_2$, 358.2]; LC/MS retention time (method B): $t_R$=1.99 min.

Example 216

(S)-2,4-dimethyl-1-(4-(2-methylquinolin-4-yl)-2-(trifluoromethyl)phenoxy)pentan-2-amine

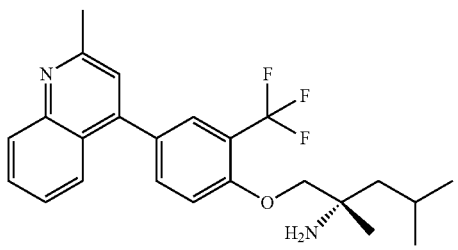 [SMILES: Cc1cc(-c2ccc(OC[C@@](C)(N)CC(C)C)c(C(F)(F)F)c2)c2ccccc2n1]

A mixture of 2N sodium carbonate solution (0.157 mL, 0.314 mmol), 1,1'-bis(diphenylphosphine)ferrocene-palladium(II)dichloride dichloromethane complex (8.97 mg, 10.99 μmol), (S)-tert-butyl (2,4-dimethyl-1-(4-(4,4,5,5-tetramethyl-1,3,2-dioxaborolan-2-yl)-2-(trifluoromethyl)phenoxy)pentan-2-yl)carbamate (0.079 g, 0.157 mmol) (prepared in Example 215, Part B) and 4-chloro-2-methylquinoline (0.05 ml, 0.248 mmol) in dioxane (1 mL) (degassed) was heated at 120° C. for 5 h. The reaction was diluted with ethyl acetate and washed with water three times. The ethyl acetate layer was dried ($Na_2SO_4$), filtered and concentrated under reduced pressure. The residue was diluted with DCM (3 mL) and was added TFA (2 mL, 26.0 mmol) at room temperature. The reaction was stirred at room temperature for 0.5 h. The solvent was removed under reduced pressure and the material was purified by reverse phase HPLC/MS to afford (S)-2,4-dimethyl-1-(4-(2-methylquinolin-4-yl)-2-(trifluoromethyl)phenoxy)pentan-2-amine (14.8 mg, 0.035 mmol, 22% yield). H NMR (500 MHz, DMSO-$d_6$) δ 8.02 (d, J=8.4 Hz, 1H), 7.83-7.73 (m, 4H), 7.55 (t, J=7.5 Hz, 1H), 7.44-7.41 (m, 2H), 3.94-3.87 (m, 2H), 3.47 (br. s., 2H), 2.70 (s, 3H), 1.87-1.79 (m, 1H), 1.42 (d, J=5.5 Hz, 2H), 1.15 (s, 3H), 0.95 (d, J=2.9 Hz, 3H), 0.93 (d, J=2.9 Hz, 3H); LCMS (ESI) m/e 417.3 [(M+H)$^+$, calcd $C_{24}H_{28}F_3N_2O$, 417.2]; LC/MS retention time (method B): $t_R$=2.26 min.

Example 217

(S)-1-(4-(6-chloroquinolin-4-yl)-2-(trifluoromethyl)phenoxy)-2,4-dimethylpentan-2-amine

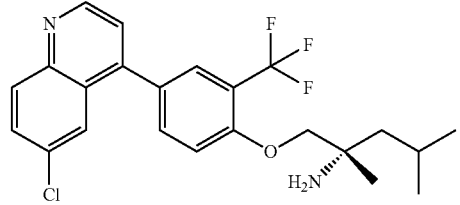 [SMILES: CC(C)C[C@](C)(N)COc1ccc(-c2ccnc3ccc(Cl)cc23)cc1C(F)(F)F]

Preparation was described as Example 19. Intermediate 6-chloro-4-(4,4,5,5-tetramethyl-1,3,2-dioxaborolan-2-yl)quinoline was prepared as described in Example 77, Part B and Part C. Obtained (S)-1-(4-(6-chloroquinolin-4-yl)-2-(trifluoromethyl)phenoxy)-2,4-dimethylpentan-2-amine (3.9 mg, 8.66 μmol, 7% yield). $^1$H NMR (500 MHz, DMSO-$d_6$) δ 8.98 (d, J=4.4 Hz, 1H), 8.16 (d, J=8.8 Hz, 1H), 7.85 (dd, J=9.0, 2.4 Hz, 2H), 7.79 (d, J=2.6 Hz, 2H), 7.59 (d, J=4.4 Hz, 1H), 7.45 (d, J=8.8 Hz, 1H), 3.97-3.89 (m, 2H), 1.83 (dt, J=12.7, 6.1 Hz, 1H), 1.43 (d, J=4.8 Hz, 2H), 1.16 (s, 3H), 0.94 (m, 6H); LCMS (ESI) m/e 419.9 [(M-$NH_2$)+, calcd $C_{23}H_{22}ClF_3NO$, 420.1]; LC/MS retention time (method B): $t_R$=2.07 min.

Example 218

(S)-1-((5-(5,7-difluoroquinolin-4-yl)-3-(trifluoromethyl)pyridin-2-yl)oxy)-2,4-dimethylpentan-2-amine

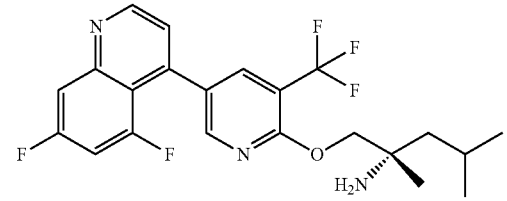

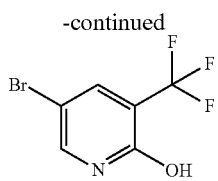

Part A: 5-Bromo-3-(trifluoromethyl)pyridin-2-ol

NBS (2.334 g, 13.11 mmol) was added portionwise to a solution of 3-(trifluoromethyl)pyridin-2-ol (1.6449 g, 10.09 mmol) in THF (15 mL) at room temperature. The reaction was stirred at room temperature over the weekend. The reaction was diluted with ethyl acetate and washed with water three times. The ethyl acetate layer was separated, dried (Na$_2$SO$_4$), filtered and concentrated under reduced pressure to give crude 5-bromo-3-(trifluoromethyl)pyridin-2-ol (2.12 g, 6.57 mmol, 65% yield) as a yellow solid. The material was carried on without further purification. LCMS (ESI) m/e 241.8 [(M+H)$^+$, calcd C$_6$H$_4$BrF$_3$NO, 241.9]; LC/MS retention time (method B): t$_R$=1.57 min.

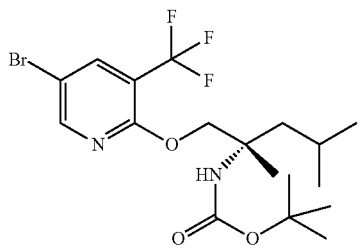 [SMILES: CC(C)C[C@@](C)(COc1ncc(Br)cc1C(F)(F)F)NC(=O)OC(C)(C)C]

Part B: (S)-tert-butyl (1-((5-bromo-3-(trifluoromethyl)pyridin-2-yl)oxy)-2,4-dimethylpentan-2-yl)carbamate A mixture of potassium carbonate (0.113 g, 0.814 mmol), (S)-tert-butyl 4-isobutyl-4-methyl-1,2,3-oxathiazolidine-3-carboxylate 2,2-dioxide (0.1593 g, 0.543 mmol) and 5-bromo-3-(trifluoromethyl)pyridin-2-ol (0.197 g, 0.814 mmol) in DMF (2 mL) was heated at 80° C. overnight. The reaction was diluted with ethyl acetate and washed with water three times. The ethyl acetate layer was separated, dried (Na$_2$SO$_4$), filtered and concentrated under reduced pressure. The residue was purified by silica gel chromatography (eluted with ethyl acetate in hexane from 0 to 10%) to give (S)-tert-butyl (1-((5-bromo-3-(trifluoromethyl)pyridin-2-yl)oxy)-2,4-dimethylpentan-2-yl)carbamate (0.059 g, 0.111 mmol, 20% yield). $^1$H NMR (400 MHz, CHLOROFORM-d) δ 8.34 (d, J=2.5 Hz, 1H), 7.95 (d, J=2.5 Hz, 1H), 4.59-4.52 (m, 2H), 4.39 (d, J=10.3 Hz, 1H), 1.89-1.72 (m, 2H), 1.54 (d, J=8.8 Hz, 1H), 1.39 (s, 9H), 1.37 (s, 3H), 0.97 (m, 6H); $^{19}$F NMR (376 MHz, CHLOROFORM-d) δ −64.11 (s, 3F). LCMS (ESI) m/e 476.9 [(M+Na)$^+$, calcd C$_{18}$H$_{26}$BrF$_3$N$_2$O$_3$Na, 477.1]; LC/MS retention time (method B): t$_R$=2.54 min.

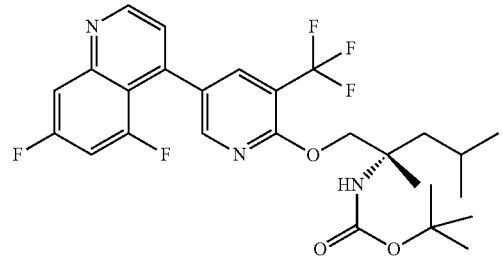 [SMILES: CC(C)C[C@@](C)(COc1ncc(-c2ccnc3cc(F)cc(F)c23)cc1C(F)(F)F)NC(=O)OC(C)(C)C]

Part C: (S)-tert-butyl (1-((5-(5,7-difluoroquinolin-4-yl)-3-(trifluoromethyl)pyridin-2-yl)oxy)-2,4-dimethylpentan-2-yl)carbamate Prepared as described in Example 193. Obtained (S)-tert-butyl (1-((5-(5,7-difluoroquinolin-4-yl)-3-(trifluoromethyl)pyridin-2-yl)oxy)-2,4-dimethylpentan-2-yl)carbamate (26.0 mg, 0.048 mmol, 80% yield). LCMS (ESI) m/e 540.2 [(M+H)$^+$, calcd C$_{27}$H$_{31}$F$_5$N$_3$O$_3$, 540.2]; LC/MS retention time (method B): t$_R$=2.53 min.

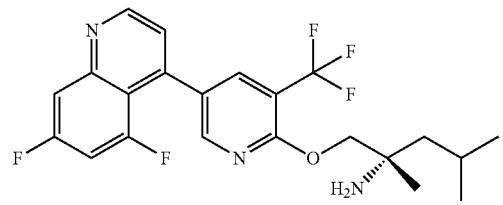 [SMILES: CC(C)C[C@](C)(N)COc1ncc(-c2ccnc3cc(F)cc(F)c23)cc1C(F)(F)F]

Part D: (S)-1-((5-(5,7-difluoroquinolin-4-yl)-3-(trifluoromethyl)pyridin-2-yl)oxy)-2,4-dimethylpentan-2-amine TFA deprotection was performed as described in Example 32. Obtained (S)-1-((5-(5,7-difluoroquinolin-4-yl)-3-(trifluoromethyl)pyridin-2-yl)oxy)-2,4-dimethylpentan-2-amine (12.5 mg, 0.025 mmol, 56% yield). $^1$H NMR (500 MHz, DMSO-d$_6$) δ 9.34 (s, 1H), 8.17-8.03 (m, 5H), 7.79 (t, J=7.5 Hz, 1H), 7.47 (d, J=8.4 Hz, 1H), 3.94 (d, J=7.3 Hz, 2H), 1.85-1.76 (m, 1H), 1.43 (m, 2H), 1.16 (s, 3H), 0.97-0.89 (m, 6H). LCMS (ESI) m/e 440.1 [(M+H)$^+$, calcd C$_{22}$H$_{23}$F$_5$N$_3$O, 440.2]; LC/MS retention time (method B): t$_R$=2.04 min.

Example 219

(S)-2,4-dimethyl-1-((5-(quinolin-4-yl)-3-(trifluoromethyl)pyridin-2-yl)oxy)pentan-2-amine

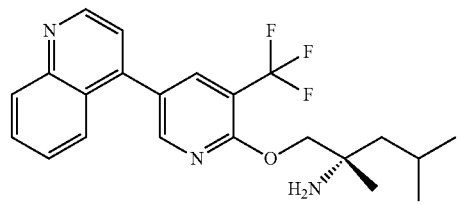

Prepared as described in Example 218. Obtained (S)-2,4-dimethyl-1-((5-(quinolin-4-yl)-3-(trifluoromethyl)pyridin-2-yl)oxy)pentan-2-amine (6.1 mg, 0.015 mmol, 60% yield) as an off-white solid. $^1$H NMR (500 MHz, DMSO-$d_6$) δ 8.99 (d, J=4.4 Hz, 1H), 8.63 (s, 1H), 8.31 (s, 1H), 8.14 (d, J=8.4 Hz, 1H), 7.88-7.82 (m, 2H), 7.66 (t, J=7.5 Hz, 1H), 7.60 (d, J=4.4 Hz, 1H), 4.25-4.18 (m, 2H), 1.84 (dt, J=12.7, 6.1 Hz, 1H), 1.42 (d, J=5.5 Hz, 2H), 1.15 (s, 3H), 0.94 (m, 6H), two exchangeable protons not observed; LCMS (ESI) m/e 404.0 [(M+H)$^+$, calcd $C_{22}H_{25}F_3N_3O$, 404.4]; LC/MS retention time (method B): $t_R$=1.77 min.

Example 220

(S)-methyl (6-((2-amino-2,4-dimethylpentyl)oxy)-5-(trifluoromethyl)-[3,4'-bipyridin]-2'-yl)carbamate

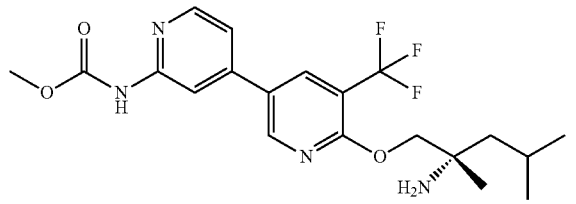 [SMILES: COC(=O)Nc1cc(-c2cnc(OC[C@@](C)(N)CC(C)C)c(C(F)(F)F)c2)ccn1]

Prepared as described in Example 218. Obtained (S)-methyl (6-((2-amino-2,4-dimethylpentyl)oxy)-5-(trifluoromethyl)-[3,4'-bipyridin]-2'-yl)carbamate (13.8 mg, 0.032 mmol, 96% yield) as an off-white solid. $^1$H NMR (500 MHz, DMSO-$d_6$) δ 10.35 (br. s., 1H), 8.79 (s, 1H), 8.38-8.32 (m, 2H), 8.11 (s, 1H), 7.48 (d, J=5.1 Hz, 1H), 4.17 (q, J=10.3 Hz, 2H), 3.38 (br. s., 3H), 1.85-1.74 (m, 1H), 1.38 (d, J=5.5 Hz, 2H), 1.11 (s, 3H), 0.91 (m, 6H), two exchangeable protons not observed; LCMS (ESI) m/e 427.0 [(M+H)$^+$, calcd $C_2H_{26}F_3N_4O_3$, 427.2]; LC/MS retention time (method B): $t_R$=1.84 min.

Example 221

(S)-2,4-dimethyl-1-((2'-methyl-5-(trifluoromethyl)-[3,4'-bipyridin]-6-yl)oxy)pentan-2-amine

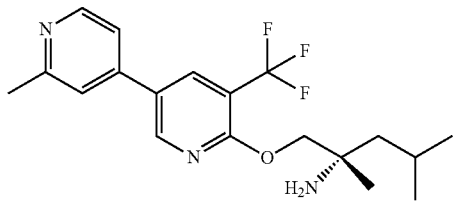 [SMILES: Cc1cc(-c2cnc(OC[C@@](C)(N)CC(C)C)c(C(F)(F)F)c2)ccn1]

Prepared as described in Example 218. Obtained (S)-2,4-dimethyl-1-((2'-methyl-5-(trifluoromethyl)-[3,4'-bipyridin]-6-yl)oxy)pentan-2-amine (4.6 mg, 0.012 mmol, 68% yield). $^1$H NMR (500 MHz, DMSO-$d_6$) δ 8.87 (s, 1H), 8.52 (d, J=5.1 Hz, 1H), 8.46 (s, 1H), 7.72 (s, 1H), 7.62 (d, J=4.0 Hz, 1H), 4.16 (q, J=10.1 Hz, 2H), 2.54 (s, 3H), 1.84-1.75 (m, 1H), 1.37 (d, J=5.5 Hz, 2H), 1.10 (s, 3H), 0.91 (m, 6H), two exchangeable protons not observed; LCMS (ESI) m/e 368.0 [(M+H)$^+$, calcd $C_{19}H_{25}F_3N_3O$, 368.2]; LC/MS retention time (method B): $t_R$=1.57 min.

Example 222

(S)-1-((5-(6-chloroquinolin-4-yl)-3-methylpyridin-2-yl)oxy)-2,4-dimethylpentan-2-amine

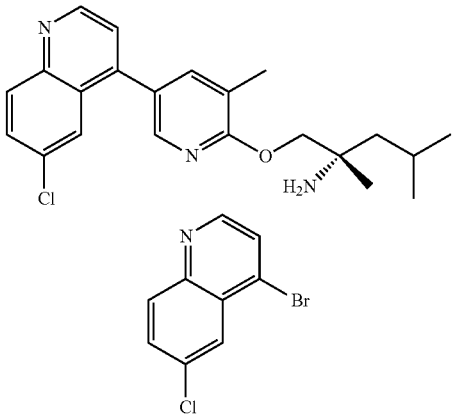

Part A: 4-Bromo-6-chloroquinoline

Prepared as described in Example 77, Part B. Obtained 4-Bromo-6-chloroquinoline (0.322 g, 1.33 mmol, 76% yield). H NMR (400 MHz, CHLOROFORM-d) δ 8.68 (d, J=4.8 Hz, 1H), 8.21 (d, J=2.3 Hz, 1H), 8.07 (d, J=8.8 Hz, 1H), 7.76-7.70 (m, 2H). LCMS (ESI) m/e 243.7 [(M+H)$^+$, calcd $C_9H_5BrNCl$, 243.5]; LC/MS retention time (method B): $t_R$=2.07 min.

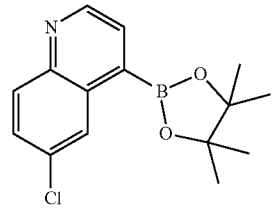 [SMILES: CC1(C)OB(c2ccnc3ccc(Cl)cc23)OC1(C)C]

Part B: 7-Chloro-4-(4,4,5,5-tetramethyl-1,3,2-dioxaborolan-2-yl)quinoline

Prepared as described in Example 77, Part C. Carried on without further purification. LCMS (ESI) m/e 207.9 [(M-NH$_2$)+, calcd $C_9H_7BNClO_2$, 207.0]; LC/MS retention time (method B): $t_R$=1.21 min.

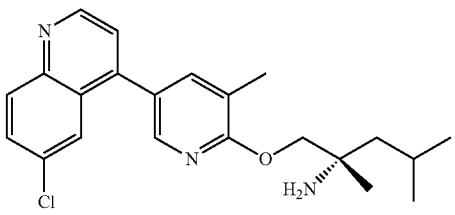

Part C: (S)-1-((5-(6-chloroquinolin-4-yl)-3-methylpyridin-2-yl)oxy)-2,4-dimethylpentan-2-amine Intermediate (S)-1-((5-bromo-3-methylpyridin-2-yl)oxy)-2,4-dimethylpentan-2-amine prepared as in Example 52, Part A. Suzuki reaction was performed as described in Example 193. Obtained (S)-1-((5-(6-chloroquinolin-4-yl)-3-methylpyridin-2-yl)oxy)-2,4-dimethylpentan-2-amine (56.7 mg, 0.143 mmol, 26% yield over two steps). $^1$H NMR (400 MHz, CHLOROFORM-d) δ 8.94 (d, J=4.5 Hz, 1H), 8.14 (d, J=9.0 Hz, 1H), 8.08 (d, J=1.8 Hz, 1H), 7.82 (d, J=2.3 Hz, 1H), 7.69 (dd, J=8.8, 2.3 Hz, 1H), 7.57-7.54 (m, 1H), 7.32 (d, J=4.5 Hz, 1H), 4.64-4.42 (m, 2H), 1.93-1.75 (m, 3H), 1.54 (s, 3H), 1.03 (d, J=6.3 Hz, 3H), 1.01 (d, J=6.3 Hz, 3H), two exchangeable protons not observed; LCMS (ESI) m/e 366.9 [(M-NH$_2$)+, calcd C$_{22}$H$_{24}$N$_2$ClO, 367.2]; LC/MS retention time (method B): $t_R$=1.88 min.

Example 223

(S)-1-((5-(6-fluoroquinolin-4-yl)-3-methylpyridin-2-yl)oxy)-2,4-dimethylpentan-2-amine

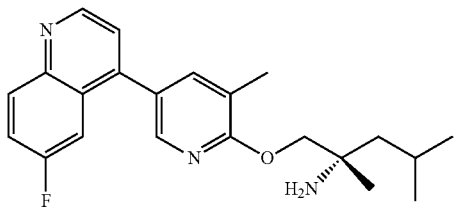 [SMILES: Cc1cc(-c2ccnc3ccc(Cl)cc23)cnc1OC[C@@](C)(N)CC(C)C]

Intermediate (S)-1-((5-bromo-3-methylpyridin-2-yl)oxy)-2,4-dimethylpentan-2-amine prepared as described in Example 52, Part A. The corresponding borolate was prepared as described in Example 77, Part C. Suzuki reaction was performed as described in Example 193. Obtained (S)-1-((5-(6-fluoroquinolin-4-yl)-3-methylpyridin-2-yl)oxy)-2,4-dimethylpentan-2-amine (9.7 mg, 0.026 mmol, 14% yield). $^1$H NMR (400 MHz, CHLOROFORM-d) δ 8.92 (d, J=4.5 Hz, 1H), 8.31-8.16 (m, 1H), 8.12 (d, J=2.0 Hz, 1H), 7.61-7.49 (m, 3H), 7.34 (d, J=4.3 Hz, 1H), 4.27-4.18 (m, 2H), 2.35 (s, 3H), 1.93-1.78 (m, 1H), 1.63-1.49 (m, 2H), 1.29 (s, 3H), 1.03 (d, J=6.8 Hz, 3H), 1.01 (d, J=6.8 Hz, 3H), two exchangeable protons not observed; LCMS (ESI) m/e 368.2 [(M+H)+, calcd C$_{22}$H$_{27}$N$_3$FO, 368.2]; LC/MS retention time (method B): $t_R$=1.78 min.

Example 224

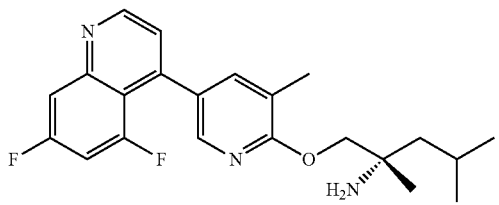

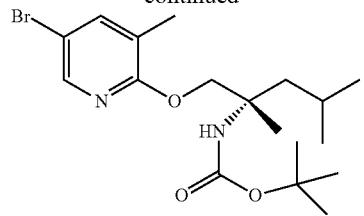

Part A: (S)-tert-butyl (1-((5-bromo-3-methylpyridin-2-yl)oxy)-2,4-dimethylpentan-2-yl)carbamate Prepared as described in Example 53, Part A. obtained (S)-1-((5-(5,7-difluoroquinolin-4-yl)-3-methylpyridin-2-yl)oxy)-2,4-dimethylpentan-2-amine (3.06 g, 7.32 mmol, 86% yield). LCMS (ESI) m/e 422.9 [(M+Na)+, calcd C$_{18}$H$_{29}$BrN$_2$O$_3$Na, 423.1]; LC/MS retention time (method B): $t_R$=2.48 min.

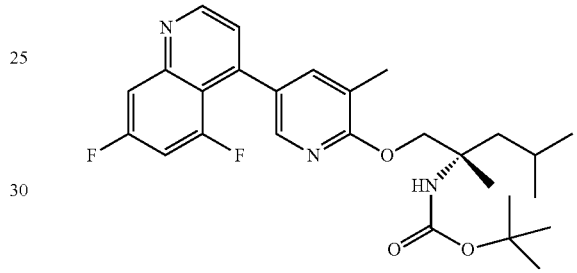

Part B: (S)-tert-butyl (1-((5-(5,7-difluoroquinolin-4-yl)-3-methylpyridin-2-yl)oxy)-2,4-dimethylpentan-2-yl)carbamate Suzuki reaction was performed as described in Example 193. Obtained (S)-tert-butyl (1-((5-(5,7-difluoroquinolin-4-yl)-3-methylpyridin-2-yl)oxy)-2,4-dimethylpentan-2-yl)carbamate (43.8 mg, 0.090 mmol, 59% yield). LCMS (ESI) m/e 486.1 [(M+H)+, calcd C$_{27}$H$_{34}$N$_3$F$_2$O$_3$, 486.3]; LC/MS retention time (method B): $t_R$=2.44 min.

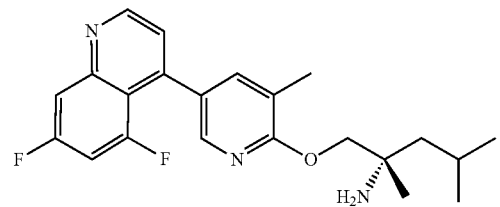 [SMILES: Cc1cc(-c2ccnc3cc(F)cc(F)c23)cnc1OC[C@@](C)(N)CC(C)C]

Part C: (S)-1-((5-(5,7-difluoroquinolin-4-yl)-3-methylpyridin-2-yl)oxy)-2,4-dimethylpentan-2-amine TFA deprotection was performed as described in Example 32. Obtained (S)-1-((5-(5,7-difluoroquinolin-4-yl)-3-methylpyridin-2-yl)oxy)-2,4-dimethylpentan-2-amine (33.9 mg, 0.088 mmol, 98% yield). $^1$H NMR (500 MHz, DMSO-d$_6$) δ 9.00 (d, J=4.4 Hz, 1H), 8.10 (s, 1H), 7.79 (d, J=9.5 Hz, 1H), 7.75 (br. s., 1H), 7.61-7.52 (m, 1H), 7.45 (d, J=4.4 Hz, 1H), 4.45-4.31 (m, 2H), 2.33 (s, 3H), 1.89-1.74 (m, 2H), 1.66 (dd, J=14.1, 5.3 Hz, 1H), 1.42 (s, 3H), 0.98 (d, J=6.6 Hz, 3H), 0.94 (d, J=6.6 Hz, 3H), two exchangeable protons not observed; LCMS (ESI) m/e 386.3 [(M+H)$^+$, calcd $C_{22}H_{26}N_3F_2O$, 386.2]; LC/MS retention time (method B): $t_R$=1.84 min.

Example 225

(S)-1-((5-(7-chloroquinolin-4-yl)-3-methylpyridin-2-yl)oxy)-2,4-dimethylpentan-2-amine

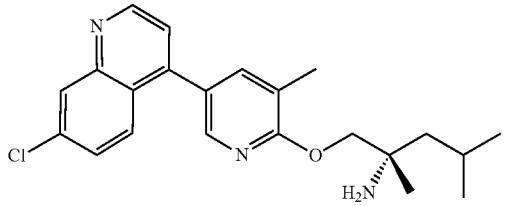 [SMILES: Cc1cc(-c2ccnc3cc(Cl)ccc23)cnc1OC[C@@](C)(N)CC(C)C]

Intermediate(S)-1-((5-bromo-3-methylpyridin-2-yl)oxy)-2,4-dimethylpentan-2-amine was prepared as described in Example 52, Part A. The corresponding borolate was prepared as described in Example 77, Part C. Suzuki reaction was performed as described in Example 193. Obtained (S)-1-((5-(7-chloroquinolin-4-yl)-3-methylpyridin-2-yl)oxy)-2,4-dimethylpentan-2-amine (22.5 mg, 0.058 mmol, 51% yield). $^1$H NMR (500 MHz, DMSO-d$_6$) δ 8.98 (d, J=4.4 Hz, 1H), 8.17 (s, 2H), 7.96-7.91 (m, 1H), 7.81 (s, 1H), 7.66 (dd, J=9.0, 2.0 Hz, 1H), 7.53 (d, J=4.4 Hz, 1H), 4.15-4.07 (m, 2H), 2.30 (s, 3H), 1.87-1.79 (m, 1H), 1.45 (t, J=6.4 Hz, 2H), 1.17 (s, 3H), 0.95 (m, 6H), two exchangeable protons not observed; LCMS (ESI) m/e 384.3 [(M+H)$^+$, calcd $C_{22}H_{27}N_3ClO$, 384.2]; LC/MS retention time (method B): $t_R$=1.98 min.

Example 226

(S)-1-((6-(5,7-difluoroquinolin-4-yl)-4-methylpyridin-3-yl)oxy)-2,4-dimethylpentan-2-amine

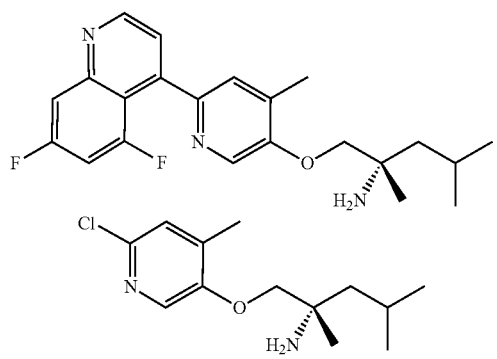

Part A: (S)-1-((6-chloro-4-methylpyridin-3-yl)oxy)-2,4-dimethylpentan-2-amine

A mixture of TFA (0.4 mL, 5.19 mmol) and (S)-tert-butyl (1-((6-chloro-4-methylpyridin-3-yl)oxy)-2,4-dimethylpentan-2-yl)carbamate (0.064 g, 0.179 mmol, 0.179 mmol) in CH$_2$Cl$_2$ (4 mL) was stirred at room temperature for 4 h. LCMS showed complete conversion to (S)-1-((6-chloro-4-methylpyridin-3-yl)oxy)-2,4-dimethylpentan-2-amine. The solvent was removed via vacuum and the material was used without further purification. LCMS (ESI) m/e 257.1 [(M+H)$^+$, calcd $C13H_{22}ClN_2O$, 257.1]; LC/MS retention time (method B): $t_R$=1.64 min.

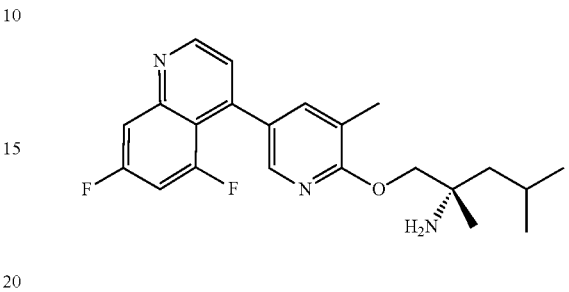

Part B: (S)-1-((6-(5,7-difluoroquinolin-4-yl)-4-methylpyridin-3-yl)oxy)-2,4-dimethylpentan-2-amine Suzuki coupling was performed as described in Example 77, Part D. Obtained (S)-1-((6-(5,7-difluoroquinolin-4-yl)-4-methylpyridin-3-yl)oxy)-2,4-dimethylpentan-2-amine (12.2 mg, 0.031 mmol, 43% yield). $^1$H NMR (500 MHz, DMSO-d6) δ 9.01 (d, J=4.4 Hz, 1H), 8.30 (s, 1H), 7.78 (d, J=8.8 Hz, 1H), 7.53 (br. s., 1H), 7.49 (d, J=4.4 Hz, 1H), 7.47 (s, 1H), 3.94 (s, 2H), 2.31 (s, 3H), 1.88-1.80 (m, 1H), 1.48 (dd, J=13.0, 5.3 Hz, 2H), 1.20 (s, 3H), 0.95 (m, 6H), two exchangeable protons not observed; LCMS (ESI) m/e 386.0 [(M+H)$^+$, calcd $C_{22}H_{26}F_2N_3O$, 386.2]; LC/MS retention time (method B): $t_R$=1.79 min.

Example 227

(S)-1-((6-(7-fluoroquinolin-4-yl)-4-methylpyridin-3-yl)oxy)-2,4-dimethylpentan-2-amine

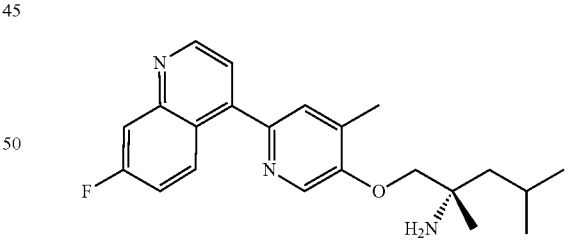

Prepared as described in Example 226. Obtained (S)-1-((6-(7-fluoroquinolin-4-yl)-4-methylpyridin-3-yl)oxy)-2,4-dimethylpentan-2-amine (6.0 mg, 0.016 mmol, 63% yield). $^1$H NMR (400 MHz, DMSO-d$_6$) δ 8.98 (d, J=4.5 Hz, 1H), 8.47 (s, 1H), 8.34 (dd, J=9.3, 6.3 Hz, 1H), 7.82 (dd, J=10.3, 2.8 Hz, 1H), 7.67 (s, 1H), 7.59 (d, J=4.5 Hz, 1H), 7.55 (td, J=8.9, 2.8 Hz, 1H), 4.10 (s, 2H), 2.37 (s, 3H), 1.86-1.78 (m, 1H), 1.63 (br. s., 1H), 1.57-1.50 (m, 1H), 1.30 (s, 3H), 0.95 (dd, J=11.7, 6.7 Hz, 6H), two exchangeable protons not observed; LCMS (ESI) m/e 368.0 [(M+H)$^+$, calcd $C_{22}H_{27}FN_3O$, 368.2]; LC/MS retention time (method B): $t_R$=1.67 min.

Example 228

(S)-1-((2',4-dimethyl-[2,4'-bipyridin]-5-yl)oxy)-2,4-dimethylpentan-2-amine

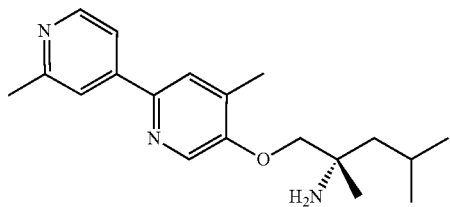

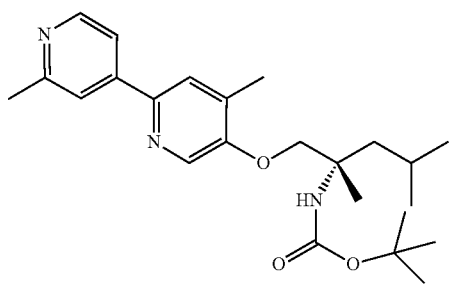

Part A: (S)-tert-butyl (1-((2',4-dimethyl-[2,4'-bipyridin]-5-yl)oxy)-2,4-dimethylpentan-2-yl)carbamate Suzuki coupling was performed as described in Example 77, Part D. The crude was used in the next reaction without purification. LCMS (ESI) m/e 414.0 [(M+H)$^+$, calcd C$_{24}$H$_{36}$N$_3$O$_3$, 414.3]; LC/MS retention time (method B): t$_R$=2.02 min.

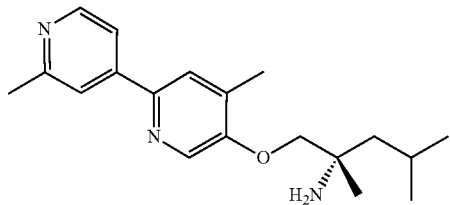 [SMILES: Cc1cc(-c2cc(C)c(OC[C@@](C)(N)CC(C)C)cn2)ccn1]

Part B: (S)-1-((2',4-dimethyl-[2,4'-bipyridin]-5-yl)oxy)-2,4-dimethylpentan-2-amine TFA deprotection as described in Example 32. Obtained (S)-1-((2',4-dimethyl-[2,4'-bipyridin]-5-yl)oxy)-2,4-dimethylpentan-2-amine (2.2 mg, 6.95 μmol, 17% yield over two steps). $^1$H NMR (600 MHz, DMSO-d$_6$) δ 8.50 (d, J=5.1 Hz, 1H), 8.34 (s, 1H), 7.96 (s, 1H), 7.86 (s, 1H), 7.78 (d, J=5.1 Hz, 1H), 3.88 (br. s., 2H), 2.54 (s, 3H), 2.31 (s, 3H), 1.82 (br. s., 1H), 1.45-1.38 (m, 2H), 1.15 (s, 3H), 0.93 (m, 6H), two exchangeable protons not observed; LCMS (ESI) m/e 314.1 [(M+H)$^+$, calcd C$_{19}$H$_{27}$N$_3$O, 314.2]; LC/MS retention time (method B): t$_R$=1.50 min.

Example 229

(S)-1-((6-(6-chloroquinolin-4-yl)-4-methylpyridin-3-yl)oxy)-2,4-dimethylpentan-2-amine

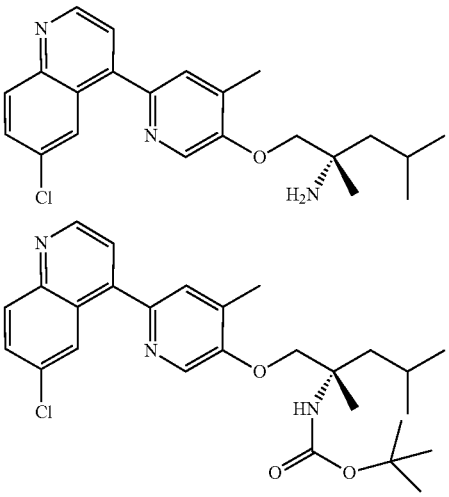

Part A: (S)-tert-butyl (1-((6-(6-chloroquinolin-4-yl)-4-methylpyridin-3-yl)oxy)-2,4-dimethylpentan-2-yl)carbamate Suzuki coupling was performed as described in Example 77, Part D. The crude was used in the next reaction without purification. LCMS (ESI) m/e 483.9 [(M+H)$^+$, calcd C$_{27}$H$_{35}$ClN$_3$O$_3$, 484.2]; LC/MS retention time (method B): t$_R$=2.24 min.

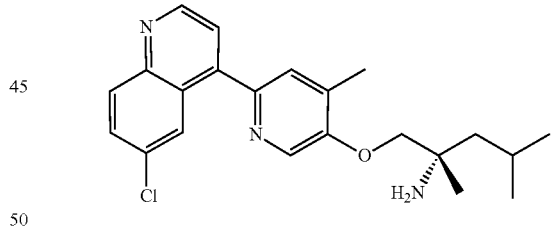

Part B: (S)-1-((6-(6-chloroquinolin-4-yl)-4-methylpyridin-3-yl)oxy)-2,4-dimethylpentan-2-amine TFA deprotection as described in Example 32. Obtained (S)-1-((6-(6-chloroquinolin-4-yl)-4-methylpyridin-3-yl)oxy)-2,4-dimethylpentan-2-amine (6.8 mg, 0.017 mmol, 16% yield over two steps). $^1$H NMR (500 MHz, DMSO-d$_6$) δ 9.00 (d, J=4.4 Hz, 1H), 8.48 (s, 1H), 8.40 (d, J=2.2 Hz, 1H), 8.12 (d, J=9.2 Hz, 1H), 7.82 (dd, J=8.8, 2.2 Hz, 1H), 7.71 (s, 1H), 7.69 (d, J=4.8 Hz, 1H), 3.95 (s, 2H), 2.35 (s, 3H), 1.84 (d, J=6.2 Hz, 1H), 1.45 (t, J=6.6 Hz, 2H), 1.18 (s, 3H), 0.95 (m, 6H), two exchangeable protons not observed; LCMS (ESI) m/e 383.9 [(M+H)$^+$, calcd C$_{22}$H$_{27}$ClN$_3$O, 384.2]; LC/MS retention time (method B): t$_R$=1.81 min.

Example 230

(S)-1-((6-(6-fluoroquinolin-4-yl)-4-methylpyridin-3-yl)oxy)-2,4-dimethylpentan-2-amine

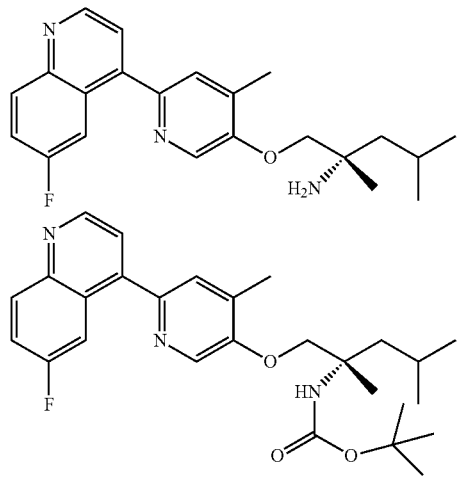

Part A: (S)-tert-butyl (1-((6-(6-fluoroquinolin-4-yl)-4-methylpyridin-3-yl)oxy)-2,4-dimethylpentan-2-yl) carbamate Suzuki coupling was performed as described in Example 77, Part D. Obtained (S)-tert-butyl (1-((6-(6-fluoroquinolin-4-yl)-4-methylpyridin-3-yl)oxy)-2,4-dimethylpentan-2-yl) carbamate (33.2 mg, 0.035 mmol, 35% yield). LCMS (ESI) m/e 468.2 [(M+H)$^+$, calcd $C_{27}H_{35}FN_3O_3$, 468.3]; LC/MS retention time (method B): $t_R$=2.22 min.

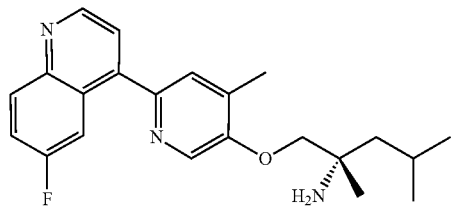 [SMILES: Cc1cc(-c2ccnc3ccc(F)cc23)ncc1OC[C@@](C)(N)CC(C)C]

Part B: (S)-1-((6-(6-fluoroquinolin-4-yl)-4-methylpyridin-3-yl)oxy)-2,4-dimethylpentan-2-amine TFA deprotection as described in Example 32. Obtained (S)-1-((6-(6-fluoroquinolin-4-yl)-4-methylpyridin-3-yl)oxy)-2,4-dimethylpentan-2-amine (21.7 mg, 0.058 mmol, 82% yield). $^1$H NMR (500 MHz, DMSO-$d_6$) δ 8.98 (d, J=4.4 Hz, 1H), 8.53 (s, 1H), 8.18 (dd, J=9.2, 5.5 Hz, 1H), 8.07 (dd, J=11.0, 2.9 Hz, 1H), 7.73 (s, 2H), 7.69 (d, J=4.4 Hz, 1H), 4.15 (d, J=4.4 Hz, 2H), 2.39 (s, 3H), 1.89-1.81 (m, 1H), 1.66 (d, J=5.1 Hz, 1H), 1.56 (dd, J=14.1, 5.3 Hz, 1H), 1.33 (s, 3H), 0.99 (d, J=6.6 Hz, 3H), 0.96 (d, J=6.6 Hz, 3H), two exchangeable protons not observed; LCMS (ESI) m/e 368.2 [(M+H)$^+$, calcd $C_{22}H_{27}FN_3O$, 368.2]; LC/MS retention time (method B): $t_R$=1.67 min.

Example 231

(S)-1-((6-(7-chloroquinolin-4-yl)-4-methylpyridin-3-yl)oxy)-2,4-dimethylpentan-2-amine

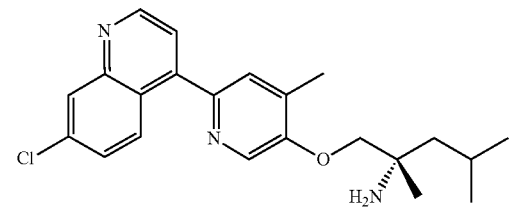 [SMILES: Cc1cc(-c2ccnc3cc(Cl)ccc23)ncc1OC[C@@](C)(N)CC(C)C]

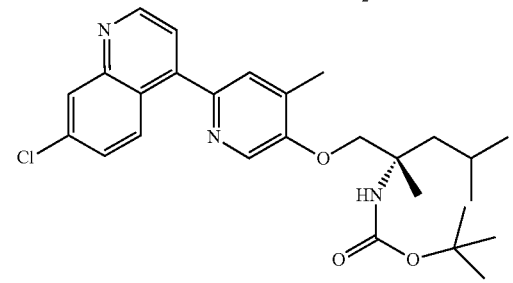

Part A: (S)-tert-butyl (1-((6-(7-chloroquinolin-4-yl)-4-methylpyridin-3-yl)oxy)-2,4-dimethylpentan-2-yl) carbamate Suzuki coupling was performed as described in Example 77, Part D. The crude was used in the next reaction without purification. LCMS (ESI) m/e 484.2 [(M+H)$^+$, calcd $C_{27}H_{35}ClN_3O_3$, 484.2]; LC/MS retention time (method B): $t_R$=2.32 min.

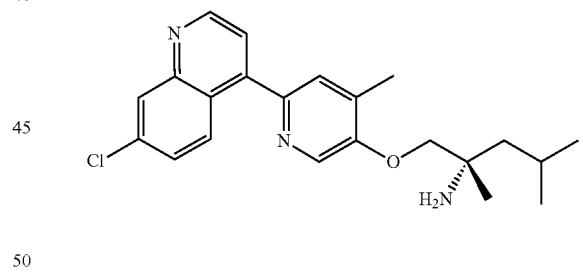

Part B: (S)-1-((6-(7-chloroquinolin-4-yl)-4-methylpyridin-3-yl)oxy)-2,4-dimethylpentan-2-amine TFA deprotection as described in Example 32. Obtained (S)-tert-butyl (1-((6-(7-chloroquinolin-4-yl)-4-methylpyridin-3-yl)oxy)-2,4-dimethylpentan-2-yl)carbamate (15.5 mg, 0.039 mmol, 34% yield over two steps). $^1$H NMR (500 MHz, DMSO-$d_6$) δ 8.98 (d, J=4.4 Hz, 1H), 8.53 (s, 1H), 8.18 (dd, J=9.2, 5.5 Hz, 1H), 8.07 (dd, J=11.0, 2.9 Hz, 1H), 7.73 (s, 2H), 7.69 (d, J=4.4 Hz, 1H), 4.15 (d, J=4.4 Hz, 2H), 2.39 (s, 3H), 1.89-1.81 (m, 1H), 1.66 (d, J=5.1 Hz, 1H), 1.56 (dd, J=14.1, 5.3 Hz, 1H), 1.33 (s, 3H), 0.99 (d, J=6.6 Hz, 3H), 0.96 (d, J=6.6 Hz, 3H), two exchangeable protons not observed; LCMS (ESI) m/e 384.1 [(M+H)$^+$, calcd $C_{22}H_{27}ClN_3O$, 384.2]; LC/MS retention time (method B): $t_R$=1.84 min.

Example 232

(S)-1-((6-(7-fluoroquinolin-4-yl)-4-methylpyridin-3-yl)oxy)-2,4-dimethylpentan-2-amine

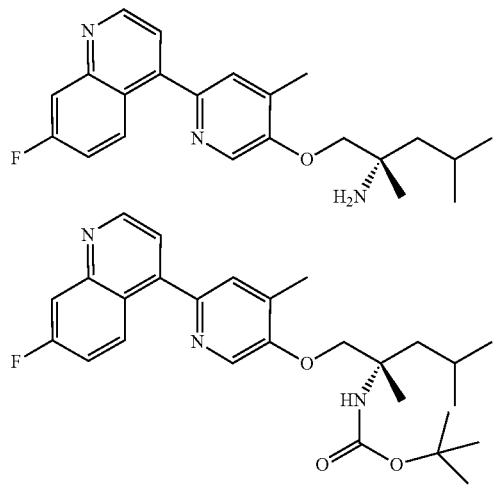

Part A: (S)-tert-butyl (1-((6-(7-fluoroquinolin-4-yl)-4-methylpyridin-3-yl)oxy)-2,4-dimethylpentan-2-yl)carbamate Suzuki coupling was performed as described in Example 77, Part D. Obtained (S)-tert-butyl (1-((6-(7-fluoroquinolin-4-yl)-4-methylpyridin-3-yl)oxy)-2,4-dimethylpentan-2-yl)carbamate (56 mg, 0.055 mmol, 27% yield). LCMS (ESI) m/e 468.0 [(M+H)$^+$, calcd $C_{27}H_{35}FN_3O_3$, 468.3]; LC/MS retention time (method B): $t_R$=2.24 min.

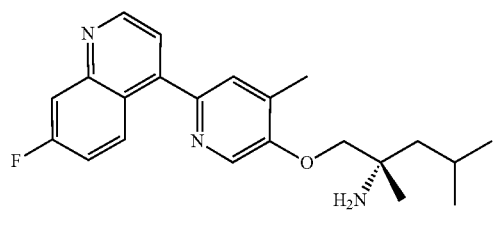 [SMILES: Cc1cc(-c2ccnc3cc(F)ccc23)ncc1OC[C@@](C)(N)CC(C)C]

Part B: (S)-1-((6-(7-fluoroquinolin-4-yl)-4-methylpyridin-3-yl)oxy)-2,4-dimethylpentan-2-amine TFA deprotection as described in Example 32. Obtained (S)-1-((6-(7-fluoroquinolin-4-yl)-4-methylpyridin-3-yl)oxy)-2,4-dimethylpentan-2-amine (36.4 mg, 0.095 mmol, 89% yield). $^1$H NMR (400 MHz, DMSO-d$_6$) δ 8.98 (d, J=4.5 Hz, 1H), 8.47 (s, 1H), 8.34 (dd, J=9.3, 6.3 Hz, 1H), 7.82 (dd, J=10.3, 2.8 Hz, 1H), 7.67 (s, 1H), 7.59 (d, J=4.5 Hz, 1H), 7.55 (td, J=8.9, 2.8 Hz, 1H), 4.10 (s, 2H), 2.37 (s, 3H), 1.86-1.78 (m, 1H), 1.63 (br. s., 1H), 1.57-1.50 (m, 1H), 1.30 (s, 3H), 0.95 (m, 6H), two exchangeable protons not observed; LCMS (ESI) m/e 368.0 [(M+H)$^+$, calcd $C_{22}H_{27}FN_3O$, 368.2]; LC/MS retention time (method B): $t_R$=1.67 min.

Example 233

(S)-1-((4-chloro-6-(5,7-difluoroquinolin-4-yl)pyridin-3-yl)oxy)-2,4-dimethylpentan-2-amine

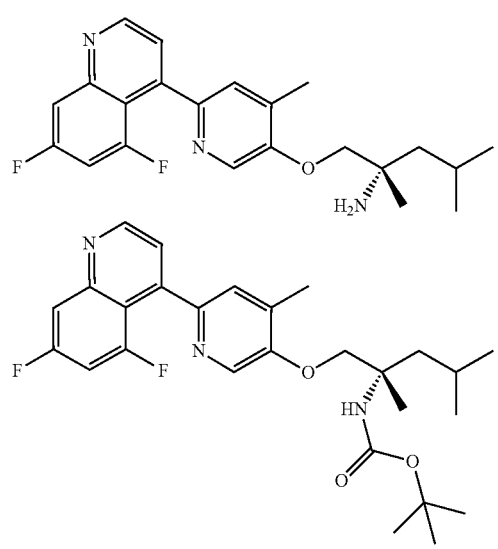

Part A: (S)-tert-butyl (1-((4-chloro-6-(5,7-difluoroquinolin-4-yl)pyridin-3-yl)oxy)-2,4-dimethylpentan-2-yl)carbamate Suzuki coupling was performed as described in Example 77, Part D. Obtained (S)-tert-butyl (1-((4-chloro-6-(5,7-difluoroquinolin-4-yl)pyridin-3-yl)oxy)-2,4-dimethylpentan-2-yl)carbamate (50.6 mg, 0.062 mmol, 62% yield). LCMS (ESI) m/e 506.2 [(M+H)$^+$, calcd $C_{26}H_{31}ClF_2N_{33}$, 506.2]; LC/MS retention time (method B): $t_R$=2.43 min.

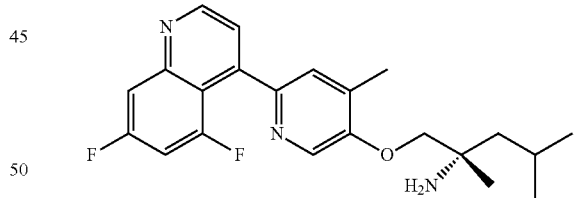

Part B: (S)-1-((4-chloro-6-(5,7-difluoroquinolin-4-yl)pyridin-3-yl)oxy)-2,4-dimethylpentan-2-amine TFA deprotection as described in Example 32. Obtained (S)-1-((4-chloro-6-(5,7-difluoroquinolin-4-yl)pyridin-3-yl)oxy)-2,4-dimethylpentan-2-amine (16.2 mg, 0.040 mmol, 40% yield). $^1$H NMR (500 MHz, DMSO-d$_6$) δ 9.04 (d, J=4.4 Hz, 1H), 8.55 (s, 1H), 7.88 (s, 1H), 7.81 (d, J=9.5 Hz, 1H), 7.61-7.53 (m, 2H), 4.04 (s, 2H), 1.88-1.77 (m, 1H), 1.52-1.40 (m, 2H), 1.20 (s, 3H), 0.95 (m, 6H), two exchangeable protons not observed; LCMS (ESI) m/e 406.1 [(M+H)$^+$, calcd $C_{21}H_{23}ClF_2N_3O$, 406.1]; LC/MS retention time (method A): $t_R$=1.82 min.

Example 234

(S)-1-((4-chloro-[2,4'-bipyridin]-5-yl)oxy)-2,4-dimethylpentan-2-amine

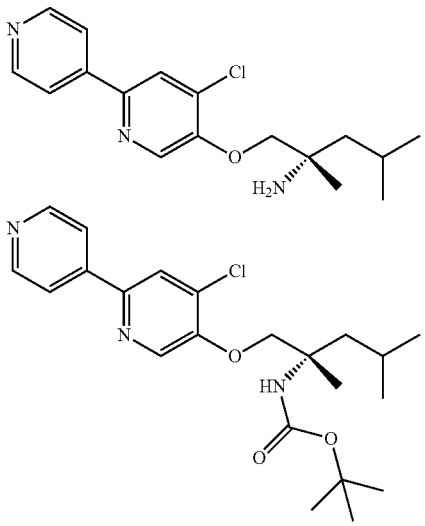

Part A: (S)-tert-butyl (1-((4-chloro-[2,4'-bipyridin]-5-yl)oxy)-2,4-dimethylpentan-2-yl)carbamate Suzuki coupling was performed as described in Example 77, Part D. Obtained (S)-tert-butyl (1-((4-chloro-[2,4'-bipyridin]-5-yl)oxy)-2,4-dimethylpentan-2-yl)carbamate (24.6 mg, 0.059 mmol, 25% yield). $^1$H NMR (400 MHz, CHLOROFORM-d) δ 8.72 (br. s., 2H), 8.41 (s, 1H), 7.83 (s, 3H), 4.59 (s, 1H), 4.41 (d, J=8.8 Hz, 1H), 4.21 (d, J=8.8 Hz, 1H), 1.95-1.80 (m, 2H), 1.56 (dd, J=13.9, 4.9 Hz, 1H), 1.44 (s, 3H), 1.40 (s, 9H), 1.01 (m, 6H). LCMS (ESI) m/e 420.2 [(M+H)$^+$, calcd $C_{22}H_{31}ClN_3O_3$, 420.2]; LC/MS retention time (method A): $t_R$=2.07 min.

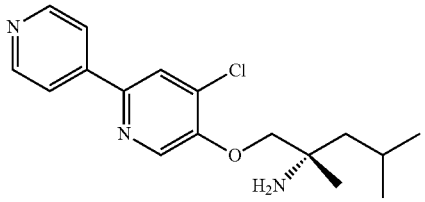 [SMILES: CC(C)C[C@](C)(N)COc1cnc(-c2ccncc2)cc1Cl]

Part B: (S)-1-((4-chloro-[2,4'-bipyridin]-5-yl)oxy)-2,4-dimethylpentan-2-amine TFA deprotection as described in Example 32. Obtained (S)-1-((4-chloro-[2,4'-bipyridin]-5-yl)oxy)-2,4-dimethylpentan-2-amine (7.2 mg, 0.022 mmol, 96% yield). $^1$H NMR (500 MHz, DMSO-d$_6$) δ 8.68 (d, J=5.9 Hz, 2H), 8.64 (s, 1H), 8.35 (s, 1H), 8.04 (d, J=5.9 Hz, 2H), 4.18 (s, 2H), 1.85-1.77 (m, 1H), 1.66-1.60 (m, 1H), 1.52 (dd, J=14.1, 5.3 Hz, 1H), 1.29 (s, 3H), 0.95 (d, J=6.6 Hz, 3H), 0.93 (d, J=6.6 Hz, 3H); LCMS (ESI) m/e 303.1 [(M-NH$_2$)+, calcd $C_{17}H_{20}ClN_2O$, 303.1]; LC/MS retention time (method B): $t_R$=1.44 min.

Example 235

(S)-1-((4-chloro-6-(6-fluoroquinolin-4-yl)pyridin-3-yl)oxy)-2,4-dimethylpentan-2-amine

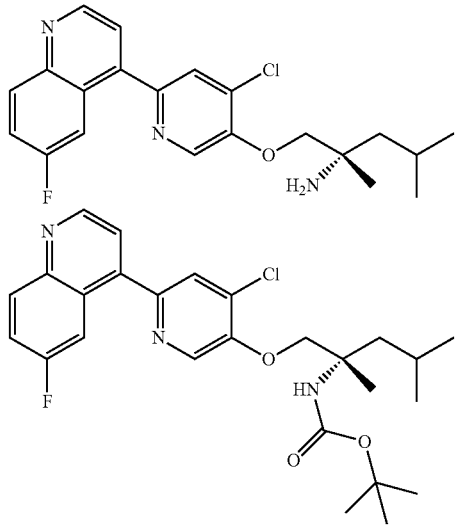

Part A: (S)-tert-butyl (1-((4-chloro-6-(6-fluoroquinolin-4-yl)pyridin-3-yl)oxy)-2,4-dimethylpentan-2-yl)carbamate Suzuki coupling was performed as described in Example 77, Part D. Obtained (S)-tert-butyl (1-((4-chloro-6-(6-fluoroquinolin-4-yl)pyridin-3-yl)oxy)-2,4-dimethylpentan-2-yl)carbamate (62.0 mg, 0.109 mmol, 45% yield). LCMS (ESI) m/e 488.2 [(M+H)$^+$, calcd $C_{26}H_{32}ClFN_3O_3$, 488.2]; LC/MS retention time (method B): $t_R$=2.37 min.

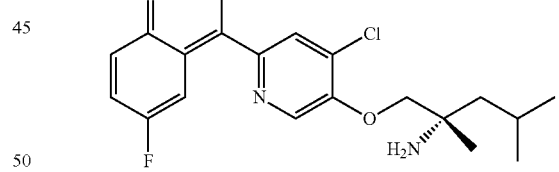

Part B: (S)-1-((4-chloro-6-(6-fluoroquinolin-4-yl)pyridin-3-yl)oxy)-2,4-dimethylpentan-2-amine TFA deprotection as described in Example 32. Obtained (S)-1-((4-chloro-6-(6-fluoroquinolin-4-yl)pyridin-3-yl)oxy)-2,4-dimethylpentan-2-amine (42.3 mg, 0.109 mmol, 86% yield). $^1$H NMR (500 MHz, DMSO-d$_6$) δ 8.99 (d, J=4.4 Hz, 1H), 8.76 (s, 1H), 8.19 (dd, J=9.2, 5.9 Hz, 1H), 8.07 (s, 1H), 8.03 (dd, J=11.0, 2.9 Hz, 1H), 7.77-7.71 (m, 2H), 4.30 (s, 2H), 1.86 (dt, J=12.5, 6.2 Hz, 1H), 1.77-1.69 (m, 1H), 1.60 (dd, J=14.1, 5.7 Hz, 1H), 1.37 (s, 3H), 0.97 (m, 6H), two exchangeable protons not observed; LCMS (ESI) m/e 388.1 [(M+H)$^+$, calcd $C_{21}H_{24}ClFN_3O$, 388.2]; LC/MS retention time (method B): $t_R$=1.75 min.

Example 236

(S)-1-((4-chloro-6-(quinolin-4-yl)pyridin-3-yl)oxy)-2,4-dimethylpentan-2-amine

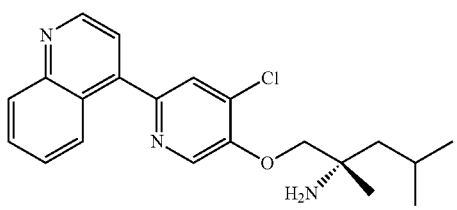 [SMILES: CC(C)C[C@](C)(N)COc1cnc(-c2ccnc3ccccc23)cc1Cl]

Prepared as described in Example 233. Obtained (S)-1-((4-chloro-6-(quinolin-4-yl)pyridin-3-yl)oxy)-2,4-dimethylpentan-2-amine (2.6 mg, 6.82 □mol, 16% yield). $^1$H NMR (500 MHz, DMSO-$d_6$) δ 9.00 (d, J=4.4 Hz, 1H), 8.70 (s, 1H), 8.21 (d, J=8.4 Hz, 1H), 8.12 (d, J=8.4 Hz, 1H), 8.00 (s, 1H), 7.82 (t, J=7.3 Hz, 1H), 7.69-7.56 (m, 2H), 4.09 (s, 2H), 1.86 (dt, J=13.0, 6.3 Hz, 1H), 1.49 (qd, J=13.9, 5.5 Hz, 2H), 1.22 (s, 3H), 0.96 (t, J=6.8 Hz, 6H), two exchangeable protons not observed; LCMS (ESI) m/e 370.0 [(M+H)$^+$, calcd $C_{21}H_{25}ClN_3O$, 370.2]; LC/MS retention time (method B): $t_R$=1.75 min.

Example 237

(S)-methyl (5-((2-amino-2,4-dimethylpentyl)oxy)-4-chloro-[2,4'-bipyridin]-2'-yl)carbamate

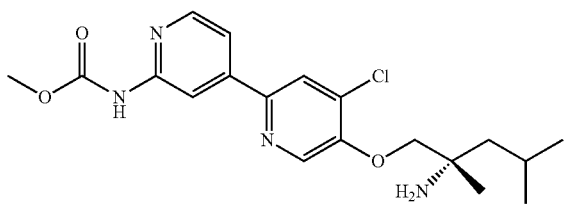 [SMILES: COC(=O)Nc1cc(-c2cc(Cl)c(OC[C@@](C)(N)CC(C)C)cn2)ccn1]

Suzuki coupling was performed as described in Example 77, Part D. Obtained (S)-methyl (5-((2-amino-2,4-dimethylpentyl)oxy)-4-chloro-[2,4'-bipyridin]-2'-yl)carbamate (8.1 mg, 0.020 mmol, 35% yield). $^1$H NMR (600 MHz, DMSO-$d_6$) δ 8.59 (s, 1H), 8.52 (s, 1H), 8.34 (d, J=5.5 Hz, 1H), 8.19 (s, 1H), 7.67 (d, J=5.5 Hz, 1H), 4.01-3.96 (m, 2H), 3.71 (s, 3H), 1.85-1.77 (m, 1H), 1.45-1.36 (m, 2H), 1.17-1.12 (m, 3H), 0.95-0.89 (m, 6H), three exchangeable protons not observed; LCMS (ESI) m/e 393.0 [(M+H)$^+$, calcd $C_{19}H_{26}ClN_4O_3$, 393.2]; LC/MS retention time (method B): $t_R$=1.63 min.

Example 238

(S)-1-((4-chloro-2'-methyl-[2,4'-bipyridin]-5-yl)oxy)-2,4-dimethylpentan-2-amine

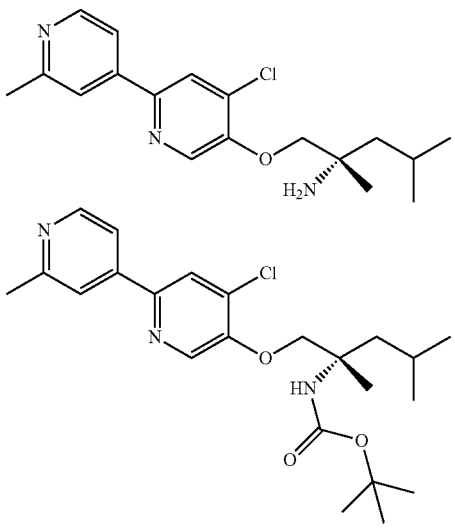

Part A: (S)-tert-butyl (1-((4-chloro-2'-methyl-[2,4'-bipyridin]-5-yl)oxy)-2,4-dimethylpentan-2-yl)carbamate Suzuki coupling was performed as described in Example 77, Part D. Obtained (S)-tert-butyl (1-((4-chloro-2'-methyl-[2,4'-bipyridin]-5-yl)oxy)-2,4-dimethylpentan-2-yl)carbamate (107.4 mg, 0.247 mmol, 49% yield). $^1$H NMR (400 MHz, CHLOROFORM-d) δ 8.57 (d, J=5.0 Hz, 1H), 8.38 (s, 1H), 7.80 (s, 1H), 7.70 (d, J=0.5 Hz, 1H), 7.59 (dd, J=5.3, 1.3 Hz, 1H), 4.39 (d, J=8.5 Hz, 1H), 4.19 (d, J=8.8 Hz, 1H), 2.64 (s, 3H), 1.95-1.77 (m, 2H), 1.55 (dd, J=13.9, 4.9 Hz, 1H), 1.43 (s, 3H), 1.39 (s, 9H), 1.00 (m, 6H), one exchangeable proton not observed; LCMS (ESI) m/e 434.2 [(M+H)$^+$, calcd $C_{23}H_{33}ClN_3O_3$, 433.2]; LC/MS retention time (method B): $t_R$=2.07 min.

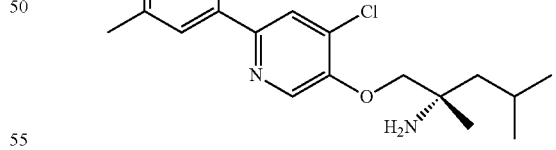

Part B: (S)-1-((4-chloro-2'-methyl-[2,4'-bipyridin]-5-yl)oxy)-2,4-dimethylpentan-2-amine TFA deprotection as described in Example 32. Obtained (S)-1-((4-chloro-2'-methyl-[2,4'-bipyridin]-5-yl)oxy)-2,4-dimethylpentan-2-amine (271.7 mg, 0.806 mmol, 81% yield). $^1$H NMR (400 MHz, CHLOROFORM-d) δ 8.59 (d, J=5.3 Hz, 1H), 8.35 (s, 1H), 7.82 (s, 1H), 7.72-7.69 (m, 1H), 7.60 (dd, J=5.3, 1.3 Hz, 1H), 3.97-3.90 (m, 2H), 2.64 (s, 3H), 1.83 (dt, J=12.7, 6.1 Hz, 1H), 1.53 (t, J=5.5 Hz, 2H), 1.28 (s, 3H), 1.04-0.96 (m, 6H), two exchangeable protons not observed; LCMS (ESI) m/e 334.3 [(M+H)+, calcd $C_{18}H_{25}ClN_3O$, 334.2]; LC/MS retention time (method B): $t_R$=1.49 min.

Example 239

(S)-1-((4-chloro-6-(6-chloroquinolin-4-yl)pyridin-3-yl)oxy)-2,4-dimethylpentan-2-amine

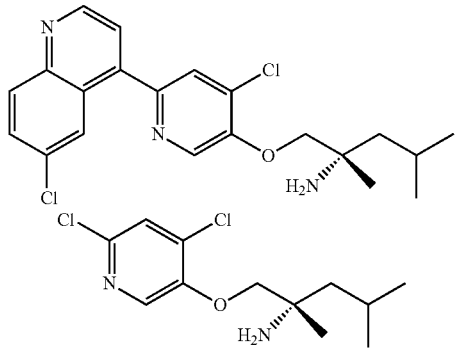

Part A: (S)-1-((4,6-dichloropyridin-3-yl)oxy)-2,4-dimethylpentan-2-amine bis(2,2,2-trifluoroacetate)

TFA (2 mL, 26.0 mmol) was added a solution of (S)-tert-butyl (1-((4,6-dichloropyridin-3-yl)oxy)-2,4-dimethylpentan-2-yl)carbamate (0.146 g, 0.387 mmol) in DCM (4 mL) at room temperature. The reaction was stirred for 1.5 h at room temperature. The solvent was removed under reduced pressure and the crude material was carried on without further purification. LCMS (ESI) m/e 259.9 [(M-NH$_2$)+, calcd $C_{12}H_{16}C_{12}NO$, 260.1]; LC/MS retention time (method B): $t_R$=1.73 min.

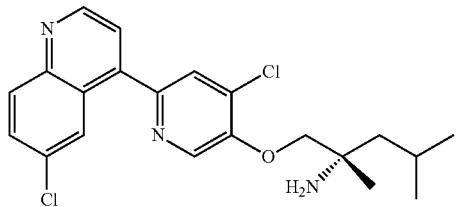 [SMILES: CC(C)C[C@](C)(N)COc1cnc(-c2ccnc3ccc(Cl)cc23)cc1Cl]

Part B: (S)-1-((4-chloro-6-(6-chloroquinolin-4-yl)pyridin-3-yl)oxy)-2,4-dimethylpentan-2-amine Suzuki coupling was performed as described in Example 77, Part D. Obtained (S)-1-((4-chloro-6-(6-chloroquinolin-4-yl)pyridin-3-yl)oxy)-2,4-dimethylpentan-2-amine (8.4 (S)-1-((4-chloro-6-(6-chloroquinolin-4-yl)pyridin-3-yl) oxy)-2,4-dimethylpentan-2-amine (mg, 0.020 mmol, 22% yield over two steps). $^1$H NMR (500 MHz, DMSO-d$_6$) δ 9.01 (d, J=4.4 Hz, 1H), 8.71 (s, 1H), 8.35 (d, J=2.2 Hz, 1H), 8.14 (d, J=9.2 Hz, 1H), 8.04 (s, 1H), 7.83 (dd, J=8.8, 2.2 Hz, 1H), 7.74 (d, J=4.4 Hz, 1H), 4.06 (s, 2H), 1.89-1.80 (m, 1H), 1.52-1.40 (m, 2H), 1.18 (s, 3H), 0.95 (m, 6H), two exchangeable protons not observed; LCMS (ESI) m/e 403.8 [(M+H)+, calcd $C_{21}H_{24}C2N_3O$, 404.1]; LC/MS retention time (method B): $t_R$=1.91 min.

Example 240

(S)-1-((2',4-dichloro-[2,4'-bipyridin]-5-yl)oxy)-2,4-dimethylpentan-2-amine

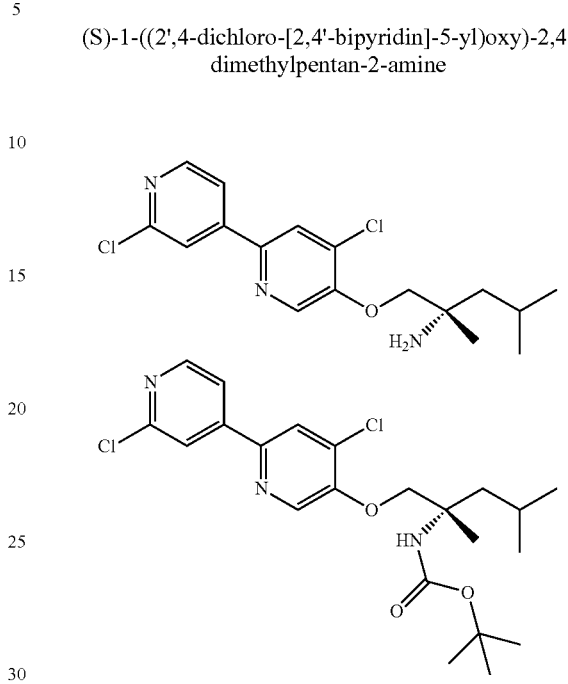

Part A: (S)-tert-butyl (1-((2',4-dichloro-[2,4'-bipyridin]-5-yl)oxy)-2,4-dimethylpentan-2-yl)carbamate Suzuki coupling was performed as described in Example 77, Part D. Obtained (S)-tert-butyl (1-((2',4-dichloro-[2,4'-bipyridin]-5-yl)oxy)-2,4-dimethylpentan-2-yl)carbamate (12.6 mg, 0.014 mmol, 7% yield). LCMS (ESI) m/e 476.1 [(M+Na)+, calcd $C_{22}H_{29}Cl_2N_{33}Na$, 476.2]; LC/MS retention time (method A): $t_R$=2.52 min.

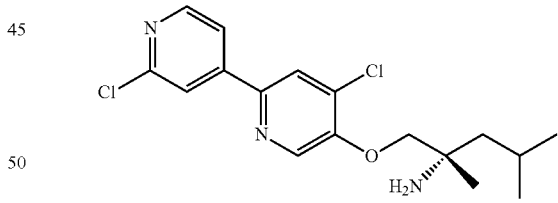

Part B: (S)-1-((2',4-dichloro-[2,4'-bipyridin]-5-yl)oxy)-2,4-dimethylpentan-2-amine TFA deprotection as described in Example 32. Obtained (S)-1-((2',4-dichloro-[2,4'-bipyridin]-5-yl)oxy)-2,4-dimethylpentan-2-amine (4.9 mg, 0.014 mmol, 100% yield). $^1$H NMR (500 MHz, DMSO-d$_6$) δ 8.60 (s, 1H), 8.51 (d, J=5.5 Hz, 1H), 8.44 (s, 1H), 8.15 (s, 1H), 8.08 (dd, J=5.1, 1.5 Hz, 1H), 1.82 (dquin, J=12.8, 6.4 Hz, 1H), 1.41 (t, J=5.3 Hz, 2H), 1.14 (s, 3H), 0.93 (m, 6H), two exchangeable protons not observed; LCMS (ESI) m/e 337.0 [(M-NH$_2$)+, calcd $C_{17}H_{19}C2N_2O$, 337.1]; LC/MS retention time (method B): $t_R$=1.98 min.

Example 241

(S)-1-((4-chloro-6-(7-fluoroquinolin-4-yl)pyridin-3-yl)oxy)-2,4-dimethylpentan-2-amine

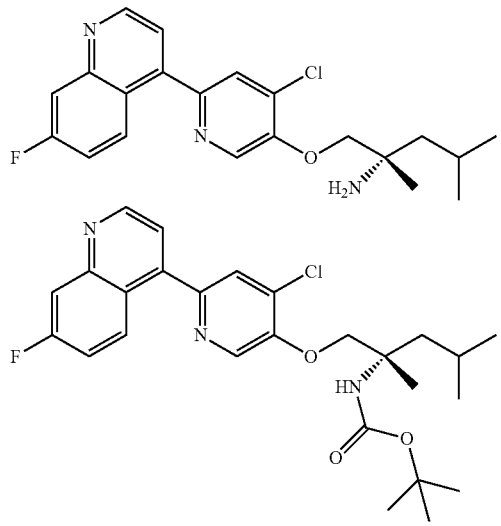

Part A: (S)-tert-butyl (1-((4-chloro-6-(7-fluoroquinolin-4-yl)pyridin-3-yl)oxy)-2,4-dimethylpentan-2-yl)carbamate Suzuki coupling was performed as described in Example 77, Part D. Obtained (S)-tert-butyl (1-((4-chloro-6-(7-fluoroquinolin-4-yl)pyridin-3-yl)oxy)-2,4-dimethylpentan-2-yl)carbamate (30.5 mg, 0.021 mmol, 20% yield). LCMS (ESI) m/e 488.2 [(M+H)$^+$, calcd C$_{26}$H$_{32}$ClFN$_3$O$_3$, 488.2]; LC/MS retention time (method B): t$_R$=2.37 min.

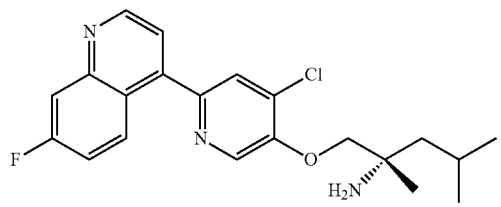 [SMILES: CC(C)C[C@](C)(N)COc1cnc(-c2ccnc3cc(F)ccc23)cc1Cl]

Part B: (S)-1-((4-chloro-6-(7-fluoroquinolin-4-yl)pyridin-3-yl)oxy)-2,4-dimethylpentan-2-amine TFA deprotection as described in Example 32. Obtained (S)-1-((4-chloro-6-(7-fluoroquinolin-4-yl)pyridin-3-yl)oxy)-2,4-dimethylpentan-2-amine (4.4 mg, 0.011 mmol, 18% yield). $^1$H NMR (500 MHz, DMSO-d$_6$) δ 9.01 (d, J=4.4 Hz, 1H), 8.68 (s, 1H), 8.33 (dd, J=9.4, 6.4 Hz, 1H), 8.01 (s, 1H), 7.85 (dd, J=10.5, 2.4 Hz, 1H), 7.66 (d, J=4.4 Hz, 1H), 7.60-7.53 (m, 1H), 4.04 (s, 2H), 1.85 (dt, J=12.7, 6.5 Hz, 1H), 1.45 (t, J=6.4 Hz, 2H), 1.18 (s, 3H), 0.96 (m, 6H), two exchangeable protons not observed; LCMS (ESI) m/e 388.1 [(M+H)$^+$, calcd C$_{21}$H$_{24}$ClFN$_3$O, 388.2]; LC/MS retention time (method B): t$_R$=1.82 min.

Example 242

(S)-1-((4-chloro-6-(7-(trifluoromethyl)quinolin-4-yl)pyridin-3-yl)oxy)-2,4-dimethylpentan-2-amine

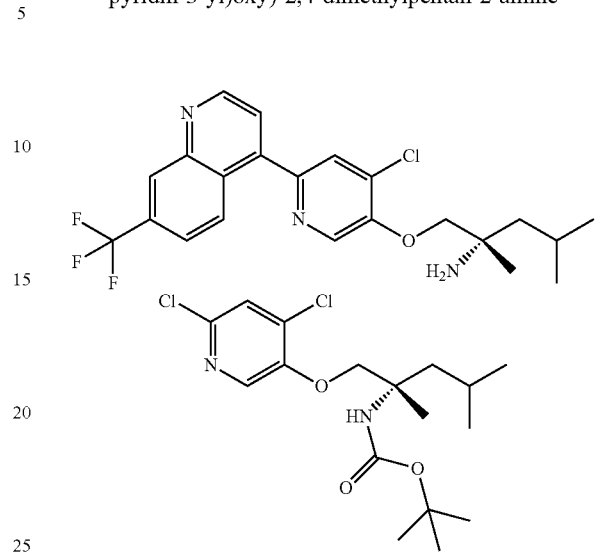

Part A: (S)-tert-butyl (1-((4,6-dichloropyridin-3-yl)oxy)-2,4-dimethylpentan-2-yl)carbamate Prepared as described in Example 53, Part A. Obtained (S)-tert-butyl (1-((4,6-dichloropyridin-3-yl)oxy)-2,4-dimethylpentan-2-yl)carbamate (765.6 mg, 2.03 mmol, 74% yield). $^1$H NMR (400 MHz, CHLOROFORM-d) δ 8.05-8.02 (m, 1H), 7.35 (s, 1H), 4.55 (s, 1H), 4.30 (d, J=8.8 Hz, 1H), 4.11 (d, J=8.8 Hz, 1H), 1.91-1.75 (m, 2H), 1.58-1.48 (m, 1H), 1.41-1.38 (m, 12H), 0.98 (m, 6H). LCMS (ESI) m/e 399.0 [(M+Na)$^+$, calcd C$_{17}$H$_{26}$C2NaN$_2$O$_3$, 399.1]; LC/MS retention time (method B): t$_R$=2.41 min.

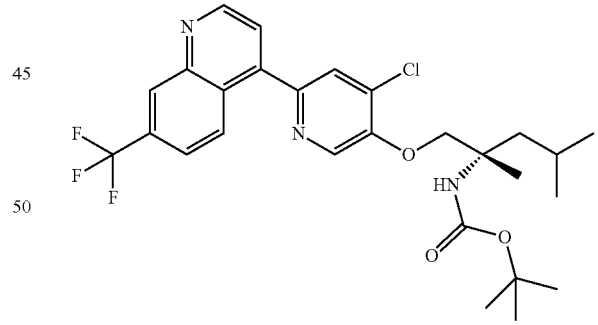

Part B: (S)-tert-butyl (1-((6-(7-fluoroquinolin-4-yl)-4-methylpyridin-3-yl)oxy)-2,4-dimethylpentan-2-yl)carbamate Suzuki coupling was performed as described in Example 77, Part D. Obtained (S)-tert-butyl (1-((6-(7-fluoroquinolin-4-yl)-4-methylpyridin-3-yl)oxy)-2,4-dimethylpentan-2-yl)carbamate (26.3 mg, 0.049 mmol, 33% yield). LCMS (ESI) m/e 538.1 [(M+H)$^+$, calcd C$_{27}$H$_{32}$ClF$_3$N$_3$O$_3$, 538.2]; LC/MS retention time (method B): t$_R$=2.51 min.

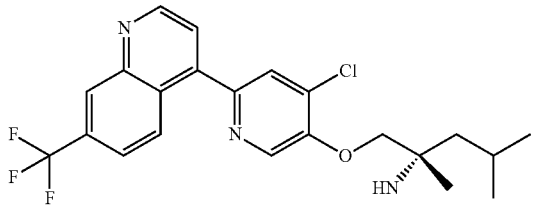 [SMILES: CC(C)C[C@](C)(N)COc1cnc(-c2ccnc3cc(C(F)(F)F)ccc23)cc1Cl]

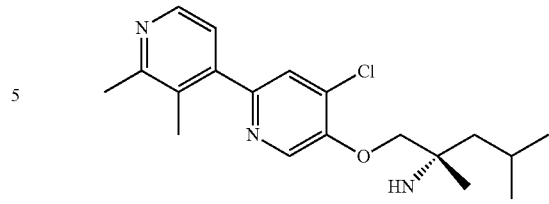

Part C: (S)-1-((4-chloro-6-(7-(trifluoromethyl)quinolin-4-yl)pyridin-3-yl)oxy)-2,4-dimethylpentan-2-amine TFA deprotection as described in Example 32. Obtained (S)-1-((4-chloro-6-(7-(trifluoromethyl)quinolin-4-yl)pyridin-3-yl)oxy)-2,4-dimethylpentan-2-amine (17.7 mg, 0.040 mmol, 83% yield). $^1$H NMR (500 MHz, DMSO-$d_6$) δ 9.14 (d, J=4.3 Hz, 1H), 8.69 (s, 1H), 8.49 (d, J=8.5 Hz, 1H), 8.45 (s, 1H), 8.06 (s, 1H), 7.90 (d, J=8.9 Hz, 1H), 7.85 (d, J=4.6 Hz, 1H), 4.04 (s, 2H), 1.85 (dt, J=12.5, 6.3 Hz, 1H), 1.45 (t, J=5.8 Hz, 2H), 1.18 (s, 3H), 0.95 (m, 6H), two exchangeable protons not observed; LCMS (ESI) m/e 438.3 [(M+H)$^+$, calcd $C_{22}H_{24}ClF_3N_3O$, 438.1]; LC/MS retention time (method A): $t_R$=1.66 min.

Example 243

(S)-1-((4-chloro-2',3'-dimethyl-[2,4'-bipyridin]-5-yl)oxy)-2,4-dimethylpentan-2-amine

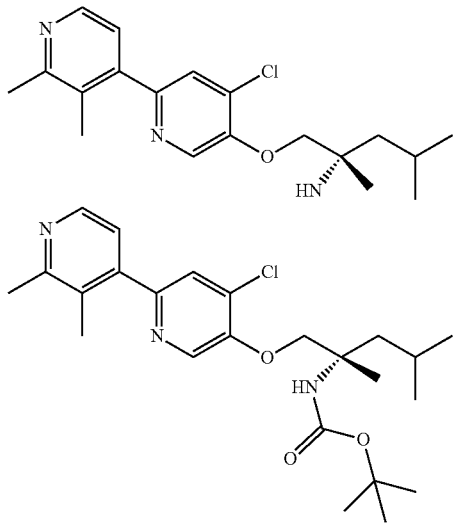

Part A: (S)-tert-butyl (1-((4-chloro-2',3'-dimethyl-[2,4'-bipyridin]-5-yl)oxy)-2,4-dimethylpentan-2-yl)carbamate Suzuki coupling was performed as described in Example 77, Part D. Obtained (S)-tert-butyl (1-((4-chloro-2',3'-dimethyl-[2,4'-bipyridin]-5-yl)oxy)-2,4-dimethylpentan-2-yl)carbamate (23 mg, 0.014 mmol, 7% yield). LCMS (ESI) m/e 448.2 [(M+H)$^+$, calcd $C_{24}H_{35}ClN_3O_3$, 448.2]; LC/MS retention time (method B): $t_R$=2.14 min.

Part B: (S)-1-((4-chloro-2',3'-dimethyl-[2,4'-bipyridin]-5-yl)oxy)-2,4-dimethylpentan-2-amine TFA deprotection as described in Example 32. Obtained (S)-1-((4-chloro-2',3'-dimethyl-[2,4'-bipyridin]-5-yl)oxy)-2,4-dimethylpentan-2-amine (1.5 mg, 4.14 □mol, 8% yield). $^1$H NMR (500 MHz, DMSO-$d_6$) δ 8.46 (d, J=5.1 Hz, 1H), 8.42 (s, 1H), 7.46 (s, 1H), 7.28 (br. s., 1H), 4.08 (br. s., 2H), 2.57 (s, 3H), 2.07 (s, 3H), 1.61 (br. s., 1H), 1.43-1.25 (m, 2H), 1.15 (br. s., 3H), 0.91-0.66 (m, 6H), two exchangeable protons not observed; LCMS (ESI) m/e 348.2 [(M+H)$^+$, calcd $C_{19}H_{27}ClN_3O$, 348.2]; LC/MS retention time (method B): $t_R$=1.34 min.

Example 244

(S)-1-((5-(difluoromethyl)-2'-methyl-[3,4'-bipyridin]-6-yl)oxy)-2,4-dimethylpentan-2-amine

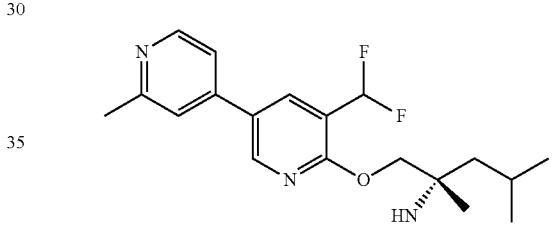

Suzuki reaction was performed as described in Example 193. Obtained (S)-1-((5-(difluoromethyl)-2'-methyl-[3,4'-bipyridin]-6-yl)oxy)-2,4-dimethylpentan-2-amine (9.8 mg, 0.028 mmol, 49% yield). $^1$H NMR (500 MHz, DMSO-$d_6$) δ 8.76 (s, 1H), 8.50 (d, J=5.2 Hz, 1H), 8.33 (s, 1H), 7.66 (s, 1H), 7.57 (d, J=4.9 Hz, 1H), 7.28 (t, J=1.0 Hz, 1H), 4.19 (s, 2H), 1.85 (s, 3H), 1.82-1.73 (m, 1H), 1.44 (qd, J=13.9, 5.5 Hz, 2H), 1.16 (s, 3H), 0.92 (d, J=6.7 Hz, 3H), 0.89 (d, J=6.4 Hz, 3H); LCMS (ESI) m/e 333.2 [(M-NH$_2$)+, calcd $C_{19}H_{23}N_2F_2O$, 333.2]; LC/MS retention time (method B): $t_R$=1.46 min.

Example 245

(R)-methyl(6-((2-amino-2,4-dimethylpentyl)oxy)-5-(difluoromethyl)-[3,4'-bipyridin]-2'-yl)carbamate

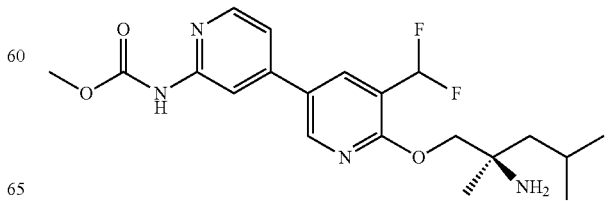

Suzuki coupling was performed as described in Example 77, Part D. Obtained (R)-methyl (6-((2-amino-2,4-dimethylpentyl)oxy)-5-(difluoromethyl)-[3,4'-bipyridin]-2'-yl)carbamate (13.3 mg, 0.032 mmol, 54% yield). $^1$H NMR (500 MHz, DMSO-$d_6$) δ 8.69 (s, 1H), 8.35 (d, J=5.1 Hz, 1H), 8.22 (s, 1H), 8.11 (s, 1H), 7.44 (d, J=3.7 Hz, 1H), 7.39-7.14 (t, J=44.0 Hz, 1H), 4.15 (d, J=2.6 Hz, 2H), 3.71 (s, 3H), 1.84-1.73 (m, 1H), 1.40 (t, J=6.1 Hz, 2H), 1.13 (s, 3H), 0.92 (m, 6H); LCMS (ESI) m/e 392.2 [(M-NH$_2$)+, calcd C$_{20}$H$_{24}$F$_2$N$_3$O$_3$, 392.2]; LC/MS retention time (method B): $t_R$=1.70 min.

Example 246

(R)-1-((3-(difluoromethyl)-5-(quinolin-4-yl)pyridin-2-yl)oxy)-2,4-dimethylpentan-2-amine

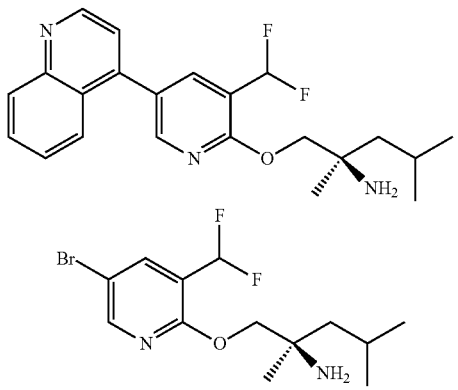

Part A: (R)-1-((5-bromo-3-(difluoromethyl)pyridin-2-yl)oxy)-2,4-dimethylpentan-2-amine Prepared as described in Example 193. Obtained (R)-1-((5-bromo-3-(difluoromethyl)pyridin-2-yl)oxy)-2,4-dimethylpentan-2-amine (275 mg, 0.465 mmol, 55% yield). LCMS (ESI) m/e 320.1 [(M-NH$_2$)+, calcd C$_{13}$H$_{17}$BrF$_2$NO, 320.1]; LC/MS retention time (method B): $t_R$=1.95 min.

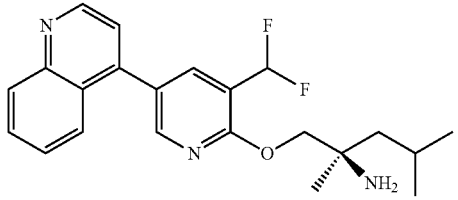 [SMILES: CC(C)C[C@@](C)(N)COc1ncc(-c2ccnc3ccccc23)cc1C(F)F]

Part B: (R)-1-((3-(difluoromethyl)-5-(quinolin-4-yl)pyridin-2-yl)oxy)-2,4-dimethylpentan-2-amine Suzuki coupling was performed as described in Example 77, Part D. Obtained (R)-1-((3-(difluoromethyl)-5-(quinolin-4-yl)pyridin-2-yl)oxy)-2,4-dimethylpentan-2-amine (6.3 mg, 0.016 mmol, 24% yield). $^1$H NMR (500 MHz, DMSO-$d_6$) δ 8.98 (d, J=4.4 Hz, 1H), 8.52 (s, 1H), 8.16-8.12 (m, 2H), 7.87-7.80 (m, 2H), 7.69-7.62 (m, 1H), 7.56 (d, J=4.4 Hz, 1H), 7.29 (t, J=1.0 Hz, 1H), 4.19 (s, 2H), 1.87-1.78 (m, 1H), 1.49-1.38 (m, 2H), 1.16 (s, 3H), 0.94 (m, 6H), two exchangeable protons not observed; LCMS (ESI) m/e 386.2 [(M+H)+, calcd C$_{22}$H$_{26}$F$_2$N$_3$O, 386.2]; LC/MS retention time (method B): $t_R$=1.65 min.

Example 247

(R)-1-((3-(difluoromethyl)-5-(2-methylpyrimidin-4-yl)pyridin-2-yl)oxy)-2,4-dimethylpentan-2-amine

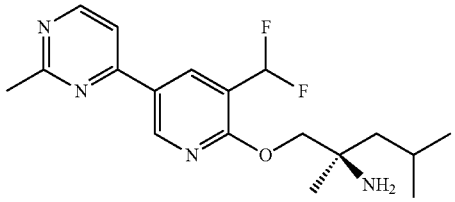 [SMILES: Cc1nccc(-c2cnc(OC[C@](C)(N)CC(C)C)c(C(F)F)c2)n1]

Suzuki coupling was performed as described in Example 77, Part D. Obtained (R)-1-((3-(difluoromethyl)-5-(2-methylpyrimidin-4-yl)pyridin-2-yl)oxy)-2,4-dimethylpentan-2-amine (7.7 mg, 0.022 mmol, 37% yield). $^1$H NMR (500 MHz, DMSO-$d_6$) δ 9.12 (s, 1H), 8.77 (d, J=5.1 Hz, 1H), 8.68 (s, 1H), 7.98 (d, J=5.5 Hz, 1H), 7.42-7.16 (t, J=55.0 Hz, 1H), 4.18 (s, 2H), 2.69 (s, 3H), 1.85-1.75 (m, 1H), 1.41 (dd, J=9.0, 5.7 Hz, 2H), 1.14 (s, 3H), 0.92 (m, 6H); LCMS (ESI) m/e 334.1 [(M-NH$_2$)+, calcd C$_{18}$H$_{22}$F$_2$N$_3$O, 334.2]; LC/MS retention time (method B): $t_R$=1.81 min.

Example 248

(R)-1-((3-(difluoromethyl)-5-(5,7-difluoroquinolin-4-yl)pyridin-2-yl)oxy)-2,4-dimethylpentan-2-amine

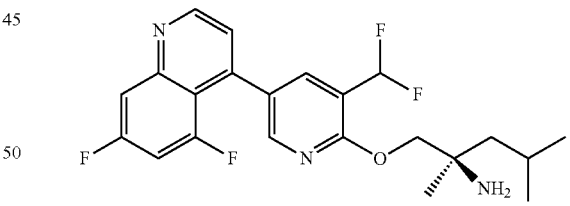

Suzuki coupling was performed as described in Example 77, Part D. Obtained (R)-1-((3-(difluoromethyl)-5-(5,7-difluoroquinolin-4-yl)pyridin-2-yl)oxy)-2,4-dimethylpentan-2-amine (8.4 mg, 0.020 mmol, 21% yield). $^1$H NMR (500 MHz, DMSO-$d_6$) δ 9.02 (d, J=4.4 Hz, 1H), 8.44 (s, 1H), 8.12 (br. s., 1H), 7.81 (d, J=9.2 Hz, 1H), 7.61 (ddd, J=12.3, 9.5, 2.4 Hz, 1H), 7.52 (d, J=4.8 Hz, 1H), 7.40-7.14 (t, J=55.0 Hz, 1H), 4.16 (s, 2H), 1.86-1.77 (m, 1H), 1.42 (dd, J=7.9, 5.7 Hz, 2H), 1.15 (s, 3H), 0.94 (m, 6H); LCMS (ESI) m/e 405.1 [(M-NH$_2$)+, calcd C$_{22}$H$_{21}$F$_4$N$_2$O, 405.2]; LC/MS retention time (method B): $t_R$=2.01 min.

Example 249

(R)-1-((5-(7-chloroquinolin-4-yl)-3-(difluoromethyl)pyridin-2-yl)oxy)-2,4-dimethylpentan-2-amine

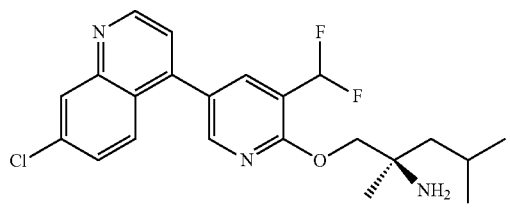 [SMILES: CC(C)C[C@@](C)(N)COc1ncc(-c2ccnc3cc(Cl)ccc23)cc1C(F)F]

Suzuki coupling was performed as described in Example 77, Part D. Obtained (R)-1-((5-(7-chloroquinolin-4-yl)-3-(difluoromethyl)pyridin-2-yl)oxy)-2,4-dimethylpentan-2-amine (16.9 mg, 0.039 mmol, 34% yield). $^1$H NMR (500 MHz, DMSO-d$_6$) δ 9.01 (d, J=4.4 Hz, 1H), 8.52 (s, 1H), 8.19 (d, J=2.2 Hz, 1H), 8.16 (s, 1H), 7.87 (d, J=9.2 Hz, 1H), 7.69 (dd, J=9.2, 2.2 Hz, 1H), 7.60 (d, J=4.4 Hz, 1H), 7.42-7.16 (t, J=55.0 Hz, 1H), 4.19 (s, 2H), 1.85-1.77 (m, 1H), 1.49-1.37 (m, 2H), 1.16 (s, 3H), 0.94 (m, 6H); LCMS (ESI) m/e 403.1 [(M-NH$_2$)+, calcd C$_{22}$H$_{22}$ClF$_2$N$_2$O, 403.1]; LC/MS retention time (method B): t$_R$=1.97 min.

Example 250

N-(4'-((2-amino-2,4-dimethylpentyl)oxy)-3'-methyl-[1,1'-biphenyl]-3-yl)acetamide

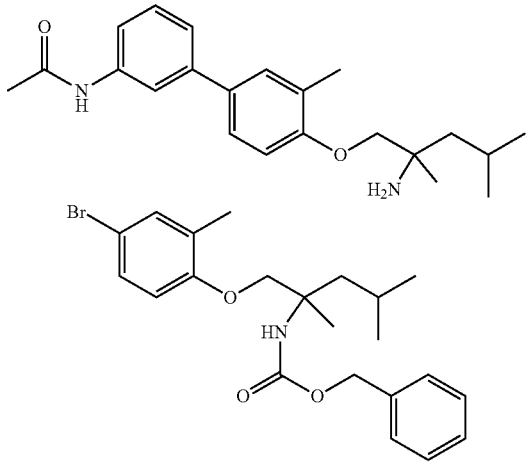

Part A: Benzyl (1-(4-bromo-2-methylphenoxy)-2,4-dimethylpentan-2-yl)carbamate Prepared as described in Example 29, Part A. Obtained benzyl (1-(4-bromo-2-methylphenoxy)-2,4-dimethylpentan-2-yl)carbamate (33 mg, 0.076 mmol, 27% yield). LCMS (ESI) m/e 456.1 [(M+Na)+, calcd C$_{22}$H$_{28}$BrNO$_3$Na, 456.1]; LC/MS retention time (method B): t$_R$=2.55 min.

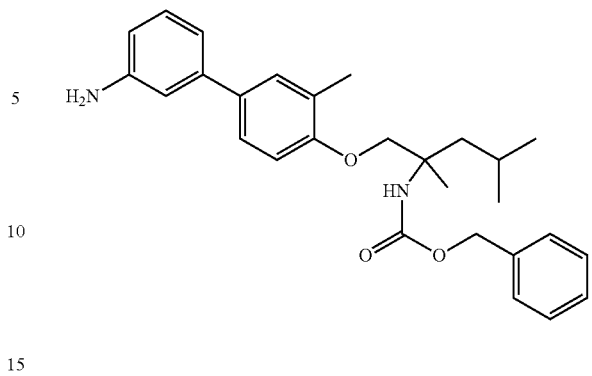

Part B: Benzyl (1-((3'-amino-3-methyl-[1,1'-biphenyl]-4-yl)oxy)-2,4-dimethylpentan-2-yl)carbamate Suzuki reaction was performed as described in Example 193. Obtained benzyl (1-((3'-amino-3-methyl-[1,1'-biphenyl]-4-yl)oxy)-2,4-dimethylpentan-2-yl)carbamate (21.1 mg, 0.047 mmol, 62% yield). $^1$H NMR (400 MHz, CHLOROFORM-d) δ 7.38-7.29 (m, 7H), 7.21 (t, J=7.8 Hz, 1H), 6.99-6.94 (m, 1H), 6.88 (t, J=1.9 Hz, 2H), 6.65 (ddd, J=7.9, 2.3, 0.9 Hz, 1H), 5.06 (s, 2H), 4.93 (s, 1H), 4.13 (d, J=8.8 Hz, 1H), 3.99 (d, J=8.8 Hz, 1H), 3.73 (br. s., 2H), 2.28 (s, 3H), 1.92-1.77 (m, 2H), 1.72-1.65 (m, 1H), 1.48 (s, 3H), 0.98 (m, 6H); LCMS (ESI) m/e 447.5 [(M+H)+, calcd C$_{28}$H$_{35}$N$_2$O$_3$, 447.6]; LC/MS retention time (method A): t$_R$=2.38 min.

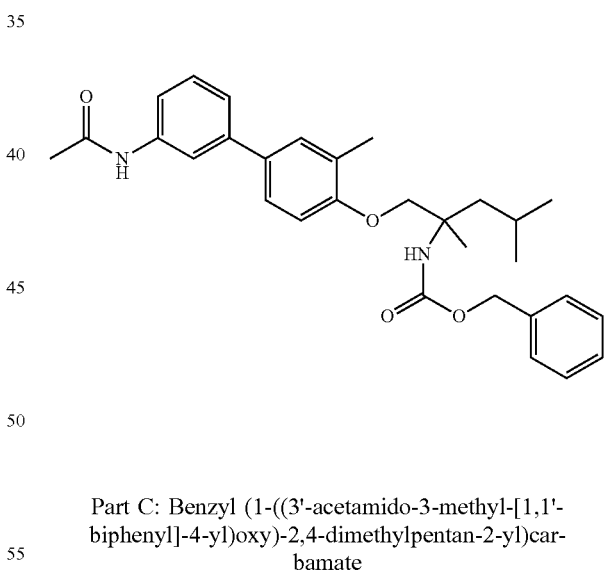

Part C: Benzyl (1-((3'-acetamido-3-methyl-[1,1'-biphenyl]-4-yl)oxy)-2,4-dimethylpentan-2-yl)carbamate Acetyl chloride (1 drop) was added to a solution of benzyl (1-((3'-amino-3-methyl-[1,1'-biphenyl]-4-yl)oxy)-2,4-dimethylpentan-2-yl)carbamate (0.0221 g, 0.049 mmol) in CH$_2$Cl$_2$ (2 mL) at room temperature. The reaction was stirred for 10 min at room temperature before addition of triethylamine (1 drop). The reaction was stirred for 2 h the concentrated under reduced pressure. The residue was carried on without further purification. LCMS (ESI) m/e 489.5 [(M+H), calcd C$_{30}$H$_{37}$N$_2$O$_4$, 489.3]; LC/MS retention time (method A): t$_R$=2.39 min.

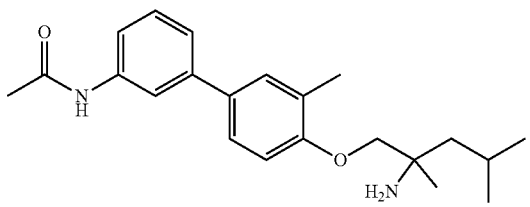 [SMILES: CC(=O)Nc1cccc(-c2ccc(OCC(C)(N)CC(C)C)c(C)c2)c1]

Part D: N-(4'-((2-amino-2,4-dimethylpentyl)oxy)-3'-methyl-[1,1'-biphenyl]-3-yl)acetamide A mixture of Pd/C (3 mg, 2.82 μmol) and benzyl (1-((3'-acetamido-3-methyl-[1,1'-biphenyl]-4-yl)oxy)-2,4-dimethylpentan-2-yl)carbamate (23.94 mg, 0.049 mmol) in ethanol (3 mL) was hydrogenated via a $H_2$ balloon at room temperature overnight. The reaction was filtered through a celite pad and washed with DCM. The filtrate was concentrated and the residue was purified by reverse phase Prep HPLC. Obtained N-(4'-((2-amino-2,4-dimethylpentyl)oxy)-3'-methyl-[1,1'-biphenyl]-3-yl)acetamide (11.4 mg, 0.031 mmol, 64% yield) as an off-white solid. $^1$H NMR (500 MHz, DMSO-$d_6$) δ 9.99 (s, 1H), 7.82 (s, 1H), 7.51 (d, J=7.9 Hz, 1H), 7.41-7.24 (m, 4H), 6.98 (d, J=8.5 Hz, 1H), 3.72 (d, J=3.1 Hz, 2H), 2.26 (s, 3H), 2.07 (s, 3H), 1.85-1.78 (m, 1H), 1.46-1.41 (m, 2H), 1.16 (s, 3H), 0.93 (t, J=6.3 Hz, 6H); LCMS (ESI) m/e 338.4 [(M-NH$_2$)+, calcd $C_{22}H_{28}NO_2$, 338.2]; LC/MS retention time (method A): $t_R$=2.03 min.

Biological Data

Methods
AAK1 Kinase Assay

The assays were performed in U-bottom 384-well plates. The final assay volume was 30 μl prepared from 15 μl additions of enzyme and substrates (fluoresceinated peptide (5-FAM)-Aha-KEEQSQITSQVTGQIGWR-NH2 and ATP) and test compounds in assay buffer (10 mM Tris-HCL pH 7.4, 10 mM MgCl$_2$, 0.01% Tween-20 and 1.0 mM DTT). The reactions were initiated by the combination of bacterially expressed, GST-Xa-hAAK1 with substrates and test compounds. The reactions were incubated at room temperature for 3 hours and terminated by adding 60 μl of 35 mM EDTA buffer to each sample. The reactions were analyzed on the Caliper LabChip 3000 (Caliper, Hopkinton, Mass.) by electrophoretic separation of the fluorescent substrate and phosphorylated product. Inhibition data were calculated by comparison to EDTA quenched control reactions for 100% inhibition and vehicle-only reactions for 0% inhibition. The final concentration of reagents in the assays are ATP, 22 μM; (5-FAM)-Aha-KEEQSQITSQVTGQIGWR-NH12, 1.5 μM; GST-Xa-hAAK1, 3.5 nM; and DMSO, 1.6%. Dose response curves were generated to determine the concentration required inhibiting 50% of kinase activity (IC$_{50}$). Compounds were dissolved at 10 mM in dimethylsulfoxide (DMSO) and evaluated at eleven concentrations. IC$_{50}$ values were derived by non-linear regression analysis. Results are shown in Table 1.

TABLE 1

| Example | AAK1 IC$_{50}$ (nM) |
| --- | --- |
| 1 | 2.7 |
| 2 | 3.0 |
| 3 | 0.30 |
| 4 | 2.8 |
| 5 | 0.50 |
| 6 | 0.47 |
| 7 | 0.42 |
| 8 | 0.53 |
| 9 | — |
| 10 | 10 |
| 11 | 3.3 |
| 12 | 1.6 |
| 13 | 1.1 |
| 14 | 0.87 |
| 15 | 0.81 |
| 16 | 6.6 |
| 17 | 24 |
| 18 | 5.0 |
| 19 | 0.36 |
| 20 | 0.34 |
| 21 | 0.74 |
| 22 | 0.65 |
| 23 | 0.76 |
| 24 | 0.63 |
| 25 | 1.0 |
| 26 | 0.69 |
| 27 | 1.0 |
| 28 | 1.2 |
| 29 | 0.67 |
| 30 | 1.4 |
| 31 | 4.5 |
| 32 | 4.5 |
| 33 | 0.32 |
| 34 | 15 |
| 35 | 0.77 |
| 36 | 0.89 |
| 37 | 0.51 |
| 38 | 0.79 |
| 39 | 3.2 |
| 40 | 8.7 |
| 41 | 3.8 |
| 42 | 3.3 |
| 43 | 0.64 |
| 44 | 2.8 |
| 45 | 1.2 |
| 46 | 0.86 |
| 47 | 0.77 |
| 48 | 4.6 |
| 49 | 2.6 |
| 50 | 0.38 |
| 63 | 24 |
| 64 | 1.1 |
| 65 | 42 |
| 66 | 0.65 |
| 67 | 4.7 |
| 68 | 2.6 |
| 69 | 0.76 |
| 70 | 2.3 |
| 71 | 0.55 |
| 72 | 0.53 |
| 73 | 0.51 |
| 74 | 0.07 |
| 75 | 34 |
| 76 | 1.7 |
| 77 | 0.92 |
| 78 | 0.49 |
| 79 | 16 |
| 80 | 19 |
| 81 | 7.8 |
| 82 | 0.85 |
| 83 | 1.8 |
| 84 | 2.2 |
| 85 | 0.32 |
| 86 | 1.2 |
| 87 | 0.87 |
| 88 | 0.46 |
| 89 | 0.66 |
| 90 | 2.6 |
| 91 | 12.1 |
| 92 | 5.4 |

TABLE 1-continued

| Example | AAK1 IC$_{50}$ (nM) |
|---|---|
| 93 | 33 |
| 94 | 4.7 |
| 95 | 39 |
| 96 | 3.0 |
| 97 | 142 |
| 98 | 10 |
| 99 | 31 |
| 100 | 6.8 |
| 101 | 27 |
| 102 | 1.3 |
| 103 | 0.68 |
| 104 | 0.83 |
| 105 | 0.72 |
| 106 | 0.62 |
| 107 | 50 |
| 108 | 106 |
| 109 | 340 |
| 110 | 3.5 |
| 111 | 650 |
| 112 | 970 |
| 113 | 43 |
| 114 | 1400 |
| 115 | 13 |
| 116 | 0.93 |
| 117 | 1.0 |
| 118 | 0.85 |
| 119 | 3.2 |
| 120 | 0.51 |
| 121 | 0.30 |
| 122 | 0.51 |
| 123 | 2.2 |
| 124 | 1.2 |
| 125 | 1.6 |
| 126 | 0.80 |
| 127 | 6.2 |
| 128 | 3.5 |
| 129 | 1.4 |
| 130 | 1.4 |
| 131 | 0.82 |
| 132 | 1.5 |
| 133 | 0.92 |
| 134 | 4.4 |
| 135 | 3.5 |
| 136 | 4.8 |
| 137 | 27 |
| 138 | 35 |
| 139 | 0.77 |
| 140 | 470 |
| 141 | 1.8 |
| 142 | 4.1 |
| 143 | 0.45 |
| 144 | 1.3 |
| 145 | 0.24 |
| 146 | 0.19 |
| 147 | 0.56 |
| 148 | 0.34 |
| 149 | 1.5 |
| 150 | 24 |
| 151 | |
| 152 | 0.68 |
| 153 | 1.9 |
| 154 | 6.8 |
| 155 | 57 |
| 156 | 110 |
| 157 | 19 |
| 158 | 5.4 |
| 159 | 1.5 |
| 160 | 0.8 |
| 161 | 1.7 |
| 162 | 530 |
| 163 | 1100 |
| 164 | 254 |
| 165 | 21 |
| 166 | 20 |
| 167 | 1040 |
| 168 | 58 |
| 169 | 101 |
| 170 | 285 |
| 171 | 48 |
| 172 | 1295 |
| 173 | 42 |
| 174 | 54 |
| 175 | 17 |
| 176 | 53 |
| 177 | 8.7 |
| 178 | 150 |
| 179 | 2.0 |
| 180 | 24 |
| 181 | 1.9 |
| 182 | 8.7 |
| 183 | 8.8 |
| 184 | 3.3 |
| 185 | 66 |
| 186 | 18 |
| 187 | 2.2 |
| 188 | 92 |
| 189 | 0.49 |
| 190 | 1.2 |
| 191 | 0.99 |
| 192 | 9.6 |
| 193 | 2.9 |
| 194 | 1.5 |
| 195 | 0.25 |
| 196 | 0.20 |
| 197 | 0.31 |
| 198 | 2.2 |
| 199 | 1.0 |
| 200 | 1.2 |
| 201 | 0.64 |
| 202 | 3.1 |
| 203 | 21 |
| 204 | 0.23 |
| 205 | 0.70 |
| 206 | 4.3 |
| 207 | 19 |
| 208 | 4.6 |
| 209 | 21 |
| 210 | 79 |
| 211 | 491 |
| 212 | 1024 |
| 213 | 22 |
| 214 | 0.86 |
| 215 | 197 |
| 216 | 25 |
| 217 | 0.56 |
| 218 | 1.0 |
| 219 | 0.59 |
| 220 | 0.38 |
| 221 | 4.1 |
| 222 | 1.2 |
| 223 | 0.88 |
| 224 | 1.1 |
| 225 | 0.74 |
| 226 | 0.93 |
| 227 | 0.93 |
| 228 | 22 |
| 229 | 1.0 |
| 230 | 1.1 |
| 231 | 0.47 |
| 232 | 0.41 |
| 233 | 0.73 |
| 234 | 3.2 |
| 235 | 0.36 |
| 236 | 0.98 |
| 237 | 1.4 |
| 238 | 2.1 |
| 239 | 0.39 |
| 240 | 2.2 |
| 241 | 0.86 |
| 242 | 1.9 |
| 243 | 1071 |
| 244 | 262 |
| 245 | 11 |
| 246 | 26 |

TABLE 1-continued

| Example | AAK1 IC$_{50}$ (nM) |
|---|---|
| 247 | 234 |
| 248 | 74 |
| 249 | 27 |
| 250 | 659 |
| 251 | 1098 |

AAK1 Knockout Mice

Mice homozygous (−/−) for the disruption of the AAK1 gene were prepared by two methods; gene trapping and homologous recombination.

Gene trapping is a method of random insertional mutagenesis that uses a fragment of DNA coding for a reporter or selectable marker gene as a mutagen. Gene trap vectors have been designed to integrate into introns or genes in a manner that allows the cellular splicing machinery to splice vector encoded exons to cellular mRNAs. Commonly, gene trap vectors contain selectable marker sequences that are preceded by strong splice acceptor sequences and are not preceded by a promoter. Thus, when such vectors integrate into a gene, the cellular splicing machinery splices exons from the trapped gene onto the 5' end of the selectable marker sequence. Typically, such selectable marker genes can only be expressed if the vector encoding the gene has integrated into an intron. The resulting gene trap events are subsequently identified by selecting for cells that can survive selective culture.

Embryonic stem cells (Lex-1 cells from derived murine strain A129), were mutated by a process involving the insertion of at least a portion of a genetically engineered vector sequence into the gene of interest, the mutated embryonic stem cells were microinjected into blastocysts which were subsequently introduced into pseudopregnant female hosts and carried to term using established methods. See, e.g., "Mouse Mutagenesis", 1998, Zambrowicz et al., eds., Lexicon Press, The Woodlands, Tex. The resulting chimeric animals were subsequently bred to produce offspring capable of germline transmission of an allele containing the engineered mutation in the gene of interest.

AAK1-gene disrupted mice were also made by homologous recombination. In this case, the second coding exon of the murine AAK1 gene (see GenBank Accession Number NM_177762) was removed by methods known in the art. See, e.g., U.S. Pat. Nos. 5,487,992, 5,627,059, and 5,789,215.

Mice homozygous (−/−) for the disruption of the AAK1 gene were studied in conjunction with mice heterozygous (+/−) for the disruption of the AAK1 gene, and wild-type (+/+) litter mates. During this analysis, the mice were subject to a medical work-up using an integrated suite of medical diagnostic procedures designed to assess the function of the major organ systems in a mammalian subject. Homozygous (−/−) "knockout" mice were studied in conjunction with their heterozygous (+/−) and wild-type (+/+) litter mates. Disruption of the AAK1 gene was confirmed by Southern analysis. Expression of the murine homolog of AAK1 was detected by RT-PCR in murine brain; spinal cord; eye; thymus; spleen; lung; kidney; liver; skeletal muscle; bone; stomach, small intestine and colon; heart; adipose; asthmatic lung; LPS liver; blood; banded heart; aortic tree; prostate; and mammary gland (5 week virgin, mature virgin, 12 DPC, 3 day post-partum (lactating), 3 day post-weaning (early involution), and 7 day post-weaning (late involution)).

AAK1 homozygous (−/−) and their wild-type (+/+) littermates were tested using the formalin paw test in order to assess their acute and tonic nociceptive responses. For these tests, Automatic Nociception Analyzers (purchased from the Ozaki lab at University of California, San Diego) were used. A metal band was placed around the left hind paw of each mouse 30 minutes prior to testing. After the 30-minute acclimation period, 20 μl of 5% formalin is subcutaneously injected in the dorsal surface of the left hind paw. Mice were individually housed in cylindrical chambers for 45 minutes. Fresh 5% formalin solution was prepared by diluting formaldehyde (Formalde-fresh 20%, Fisher Scientific, Fair Lawn, N.J.) with distilled water. Investigatory compounds were administered 30 minutes prior to formalin injection.

A computer recorded flinches per minute, total flinches for phase I (acute phase=first 8 minutes), and total flinches for phase II (tonic phase=time between minutes 20-40) through an electromagnetic field. See Yaksh T L, Ozaki G, McCumber D, Rathbun M, Svensson C, Malkmus S, Yaksh M C. *An automated flinch detecting system for use in the formalin nociceptive bioassay. J Appl Physiol.*, 2001; 90:2386-402. As shown in FIG. 1, phase 1 and phase 2 data were obtained using homozygous (−/−) mice females (n=16), wild-type females (n=15), homozygous (−/−) mice males (n=9), and wild-type males (n=18). In all groups and in both phases, the AAK1 homozygous (−/−) mice exhibited significantly less recorded paw flinching than their wild-type (+/+) littermates.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The invention claimed is:

1. A method for treating or managing a disease or a disorder mediated by AAK1 activity, the method comprising administering to a patient in need thereof a therapeutically effective amount of (S)-1-((2',6-bis(difluoromethyl)-[2,4'-bipyridin]-5-yl)oxy)-2,4-dimethylpentan-2-amine, or a pharmaceutically acceptable salt thereof, and a glucocorticoid, wherein the disease or disorder mediated by AAK1 activity is pain.

2. The method of claim 1, wherein the glucocorticoid is dexamethasone.

* * * * *